United States Patent
Beil et al.

(10) Patent No.: US 11,254,737 B2
(45) Date of Patent: Feb. 22, 2022

(54) MULTISPECIFIC BINDING MOLECULES HAVING SPECIFICITY TO DYSTROGLYCAN AND LAMININ-2

(71) Applicant: Sanofi, Paris (FR)

(72) Inventors: Christian Beil, Frankfurt am Main (DE); William H. Brondyk, Mansfield, MA (US); Yangde Chen, Wellesley, MA (US); Seng H. Cheng, Natick, MA (US); Timothy D. Connors, Shrewsbury, MA (US); Catherine Devaud, Malakoff (FR); Dietmar Hoffmann, Ashland, MA (US); Christian Lange, Frankfurt am Main (DE); Maureen Magnay, Westborough, MA (US); Tristan Magnay, Westborough, MA (US); Catherine Prades, Choisy le Roi (FR); Ercole Rao, Morfelden-Walldorf (DE); Leila Sevigny, Westborough, MA (US); Ronnie Wei, Needham, MA (US); Hongmei Zhao, Southborough, MA (US); Yunxiang Zhu, Wayland, MA (US)

(73) Assignee: SANOFI, Paris (FR)

( * ) Notice: Subject to any disclaimer, the term of this patent is extended or adjusted under 35 U.S.C. 154(b) by 21 days.

(21) Appl. No.: 16/818,304

(22) Filed: Mar. 13, 2020

(65) Prior Publication Data

US 2020/0317761 A1    Oct. 8, 2020

Related U.S. Application Data

(62) Division of application No. 15/932,251, filed on Feb. 16, 2018, now Pat. No. 10,626,169.
(Continued)

(30) Foreign Application Priority Data

Feb. 16, 2018    (EP) .................................... 18305168

(51) Int. Cl.
*C12N 15/11* (2006.01)
*C12N 15/63* (2006.01)
(Continued)

(52) U.S. Cl.
CPC .............. *C07K 16/18* (2013.01); *A61P 21/00* (2018.01); *C07K 16/28* (2013.01); *C12N 15/11* (2013.01);
(Continued)

(58) Field of Classification Search
CPC .... C07K 16/18; C07K 16/28; C07K 2317/24; C07K 2317/31; C07K 2317/34;
(Continued)

(56) References Cited

U.S. PATENT DOCUMENTS 5,565,332 A    10/1996    Hoogenboom et al.
5,589,205 A    12/1996    Ishikawa et al.
(Continued)

FOREIGN PATENT DOCUMENTS

EP    2691416 B1    5/2016
WO    WO-1996/027011 A1    9/1996
(Continued)

OTHER PUBLICATIONS

Atwell, S. et al. (Jul. 4, 1997). "Stable Heterodimers from Remodeling the Domain Interface of a Homodimer Using a Phage Display Library," *J. Mol. Biol.* 270(1):26-35.
(Continued)

*Primary Examiner* — Kimberly Ballard
(74) *Attorney, Agent, or Firm* — Morrison & Foerster LLP

(57) ABSTRACT

Provided herein multispecific (e.g., bispecific) binding molecules comprising a first binding domain that binds an
(Continued)

extracellular portion of dystroglycan and a second binding domain that binds laminin-2. Further provided herein are methods for making such binding molecules and uses of such binding molecules for treating and/or preventing alpha-dystroglycanopathies.

38 Claims, 39 Drawing Sheets

Specification includes a Sequence Listing.

Related U.S. Application Data

(60) Provisional application No. 62/460,663, filed on Feb. 17, 2017.

(51) Int. Cl.
| | |
|---|---|
| C07K 16/18 | (2006.01) |
| C07K 16/28 | (2006.01) |
| A61P 21/00 | (2006.01) |
| A61K 39/00 | (2006.01) |

(52) U.S. Cl.
CPC ........ C12N 15/63 (2013.01); A61K 2039/505 (2013.01); C07K 2317/24 (2013.01); C07K 2317/31 (2013.01); C07K 2317/34 (2013.01); C07K 2317/35 (2013.01); C07K 2317/524 (2013.01); C07K 2317/526 (2013.01); C07K 2317/55 (2013.01); C07K 2317/56 (2013.01); C07K 2317/565 (2013.01); C07K 2317/624 (2013.01); C07K 2317/66 (2013.01); C07K 2317/92 (2013.01)

(58) Field of Classification Search
CPC .......... C07K 2317/35; C07K 2317/524; C07K 2317/526; C07K 2317/55; C07K 2317/56; C07K 2317/565; C07K 2317/624; C07K 2317/66; C07K 2317/92; A61K 2039/505; A61P 21/00; C12N 15/11; C12N 15/63
See application file for complete search history.

(56) References Cited

U.S. PATENT DOCUMENTS

| | | | |
|---|---|---|---|
| 5,989,830 | A | 11/1999 | Davis et al. |
| 6,180,370 | B1 | 1/2001 | Queen et al. |
| 6,632,927 | B2 | 10/2003 | Adair et al. |
| 7,083,784 | B2 | 8/2006 | Dall'Acqua et al. |
| 7,241,877 | B2 | 7/2007 | Adair et al. |
| 7,244,615 | B2 | 7/2007 | Adair et al. |
| 7,244,832 | B2 | 7/2007 | Adair et al. |
| 7,262,050 | B2 | 8/2007 | Adair et al. |
| 7,612,181 | B2 | 11/2009 | Wu et al. |
| 9,221,917 | B2 | 12/2015 | Baurin et al. |
| 9,790,268 | B2 | 10/2017 | Pan et al. |
| 10,626,169 | B2 | 4/2020 | Beil et al. |
| 2003/0224981 | A1* | 12/2003 | Ruegg ................ G01N 33/5088 514/1.1 |
| 2004/0236078 | A1 | 11/2004 | Carter et al. |
| 2010/0226923 | A1 | 9/2010 | Rao et al. |
| 2010/0331527 | A1 | 12/2010 | Davis et al. |
| 2013/0039913 | A1 | 2/2013 | Labrijn et al. |
| 2016/0200811 | A1 | 7/2016 | Baurin |
| 2017/0320967 | A1 | 11/2017 | Yang et al. |
| 2018/0237511 | A1 | 8/2018 | Beil et al. |

FOREIGN PATENT DOCUMENTS

| | | | |
|---|---|---|---|
| WO | WO-2011/131746 | A2 | 10/2011 |
| WO | WO-2012135345 | A1 * | 10/2012 ......... C07K 16/2803 |
| WO | WO-2017/074878 | A1 | 5/2017 |
| WO | WO-2017/180913 | A2 | 10/2017 |

OTHER PUBLICATIONS

Barone, R. et al. (Oct. 2012; e-published on Apr. 24, 2012). "DPM2-CDG: A Muscular Dystrophy-Dystroglycanopathy Syndrome with Severe Epilepsy," *Ann. Neurol.* 72(4):550-558.

Barresi, R. et al. (Jan. 15, 2006). "Dystroglycan: From Biosynthesis to Pathogenesis of Human Disease," *J Cell. Sci.* 119(pt. 2):199-207.

Carter, P. et al. (May 1992). "Humanization of an Anti-p185$^{HER2}$ Antibody for Human Cancer Therapy," *Proc. Natl. Acad. Sci. USA* 89:4285-4289.

Carter, P. (Feb. 1, 2001). "Bispecific Human IgG by Design," *J. Jmmunol. Methods* 248(1-2)7-15.

Cheng, S.H. et al. (Sep. 2017). "AB008. Bifunctional antibody as a Surrogate Molecular Linker for the Treatment of Alpha-Dystroglycan Related Muscular Dystrophies", *Annals of Translational Medicine* 5(S2):29, one page.

Chothia, C. et al. (Aug. 20, 1987). "Canonical Structures for the Hypervariable Regions of Immunoglobulins," *J. Mol. Biol.* 196(4):901-917.

Chothia, C. et al. (Dec. 21-28, 1989). "Conformations of Immunoglobulin Hypervariable Regions," *Nature* 342(6252): 877-883.

Clement, E.M. et al. (Jan. 2008). "Mild POMGnT1 Mutations Underlie a Novel Limb-Girdle Muscular Dystrophy Variant," *Arch. Neurol.* 65(1):137-141.

Davis, J.H. et al. (2010). "SEEDbodies: Fusion Proteins Based on Strand-Exchange Engineered Domain (SEED) $C_H3$ Heterodimers In An Fc Analogue Platform For Asymmetric Binders Or Immunofusions And Bispecific Antibodies," *Protein Eng. Des. Sel.* 23(4): 195-202.

Durocher et al. (2002). "High-Level and High-Throughput Recombinant Protein Production by Transient Transfection of Suspension-Growing Human 293-EBNA1 Cells," *Nucl. Acids Res.* 30(2):E9, pp. 1-9.

Edwards, B.M. et al. (2003). "The Remarkable Flexibility of the Human Antibody Repertoire; Isolation of Over One Thousand Different Antibodies to a Single Protein, BLyS," *J. Mol. Biol.* 334:103-118.

Endo, T. et al. (2010). "Chapter Nineteen—POMGnTI, POMT1, and POMT2 Mutations in Congenital Muscular Dystrophies," *Methods Enzymol.* 479:343-352.

Fortunato, M.J. et al. (May 13, 2014). "Development of Rabbit Monoclonal Antibodies for Detection of Alpha-Dystroglycan in Normal and Dystrophic Tissue," *PLOS One* 9(5):e97567, pp. 1-10.

Godfrey, C. et al. (Oct. 1, 2007, e-pub. Aug. 18, 2007). "Refining Genotype—Phenotype Correlations in Muscular Dystrophies with Defective Glycosylation of Dystroglycan," *Brain* 130(10):2725-2735.

Godfrey, C. et al. (Jun. 2011; e-published on Mar. 11, 2011). "Dystroglycanopathies Coming into Focus,"*Curr. Opin. Genet. Dev.* 21(3):278-285.

Gunasekaran, K. et al. (Jun. 18, 2010; e-published on Apr. 16, 2010). "Enhancing Antibody Fc Heterodimer Formation Through Electrostatic Steering Effects—Applications to Bispecific Molecules and Monovalent IgG,"*J. Biol. Chem.* 285(25):19637-19646.

Han, R. et al. (Aug. 4, 2009). "Basal Lamina Strengthens Cell Membrane Integrity Via the Laminin G Domain-Binding Motif of α-Dystroglycan," *PNAS* 106(31):12573-12579.

Hara, Y. et al. (Mar. 10, 2011). "A Dystroglycan Mutation Associated with Limb-Girdle Muscular Dystrophy," *N. Engl. J Med.* 364(10): 939-946.

Hewitt, J. E. (Sep. 2009; e-published on Jun. 17, 2009). "Abnormal Glycosylation of Dystroglycan in Human Genetic Disease,"*Biochim. Bio phys. Acta.* 1792(9):853-861.

Hinton, P.R. et al. (Jan. 1, 2006). "An Engineered Human IgG1 Antibody With Longer Serum Half-Life," *J. Immunol.* 176(1):346-356.

Holt, K.H. et al. (Feb. 18, 2000). "Biosynthesis of Dystroglycan: Processing of a Precursor Propeptide," *FEBS Lett.* 468(1):79-83.

Humphrey, E.L. et al. (Jan. 1, 2015). "A New Monoclonal Antibody DAG-6F4 Against Human Alpha-Dystroglycan Reveals Reduced Core Protein in Some, But Not All, Dystroglycanopathy Patients," *Neuromuscular Disorders* 25(1):32-42.

(56) References Cited

OTHER PUBLICATIONS

Inamori, K. et al. (Jan. 6, 2012). "Dystroglycan Function Requires Xylosyl- and Glucuronyltransferase Activities of LARGE," *Science* 335(6064):93-96, eight pages.

Jones, P.T. et al. (May 29, 1986). "Replacing the Complementarity-Determining Regions in a Human Antibody with those from a Mouse," *Nature* 321:522-525.

Kanagawa, M. et al. (Mar. 8, 2016). "Identification of a Post-translational Modification with Ribitol-Phosphate and Its Defect in Muscular Dystrophy," *Cell. Rep.* 14(9):2209-2223.

Kim, D.-S. et al. (Mar. 23, 2004). "POMT1 Mutation Results in Defective Glycosylation and Loss of Laminin-Binding Activity in α-DG," *Neurology* 62(6):1009-1011.

Labrun, A.F. et al. (Mar. 26, 2013). "Efficient Generation of Stable Bispecific IgG1 by Controlled Fab-arm Exchange," *Proc. Natl. Acad. Sci.* 110(13):5145-5150.

Lefeber, D.J. et al. (Jul. 10, 2009). "Deficiency of Dol-P-Man Synthase Subunit DPM3 Bridges the Congenital Disorders of Glycosylation with the Dystroglycanopathies," *Am. J. Hum. Genet.* 85(1):76-86.

Lefranc, M.P. et al. (Jan. 2003). "IMGT Unique Numbering For Immunoglobulin And T Cell Receptor Variable Domains And Ig Superfamily V-Like Domains," *Dev. Comp. Immunol.* 27(1):55-77.

Longman, C. et al. (Nov. 1, 2003). "Mutations in the Human LARGE Gene Cause MDC1D, a Novel Form of Congenital Muscular Dystrophy with Severe Mental Retardation and Abnormal Glycosylation of α-dystroglycan," *Hum. Mot. Genet.* 12(21):2853-2861.

Lloyd, C. et al. (2009; e-pub. Oct. 29, 2008). "Modelling the Human Immune Response Performance of a 10" Human Antibody Repertoire Against a Broad Panel of Therapeutically Relevant Antigens," *Protein Engineering, Design & Selection* 22(3):159-168.

MacCallum, R.M et al. (Oct. 11, 1996). "Antibody-Antigen Interactions: Contact Analysis and Binding Site Topography," *J. Mol. Biol.* 262(5):732-745.

Masui, S. et al. (Mar. 1, 2005). "An Efficient System to Establish Multiple Embryonic Stem Cell Lines Carrying an Inducible Expression Unit," *Nucleic Acids Res.* 33(4):e43, pp. 1-8.

Matsumura, K. et al. (1993). "The Role of the Dystrophin-Glycoprotein Complex in the Molecular Pathogenesis of Muscular Dystrophies," *Neuromuscul. Disord.* 3(5-6):533-535.

Mazor, Y. et al. (2015; e-published on Jan. 15, 2015). "Improving Target Cell Specificity Using a Novel Monovalent Bispecific IgG Design," *Mabs* 7(2):377-389.

Merchant, A.M. et al. (Jul. 1998). "An Efficient Route to Human Bispecific IgG," *Nature Biotechnol.* 16(7):677-681.

Michele, D.E. et al. (Jul. 25, 2002). "Post-Translational Disruption of Dystroglycan-Ligand Interactions in Congenital Muscular Dystrophies," *Nature* 418(6896):417-422.

Muntoni, F. (Sep. 1, 2004). "Journey Into Muscular Dystrophies Caused by Abnormal Glycosylation," *Acta. Myol.* 23(2):79-84.

Muntoni, F. et al. (Nov. 2, 2002). "Defective Glycosylation in Muscular Dystrophy," *Lancet* 360(9343):1419-1421.

Muntoni, F. et al. (Dec. 2007). "Muscular Dystrophies Due to Defective Glycosylation of Dystroglycan,"*Acta. Myol.* 26(3): 129-135.

Murakami, T. et al. (Jun. 2009; e-published on Sep. 19, 2008). "A Novel POMT2 Mutation Causes Mild Congenital Muscular Dystrophy with Normal Brain MRI," *Brain Dev.* 31(6):465-468, seven pages.

Niwa, H. et al. (Dec. 15, 1991). "Efficient Selection for High-Expression Transfectants with a Novel Eukaryotic Vector," *Gene* 108(2):193-199.

Padlan, E.A. et al. (Jan. 1995). "Identification of Specificity-Determining Residues in Antibodies," *FASEB J.* 9(1): 133-139.

Presta, L.G. et al. (Sep. 1, 1993). "Humanization of an Antibody Directed Against IgE," *J Immunol* 151 (5):2623-2632.

Puckett, R.L. et al. (May 2009; e-published on Apr. 1, 2009). "Further Evidence of Fukutin Mutations as a Cause of Childhood Onset Limb-Girdle Muscular Dystrophy Without Mental Retardation," *Neuromuscul. Disord.* 19(5):352-356, twelve pages.

Qiao, C. et al. (Aug. 23, 2005). "Amelioration of Laminin- α2-Deficient Congenital Muscular Dystrophy by Somatic Gene Transfer of Miniagrin," *Proceedings of the National Academy of Sciences* 102(34) :11999-12004.

Ridgway, J.B. et al. (Jul. 1996). "'Knobs-lnto-Holes' Engineering of Antibody $C_H3$ Domains For Heavy Chain Heterodimerization," *Protein Eng.* 9(7):617-621.

Saredi, S. et al. (Jul. 15, 2012). "Novel POMGNT1 Point Mutations And Intragenic Rearrangements Associated With Muscle-Eye-Brain Disease," *J Neurol. Sci.* 318(1-2):45-50, fifteen pages.

Sims, M.J. et al. (Aug. 15, 1993). "A Humanized CD18 Antibody Can Block Function Without Cell Destruction," *J Immunol.* 151(4):2296-2308.

Smith, E.J. et al. (Dec. 11, 2015). "A Novel, Native-Format Bispecific Antibody Triggering T-Cell Killing of B-Cells is Robustly Active in Mouse Tumor Models and Cynomolgus Monkeys," *Sci. Rep.* 5:17943, pp. 1-12.

Thompson, J.D. (Nov. 11, 1994). "Clustal W: Improving the Sensitivity of Progressive Multiple Sequence Alignment Through Sequence Weighting, Position-Specific Gap Penalties and Weight Matrix Choice," *Nucleic Acids Res.* 22(22):4673-4680.

Toda, T. (Nov. 2005). "α-Dystroglycanopathy (FCMD, MEB, etc): Abnormal Glycosylation and Muscular Dystrophy,"*Rinsho Shinkeigaku (Clinical Neurology*), The 46th Annual Meeting of the Japanese Society of Neurology 45(11):932-934, (English Abstract Only).

Toda, T. (2007). "Hint and Luck for Identification of a Gene For Fukuyama Muscular Dystrophy, Fukutin," *Rinsho Shinkeigaku (Clinical Neurology*), The 48th Annual Meeting of the Japanese Society of Neurology 47(11):743-748, (English Abstract Only).

Toda, T. (2009). "Pathomechanism and Therapeutic Strategy of Fukuyama Congenital Muscular Dystrophy and Related Disorders," *Rinsho Shinkeigaku (Clinical Neurology*) 49(11):859-862, (English Abstract only).

Toda, T. et al. (Jun. 2003). "Fukuyama-Type Congenital Muscular Dystrophy (FCMD) and α-Dystroglycanopathy," *Congenit. Anom. (Kyoto*) 43(2):97-104.

Vannoy, C.H. et al. (Feb. 2017). "Adeno-Associated Virus-Mediated Mini-Agrin Delivery Is Unable to Rescue Disease Phenotype in a Mouse Model of Limb Girdle Muscular Dystrophy Type 21", *The American Journal of Pathology* 187(2):431 -440.

Van Reeuwijk, J. et al. (2005; e-published on May 13, 2005). "POMT2 Mutations Cause α-Dystroglycan Hypoglycosylation and Walker-Warburg Syndrome," *J Med. Genet.* 42(12):907-912.

Verhoeyen, M. et al. (Mar. 25, 1988). "Reshaping Human Antibodies: Grafting an Antilysozyme Activity," *Science* 239(4847):1534-1536.

Yamamoto, T. et al. (Jun. 1, 2010). "Functions of Fukutin, a Gene Responsible for Fukuyama Type Congenital Muscular Dystrophy, in Neuromuscular System and Other Somatic Organs," *Cent. Nerv. Syst. Agents. Med. Chem.* 10(2):169-179.

Yanagisawa, A. et al. (Jul.-Aug. 2009; e-published on Dec. 27, 2008). "POMT2 Intragenic Deletions and Splicing Abnormalities Causing Congenital Muscular Dystrophy With Mental Retardation," *Eur. J Med. Genet.* 52(4):201-206.

Yoshida-Moriguchi, T. et al. (Aug. 23, 2013; e-published on Aug. 8, 2013). "SGK196 Is a Glycosylation-Specific O-Mannose Kinase Required for Dystroglycan Function," *Science* 341 (6148):896-899, ten pages.

International Search Report and Written Opinion of the International Searching Authority dated May 16, 2018 for PCT Application No. PCT/US2018/000056 filed on Feb. 16, 2018, sixteen pages.

U.S. Appl. No. 15/770,471, filed Apr. 23, 2018, by Yan et al. (Copy not submitted herewith pursuant to the waiver of 37 C.F.R. § 1.98 (a)(2)(iii) issued by the Office on Sep. 21, 2004.).

\* cited by examiner

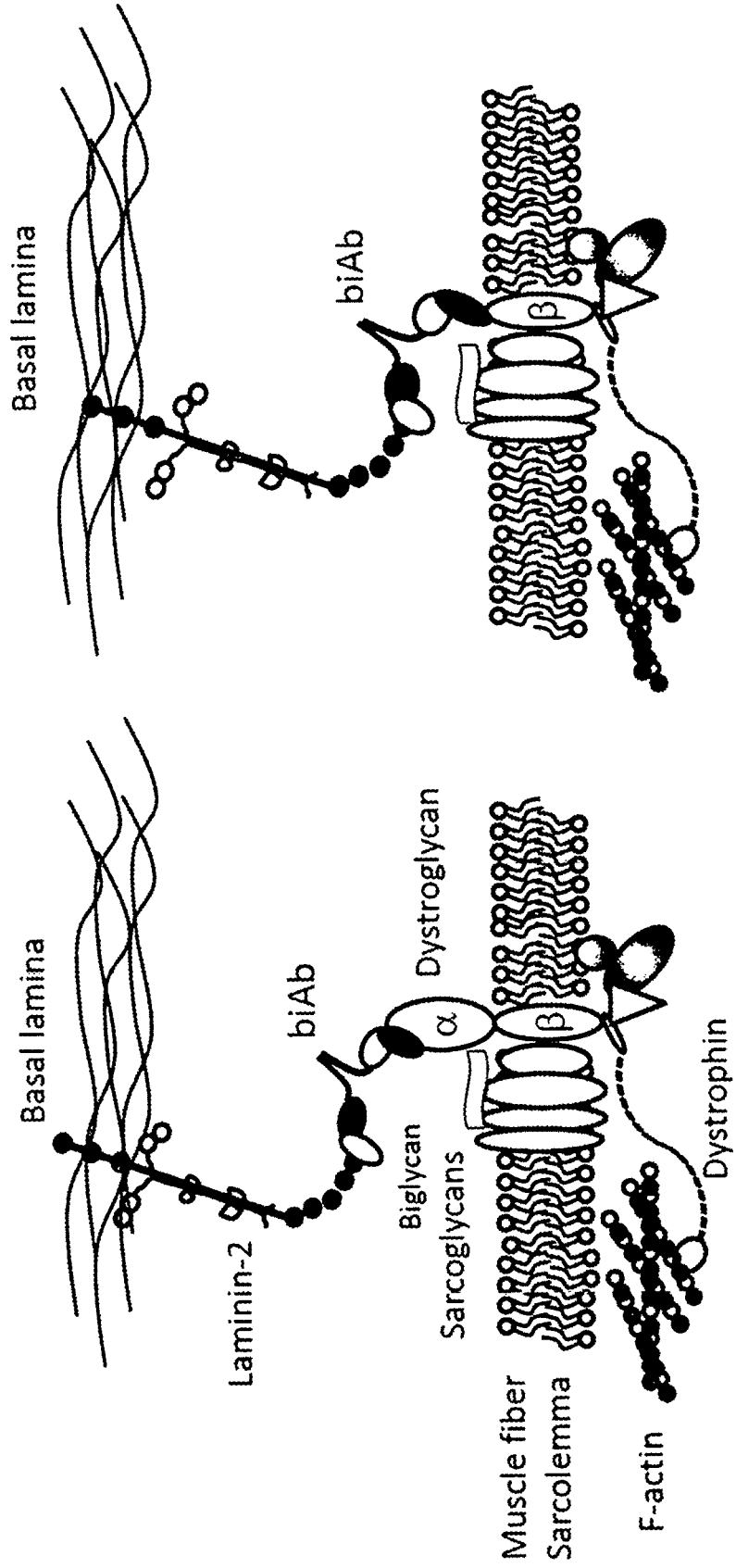

Human/mouse LG domain4/5

Human
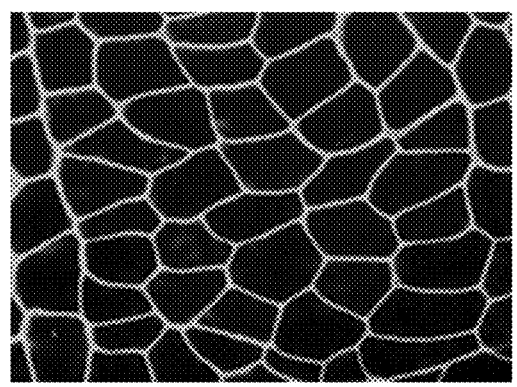
Mouse
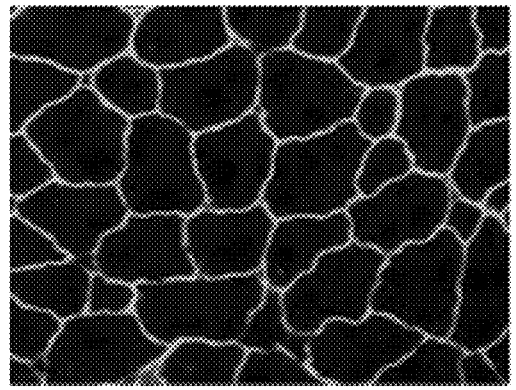
FIG. 4A
Human
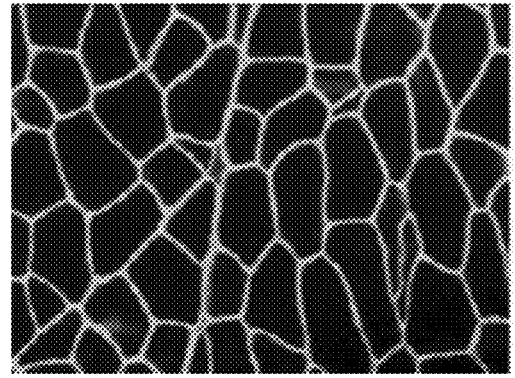
Mouse
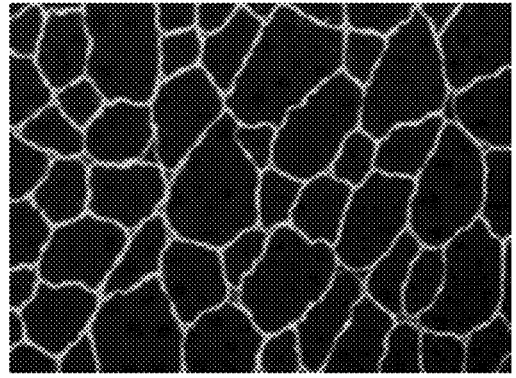
FIG. 4B

Human
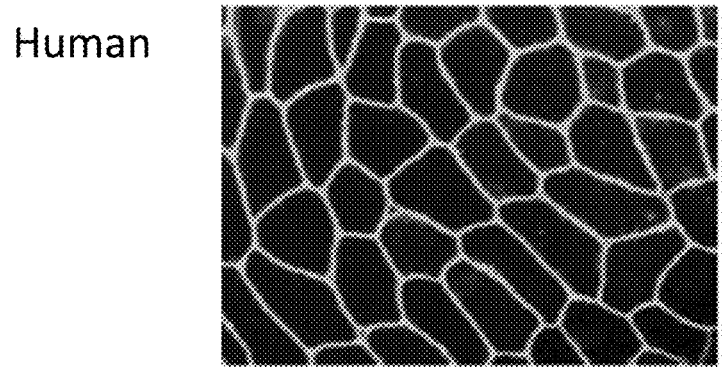
Mouse
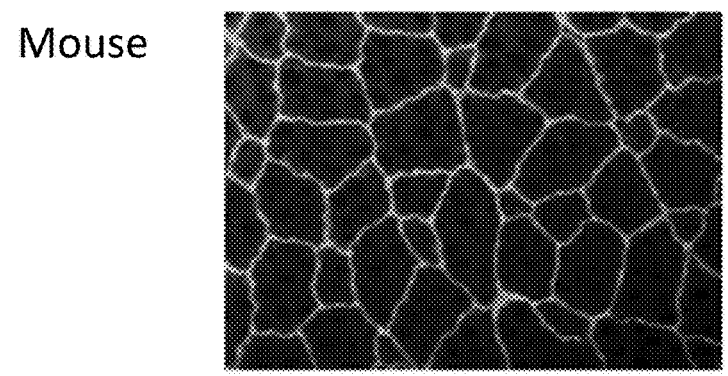
FIG. 4C
Human
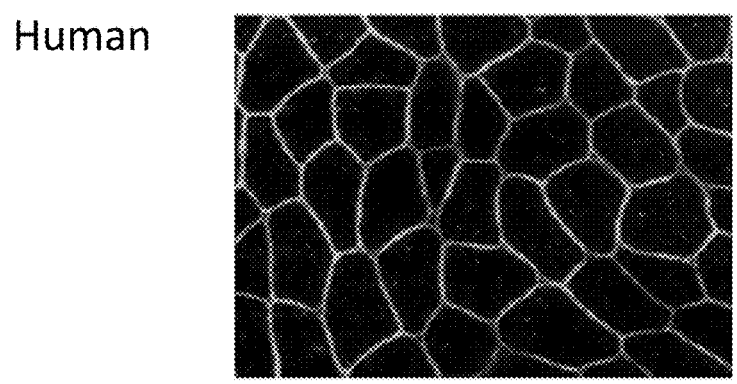
Mouse
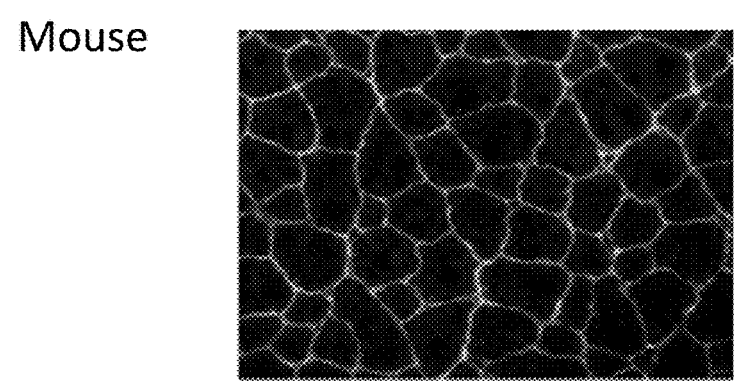
FIG. 4D

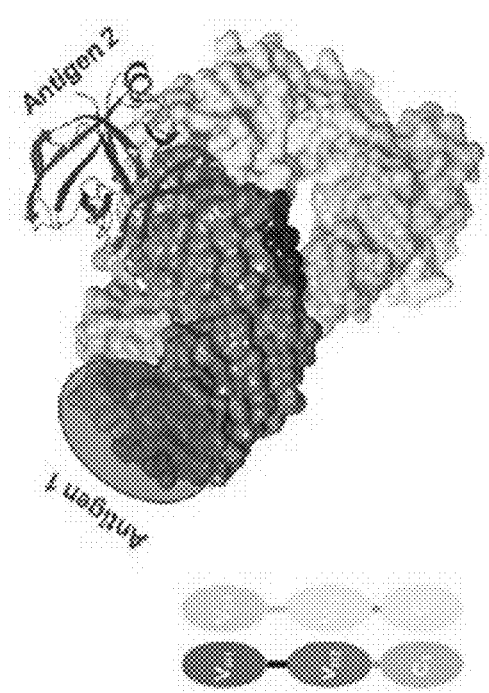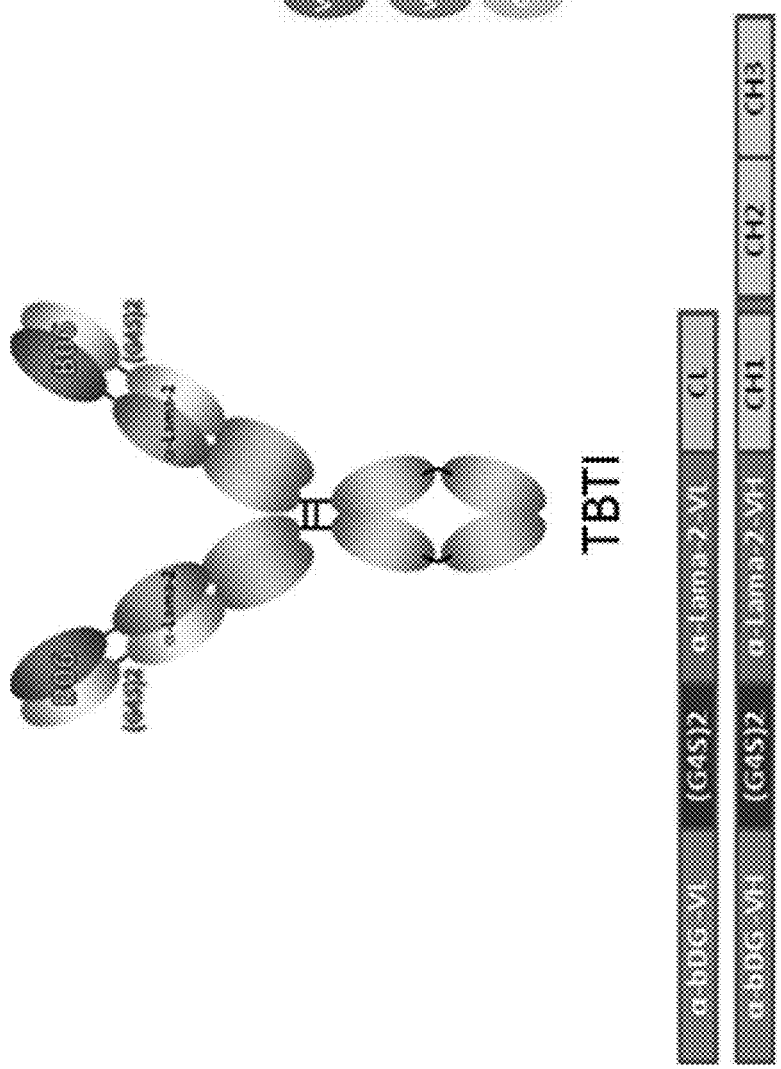
FIG. 5A

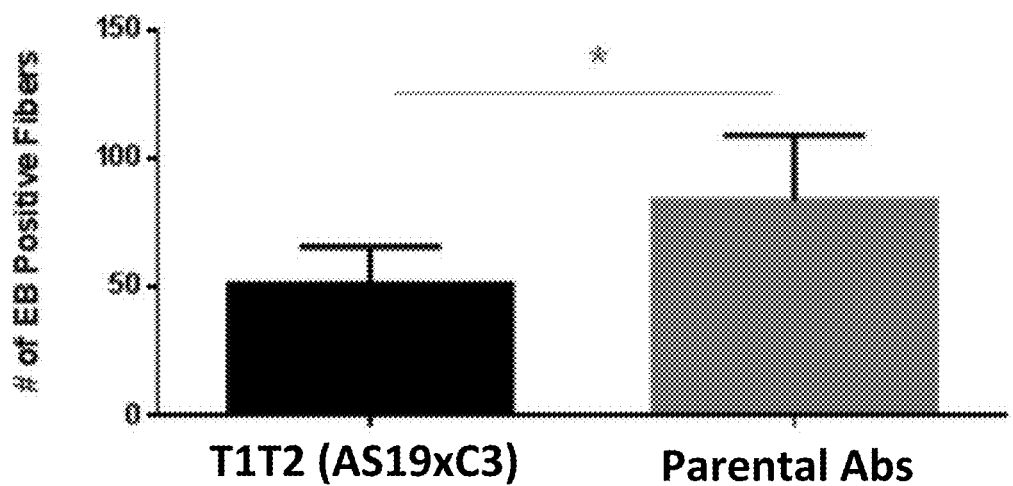
FIG. 8D
FIG. 8E
T1T2 (AS19xC3)
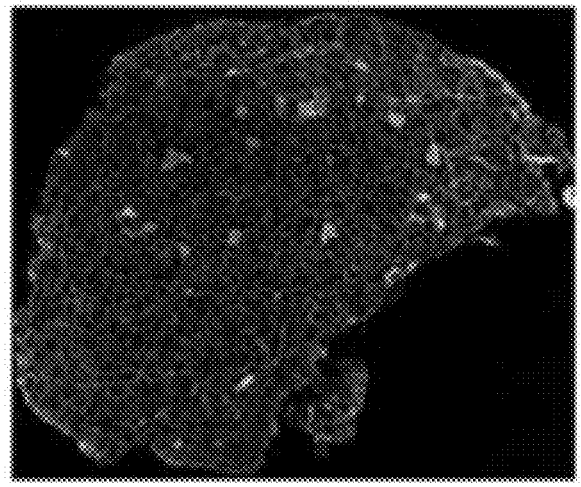
Parental Abs
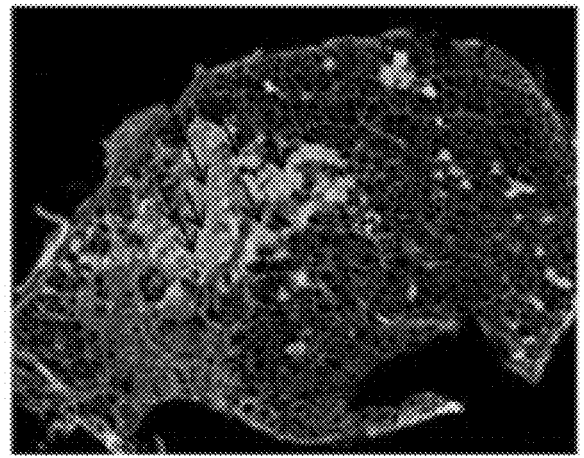

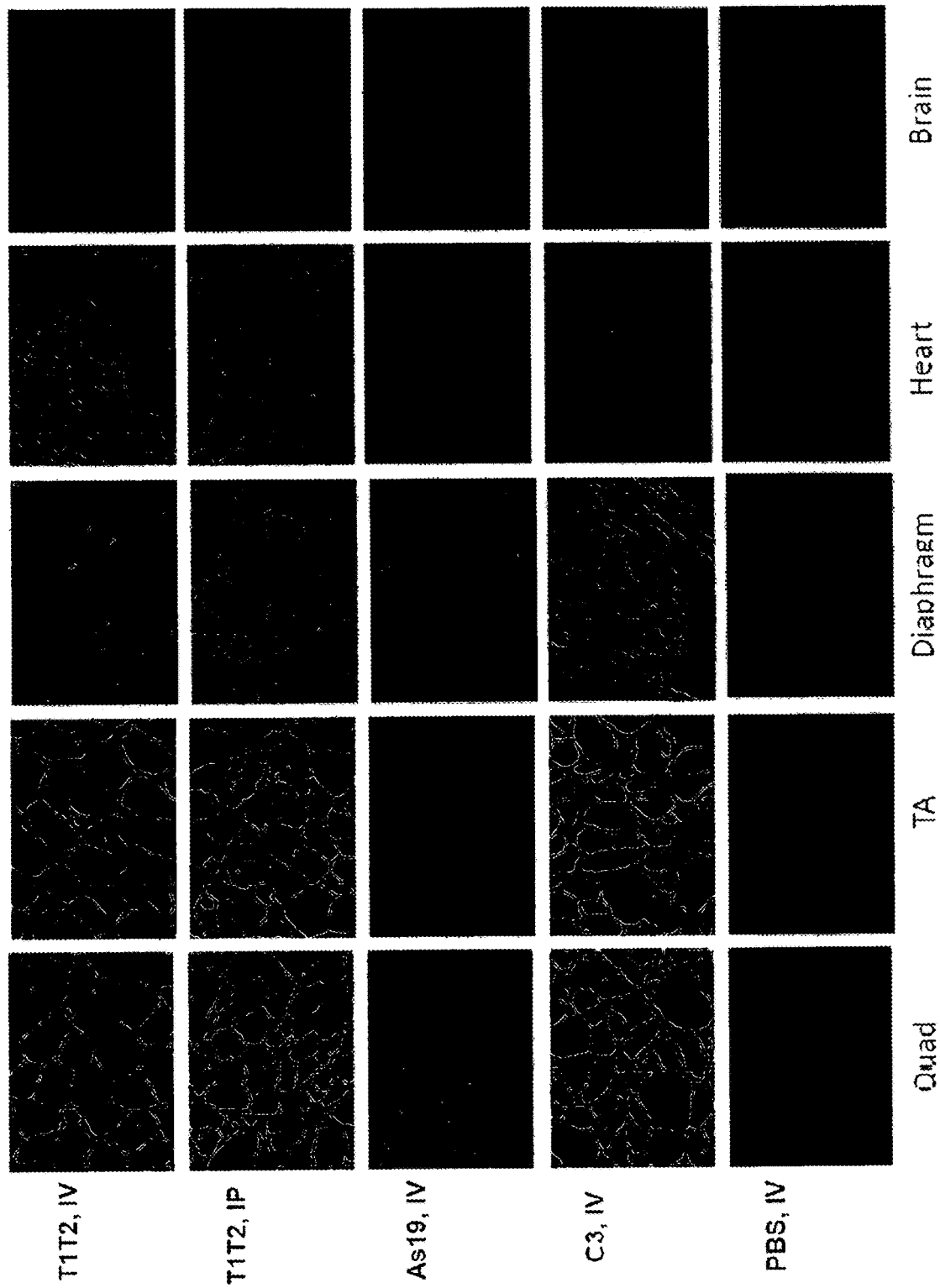

MULTISPECIFIC BINDING MOLECULES HAVING SPECIFICITY TO DYSTROGLYCAN AND LAMININ-2

CROSS-REFERENCE TO RELATED APPLICATIONS

This application is a divisional of U.S. patent application Ser. No. 15/932,251, issued as U.S. Pat. No. 10,626,169 on Apr. 21, 2020 and filed Feb. 16, 2018, which claims the priority benefit of U.S. Provisional Application No. 62/460,663, filed Feb. 17, 2017, and EP Application No. EP18305168.9, filed Feb. 16, 2018, each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 183952028110SEQLIST.txt, date recorded: Mar. 6, 2020, size: 315 KB).

FIELD

The disclosure relates to multispecific (e.g., multispecific and trivalent, or bispecific and bivalent or tetravalent) binding molecules comprising a first binding domain that binds an extracellular portion of dystroglycan and a second binding domain that binds laminin-2. The disclosure also relates to methods for making such binding molecules and uses of such binding molecules for treating and/or preventing alpha-dystroglycanopathies.

BACKGROUND

Alpha-dystroglycanopathy is a subgroup of congenital muscular dystrophy (CMD) characterized by reduced or absence of O-glycosylation in the mucin-like domain in alpha-dystroglycan (alpha-DG) (Muntoni, F. (2004) Acta. Myol. 23(2), 79-84; Toda, T. (2005) Rinsho Shinkeigaku 45(11), 932-934; Muntoni, F., et al. (2007) Acta. Myol. 26(3), 129-135; Hewitt, J. E. (2009). Biochim. Biophys. Acta. 1792(9), 853-861; Godfrey, C., et al. (2011) Curr. Opin. Genet. Dev. 21(3), 278-285). The lack or hypoglycosylation on alpha-dystroglycan leads to the loss or decreased binding of its ligands, which include laminin-2, agrin and perlecan in skeletal muscle, neurexin in the brain, and pikachurin in the eye. Alpha-dystroglycan is a peripheral membrane component of the dystrophin-glycoprotein complex (DGC) (FIG. 1A) common to all muscles and the heart (Matsumura, K., et al. (1993) Neuromuscul. Disord. 3(5-6), 533-535). In these tissues, the DGC complex functions to link the filamentous actin (F-actin)-associated cytoskeleton of the muscle fiber via dystrophin to the extracellular matrix (ECM, also called basal lamina) via laminin-2 (FIG. 1B).

In alpha-dystroglycanopathies, mutations in at least 18 genes identified to date are linked to aberrant processing of O-glycosylation on alpha-DG and lack of binding to its ligands, leading to diseases. See, e.g., Hara, Y., et al. (2011) N. Engl. J. Med. 364(10), 939-946; Kim, D. S., et al. (2004) Neurology 62(6), 1009-1011; van Reeuwijk, J., et al. (2005) J. Med. Genet. 42(12), 907-912; Murakami, T., et al. (2009) Brain Dev. 31(6), 465-468; Yanagisawa, A., et al. (2009) Eur. J. Med. Genet. 52(4), 201-206; Clement, E. M., et al. (2008) Arch. Neurol. 65(1), 137-141; Endo, T., et al. (2010) Methods Enzymol. 479, 343-352; Saredi, S., et al. (2012) J. Neurol. Sci. 318(1-2), 45-50; Longman, C., et al. (2003) Hum. Mol. Genet. 12(21), 2853-2861; Lefeber, D. J., et al. (2009) Am. J. Hum. Genet. 85(1), 76-86; Barone, R., et al. (2012) Ann. Neurol. 72(4), 550-558; Toda, T., et al. (2003) Congenit. Anom. (Kyoto) 43(2), 97-104; Toda, T. (2007). Rinsho Shinkeigaku 47(11), 743-748; Puckett, R. L., et al. (2009) Neuromuscul. Disord. 19(5), 352-356; Toda, T. (2009). Rinsho Shinkeigaku 49(11), 859-862; Yamamoto, T., et al. (2010) Cent. Nerv. Syst. Agents. Med. Chem. 10(2), 169-179; Kanagawa, M., et al. (2016) Cell. Rep. 14(9), 2209-2223; Yoshida-Moriguchi, T., et al. (2013) Science 341(6148), 896-899). These genes include, for instance, many glycosyltransferases, such as LARGE, which encodes a xylosyl- and glucuronyl-dual transferase responsible for adding xylose-glucuronic acid repeats to glycans to facilitate ligand binding (Inamori, K., et al. (2012) Science 335(6064), 93-96; Longman, C., et al. (2003) Hum. Mol. Genet. 12(21), 2853-2861). The main biological function of glycosyltransferases in this pathway (e.g. LARGE) are to properly assemble the O-glycosylation in the mucin-like domain in alpha-DG, which is necessary for tight binding to laminin-2 in the basal lamina of muscles, agrin and perlecan in neuromuscular junction, neurexin in the CNS, and pikachurin in the eye (Michele, D. E., et al. (2002) Nature 418 (6896), 417-422; Muntoni, F., et al. (2002) Lancet 360 (9343), 1419-1421). In the absence of proper O-glycosylation due to a defect in any of the aforementioned genes, binding of alpha-DG to laminin-2 in the extracellular matrix (ECM) is compromised or lost (FIG. 1C), causing a breakage of the mechanical link that is necessary for sarcolemma integrity. This renders the muscles prone to contraction-induced injury, resulting in damage to the sarcolemma of the muscle fiber and consequent muscular dystrophy (Barresi, R. and Campbell. K. P. (2006) J. Cell. Sci. 119, 199-207).

Due to the genetic heterogeneity, alpha-dystroglycanopathies include many subtypes of diseases which exhibit diverse yet overlapping clinical manifestations from very severe muscular dystrophy with central nervous system (CNS) and eye abnormalities to relatively mild muscular dystrophic phenotype without CNS manifestation or eye problem. There is no strict genetic and phenotypic correlation between different subtypes of alpha-dystroglycanopathies. Mutations in one gene can cause different subtypes of diseases with overlapping clinical manifestations, and mutations in different genes may lead to the same or similar disease (Godfrey, C., et al. (2007) Brain 130, 2725-2735). Because of this heterogeneity, strategies to treat individual alpha-dystroglycanopathies caused by mutations in individual genes have not been attractive for drug development due to the low cost effectiveness.

Alpha-dystroglycan and beta-dystroglycan are encoded by the same gene DAG1 and translated from a single mRNA as an intact type-1 transmembrane protein, dystroglycan. En route to the cell surface, dystroglycan is proteolytically cleaved to generate the transmembrane stud beta-dystroglycan and the noncovalently associated alpha-dystroglycan (Holt, K. H., et al. (2000) FEBS Lett. 468(1), 79-83). Theoretically, recombinant alpha-dystroglycan with proper O-glycosylation has been proposed as a protein replacement therapy for alpha-dystroglycanopathies. However, systemic delivery of recombinant alpha-dystroglycan indicated that this protein failed to reach the muscle interstitial space to be incorporated onto to the sarcolemma (Han, R., et al. (2009) PNAS 106(31), 12573-12579). Utilizing recombinant alpha-dystroglycan as protein replacement therapy for alpha-dystroglycanopathies is therefore thought to be technically impractical.

Therefore, a need exists for therapeutic molecules for preventing and/or treating alpha-dystroglycanopathies and their associated pathologies.

All references cited herein, including patent applications, patent publications, and UniProtKB/Swiss-Prot Accession numbers are herein incorporated by reference in their entirety, as if each individual reference were specifically and individually indicated to be incorporated by reference.

BRIEF SUMMARY

To meet this and other needs, provided herein, inter alia, are multispecific and bispecific binding molecules (e.g., bispecific antibodies) and bifunctional biologics that can bind to laminin-2 and dystroglycan(s) simultaneously. When such a multispecific/bispecific antibody or bifunctional biologic is administered into patients with alpha-dystroglycanopathies, its concurrent binding to laminin-2 in the basal lamina and dystroglycan (alpha- or beta-) on the sarcolemma can restore the missing linkage (FIGS. 1D and 1E). The present disclosure demonstrates that such an approach can ameliorate characteristic symptoms of alpha-dystroglycanopathies in an in vivo animal model system. In particular, antibodies are known to have prolonged circulation half-life (long pharmacokinetics) in vivo owing to their binding to neonatal Fc receptor, which mediates antibody recycling. Therefore, this multispecific/bispecific antibody strategy (or alternatively, bifunctional biologics strategy) represents a novel therapeutic approach for treating alpha-dystroglycanopathies.

In some embodiments, the disclosure provides a multispecific binding molecule comprising at least a first binding domain that binds an extracellular portion of dystroglycan and at least a second binding domain that binds laminin-2. In some embodiments, the multispecific binding molecule is a multispecific binding protein comprising one or more polypeptide chains.

In some embodiments, the multispecific binding molecule is a multispecific, trivalent binding protein comprising three antigen binding sites. In some embodiments, the binding protein comprises four polypeptide chains, wherein a first polypeptide chain comprises a structure represented by the formula:

$$V_{L2}\text{-}L_1\text{-}V_{L1}\text{-}L_2\text{-}C_L \quad [\text{I}]$$

and a second polypeptide chain comprises a structure represented by the formula:

$$V_{H1}\text{-}L_3\text{-}V_{H2}\text{-}L_4\text{-}C_{H1}\text{-hinge-}C_{H2}\text{—}C_{H3} \quad [\text{II}]$$

and a third polypeptide chain comprises a structure represented by the formula:

$$V_{H3}\text{—}C_{H1}\text{-hinge-}C_{H2}\text{—}C_{H3} \quad [\text{III}]$$

and a fourth polypeptide chain comprises a structure represented by the formula:

$$V_{L3}\text{—}C_L \quad [\text{IV}]$$

wherein:

$V_{L1}$ is a first immunoglobulin light chain variable domain;
$V_{L2}$ is a second immunoglobulin light chain variable domain;
$V_{L3}$ is a third immunoglobulin light chain variable domain;
$V_{H1}$ is a first immunoglobulin heavy chain variable domain;
$V_{H2}$ is a second immunoglobulin heavy chain variable domain;
$V_{H3}$ is a third immunoglobulin heavy chain variable domain;
$C_L$ is an immunoglobulin light chain constant domain;
$C_{H1}$ is an immunoglobulin $C_{H1}$ heavy chain constant domain;
$C_{H2}$ is an immunoglobulin $C_{H2}$ heavy chain constant domain;
$C_{H3}$ is an immunoglobulin $C_{H3}$ heavy chain constant domain;
hinge is an immunoglobulin hinge region connecting the $C_{H1}$ and $C_{H2}$ domains; and
$L_1$, $L_2$, $L_3$ and $L_4$ are amino acid linkers;
wherein the polypeptide of formula I and the polypeptide of formula II form a cross-over light chain-heavy chain pair; and wherein $V_{H1}$ and $V_{L1}$ form an antigen binding site, wherein $V_{H2}$ and $V_{L2}$ form an antigen binding site, and wherein $V_{H3}$ and $V_{L3}$ form an antigen binding site for a total of three antigen binding sites, and wherein the three antigen binding sites comprise at least one antigen binding site that binds the extracellular portion of dystroglycan and at least one antigen binding site that binds laminin-2.

In some embodiments, the multispecific binding molecule comprises one antigen binding site that binds the extracellular portion of dystroglycan and two antigen binding sites that bind laminin-2. In some embodiments, the two antigen binding sites that bind laminin-2 bind different epitopes of laminin-2. In some embodiments, the two antigen binding sites that bind laminin-2 bind the same epitope of laminin-2. In some embodiments, $V_{H1}$ and $V_{L1}$ form a first antigen binding site that binds laminin-2, $V_{H2}$ and $V_{L2}$ form a second antigen binding site that binds laminin-2, and $V_{H3}$ and $V_{L3}$ form a third antigen binding site that binds the extracellular portion of dystroglycan.

In some embodiments, the multispecific binding molecule comprises two antigen binding sites that bind the extracellular portion of dystroglycan and one antigen binding site that binds laminin-2. In some embodiments, the two antigen binding sites that bind the extracellular portion of dystroglycan bind different epitopes of the extracellular portion of dystroglycan. In some embodiments, the two antigen binding sites that bind the extracellular portion of dystroglycan bind the same epitope of the extracellular portion of dystroglycan. In some embodiments, $V_{H1}$ and $V_{L1}$ form a first antigen binding site that binds the extracellular portion of dystroglycan, $V_{H2}$ and $V_{L2}$ form a second antigen binding site that binds the extracellular portion of dystroglycan, and $V_{H3}$ and $V_{L3}$ form a third antigen binding site that binds laminin-2.

In some embodiments, the at least one antigen binding site that binds the extracellular portion of dystroglycan binds the extracellular portion of dystroglycan with an equilibrium dissociation constant ($K_D$) lower than about 1 µM when assayed as part of a multispecific binding protein. In some embodiments, the at least one antigen binding site that binds the extracellular portion of dystroglycan binds the extracellular portions of human and mouse dystroglycan. In some embodiments, the at least one antigen binding site that binds the extracellular portion of dystroglycan binds beta-dystroglycan. In some embodiments, the at least one antigen binding site that binds the extracellular portion of dystroglycan binds a polypeptide comprising the sequence SIVVEWTNN TLPLEPCPKE QIIGLSRRIA DENGKPRPAF SNALEPDFKA LSIAVTGSGS CRHLQFIPVA PPSPGS- SAAP ATEVPDRDPE KSSEDD (SEQ ID NO:290). In some embodiments, the at least one antigen binding site that binds the extracellular portion of dystroglycan binds a polypeptide comprising the sequence SIVVEWT NNTLPLEPCP KEQIAGLSRR IAEDDGKPRP AFSNALEPDF KATSITVTGS GSCRHLQFIP VVPPRRVPSE APPTEVPDRD PEKSSEDDV (SEQ ID NO:291). In some embodiments, the at least one antigen binding site that binds the extracellular portion of dystroglycan binds alpha-dystroglycan. In some embodiments, the at least one antigen binding site that binds the extracellular portion of dystroglycan binds a polypeptide comprising the sequence SIVVEWT NNTLPLEPCP KEQIAGLSRR IAEDDGKPRP AFSNALEPDF KATSITVTGS GSCRHLQFIP VVPPRRVPSE APPTEVPDRD PEKSSEDDV (SEQ ID NO:291).

In some embodiments, the at least one antigen binding site that binds laminin-2 binds human laminin-2. In some embodiments, the at least one antigen binding site that binds laminin-2 binds human laminin-2 with an equilibrium dissociation constant ($K_D$) lower than about 1 μM when assayed as part of a multispecific binding protein. In some embodiments, the at least one antigen binding site that binds laminin-2 binds mouse and human laminin-2. In some embodiments, the at least one antigen binding site that binds laminin-2 binds a polypeptide comprising a laminin G-like (LG) domain 4 of laminin-2, a laminin G-like (LG) domain 5 of laminin-2, or both. In some embodiments, the at least one antigen binding site that binds laminin-2 binds a polypeptide comprising the laminin G-like (LG) domain 4 and laminin G-like (LG) domain 5 of laminin-2. In some embodiments, the at least one antigen binding site that binds laminin-2 binds a polypeptide comprising the sequence VQPQPV PTPAFPFPAP TMVHGPCVAE SEPALLTGSK QFGLSRNSHI AIAFDDTKVK NRLTIELEVR TEAESGLLFY MARINHADFA TVQLRNGFPY FSYDLGSGDT STMIPTKIND GQWHKIKIVR VKQEGILYVD DASSQTISPK KADILDVVGI LYVGGLPINY TTRRIGPVTY SLDGCVRNLH MEQAPVDLDQ PTSSFHVGTC FANAESGTYF DGTGFAKAVG GFKVGLDLLV EFEFRTTRPT GVLLGVSSQK MDGMGIEMID EKLMFHVDNG AGRFTAIYDA GIPGHMCNGQ WHKVTAKKIK NRLELVVDGN QVDAQSPNSA STSADTNDPV FVGGFPGGLN QFGLTTNIRF RGCIRSLKLT KGTGKPLEVN FAKALELRGV QPVSCPTT (SEQ ID NO:300). In some embodiments, the at least one antigen binding site that binds laminin-2 binds a polypeptide comprising the sequence Q PEPVPTPAFP TPTPVLTHGP CAAESEPALL IGSKQFGLSR NSHIAIAFDD TKVKNRLTIE LEVRTEAESG LLFYMARINH ADFATVQLRN GLPYFSYDLG SGDTHTMIPT KINDGQWHKI KIMRSKQEGI LYVDGASNRT ISPKKADILD VVGMLYVGGL PINYTTRRIG PVTYSIDGCV RNLHMAEAPA DLEQPTSSFH VGTCFANAQR GTYFDGTGFA KAVGGFKVGL DLLVEFEFRT TTTTGVLLGI SSQKMDGMGI EMIDEKLMFH VDNGAGRFTA VYDAGVPGHL CDGQWHKVTA NKIKHRIELT VDGNQVEAQS PNPASTSADT NDPVFVGGFP DDLKQFGLTT SIPFRGCIRS LKLTKGTGKP LEVNFAKALE LRGVQPVSCP AN (SEQ ID NO:301). In some embodiments, the at least one antigen binding site that binds laminin-2 binds a polypeptide comprising the laminin G-like (LG) domain 5 of laminin-2. In some embodiments, the at least one antigen binding site that binds laminin-2 binds a polypeptide comprising the sequence ANAESGTYF DGTGFAKAVG GFKVGLDLLV EFEFRTTRPT GVLLGVSSQK MDGMGIEMID EKLMFHVDNG AGRFTAIYDA GIPGHMCNGQ WHKVTAKKIK NRLELVVDGN QVDAQSPNSA STSADTNDPV FVGGFPGGLN QFGLTTNIRF RGCIRSLKLT KGTGKPLEVN FAKALELRGV QPVSCPTT (SEQ ID NO:292). In some embodiments, the at least one antigen binding site that binds laminin-2 binds a polypeptide comprising the sequence ANAQR GTYFDGTGFA KAVGGFKVGL DLLVEFEFRT TTTTGVLLGI SSQKMDGMGI EMIDEKLMFH VDNGAGRFTA VYDAGVPGHL CDGQWHKVTA NKIKHRIELT VDGNQVEAQS PNPASTSADT NDPVFVGGFP DDLKQFGLTT SIPFRGCIRS LKLTKGTGKP LEVNFAKALE LRGVQPVSCP AN (SEQ ID NO:293).

In some embodiments, the at least one antigen binding site that binds the extracellular portion of dystroglycan comprises: (a) a heavy chain variable domain (VH) comprising a CDR-H1 comprising an amino acid sequence selected from the group consisting of SEQ ID NOs:1-8, a CDR-H2 comprising an amino acid sequence selected from the group consisting of SEQ ID NOs:9-17, and a CDR-H3 comprising an amino acid sequence selected from the group consisting of SEQ ID NOs:18-27; and (b) a light chain variable domain (VL) comprising a CDR-L1 comprising an amino acid sequence selected from the group consisting of SEQ ID NOs:28-37, a CDR-L2 comprising an amino acid sequence selected from the group consisting of SEQ ID NOs:38-42, and a CDR-L3 comprising an amino acid sequence selected from the group consisting of SEQ ID NOs:43-50. In some embodiments, the VH domain of the at least one antigen binding site that binds the extracellular portion of dystroglycan comprises a sequence selected from the group consisting of SEQ ID NOs:170, 172, 174, 176, 178, 180, 182, 184, 186, and 188; and the VL domain of the at least one antigen binding site that binds the extracellular portion of dystroglycan comprises a sequence selected from the group consisting of SEQ ID NOs:171, 173, 175, 177, 179, 181, 183, 185, 187, and 189. In some embodiments, the at least one antigen binding site that binds the extracellular portion of dystroglycan comprises: (a) a heavy chain variable domain (VH) comprising a CDR-H1 comprising the sequence of SEQ ID NO:316, a CDR-H2 comprising the sequence of SEQ ID NO:318, and a CDR-H3 comprising the sequence of SEQ ID NO:320; and (b) a light chain variable domain (VL) comprising a CDR-L1 comprising the sequence of SEQ ID NO:332, a CDR-L2 comprising the sequence of SEQ ID NO:334, and a CDR-L3 comprising the sequence of SEQ ID NO:336. In some embodiments, the at least one antigen binding site that binds the extracellular portion of dystroglycan comprises a humanized VH domain and a humanized VL domain. In some embodiments, the VH domain of the at least one antigen binding site that binds the extracellular portion of dystroglycan comprises the sequence of SEQ ID NO:314; and the VL domain of the at least one antigen binding site that binds the extracellular portion of dystroglycan comprises the sequence of SEQ ID NO:330. In some embodiments, the VH domain of the at least one antigen binding site that binds the extracellular portion of dystroglycan comprises the sequence of SEQ ID NO:346; and the VL domain of the at least one antigen binding site that binds the extracellular portion of dystroglycan comprises the sequence of SEQ ID NO:362. In some embodiments, the at least one antigen binding site that binds the extracellular portion of dystroglycan comprises: (a) a heavy chain variable domain (VH) comprising a CDR-H1, a CDR-H2, and a CDR-H3 of AS30SS_Hu6 or AS30SS_Hu9 shown in Table A2, D2, or I4; and (b) a light chain variable domain (VL) comprising a CDR-L1, a CDR- L2, and a CDR-L3 of AS30SS_Hu6 or AS30SS_Hu9 shown in Table A2, D2, or I4. In some embodiments, the VH domain of the at least one antigen binding site that binds the extracellular portion of dystroglycan comprises the sequence of an AS30SS_Hu6 or AS30SS_Hu9 VH domain shown in Table D2 or I4; and the VL domain of the at least one antigen binding site that binds the extracellular portion of dystroglycan comprises the sequence of an AS30SS_Hu6 or AS30SS_Hu9 VL domain shown in Table D2 or I4.

In some embodiments, the at least one antigen binding site that binds laminin-2 comprises: (a) a heavy chain variable domain (VH) comprising a CDR-H1 comprising an amino acid sequence selected from the group consisting of SEQ ID NOs:51-55 and 81-95, a CDR-H2 comprising an amino acid sequence selected from the group consisting of SEQ ID NOs:56-60 and 96-110, and a CDR-H3 comprising an amino acid sequence selected from the group consisting of SEQ ID NOs:61-65 and 111-125; and (b) a light chain variable domain (VL) comprising a CDR-L1 comprising an amino acid sequence selected from the group consisting of SEQ ID NOs:66-70 and 126-140, a CDR-L2 comprising an amino acid sequence selected from the group consisting of SEQ ID NOs:38, 71-75, and 141-154, and a CDR-L3 comprising an amino acid sequence selected from the group consisting of SEQ ID NOs:76-80 and 155-169. In some embodiments, the VH domain of the at least one antigen binding site that binds laminin-2 comprises a sequence selected from the group consisting of SEQ ID NOs:190, 192, 194, 196, 198, 200, 202, 204, 206, 208, 210, 212, 214, 216, 218, 220, 222, 224, 226, and 228; and the VL domain of the at least one antigen binding site that binds laminin-2 comprises a sequence selected from the group consisting of SEQ ID NOs: 191, 193, 195, 197, 199, 201, 203, 205, 207, 209, 211, 213, 215, 217, 219, 221, 223, 225, 227, and 229. In some embodiments, the at least one antigen binding site that binds laminin-2 comprises: (a) a heavy chain variable domain (VH) comprising a CDR-H1 comprising the sequence of SEQ ID NO:380, a CDR-H2 comprising the sequence of SEQ ID NO:382, and a CDR-H3 comprising the sequence of SEQ ID NO:384; and (b) a light chain variable domain (VL) comprising a CDR-L1 comprising the sequence of SEQ ID NO:396, a CDR-L2 comprising the sequence of SEQ ID NO:398, and a CDR-L3 comprising the sequence of SEQ ID NO:400. In some embodiments, the at least one antigen binding site that binds laminin-2 comprises a humanized VH domain and a humanized VL domain. In some embodiments, the VH domain of the at least one antigen binding site that binds laminin-2 comprises the sequence of SEQ ID NO:378; and the VL domain of the at least one antigen binding site that binds laminin-2 comprises the sequence of SEQ ID NO:394. In some embodiments, the at least one antigen binding site that binds laminin-2 comprises: (a) a heavy chain variable domain (VH) comprising a CDR-H1 comprising the sequence of SEQ ID NO:380, a CDR-H2 comprising the sequence of SEQ ID NO:382, and a CDR-H3 comprising the sequence of SEQ ID NO:384; and (b) a light chain variable domain (VL) comprising a CDR-L1 comprising the sequence of SEQ ID NO:428, a CDR-L2 comprising the sequence of SEQ ID NO:398, and a CDR-L3 comprising the sequence of SEQ ID NO:400. In some embodiments, the at least one antigen binding site that binds laminin-2 comprises a humanized VH domain and a humanized VL domain. In some embodiments, the VH domain of the at least one antigen binding site that binds laminin-2 comprises the sequence of SEQ ID NO:410; and the VL domain of the at least one antigen binding site that binds laminin-2 comprises the sequence of SEQ ID NO:426. In some embodiments, the at least one antigen binding site that binds laminin-2 comprises: (a) a heavy chain variable domain (VH) comprising a CDR-H1 comprising the sequence of SEQ ID NO:444, a CDR-H2 comprising the sequence of SEQ ID NO:446, and a CDR-H3 comprising the sequence of SEQ ID NO:448; and (b) a light chain variable domain (VL) comprising a CDR-L1 comprising the sequence of SEQ ID NO:460, a CDR-L2 comprising the sequence of SEQ ID NO:462, and a CDR-L3 comprising the sequence of SEQ ID NO:464. In some embodiments, the at least one antigen binding site that binds laminin-2 comprises a humanized VH domain and a humanized VL domain. In some embodiments, the VH domain of the at least one antigen binding site that binds laminin-2 comprises the sequence of SEQ ID NO:442; and the VL domain of the at least one antigen binding site that binds laminin-2 comprises the sequence of SEQ ID NO:458. In some embodiments, the at least one antigen binding site that binds laminin-2 comprises: (a) a heavy chain variable domain (VH) comprising a CDR-H1 comprising the sequence of SEQ ID NO:444, a CDR-H2 comprising the sequence of SEQ ID NO:478, and a CDR-H3 comprising the sequence of SEQ ID NO:448; and (b) a light chain variable domain (VL) comprising a CDR-L1 comprising the sequence of SEQ ID NO:460, a CDR-L2 comprising the sequence of SEQ ID NO:462, and a CDR-L3 comprising the sequence of SEQ ID NO:464. In some embodiments, the at least one antigen binding site that binds laminin-2 comprises a humanized VH domain and a humanized VL domain. In some embodiments, the VH domain of the at least one antigen binding site that binds laminin-2 comprises the sequence of SEQ ID NO:474; and the VL domain of the at least one antigen binding site that binds laminin-2 comprises the sequence of SEQ ID NO:490. In some embodiments, the at least one antigen binding site that binds laminin-2 comprises: (a) a heavy chain variable domain (VH) comprising a CDR-H1, a CDR-H2, and a CDR-H3 of C3_Hu10, C3_Hu11, C21_Hu11, or C21_Hu21 shown in Table A2, D2, or I4; and (b) a light chain variable domain (VL) comprising a CDR-L1, a CDR-L2, and a CDR-L3 of C3_Hu10, C3_Hu11, C21_Hu11, or C21_Hu21 shown in Table A2, D2, or I4. In some embodiments, the VH domain of the at least one antigen binding site that binds laminin-2 comprises the sequence of a C3_Hu10, C3_Hu11, C21_Hu11, or C21_Hu21 VH domain shown in Table D2 or I4; and the VL domain of the at least one antigen binding site that binds laminin-2 comprises the sequence of a C3_Hu10, C3_Hu11, C21_Hu11, or C21_Hu21 VL domain shown in Table D2 or I4.

In some embodiments, $V_{H1}$ comprises a CDR-H1 comprising the sequence of SEQ ID NO:380, a CDR-H2 comprising the sequence of SEQ ID NO:382, and a CDR-H3 comprising the sequence of SEQ ID NO:384, and $V_{L1}$ comprises a CDR-L1 comprising the sequence of SEQ ID NO:396, a CDR-L2 comprising the sequence of SEQ ID NO:398, and a CDR-L3 comprising the sequence of SEQ ID NO:400; $V_{H2}$ comprises a CDR-H1 comprising the sequence of SEQ ID NO:380, a CDR-H2 comprising the sequence of SEQ ID NO:382, and a CDR-H3 comprising the sequence of SEQ ID NO:384, and $V_{L1}$ comprises a CDR-L1 comprising the sequence of SEQ ID NO:396, a CDR-L2 comprising the sequence of SEQ ID NO:398, and a CDR-L3 comprising the sequence of SEQ ID NO:400; and $V_{H3}$ comprises a CDR-H1 comprising the sequence of SEQ ID NO:316, a CDR-H2 comprising the sequence of SEQ ID NO:318, and a CDR-H3 comprising the sequence of SEQ ID NO:320, and $V_{L3}$ comprises a CDR-L1 comprising the sequence of SEQ ID NO:332, a CDR-L2 comprising the sequence of SEQ ID NO:334, and a CDR-L3 comprising the sequence of SEQ ID NO:336. In some embodiments, $V_{H1}$ comprises the sequence of SEQ ID NO:378, and $V_{L1}$ comprises the sequence of SEQ ID NO:394; $V_{H2}$ comprises the sequence of SEQ ID NO:378, and $V_{L2}$ comprises the sequence of SEQ ID NO:394; and $V_{H3}$ comprises the sequence of SEQ ID NO:314, and $V_{L3}$ comprises the sequence of SEQ ID NO:330. In some embodiments, $V_{H1}$ comprises a CDR-H1 comprising the sequence of SEQ ID NO:380, a CDR-H2 comprising the sequence of SEQ ID NO:382, and a CDR-H3 comprising the sequence of SEQ ID NO:384, and $V_{L1}$ comprises a CDR-L1 comprising the sequence of SEQ ID NO:396, a CDR-L2 comprising the sequence of SEQ ID NO:398, and a CDR-L3 comprising the sequence of SEQ ID NO:400; $V_{H2}$ comprises a CDR-H1 comprising the sequence of SEQ ID NO:444, a CDR-H2 comprising the sequence of SEQ ID NO:446, and a CDR-H3 comprising the sequence of SEQ ID NO:448, and $V_{L2}$ comprises a CDR-L1 comprising the sequence of SEQ ID NO:460, a CDR-L2 comprising the sequence of SEQ ID NO:462, and a CDR-L3 comprising the sequence of SEQ ID NO:464; and $V_{H3}$ comprises a CDR-H1 comprising the sequence of SEQ ID NO:316, a CDR-H2 comprising the sequence of SEQ ID NO:318, and a CDR-H3 comprising the sequence of SEQ ID NO:320, and $V_{L3}$ comprises a CDR-L1 comprising the sequence of SEQ ID NO:332, a CDR-L2 comprising the sequence of SEQ ID NO:334, and a CDR-L3 comprising the sequence of SEQ ID NO:336. In some embodiments, $V_{H1}$ comprises the sequence of SEQ ID NO:378, and $V_{L1}$ comprises the sequence of SEQ ID NO:394; $V_{H2}$ comprises the sequence of SEQ ID NO:442, and $V_{L2}$ comprises the sequence of SEQ ID NO:458; and $V_{H3}$ comprises the sequence of SEQ ID NO:314, and $V_{L3}$ comprises the sequence of SEQ ID NO:330. In some embodiments, $V_{H1}$ comprises a CDR-H1 comprising the sequence of SEQ ID NO:380, a CDR-H2 comprising the sequence of SEQ ID NO:382, and a CDR-H3 comprising the sequence of SEQ ID NO:384, and $V_{L1}$ comprises a CDR-L1 comprising the sequence of SEQ ID NO:428, a CDR-L2 comprising the sequence of SEQ ID NO:398, and a CDR-L3 comprising the sequence of SEQ ID NO:400; $V_{H2}$ comprises a CDR-H1 comprising the sequence of SEQ ID NO:444, a CDR-H2 comprising the sequence of SEQ ID NO:478, and a CDR-H3 comprising the sequence of SEQ ID NO:448, and $V_{L2}$ comprises a CDR-L1 comprising the sequence of SEQ ID NO:460, a CDR-L2 comprising the sequence of SEQ ID NO:462, and a CDR-L3 comprising the sequence of SEQ ID NO:464; and $V_{H3}$ comprises a CDR-H1 comprising the sequence of SEQ ID NO:316, a CDR-H2 comprising the sequence of SEQ ID NO:318, and a CDR-H3 comprising the sequence of SEQ ID NO:320, and $V_{L3}$ comprises a CDR-L1 comprising the sequence of SEQ ID NO:332, a CDR-L2 comprising the sequence of SEQ ID NO:334, and a CDR-L3 comprising the sequence of SEQ ID NO:336. In some embodiments, $V_{H1}$ comprises the sequence of SEQ ID NO:410, and $V_{L1}$ comprises the sequence of SEQ ID NO:426; $V_{H2}$ comprises the sequence of SEQ ID NO:474, and $V_{L2}$ comprises the sequence of SEQ ID NO:490; and $V_{H3}$ comprises the sequence of SEQ ID NO:314, and $V_{L3}$ comprises the sequence of SEQ ID NO:330. In some embodiments, $V_{H1}$ comprises a CDR-H1 comprising the sequence of SEQ ID NO:444, a CDR-H2 comprising the sequence of SEQ ID NO:446, and a CDR-H3 comprising the sequence of SEQ ID NO:448, and $V_{L1}$ comprises a CDR-L1 comprising the sequence of SEQ ID NO:460, a CDR-L2 comprising the sequence of SEQ ID NO:462, and a CDR-L3 comprising the sequence of SEQ ID NO:464; $V_{H2}$ comprises a CDR-H1 comprising the sequence of SEQ ID NO:380, a CDR-H2 comprising the sequence of SEQ ID NO:382, and a CDR-H3 comprising the sequence of SEQ ID NO:384, and $V_{L2}$ comprises a CDR-L1 comprising the sequence of SEQ ID NO:428, a CDR-L2 comprising the sequence of SEQ ID NO:398, and a CDR-L3 comprising the sequence of SEQ ID NO:400; and $V_{H3}$ comprises a CDR-H1 comprising the sequence of SEQ ID NO:316, a CDR-H2 comprising the sequence of SEQ ID NO:318, and a CDR-H3 comprising the sequence of SEQ ID NO:320, and $V_{L3}$ comprises a CDR-L1 comprising the sequence of SEQ ID NO:332, a CDR-L2 comprising the sequence of SEQ ID NO:334, and a CDR-L3 comprising the sequence of SEQ ID NO:336. In some embodiments, $V_{H1}$ comprises the sequence of SEQ ID NO:442, and $V_{L1}$ comprises the sequence of SEQ ID NO:458; $V_{H2}$ comprises the sequence of SEQ ID NO:410, and $V_{L2}$ comprises the sequence of SEQ ID NO:426; and $V_{H3}$ comprises the sequence of SEQ ID NO:314, and $V_{L3}$ comprises the sequence of SEQ ID NO:330. In some embodiments, $V_{H1}$ comprises a CDR-H1 comprising the sequence of SEQ ID NO:444, a CDR-H2 comprising the sequence of SEQ ID NO:478, and a CDR-H3 comprising the sequence of SEQ ID NO:448, and $V_{L1}$ comprises a CDR-L1 comprising the sequence of SEQ ID NO:460, a CDR-L2 comprising the sequence of SEQ ID NO:462, and a CDR-L3 comprising the sequence of SEQ ID NO:464; $V_{H2}$ comprises a CDR-H1 comprising the sequence of SEQ ID NO:380, a CDR-H2 comprising the sequence of SEQ ID NO:382, and a CDR-H3 comprising the sequence of SEQ ID NO:384, and $V_{L2}$ comprises a CDR-L1 comprising the sequence of SEQ ID NO:396, a CDR-L2 comprising the sequence of SEQ ID NO:398, and a CDR-L3 comprising the sequence of SEQ ID NO:400; and $V_{H3}$ comprises a CDR-H1 comprising the sequence of SEQ ID NO:316, a CDR-H2 comprising the sequence of SEQ ID NO:318, and a CDR-H3 comprising the sequence of SEQ ID NO:320, and $V_{L3}$ comprises a CDR-L1 comprising the sequence of SEQ ID NO:332, a CDR-L2 comprising the sequence of SEQ ID NO:334, and a CDR-L3 comprising the sequence of SEQ ID NO:336. In some embodiments, $V_{H1}$ comprises the sequence of SEQ ID NO:474, and $V_{L1}$ comprises the sequence of SEQ ID NO:490; $V_{H2}$ comprises the sequence of SEQ ID NO:378, and $V_{L2}$ comprises the sequence of SEQ ID NO:394; and $V_{H3}$ comprises the sequence of SEQ ID NO:314, and $V_{L3}$ comprises the sequence of SEQ ID NO:330.

In some embodiments of any of the above embodiments, $L_1$ and $L_2$ comprise the sequence DKTHT (SEQ ID NO: 534). In some embodiments, $L_3$ and $L_4$ comprise the sequence DKTHT (SEQ ID NO: 534). In some embodiments, $L_1$, $L_2$, $L_3$, and $L_4$ comprise the sequence DKTHT (SEQ ID NO: 534).

In some embodiments of any of the above embodiments, the $C_{H3}$ domain of the second polypeptide chain comprises amino acid substitutions at positions corresponding to positions 354 and 366 of human IgG1 or IgG4 according to EU Index, wherein the amino acid substitutions are S354C and T366W; and wherein the $C_{H3}$ domain of the third polypeptide chain comprises amino acid substitutions at positions corresponding to positions 349, 366, 368, and 407 of human IgG1 or IgG4 according to EU Index, wherein the amino acid substitutions are Y349C, T366S, L368A, and Y407V. In some embodiments, the $C_{H3}$ domain of the second polypeptide chain comprises amino acid substitutions at positions corresponding to positions 349, 366, 368, and 407 of human IgG1 or IgG4 according to EU Index, wherein the amino acid substitutions are Y349C, T366S, L368A, and Y407V; and wherein the $C_{H3}$ domain of the third polypeptide chain comprises amino acid substitutions at positions corresponding to positions 354 and 366 of human IgG1 or IgG4 according to EU Index, wherein the amino acid substitutions are S354C and T366W. In some embodiments, the $C_{H3}$ domains of the second and the third polypeptide chains are human IgG1 or IgG4 $C_{H3}$ domains, and wherein only one of the $C_{H3}$ domains comprises amino acid substitutions at positions corresponding to positions 435 and 436 of human IgG1 or IgG4 according to EU Index, wherein the amino acid substitutions are H435R and Y436F. In some embodiments, the $C_{H2}$ domains of the second and the third polypeptide chains are human IgG1 or IgG4 $C_{H2}$ domains comprising an asparagine residue at position 297, an asparagine residue at position 298, an alanine residue at position 299, and a serine or threonine residue at position 300, numbering according to EU Index. In some embodiments, the $C_{H2}$ domains of the second and the third polypeptide chains are human IgG1 or IgG4 $C_{H2}$ domains comprising a tyrosine residue at position 252, a threonine residue at position 254, and a glutamic acid residue at position 256, numbering according to EU Index.

In some embodiments, the first polypeptide chain comprises the sequence of SEQ ID NO:500, the second polypeptide chain comprises the sequence of SEQ ID NO:498, the third polypeptide chain comprises the sequence of SEQ ID NO:499, and the fourth polypeptide chain comprises the sequence of SEQ ID NO:501. In some embodiments, the first polypeptide chain comprises the sequence of SEQ ID NO:504, the second polypeptide chain comprises the sequence of SEQ ID NO:502, the third polypeptide chain comprises the sequence of SEQ ID NO:503, and the fourth polypeptide chain comprises the sequence of SEQ ID NO:505. In some embodiments, the first polypeptide chain comprises the sequence of SEQ ID NO:508, the second polypeptide chain comprises the sequence of SEQ ID NO:506, the third polypeptide chain comprises the sequence of SEQ ID NO:507, and the fourth polypeptide chain comprises the sequence of SEQ ID NO:509. In some embodiments, the first polypeptide chain comprises the sequence of SEQ ID NO:512, the second polypeptide chain comprises the sequence of SEQ ID NO:510, the third polypeptide chain comprises the sequence of SEQ ID NO:511, and the fourth polypeptide chain comprises the sequence of SEQ ID NO:513. In some embodiments, the first polypeptide chain comprises the sequence of SEQ ID NO:516, the second polypeptide chain comprises the sequence of SEQ ID NO:514, the third polypeptide chain comprises the sequence of SEQ ID NO:515, and the fourth polypeptide chain comprises the sequence of SEQ ID NO:517. In some embodiments, the binding protein comprises one, two, three, or four polypeptides of triAb 3407, 3423, 3429, 3437, or 3439, as shown in Table I2 or I4.

In some embodiments, the binding protein comprises (a) a first antibody heavy chain comprising a first heavy chain variable (VH) domain and a first Fc region of an immunoglobulin comprising a first $C_{H3}$ region, and a first antibody light chain comprising a first light chain variable (VL) domain, wherein the first VH and VL domains form a first antigen binding domain that binds an extracellular portion of dystroglycan, and (b) a second antibody heavy chain comprising a second heavy chain variable (VH) domain and a second Fc region of an immunoglobulin comprising a second $C_{H3}$ region, and a second antibody light chain comprising a second light chain variable (VL) domain, wherein the second VH and VL domains form a second antigen binding domain that binds laminin-2; wherein the sequences of said first and second $C_{H3}$ regions are different and are such that the heterodimeric interaction between said first and second $C_{H3}$ regions is stronger than each of the homodimeric interactions of said first and second $C_{H3}$ regions, and wherein said first homodimeric protein has an amino acid other than Lys, Leu or Met at position 409 and said second homodimeric protein has an amino-acid substitution at a position selected from the group consisting of: 366, 368, 370, 399, 405 and 407 and/or wherein the sequences of said first and second $C_{H3}$ regions are such that the dissociation constants of homodimeric interactions of each of the $C_{H3}$ regions are between 0.01 and 10 micromolar. In some embodiments, the first antibody heavy chain comprises the sequence of SEQ ID NO:518, wherein the second antibody heavy chain comprises the sequence of SEQ ID NO:519, wherein the first antibody light chain comprises the sequence of SEQ ID NO:520, and wherein the second antibody light chain comprises the sequence of SEQ ID NO:521. In some embodiments, the binding protein comprises one, two, three, or four polypeptides of AS30_Hu6× C3_Hu10 Duobody, AS30_Hu6×C21_Hu11 Duetmab, AS30_Hu6×C3_Hu10 TBTI, AS30_Hu6×C21_Hu11 TBTI, AS30_Hu9×C3_Hu11 CODV, or AS30_Hu9×C21_Hu21 CODV, as shown in Table I3 or I4.

Further provided herein are isolated nucleic acid molecules comprising a nucleotide sequence encoding the multispecific binding molecule of any one of the above embodiments. Also provided are isolated nucleic acid molecules comprising a nucleotide sequence of Table G2 or I4. Also provided are expression vectors comprising the nucleic acid molecules of any one of the above embodiments. Also provided are host cells (e.g., isolated host cells) comprising the nucleic acid molecules or expression vectors of any one of the above embodiments. Also provided is a vector system comprising one or more vectors encoding a first, second, third, and fourth polypeptide chain of a multispecific binding molecule of any one of the above embodiments. Also provided is a host cell (e.g., an isolated host cell) comprising the vector system of any one of the above embodiments. Also provided is a method of producing a multispecific binding molecule, the method comprising: culturing a host cell of any one of the above embodiments under conditions such that the host cell expresses the multispecific binding molecule; and isolating the multispecific binding molecule from the host cell.

Further provided herein are methods for treating or preventing an alpha-dystroglycanopathy in an individual, the method comprising administering to the individual the multispecific binding molecule of any one of the above embodiments. Also provided herein are methods for providing linkage between laminin-2 and an extracellular portion of dystroglycan in an individual, the method comprising administering to the individual the multispecific binding molecule of any one of the above embodiments. Also provided herein is a use of the multispecific binding molecule of any one of the above embodiments for treating or preventing an alpha-dystroglycanopathy in an individual. Also provided herein is a use of the multispecific binding molecule of any one of the above embodiments for providing linkage between laminin-2 and an extracellular portion of dystroglycan in an individual. Also provided herein is a use of the multispecific binding molecule of any one of the above embodiments in the manufacture of a medicament for treating or preventing an alpha-dystroglycanopathy in an individual. Also provided herein is a use of the multispecific binding molecule of any one of the above embodiments in the manufacture of a medicament for providing linkage between laminin-2 and an extracellular portion of dystroglycan in an individual.

In some embodiments of any of the above embodiments, the individual has reduced expression of alpha-dystroglycan. In some embodiments, alpha-dystroglycan expressed in the individual has impaired or aberrant O-glycosylation. In some embodiments, the individual has a mutation in a gene selected from the group consisting of: dystroglycan (DAG1), protein O-mannosyltransferase-1 (POMT1), protein O-mannosyltransferase-2 (POMT2), protein O-linked mannose beta1,2-N-acetylglucosylaminyltransferase subunit 1 (POMGNT1), protein O-linked mannose beta1,4-N-acetylglucosylaminyltransferase subunit 2 (POMGNT2), xylosyl- and glucuronyltransferase 1 (LARGE1), xylosyl- and glucuronyltransferase 2 (LARGE2), dolichyl-phosphate mannosyltransferase subunit 1 (DPM1), dolichyl-phosphate mannosyltransferase subunit 2 (DPM2), dolichyl-phosphate mannosyltransferase subunit 3 (DPM3), fukutin, fukutin related protein (FKRP), isprenoid synthase domain containing (ISPD), protein O-mannose kinase (POMK), beta-1,3-N-acetylgalactosaminyltransferase 2 (B3GALNT2), beta-1,4-glucuronyltransferase 1 (B4GAT1), dolichol kinase (DOLK), transmembrane protein 5 (TMEM5), and GDP-mannose pyrophosphorylase B (GMPPB). In some embodiments, the multispecific binding molecule is administered via intravenous infusion. In some embodiments, the multispecific binding molecule is administered via intramuscular, intraperitoneal, or subcutaneous injection. In some embodiments, the individual is a human.

Further provided herein is a pharmaceutical composition comprising the multispecific binding molecule of any one of the above embodiments and a pharmaceutically acceptable carrier. Also provided is a kit comprising the multispecific binding molecule of any one of the above embodiments and instructions for use in treating or preventing an alpha-dystroglycanopathy in an individual. In some embodiments, the individual has reduced expression of alpha-dystroglycan. In some embodiments, alpha-dystroglycan expressed in the individual has impaired or aberrant O-glycosylation. In some embodiments, the individual has a mutation in a gene selected from the group consisting of: dystroglycan (DAG1), protein O-mannosyltransferase-1 (POMT1), protein O-mannosyltransferase-2 (POMT2), protein O-linked mannose beta1,2-N-acetylglucosylaminyltransferase subunit 1 (POMGNT1), protein O-linked mannose beta1,4-N-acetylglucosylaminyltransferase subunit 2 (POMGNT2), xylosyl- and glucuronyltransferase 1 (LARGE1), xylosyl- and glucuronyltransferase 2 (LARGE2), dolichyl-phosphate mannosyltransferase subunit 1 (DPM1), dolichyl-phosphate mannosyltransferase subunit 2 (DPM2), dolichyl-phosphate mannosyltransferase subunit 3 (DPM3), fukutin, fukutin related protein (FKRP), isprenoid synthase domain containing (ISPD), protein O-mannose kinase (POMK), beta-1,3-N-acetylgalactosaminyltransferase 2 (B3GALNT2), beta-1,4-glucuronyltransferase 1 (B4GAT1), dolichol kinase (DOLK), transmembrane protein 5 (TMEM5), and GDP-mannose pyrophosphorylase B (GMPPB). In some embodiments, the individual is a human.

Further provided herein is an antibody that binds an extracellular portion of dystroglycan, wherein the antibody comprises: (a) an antibody heavy chain comprising a heavy chain variable domain (VH) comprising a CDR-H1 comprising an amino acid sequence selected from the group consisting of SEQ ID NOs:1-8, a CDR-H2 comprising an amino acid sequence selected from the group consisting of SEQ ID NOs:9-17, and a CDR-H3 comprising an amino acid sequence selected from the group consisting of SEQ ID NOs:18-27; and (b) an antibody light chain comprising a light chain variable domain (VL) comprising a CDR-L1 comprising an amino acid sequence selected from the group consisting of SEQ ID NOs:28-37, a CDR-L2 comprising an amino acid sequence selected from the group consisting of SEQ ID NOs:38-42, and a CDR-L3 comprising an amino acid sequence selected from the group consisting of SEQ ID NOs:43-50. In some embodiments, the VH domain comprises an amino acid sequence selected from the group consisting of SEQ ID NOs:170, 172, 174, 176, 178, 180, 182, 184, 186, and 188; and the VL domain comprises an amino acid sequence selected from the group consisting of SEQ ID NOs:171, 173, 175, 177, 179, 181, 183, 185, 187, and 189. In some embodiments, the antibody comprises 1, 2, 3, 4, 5, or 6 CDR sequences of a binding domain shown in Table A2, D2, or I4, or a VH and/or VL domain sequence of a binding domain shown in Table D2 or I4 or encoded by a polynucleotide sequence shown in Table G2.

Further provided herein is an antibody that binds an extracellular portion of dystroglycan, wherein the antibody comprises: (a) an antibody heavy chain comprising a heavy chain variable domain (VH) comprising a CDR-H1 comprising the sequence of SEQ ID NO:316, a CDR-H2 comprising the sequence of SEQ ID NO:318, and a CDR-H3 comprising the sequence of SEQ ID NO:320; and (b) an antibody light chain comprising a light chain variable domain (VL) comprising a CDR-L1 comprising the sequence of SEQ ID NO:332, a CDR-L2 comprising the sequence of SEQ ID NO:334, and a CDR-L3 comprising the sequence of SEQ ID NO:336. In some embodiments, the VH domain comprises the amino acid sequence of SEQ ID NO:314, and the VL domain comprises the amino acid sequence of SEQ ID NO:330; or the VH domain comprises the amino acid sequence of SEQ ID NO:346, and the VL domain comprises the amino acid sequence of SEQ ID NO:362. In some embodiments, the antibody comprises 1, 2, 3, 4, 5, or 6 CDR sequences of a binding domain shown in Table A2, D2, or I4, or a VH and/or VL domain sequence of a binding domain shown in Table D2 or I4 or encoded by a polynucleotide sequence shown in Table G2.

Further provided herein is an antibody that binds laminin-2, wherein the antibody comprises: (a) an antibody heavy chain comprising a CDR-H1 comprising an amino acid sequence selected from the group consisting of SEQ ID NOs:51-55 and 81-95, a CDR-H2 comprising an amino acid sequence selected from the group consisting of SEQ ID NOs:56-60 and 96-110, and a CDR-H3 comprising an amino acid sequence selected from the group consisting of SEQ ID NOs:61-65 and 111-125; and (b) an antibody light chain comprising a light chain variable domain (VL) comprising a CDR-L1 comprising an amino acid sequence selected from the group consisting of SEQ ID NOs:66-70 and 126-140, a CDR-L2 comprising an amino acid sequence selected from the group consisting of SEQ ID NOs:38, 71-75, and 141-154, and a CDR-L3 comprising an amino acid sequence selected from the group consisting of SEQ ID NOs:76-80 and 155-169. In some embodiments, the VH domain comprises an amino acid sequence selected from the group consisting of SEQ ID NOs:190, 192, 194, 196, 198, 200, 202, 204, 206, 208, 210, 212, 214, 216, 218, 220, 222, 224, 226, and 228; and the VL domain comprises an amino acid sequence selected from the group consisting of SEQ ID NOs: 191, 193, 195, 197, 199, 201, 203, 205, 207, 209, 211, 213, 215, 217, 219, 221, 223, 225, 227, and 229. In some embodiments, the antibody comprises 1, 2, 3, 4, 5, or 6 CDR sequences of a binding domain shown in Table A2, D2, or I4, or a VH and/or VL domain sequence of a binding domain shown in Table D2 or I4 or encoded by a polynucleotide sequence shown in Table G2.

Further provided herein is an antibody that binds laminin-2, wherein the antibody comprises: (a) an antibody heavy chain comprising a heavy chain variable domain (VH) comprising a CDR-H1 comprising the sequence of SEQ ID NO:380, a CDR-H2 comprising the sequence of SEQ ID NO:382, and a CDR-H3 comprising the sequence of SEQ ID NO:384, and an antibody light chain comprising a light chain variable domain (VL) comprising a CDR-L1 comprising the sequence of SEQ ID NO:428, a CDR-L2 comprising the sequence of SEQ ID NO:398, and a CDR-L3 comprising the sequence of SEQ ID NO:400; (b) an antibody heavy chain comprising a heavy chain variable domain (VH) comprising a CDR-H1 comprising the sequence of SEQ ID NO:380, a CDR-H2 comprising the sequence of SEQ ID NO:382, and a CDR-H3 comprising the sequence of SEQ ID NO:384, and an antibody light chain comprising a light chain variable domain (VL) comprising a CDR-L1 comprising the sequence of SEQ ID NO:428, a CDR-L2 comprising the sequence of SEQ ID NO:398, and a CDR-L3 comprising the sequence of SEQ ID NO:400; (c) an antibody heavy chain comprising a heavy chain variable domain (VH) comprising a CDR-H1 comprising the sequence of SEQ ID NO:444, a CDR-H2 comprising the sequence of SEQ ID NO:446, and a CDR-H3 comprising the sequence of SEQ ID NO:448, and an antibody light chain comprising a light chain variable domain (VL) comprising a CDR-L1 comprising the sequence of SEQ ID NO:460, a CDR-L2 comprising the sequence of SEQ ID NO:462, and a CDR-L3 comprising the sequence of SEQ ID NO:464; or (d) an antibody heavy chain comprising a heavy chain variable domain (VH) comprising a CDR-H1 comprising the sequence of SEQ ID NO:444, a CDR-H2 comprising the sequence of SEQ ID NO:478, and a CDR-H3 comprising the sequence of SEQ ID NO:448, and an antibody light chain comprising a light chain variable domain (VL) comprising a CDR-L1 comprising the sequence of SEQ ID NO:460, a CDR-L2 comprising the sequence of SEQ ID NO:462, and a CDR-L3 comprising the sequence of SEQ ID NO:464. In some embodiments, (a) the VH domain comprises the amino acid sequence of SEQ ID NO:378, and the VL domain comprises the amino acid sequence of SEQ ID NO:394; (b) the VH domain comprises the amino acid sequence of SEQ ID NO:410, and the VL domain comprises the amino acid sequence of SEQ ID NO:426; (c) the VH domain comprises the amino acid sequence of SEQ ID NO:442, and the VL domain comprises the amino acid sequence of SEQ ID NO:458; or (d) the VH domain comprises the amino acid sequence of SEQ ID NO:474, and the VL domain comprises the amino acid sequence of SEQ ID NO:490. In some embodiments, the antibody comprises 1, 2, 3, 4, 5, or 6 CDR sequences of a binding domain shown in Table A2, D2, or I4, or a VH and/or VL domain sequence of a binding domain shown in Table D2 or I4 or encoded by a polynucleotide sequence shown in Table G2.

Further provided herein are isolated nucleic acid molecules comprising a nucleotide sequence encoding the antibody of any one of the above embodiments. Also provided are expression vectors comprising the nucleic acid molecules of any one of the above embodiments. Also provided are host cells (e.g., isolated host cells) comprising the nucleic acid molecules or expression vectors of any one of the above embodiments. Also provided is a method of producing an antibody, the method comprising: culturing a host cell of any one of the above embodiments under conditions such that the host cell expresses the antibody; and isolating the antibody from the host cell.

In one embodiment, the disclosure provides a bispecific binding molecule comprising a first binding domain that binds an extracellular portion of dystroglycan and a second binding domain that binds laminin-2. In some embodiments, the bispecific binding molecule is a bispecific binding protein comprising one or more polypeptide chains.

In some embodiments, the bispecific binding molecule is a bispecific, bivalent or tetravalent binding protein comprising two or four antigen binding sites. In some embodiments, the bispecific binding protein comprises a first binding domain that binds to an extracellular portion of dystroglycan, wherein the first binding domain comprises a first immunoglobulin heavy chain variable domain ($V_{H1}$) and a first immunoglobulin light chain variable domain ($V_{L1}$), and a second binding domain that binds to laminin-2, wherein the second binding domain comprises a second immunoglobulin heavy chain variable domain ($V_{H2}$) and a second immunoglobulin light chain variable domain ($V_{L2}$). In some embodiments, the $V_{H1}$ domain comprises at least 1, at least 2, at least 3, at least 4, at least 5, or 6 CDR sequences of an antibody shown in Table A and/or the $V_{L1}$ domain comprises at least 1, at least 2, at least 3, at least 4, at least 5, or 6 CDR sequences of an antibody shown in Table A. In some embodiments, the $V_{H2}$ domain comprises at least 1, at least 2, at least 3, at least 4, at least 5, or 6 CDR sequences of an antibody shown in Table B or Table C and/or the $V_{L2}$ domain comprises at least 1, at least 2, at least 3, at least 4, at least 5, or 6 CDR sequences of an antibody shown in Table B or Table C.

In some embodiments, the bispecific binding molecule comprises four polypeptide chains that form four antigen binding sites, wherein two polypeptide chains comprise a structure represented by the formula:

$$V_{L1}\text{-}L_1\text{-}V_{L2}\text{-}L_2\text{-}C_L \qquad [I]$$

and two polypeptide chains comprise a structure represented by the formula:

$$V_{H2}\text{-}L_3\text{-}V_{H1}\text{-}L_4\text{-}C_{H1}\text{-hinge-}C_{H2}\text{—}C_{H3} \qquad [II]$$

wherein:

$V_{L1}$ is a first immunoglobulin light chain variable domain;
$V_{L2}$ is a second immunoglobulin light chain variable domain;
$V_{H1}$ is a first immunoglobulin heavy chain variable domain;
$V_{H2}$ is a second immunoglobulin heavy chain variable domain;
$C_L$ is an immunoglobulin light chain constant domain;
$C_{H1}$ is an immunoglobulin $C_{H1}$ heavy chain constant domain;
$C_{H2}$ is an immunoglobulin $C_{H2}$ heavy chain constant domain;
$C_{H3}$ is an immunoglobulin $C_{H3}$ heavy chain constant domain;
hinge is an immunoglobulin hinge region connecting the $C_{H1}$ and $C_{H2}$ domains; and
$L_1$, $L_2$, $L_3$, and $L_4$ are amino acid linkers; wherein the $V_{H1}$ and $V_{L1}$ domains form a $V_{H1}/V_{L1}$ binding pair, and wherein the $V_{H2}$ and $V_{L2}$ domains form a $V_{H2}/V_{L2}$ binding pair.

In some embodiments, the $V_{H1}$ and $V_{L1}$ domains cross-over to form the $V_{H1}/V_{L1}$ binding pair. In some embodiments, the $V_{H2}$ and $V_{L2}$ domains cross-over to form the $V_{H2}/V_{L2}$ binding pair. In some embodiments, $L_1$, $L_2$, $L_3$, and $L_4$ are each 0 to 50 amino acid residues in length. In some embodiments, $L_1$, $L_2$, $L_3$, and $L_4$ are each 0 to 25 amino acid residues in length. In some embodiments, $L_1$, $L_2$, $L_3$, and $L_4$ are each 0 to 14 amino acid residues in length. In some embodiments, $L_1$ is 5 amino acid residues in length; $L_2$ is 5 amino acid residues in length; $L_3$ is 5 amino acid residues in length; and $L_4$ is 5 amino acid residues in length. In some embodiments, $L_1$ is 14 amino acid residues in length; $L_2$ is 2 amino acid residues in length; $L_3$ is 14 amino acid residue in length; and $L_4$ is 2 amino acid residues in length. In some embodiments, $L_1$ and $L_3$ each comprise the sequence EPKSDKTHTSPPSP (SEQ ID NO:296), and wherein $L_2$ and $L_4$ each comprise the sequence GG. In some embodiments, $L_1$ is 7 amino acid residues in length; $L_2$ is 5 amino acid residues in length; $L_3$ is 1 amino acid residue in length; and $L_4$ is 2 amino acid residues in length. In some embodiments, $L_1$ comprises the sequence GQPKAAP (SEQ ID NO:297); $L_2$ comprises the sequence TKGPS (SEQ ID NO:298); $L_3$ comprises a serine residue; and $L_4$ comprises the sequence RT. In some embodiments, $L_1$ is 10 amino acid residues in length; $L_2$ is 10 amino acid residues in length; $L_3$ is 0 amino acid residues in length; and $L_4$ is 0 amino acid residues in length. In some embodiments, $L_1$ and $L_2$ each comprise the sequence GGSGSSGSGG (SEQ ID NO:299). In some embodiments, one or both of the variable domains of the polypeptides of formula I and/or formula II are human, humanized, or mouse variable domains.

In some embodiments, the bispecific binding molecule comprises two light chains comprising a structure represented by the formula:

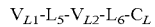    [III]

and two heavy chains comprising a structure represented by the formula:

    [IV]

wherein:
$V_{L1}$ is a first immunoglobulin light chain variable domain;
$V_{L2}$ is a second immunoglobulin light chain variable domain;
$V_{H1}$ is a first immunoglobulin heavy chain variable domain;
$V_{H2}$ is a second immunoglobulin heavy chain variable domain;
$C_L$ is an immunoglobulin light chain constant domain;
$C_{H1}$ is an immunoglobulin $C_{H1}$ heavy chain constant domain;
$C_{H2}$ is an immunoglobulin $C_{H2}$ heavy chain constant domain;
$C_{H3}$ is an immunoglobulin $C_{H3}$ heavy chain constant domain;
hinge is an immunoglobulin hinge region connecting the $C_{H1}$ and $C_{H2}$ domains; and
$L_5$, $L_6$, $L_7$, and $L_8$ are amino acid linkers; wherein the $V_{H1}$ and $V_{L1}$ domains form a $V_{H1}/V_{L1}$ binding pair, and wherein the $V_{H2}$ and $V_{L2}$ domains form a $V_{H2}/V_{L2}$ binding pair.

In some embodiments, $L_5$, $L_6$, $L_7$, and $L_8$ are each 0 to 50 amino acid residues in length. In some embodiments, $L_5$, $L_6$, $L_7$, and $L_8$ are each 0 to 25 amino acid residues in length. In some embodiments, $L_5$, $L_6$, $L_7$, and $L_8$ are each 0 to 14 amino acid residues in length. In some embodiments, the $L_5$ and $L_7$ linkers comprise the amino acid sequence of GGGGSGGGGS (SEQ ID NO:294), and wherein the $L_6$ and $L_8$ linkers are each 0 amino acid residues in length. In some embodiments, one or both of the variable domains of the polypeptides of formula III and/or formula IV are human, humanized, or mouse variable domains.

In some embodiments of any of the above embodiments, the $V_{H1}/V_{L1}$ binding pair binds the extracellular portion of dystroglycan, and wherein the $V_{H2}/V_{L2}$ binding pair binds laminin-2. In some embodiments, the $V_{H1}/V_{L1}$ binding pair binds the extracellular portion of human dystroglycan. In some embodiments, the $V_{H1}/V_{L1}$ binding pair binds the extracellular portion of human dystroglycan with an equilibrium dissociation constant ($K_D$) lower than about 1 μM. In some embodiments, the $V_{H1}/V_{L1}$ binding pair binds the extracellular portions of human and mouse dystroglycan. In some embodiments, the $V_{H1}/V_{L1}$ binding pair binds beta-dystroglycan. In some embodiments, the $V_{H1}/V_{L1}$ binding pair binds a polypeptide comprising the sequence SIVVEWTNN TLPLEPCPKE QIIGLSRRIA DENGKPRPAF SNALEPDFKA LSIAVTGSGS CRHLQFIPVA PPSPGSSAAP ATEVPDRDPE KSSEDD (SEQ ID NO:290). In some embodiments, the $V_{H1}/V_{L1}$ binding pair binds a polypeptide comprising the sequence SIVVEWT NNTLPLEPCP KEQIAGLSRR IAEDDGKPRP AFSNALEPDF KATSITVTGS GSCRHLQFIP VVPPRRVPSE APPTEVPDRD PEKSSEDDV (SEQ ID NO:291). In some embodiments, the $V_{H1}/V_{L1}$ binding pair binds alpha-dystroglycan. In some embodiments, the $V_{H2}/V_{L2}$ binding pair binds human laminin-2. In some embodiments, the $V_{H2}/V_{L2}$ binding pair binds human laminin-2 with an equilibrium dissociation constant ($K_D$) lower than about 1 μM. In some embodiments, the $V_{H2}/V_{L2}$ binding pair binds mouse and human laminin-2. In some embodiments, the $V_{H2}/V_{L2}$ binding pair binds a polypeptide comprising a laminin G-like (LG) domain 4 of laminin-2, a laminin G-like (LG) domain 5 of laminin-2, or both. In some embodiments, the $V_{H2}/V_{L2}$ binding pair binds a polypeptide comprising the laminin G-like (LG) domain 4 and laminin G-like (LG) domain 5 of laminin-2. In some embodiments, the $V_{H2}/V_{L2}$ binding pair binds a polypeptide comprising the sequence VQPQPV PTPAFPFPAP TMVHGPCVAE SEPALLTGSK QFGLSRNSHI AIAFDDTKVK NRLTIELEVR TEAESGLLFY MARINHADFA TVQLRNGFPY FSYDLGSGDT STMIPTKIND GQWHKIKIVR VKQEGILYVD DASSQTISPK KADILDVVGI LYVGGLPINY TTRRIGPVTY SLDGCVRNLH MEQAPVDLDQ PTSSFHVGTC FANAESGTYF DGTGFAKAVG GFKVGLDLLV EFEFRTTRPT GVLLGVSSQK MDGMGIEMID EKLMFHVDNG AGRFTAIYDA GIPGHMCNGQ WHKVTAKKIK NRLELVVDGN QVDAQSPNSA STSADTNDPV FVGGFPGGLN QFGLTTNIRF RGCIRSLKLT KGTGKPLEVN FAKALELRGV QPVSCPTT (SEQ ID NO:300). In some embodiments, the $V_{H2}/V_{L2}$ binding pair binds a polypeptide comprising the sequence Q PEPVPTPAFP TPTPVLTHGP CAAESEPALL IGSKQFGLSR NSHIAIAFDD TKVKNRLTIE LEVRTEAESG LLFYMARINH ADFATVQLRN GLPYFSYDLG SGDTHTMIPT KINDGQWHKI KIMRSKQEGI LYVDGASNRT ISPKKADILD VVGMLYVGGL PINYTTRRIG PVTYSIDGCV RNLHMAEAPA DLEQPTSSFH VGTCFANAQR GTYFDGTGFA KAVGGFKVGL DLLVEFEFRT TTTTGVLLGI SSQKMDGMGI EMIDEKLMFH VDNGAGRFTA VYDAGVPGHL CDGQWHKVTA NKIKHRIELT VDGNQVEAQS PNPASTSADT NDPVFVGGFP DDLKQFGLTT SIPFRGCIRS LKLTKGTGKP LEVNFAKALE LRGVQPVSCP AN (SEQ ID NO:301). In some embodiments, the $V_{H2}/V_{L2}$ binding pair binds a polypeptide comprising the laminin G-like (LG) domain 5 of laminin-2. In some embodiments, the $V_{H2}/V_{L2}$ binding pair binds a polypeptide comprising the sequence ANAESGTYF DGTGFAKAVG GFKVGLDLLV EFEFRTTRPT GVLLGVSSQK MDGMGIEMID EKLMFHVDNG AGRFTAIYDA GIPGHMCNGQ WHKVTAKKIK NRLELVVDGN QVDAQSPNSA STSADTNDPV FVGGFPGGLN QFGLTTNIRF RGCIRSLKLT KGTGKPLEVN FAKALELRGV QPVSCPTT (SEQ ID NO:292). In some embodiments, the $V_{H2}/V_{L2}$ binding pair binds a polypeptide comprising the sequence ANAQR GTYFDGTGFA KAVGGFKVGL DLLVEFEFRT TTTTGVLLGI SSQKMDGMGI EMIDEKLMFH VDNGAGRFTA VYDAGVPGHL CDGQWHKVTA NKIKHRIELT VDGNQVEAQS PNPASTSADT NDPVFVGGFP DDLKQFGLTT SIPFRGCIRS LKLTKGTKGP LEVN-FAKALE LRGVQPVSCP AN (SEQ ID NO:293).

In some embodiments, the $V_{H1}$ domain comprises a CDR-H1 comprising an amino acid sequence selected from the group consisting of SEQ ID NOs:1-8, a CDR-H2 comprising an amino acid sequence selected from the group consisting of SEQ ID NOs:9-17, and a CDR-H3 comprising an amino acid sequence selected from the group consisting of SEQ ID NOs:18-27; and/or wherein the $V_{L1}$ domain comprises a CDR-L1 comprising an amino acid sequence selected from the group consisting of SEQ ID NOs:28-37, a CDR-L2 comprising an amino acid sequence selected from the group consisting of SEQ ID NOs:38-42, and a CDR-L3 comprising an amino acid sequence selected from the group consisting of SEQ ID NOs:43-50. In some embodiments, the $V_{H1}$ domain comprises an amino acid sequence selected from the group consisting of SEQ ID NOs:170, 172, 174, 176, 178, 180, 182, 184, 186, and 188. In some embodiments, the $V_{L1}$ domain comprises an amino acid sequence selected from the group consisting of SEQ ID NOs:171, 173, 175, 177, 179, 181, 183, 185, 187, and 189. In some embodiments, the $V_{H1}$ domain is encoded by a nucleic acid sequence selected from the group consisting of SEQ ID NOs:230, 232, 234, 236, 238, 240, 242, 244, 246, and 248. In some embodiments, the $V_{L1}$ domain is encoded by a nucleic acid sequence selected from the group consisting of SEQ ID NOs:231, 233, 235, 237, 239, 241, 243, 245, 247, and 249. In some embodiments, the $V_{H2}$ domain comprises a CDR-H1 comprising an amino acid sequence selected from the group consisting of SEQ ID NOs:51-55 and 81-95, a CDR-H2 comprising an amino acid sequence selected from the group consisting of SEQ ID NOs:56-60 and 96-110, and a CDR-H3 comprising an amino acid sequence selected from the group consisting of SEQ ID NOs:61-65 and 111-125; and/or wherein the $V_{L2}$ domain comprises a CDR-L1 comprising an amino acid sequence selected from the group consisting of SEQ ID NOs:66-70 and 126-140, a CDR-L2 comprising an amino acid sequence selected from the group consisting of SEQ ID NOs:38, 71-75, and 141-154, and a CDR-L3 comprising an amino acid sequence selected from the group consisting of SEQ ID NOs:76-80 and 155-169. In some embodiments, the $V_{H2}$ domain comprises an amino acid sequence selected from the group consisting of SEQ ID NOs:190, 192, 194, 196, 198, 200, 202, 204, 206, 208, 210, 212, 214, 216, 218, 220, 222, 224, 226, and 228. In some embodiments, the $V_{L2}$ domain comprises an amino acid sequence selected from the group consisting of SEQ ID NOs: 191, 193, 195, 197, 199, 201, 203, 205, 207, 209, 211, 213, 215, 217, 219, 221, 223, 225, 227, and 229. In some embodiments, the $V_{H2}$ domain is encoded by a nucleic acid sequence selected from the group consisting of SEQ ID NOs:250, 252, 254, 256, 258, 260, 262, 264, 266, 268, 270, 272, 274, 276, 278, 280, 282, 284, 286, and 288. In some embodiments, the $V_{L2}$ domain is encoded by a nucleic acid sequence selected from the group consisting of SEQ ID NOs:251, 253, 255, 257, 259, 261, 263, 265, 267, 269, 271, 273, 275, 277, 279, 281, 283, 285, 287, and 289.

In some embodiments of any of the above embodiments, the $V_{H1}/V_{L1}$ binding pair binds laminin-2, and wherein the $V_{H2}/V_{L2}$ binding pair binds the extracellular portion of dystroglycan. In some embodiments, the $V_{H2}/V_{L2}$ binding pair binds the extracellular portion of human dystroglycan. In some embodiments, the $V_{H2}/V_{L2}$ binding pair binds the extracellular portion of human dystroglycan with an equilibrium dissociation constant ($K_D$) lower than about 1 μM. In some embodiments, the $V_{H2}/V_{L2}$ binding pair binds the extracellular portions of human and mouse dystroglycan. In some embodiments, the $V_{H2}/V_{L2}$ binding pair binds beta-dystroglycan. In some embodiments, the $V_{H2}/V_{L2}$ binding pair binds a polypeptide comprising the sequence SIV-VEWTNN TLPLEPCPKE QIIGLSRRIA DENGKPRPAF SNALEPDFKA LSIAVTGSGS CRHLQFIPVA PPSPGS-SAAP ATEVPDRDPE KSSEDD (SEQ ID NO:290). In some embodiments, the $V_{H2}/V_{L2}$ binding pair binds a polypeptide comprising the sequence SIVVEWT NNTLPLEPCP KEQIAGLSRR IAEDDGKPRP AFSN-ALEPDF KATSITVTGS GSCRHLQFIP VVPPRRVPSE APPTEVPDRD PEKSSEDDV (SEQ ID NO:291). In some embodiments, the $V_{H2}/V_{L2}$ binding pair binds alpha-dystroglycan. In some embodiments, the $V_{H1}/V_{L1}$ binding pair binds human laminin-2. In some embodiments, the $V_{H1}/V_{L1}$ binding pair binds human laminin-2 with an equilibrium dissociation constant ($K_D$) lower than about 1 μM. In some embodiments, the $V_{H1}/V_{L1}$ binding pair binds mouse and human laminin-2. In some embodiments, the $V_{H1}/V_{L1}$ binding pair binds a polypeptide comprising a laminin G-like (LG) domain 4 of laminin-2, a laminin G-like (LG) domain 5 of laminin-2, or both. In some embodiments, the $V_{H1}/V_{L1}$ binding pair binds a polypeptide comprising the laminin G-like (LG) domain 4 and laminin G-like (LG) domain 5 of laminin-2. In some embodiments, the $V_{H1}/V_{L1}$ binding pair binds a polypeptide comprising the sequence VQPQPV PTPAFPFPAP TMVHGPCVAE SEPALLTGSK QFGLSRNSHI AIAFDDTKVK NRLTIELEVR TEAESGLLFY MARINHADFA TVQLRNGFPY FSYDLGSGDT STMIPTKIND GQWHKIKIVR VKQEGI-LYVD DASSQTISPK KADILDVVGI LYVGGLPINY TTRRIGPVTY SLDGCVRNLH MEQAPVDLDQ PTSSFHVGTC FANAESGTYF DGTGFAKAVG GFKVGLDLLV EFEFRTTRPT GVLLGVSSQK MDGMGIEMID EKLMFHVDNG AGRFTAIYDA GIPGHMCNGQ WHKVTAKKIK NRLELVVDGN QVDAQSPNSA STSADTNDPV FVGGFPGGLN QFGLTTNIRF RGCIRSLKLT KGTGKPLEVN FAKA-LELRGV QPVSCPTT (SEQ ID NO:300). In some embodiments, the $V_{H1}/V_{L1}$ binding pair binds a polypeptide comprising the sequence Q PEPVPTPAFP TPTPVLTHGP CAAESEPALL IGSKQFGLSR NSHIAIAFDD TKVKNRLTIE LEVRTEAESG LLFYMARINH ADFA-TVQLRN GLPYFSYDLG SGDTHTMIPT KINDGQWHKI KIMRSKQEGI LYVDGASNRT ISPK-KADILD VVGMLYVGGL PINYTTRRIG PVTYSIDGCV RNLHMAEAPA DLEQPTSSFH VGTCFANAQR GTYFDGTGFA KAVGGFKVGL DLLVEFEFRT TTTTGVLLGI SSQKMDGMGI EMIDEKLMFH VDN-GAGRFTA VYDAGVPGHL CDGQWHKVTA NKIKHRI-ELT VDGNQVEAQS PNPASTSADT NDPVFVGGFP DDLKQFGLTT SIPFRGCIRS LKLTKGTGKP LEVN-FAKALE LRGVQPVSCP AN (SEQ ID NO:301). In some embodiments, the $V_{H1}/V_{L1}$ binding pair binds a polypeptide comprising the laminin G-like (LG) domain 5 of laminin-2. In some embodiments, the $V_{H1}/V_{L1}$ binding pair binds a polypeptide comprising the sequence ANAESGTYF DGTGFAKAVG GFKVGLDLLV EFEFRTTRPT GVLLGVSSQK MDGMGIEMID EKLMFHVDNG AGRFTAIYDA GIPGHMCNGQ WHKVTAKKIK NRLELVVDGN QVDAQSPNSA STSADTNDPV FVGGFPGGLN QFGLTTNIRF RGCIRSLKLT KGTGKPLEVN FAKALELRGV QPVSCPTT (SEQ ID NO:292). In some embodiments, the $V_{H1}/V_{L1}$ binding pair binds a polypeptide comprising the sequence ANAQR GTYFDGTGFA KAVGGFKVGL DLLVEFEFRT TTTTGVLLGI SSQKMDGMGI EMIDEKLMFH VDNGAGRFTA VYDAGVPGHL CDGQWHKVTA NKIKHRIELT VDGNQVEAQS PNPASTSADT NDPVFVGGFP DDLKQFGLTT SIPFRGCIRS LKLTKGTGKP LEVNFAKALE LRGVQPVSCP AN (SEQ ID NO:293).

In some embodiments, the $V_{H2}$ domain comprises a CDR-H1 comprising an amino acid sequence selected from the group consisting of SEQ ID NOs:1-8, a CDR-H2 comprising an amino acid sequence selected from the group consisting of SEQ ID NOs:9-17, and a CDR-H3 comprising an amino acid sequence selected from the group consisting of SEQ ID NOs:18-27; and/or wherein the $V_{L2}$ domain comprises a CDR-L1 comprising an amino acid sequence selected from the group consisting of SEQ ID NOs:28-37, a CDR-L2 comprising an amino acid sequence selected from the group consisting of SEQ ID NOs:38-42, and a CDR-L3 comprising an amino acid sequence selected from the group consisting of SEQ ID NOs:43-50. In some embodiments, the $V_{H2}$ domain comprises an amino acid sequence selected from the group consisting of SEQ ID NOs:170, 172, 174, 176, 178, 180, 182, 184, 186, and 188. In some embodiments, the $V_{L2}$ domain comprises an amino acid sequence selected from the group consisting of SEQ ID NOs:171, 173, 175, 177, 179, 181, 183, 185, 187, and 189. In some embodiments, the $V_{H2}$ domain is encoded by a nucleic acid sequence selected from the group consisting of SEQ ID NOs:230, 232, 234, 236, 238, 240, 242, 244, 246, and 248. In some embodiments, the $V_{L2}$ domain is encoded by a nucleic acid sequence selected from the group consisting of SEQ ID NOs:231, 233, 235, 237, 239, 241, 243, 245, 247, and 249. In some embodiments, the $V_{H1}$ domain comprises a CDR-H1 comprising an amino acid sequence selected from the group consisting of SEQ ID NOs:51-55 and 81-95, a CDR-H2 comprising an amino acid sequence selected from the group consisting of SEQ ID NOs:56-60 and 96-110, and a CDR-H3 comprising an amino acid sequence selected from the group consisting of SEQ ID NOs:61-65 and 111-125; and/or wherein the $V_{L1}$ domain comprises a CDR-L1 comprising an amino acid sequence selected from the group consisting of SEQ ID NOs:66-70 and 126-140, a CDR-L2 comprising an amino acid sequence selected from the group consisting of SEQ ID NOs:38, 71-75, and 141-154, and a CDR-L3 comprising an amino acid sequence selected from the group consisting of SEQ ID NOs:76-80 and 155-169. In some embodiments, the $V_{H2}$ domain comprises an amino acid sequence selected from the group consisting of SEQ ID NOs:190, 192, 194, 196, 198, 200, 202, 204, 206, 208, 210, 212, 214, 216, 218, 220, 222, 224, 226, and 228. In some embodiments, the $V_{L2}$ domain comprises an amino acid sequence selected from the group consisting of SEQ ID NOs: 191, 193, 195, 197, 199, 201, 203, 205, 207, 209, 211, 213, 215, 217, 219, 221, 223, 225, 227, and 229. In some embodiments, the $V_{H2}$ domain is encoded by a nucleic acid sequence selected from the group consisting of SEQ ID NOs:250, 252, 254, 256, 258, 260, 262, 264, 266, 268, 270, 272, 274, 276, 278, 280, 282, 284, 286, and 288. In some embodiments, the $V_{L2}$ domain is encoded by a nucleic acid sequence selected from the group consisting of SEQ ID NOs:251, 253, 255, 257, 259, 261, 263, 265, 267, 269, 271, 273, 275, 277, 279, 281, 283, 285, 287, and 289.

In one embodiment, the disclosure provides an isolated nucleic acid molecule comprising a nucleotide sequence encoding the bispecific binding molecule according to any one of the above embodiments. In one embodiment, the disclosure provides an expression vector comprising a nucleotide sequence encoding the bispecific binding molecule according to any one of the above embodiments. In one embodiment, the disclosure provides an isolated host cell comprising a nucleotide sequence encoding the bispecific binding molecule according to any one of the above embodiments or comprising an expression vector comprising a nucleotide sequence encoding the bispecific binding molecule according to any one of the above embodiments. In one embodiment, the disclosure provides a vector system comprising one or more vectors encoding a first, second, third, and fourth polypeptide chain of a bispecific binding molecule according to any one of the above embodiments. In one embodiment, the disclosure provides a vector system comprising one or more vectors encoding two light chains and two heavy chains of a bispecific binding molecule according to any one of the above embodiments. In one embodiment, the disclosure provides an isolated host cell comprising the vector system according to any one of the above embodiments.

In one embodiment, the disclosure provides a method of producing a bispecific binding molecule, the method comprising: a) culturing a host cell according to any one of the above embodiments under conditions such that the host cell expresses the bispecific binding molecule; and b) isolating the bispecific binding molecule from the host cell. In one embodiment, the disclosure provides a method of producing a bispecific binding protein comprising a first binding domain that binds an extracellular portion of dystroglycan and a second binding domain that binds laminin-2, the method comprising: a) culturing a first host cell that comprises a nucleic acid molecule encoding a first polypeptide chain comprising the first binding domain under conditions such that the host cell expresses the first polypeptide chain as part of a first monospecific binding protein with a first CH3 domain; b) culturing a second host cell that comprises a nucleic acid molecule encoding a second polypeptide chain comprising the second binding domain conditions such that the host cell expresses the second polypeptide chain as part of a second monospecific binding protein with a second CH3 domain; c) isolating the first monospecific binding protein from the first host cell; d) isolating the second monospecific binding protein from the second host cell; e) incubating the isolated first and second monospecific binding proteins under reducing conditions sufficient to allow cysteines in the hinge region to undergo disulfide bond isomerization; and f) obtaining the bispecific binding protein, wherein the first and second CH3 domains are different and are such that the heterodimeric interaction between said first and second CH3 domains is stronger than each of the homodimeric interactions of said first and second CH3 domains.

In one embodiment, the disclosure provides a method for treating or preventing an alpha-dystroglycanopathy in an individual, the method comprising administering to the individual the bispecific binding molecule according to any one of the above embodiments. In one embodiment, the disclosure provides a method for providing linkage between laminin-2 and an extracellular portion of dystroglycan in an individual, the method comprising administering to the individual the bispecific binding molecule according to any one of the above embodiments. In some embodiments, the individual has reduced expression of alpha-dystroglycan. In some embodiments, alpha-dystroglycan expressed in the individual has impaired or aberrant O-glycosylation. In some embodiments, the individual has a mutation in a gene selected from the group consisting of: dystroglycan (DAG1), protein O-mannosyltransferase-1 (POMT1), protein O-mannosyltransferase-2 (POMT2), protein O-linked mannose beta1,2-N-acetylglucosylaminyltransferase subunit 1 (POMGNT1), protein O-linked mannose beta1,4-N-acetylglucosylaminyltransferase subunit 2 (POMGNT2), xylosyl- and glucuronyltransferase 1 (LARGE1), xylosyl- and glucuronyltransferase 2 (LARGE2), dolichyl-phosphate mannosyltransferase subunit 1 (DPM1), dolichyl-phosphate mannosyltransferase subunit 2 (DPM2), dolichyl-phosphate mannosyltransferase subunit 3 (DPM3), fukutin, fukutin related protein (FKRP), isprenoid synthase domain containing (ISPD), protein O-mannose kinase (POMK), beta-1,3-N-acetylgalactosaminyltransferase 2 (B3GALNT2), beta-1, 4-glucuronyltransferase 1 (B4GAT1), dolichol kinase (DOLK), transmembrane protein 5 (TMEM5), and GDP-mannose pyrophosphorylase B (GMPPB). In some embodiments, the bispecific binding molecule is administered via intravenous infusion. In some embodiments, the bispecific binding molecule is administered via intramuscular, intraperitoneal, or subcutaneous injection. In some embodiments, the individual is a human.

In one embodiment, the disclosure provides a pharmaceutical composition comprising the bispecific binding molecule according to any one of the above embodiments and a pharmaceutically acceptable carrier. In one embodiment, the disclosure provides a kit comprising the bispecific binding molecule according to any one of the above embodiments and instructions for use in treating or preventing an alpha-dystroglycanopathy in an individual. In some embodiments, the individual has reduced expression of alpha-dystroglycan. In some embodiments, alpha-dystroglycan expressed in the individual has impaired or aberrant O-glycosylation. In some embodiments, the individual has a mutation in a gene selected from the group consisting of: dystroglycan (DAG1), protein O-mannosyltransferase-1 (POMT1), protein O-mannosyltransferase-2 (POMT2), protein O-linked mannose beta1,2-N-acetylglucosylaminyltransferase subunit 1 (POMGNT1), protein O-linked mannose beta1,4-N-acetylglucosylaminyltransferase subunit 2 (POMGNT2), xylosyl- and glucuronyltransferase 1 (LARGE1), xylosyl- and glucuronyltransferase 2 (LARGE2), dolichyl-phosphate mannosyltransferase subunit 1 (DPM1), dolichyl-phosphate mannosyltransferase subunit 2 (DPM2), dolichyl-phosphate mannosyltransferase subunit 3 (DPM3), fukutin, fukutin related protein (FKRP), isprenoid synthase domain containing (ISPD), protein O-mannose kinase (POMK), beta-1,3-N-acetylgalactosaminyltransferase 2 (B3GALNT2), beta-1, 4-glucuronyltransferase 1 (B4GAT1), dolichol kinase (DOLK), transmembrane protein 5 (TMEM5), and GDP-mannose pyrophosphorylase B (GMPPB). In some embodiments, the individual is a human.

Specific embodiments of the invention will become evident from the following more detailed description of certain embodiments and the claims.

It is to be understood that one, some, or all of the properties of the various embodiments described herein may be combined to form other embodiments of the present invention. These and other aspects of the invention will become apparent to one of skill in the art.

BRIEF DESCRIPTION OF THE DRAWINGS

FIG. 1A shows the dystrophin associated glycoprotein complex, where dystroglycan is O-glycosylated normally. FIG. 1B shows laminin-2 in the basal lamina interacting with O-glycoslyated alpha-dystroglycan. Beta-dystroglycan interacts with dystrophin, which in turn is associated with filamentous actin inside the cellular membrane.

FIGS. 1D and 1E show the strategy of employing multispecific of bispecific antibodies to treat alpha-dystroglycanopathy. Bispecific and multispecific antibodies specifically recognize and bind to laminin-2 with one or more arms and alpha-dystroglycan (FIG. 1D) or beta-dystroglycan (FIG. 1E) with one or more other arms, thus restoring the linkage between laminin-2 and dystroglycan for treating alpha-dystroglycanopathies.

FIGS. 4A and 4B show unfixed frozen human and mouse muscle tissue sections stained with anti-laminin-2 antibody derived from hybridoma clones C21 (FIG. 4A) and C3 (FIG. 4B), then detected with fluorescently labeled anti-mouse IgG secondary antibody. Secondary antibody only did not reveal any staining (not shown).

FIGS. 4C and 4D show unfixed frozen human and mouse muscle tissue sections stained with anti-beta-DG antibody derived from hybridoma clones AS30 (FIG. 4C) and AS19 (FIG. 4D), then detected with fluorescently labeled anti-mouse IgG secondary antibody. Secondary antibody only did not reveal any staining (not shown).

FIG. 5A shows a schematic design for tetravalent bispecific tandem IgG format antibodies (TBTI antibodies) that are specific to beta-DG and laminin-2, in accordance with some embodiments.

FIG. 8D shows the average number of Evans blue positive (i.e. damaged) muscle fibers for treatment with bispecific antibody T1T2 versus a mixture of parental monoclonal antibodies (AS19 and C3). Less damage was seen with bispecific antibody treatment than with the control parental antibody treatment.

FIG. 8E shows stained muscle tissue of LARGE$^{myd-3J/GrsrJ}$ mice that were treated with bispecific antibody T1T2 or a mixture of parental monoclonal antibodies (AS19 and C3). Staining with Evans blue dye (arrows) is much more prominent in tissue treated with parental monoclonal antibodies than with bispecific antibody T1T2. Staining of bispecific antibody T1T2 or a mixture of parental monoclonal antibodies (AS19 and C3) using a fluorescent secondary antibody is shown.

FIG. 9A shows that bispecific antibody-treated LARGE$^{myd-3J/GrsrJ}$ mice showed improvement in the grip strength test compared to untreated LARGE$^{myd-3J/GrsrJ}$ mice. FIG. 9B shows that bispecific antibody-treated LARGE$^{myd-3J/GrsrJ}$ mice showed improvement in the wire hang test compared to untreated LARGE$^{myd-3J/GrsrJ}$ mice. FIG. 9C shows that bispecific antibody-treated LARGE$^{myd-3J/GrsrJ}$ mice showed improvement in the run time test over untreated LARGE$^{myd-3J/GrsrJ}$ mice.

FIG. 11 shows immunofluorescence staining of LARGE$^{myd-3J/GrsrJ}$ mouse tissues 4 days after injection with bispecific antibody T1T2, parental monoclonal antibody AS19 or C3, or PBS as a negative control. Slides were washed and mounted using Vectashield mounting media with DAPI (Vector Labs). IV: intravenous injection; IP: intraperitoneal injection.

In FIG. 14A, plates were coated with biotinylated N'Avi-HPC4-human LG4/5, and binding to human beta-DG was detected. In FIG. 14B, plates were coated with human-beta DG-HPC4-Avi-C', and binding to human human LG4/5 was detected.

DETAILED DESCRIPTION

Figure 1B:
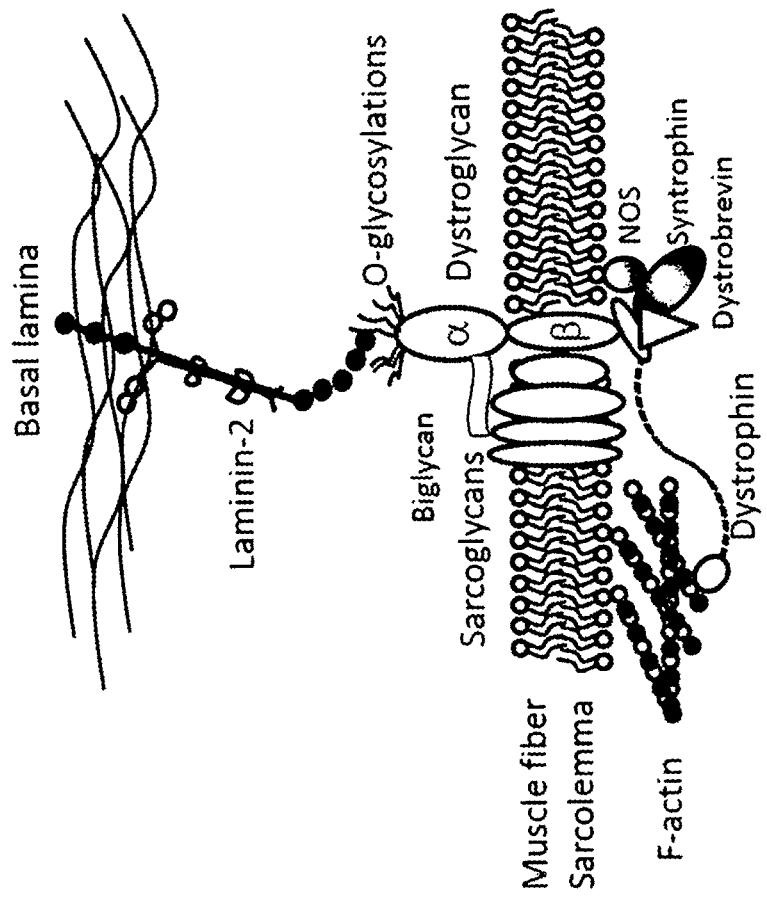
FIGS. 1A and 1B show the normal protein interactions and functions of the dystrophin associated glycoprotein complex. The O-linked glycans in the mucin-like domain of alpha-dystroglycan serve as receptors for several ligands, including laminin-2 in muscles.

The present disclosure provides multispecific and bispecific binding molecules comprising a first binding domain that binds an extracellular portion of dystroglycan and a second binding domain that binds laminin-2. In some embodiments, the binding molecules are bispecific and comprise a first binding domain that binds an extracellular portion of dystroglycan and a second binding domain that binds laminin-2. In some embodiments, the binding molecules are multispecific and comprise a first binding domain that binds an extracellular portion of dystroglycan, a second binding domain that binds laminin-2, and one or more additional binding domains that bind one or more additional targets. The present disclosure provides multiple configurations of multispecific/bispecific binding molecules that are able to bind dystroglycan and laminin-2 simultaneously and ameliorate the symptoms of alpha-dystroglycanopathy in an in vivo model system.

The following description sets forth exemplary methods, parameters, and the like. It should be recognized, however, that such description is not intended as a limitation on the scope of the present disclosure but is instead provided as a description of exemplary embodiments.

Definitions

As utilized in accordance with the present disclosure, the following terms, unless otherwise indicated, shall be understood to have the following meanings. Unless otherwise required by context, singular terms shall include pluralities and plural terms shall include the singular.

The term "antigen" or "target antigen" or "antigen target" as used herein refers to a molecule or a portion of a molecule that is capable of being bound by a binding protein, and additionally is capable of being used in an animal to produce antibodies capable of binding to an epitope of that antigen. A target antigen may have one or more epitopes. With respect to each target antigen recognized by a binding protein, the binding protein is capable of competing with an intact antibody that recognizes the target antigen. Exemplary target antigens described herein include dystroglycan (e.g., an extracellular portion thereof) and laminin-2.

The term "epitope" includes any determinant, for example a polypeptide determinant, capable of specifically binding to an immunoglobulin or T-cell receptor. In certain embodiments, epitope determinants include chemically active surface groupings of molecules such as amino acids, sugar side chains, phosphoryl groups, or sulfonyl groups, and, in certain embodiments, may have specific three-dimensional structural characteristics and/or specific charge characteristics. An epitope is a region of an antigen that is bound by an antibody or binding protein. In certain embodiments, a binding protein is said to specifically bind an antigen when it preferentially recognizes its target antigen in a complex mixture of proteins and/or macromolecules. In some embodiments, a binding protein is said to specifically bind an antigen when the equilibrium dissociation constant is $\leq 10^{-6}$ M, for example when the equilibrium dissociation constant is $\leq 10^{-9}$ M, and for example when the dissociation constant is $\leq 10^{-10}$ M.

The dissociation constant ($K_D$) of a binding protein can be determined, for example, by surface plasmon resonance. Generally, surface plasmon resonance analysis measures real-time binding interactions between ligand (a target antigen on a biosensor matrix) and analyte (a binding protein in solution) by surface plasmon resonance (SPR) using the BIAcore system (Pharmacia Biosensor; Piscataway, N.J.). Surface plasmon analysis can also be performed by immobilizing the analyte (binding protein on a biosensor matrix) and presenting the ligand (target antigen). The term "$K_D$," as used herein refers to the dissociation constant of the interaction between a particular binding protein and a target antigen.

The term "specifically binds" as used herein refers to the ability of a binding protein or an antigen-binding fragment thereof to bind to an antigen containing an epitope with an $K_D$ of at least about $1 \times 10^{-6}$ M, $1 \times 10^{-7}$ M, $1 \times 10^{-8}$ M, $1 \times 10^{-9}$ M, $1 \times 10^{-10}$ M, $1 \times 10^{-11}$ M, $1 \times 10^{-12}$ M, or more, and/or to bind to an epitope with an affinity that is at least two-fold greater than its affinity for a nonspecific antigen.

The term "binding protein" as used herein refers to a non-naturally occurring (or recombinant or engineered) molecule that specifically binds to at least one target antigen.

The term "monospecific binding protein" refers to a binding protein that specifically binds to one antigen target.

The term "monovalent binding protein" refers to a binding protein that has one antigen binding site.

The term "bispecific binding protein" refers to a binding protein that specifically binds to two different antigen targets. A bispecific or bifunctional antibody typically is an artificial hybrid antibody having two different heavy chain/light chain pairs and two different binding sites or epitopes. Bispecific antibodies may be produced by a variety of methods including, but not limited to, fusion of hybridomas or linking of F(ab') fragments.

The term "bivalent binding protein" refers to a binding protein that has two binding sites or domains.

The term "polynucleotide" as used herein refers to single-stranded or double-stranded nucleic acid polymers of at least 10 nucleotides in length. In certain embodiments, the nucleotides comprising the polynucleotide can be ribonucleotides or deoxyribonucleotides or a modified form of either type of nucleotide. Such modifications include base modifications such as bromuridine, ribose modifications such as arabinoside and 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single-stranded and double-stranded forms of DNA.

An "isolated polynucleotide" is a polynucleotide of genomic, cDNA, or synthetic origin or some combination thereof, which: (1) is not associated with all or a portion of a polynucleotide in which the isolated polynucleotide is found in nature, (2) is linked to a polynucleotide to which it is not linked in nature, or (3) does not occur in nature as part of a larger sequence.

An "isolated polypeptide" is one that: (1) is free of at least some other polypeptides with which it would normally be found, (2) is essentially free of other polypeptides from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a polypeptide with which the "isolated polypeptide" is associated in nature, (6) is operably associated (by covalent or noncovalent interaction) with a polypeptide with which it is not associated in nature, or (7) does not occur in nature. Such an isolated polypeptide can be encoded by genomic DNA, cDNA, mRNA or other RNA, of synthetic origin, or any combination thereof. In some embodiments, the isolated polypeptide is substantially free from polypeptides or other contaminants that are found in its natural environment that would interfere with its use (therapeutic, diagnostic, prophylactic, research or otherwise).

Naturally occurring antibodies typically comprise a tetramer. Each such tetramer is typically composed of two identical pairs of polypeptide chains, each pair having one full-length "light" chain (typically having a molecular weight of about 25 kDa) and one full-length "heavy" chain (typically having a molecular weight of about 50-70 kDa). The terms "heavy chain" and "light chain" as used herein refer to any immunoglobulin polypeptide having sufficient variable domain sequence to confer specificity for a target antigen. The amino-terminal portion of each light and heavy chain typically includes a variable domain of about 100 to 110 or more amino acids that typically is responsible for antigen recognition. The carboxy-terminal portion of each chain typically defines a constant domain responsible for effector function. Thus, in a naturally occurring antibody, a full-length heavy chain immunoglobulin polypeptide includes a variable domain ($V_H$) and three constant domains ($C_{H1}$, $C_{H2}$, and $C_{H3}$), wherein the $V_H$ domain is at the amino-terminus of the polypeptide and the $C_{H3}$ domain is at the carboxyl-terminus, and a full-length light chain immunoglobulin polypeptide includes a variable domain ($V_L$) and a constant domain ($C_L$), wherein the $V_L$ domain is at the amino-terminus of the polypeptide and the $C_L$ domain is at the carboxyl-terminus.

Human light chains are typically classified as kappa and lambda light chains, and human heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, the variable and constant domains typically are joined by a "J" region of about 12 or more amino acids, with the heavy chain also including a "D" region of about 10 more amino acids. See, e.g., FUNDAMENTAL IMMUNOLOGY (Paul, W., ed., Raven Press, 2nd ed., 1989), which is incorporated by reference in its entirety for all purposes. The variable regions of each light/heavy chain pair typically form an antigen binding site. The variable domains of naturally occurring antibodies typically exhibit the same general structure of relatively conserved framework regions (FR) joined by three hypervariable regions, also called complementarity determining regions or CDRs. The CDRs from the two chains of each pair typically are aligned by the framework regions, which may enable binding to a specific epitope. From the amino-terminus to the carboxyl-terminus, both light and heavy chain variable domains typically comprise the domains FR1, CDR1, FR2, CDR2, FR3, CDR3, and FR4.

The term "CDR set" refers to a group of three CDRs that occur in a single variable region capable of binding the antigen. The exact boundaries of these CDRs have been defined differently according to different systems. The system described by Kabat (Kabat et al., SEQUENCES OF PROTEINS OF IMMUNOLOGICAL INTEREST (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia and Lesk, 1987, *J. Mol. Biol.* 196: 901-17; Chothia et al., 1989, *Nature* 342: 877-83) found that certain sub-portions within Kabat CDRs adopt nearly identical peptide backbone conformations, despite having great diversity at the level of amino acid sequence. These sub-portions were designated as L1, L2, and L3 or H1, H2, and H3 where the "L" and the "H" designates the light chain and the heavy chain regions, respectively. These regions may be referred to as Chothia CDRs, which have boundaries that overlap with Kabat CDRs. Other boundaries defining CDRs overlapping with the Kabat CDRs have been described by Padlan, 1995, *FASEB J.* 9: 133-39; MacCallum, 1996, *J. Mol. Biol.* 262(5): 732-45; and Lefranc, 2003, *Dev. Comp. Immunol.* 27: 55-77. Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat or Chothia defined CDRs. Identification of predicted CDRs using the amino acid sequence is well known in the field, such as in Martin, A. C. "Protein sequence and structure analysis of antibody variable domains," In *Antibody Engineering*, Vol. 2. Kontermann R., Dübel S., eds. Springer-Verlag, Berlin, p. 33-51 (2010). The amino acid sequence of the heavy and/or light chain variable domain may be also inspected to identify the sequences of the CDRs by other conventional methods, e.g., by comparison to known amino acid sequences of other heavy and light chain variable regions to determine the regions of sequence hypervariability. The numbered sequences may be aligned by eye, or by employing an alignment program such as one of the CLUSTAL suite of programs, as described in Thompson, 1994, *Nucleic Acids Res.* 22: 4673-80. Molecular models are conventionally used to correctly delineate framework and CDR regions and thus correct the sequence-based assignments.

The term "Fc" as used herein refers to a molecule comprising the sequence of a non-antigen-binding fragment resulting from digestion of an antibody or produced by other means, whether in monomeric or multimeric form, and can contain the hinge region. In some embodiments, the original immunoglobulin source of the native Fc is of human origin and can be any of the immunoglobulins, for example IgG1 and IgG2. Fc molecules are made up of monomeric polypeptides that can be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, and IgE) or subclass (e.g., IgG1, IgG2, IgG3, IgA1, and IgA2). One example of a Fc is a disulfide-bonded dimer resulting from papain digestion of an IgG. The term "Fc" as used herein is generic to the monomeric, dimeric, and multimeric forms.

A F(ab) fragment typically includes one light chain and the $V_H$ and $C_{H1}$ domains of one heavy chain, wherein the $V_H$—$C_{H1}$ heavy chain portion of the F(ab) fragment cannot form a disulfide bond with another heavy chain polypeptide. As used herein, a F(ab) fragment can also include one light chain containing two variable domains separated by an amino acid linker and one heavy chain containing two variable domains separated by an amino acid linker and a $C_{H1}$ domain.

A F(ab') fragment typically includes one light chain and a portion of one heavy chain that contains more of the constant region (between the $C_{H1}$ and $C_{H2}$ domains), such that an interchain disulfide bond can be formed between two heavy chains to form a $F(ab')_2$ molecule.

A "recombinant" molecule is one that has been prepared, expressed, created, or isolated by recombinant means.

One embodiment of the disclosure provides binding proteins having biological and immunological specificity to between one and three target antigens. Another embodiment of the disclosure provides nucleic acid molecules comprising nucleotide sequences encoding polypeptide chains that form such binding proteins. Another embodiment of the disclosure provides expression vectors comprising nucleic acid molecules comprising nucleotide sequences encoding polypeptide chains that form such binding proteins. Yet another embodiment of the disclosure provides host cells that express such binding proteins (i.e., comprising nucleic acid molecules or vectors encoding polypeptide chains that form such binding proteins).

The term "swapability" as used herein refers to the interchangeability of variable domains within the binding protein format and with retention of folding and ultimate binding affinity. "Full swapability" refers to the ability to swap the order of both $V_{H1}$ and $V_{H2}$ domains, and therefore the order of $V_{L1}$ and $V_{L2}$ domains, in the polypeptide chain of formula I or the polypeptide chain of formula II (i.e., to reverse the order) while maintaining full functionality of the binding protein as evidenced by the retention of binding affinity. Furthermore, it should be noted that the designations $V_H$ and $V_L$ refer only to the domain's location on a particular protein chain in the final format. For example, $V_{H1}$ and $V_{H2}$ could be derived from $V_{L1}$ and $V_{L2}$ domains in parent antibodies and placed into the $V_{H1}$ and $V_{H2}$ positions in the binding protein. Likewise, $V_{L1}$ and $V_{L2}$ could be derived from $V_{H1}$ and $V_{H2}$ domains in parent antibodies and placed in the $V_{H1}$ and $V_{H2}$ positions in the binding protein. Thus, the $V_H$ and $V_L$ designations refer to the present location and not the original location in a parent antibody. $V_H$ and $V_L$ domains are therefore "swappable."

An "isolated" binding molecule or protein is one that has been identified and separated and/or recovered from a component of its natural environment. Contaminant components of its natural environment are materials that would interfere with diagnostic or therapeutic uses for the binding protein, and may include enzymes, hormones, and other proteinaceous or non-proteinaceous solutes. In some embodiments, the binding molecule or protein will be purified: (1) to greater than 95% by weight of antibody as determined by the Lowry method, and in some embodiments more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated binding molecules or proteins include the molecules/proteins in situ within recombinant cells since at least one component of the natural environment will not be present.

The terms "substantially pure" or "substantially purified" as used herein refer to a compound or species that is the predominant species present (i.e., on a molar basis it is more abundant than any other individual species in the composition). In some embodiments, a substantially purified fraction is a composition wherein the species comprises at least about 50% (on a molar basis) of all macromolecular species present. In other embodiments, a substantially pure composition will comprise more than about 80%, 85%, 90%, 95%, or 99% of all macromolar species present in the composition. In still other embodiments, the species is purified to essential homogeneity (contaminant species cannot be detected in the composition by conventional detection methods) wherein the composition consists essentially of a single macromolecular species.

The term "vector" as used herein refers to any molecule (e.g., nucleic acid, plasmid, or virus) that is used to transfer coding information to a host cell. The term "vector" includes a nucleic acid molecule that is capable of transporting another nucleic acid to which it has been linked. One type of vector is a "plasmid," which refers to a circular double-stranded DNA molecule into which additional DNA segments may be inserted. Another type of vector is a viral vector, wherein additional DNA segments may be inserted into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell and thereby are replicated along with the host genome. In addition, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. The terms "plasmid" and "vector" may be used interchangeably herein, as a plasmid is the most commonly used form of vector. However, the disclosure is intended to include other forms of expression vectors, such as viral vectors (e.g., replication defective retroviruses, adenoviruses, and adeno-associated viruses), which serve equivalent functions.

The phrase "recombinant host cell" (or "host cell") as used herein refers to a cell into which a recombinant expression vector has been introduced. A recombinant host cell or host cell is intended to refer not only to the particular subject cell, but also to the progeny of such a cell. Because certain modifications may occur in succeeding generations due to either mutation or environmental influences, such progeny may not, in fact, be identical to the parent cell, but such cells are still included within the scope of the term "host cell" as used herein. A wide variety of host cell expression systems can be used to express the binding proteins, including bacterial, yeast, baculoviral, and mammalian expression systems (as well as phage display expression systems). An example of a suitable bacterial expression vector is pUC19. To express a binding protein recombinantly, a host cell is transformed or transfected with one or more recombinant expression vectors carrying DNA fragments encoding the polypeptide chains of the binding protein such that the polypeptide chains are expressed in the host cell and secreted into the medium in which the host cells are cultured, from which medium the binding protein can be recovered.

The term "transformation" as used herein refers to a change in a cell's genetic characteristics, and a cell has been transformed when it has been modified to contain a new DNA. For example, a cell is transformed where it is genetically modified from its native state. Following transformation, the transforming DNA may recombine with that of the cell by physically integrating into a chromosome of the cell, or may be maintained transiently as an episomal element without being replicated, or may replicate independently as a plasmid. A cell is considered to have been stably transformed when the DNA is replicated with the division of the cell. The term "transfection" as used herein refers to the uptake of foreign or exogenous DNA by a cell, and a cell has been "transfected" when the exogenous DNA has been introduced inside the cell membrane. A number of transfection techniques are well known in the art. Such techniques can be used to introduce one or more exogenous DNA molecules into suitable host cells.

The term "naturally occurring" as used herein and applied to an object refers to the fact that the object can be found in nature and has not been manipulated by man. For example, a polynucleotide or polypeptide that is present in an organism (including viruses) that can be isolated from a source in nature and that has not been intentionally modified by man is naturally-occurring. Similarly, "non-naturally occurring" as used herein refers to an object that is not found in nature or that has been structurally modified or synthesized by man.

As used herein, the twenty conventional amino acids and their abbreviations follow conventional usage. Stereoisomers (e.g., D-amino acids) of the twenty conventional amino acids; unnatural amino acids and analogs such as α-,α-disubstituted amino acids, N-alkyl amino acids, lactic acid, and other unconventional amino acids may also be suitable components for the polypeptide chains of the binding proteins. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

Naturally occurring residues may be divided into classes based on common side chain properties:
(1) hydrophobic: Met, Ala, Val, Leu, Ile, Phe, Trp, Tyr, Pro;
(2) polar hydrophilic: Arg, Asn, Asp, Gln, Glu, His, Lys, Ser, Thr;
(3) aliphatic: Ala, Gly, Ile, Leu, Val, Pro;
(4) aliphatic hydrophobic: Ala, Ile, Leu, Val, Pro;
(5) neutral hydrophilic: Cys, Ser, Thr, Asn, Gln;
(6) acidic: Asp, Glu;
(7) basic: His, Lys, Arg;
(8) residues that influence chain orientation: Gly, Pro;
(9) aromatic: His, Trp, Tyr, Phe; and
(10) aromatic hydrophobic: Phe, Trp, Tyr.

Conservative amino acid substitutions may involve exchange of a member of one of these classes with another member of the same class. Non-conservative substitutions may involve the exchange of a member of one of these classes for a member from another class.

A skilled artisan will be able to determine suitable variants of the polypeptide chains of the binding proteins using well-known techniques. For example, one skilled in the art may identify suitable areas of a polypeptide chain that may be changed without destroying activity by targeting regions not believed to be important for activity. Alternatively, one skilled in the art can identify residues and portions of the molecules that are conserved among similar polypeptides. In addition, even areas that may be important for biological activity or for structure may be subject to conservative amino acid substitutions without destroying the biological activity or without adversely affecting the polypeptide structure.

The term "patient" (the terms "individual" and "subject" can be used interchangeably herein) as used herein includes human and animal (e.g., mammals, including but not limited to dogs, cats, and other domestic pets; horses, cows, goats, rabbits, buffalos, and other livestock; and research animals such as non-human primates, mice, etc.) subjects.

In some embodiments, the terms "treatment" or "treat" as used herein refer to therapeutic treatment, e.g., reducing or mitigating the severity or presence of one or more symptoms.

In other embodiments, the term "prevent" as used herein can refer to prophylactic or preventative measures, e.g., preventing or delaying onset of one or more symptoms, for instance in an individual at risk for developing a pathological condition described herein.

The terms "pharmaceutical composition" or "therapeutic composition" as used herein refer to a compound or composition capable of inducing a desired therapeutic effect when properly administered to a patient.

The term "pharmaceutically acceptable carrier" or "physiologically acceptable carrier" as used herein refers to one or more formulation materials suitable for accomplishing or enhancing the delivery of a binding protein.

The terms "effective amount" and "therapeutically effective amount" when used in reference to a pharmaceutical composition comprising one or more binding proteins refer to an amount or dosage sufficient to produce a desired therapeutic result. More specifically, a therapeutically effective amount is an amount of a binding protein sufficient to inhibit, for some period of time, one or more of the clinically defined pathological processes associated with the condition being treated. The effective amount may vary depending on the specific binding protein that is being used, and also depends on a variety of factors and conditions related to the patient being treated and the severity of the disorder. For example, if the binding protein is to be administered in vivo, factors such as the age, weight, and health of the patient as well as dose response curves and toxicity data obtained in preclinical animal work would be among those factors considered. The determination of an effective amount or therapeutically effective amount of a given pharmaceutical composition is well within the ability of those skilled in the art.

One embodiment of the disclosure provides a pharmaceutical composition comprising a pharmaceutically acceptable carrier and a therapeutically effective amount of a binding molecule.

Binding Molecules

Certain aspects of the present disclosure relate to multispecific binding molecules comprising one or more binding domain(s) that bind an extracellular portion of dystroglycan and one or more binding domain(s) that bind laminin-2. In some embodiments, the multispecific binding molecule is a multispecific binding protein comprising one or more polypeptide chains. In some embodiments, the multispecific binding molecule is a bivalent or tetravalent bispecific binding molecule comprising two or four antigen binding sites. In some embodiments, the multispecific binding molecule is a trivalent multispecific binding molecule comprising three antigen binding sites. The terms "binding domain" and "binding site" are used interchangeably herein.

Various formats and configurations for multispecific binding proteins are known in the art and suitable for use as described herein. Descriptions of exemplary and non-limiting formats are provided below. Any of the formats and optional features thereof described in International Publication No. WO2017/180913 may be used in the binding proteins (e.g., multispecific binding proteins) described herein.

Multispecific, Trivalent Binding Proteins

In some embodiments, the binding protein is a multispecific binding protein. In some embodiments, the multispecific binding protein is a trivalent binding protein comprising three antigen binding sites and collectively targeting two or more target antigens. In some embodiments, the binding protein (e.g., multispecific binding protein) comprises four polypeptide chains, wherein a first polypeptide chain comprises a structure represented by the formula:

$$V_{L2}\text{-}L_1\text{-}V_{L1}\text{-}L_2\text{-}C_L \quad [\text{I}]$$

and a second polypeptide chain comprises a structure represented by the formula:

$$V_{H1}\text{-}L_3\text{-}V_{H2}\text{-}L_4\text{-}C_{H1}\text{-}\text{hinge}\text{-}C_{H2}\text{—}C_{H3} \quad [\text{II}]$$

and a third polypeptide chain comprises a structure represented by the formula:

$$V_{H3}\text{—}C_{H1}\text{-}\text{hinge}\text{-}C_{H2}\text{—}C_{H3} \quad [\text{III}]$$

and a fourth polypeptide chain comprises a structure represented by the formula:

$$V_{L3}\text{—}C_L \quad [\text{IV}]$$

where:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers.

In some embodiments, the polypeptide of formula I and the polypeptide of formula II form a cross-over light chain-heavy chain pair. In some embodiments, $V_{H1}$ and $V_{L1}$ form an antigen binding site, $V_{H2}$ and $V_{L2}$ form an antigen binding site, and $V_{H3}$ and $V_{L3}$ form an antigen binding site for a total of three antigen binding sites. In some embodiments, the three antigen binding sites comprise at least one antigen binding site that binds the extracellular portion of dystroglycan and at least one antigen binding site that binds laminin-2 (e.g., one antigen binding site that binds the extracellular portion of dystroglycan and two antigen binding sites that bind laminin-2, or two antigen binding sites that bind the extracellular portion of dystroglycan and one antigen binding site that binds laminin-2).

In some embodiments, the two antigen binding sites that bind laminin-2 bind different epitopes of laminin-2. In some embodiments, the two antigen binding sites that bind laminin-2 bind the same or overlapping epitopes of laminin-2. In some embodiments, $V_{H1}$ and $V_{L1}$ form a first antigen binding site that binds laminin-2, $V_{H2}$ and $V_{L2}$ form a second antigen binding site that binds laminin-2, and $V_{H3}$ and $V_{L3}$ form a third antigen binding site that binds the extracellular portion of dystroglycan.

In some embodiments, the two antigen binding sites that bind the extracellular portion of dystroglycan bind different epitopes of the extracellular portion of dystroglycan. In some embodiments, the two antigen binding sites that bind the extracellular portion of dystroglycan bind the same or overlapping epitopes of the extracellular portion of dystroglycan. In some embodiments, $V_{H1}$ and $V_{L1}$ form a first antigen binding site that binds the extracellular portion of dystroglycan, $V_{H2}$ and $V_{L2}$ form a second antigen binding site that binds the extracellular portion of dystroglycan, and $V_{H3}$ and $V_{L3}$ form a third antigen binding site that binds laminin-2.

Any of the antigen binding sites described herein may find use in the binding proteins (e.g., multispecific binding proteins) described herein, e.g., including but not limited to, binding proteins comprising polypeptide(s) according to formulas I, II, III, and/or IV described supra.

In some embodiments, a binding protein (e.g., multispecific binding protein) of the present disclosure comprises: a heavy chain variable domain (VH) comprising a CDR-H1 comprising the sequence of GFTFTDSV (SEQ ID NO:316), a CDR-H2 comprising the sequence of IYPGSGNF (SEQ ID NO:318), and a CDR-H3 comprising the sequence of AMRRSS (SEQ ID NO:320); and a light chain variable domain (VL) comprising a CDR-L1 comprising the sequence of QTIVHSNSKTY (SEQ ID NO:332), a CDR-L2 comprising the sequence of KVS (SEQ ID NO:334), and a CDR-L3 comprising the sequence of FQGSHVPLT (SEQ ID NO:336). In some embodiments, the VH and VL domains form an antigen binding site (e.g., $V_{H1}$ and $V_{L1}$, $V_{H2}$ and $V_{L2}$, or $V_{H3}$ and $V_{L3}$) that binds the extracellular portion of dystroglycan. In some embodiments, a binding protein (e.g., multispecific binding protein) of the present disclosure comprises 1, 2, 3, 4, 5, or 6 CDR sequences of antibody AS30SS_Hu6 or AS30SS_Hu9 as shown in Table A2.

In some embodiments, the VH and/or VL domain are humanized. In some embodiments, a binding protein (e.g., multispecific binding protein) of the present disclosure comprises a VH domain sequence having at least 90%, 91%, 92%, 93%, 94%, 95%, 96%, 97%, 98%, 99%, or 100% sequence identity to the amino acid sequence of SEQ ID NO: 314 and/or a VL domain sequence having at least 90%, 91%, 92%, 93%, 94%, 95%, 96%, 97%, 98%, 99%, or 100% sequence identity to the amino acid sequence of SEQ ID NO:330. In some embodiments, a binding protein (e.g., multispecific binding protein) of the present disclosure comprises a VH domain sequence having at least 90%, 91%, 92%, 93%, 94%, 95%, 96%, 97%, 98%, 99%, or 100% sequence identity to the amino acid sequence of SEQ ID NO: 346 and/or a VL domain sequence having at least 90%, 91%, 92%, 93%, 94%, 95%, 96%, 97%, 98%, 99%, or 100% sequence identity to the amino acid sequence of SEQ ID NO:362. In some embodiments, a binding protein (e.g., multispecific binding protein) of the present disclosure comprises a VH and/or VL domain sequence of antibody AS30SS_Hu6 or AS30SS_Hu9 as shown in Table D2. In some embodiments, a binding protein (e.g., multispecific binding protein) of the present disclosure comprises a VH domain encoded by the polynucleotide sequence of SEQ ID NO:306 and/or a VL domain encoded by the polynucleotide sequence of SEQ ID NO:322. In some embodiments, a binding protein (e.g., multispecific binding protein) of the present disclosure comprises a VH domain encoded by the polynucleotide sequence of SEQ ID NO:338 and/or a VL domain encoded by the polynucleotide sequence of SEQ ID NO:354.

In some embodiments, a binding protein (e.g., multispecific binding protein) of the present disclosure comprises: a heavy chain variable domain (VH) comprising a CDR-H1 comprising the sequence of GFTFSSYT (SEQ ID NO:380), a CDR-H2 comprising the sequence of ISSSGSNT (SEQ ID NO:382), and a CDR-H3 comprising the sequence of ARFDYGSSLDS (SEQ ID NO:384); and a light chain variable domain (VL) comprising a CDR-L1 comprising the sequence of QSISNN (SEQ ID NO:396), a CDR-L2 comprising the sequence of YAS (SEQ ID NO:398), and a CDR-L3 comprising the sequence of QQSKSWPRT (SEQ ID NO:400). In some embodiments, the VH and VL domains form an antigen binding site (e.g., $V_{H1}$ and $V_{L1}$, $V_{H2}$ and $V_{L2}$, or $V_{H3}$ and $V_{L3}$) that binds laminin-2. In some embodiments, a binding protein (e.g., multispecific binding protein) of the present disclosure comprises 1, 2, 3, 4, 5, or 6 CDR sequences of antibody C3_Hu10 as shown in Table A2.

In some embodiments, the VH and/or VL domain are humanized. In some embodiments, a binding protein (e.g., multispecific binding protein) of the present disclosure comprises a VH domain sequence having at least 90%, 91%, 92%, 93%, 94%, 95%, 96%, 97%, 98%, 99%, or 100% sequence identity to the amino acid sequence of SEQ ID NO: 378 and/or a VL domain sequence having at least 90%, 91%, 92%, 93%, 94%, 95%, 96%, 97%, 98%, 99%, or 100% sequence identity to the amino acid sequence of SEQ ID NO:394. In some embodiments, a binding protein (e.g., multispecific binding protein) of the present disclosure comprises a VH and/or VL domain sequence of antibody C3_Hu10 as shown in Table D2. In some embodiments, a binding protein (e.g., multispecific binding protein) of the present disclosure comprises a VH domain encoded by the polynucleotide sequence of SEQ ID NO:370 and/or a VL domain encoded by the polynucleotide sequence of SEQ ID NO:386.

In some embodiments, a binding protein (e.g., multispecific binding protein) of the present disclosure comprises: a heavy chain variable domain (VH) comprising a CDR-H1 comprising the sequence of GFTFSSYT (SEQ ID NO:380), a CDR-H2 comprising the sequence of ISSSGSNT (SEQ ID NO:382), and a CDR-H3 comprising the sequence of ARFDYGSSLDS (SEQ ID NO:384); and a light chain variable domain (VL) comprising a CDR-L1 comprising the sequence of QSIGNN (SEQ ID NO:428), a CDR-L2 comprising the sequence of YAS (SEQ ID NO:398), and a CDR-L3 comprising the sequence of QQSKSWPRT (SEQ ID NO:400). In some embodiments, the VH and VL domains form an antigen binding site (e.g., $V_{H1}$ and $V_{L1}$, $V_{H2}$ and $V_{L2}$, or $V_{H3}$ and $V_{L3}$) that binds laminin-2. In some embodiments, a binding protein (e.g., multispecific binding protein) of the present disclosure comprises 1, 2, 3, 4, 5, or 6 CDR sequences of antibody C3_Hu11 as shown in Table A2.

In some embodiments, the VH and/or VL domain are humanized. In some embodiments, a binding protein (e.g., multispecific binding protein) of the present disclosure comprises a VH domain sequence having at least 90%, 91%, 92%, 93%, 94%, 95%, 96%, 97%, 98%, 99%, or 100% sequence identity to the amino acid sequence of SEQ ID NO: 410 and/or a VL domain sequence having at least 90%, 91%, 92%, 93%, 94%, 95%, 96%, 97%, 98%, 99%, or 100% sequence identity to the amino acid sequence of SEQ ID NO:426. In some embodiments, a binding protein (e.g., multispecific binding protein) of the present disclosure comprises a VH and/or VL domain sequence of antibody C3_Hu11 as shown in Table D2. In some embodiments, a binding protein (e.g., multispecific binding protein) of the present disclosure comprises a VH domain encoded by the polynucleotide sequence of SEQ ID NO:402 and/or a VL domain encoded by the polynucleotide sequence of SEQ ID NO:418.

In some embodiments, a binding protein (e.g., multispecific binding protein) of the present disclosure comprises: a heavy chain variable domain (VH) comprising a CDR-H1 comprising the sequence of GFTFSSYT (SEQ ID NO:444), a CDR-H2 comprising the sequence of ISSSGSNT (SEQ ID NO:446), and a CDR-H3 comprising the sequence of ARFDYGSSLDS (SEQ ID NO:448); and a light chain variable domain (VL) comprising a CDR-L1 comprising the sequence of QSISNY (SEQ ID NO:460), a CDR-L2 comprising the sequence of YAS (SEQ ID NO:462), and a CDR-L3 comprising the sequence of QQSKSWPRT (SEQ ID NO:464). In some embodiments, the VH and VL domains form an antigen binding site (e.g., $V_{H1}$ and $V_{L1}$, $V_{H2}$ and $V_{L2}$, or $V_{H3}$ and $V_{L3}$) that binds laminin-2. In some embodiments, a binding protein (e.g., multispecific binding protein) of the present disclosure comprises 1, 2, 3, 4, 5, or 6 CDR sequences of antibody C21_Hu11 as shown in Table A2.

In some embodiments, the VH and/or VL domain are humanized. In some embodiments, a binding protein (e.g., multispecific binding protein) of the present disclosure comprises a VH domain sequence having at least 90%, 91%, 92%, 93%, 94%, 95%, 96%, 97%, 98%, 99%, or 100% sequence identity to the amino acid sequence of SEQ ID NO: 442 and/or a VL domain sequence having at least 90%, 91%, 92%, 93%, 94%, 95%, 96%, 97%, 98%, 99%, or 100% sequence identity to the amino acid sequence of SEQ ID NO:458. In some embodiments, a binding protein (e.g., multispecific binding protein) of the present disclosure comprises a VH and/or VL domain sequence of antibody C21_Hu11 as shown in Table D2. In some embodiments, a binding protein (e.g., multispecific binding protein) of the present disclosure comprises a VH domain encoded by the polynucleotide sequence of SEQ ID NO:434 and/or a VL domain encoded by the polynucleotide sequence of SEQ ID NO:450.

In some embodiments, a binding protein (e.g., multispecific binding protein) of the present disclosure comprises: a heavy chain variable domain (VH) comprising a CDR-H1 comprising the sequence of GFTFSSYT (SEQ ID NO:444), a CDR-H2 comprising the sequence of ISSSGDNT (SEQ ID NO:478), and a CDR-H3 comprising the sequence of ARFDYGSSLDS (SEQ ID NO:448); and a light chain variable domain (VL) comprising a CDR-L1 comprising the sequence of QSISNY (SEQ ID NO:460), a CDR-L2 comprising the sequence of YAS (SEQ ID NO:462), and a CDR-L3 comprising the sequence of QQSKSWPRT (SEQ ID NO:464). In some embodiments, the VH and VL domains form an antigen binding site (e.g., $V_{H1}$ and $V_{L1}$, $V_{H2}$ and $V_{L2}$, or $V_{H3}$ and $V_{L3}$) that binds laminin-2. In some embodiments, a binding protein (e.g., multispecific binding protein) of the present disclosure comprises 1, 2, 3, 4, 5, or 6 CDR sequences of antibody C21_Hu21 as shown in Table A2.

In some embodiments, the VH and/or VL domain are humanized. In some embodiments, a binding protein (e.g., multispecific binding protein) of the present disclosure comprises a VH domain sequence having at least 90%, 91%, 92%, 93%, 94%, 95%, 96%, 97%, 98%, 99%, or 100% sequence identity to the amino acid sequence of SEQ ID NO: 474 and/or a VL domain sequence having at least 90%, 91%, 92%, 93%, 94%, 95%, 96%, 97%, 98%, 99%, or 100% sequence identity to the amino acid sequence of SEQ ID NO:490. In some embodiments, a binding protein (e.g., multispecific binding protein) of the present disclosure comprises a VH and/or VL domain sequence of antibody C21_Hu21 as shown in Table D2. In some embodiments, a binding protein (e.g., multispecific binding protein) of the present disclosure comprises a VH domain encoded by the polynucleotide sequence of SEQ ID NO:466 and/or a VL domain encoded by the polynucleotide sequence of SEQ ID NO:482.

In some embodiments, $V_{H1}$ comprises a CDR-H1 comprising the sequence of SEQ ID NO:380, a CDR-H2 comprising the sequence of SEQ ID NO:382, and a CDR-H3 comprising the sequence of SEQ ID NO:384, and $V_{L1}$ comprises a CDR-L1 comprising the sequence of SEQ ID NO:396, a CDR-L2 comprising the sequence of SEQ ID NO:398, and a CDR-L3 comprising the sequence of SEQ ID NO:400; $V_{H2}$ comprises a CDR-H1 comprising the sequence of SEQ ID NO:380, a CDR-H2 comprising the sequence of SEQ ID NO:382, and a CDR-H3 comprising the sequence of SEQ ID NO:384, and $V_{L1}$ comprises a CDR-L1 comprising the sequence of SEQ ID NO:396, a CDR-L2 comprising the sequence of SEQ ID NO:398, and a CDR-L3 comprising the sequence of SEQ ID NO:400; and $V_{H3}$ comprises a CDR-H1 comprising the sequence of SEQ ID NO:316, a CDR-H2 comprising the sequence of SEQ ID NO:318, and a CDR-H3 comprising the sequence of SEQ ID NO:320, and $V_{L3}$ comprises a CDR-L1 comprising the sequence of SEQ ID NO:332, a CDR-L2 comprising the sequence of SEQ ID NO:334, and a CDR-L3 comprising the sequence of SEQ ID NO:336. In some embodiments, $V_{H1}$ comprises the sequence of SEQ ID NO:378, and $V_{L1}$ comprises the sequence of SEQ ID NO:394; $V_{H2}$ comprises the sequence of SEQ ID NO:378, and $V_{L2}$ comprises the sequence of SEQ ID NO:394; and $V_{H3}$ comprises the sequence of SEQ ID NO:314, and $V_{L3}$ comprises the sequence of SEQ ID NO:330. In some embodiments, a binding protein (e.g., multispecific binding protein) of the present disclosure comprises a first polypeptide chain that comprises the sequence of SEQ ID NO:500, a second polypeptide chain that comprises the sequence of SEQ ID NO:498, a third polypeptide chain that comprises the sequence of SEQ ID NO:499, and a fourth polypeptide chain that comprises the sequence of SEQ ID NO:501. In some embodiments, the binding protein comprises 1, 2, 3, or 4 polypeptide chains of triAb 3407, e.g., as shown in Table I2 or I4.

In some embodiments, $V_{H1}$ comprises a CDR-H1 comprising the sequence of SEQ ID NO:380, a CDR-H2 comprising the sequence of SEQ ID NO:382, and a CDR-H3 comprising the sequence of SEQ ID NO:384, and $V_{L1}$ comprises a CDR-L1 comprising the sequence of SEQ ID NO:396, a CDR-L2 comprising the sequence of SEQ ID NO:398, and a CDR-L3 comprising the sequence of SEQ ID NO:400; $V_{H2}$ comprises a CDR-H1 comprising the sequence of SEQ ID NO:444, a CDR-H2 comprising the sequence of SEQ ID NO:446, and a CDR-H3 comprising the sequence of SEQ ID NO:448, and $V_{L2}$ comprises a CDR-L1 comprising the sequence of SEQ ID NO:460, a CDR-L2 comprising the sequence of SEQ ID NO:462, and a CDR-L3 comprising the sequence of SEQ ID NO:464; and $V_{H3}$ comprises a CDR-H1 comprising the sequence of SEQ ID NO:316, a CDR-H2 comprising the sequence of SEQ ID NO:318, and a CDR-H3 comprising the sequence of SEQ ID NO:320, and $V_{L3}$ comprises a CDR-L1 comprising the sequence of SEQ ID NO:332, a CDR-L2 comprising the sequence of SEQ ID NO:334, and a CDR-L3 comprising the sequence of SEQ ID NO:336. In some embodiments, $V_{H1}$ comprises the sequence of SEQ ID NO:378, and $V_{L1}$ comprises the sequence of SEQ ID NO:394; $V_{H2}$ comprises the sequence of SEQ ID NO:442, and $V_{L2}$ comprises the sequence of SEQ ID NO:458; and $V_{H3}$ comprises the sequence of SEQ ID NO:314, and $V_{L3}$ comprises the sequence of SEQ ID NO:330. In some embodiments, a binding protein (e.g., multispecific binding protein) of the present disclosure comprises a first polypeptide chain that comprises the sequence of SEQ ID NO:504, a second polypeptide chain that comprises the sequence of SEQ ID NO:502, a third polypeptide chain that comprises the sequence of SEQ ID NO:503, and a fourth polypeptide chain that comprises the sequence of SEQ ID NO:505. In some embodiments, the binding protein comprises 1, 2, 3, or 4 polypeptide chains of triAb 3423, e.g., as shown in Table I2 or I4.

In some embodiments, $V_{H1}$ comprises a CDR-H1 comprising the sequence of SEQ ID NO:380, a CDR-H2 comprising the sequence of SEQ ID NO:382, and a CDR-H3 comprising the sequence of SEQ ID NO:384, and $V_{L1}$ comprises a CDR-L1 comprising the sequence of SEQ ID NO:428, a CDR-L2 comprising the sequence of SEQ ID NO:398, and a CDR-L3 comprising the sequence of SEQ ID NO:400; $V_{H2}$ comprises a CDR-H1 comprising the sequence of SEQ ID NO:444, a CDR-H2 comprising the sequence of SEQ ID NO:478, and a CDR-H3 comprising the sequence of SEQ ID NO:448, and $V_{L2}$ comprises a CDR-L1 comprising the sequence of SEQ ID NO:460, a CDR-L2 comprising the sequence of SEQ ID NO:462, and a CDR-L3 comprising the sequence of SEQ ID NO:464; and $V_{H3}$ comprises a CDR-H1 comprising the sequence of SEQ ID NO:316, a CDR-H2 comprising the sequence of SEQ ID NO:318, and a CDR-H3 comprising the sequence of SEQ ID NO:320, and $V_{L3}$ comprises a CDR-L1 comprising the sequence of SEQ ID NO:332, a CDR-L2 comprising the sequence of SEQ ID NO:334, and a CDR-L3 comprising the sequence of SEQ ID NO:336. In some embodiments, $V_{H1}$ comprises the sequence of SEQ ID NO:410, and $V_{L1}$ comprises the sequence of SEQ ID NO:426; $V_{H2}$ comprises the sequence of SEQ ID NO:474, and $V_{L2}$ comprises the sequence of SEQ ID NO:490; and $V_{H3}$ comprises the sequence of SEQ ID NO:314, and $V_{L3}$ comprises the sequence of SEQ ID NO:330. In some embodiments, a binding protein (e.g., multispecific binding protein) of the present disclosure comprises a first polypeptide chain that comprises the sequence of SEQ ID NO:508, a second polypeptide chain that comprises the sequence of SEQ ID NO:506, a third polypeptide chain that comprises the sequence of SEQ ID NO:507, and a fourth polypeptide chain that comprises the sequence of SEQ ID NO:509. In some embodiments, the binding protein comprises 1, 2, 3, or 4 polypeptide chains of triAb 3429, e.g., as shown in Table I2 or I4.

In some embodiments, $V_{H1}$ comprises a CDR-H1 comprising the sequence of SEQ ID NO:444, a CDR-H2 comprising the sequence of SEQ ID NO:446, and a CDR-H3 comprising the sequence of SEQ ID NO:448, and $V_{L1}$ comprises a CDR-L1 comprising the sequence of SEQ ID NO:460, a CDR-L2 comprising the sequence of SEQ ID NO:462, and a CDR-L3 comprising the sequence of SEQ ID NO:464; $V_{H2}$ comprises a CDR-H1 comprising the sequence of SEQ ID NO:380, a CDR-H2 comprising the sequence of SEQ ID NO:382, and a CDR-H3 comprising the sequence of SEQ ID NO:384, and $V_{L2}$ comprises a CDR-L1 comprising the sequence of SEQ ID NO:428, a CDR-L2 comprising the sequence of SEQ ID NO:398, and a CDR-L3 comprising the sequence of SEQ ID NO:400; and $V_{H3}$ comprises a CDR-H1 comprising the sequence of SEQ ID NO:316, a CDR-H2 comprising the sequence of SEQ ID NO:318, and a CDR-H3 comprising the sequence of SEQ ID NO:320, and $V_{L3}$ comprises a CDR-L1 comprising the sequence of SEQ ID NO:332, a CDR-L2 comprising the sequence of SEQ ID NO:334, and a CDR-L3 comprising the sequence of SEQ ID NO:336. In some embodiments, $V_{H1}$ comprises the sequence of SEQ ID NO:442, and $V_{L1}$ comprises the sequence of SEQ ID NO:458; $V_{H2}$ comprises the sequence of SEQ ID NO:410, and $V_{L2}$ comprises the sequence of SEQ ID NO:426; and $V_{H3}$ comprises the sequence of SEQ ID NO:314, and $V_{L3}$ comprises the sequence of SEQ ID NO:330. In some embodiments, a binding protein (e.g., multispecific binding protein) of the present disclosure comprises a first polypeptide chain that comprises the sequence of SEQ ID NO:512, a second polypeptide chain that comprises the sequence of SEQ ID NO:510, a third polypeptide chain that comprises the sequence of SEQ ID NO:511, and a fourth polypeptide chain that comprises the sequence of SEQ ID NO:513. In some embodiments, the binding protein comprises 1, 2, 3, or 4 polypeptide chains of triAb 3437, e.g., as shown in Table I2 or I4.

In some embodiments, $V_{H1}$ comprises a CDR-H1 comprising the sequence of SEQ ID NO:444, a CDR-H2 comprising the sequence of SEQ ID NO:478, and a CDR-H3 comprising the sequence of SEQ ID NO:448, and $V_{L1}$ comprises a CDR-L1 comprising the sequence of SEQ ID NO:460, a CDR-L2 comprising the sequence of SEQ ID NO:462, and a CDR-L3 comprising the sequence of SEQ ID NO:464; $V_{H2}$ comprises a CDR-H1 comprising the sequence of SEQ ID NO:380, a CDR-H2 comprising the sequence of SEQ ID NO:382, and a CDR-H3 comprising the sequence of SEQ ID NO:384, and $V_{L2}$ comprises a CDR-L1 comprising the sequence of SEQ ID NO:396, a CDR-L2 comprising the sequence of SEQ ID NO:398, and a CDR-L3 comprising the sequence of SEQ ID NO:400; and $V_{H3}$ comprises a CDR-H1 comprising the sequence of SEQ ID NO:316, a CDR-H2 comprising the sequence of SEQ ID NO:318, and a CDR-H3 comprising the sequence of SEQ ID NO:320, and $V_{L3}$ comprises a CDR-L1 comprising the sequence of SEQ ID NO:332, a CDR-L2 comprising the sequence of SEQ ID NO:334, and a CDR-L3 comprising the sequence of SEQ ID NO:336. In some embodiments, $V_{H1}$ comprises the sequence of SEQ ID NO:474, and $V_{L1}$ comprises the sequence of SEQ ID NO:490; $V_{H2}$ comprises the sequence of SEQ ID NO:378, and $V_{L2}$ comprises the sequence of SEQ ID NO:394; and $V_{H3}$ comprises the sequence of SEQ ID NO:314, and $V_{L3}$ comprises the sequence of SEQ ID NO:330. In some embodiments, a binding protein (e.g., multispecific binding protein) of the present disclosure comprises a first polypeptide chain that comprises the sequence of SEQ ID NO:516, a second polypeptide chain that comprises the sequence of SEQ ID NO:514, a third polypeptide chain that comprises the sequence of SEQ ID NO:515, and a fourth polypeptide chain that comprises the sequence of SEQ ID NO:517. In some embodiments, the binding protein comprises 1, 2, 3, or 4 polypeptide chains of triAb 3439, e.g., as shown in Table I2 or I4.

Bispecific Binding Proteins

In some embodiments, the binding protein is a bispecific binding protein. In some embodiments, the bispecific binding protein is a bivalent binding protein comprising two antigen binding sites and collectively targeting two target antigens. In some embodiments, the bispecific binding protein is a tetravalent binding protein comprising four antigen binding sites and collectively targeting two target antigens.

In some embodiments, the bispecific binding molecule comprises a first binding domain that binds to an extracellular portion of dystroglycan, wherein the first binding domain comprises a first immunoglobulin heavy chain variable domain ($V_{H1}$) and a first immunoglobulin light chain variable domain ($V_{L1}$), and a second binding domain that binds to laminin-2, wherein the second binding domain comprises a second immunoglobulin heavy chain variable domain ($V_{H2}$) and a second immunoglobulin light chain variable domain ($V_{L2}$). In some embodiments, the bispecific binding molecule is a bispecific binding protein, such as a bispecific antibody.

In some embodiments, the bispecific binding molecule comprises four polypeptide chains that form four antigen binding sites, wherein two polypeptide chains comprise a structure represented by the formula:

$$V_{L1}\text{-}L_1\text{-}V_{L2}\text{-}L_2\text{-}C_L \qquad [I]$$

and two polypeptide chains comprise a structure represented by the formula:

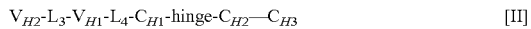

$$V_{H2}\text{-}L_3\text{-}V_{H1}\text{-}L_4\text{-}C_{H1}\text{-hinge-}C_{H2}\text{—}C_{H3} \qquad [II]$$

wherein:
$V_{L1}$ is a first immunoglobulin light chain variable domain;
$V_{L2}$ is a second immunoglobulin light chain variable domain;
$V_{H1}$ is a first immunoglobulin heavy chain variable domain;
$V_{H2}$ is a second immunoglobulin heavy chain variable domain;
$C_L$ is an immunoglobulin light chain constant domain;
$C_{H1}$ is an immunoglobulin $C_{H1}$ heavy chain constant domain;
$C_{H2}$ is an immunoglobulin $C_{H2}$ heavy chain constant domain;
$C_{H3}$ is an immunoglobulin $C_{H3}$ heavy chain constant domain;
hinge is an immunoglobulin hinge region connecting the $C_{H1}$ and $C_{H2}$ domains; and
$L_1$, $L_2$, $L_3$, and $L_4$ are amino acid linkers;
wherein the $V_{H1}$ and $V_{L1}$ domains form a $V_{H1}/V_{L1}$ binding pair, and wherein the $V_{H2}$ and $V_{L2}$ domains form a $V_{H2}/V_{L2}$ binding pair.

In some embodiments, formulae I and II describe the arrangement of domains within the respective polypeptide chains in order from N-terminus to C-terminus. In some embodiments, one or more of the polypeptide chains can comprise additional sequence(s), e.g., at the N-terminal or C-terminal ends.

For exemplary descriptions of this format, see, e.g., International Pub. No. WO2012/135345, U.S. Pat. No. 9,221,917, and EP Pat. No. EP2691416B1.

In some embodiments, the bispecific binding molecule comprises two polypeptide chains according to formula II comprising the sequence of SEQ ID NO:530 and two polypeptide chains according to formula I comprising the sequence of SEQ ID NO:531. In some embodiments, the bispecific binding molecule comprises two polypeptide chains according to formula II comprising the sequence of SEQ ID NO:532 and two polypeptide chains according to formula I comprising the sequence of SEQ ID NO:533. In some embodiments, the binding protein comprises two polypeptide chains shown for AS30_Hu9×C3_Hu11 CODV or AS30_Hu9×C21_Hu21 CODV in Table I3 or I4. In some embodiments, the binding protein comprises a variable domain comprising 1, 2, 3, 4, 5, or 6 CDR sequences shown in Table A2. In some embodiments, the binding protein comprises 1, 3, or 4 variable domains shown in Table D2 I3, or I4.

In some embodiments, the $V_{H1}/V_{L1}$ binding pair binds the extracellular portion of dystroglycan, and the $V_{H2}/V_{L2}$ binding pair binds laminin-2. In other embodiments, the $V_{H2}/V_{L2}$ binding pair binds the extracellular portion of dystroglycan, and the $V_{H1}/V_{L1}$ binding pair binds laminin-2.

In some embodiments of any of the multispecific and/or bispecific binding molecules described supra, the polypeptides of formula I and the polypeptides of formula II form a cross-over light chain-heavy chain pair. In some embodiments, the $V_{H1}$ and $V_{L1}$ domains cross-over to form the $V_{H1}/V_{L1}$ binding pair. In some embodiments, the $V_{H2}$ and $V_{L2}$ domains cross-over to form the $V_{H2}/V_{L2}$ binding pair. In some embodiments, the term linker as used herein in reference to the format above refers to one or more amino acid residues inserted between immunoglobulin domains to provide sufficient mobility for the domains of the light and heavy chains to fold into cross over dual variable region immunoglobulins. A linker is inserted at the transition between variable domains or between variable and constant domains, respectively, at the sequence level. The transition between domains can be identified because the approximate size of the immunoglobulin domains are well understood. The precise location of a domain transition can be determined by locating peptide stretches that do not form secondary structural elements such as beta-sheets or alpha-helices as demonstrated by experimental data or as can be assumed by techniques of modeling or secondary structure prediction. The linkers $L_1$, $L_2$, $L_3$, and $L_4$ are independent, but they may in some cases have the same sequence and/or length.

In some embodiments, a linker of the present disclosure comprises the sequence DKTHT (SEQ ID NO: 534). In some embodiments, $L_1$ and $L_2$ comprise the sequence DKTHT (SEQ ID NO: 534). In some embodiments, $L_3$ and $L_4$ comprise the sequence DKTHT (SEQ ID NO: 534). In some embodiments, $L_1$, $L_2$, $L_3$, and $L_4$ comprise the sequence DKTHT (SEQ ID NO: 534). Any of the linkers and linker combinations described in International Publication No. WO2017/180913 may be used in the binding proteins (e.g., multispecific binding proteins) described herein.

In some embodiments, $L_1$, $L_2$, $L_3$, and $L_4$ are each 0 to 50 amino acid residues in length, 0 to 40 amino acid residues in length, 0 to 30 amino acid residues in length, 0 to 25 amino acid residues in length, 0 to 20 amino acid residues in length, 0 to 18 amino acid residues in length, 0 to 16 amino acid residues in length, or 0 to 14 amino acid residues in length. In some embodiments, the linkers $L_1$, $L_2$, $L_3$, and $L_4$ range from no amino acids (length=0) to about 100 amino acids long, or less than 100, 50, 40, 30, 20, or 15 amino acids or less. The linkers can also be 10, 9, 8, 7, 6, 5, 4, 3, 2, or 1 amino acids long. $L_1$, $L_2$, $L_3$, and $L_4$ in one binding protein may all have the same amino acid sequence or may all have different amino acid sequences.

In certain embodiments, $L_1$ is 5 amino acid residues in length, $L_2$ is 5 amino acid residues in length, $L_3$ is 5 amino acid residues in length, $L_4$ is 5 amino acid residues in length. In certain embodiments, $L_1$ is 14 amino acid residues in length, $L_2$ is 2 amino acid residues in length, $L_3$ is 14 amino acid residues in length, $L_4$ is 2 amino acid residues in length. In some embodiments, $L_1$ and $L_3$ each comprise the sequence EPKSDKTHTSPPSP (SEQ ID NO:296), and/or $L_2$ and $L_4$ each comprise the sequence GG. In certain embodiments, $L_1$ is 7 amino acid residues in length, $L_2$ is 5 amino acid residues in length, $L_3$ is 1 amino acid residue in length, and $L_4$ is 2 amino acid residues in length. In some embodiments, $L_1$ comprises the sequence GQPKAAP (SEQ ID NO:297), $L_2$ comprises the sequence TKGPS (SEQ ID NO:298), $L_3$ comprises a serine residue (e.g., the sequence S), and $L_4$ comprises the sequence RT. In certain embodiments, $L_1$ is 10 amino acid residues in length, $L_2$ is 10 amino acid residues in length, $L_3$ is 0 amino acid residues in length, and $L_4$ is 0 amino acid residues in length. In some embodiments, $L_1$ and $L_2$ each comprise the sequence GGSGSSGSGG (SEQ ID NO:299).

In some embodiments, one or both of the variable domains of the polypeptides of formula I and/or formula II are human, humanized, or mouse variable domains.

In some embodiments, the bispecific binding molecule comprises two light chains comprising a structure represented by the formula:

$$V_{L1}\text{-}L_5\text{-}V_{L2}\text{-}L_6\text{-}C_L \qquad [III]$$

and two heavy chains comprising a structure represented by the formula:

$$V_{H1}\text{-}L_7\text{-}V_{H2}\text{-}L_8\text{-}C_{H1}\text{-hinge-}C_{H2}\text{—}C_{H3} \qquad [IV]$$

wherein:
$V_{L1}$ is a first immunoglobulin light chain variable domain;
$V_{L2}$ is a second immunoglobulin light chain variable domain;
$V_{H1}$ is a first immunoglobulin heavy chain variable domain;
$V_{H2}$ is a second immunoglobulin heavy chain variable domain;
$C_L$ is an immunoglobulin light chain constant domain;
$C_{H1}$ is an immunoglobulin $C_{H1}$ heavy chain constant domain;
$C_{H2}$ is an immunoglobulin $C_{H2}$ heavy chain constant domain;
$C_{H3}$ is an immunoglobulin $C_{H3}$ heavy chain constant domain;
hinge is an immunoglobulin hinge region connecting the $C_{H1}$ and $C_{H2}$ domains; and
$L_5$, $L_6$, $L_7$, and $L_8$ are amino acid linkers;
wherein the $V_{H1}$ and $V_{L1}$ domains form a $V_{H1}/V_{L1}$ binding pair, and wherein the $V_{H2}$ and $V_{L2}$ domains form a $V_{H2}/V_{L2}$ binding pair.

In some embodiments, formulae III and IV describe the arrangement of domains within the respective polypeptide chains in order from N-terminus to C-terminus. In some embodiments, one or more of the polypeptide chains can comprise additional sequence(s), e.g., at the N-terminal or C-terminal ends.

For exemplary descriptions of this format, see, e.g., US PG Pub. No. US20130209469.

In some embodiments, the bispecific binding molecule comprises two heavy chains comprising the sequence of SEQ ID NO:522 and two light chains comprising the sequence of SEQ ID NO:523. In some embodiments, the bispecific binding molecule comprises two heavy chains comprising the sequence of SEQ ID NO:528 and two light chains comprising the sequence of SEQ ID NO:529. In some embodiments, the binding protein comprises two polypeptide chains shown for AS30_Hu6×C3_Hu10 or AS30_Hu6× C21_Hu11 in Table I3 or I4. In some embodiments, the binding protein comprises a variable domain comprising 1, 2, 3, 4, 5, or 6 CDR sequences shown in Table A2. In some embodiments, the binding protein comprises 1, 2, 3, or 4 variable domains shown in Table D2, I3, or I4.

In some embodiments, the $V_{H1}/V_{L1}$ binding pair binds the extracellular portion of dystroglycan, and the $V_{H2}/V_{L2}$ binding pair binds laminin-2. In other embodiments, the $V_{H2}/V_{L2}$ binding pair binds the extracellular portion of dystroglycan, and the $V_{H1}/V_{L1}$ binding pair binds laminin-2.

In some embodiments, one or both of the variable domains of the polypeptides of formula III and/or formula IV are human, humanized, or mouse variable domains.

Linkers

In some embodiments, $L_5$, $L_6$, $L_7$, and $L_8$ are each 0 to 50 amino acid residues in length, 0 to 40 amino acid residues in length, 0 to 30 amino acid residues in length, 0 to 25 amino acid residues in length, 0 to 20 amino acid residues in length, 0 to 18 amino acid residues in length, 0 to 16 amino acid residues in length, or 0 to 14 amino acid residues in length. In some embodiments, the linkers $L_5$, $L_6$, $L_7$, and $L_8$ range from no amino acids (length=0) to about 100 amino acids long, or less than 100, 50, 40, 30, 20, or 15 amino acids or less. The linkers can also be 10, 9, 8, 7, 6, 5, 4, 3, 2, or 1 amino acids long. $L_5$, $L_6$, $L_7$, and $L_8$ in one binding protein may all have the same amino acid sequence or may all have different amino acid sequences.

In some embodiments, a linker of the present disclosure comprises the sequence DKTHT (SEQ ID NO: 534). In some embodiments, $L_1$ and $L_2$ comprise the sequence DKTHT (SEQ ID NO: 534). In some embodiments, $L_3$ and $L_4$ comprise the sequence DKTHT (SEQ ID NO: 534). In some embodiments, $L_1$, $L_2$, $L_3$, and $L_4$ comprise the sequence DKTHT (SEQ ID NO: 534). Any of the linkers and linker combinations described in International Publication No. WO2017/180913 may be used in the binding proteins (e.g., multispecific binding proteins) described herein.

In some embodiments, $L_1$, $L_2$, $L_3$, and $L_4$ are each 0 to 50 amino acid residues in length, 0 to 40 amino acid residues in length, 0 to 30 amino acid residues in length, 0 to 25 amino acid residues in length, 0 to 20 amino acid residues in length, 0 to 18 amino acid residues in length, 0 to 16 amino acid residues in length, or 0 to 14 amino acid residues in length. In some embodiments, the linkers $L_1$, $L_2$, $L_3$, and $L_4$ range from no amino acids (length=0) to about 100 amino acids long, or less than 100, 50, 40, 30, 20, or 15 amino acids or less. The linkers can also be 10, 9, 8, 7, 6, 5, 4, 3, 2, or 1 amino acids long. $L_1$, $L_2$, $L_3$, and $L_4$ in one binding protein may all have the same amino acid sequence or may all have different amino acid sequences.

In certain embodiments, $L_1$ is 5 amino acid residues in length, $L_2$ is 5 amino acid residues in length, $L_3$ is 5 amino acid residues in length, $L_4$ is 5 amino acid residues in length. In certain embodiments, $L_1$ is 14 amino acid residues in length, $L_2$ is 2 amino acid residues in length, $L_3$ is 14 amino acid residues in length, $L_4$ is 2 amino acid residues in length. In some embodiments, $L_1$ and $L_3$ each comprise the sequence EPKSDKTHTSPPSP (SEQ ID NO:296), and/or $L_2$ and $L_4$ each comprise the sequence GG. In certain embodiments, $L_1$ is 7 amino acid residues in length, $L_2$ is 5 amino acid residues in length, $L_3$ is 1 amino acid residue in length, and $L_4$ is 2 amino acid residues in length. In some embodiments, $L_1$ comprises the sequence GQPKAAP (SEQ ID NO:297), $L_2$ comprises the sequence TKGPS (SEQ ID NO:298), $L_3$ comprises a serine residue (e.g., the sequence S), and $L_4$ comprises the sequence RT. In certain embodiments, $L_1$ is 10 amino acid residues in length, $L_2$ is 10 amino acid residues in length, $L_3$ is 0 amino acid residues in length, and $L_4$ is 0 amino acid residues in length. In some embodiments, $L_1$ and $L_2$ each comprise the sequence GGSGSSGSGG (SEQ ID NO:299).

In certain embodiments, the $L_5$ and $L_7$ linkers comprise the amino acid sequence of GGGGSGGGGS (SEQ ID NO:294), and/or the $L_6$ and $L_8$ linkers are each 0 amino acid residues in length.

The examples listed above (e.g., for $L_1$, $L_2$, $L_3$, $L_4$, $L_5$, $L_6$, $L_7$, or $L_8$) are not intended to limit the scope of the disclosure in any way, and linkers comprising randomly selected amino acids selected from the group consisting of valine, leucine, isoleucine, serine, threonine, lysine, arginine, histidine, aspartate, glutamate, asparagine, glutamine, glycine, and proline are suitable in the binding proteins.

The identity and sequence of amino acid residues in the linker may vary depending on the type of secondary structural element necessary to achieve in the linker. For example, glycine, serine, and alanine are used for flexible linkers. Some combination of glycine, proline, threonine, and serine are useful if a more rigid and extended linker is necessary. Any amino acid residue may be considered as a linker in combination with other amino acid residues to construct larger peptide linkers as necessary depending on the desired properties.

Constant/Fc Regions

In some embodiments, a binding protein (e.g., multispecific binding protein) of the present disclosure comprises a "knob" mutation on the second polypeptide chain and a "hole" mutation on the third polypeptide chain. In some embodiments, a binding protein of the present disclosure comprises a "knob" mutation on the third polypeptide chain and a "hole" mutation on the second polypeptide chain. In some embodiments, the "knob" mutation comprises substitution(s) at positions corresponding to positions 354 and/or 366 of human IgG1 or IgG4 according to EU Index. In some embodiments, the amino acid substitutions are S354C, T366W, T366Y, S354C and T366W, or S354C and T366Y. In some embodiments, the "knob" mutation comprises substitutions at positions corresponding to positions 354 and 366 of human IgG1 or IgG4 according to EU Index. In some embodiments, the amino acid substitutions are S354C and T366W. In some embodiments, the "hole" mutation comprises substitution(s) at positions corresponding to positions 407 and, optionally, 349, 366, and/or 368 and of human IgG1 or IgG4 according to EU Index. In some embodiments, the amino acid substitutions are Y407V or Y407T and optionally Y349C, T366S, and/or L368A. In some embodiments, the "hole" mutation comprises substitutions at positions corresponding to positions 349, 366, 368, and 407 of human IgG1 or IgG4 according to EU Index. In some embodiments, the amino acid substitutions are Y349C, T366S, L368A, and Y407V.

In some embodiments, the $C_{H3}$ domain of the second polypeptide chain comprises amino acid substitutions at positions corresponding to positions 354 and 366 of human IgG1 or IgG4 according to EU Index (e.g., S354C and T366W); and the $C_{H3}$ domain of the third polypeptide chain comprises amino acid substitutions at positions corresponding to positions 349, 366, 368, and 407 of human IgG1 or IgG4 according to EU Index (e.g., Y349C, T366S, L368A, and Y407V). In some embodiments, the $C_{H3}$ domain of the second polypeptide chain comprises amino acid substitutions at positions corresponding to positions 349, 366, 368, and 407 of human IgG1 or IgG4 according to EU Index (e.g., Y349C, T366S, L368A, and Y407V); and the $C_{H3}$ domain of the third polypeptide chain comprises amino acid substitutions at positions corresponding to positions 354 and 366 of human IgG1 or IgG4 according to EU Index (e.g., S354C and T366W).

In some embodiments, a binding protein (e.g., multispecific binding protein) of the present disclosure comprises one or more mutations to improve purification, e.g., by modulating the affinity for a purification reagent. For example, it is known that heterodimeric binding proteins can be selectively purified away from their homodimeric forms if one of the two Fc regions of the heterodimeric form contains mutation(s) that reduce or eliminate binding to Protein A, because the heterodimeric form will have an intermediate affinity for Protein A-based purification than either homodimeric form and can be selectively eluted from Protein A, e.g., by use of a different pH (See e.g., Smith, E. J. et al. (2015) Sci. Rep. 5:17943). In some embodiments, the first and/or second Fc regions are human IgG1 Fc regions. In some embodiments, the first and/or second Fc regions are human IgG4 Fc regions. In some embodiments, the mutation comprises substitutions at positions corresponding to positions 435 and 436 of human IgG1 or IgG4 according to EU Index, wherein the amino acid substitutions are H435R and Y436F. In some embodiments, the $C_{H3}$ domains of the second and the third polypeptide chains are human IgG1 or IgG4 $C_{H3}$ domains, and only one of the $C_{H3}$ domains comprises amino acid substitutions at positions corresponding to positions 435 and 436 of human IgG1 or IgG4 according to EU Index (e.g., H435R and Y436F). In some embodiments, a binding protein of the present disclosure comprises knob and hole mutations and one or more mutations to improve purification.

In some embodiments, a binding protein (e.g., multispecific binding protein) of the present disclosure comprises one or more mutations to increase half-life, e.g., in vivo half-life. In some embodiments, a binding protein comprises one or more of the mutations described in U.S. Pat. No. 7,083,784. For example, in some embodiments, the $C_{H2}$ domains of the second and the third polypeptide chains are human IgG1 or IgG4 $C_{H2}$ domains comprising a tyrosine residue at position 252, a threonine residue at position 254, and a glutamic acid residue at position 256, numbering according to EU Index.

In some embodiments, a binding protein (e.g., multispecific binding protein) of the present disclosure comprises one or more mutations resulting in an Fc region with altered glycosylation and/or reduced effector function. In some embodiments, a binding protein comprises one or more of the mutations described in U.S. Pat. No. 9,790,268. For example, in some embodiments, the $C_{H2}$ domains of the second and the third polypeptide chains are human IgG1 or IgG4 $C_{H2}$ domains comprising an asparagine residue at position 297, an asparagine residue at position 298, an alanine residue at position 299, and a serine or threonine residue at position 300, numbering according to EU Index.

Another bispecific binding protein platform contemplated for use herein is described in US PG Pub. No. US2013/0039913 and Labrijn, A. F. et al. (2013) Proc. Natl. Acad. Sci. 110:5145-5150. In this approach, each binding domain is produced in a homodimeric form, then assembled in vitro to form a heterodimeric bispecific binding protein. This approach employs specific mutations (e.g., in the antibody CH3 domain) to promote Fab-arm exchange, leading to heterodimeric binding proteins that are more stable than either homodimeric form. In some embodiments, these mutations occur, e.g., at positions 366, 368, 370, 399, 405, 407 and/or 409, according to the EU-index as described in Kabat et al. Specific mutations are described in greater detail in US PG Pub. No. US2013/0039913 and Labrijn, A. F. et al. (2013) Proc. Natl. Acad. Sci. 110:5145-5150.

Additional bispecific binding protein platforms contemplated for use herein are described briefly below. One strategy was proposed by Carter et al. (Ridgway et al., 1996, Protein Eng. 9(7): 617-21; Carter, 2011, J. Immunol. Methods 248(1-2): 7-15) to produce a Fc heterodimer using a set of "knob-into-hole" mutations in the $C_{H3}$ domain of Fc. These mutations lead to the alteration of residue packing complementarity between the $C_{H3}$ domain interface within the structurally conserved hydrophobic core so that formation of the heterodimer is favored as compared with homodimers, which achieves good heterodimer expression from mammalian cell culture. Although the strategy led to higher heterodimer yield, the homodimers were not completely suppressed (Merchant et al., 1998, *Nat. Biotechnol.* 16(7): 677-81).

To improve the yields of the binding proteins, in some embodiments, the $C_{H3}$ domains can be altered by the "knob-into-holes" technology which is described in detail with several examples in, for example, International Publication No. WO 96/027011, Ridgway et al., 1996, *Protein Eng.* 9: 617-21; and Merchant et al., 1998, *Nat. Biotechnol.* 16: 677-81. Specifically, the interaction surfaces of the two $C_{H3}$ domains are altered to increase the heterodimerisation of both heavy chains containing these two $C_{H3}$ domains. Each of the two $C_{H3}$ domains (of the two heavy chains) can be the "knob," while the other is the "hole." The introduction of a disulfide bridge further stabilizes the heterodimers (Merchant et al., 1998; Atwell et al., 1997, *J. Mol. Biol.* 270: 26-35) and increases the yield. In particular embodiments, the knob is on the CH3 domain of one polypeptide chain. In other embodiments, the knob is on the first pair of polypeptides having the cross-over orientation. In yet other embodiments, the $C_{H3}$ domains do not include a knob in hole.

In some embodiments, a binding protein of the present disclosure comprises a "knob" mutation on one polypeptide chain and a "hole" mutation on the other polypeptide chain. In some embodiments, the "knob" mutation comprises substitutions at positions corresponding to positions 354 and 366 of human IgG1 according to EU Index. In some embodiments, the amino acid substitutions are S354C and T366W. In some embodiments, the "hole" mutation comprises substitutions at positions corresponding to positions 349, 366, 368, and 407 of human IgG1 according to EU Index. In some embodiments, the amino acid substitutions are Y349C, T366S, L368A, and Y407V.

In some embodiments, a binding protein of the present disclosure comprises one or more mutations to improve serum half-life (See e.g., Hinton, P. R. et al. (2006) *J. Immunol.* 176(1):346-56). In some embodiments, the mutation comprises substitutions at positions corresponding to positions 428 and 434 of human IgG1 according to EU Index, wherein the amino acid substitutions are M428L and N434S. In some embodiments, a binding protein of the present disclosure comprises knob and hole mutations and one or more mutations to improve serum half-life.

Another bispecific binding protein platform contemplated for use herein is the heterodimeric, bivalent antibody Fc-containing format described in WO2011131746. Any of the antigen binding sites described herein may be combined in this heterodimeric, bispecific format. In some embodiments, a multispecific (e.g., bispecific) binding protein of the present disclosure comprises a first antibody heavy chain comprising a first heavy chain variable (VH) domain and a first Fc region of an immunoglobulin comprising a first $C_{H3}$ region, and a first antibody light chain comprising a first light chain variable (VL) domain, wherein the first VH and VL domains form a first antigen binding domain that binds an extracellular portion of dystroglycan, and a second antibody heavy chain comprising a second heavy chain variable (VH) domain and a second Fc region of an immunoglobulin comprising a second $C_{H3}$ region, and a second antibody light chain comprising a second light chain variable (VL) domain, wherein the second VH and VL domains form a second antigen binding domain that binds laminin-2. In some embodiments, the sequences of said first and second $C_{H3}$ regions are different and are such that the heterodimeric interaction between said first and second $C_{H3}$ regions is stronger than each of the homodimeric interactions of said first and second $C_{H3}$ regions. In some embodiments, the first homodimeric protein has an amino acid other than Lys, Leu or Met at position 409 and the second homodimeric protein has an amino-acid substitution at a position selected from: 366, 368, 370, 399, 405 and 407, and/or the sequences of said first and second $C_{H3}$ regions are such that the dissociation constants of homodimeric interactions of each of the $C_{H3}$ regions are between 0.01 and 10 micromolar. In some embodiments, the first antibody heavy chain comprises the sequence of SEQ ID NO:518, the second antibody heavy chain comprises the sequence of SEQ ID NO:519, the first antibody light chain comprises the sequence of SEQ ID NO:520, and the second antibody light chain comprises the sequence of SEQ ID NO:521. In some embodiments, the binding protein comprises two antibody light chains and two antibody heavy chains shown for AS30_Hu6×C3_Hu10 duobody in Table I3.

Another bispecific binding protein platform contemplated for use herein is the "DuetMab" design (Mazor, Y. et al. (2015) *MAbs* 7:377-389). Briefly, the "knob-into-hole" approach described above is combined with replacing a native disulfide bond in one of the CH1-CL interfaces with an engineered disulfide bond to increase the efficiency of cognate heavy and light chain pairing. In some embodiments, the heavy chain of one binding domain bears an F126C mutation, and the cognate light chain for that binding domain bears an S121C mutation, numbering according to Kabat. For example, in some embodiments, a multispecific (e.g., bispecific) binding protein of the present disclosure comprises a first antibody heavy chain comprising the sequence of SEQ ID NO:524, a second antibody heavy chain comprising the sequence of SEQ ID NO:525, a first antibody light chain comprising the sequence of SEQ ID NO:526, and a second antibody light chain comprising the sequence of SEQ ID NO:527. In some embodiments, the binding protein comprises two antibody light chains and two antibody heavy chains shown for AS30_Hu6×C21_Hu11 duetmab in Table I3.

Gunasekaran et al. explored the feasibility of retaining the hydrophobic core integrity while driving the formation of Fc heterodimer by changing the charge complementarity at the $C_{H3}$ domain interface (Gunasekaran et al., 2010, *J. Biol. Chem.* 285(25): 19637-46). Taking advantage of the electrostatic steering mechanism, these constructs showed efficient promotion of Fc heterodimer formation with minimum contamination of homodimers through mutation of two pairs of peripherally located charged residues. In contrast to the knob-into-hole design, the homodimers were evenly suppressed due to the nature of the electrostatic repulsive mechanism, but not totally avoided.

Davis et al. describe an antibody engineering approach to convert Fc homodimers into heterodimers by interdigitating β-strand segments of human IgG and IgA $C_{H3}$ domains, without the introduction of extra interchain disulfide bonds (Davis et al., 2010, *Protein Eng. Des. Sel.* 23(4): 195-202). Expression of SEEDbody (Sb) fusion proteins by mammalian cells yields Sb heterodimers in high yield that are readily purified to eliminate minor by-products.

U.S. Patent Application Publication No. US 2010/331527 A1 describes a bispecific antibody based on heterodimerization of the $C_{H3}$ domain, introducing in one heavy chain the mutations H95R and Y96F within the $C_{H3}$ domain. These amino acid substitutions originate from the $C_{H3}$ domain of the IgG3 subtype and will heterodimerize with an IgG1 backbone. A common light chain prone to pair with every heavy chain is a prerequisite for all formats based on heterodimerization through the $C_{H3}$ domain. A total of three types of antibodies are therefore produced: 50% having a pure IgG1 backbone, one-third having a pure H95R and Y96F mutated backbone, and one-third having two different heavy chains (bispecific). The desired heterodimer can be purified from this mixture because its binding properties to Protein A are different from those of the parental antibodies: IgG3-derived $C_{H3}$ domains do not bind to Protein A, whereas the IgG1 does. Consequently, the heterodimer binds to Protein A, but elutes at a higher pH than the pure IgG1 homodimer, and this makes selective purification of the bispecific heterodimer possible.

U.S. Pat. No. 7,612,181 describes a Dual-Variable-Domain IgG (DVD-IgG) bispecific antibody that is based on the Dual-Fv format described in U.S. Pat. No. 5,989,830. A similar bispecific format was also described in U.S. Patent Application Publication No. US 2010/0226923 A1. The addition of constant domains to respective chains of the Dual-Fv ($C_{H1}$-Fc to the heavy chain and kappa or lambda constant domain to the light chain) led to functional bispecific antibodies without any need for additional modifications (i.e., obvious addition of constant domains to enhance stability). Some of the antibodies expressed in the DVD-Ig/TBTI format show a position effect on the second (or innermost) antigen binding position (Fv2). Depending on the sequence and the nature of the antigen recognized by the Fv2 position, this antibody domain displays a reduced affinity to its antigen (i.e, loss of on-rate in comparison to the parental antibody). One possible explanation for this observation is that the linker between $V_{L1}$ and $V_{L2}$ protrudes into the CDR region of Fv2, making the Fv2 somewhat inaccessible for larger antigens.

The second configuration of a bispecific antibody fragment described in U.S. Pat. No. 5,989,830 is the cross-over double head (CODH), having the following orientation of variable domains expressed on two chains:

$V_{L1}$-linker-$V_{L2}$ for the light chain, and
$V_{H2}$-linker-$V_{H1}$ for the heavy chain.

CDR, VH, and VL Domain Sequences

Described infra are exemplary CDR, VH domain, and VL domain sequences that may be used in any of the multispecific or bispecific binding proteins of the present disclosure in any number, combination, or configuration.

In some embodiments of any of the formats described herein, a $V_{H1}/V_{L1}$ binding pair of the present disclosure binds the extracellular portion of dystroglycan, and a $V_{H2}/V_{L2}$ binding pair of the present disclosure binds laminin-2.

In some embodiments, the $V_{H1}$ domain comprises a CDR-H1 comprising an amino acid sequence selected from the group consisting of SEQ ID NOs:1-8, a CDR-H2 comprising an amino acid sequence selected from the group consisting of SEQ ID NOs:9-17, and a CDR-H3 comprising an amino acid sequence selected from the group consisting of SEQ ID NOs:18-27; and/or wherein the $V_{L1}$ domain comprises a CDR-L1 comprising an amino acid sequence selected from the group consisting of SEQ ID NOs:28-37, a CDR-L2 comprising an amino acid sequence selected from the group consisting of SEQ ID NOs:38-42, and a CDR-L3 comprising an amino acid sequence selected from the group consisting of SEQ ID NOs:43-50. In some embodiments of any of the formats described herein, the $V_{H1}$ domain comprises an amino acid sequence selected from the group consisting of SEQ ID NOs:170, 172, 174, 176, 178, 180, 182, 184, 186, and 188. In some embodiments, the $V_{L1}$ domain comprises an amino acid sequence selected from the group consisting of SEQ ID NOs:171, 173, 175, 177, 179, 181, 183, 185, 187, and 189. In some embodiments, the $V_{H1}$ domain is encoded by a nucleic acid sequence selected from the group consisting of SEQ ID NOs:230, 232, 234, 236, 238, 240, 242, 244, 246, and 248. In some embodiments, the $V_{L1}$ domain is encoded by a nucleic acid sequence selected from the group consisting of SEQ ID NOs:231, 233, 235, 237, 239, 241, 243, 245, 247, and 249.

In some embodiments of any of the formats described herein, a $V_{H1}/V_{L1}$ binding pair of the present disclosure binds the extracellular portion of dystroglycan, and a $V_{H2}/V_{L2}$ binding pair of the present disclosure binds laminin-2 (e.g., a laminin G-like (LG) domain 5, or LG-5). In some embodiments of any of the formats described herein, the $V_{H2}$ domain comprises a CDR-H1 comprising an amino acid sequence selected from the group consisting of SEQ ID NOs:51-55, a CDR-H2 comprising an amino acid sequence selected from the group consisting of SEQ ID NOs:56-60, and a CDR-H3 comprising an amino acid sequence selected from the group consisting of SEQ ID NOs:61-65; and/or wherein the $V_{L2}$ domain comprises a CDR-L1 comprising an amino acid sequence selected from the group consisting of SEQ ID NOs:66-70, a CDR-L2 comprising an amino acid sequence selected from the group consisting of SEQ ID NOs: 71-75, and a CDR-L3 comprising an amino acid sequence selected from the group consisting of SEQ ID NOs:76-80. In some embodiments, the $V_{H2}$ domain comprises an amino acid sequence selected from the group consisting of SEQ ID NOs:190, 192, 194, 196, and 198. In some embodiments, the $V_{L2}$ domain comprises an amino acid sequence selected from the group consisting of SEQ ID NOs: 191, 193, 195, 197, and 199. In some embodiments, the $V_{H2}$ domain is encoded by a nucleic acid sequence selected from the group consisting of SEQ ID NOs:250, 252, 254, 256, and 258. In some embodiments, the $V_{L2}$ domain is encoded by a nucleic acid sequence selected from the group consisting of SEQ ID NOs:251, 253, 255, 257, and 259.

In some embodiments of any of the formats described herein, a $V_{H1}/V_{L1}$ binding pair of the present disclosure binds the extracellular portion of dystroglycan, and a $V_{H2}/V_{L2}$ binding pair of the present disclosure binds laminin-2 (e.g., laminin G-like (LG) 4 and/or 5 domains, or LG-4/5). In some embodiments of any of the formats described herein, the $V_{H2}$ domain comprises a CDR-H1 comprising an amino acid sequence selected from the group consisting of SEQ ID NOs:81-95, a CDR-H2 comprising an amino acid sequence selected from the group consisting of SEQ ID NOs:96-110, and a CDR-H3 comprising an amino acid sequence selected from the group consisting of SEQ ID NOs:111-125; and/or wherein the $V_{L2}$ domain comprises a CDR-L1 comprising an amino acid sequence selected from the group consisting of SEQ ID NOs:126-140, a CDR-L2 comprising an amino acid sequence selected from the group consisting of SEQ ID NOs:38 and 141-154, and a CDR-L3 comprising an amino acid sequence selected from the group consisting of SEQ ID NOs:155-169. In some embodiments, the $V_{H2}$ domain comprises an amino acid sequence selected from the group consisting of SEQ ID NOs:200, 202, 204, 206, 208, 210, 212, 214, 216, 218, 220, 222, 224, 226, and 228. In some embodiments, the $V_{L2}$ domain comprises an amino acid sequence selected from the group consisting of SEQ ID NOs:201, 203, 205, 207, 209, 211, 213, 215, 217, 219, 221, 223, 225, 227, and 229. In some embodiments, the $V_{H2}$ domain is encoded by a nucleic acid sequence selected from the group consisting of SEQ ID NOs:260, 262, 264, 266, 268, 270, 272, 274, 276, 278, 280, 282, 284, 286, and 288. In some embodiments, the $V_{L2}$ domain is encoded by a nucleic acid sequence selected from the group consisting of SEQ ID NOs:261, 263, 265, 267, 269, 271, 273, 275, 277, 279, 281, 283, 285, 287, and 289.

In some embodiments of any of the formats described herein, a $V_{H2}/V_{L2}$ binding pair of the present disclosure binds the extracellular portion of dystroglycan, and a $V_{H1}/V_{L1}$ binding pair of the present disclosure binds laminin-2. In some embodiments of any of the formats described herein, the $V_{H2}$ domain comprises a CDR-H1 comprising an amino acid sequence selected from the group consisting of SEQ ID NOs:1-8, a CDR-H2 comprising an amino acid sequence selected from the group consisting of SEQ ID NOs:9-17, and a CDR-H3 comprising an amino acid sequence selected from the group consisting of SEQ ID NOs:18-27; and/or wherein the $V_{L2}$ domain comprises a CDR-L1 comprising an amino acid sequence selected from the group consisting of SEQ ID NOs:28-37, a CDR-L2 comprising an amino acid sequence selected from the group consisting of SEQ ID NOs:38-42, and a CDR-L3 comprising an amino acid sequence selected from the group consisting of SEQ ID NOs:43-50. In some embodiments of any of the formats described herein, the $V_{H2}$ domain comprises an amino acid sequence selected from the group consisting of SEQ ID NOs:170, 172, 174, 176, 178, 180, 182, 184, 186, and 188. In some embodiments, the $V_{L2}$ domain comprises an amino acid sequence selected from the group consisting of SEQ ID NOs:171, 173, 175, 177, 179, 181, 183, 185, 187, and 189. In some embodiments, the $V_{H2}$ domain is encoded by a nucleic acid sequence selected from the group consisting of SEQ ID NOs:230, 232, 234, 236, 238, 240, 242, 244, 246, and 248. In some embodiments, the $V_{L2}$ domain is encoded by a nucleic acid sequence selected from the group consisting of SEQ ID NOs:231, 233, 235, 237, 239, 241, 243, 245, 247, and 249.

In some embodiments of any of the formats described herein, a $V_{H2}/V_{L2}$ binding pair of the present disclosure binds the extracellular portion of dystroglycan, and a $V_{H1}/V_{L1}$ binding pair of the present disclosure binds laminin-2 (e.g., a laminin G-like (LG) domain 5, or LG-5). In some embodiments of any of the formats described herein, the $V_{H2}$ domain comprises a CDR-H1 comprising an amino acid sequence selected from the group consisting of SEQ ID NOs:51-55, a CDR-H2 comprising an amino acid sequence selected from the group consisting of SEQ ID NOs:56-60, and a CDR-H3 comprising an amino acid sequence selected from the group consisting of SEQ ID NOs:61-65; and/or wherein the $V_{L2}$ domain comprises a CDR-L1 comprising an amino acid sequence selected from the group consisting of SEQ ID NOs:66-70, a CDR-L2 comprising an amino acid sequence selected from the group consisting of SEQ ID NOs: 71-75, and a CDR-L3 comprising an amino acid sequence selected from the group consisting of SEQ ID NOs:76-80. In some embodiments, the $V_{H2}$ domain comprises an amino acid sequence selected from the group consisting of SEQ ID NOs:190, 192, 194, 196, and 198. In some embodiments, the $V_{L2}$ domain comprises an amino acid sequence selected from the group consisting of SEQ ID NOs: 191, 193, 195, 197, and 199. In some embodiments, the $V_{H2}$ domain is encoded by a nucleic acid sequence selected from the group consisting of SEQ ID NOs:250, 252, 254, 256, and 258. In some embodiments, the $V_{L2}$ domain is encoded by a nucleic acid sequence selected from the group consisting of SEQ ID NOs:251, 253, 255, 257, and 259.

In some embodiments of any of the formats described herein, a $V_{H2}/V_{L2}$ binding pair of the present disclosure binds the extracellular portion of dystroglycan, and a $V_{H1}/V_{L1}$ binding pair of the present disclosure binds laminin-2 (e.g., laminin G-like (LG) 4 and/or 5 domains, or LG-4/5). In some embodiments of any of the formats described herein, the $V_{H2}$ domain comprises a CDR-H1 comprising an amino acid sequence selected from the group consisting of SEQ ID NOs:81-95, a CDR-H2 comprising an amino acid sequence selected from the group consisting of SEQ ID NOs:96-110, and a CDR-H3 comprising an amino acid sequence selected from the group consisting of SEQ ID NOs:111-125; and/or wherein the $V_{L2}$ domain comprises a CDR-L1 comprising an amino acid sequence selected from the group consisting of SEQ ID NOs:126-140, a CDR-L2 comprising an amino acid sequence selected from the group consisting of SEQ ID NOs:38 and 141-154, and a CDR-L3 comprising an amino acid sequence selected from the group consisting of SEQ ID NOs:155-169. In some embodiments, the $V_{H2}$ domain comprises an amino acid sequence selected from the group consisting of SEQ ID NOs:200, 202, 204, 206, 208, 210, 212, 214, 216, 218, 220, 222, 224, 226, and 228. In some embodiments, the $V_{L2}$ domain comprises an amino acid sequence selected from the group consisting of SEQ ID NOs:201, 203, 205, 207, 209, 211, 213, 215, 217, 219, 221, 223, 225, 227, and 229. In some embodiments, the $V_{H2}$ domain is encoded by a nucleic acid sequence selected from the group consisting of SEQ ID NOs:260, 262, 264, 266, 268, 270, 272, 274, 276, 278, 280, 282, 284, 286, and 288. In some embodiments, the $V_{L2}$ domain is encoded by a nucleic acid sequence selected from the group consisting of SEQ ID NOs:261, 263, 265, 267, 269, 271, 273, 275, 277, 279, 281, 283, 285, 287, and 289.

Exemplary CDR sequences suitable for use in the binding proteins of the present disclosure are provided in Tables A-C below. Exemplary VH and VL sequences (polypeptide and nucleic acid) suitable for use in the binding proteins of the present disclosure are provided in Tables D-I below. In some embodiments, a bispecific binding protein of the present disclosure comprises a binding domain that binds an extracellular portion of dystroglycan, wherein the binding domain comprises a VH domain comprising at least 1, at least 2, at least 3, at least 4, at least 5, or 6 CDR sequences of an antibody shown in Table A below and/or a VL domain comprising at least 1, at least 2, at least 3, at least 4, at least 5, or 6 CDR sequences of an antibody shown in Table A below. In some embodiments, a bispecific binding protein of the present disclosure comprises a binding domain that binds laminin-2, wherein the binding domain comprises a VH domain comprising at least 1, at least 2, at least 3, at least 4, at least 5, or 6 CDR sequences of an antibody shown in Table B or Table C below and/or a VL domain comprising at least 1, at least 2, at least 3, at least 4, at least 5, or 6 CDR sequences of an antibody shown in Table B or Table C below. In some embodiments, a bispecific binding protein of the present disclosure comprises a binding domain that binds an extracellular portion of dystroglycan, wherein the binding domain comprises a VH domain comprising a sequence that is at least 90%, at least 91%, at least 92%, at least 93%, at least 94%, at least 95%, at least 96%, at least 97%, at least 98%, at least 99%, or 100% identical to a VH sequence shown in Table D below and/or a VL domain comprising a sequence that is at least 90%, at least 91%, at least 92%, at least 93%, at least 94%, at least 95%, at least 96%, at least 97%, at least 98%, at least 99%, or 100% identical to a VL sequence shown in Table D below. In some embodiments, a bispecific binding protein of the present disclosure comprises a binding domain that binds laminin-2, wherein the binding domain comprises a VH domain comprising a sequence that is at least 90%, at least 91%, at least 92%, at least 93%, at least 94%, at least 95%, at least 96%, at least 97%, at least 98%, at least 99%, or 100% identical to a VH sequence shown in Table E or Table F below and/or a VL domain comprising a sequence that is at least 90%, at least 91%, at least 92%, at least 93%, at least 94%, at least 95%, at least 96%, at least 97%, at least 98%, at least 99%, or 100% identical to a VL sequence shown in Table E or Table F below. In some embodiments, a bispecific binding protein of the present disclosure comprises a binding domain that binds an extracellular portion of dystroglycan, wherein the binding domain comprises a VH domain comprising a sequence that is at least 90%, at least 91%, at least 92%, at least 93%, at least 94%, at least 95%, at least 96%, at least 97%, at least 98%, at least 99%, or 100% identical to a VH sequence encoded by a polynucleotide sequence shown in Table G below and/or a VL domain comprising a sequence that is at least 90%, at least 91%, at least 92%, at least 93%, at least 94%, at least 95%, at least 96%, at least 97%, at least 98%, at least 99%, or 100% identical to a VL sequence encoded by a polynucleotide sequence shown in Table G below. In some embodiments, a bispecific binding protein of the present disclosure comprises a binding domain that binds laminin-2, wherein the binding domain comprises a VH domain comprising a sequence that is at least 90%, at least 91%, at least 92%, at least 93%, at least 94%, at least 95%, at least 96%, at least 97%, at least 98%, at least 99%, or 100% identical to a VH sequence encoded by a polynucleotide sequence shown in Table H or Table I below and/or a VL domain comprising a sequence that is at least 90%, at least 91%, at least 92%, at least 93%, at least 94%, at least 95%, at least 96%, at least 97%, at least 98%, at least 99%, or 100% identical to a VL sequence encoded by a polynucleotide sequence shown in Table H or Table I below.

In some embodiments, a bispecific binding protein of the present disclosure comprises (a) a VH domain comprising (i) CDR-H1 comprising the amino acid sequence of SEQ ID NO:1, (ii) CDR-H2 comprising the amino acid sequence of SEQ ID NO:9, and (iii) CDR-H3 comprising the amino acid sequence of SEQ ID NO:18; and/or (b) a VL domain comprising (i) CDR-L1 comprising the amino acid sequence of SEQ ID NO:28, (ii) CDR-L2 comprising the amino acid sequence of SEQ ID NO:38, and (iii) CDR-L3 comprising the amino acid sequence of SEQ ID NO:43. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:170 and/or a VL domain sequence having at least 90%, 91%, 92%, 93%, 94%, 95%, 96%, 97%, 98%, 99%, or 100% sequence identity to the amino acid sequence of SEQ ID NO:171. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:230 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:231.

In some embodiments, a bispecific binding protein of the present disclosure comprises (a) a VH domain comprising (i) CDR-H1 comprising the amino acid sequence of SEQ ID NO:1, (ii) CDR-H2 comprising the amino acid sequence of SEQ ID NO:10, and (iii) CDR-H3 comprising the amino acid sequence of SEQ ID NO:19; and/or (b) a VL domain comprising (i) CDR-L1 comprising the amino acid sequence of SEQ ID NO:29, (ii) CDR-L2 comprising the amino acid sequence of SEQ ID NO:38, and (iii) CDR-L3 comprising the amino acid sequence of SEQ ID NO:43. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:172 and/or a VL domain sequence having at least 90%, 91%, 92%, 93%, 94%, 95%, 96%, 97%, 98%, 99%, or 100% sequence identity to the amino acid sequence of SEQ ID NO:173. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:232 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:233.

In some embodiments, a bispecific binding protein of the present disclosure comprises (a) a VH domain comprising (i) CDR-H1 comprising the amino acid sequence of SEQ ID NO:2, (ii) CDR-H2 comprising the amino acid sequence of SEQ ID NO:11, and (iii) CDR-H3 comprising the amino acid sequence of SEQ ID NO:20; and/or (b) a VL domain comprising (i) CDR-L1 comprising the amino acid sequence of SEQ ID NO:30, (ii) CDR-L2 comprising the amino acid sequence of SEQ ID NO:39, and (iii) CDR-L3 comprising the amino acid sequence of SEQ ID NO:44. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:174 and/or a VL domain sequence having at least 90%, 91%, 92%, 93%, 94%, 95%, 96%, 97%, 98%, 99%, or 100% sequence identity to the amino acid sequence of SEQ ID NO:175. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:234 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:235.

In some embodiments, a bispecific binding protein of the present disclosure comprises (a) a VH domain comprising (i) CDR-H1 comprising the amino acid sequence of SEQ ID NO:3, (ii) CDR-H2 comprising the amino acid sequence of SEQ ID NO:12, and (iii) CDR-H3 comprising the amino acid sequence of SEQ ID NO:21; and/or (b) a VL domain comprising (i) CDR-L1 comprising the amino acid sequence of SEQ ID NO:31, (ii) CDR-L2 comprising the amino acid sequence of SEQ ID NO:40, and (iii) CDR-L3 comprising the amino acid sequence of SEQ ID NO:45. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:176 and/or a VL domain sequence having at least 90%, 91%, 92%, 93%, 94%, 95%, 96%, 97%, 98%, 99%, or 100% sequence identity to the amino acid sequence of SEQ ID NO:177. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:236 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:237.

In some embodiments, a bispecific binding protein of the present disclosure comprises (a) a VH domain comprising (i) CDR-H1 comprising the amino acid sequence of SEQ ID NO:4, (ii) CDR-H2 comprising the amino acid sequence of SEQ ID NO:13, and (iii) CDR-H3 comprising the amino acid sequence of SEQ ID NO:22; and/or (b) a VL domain comprising (i) CDR-L1 comprising the amino acid sequence of SEQ ID NO:32, (ii) CDR-L2 comprising the amino acid sequence of SEQ ID NO:41, and (iii) CDR-L3 comprising the amino acid sequence of SEQ ID NO:46. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:178 and/or a VL domain sequence having at least 90%, 91%, 92%, 93%, 94%, 95%, 96%, 97%, 98%, 99%, or 100% sequence identity to the amino acid sequence of SEQ ID NO:179. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:238 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:239.

In some embodiments, a bispecific binding protein of the present disclosure comprises (a) a VH domain comprising (i) CDR-H1 comprising the amino acid sequence of SEQ ID NO:4, (ii) CDR-H2 comprising the amino acid sequence of SEQ ID NO:13, and (iii) CDR-H3 comprising the amino acid sequence of SEQ ID NO:23; and/or (b) a VL domain comprising (i) CDR-L1 comprising the amino acid sequence of SEQ ID NO:33, (ii) CDR-L2 comprising the amino acid sequence of SEQ ID NO:41, and (iii) CDR-L3 comprising the amino acid sequence of SEQ ID NO:46. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:180 and/or a VL domain sequence having at least 90%, 91%, 92%, 93%, 94%, 95%, 96%, 97%, 98%, 99%, or 100% sequence identity to the amino acid sequence of SEQ ID NO:181. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:240 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:241.

In some embodiments, a bispecific binding protein of the present disclosure comprises (a) a VH domain comprising (i) CDR-H1 comprising the amino acid sequence of SEQ ID NO:5, (ii) CDR-H2 comprising the amino acid sequence of SEQ ID NO:14, and (iii) CDR-H3 comprising the amino acid sequence of SEQ ID NO:24; and/or (b) a VL domain comprising (i) CDR-L1 comprising the amino acid sequence of SEQ ID NO:34, (ii) CDR-L2 comprising the amino acid sequence of SEQ ID NO:42, and (iii) CDR-L3 comprising the amino acid sequence of SEQ ID NO:47. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:182 and/or a VL domain sequence having at least 90%, 91%, 92%, 93%, 94%, 95%, 96%, 97%, 98%, 99%, or 100% sequence identity to the amino acid sequence of SEQ ID NO:183. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:242 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:243.

In some embodiments, a bispecific binding protein of the present disclosure comprises (a) a VH domain comprising (i) CDR-H1 comprising the amino acid sequence of SEQ ID NO:6, (ii) CDR-H2 comprising the amino acid sequence of SEQ ID NO:15, and (iii) CDR-H3 comprising the amino acid sequence of SEQ ID NO:25; and/or (b) a VL domain comprising (i) CDR-L1 comprising the amino acid sequence of SEQ ID NO:35, (ii) CDR-L2 comprising the amino acid sequence of SEQ ID NO:40, and (iii) CDR-L3 comprising the amino acid sequence of SEQ ID NO:48. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:184 and/or a VL domain sequence having at least 90%, 91%, 92%, 93%, 94%, 95%, 96%, 97%, 98%, 99%, or 100% sequence identity to the amino acid sequence of SEQ ID NO:185. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:244 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:245.

In some embodiments, a bispecific binding protein of the present disclosure comprises (a) a VH domain comprising (i) CDR-H1 comprising the amino acid sequence of SEQ ID NO:7, (ii) CDR-H2 comprising the amino acid sequence of SEQ ID NO:16, and (iii) CDR-H3 comprising the amino acid sequence of SEQ ID NO:26; and/or (b) a VL domain comprising (i) CDR-L1 comprising the amino acid sequence of SEQ ID NO:36, (ii) CDR-L2 comprising the amino acid sequence of SEQ ID NO:40, and (iii) CDR-L3 comprising the amino acid sequence of SEQ ID NO:49. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:186 and/or a VL domain sequence having at least 90%, 91%, 92%, 93%, 94%, 95%, 96%, 97%, 98%, 99%, or 100% sequence identity to the amino acid sequence of SEQ ID NO:187. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:246 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:247.

In some embodiments, a bispecific binding protein of the present disclosure comprises (a) a VH domain comprising (i) CDR-H1 comprising the amino acid sequence of SEQ ID NO:8, (ii) CDR-H2 comprising the amino acid sequence of SEQ ID NO:17, and (iii) CDR-H3 comprising the amino acid sequence of SEQ ID NO:27; and/or (b) a VL domain comprising (i) CDR-L1 comprising the amino acid sequence of SEQ ID NO:37, (ii) CDR-L2 comprising the amino acid sequence of SEQ ID NO:40, and (iii) CDR-L3 comprising the amino acid sequence of SEQ ID NO:50. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:188 and/or a VL domain sequence having at least 90%, 91%, 92%, 93%, 94%, 95%, 96%, 97%, 98%, 99%, or 100% sequence identity to the amino acid sequence of SEQ ID NO:189. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:248 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:249.

In some embodiments, a bispecific binding protein of the present disclosure comprises (a) a VH domain comprising (i) CDR-H1 comprising the amino acid sequence of SEQ ID NO:51, (ii) CDR-H2 comprising the amino acid sequence of SEQ ID NO:56, and (iii) CDR-H3 comprising the amino acid sequence of SEQ ID NO:61; and/or (b) a VL domain comprising (i) CDR-L1 comprising the amino acid sequence of SEQ ID NO:66, (ii) CDR-L2 comprising the amino acid sequence of SEQ ID NO:71, and (iii) CDR-L3 comprising the amino acid sequence of SEQ ID NO:76. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:190 and/or a VL domain sequence having at least 90%, 91%, 92%, 93%, 94%, 95%, 96%, 97%, 98%, 99%, or 100% sequence identity to the amino acid sequence of SEQ ID NO:191. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:250 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:251.

In some embodiments, a bispecific binding protein of the present disclosure comprises (a) a VH domain comprising (i) CDR-H1 comprising the amino acid sequence of SEQ ID NO:52, (ii) CDR-H2 comprising the amino acid sequence of SEQ ID NO:57, and (iii) CDR-H3 comprising the amino acid sequence of SEQ ID NO:62; and/or (b) a VL domain comprising (i) CDR-L1 comprising the amino acid sequence of SEQ ID NO:67, (ii) CDR-L2 comprising the amino acid sequence of SEQ ID NO:72, and (iii) CDR-L3 comprising the amino acid sequence of SEQ ID NO:77. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:192 and/or a VL domain sequence having at least 90%, 91%, 92%, 93%, 94%, 95%, 96%, 97%, 98%, 99%, or 100% sequence identity to the amino acid sequence of SEQ ID NO:193. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:252 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:253.

In some embodiments, a bispecific binding protein of the present disclosure comprises (a) a VH domain comprising (i) CDR-H1 comprising the amino acid sequence of SEQ ID NO:53, (ii) CDR-H2 comprising the amino acid sequence of SEQ ID NO:58, and (iii) CDR-H3 comprising the amino acid sequence of SEQ ID NO:63; and/or (b) a VL domain comprising (i) CDR-L1 comprising the amino acid sequence of SEQ ID NO:68, (ii) CDR-L2 comprising the amino acid sequence of SEQ ID NO:73, and (iii) CDR-L3 comprising the amino acid sequence of SEQ ID NO:78. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:194 and/or a VL domain sequence having at least 90%, 91%, 92%, 93%, 94%, 95%, 96%, 97%, 98%, 99%, or 100% sequence identity to the amino acid sequence of SEQ ID NO:195. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:254 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:255.

In some embodiments, a bispecific binding protein of the present disclosure comprises (a) a VH domain comprising (i) CDR-H1 comprising the amino acid sequence of SEQ ID NO:54, (ii) CDR-H2 comprising the amino acid sequence of SEQ ID NO:59, and (iii) CDR-H3 comprising the amino acid sequence of SEQ ID NO:64; and/or (b) a VL domain comprising (i) CDR-L1 comprising the amino acid sequence of SEQ ID NO:69, (ii) CDR-L2 comprising the amino acid sequence of SEQ ID NO:74, and (iii) CDR-L3 comprising the amino acid sequence of SEQ ID NO:79. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:196 and/or a VL domain sequence having at least 90%, 91%, 92%, 93%, 94%, 95%, 96%, 97%, 98%, 99%, or 100% sequence identity to the amino acid sequence of SEQ ID NO:197. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:256 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:257.

In some embodiments, a bispecific binding protein of the present disclosure comprises (a) a VH domain comprising (i) CDR-H1 comprising the amino acid sequence of SEQ ID NO:55, (ii) CDR-H2 comprising the amino acid sequence of SEQ ID NO:60, and (iii) CDR-H3 comprising the amino acid sequence of SEQ ID NO:65; and/or (b) a VL domain comprising (i) CDR-L1 comprising the amino acid sequence of SEQ ID NO:70, (ii) CDR-L2 comprising the amino acid sequence of SEQ ID NO:75, and (iii) CDR-L3 comprising the amino acid sequence of SEQ ID NO:80. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:198 and/or a VL domain sequence having at least 90%, 91%, 92%, 93%, 94%, 95%, 96%, 97%, 98%, 99%, or 100% sequence identity to the amino acid sequence of SEQ ID NO:199. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:258 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:259.

In some embodiments, a bispecific binding protein of the present disclosure comprises (a) a VH domain comprising (i) CDR-H1 comprising the amino acid sequence of SEQ ID NO:81, (ii) CDR-H2 comprising the amino acid sequence of SEQ ID NO:96, and (iii) CDR-H3 comprising the amino acid sequence of SEQ ID NO:111; and/or (b) a VL domain comprising (i) CDR-L1 comprising the amino acid sequence of SEQ ID NO:126, (ii) CDR-L2 comprising the amino acid sequence of SEQ ID NO:141, and (iii) CDR-L3 comprising the amino acid sequence of SEQ ID NO:155. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:200 and/or a VL domain sequence having at least 90%, 91%, 92%, 93%, 94%, 95%, 96%, 97%, 98%, 99%, or 100% sequence identity to the amino acid sequence of SEQ ID NO:201. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:260 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:261.

In some embodiments, a bispecific binding protein of the present disclosure comprises (a) a VH domain comprising (i) CDR-H1 comprising the amino acid sequence of SEQ ID NO:82, (ii) CDR-H2 comprising the amino acid sequence of SEQ ID NO:97, and (iii) CDR-H3 comprising the amino acid sequence of SEQ ID NO:112; and/or (b) a VL domain comprising (i) CDR-L1 comprising the amino acid sequence of SEQ ID NO:127, (ii) CDR-L2 comprising the amino acid sequence of SEQ ID NO:142, and (iii) CDR-L3 comprising the amino acid sequence of SEQ ID NO:156. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:202 and/or a VL domain sequence having at least 90%, 91%, 92%, 93%, 94%, 95%, 96%, 97%, 98%, 99%, or 100% sequence identity to the amino acid sequence of SEQ ID NO:203. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:262 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:263.

In some embodiments, a bispecific binding protein of the present disclosure comprises (a) a VH domain comprising (i) CDR-H1 comprising the amino acid sequence of SEQ ID NO:83, (ii) CDR-H2 comprising the amino acid sequence of SEQ ID NO:98, and (iii) CDR-H3 comprising the amino acid sequence of SEQ ID NO:113; and/or (b) a VL domain comprising (i) CDR-L1 comprising the amino acid sequence of SEQ ID NO:128, (ii) CDR-L2 comprising the amino acid sequence of SEQ ID NO:143, and (iii) CDR-L3 comprising the amino acid sequence of SEQ ID NO:157. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:204 and/or a VL domain sequence having at least 90%, 91%, 92%, 93%, 94%, 95%, 96%, 97%, 98%, 99%, or 100% sequence identity to the amino acid sequence of SEQ ID NO:205. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:264 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:265.

In some embodiments, a bispecific binding protein of the present disclosure comprises (a) a VH domain comprising (i) CDR-H1 comprising the amino acid sequence of SEQ ID NO:84, (ii) CDR-H2 comprising the amino acid sequence of SEQ ID NO:99, and (iii) CDR-H3 comprising the amino acid sequence of SEQ ID NO:114; and/or (b) a VL domain comprising (i) CDR-L1 comprising the amino acid sequence of SEQ ID NO:129, (ii) CDR-L2 comprising the amino acid sequence of SEQ ID NO:144, and (iii) CDR-L3 comprising the amino acid sequence of SEQ ID NO:158. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:206 and/or a VL domain sequence having at least 90%, 91%, 92%, 93%, 94%, 95%, 96%, 97%, 98%, 99%, or 100% sequence identity to the amino acid sequence of SEQ ID NO:207. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:266 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:267.

In some embodiments, a bispecific binding protein of the present disclosure comprises (a) a VH domain comprising (i) CDR-H1 comprising the amino acid sequence of SEQ ID NO:85, (ii) CDR-H2 comprising the amino acid sequence of SEQ ID NO:100, and (iii) CDR-H3 comprising the amino acid sequence of SEQ ID NO:115; and/or (b) a VL domain comprising (i) CDR-L1 comprising the amino acid sequence of SEQ ID NO:130, (ii) CDR-L2 comprising the amino acid sequence of SEQ ID NO:145, and (iii) CDR-L3 comprising the amino acid sequence of SEQ ID NO:159. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:208 and/or a VL domain sequence having at least 90%, 91%, 92%, 93%, 94%, 95%, 96%, 97%, 98%, 99%, or 100% sequence identity to the amino acid sequence of SEQ ID NO:209. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:268 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:269.

In some embodiments, a bispecific binding protein of the present disclosure comprises (a) a VH domain comprising (i) CDR-H1 comprising the amino acid sequence of SEQ ID NO:86, (ii) CDR-H2 comprising the amino acid sequence of SEQ ID NO:101, and (iii) CDR-H3 comprising the amino acid sequence of SEQ ID NO:116; and/or (b) a VL domain comprising (i) CDR-L1 comprising the amino acid sequence of SEQ ID NO:131, (ii) CDR-L2 comprising the amino acid sequence of SEQ ID NO:146, and (iii) CDR-L3 comprising the amino acid sequence of SEQ ID NO:160. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:210 and/or a VL domain sequence having at least 90%, 91%, 92%, 93%, 94%, 95%, 96%, 97%, 98%, 99%, or 100% sequence identity to the amino acid sequence of SEQ ID NO:211. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:270 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:271.

In some embodiments, a bispecific binding protein of the present disclosure comprises (a) a VH domain comprising (i) CDR-H1 comprising the amino acid sequence of SEQ ID NO:87, (ii) CDR-H2 comprising the amino acid sequence of SEQ ID NO:102, and (iii) CDR-H3 comprising the amino acid sequence of SEQ ID NO:117; and/or (b) a VL domain comprising (i) CDR-L1 comprising the amino acid sequence of SEQ ID NO:132, (ii) CDR-L2 comprising the amino acid sequence of SEQ ID NO:147, and (iii) CDR-L3 comprising the amino acid sequence of SEQ ID NO:161. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:212 and/or a VL domain sequence having at least 90%, 91%, 92%, 93%, 94%, 95%, 96%, 97%, 98%, 99%, or 100% sequence identity to the amino acid sequence of SEQ ID NO:213. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:272 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:273.

In some embodiments, a bispecific binding protein of the present disclosure comprises (a) a VH domain comprising (i) CDR-H1 comprising the amino acid sequence of SEQ ID NO:88, (ii) CDR-H2 comprising the amino acid sequence of SEQ ID NO:103, and (iii) CDR-H3 comprising the amino acid sequence of SEQ ID NO:118; and/or (b) a VL domain comprising (i) CDR-L1 comprising the amino acid sequence of SEQ ID NO:133, (ii) CDR-L2 comprising the amino acid sequence of SEQ ID NO:148, and (iii) CDR-L3 comprising the amino acid sequence of SEQ ID NO:162. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:214 and/or a VL domain sequence having at least 90%, 91%, 92%, 93%, 94%, 95%, 96%, 97%, 98%, 99%, or 100% sequence identity to the amino acid sequence of SEQ ID NO:215. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:274 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:275.

In some embodiments, a bispecific binding protein of the present disclosure comprises (a) a VH domain comprising (i) CDR-H1 comprising the amino acid sequence of SEQ ID NO:89, (ii) CDR-H2 comprising the amino acid sequence of SEQ ID NO:104, and (iii) CDR-H3 comprising the amino acid sequence of SEQ ID NO:119; and/or (b) a VL domain comprising (i) CDR-L1 comprising the amino acid sequence of SEQ ID NO:134, (ii) CDR-L2 comprising the amino acid sequence of SEQ ID NO:149, and (iii) CDR-L3 comprising the amino acid sequence of SEQ ID NO:163. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:216 and/or a VL domain sequence having at least 90%, 91%, 92%, 93%, 94%, 95%, 96%, 97%, 98%, 99%, or 100% sequence identity to the amino acid sequence of SEQ ID NO:217. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:276 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:277.

In some embodiments, a bispecific binding protein of the present disclosure comprises (a) a VH domain comprising (i) CDR-H1 comprising the amino acid sequence of SEQ ID NO:90, (ii) CDR-H2 comprising the amino acid sequence of SEQ ID NO:105, and (iii) CDR-H3 comprising the amino acid sequence of SEQ ID NO:120; and/or (b) a VL domain comprising (i) CDR-L1 comprising the amino acid sequence of SEQ ID NO:135, (ii) CDR-L2 comprising the amino acid sequence of SEQ ID NO:150, and (iii) CDR-L3 comprising the amino acid sequence of SEQ ID NO:164. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:218 and/or a VL domain sequence having at least 90%, 91%, 92%, 93%, 94%, 95%, 96%, 97%, 98%, 99%, or 100% sequence identity to the amino acid sequence of SEQ ID NO:219. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:278 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:279.

In some embodiments, a bispecific binding protein of the present disclosure comprises (a) a VH domain comprising (i) CDR-H1 comprising the amino acid sequence of SEQ ID NO:91, (ii) CDR-H2 comprising the amino acid sequence of SEQ ID NO:106, and (iii) CDR-H3 comprising the amino acid sequence of SEQ ID NO:121; and/or (b) a VL domain comprising (i) CDR-L1 comprising the amino acid sequence of SEQ ID NO:136, (ii) CDR-L2 comprising the amino acid sequence of SEQ ID NO:151, and (iii) CDR-L3 comprising the amino acid sequence of SEQ ID NO:165. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:220 and/or a VL domain sequence having at least 90%, 91%, 92%, 93%, 94%, 95%, 96%, 97%, 98%, 99%, or 100% sequence identity to the amino acid sequence of SEQ ID NO:221. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:280 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:281.

In some embodiments, a bispecific binding protein of the present disclosure comprises (a) a VH domain comprising (i) CDR-H1 comprising the amino acid sequence of SEQ ID NO:92, (ii) CDR-H2 comprising the amino acid sequence of SEQ ID NO:107, and (iii) CDR-H3 comprising the amino acid sequence of SEQ ID NO:122; and/or (b) a VL domain comprising (i) CDR-L1 comprising the amino acid sequence of SEQ ID NO:137, (ii) CDR-L2 comprising the amino acid sequence of SEQ ID NO:152, and (iii) CDR-L3 comprising the amino acid sequence of SEQ ID NO:166. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:222 and/or a VL domain sequence having at least 90%, 91%, 92%, 93%, 94%, 95%, 96%, 97%, 98%, 99%, or 100% sequence identity to the amino acid sequence of SEQ ID NO:223. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:282 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:283.

In some embodiments, a bispecific binding protein of the present disclosure comprises (a) a VH domain comprising (i) CDR-H1 comprising the amino acid sequence of SEQ ID NO:93, (ii) CDR-H2 comprising the amino acid sequence of SEQ ID NO:108, and (iii) CDR-H3 comprising the amino acid sequence of SEQ ID NO:123; and/or (b) a VL domain comprising (i) CDR-L1 comprising the amino acid sequence of SEQ ID NO:138, (ii) CDR-L2 comprising the amino acid sequence of SEQ ID NO:153, and (iii) CDR-L3 comprising the amino acid sequence of SEQ ID NO:167. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:224 and/or a VL domain sequence having at least 90%, 91%, 92%, 93%, 94%, 95%, 96%, 97%, 98%, 99%, or 100% sequence identity to the amino acid sequence of SEQ ID NO:225. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:284 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:285.

In some embodiments, a bispecific binding protein of the present disclosure comprises (a) a VH domain comprising (i) CDR-H1 comprising the amino acid sequence of SEQ ID NO:94, (ii) CDR-H2 comprising the amino acid sequence of SEQ ID NO:109, and (iii) CDR-H3 comprising the amino acid sequence of SEQ ID NO:124; and/or (b) a VL domain comprising (i) CDR-L1 comprising the amino acid sequence of SEQ ID NO:139, (ii) CDR-L2 comprising the amino acid sequence of SEQ ID NO:38, and (iii) CDR-L3 comprising the amino acid sequence of SEQ ID NO:168. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:226 and/or a VL domain sequence having at least 90%, 91%, 92%, 93%, 94%, 95%, 96%, 97%, 98%, 99%, or 100% sequence identity to the amino acid sequence of SEQ ID NO:227. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:286 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:287.

In some embodiments, a bispecific binding protein of the present disclosure comprises (a) a VH domain comprising (i) CDR-H1 comprising the amino acid sequence of SEQ ID NO:95, (ii) CDR-H2 comprising the amino acid sequence of SEQ ID NO:110, and (iii) CDR-H3 comprising the amino acid sequence of SEQ ID NO:125; and/or (b) a VL domain comprising (i) CDR-L1 comprising the amino acid sequence of SEQ ID NO:140, (ii) CDR-L2 comprising the amino acid sequence of SEQ ID NO:154, and (iii) CDR-L3 comprising the amino acid sequence of SEQ ID NO:169. In some embodiments, a bispecific binding protein of the present disclosure comprises a VH domain sequence having at least 90%, 91%, 92%, 93%, 94%, 95%, 96%, 97%, 98%, 99%, or 100% sequence identity to the amino acid sequence of SEQ ID NO:228 and/or a VL domain sequence having at least 90%, 91%, 92%, 93%, 94%, 95%, 96%, 97%, 98%, 99%, or 100% sequence identity to the amino acid sequence of SEQ ID NO:229. In some embodiments, a bispecific binding protein of the present disclosure comprises a VH domain sequence having at least 90%, 91%, 92%, 93%, 94%, 95%, 96%, 97%, 98%, 99%, or 100% sequence identity to a VH domain sequence encoded by the polynucleotide sequence of SEQ ID NO:288 and/or a VL domain sequence having at least 90%, 91%, 92%, 93%, 94%, 95%, 96%, 97%, 98%, 99%, or 100% sequence identity to a VL domain sequence encoded by the polynucleotide sequence of SEQ ID NO:289.

It will be appreciated by one of skill in the art that the CDRs and/or VH/VL domains of any of the anti-dystroglycan antibodies described herein may be combined in a bispecific binding protein with the CDRs and/or VH/VL domains of any of the anti-laminin-2 antibodies (e.g., antibodies that bind the LG-4/5 and/or LG-5 domains of laminin-2) described herein in any combination or configuration (e.g., having a $V_{H1}/V_{L1}$ binding pair specific for the extracellular domain of dystroglycan and a $V_{H2}/V_{L2}$ binding pair specific for laminin-2, or having a $V_{H2}/V_{L2}$ binding pair specific for the extracellular domain of dystroglycan and a $V_{H1}/V_{L1}$ binding pair specific for laminin-2).

It will be appreciated by one of skill in the art that the CDRs and/or VH/VL domains of any of the anti-dystroglycan antibodies described herein may be combined in a multispecific binding protein with the CDRs and/or VH/VL domains of any of the anti-laminin-2 antibodies (e.g., antibodies that bind the LG-4/5 and/or LG-5 domains of laminin-2) described herein in any combination or configuration. In some embodiments, a binding protein (e.g., multispecific binding protein) of the present disclosure comprises 1, 2, 3, 4, 5, 6, or more CDRs shown in Table A2 or from a variable domain or polypeptide sequence shown in Tables D2, I2, I3, or I4. In some embodiments, a binding protein (e.g., multispecific binding protein) of the present disclosure comprises a 1, 2, 3, 4, 5, or 6 variable domain sequences shown in Tables D2, I2, I3, or I4, or a 1, 2, 3, 4, 5, or 6 variable domain sequences encoded by a polynucleotide shown in Table G2 (e.g., 1, 2, or 3 VH/VL binding pairs, each comprising a VH and VL domain). In some embodiments, a binding protein (e.g., multispecific binding protein) of the present disclosure comprises 1, 2, 3, or 4 variable domain framework sequences shown in Table I4.

TABLE A

CDR sequences of anti-beta-DG VH and VL regions.

| bDG | Variable Heavy Chain (VH) | | | | | | Variable Light Chain (VL) | | | | | |
|---|---|---|---|---|---|---|---|---|---|---|---|---|
| | CDR 1 | SEQ ID NO | CDR 2 | SEQ ID NO | CDR 3 | SEQ ID NO | CDR 1 | SEQ ID NO | CDR 2 | SEQ ID NO | CDR 3 | SEQ ID NO |
| AS19 | GFTFTDSV | 1 | IYPGSGSI | 9 | AMRRSY | 18 | QSIVHS NGNTY | 28 | KVS | 38 | FQGSHVPLT | 43 |
| AS30 S/S | GFTFTDSV | 1 | IYPGSGNF | 10 | AMRRSS | 19 | QTIVHS NSKTY | 29 | KVS | 38 | FQGSHVPLT | 43 |
| B04 | GFTFSSYA | 2 | ISGSGGST | 11 | ARLGYCSST SCYLSAFDI | 20 | QSISSW | 30 | DAS | 39 | QQYNSYPLT | 44 |
| B06 | GYSFSNYW | 3 | IYPGDSDT | 12 | ARGVIING TTSGFDY | 21 | QSVSSN | 31 | GAS | 40 | QHYNNLPLT | 45 |
| C107 | GFNIKDTY | 4 | IDPANGNT | 13 | GRSGG NYVGY | 22 | QSLLDSG NQKNY | 32 | WAS | 41 | QQYYTYPWT | 46 |
| D87/ D39/ D173 | GFNIKDTY | 4 | IDPANGNT | 13 | GRSRG NYFDY | 23 | QSLLYSS NQKNY | 33 | WAS | 41 | QQYYTYPWT | 46 |
| TDG-2 | GYTFTTYY | 5 | INPSAGNT | 14 | ARELDI | 24 | QDIRND | 34 | AAS | 42 | LQDFNFPFT | 47 |
| TDI-11 | GFTFSSYG | 6 | IWYDGSNK | 15 | AREGMVR GALFDY | 25 | QSVSSSY | 35 | GAS | 40 | QQDYNLPYT | 48 |
| TDI-23 | GYSFTSYW | 7 | IYPGDSDT | 16 | ARQLRD YYGMDV | 26 | QTISSNY | 36 | GAS | 40 | QQDYNLPRT | 49 |
| TDI-38 | GYSFTSYW | 8 | IYPG DSDT | 17 | ARQLRD YYSMDV | 27 | QSVSSSY | 37 | GAS | 40 | QQDYNLPRT | 50 |

TABLE A2

CDR sequences of humanized antibodies.

| | Variable Heavy Chain (VH) | | | | | | Variable Light Chain (VL) | | | | | |
|---|---|---|---|---|---|---|---|---|---|---|---|---|
| | CDR 1 | SEQ ID NO | CDR 2 | SEQ ID NO | CDR 3 | SEQ ID NO | CDR 1 | SEQ ID NO | CDR 2 | SEQ ID NO | CDR 3 | SEQ ID NO |
| bDG | | | | | | | | | | | | |
| AS30SS_Hu6 | GFTFTDSV | 316 | IYPGSGNF | 318 | AMRRSS | 320 | QTIVHSNSKTY | 332 | KVS | 334 | FQGSHVPLT | 336 |
| AS30SS_Hu9 | GFTFTDSV | 316 | IYPGSGNF | 318 | AMRRSS | 320 | QTIVHSNSKTY | 332 | KVS | 334 | FQGSHVPLT | 336 |
| L-4/5 | | | | | | | | | | | | |
| C3_Hu10 | GFTFSSYT | 380 | ISSSGSNT | 382 | ARFDYGSSLDS | 384 | QSISNN | 396 | YAS | 398 | QQSKSWPRT | 400 |
| CE_Hu11 | GFTFSSYT | 412 | ISSSGSNT | 414 | ARFDYGSSLDS | 416 | QSIGNN | 428 | YAS | 430 | QQSKSWPRT | 432 |
| C21_Hu11 | GFTFSSYT | 444 | ISSSGSNT | 446 | ARFDYGSSLDS | 448 | QSISNY | 460 | YAS | 462 | QQSKSWPRT | 464 |
| C21_Hu21 | GFTFSSYT | 476 | ISSSGDNT | 478 | ARFDYGSSLDS | 480 | QSISNY | 492 | YAS | 494 | QQSKSWPRT | 496 |

TABLE B

CDR sequences of anti-LG-5 VH and VL regions.

| | Variable Heavy Chain (VH) | | | | | | Variable Light Chain (VL) | | | | | |
|---|---|---|---|---|---|---|---|---|---|---|---|---|
| L-5 | CDR 1 | SEQ ID NO | CDR 2 | SEQ ID NO | CDR 3 | SEQ ID NO | CDR 1 | SEQ ID NO | CDR 2 | SEQ ID NO | CDR 3 | SEQ ID NO |
| AN01 | GYTFTSYN | 51 | INPYNDGT | 56 | AIYGNSY | 61 | KSLLHSNGNTY | 66 | YMS | 71 | MQGLEYPYT | 76 |
| C3 | GFTFSSYT | 52 | ISSGGGNT | 57 | ARFDYGSSLDS | 62 | QSISNN | 67 | YAS | 72 | QQSKNWPRT | 77 |
| C21 | GFTFSSYT | 53 | ISSGGDNT | 58 | ARFDYGSSLDC | 63 | QSISNY | 68 | YAS | 73 | QQSKSWPRT | 78 |
| TLF39 | GYSFTSYW | 54 | IYPGDSDT | 59 | ARRGYRSSWYFDY | 64 | QGIRND | 69 | AAS | 74 | LQDYNYPLT | 79 |
| TLF86 | GFTFDDYG | 55 | INWNGGST | 60 | AREGGELLMDY | 65 | QSVSTY | 70 | DAS | 75 | QQRSNWPPT | 80 |

TABLE C

CDR sequences of anti-LG-4/5 VH and VL regions.

| | Variable Heavy Chain (VH) | | | | | | Variable Light Chain (VL) | | | | | |
|---|---|---|---|---|---|---|---|---|---|---|---|---|
| L-4/5 | CDR 1 | SEQ ID NO | CDR 2 | SEQ ID NO | CDR 3 | SEQ ID NO | CDR 1 | SEQ ID NO | CDR 2 | SEQ ID NO | CDR 3 | SEQ ID NO |
| CL-40968 | GFTFSHYS | 81 | IYPSGGT | 96 | ARHWRGYSSSWYHPAYFDY | 111 | QSVSSY | 126 | DAS | 141 | QQRSNWPLT | 155 |
| CL-40992 | GFTFSWYP | 82 | IYPSGGTT | 97 | ARSYYYDSSGYYSHDAFDI | 112 | QSIDTY | 127 | AAS | 142 | QQSYSSPGIT | 156 |

TABLE C-continued

CDR sequences of anti-LG-4/5 VH and VL regions.

| L-4/5 | Variable Heavy Chain (VH) | | | | | | Variable Light Chain (VL) | | | | | |
|---|---|---|---|---|---|---|---|---|---|---|---|---|
| | CDR 1 | SEQ ID NO | CDR 2 | SEQ ID NO | CDR 3 | SEQ ID NO | CDR 1 | SEQ ID NO | CDR 2 | SEQ ID NO | CDR 3 | SEQ ID NO |
| CL-41136 | GFTFSDYE | 83 | IWPSGGLT | 98 | ARDSYYYDSSGALGY | 113 | QSVSNW | 128 | KAS | 143 | LQYVSYPLT | 157 |
| CL-41400 | GFTFSYYD | 84 | IYSSGGHT | 99 | ARPGYSSGWYDGTYFDY | 114 | QSIDTW | 129 | SAS | 144 | QQYKTYPFT | 158 |
| CL-41500 | GFTFSHYQ | 85 | ISPSGGFT | 100 | TREPGRLWAFDI | 115 | QDIRNW | 130 | AAS | 145 | QQADSSPRT | 159 |
| TLG3/TLG4 | GYTFTGYY | 86 | INPNSGGT | 101 | AVFGSGSS | 116 | QGISNS | 131 | AAS | 146 | QQYKSYPYT | 160 |
| TLG26 | GNTFTGYY | 87 | IKPSTGDT | 102 | AVFGSGSS | 117 | QGISNY | 132 | AAS | 147 | QQYKTYPYT | 161 |
| TLI-3 | GFTFSSYG | 88 | IWYDGSNK | 103 | AREGGWYGGDYYYGMDV | 118 | QGISSA | 133 | DAS | 148 | HQFNNYPFT | 162 |
| TLI-7 | GFTFSSYA | 89 | ISGRGGSP | 104 | AKDGDSGPPYYFDY | 119 | QGISSW | 134 | AAS | 149 | QQYNSYPYT | 163 |
| TTLK71-4-6 | GFTFSGYG | 90 | IWSDGSNR | 105 | ARDRGITMVRGLIIKYYYYYGLDV | 120 | QSVSSY | 135 | DAS | 150 | QQRSNWWT | 164 |
| TTLK123-3 | GFTFSSFG | 91 | IYYDGSNK | 106 | ARDDNWNDGDFDY | 121 | QGISSY | 136 | AAS | 151 | QQLNSYPRT | 165 |
| TTLK145-6-3 | GFTFNRFV | 92 | ISGSGGST | 107 | AKDFTYYYGSGNYYNWFDP | 122 | QSISSW | 137 | KAS | 152 | QQYNSYSRT | 166 |
| TTLK170-2 | GGSFSGYY | 93 | INHSGGT | 108 | ARTSDYDYYYYGMDV | 123 | SGINLGRYR | 138 | YYSDSSK | 153 | MIWHRSALFI | 167 |
| WJL10 | GYTFTSYE | 94 | IYPRDGDT | 109 | ARHTPGAF | 124 | QSLVHSNGDTY | 139 | KVS | 38 | SQSTHVPYT | 168 |
| WJL48 | GFTFSRYA | 95 | ISSGGDYI | 110 | TRVLFYYYGSSYVFFDY | 125 | QDISNF | 140 | YTS | 154 | QQGHTLPYT | 169 |

TABLE D

Amino acid sequences of anti-beta-DG VH and VL regions.

| bDG | Chain | | SEQ ID NO |
|---|---|---|---|
| AS19 | VH | QVQLQQSGPELVKPGASVKMSCKASGFTFTDSVISWVKQRTGQGLEWIGEIYPGSGSIYYNEKFKGKATLTADKSSNTAYMQLRSLTSEDSAVYFCAMRRSYWGQGTLVTVSA | 170 |
| | VL | DVLMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVPLTFGAGTKLELK | 171 |
| AS30 S/S | VH | QIQLQQSGPELVKPGASVKMSCEASGFTFTDSVITWVKQRPGQGLEWIGEIYPGSGNFYYNEKFKGKATLTADKSSNTAYMQLRSLTSEDSAVYFCAMRRSSWGQGTLVTVSA | 172 |
| | VL | DVLMTQTPLSLPVSLGDQASISCRSSQTIVHSNSKTYLEWYLQKPGQSPKLLIYKVSNRFSGVPDRFSGSGSGTDFTLKISRVEAEDLGVYYCFQGSHVPLTFGAGTKLELK | 173 |
| B04 | VH | QVQLQQSGGGLVQPGGSLRLSCAASGFTFSSYAMSWVRQAPGKGLEWVSAISGSGGSTYYADSVKGRFTVSRDNSKNTLYLQMNSLRAEDTAVYYCARLGYCSSTSCYLSAFDIWGQGTMVTVSS | 174 |
| | VL | EIVLTQSPSTLSASVGDRVTITCRASQSISSWLAWYQQKPGKAPKLLIYDASSLESGVPSRFSGSGSGTEFTLTISSLQPDDFATYYCQQYNSYPLTFGGGTKVEIK | 175 |
| B06 | VH | QIQLVQSGAEVKKPGKSLKIACKGSGYSFSNYWIGWVRQMPGKGLEWMGIIYPGDSDTRYSPSFHGQVTISADKSISTAYLQWSSLKASDTAMYYCARGVIINGTTSGFDYWGQGTLVIVSS | 176 |
| | VL | ETTLTQSPATLSVSPGERATLSCRASQSVSSNLAWYQQKPGQAPRLLMYGASTRATGIPARFSGSGSGTEFTLTISSLQSEDFAVYYCQHYNNLPLTFGGGTKVDLK | 177 |
| C107 | VH | EVQLQQSGAELVKPGASVKLSCTASGFNIKDTYIHWVKQRPEQGLEWIGRIDPANGNTKYDPKFQGKATITADTSSNIVYVQFSSLTSEDTAVYYCGRSGGNYVGYWGQGTTLTVSS | 178 |
| | VL | DIVMSQSPSSPTVSVGEKVTMTCKSSQSLLDSGNQKNYLAWYQQKPGQSPKLLIYWASTRKSGVPDRFTGSGSGTDFTLSISSVKAEDLAVYYCQQYYTYPWTFGGGTKLEIK | 179 |

TABLE D-continued

Amino acid sequences of anti-beta-DG VH and VL regions.

| bDG | Chain | | SEQ ID NO |
|---|---|---|---|
| D87/D39/D173 | VH | EVQLQQSGAELVKPGASVKLSCTASGFNIKDTY MHWVKERPEQGLEWIGRIDPANGNTKYDPKFQG KATITADTSSNTAYLQLSSLTSEDTAVYYCGRS RGNYFDYWGQGTTLTVSS | 180 |
| | VL | DIVMSQPPSSLAVSVGEKVTMTCKSSQSLLYSSNQ KNYLAWYQQKPGQSPKLLIYWASTRESGVPDRFTG SGSGTDFTLTISSVKAEDLAVYYCQQYYTYPWTFG GGTKLEIK | 181 |
| TDG-2 | VH | QVQLVQSGAEVKKPGTSVKVSCKASGYTFTTYYMH WVRQAPGQGLEWMGLINPSAGNTRNAQKFQGRVTM TRDTSTNTVYMELSSLRSEDTAVYYCARELDIWGQ GTKVTVSS | 182 |
| | VL | AIQMTQSPSSLSASVGDRVTITCRASQDIRNDLGW YQQKPGKAPKLLIYAASSLQSGVPSRFSGNGSGTD FTLTINSLQPEDFATYYCLQDFNFPFTFGPGTTVD IN | 183 |
| TDI-11 | VH | QVQLVESGGGVVQSGRSLRLSCAASGFTFSSYGMH WVRQAPGKGLEWVAVIWYDGSNKYYADSVKDRFTI SRDNSKKTVYLQMNSLRAEDTAVYYCAREGMVRGA LFDYWGQGTLVTVSS | 184 |

TABLE D-continued

Amino acid sequences of anti-beta-DG VH and VL regions.

| bDG | Chain | | SEQ ID NO |
|---|---|---|---|
| | VL | EIVMTQSPATLSLSPGERATLSCRASQSVSSSYLS WYQQKPGQAPRLLIYGASTRATGIPARFSGSGSGP DLTLTISSLQPEDFAVYYCQQDYNLPYTFGQGTKL EIK | 185 |
| TDI-23 | VH | EVQLVQSGAEVKKPGESLKISCKGSGYSFTSYWIG WVRQMPGKGLEWMGVIYPGDSDTRYSPSFQGQVTM SADKSISTAYLQWSSLKASDSAMYYCARQLRDYYG MDVWGQGTTVTVSS | 186 |
| | VL | EIVMTQSPATLSLSPGERATLSCRASQTISSNYFS WYQQKPGQAPRLLIYGASTRATGIPARFSGSGSET DFTLTISSLQPEDFAVYYCQQDYNLPRTFGQGTKV EIK | 187 |
| TDI-38 | VH | EVQLVQSGAEVKKPGESLKISCKGSGYSFTSYWIG WVRQMPGKGLEWMGIIYPGDSDTRYSPSFQGQVTI SADKSISTAYLHWSSLKASDTAMYYCARQLRDYYS MDVWGQGTTVTVSS | 188 |
| | VL | EIVMTQSPATLSLSPGERATLSCRASQSVSSSYLS WYQQKPGQAPRLLIYGASTRATGIAARFSGSGSGT DFTLTISSLQPEDFAVYYCQQDYNLPRTFGQGTKV EIK | 189 |

TABLE D2

Amino acid sequences of humanized VH and VL regions.

| | Chain | | SEQ ID NO |
|---|---|---|---|
| AS30SS_Hu6 | VH | QVQLVQSGAEVVKPGSSVKVSCEASGFTFTDSVITWVRQRPGQGLEWIGEIYP GSGNFYYNEKFQGRVTITADKSTSTAYMELSSLRSEDTAVYFCAMRRSSWGQ GTLVTVSS | 314 |
| | VL | DVVMTQTPLSLSVTPGQPASISCKSSQTIVHSNSKTYLEWYLQKPGQSPQLLIY KVSSRFSGVPDRFSGSGSGTDFTLKISRVEAEDVGVYYCFQGSHVPLTFGQGT KLEIK | 330 |
| AS30SS_Hu9 | VH | QVQLVQSGAEVVKPGSSVKVSCEASGFTFTDSVITWVRQRPGQGLEWIGEIYP GSGNFYYNEKFQGRVTITADKSTSTAYMELSSLRSEDTAVYFCAMRRSSWGQ GTLVTVSS | 346 |
| | VL | DVVMTQTPLSLSVTPGQPASISCRSSQTIVHSNSKTYLEWYLQKPGQSPQLLIY KVSNRFSGVPDRFSGSGSGTDFTLKISRVEAEDVGVYYCFQGSHVPLTFGAGT KLEIK | 362 |
| C3_Hu10 | VH | EVQLVESGGGLVKPGGSLRLSCAASGFTFSSYTMSWVRQAPGKGLEWVASIS SSGSNTYYPDSVKGRFTISRDNAKNNLYLQMNSLRAEDTALYYCARFDYGSSL DSWGQGTLLTVSS | 378 |
| | VL | EIVLTQSPDFLSVTPKEKVTLTCRASQSISNNLHWYQQKSDQSPKLLIKYASQSI SGIPSRFSGSGSGTDFTLTINSVEAEDAATYFCQQSKSWPRTFGGGTKLEIK | 394 |
| C3_Hu11 | VH | EVQLVESGGGLVKPGGSLRLSCAASGFTFSSYTMSWVRQAPGKGLEWVASIS SSGSNTYYPDSVKGRFTISRDNAKNNLYLQMNSLRAEDTALYYCARFDYGSSL DSWGQGTLLTVSS | 410 |
| | VL | EIVLTQSPDFLSVTPKEKVTLTCRASQSIGNNLHWYQQKSDQSPKLLIKYASQSI SGIPSRFSGSGSGTDFTLTINSVEAEDAATYFCQQSKSWPRTFGGGTKLEIK | 426 |
| C21_Hu11 | VH | EVQLVESGGGLVKPGGSLRLSCAASGFTFSSYTMSWVRQAPGKGLEWVASIS SSGSNTYYPDSVKGRFTISRDNAKNNLYLQMNSLRAEDTALYYCARFDYGSSL DSWGQGTLLTVSS | 442 |
| | VL | EIVLTQSPDFLSVTPKEKVTLSCRASQSISNYLHWYQQKSDQSPKLLIKYASQSI SGIPSRFSGSGSGTDFTLSINSVEAEDAATYFCQQSKSWPRTFGGGTKLEIK | 458 |
| C21_Hu21 | VH | EVQLVESGGGLVQPGGSLRLSCAASGFTFSSYTMSWVRQAPGKGLEWVATIS SSGDNTYYPDSVKGRFTISRDNSKNTLYLQMSSLRAEDTALYYCARFDYGSSL DSWGQGTLVTVSS | 474 |
| | VL | EIVLTQSPDFLSVTPGEKVTLTCRASQSISNYLHWYQQKSDQSPKLLIKYASQSI SGVPSRFSGSGSGTDFTLTISSVEAEDFATYFCQQSKSWPRTFGGGTKLEIK | 490 |

TABLE E

Amino acid sequences of anti-LG-5 VH and VL regions.

| LG-5 | Chain | Amino Acid Sequence | SEQ ID NO |
|---|---|---|---|
| AN01 | VH | EVQLQQSGPELVKPGASVKMSCKASGYTFTSYNIHWVKQKPGQGLEWIGYINPYN DGTKYSEKFKGKATLTSDRSSSTAYMEVSSLTSEDSAVYYCAIYGNSYWGQGSTLTVS S | 190 |
|  | VL | DIVMTQAAPSIPVTPGESVSISCRSSKSLLHSNGNTYLYWFLQRPGQSPQRLIYYMSN LDSGVPDRFSGRGSGTDFTLRISRVEAEDVGVYYCMQGLEYPYTFGGGTKLEIK | 191 |
| C3 | VH | DVMLVESGGDLVKPGGSLKLSCAASGFTFSSYTMSWVRQTPEKRLEWVASISSGGG NTYYPDSVKGRFTISRDNAKNNLYLQMSSLRSEDTALYYCARFDYGSSLDSWGQGT TLTVSS | 192 |
|  | VL | DIVLTQSPATLSVTPGDSVSLSCRASQSISNNLHWYQQKSHESPRLLIKYASQSISGIP SRFSGSGSGTDFTLSINSVETEDFGMYFCQQSKNWPRTFGGGTKLEIK | 193 |
| C21 | VH | EVMLVESGGGLVKPGGSLKLSCAASGFTFSSYTMSWVRQTPEKRLEWVATISSGGD NTYYPDSVKGRFTISRDNAKNNLYLQMSSLRSEDTALYYCARFDYGSSLDCWGQGT TLTVSS | 194 |
|  | VL | DIVLTQSPATLSVTPGDSVSLSCRASQSISNYLHWYQQKSHESPRLLIKYASQSISGIPS RFSGSGSGTDFTLSINSVETEDFGMYFCQQSKSWPRTFGGGTELEIK | 195 |
| TLF39 | VH | EVQLVQSGAEVKKPGESLKISCKGSGYSFTSYWIGWVRQMPGKGLEWMGIIYPGD SDTRYSPSFQGQVTISADKSISTAYLQWSSLKASDTAMYYCARRGYRSSWYFDYWG QGTLVTVSS | 196 |
|  | VL | AIQMTQSPSSLSASVGDRVTITCRASQGIRNDLGWYQQKPGKAPKLLIYAASSLQSG VPSRFSGSGSGTDFTFTISSLQPEDFATYYCLQDYNYPLTFGGGTKVEIK | 197 |
| TLF86 | VH | EVQLVESGGGVVRPGGSLRLSCAASGFTFDDYGMSWVRQAPGKGLEWVSGINW NGGSTGYADSVKGRFTISRDNAKNSLYLQMNSLRAEDTALYHCAREGGELLMDYW GQGTLVTVSS | 198 |
|  | VL | EIVLTQSPATLSLSPGERATLSCRASQSVSTYLAWYQQKPGQAPRLLIYDASNRATGI PPRFSGSGSGTDFTLTISSLEPEDFAVYYCQQRSNWPPTFGGGTTVEIK | 199 |

TABLE F

Amino acid sequences of anti-LG-4/5 VH and VL regions.

| LG-4/5 | Chain | Amino Acid Sequence | SEQ ID NO |
|---|---|---|---|
| CL-40968 | VH | EVQLLESGGGLVQPGGSLRLSCAASGFTFSHYSMVWVRQAPGKGLEWVSYIYPSG GTSYADSVKGRFTISRDNSKNTLYLQMNSLRAEDTAVYYCARHWRGYSSSWYHPAY FDYWGQGTLVTVSS | 200 |
|  | VL | DIQMTQSPATLSLSPGERATLSCRASQSVSSYLAWYQQKPGQAPRLLIYDASNRATG IPARFSGSGSGTDFTLTISSLEPEDFAVYYCQQRSNWPLTFGGGTKVEIK | 201 |
| CL-40992 | VH | EVQLLESGGGLVQPGGSLRLSCAASGFTFSWYPMMWVRQAPGKGLEWVSSIYPS GGTTTYADSVKGRFTISRDNSKNTLYLQMNSLRAEDTAVYYCARSYYYDSSGYYSHD AFDIWGQGTMVTVSS | 202 |
|  | VL | DIQMTQSPSSLSASVGDRVAITCRASQSIDTYLNWYQQKPGKAPKLLIYAASKLEDG VPSRFSGSGTGTDFTLTIRSLQPEDFASYFCQQSYSSPGITFGPGTKVEIK | 203 |
| CL-41136 | VH | EVQLLESGGGLVQPGGSLRLSCAASGFTFSDYEMHWVRQAPGKGLEWVSSIWPSG GLTKYADPVKGRFTISRDNSKNTLYLQMNSLRAEDTAVYYCARDSYYYDSSGALGY WGQGTLVTVSS | 204 |
|  | VL | DIQMTQSPSTLSASVGDRVTITCRASQSVSNWLAWYQQKPGKAPKLLIYKASSLESG VPSRFSGSGSGTEFTLTISSLQPDDFATYYCLQYVSYPLTFGGGTKVDIK | 205 |
| CL-41400 | VH | EVQLLESGGGLVQPGGSLRLSCAASGFTFSYYDMYWVRQAPGKGLEWVSRIYSSGG HTWYADSVKGRFTISRDNSKNTLYLQMNSLRAEDTAVYYCARPGYSSGWYDGTYF DYWGQGTLVTVSS | 206 |
|  | VL | DIQMTQSPSTLSASVGDRVTITCRASQSIDTWLAWYRQKPGKAPNVVIHSASTLQS GVPARFSGSGFGTEWTLTITNLQPDDFATYYCQQYKTYPFTFGQGTKLEIK | 207 |
| CL-41500 | VH | EVQLLESGGGLVQPGGSLRLSCAASGFTFSHYQMEWVRQAPGKGLEWVSSISPSG GFTSYADSVKGRFTISRDNSKNTLYLQMNSLRAEDTAVYYCTREPGRLWAFDIWGQ GTMVTVSS | 208 |
|  | VL | DIQMTQSPSFVSASVGDRVTITCRASQDIRNWLAWYQQESGKAPRLLISAASSRHS GVSSRFSGSGSGTDFTLTITSLQPEDSATYFCQQADSPRTFGQGTKVEIK | 209 |

TABLE F-continued

Amino acid sequences of anti-LG-4/5 VH and VL regions.

| LG-4/5 | Chain | Amino Acid Sequence | SEQ ID NO |
|---|---|---|---|
| TLG3/ TLG4 | VH | QVQLVQSGAEVKKPGASVKVSCKASGYTFTGYYMHWVRQAPGQGLEWMGWIN PNSGGTNYAQKFQGRVTMTRDTSINTAYMELSRLRSDDTAVYYCAVFGSGSSWGQ GTLVTVSS | 210 |
|  | VL | DIQMTQSPSSLSASVGDRVTITCRASQGISNSLAWFQQKPGKAPKSLIYAASSLQSG VPSKFSGSGSGTDFTLTISSLQPEDFATYYCQQYKSYPYTFGQGTKLEIK | 211 |
| TLG26 | VH | QVQLVQSGAEVKKPGASVKVSCKASGNTFTGYYIHWVRQAPGQGLEWMGWIKPS TGDTNYAQNFLDRVTMTRDTSISTAYMELSRLRSDDTAVYYCAVFGSGSSWGQGT LVTVSS | 212 |
|  | VL | DIHMTQSPSSLSAFVGDRVTITCRASQGISNYLAWFQQKPGKAPKSLIYAASSLQSG VPSKFSGSGSGTDFTLTINNLQPEDFATYYCQQYKTYPYTFGQGTKLEIK | 213 |
| TLI-3 | VH | QVQLVESGGGVVQPGRSLRLSCAASGFTFSSYGMHWVRQAPGKGLEWVAVIWYD GSNKYYADSVKGRFTISRDNSKNTLYLQMNSLRAEDAAVYYCAREGGWYGGDYYY GMDVWGQGTTVTVSS | 214 |
|  | VL | AIQLTQSPSSLSASVGDRVTITCRASQGISSALAWYQQKPGKAPKLLIYDASSLESGVP SRFSGSGSGTDFTLTISSLQPEDFATYYCHQFNNYPFTFGPGTKVDIK | 215 |
| TLI-7 | VH | EVQLLESGGGLVQPGGSLRLSCVASGFTFSSYAMSWVRQAPGKGLEWVSGISRG GSPNYADSVKGRFTISRDNSKNTLYLQMNSLRAEDTAVYYCAKDGDGSGPPYYFDY WGQGTLVTVSS | 216 |
|  | VL | DIQMTQSPSSLSASVGDRVTITCRASQGISSWLAWYQQKPEKAPKSLIYAASSLQSG VPSRFSGSGSGTDFTLTISSLQPEDFATYYCQQYNSYPYTFGQGTKLEIK | 217 |
| TTLK71-4-6 | VH | QVQLMESGGGVVQPGRSLRLSCAASGFTFSGYGMHWVRQAPGKGLEWVAVIWS DGSNRYYTDSVKGRFTISRDNSKNTLSLQMNSLRAEDTAVYYCARDRGITMVRGLII KYYYYYGLDVWGQGTSVTVSS | 218 |
|  | VL | EIVLTQSPATLSLSPGERATLSCRASQSVSSYLAWYQQKPGQAPRLLIYDASNRATGI PARFSGSGSGTDFTLTISSLEPEDFAVYYCQQRSNWWTFGQGTKVEIK | 219 |
| TTLK123-3 | VH | QVQLVESGGGVVQPGRSLRLSCAASGFTFSSFGMHWVRQAPGKGLEWVAVIYYD GSNKYYADSVKGRFTISRDNSKNTLYLQMNSLRAEDTAVYYCARDDNWNDGDFDY WGQGTLVTVSS | 220 |
|  | VL | DIQLTQSPSFLSASVGDRVTITCRASQGISSYLAWYQQKPGKAPKLLIYAASTLQSGV PSRFSGSGSGTEFTLTISSLQPEDFATYYCQQLNSYPRTFGQGTKVEIK | 221 |
| TTLK145-6-3 | VH | EVQLLESGGGLVQPGESLRLSCAASGFTFNRFVMSWVRQAPGKGLEWVSTISGSG GSTYYADSVKGRFTISRDNSKNTLYLQMNSLRAEDTAVYYCAKDFTYYYGSGNYYN WFDPRGQGTLVTVSS | 222 |
|  | VL | DIQMTQSPSTLSTSVGDRVTITCRASQSISSWLAWYQQKPGKAPKLLIYKASSLESGV PSRFSGSGSGTEFTLTISSLQPDDFATYYCQQYNSYSRTFGQGTKVEIK | 223 |
| TTLK170-2 | VH | QVQLQQWGAGLLKPSETLSLTCAVYGGSFSGYYWSWIRQPPGKGLEWIGEINHSG GTNYNPSLKSRVTISVDTSKNHFSLKLSSVTAADTAVYYCARTSDYDYYYYGMDVW GQGTTVTVSS | 224 |
|  | VL | QPVLTQPTSLSASPGASARLTCTLRSGINLGRYRIFWYQQKPESPPRYLLSYYSDSSKH QGSGVPSRFSGSKDASSNAGILVISGLQSEDEADYYCMIWHRSALFIFGSGTKVTVL | 225 |
| WJL10 | VH | QVQLQQSGPELVKPGASVKLSCKASGYTFTSYEINWLKQRPGQGLEWIGLIYPRDG DTKYNEKFKGKATLTADTSSSTAYMELHSLTSEDSAVYFCARHTPGAFWGQGTLVT VSA | 226 |
|  | VL | DVVMTQTPLSLPVSLGDQASISCRSSQSLVHSNGDTYLHWYLQKPGQSPKLLIYKVS NRFSGVPDRFSGSGSGTDFTLKISRVEAEDLEIYFCSQSTHVPYTFGGGTKLEIK | 227 |
| WJL48 | VH | DVKLVESGEGLVKPGGSLKLSCAASGFTFSRYAMSWVRQTPEKRLEWVAYISSGGD YIHYGETVKGRFTISRDNARNTLYLQMSSLKSEDTAMYYCTRVLFYYYGSSYVFFDY WGQGTTLTVSS | 228 |
|  | VL | DIQMTQTTSSLSVSLGDRVTISCRASQDISNFLNWYQQKPDGTVNLLIYYTSKLHSGV PSRFSGGGSGRDYSLTINNLEQEDIASYFCQQGHTLPYTFGGGTKLEIK | 229 |

TABLE G

Nucleic acid sequences of anti-beta-DG VH and VL regions.

| bDG | Chain | Nucleotide Sequence | SEQ ID NO |
|---|---|---|---|
| AS19 | VH | CAGGTGCAGCTGCAGCAGAGCGGTCCCGAGCTGGTGAAACCTGGCGCATCAGT CAAAATGAGCTGCAAGGCCTCCGGCTTCACTTTTACCGACTCAGTGATCAGCTG | 230 |

TABLE G-continued

Nucleic acid sequences of anti-beta-DG VH and VL regions.

| bDG | Chain | Nucleotide Sequence | SEQ ID NO |
|---|---|---|---|
| | | GGTCAAGCAGCGAACCGGTCAGGGACTGGAGTGGATCGGAGAAATCTACCCTG GATCTGGGAGTATCTACTATAACGAGAAGTTCAAAGGGAAGGCAACACTGACT GCCGACAAAAGCTCCAATACAGCCTATATGCAGCTGCGATCCCTGACTTCTGAA GATAGCGCCGTGTACTTTTGCGCAATGCGGAGGTCCTATTGGGGTCAGGGCACC CTGGTGACAGTCTCTGCT | |
| | VL | GACGTGCTGATGACCCAGACACCCCTGAGTCTGCCTGTCTCACTGGGAGATCAG GCTTCTATCAGTTGCCGAAGCTCCCAGAGCATCGTGCATTCCAACGGAAATACCT ACCTGGAGTGGTATCTGCAGAAGCCAGGGCAGTCCCCCAAGCTGCTGATCTACA AAGTGTCTAACCGGTTCAGTGGCGTCCCAGACAGGTTTTCAGGTAGCGGCTCCG GAACTGATTTCACCCTGAAAATTTCCCGGTGGAGGCAGAAGACCTGGGTGTCT ACTATTGCTTCCAGGGCAGCCATGTGCCCCTGACTTTTGGGGCCGGTACCAAGCT GGAGCTGAAA | 231 |
| AS30 S/S | VH | CAGATCCAGCTGCAGCAGTCCGGTCCCGAGCTGGTGAAACCTGGCGCATCTGTC AAGATGAGTTGCAAGCCTCAGGCTTCACTTTTACCGACTCCGTGATTACCTGGG TCAAACAGCGCCCAGGCCAGGGACTGGAGTGGATCGGAGAAATCTACCCCGGA TCTGGGAACTTCTACTATAATGAGAAGTTTAAAGGGAAGGCAACACTGACTGCC GACAAGAGCTCCAACACCGCCTACATGCAGCTGCGATCACTGACAAGCGAAGAT AGCGCCGTGTACTTCTGCGCAATGCGGAGGTCTAGTTGGGGTCAGGGCACCCTG GTGACAGTCTCTGCT | 232 |
| | VL | GACGTGCTGATGACCCAGACACCCCTGTCTCTGCCTGTCAGTCTGGGAGATCAG GCTTCTATCAGTTGCCGAAGCTCCCAGACCATCGTGCATTCAAACAGCAAGACAT ACCTGGAGTGGTATCTGCAGAAACCAGGCCAGTCCCCCAAGCTGCTGATCTACA AAGTGTCAAATCGGTTCTCTGGAGTCCCAGACAGGTTTTCCGGTTCTGGCAGTG GAACTGATTTCACCCTGAAGATTTCTCGGGTGGAGGCAGAAGACCTGGGTGTCT ACTATTGCTTCCAGGGGAGCCATGTGCCCCTGACTTTTGGGGCCGGTACCAAGC TGGAGCTGAAA | 233 |
| B04 | VH | CAGGTGCAGCTGCAGCAGTCGGGGGAGGCTTGGTACAGCCTGGGGGGTCCCT GAGACTCTCCTGTGCAGCCTCTGGATTCACCTTTAGCAGCTATGCCATGAGCTGG GTCCGCCAGGCTCCAGGGAAGGGGCTGGAGTGGGTCTCAGCTATTAGTGGTAG TGGTGGTAGCACATACTACGCAGACTCCGTGAAGGGCCGGTTCACCGTCTCCAG AGACAATTCCAAGAACACGCTGTATCTGCAAATGAACAGCCTGAGAGCCGAGG ACACGGCCGTATATTACTGTGCGAGGCTAGGATATTGTAGTAGTACCAGCTGCT ATTTGTCTGCTTTTGATATCTGGGGCCAAGGGACAATGGTCACCGTCTCTTCA | 234 |
| | VL | GAAATTGTGTTGACACAGTCTCCTTCCACCCTGTCTGCATCTGTAGGAGACAGAG TCACCATCACTTGCCGGGCCAGTCAGAGTATTAGTAGCTGGTTGGCCTGGTATC AGCAGAAACCAGGGAAAGCCCCTAAGCTCCTGATCTATGATGCCTCCAGTTTGG AAAGTGGGGTCCCATCAAGGTTCAGCGGCAGTGGATCTGGGACAGAATTCACT CTCACCATCAGCAGCCTGCAGCCTGATGATTTTGCAACTTATTACTGCCAACAGT ATAATAGTTACCCGCTCACTTTCGGCGGAGGGACCAAGGTGGAGATCAAA | 235 |
| B06 | VH | CAGATCCAGCTGGTGCAGTCTGGCGCCGAAGTGAAGAAGCCTGGCAAGAGCCT GAAGATCGCCTGCAAGGGCTCCGGCTACACAGCTTCAGCAACTACTGGATCGGCTG GGTGCGCCAGATGCCTGGAAAAGGACTGGAATGGATGGGCATTATCTACCCTG GCGACAGCGACACCCGGTACAGCCCCAGCTTCCACGGCCAGGTGACAATCAGC GCCGACAAGAGCATCTCCACCGCCTACCTGCAGTGGTCCTCCCTGAAGGCCAGC GACACCGCCATGTACTATTGTGCCAGAGGCGTGATCATCAACGGCACCACCAGC GGCTTCGACTATTGGGGACAGGGCACCCTGGTGATCGTGTCCTCC | 236 |
| | VL | GAGACAACCCTGACCCAGAGCCCCGCCACCCTGTCCGTGTCTCCAGGCGAGAGA GCCACCCTGAGCTGCAGAGCCAGCCAGAGCGTGTCCAGCAACCTGGCCTGGTAT CAGCAGAAGCCCGGCCAGGCCCCCAGACTGCTGATGTACGGCGCCAGCACCAG AGCCACCGGCATCCCTGCCAGATTCAGCGGCAGCGGCTCCGGCACCGAGTTCAC CCTGACCATCAGCAGCCTGCAGAGCGAGGACTTCGCCGTGTACTACTGCCAGCA CTACAACAACCTGCCCCTGACCTTCGGCGGAGGCACCAAGGTGGACCTGAAG | 237 |
| C107 | VH | GAAGTCCAACTCCAACAGTCTGGGGCAGAACTTGTCAAACCTGGGGCTTCAGTA AAATTGAGTTGCACAGCAAGTGGCTTTAACATCAAAGACACATATATTCATTGG GTGAAGCAACGACCAGAACAAGGCTTGGAGTGGATCGGTAGGATTGACCCTGC AAACGGGAATACAAAATATGACCCTAAATTCCAGGGAAAGGCTACAATAACAGC AGACACCAGCAGTAACATTGTCTATGTGCAATTTAGCTCTCTTACCTCTGAGGAC ACTGCTGTCTATTATTGCGGACGTAGTGGCGGGAATTATGTGGGTTATTGGGGC CAGGGGACAACACTCACCGTATCCTCT | 238 |
| | VL | GATATAGTAATGTCCCAGTCTCCTTCATCACCTACTGTGTCAGTTGGAGAAAAAG TCACCATGACCTGTAAGTCCTCACAGTCCCTTGGACAGCGGGAATCAGAAAA ATTATCTCGCATGGTATCAGCAAAAGCCAGGGCAGTCCCCTAAGCTGTTGATCTA TTGGGCAAGTACAAGGAAAAGTGGCGTGCCTGATAGATTCACAGGGAGCGGCA GCGGGACAGACTTCACTTTGAGCATCTCTTCAGTAAAAGCCGAAGACCTGGCAG TGTACTACTGTCAGCAATATTATACCTACCCTTGGACTTTTGGTGGCGGGACCAA ACTGGAAATAAAA | 239 |
| D87/D39/ D173 | VH | GAGGTTCAACTTCAGCAATCAGGGGCTGAGCTTGTAAAACCTGGAGCCTCTGTA AAACTCTCTTGTACCGCCTCCGGGTTCAACATAAAAGATACATATATGCACTGGG TAAAGGAGCGGCCCGAACAGGGACTCGAATGGATCGGGAGGATTGACCCAGCT | 240 |

TABLE G-continued

Nucleic acid sequences of anti-beta-DG VH and VL regions.

| bDG | Chain | Nucleotide Sequence | SEQ ID NO |
|---|---|---|---|
| | | AACGGAAATACCAAGTATGATCCAAAATTTCAGGGGAAAGCTACAATAACCGCC GATACTTCTAGTAATACAGCATATCTTCAGCTCAGCAGCTTGACAAGCGAAGATA CCGCAGTTTACTACTGCGGTCGATCCCGAGGGAATTATTTTGACTACTGGGGCC AGGGTACTACTCTCACAGTAAGTAGC | |
| | VL | GACATAGTAATGAGCCAGCCACCTAGTTCACTTGCCGTAAGTGTGGGTGAAAAG GTGACTATGACCTGTAAAAGTAGTCAGAGCCTCCTTTACTCATCAAATCAGAAGA ATTACTTGGCCTGGTATCAACAGAAACCTGGACAAAGCCCCAAACTCCTCATATA CTGGGCCTCTACCCGAGAGTCCGGCGTACCAGATCGGTTTACCGGTTCTGGATC AGGTACAGACTTTACACTTACCATCTCTTCAGTGAAGGCTGAGGACTTGGCCGT GTATTATTGTCAACAATATTATACATATCCTTGGACTTTTGGCGGAGGGACAAAG CTCGAAATAAAG | 241 |
| TDG-2 | VH | CAGGTGCAGCTGGTGCAGTCTGGCGCCGAAGTGAAGAAACCCGGCACCTCCGT GAAGGTGTCCTGCAAGGCTTCCGGCTACACCTTTACCACCTACTACATGCACTGG GTGCGACAGGCCCCTGGACAGGGCCTGGAATGGATGGGCCTGATCAACCCTTC CGCCGGCAACACCAGAAACGCCCAGAAATTCCAGGGCAGAGTGACCATGACCC GGGACACCTCCACCAACACCGTGTACATGGAACTGTCCTCCCTGCGGAGCGAGG ACACCGCCGTGTACTACTGTGCCAGAGAGCTGGACATCTGGGGCCAGGGCACC AAAGTGACCGTGTCCTCT | 242 |
| | VL | GCCATCCAGATGACCCAGTCCCCCAGCTCCCTGTCTGCCTCTGTGGGCGACAGA GTGACCATCACCTGTCGGGCCTCTCAGGACATCCGGAACGACCTGGGCTGGTAT CAGCAGAAGCCTGGCAAGGCCCCCAAGCTGCTGATCTACGCCGCTTCCAGTCTC CAGTCCGGCGTGCCCTCCAGATTCTCCGGCAATGGCTCTGGCACCGACTTCACCC TGACCATCAACTCCCTCCAGCCCGAGGACTTCGCCACCTACTACTGTCTCCAAGA CTTCAACTTCCCCTTCACCTTCGGCCCTGGCACCACCGTGGACATCAAC | 243 |
| TDI-11 | VH | CAGGTGCAGCTGGTGGAGTCTGGGGGAGGCGTGGTCCAGTCTGGGAGGTCCCT GAGACTCTCCTGTGCAGCGTCTGGATTCACCTTCAGTAGTTATGGCATGCACTGG GTCCGCCAGGCTCCAGGCAAGGGGCTGGAGTGGGTGGCAGTTATATGGTATGA TGGAAGTAATAAATACTATGCAGACTCCGTGAAGGACCGATTCACCATCTCCAG AGACAATTCCAAGAAAACGGTGTATCTGCAAATGAACAGTCTGAGAGCCGAGG ACACGGCTGTTTATTACTGTGCGAGAGAAGGGATGGTTCGGGGAGCCCTCTTTG ACTACTGGGGTCAGGGAACCCTGGTCACCGTCTCCTCA | 244 |
| | VL | GAAATTGTAATGACACAGTCTCCAGCCACCCTGTCTTTGTCTCCAGGGGAAAGA GCCACCCTCTCCTGCAGGGCCAGTCAGAGTGTTAGCAGCAGCTACTTATCCTGGT ACCAACAGAAACCTGGGCAGGCTCCCAGGCTCCTCATCTATGGTGCATCCACCA GGGCCACTGGCATCCCAGCCAGGTTCAGTGGCAGTGGGTCTGGGCCAGACCTC ACTCTCACCATCAGCAGCCTGCAGCCTGAAGATTTTGCAGTTTATTACTGTCAGC AGGATTATAACTTACCGTACACTTTTGGCCAGGGGACCAAGCTGGAGATCAAA | 245 |
| TDI-23 | VH | GAGGTGCAGCTGGTGCAGTCTGGAGCAGAGGTGAAAAAGCCCGGGGAGTCTCT GAAGATCTCCTGTAAGGGTTCTGGATACAGTTTTACTAGTTACTGGATCGGCTG GGTGCGCCAGATGCCCGGGAAAGGCCTGGAGTGGATGGGAGTCATCTATCCTG GTGACTCTGATACCAGATATAGCCCGTCCTTCCAAGGCCAGGTCACCATGTCAGC CGACAAGTCCATCAGTACCGCCTACCTGCAGTGGAGCAGCCTGAAGGCCTCGGA CAGCGCCATGTATTACTGTGCGAGACAGCTACGAGACTACTACGGTATGGACGT CTGGGGCCAAGGGACCACGGTCACCGTCTCCTCA | 246 |
| | VL | GAAATTGTAATGACACAGTCTCCAGCCACCCTGTCTTTGTCTCCAGGGGAAAGA GCCACCCTCTCCTGCAGGGCCAGTCAGACTATCAGCAGCAACTACTTTTCCTGGT ACCAGCAGAAACCTGGGCAGGCTCCCAGGCTCCTCATCTATGGTGCATCCACCA GGGCCACTGGCATTCCAGCCAGGTTCAGTGGCAGTGGGTCTGAGACAGACTTCA CTCTCACCATCAGCAGCCTGCAGCCTGAAGATTTTGCAGTTTATTACTGTCAGCA GGATTATAACTTACCTCGGACGTTCGGCCAAGGGACCAAGGTGGAAATCAAA | 247 |
| TDI-38 | VH | GAGGTGCAGCTGGTGCAGTCTGGAGCAGAGGTGAAAAAGCCCGGGGAGTCTCT GAAGATCTCCTGTAAGGGTTCTGGATACAGTTTTACCAGCTACTGGATCGGCTG GGTGCGCCAGATGCCCGGGAAAGGCCTGGAGTGGATGGGGATCATCTATCCTG GTGACTCTGATACCAGATACAGCCCGTCCTTCCAAGGCCAGGTCACCATCTCAGC CGACAAGTCCATCAGCACCGCCTACCTGCACTGGAGCAGCCTGAAGGCCTCGGA CACCGCCATGTATTACTGTGCGAGACAGCTACGAGACTACTACAGTATGGACGT CTGGGGCCAAGGGACCACGGTCACCGTCTCCTCA | 248 |
| | VL | GAAATTGTAATGACACAGTCTCCAGCCACCCTGTCTTTGTCTCCAGGGGAAAGA GCCACCCTCTCCTGCAGGGCCAGTCAGAGTGTTAGCAGCAGCTACTTATCCTGGT ACCAGCAGAAACCTGGGCAGGCTCCCAGGCTCCTCATCTATGGTGCATCCACCA GGGCCACTGGCATTCAGCCAGGTTCAGTGGCAGTGGGTCTGGACAGACTTC ACTCTCACCATCAGCAGCCTGCAGCCTGAAGATTTTGCAGTTTATTACTGTCAGC AGGATTATAACTTACCTCGGACGTTCGGCCAAGGGACCAAGGTGGAAATCAAA | 249 |

TABLE G2

Nucleic acid sequences of humanized VH and VL regions.

| Domain | | Nucleotide Sequence | SEQ ID NO |
|---|---|---|---|
| AS30SS_Hu6 | VH | CAAGTACAACTGGTTCAATCAGGCGCAGAAGTCGTAAAACCTGGTTCCAGCGTA AAAGTCAGTTGTGAGGCTAGTGGATTCACCTTCACCGATAGCGTTATTACATGG GTTCGTCAGCGCCCAGGTCAAGGGCTCGAGTGGATTGGGGAAATTTACCCAGG AAGTGGAAATTTCTACTACAATGAAAAATTTCAAGGCCGGGTGACCATCACTGC TGATAAAAGCACTTCAACAGCCTATATGGAATTGTCCAGCTTGCGCTCCGAAGAC ACTGCCGTTTATTTCTGCGCCATGCGTAGGTCTTCCTGGGGACAGGGTACACTTG TAACTGTCAGCTCT | 306 |
| | VL | GACGTCGTAATGACTCAAACACCCCTCTCTCTTTCTGTTACCCCCGGACAGCCTG CTTCAATCAGTTGTAAATCATCCCAAACCATAGTTCATTCTAATAGTAAACTTAC CTCGAATGGTATCTCCAAAAACCTGGTCAGTCACCACAGCTCCTTATTTACAAGG TTAGTTCCAGATTCTCTGGCGTCCCTGACCGCTTCTCTGGCTCCGGTTCAGGCAC CGACTTTACTCTGAAAATCTCACGGGTTGAAGCTGAAGATGTTGGAGTGTACTA CTGCTTCCAGGGTTCTCACGTCCCATTGACCTTTGGACAGGGAACTAAGCTCGAA ATAAAA | 322 |
| AS30SS_Hu9 | VH | CAAGTACAACTGGTTCAATCAGGCGCAGAAGTCGTAAAACCTGGTTCCAGCGTA AAAGTCAGTTGTGAGGCTAGTGGATTCACCTTCACCGATAGCGTTATTACATGG GTTCGTCAGCGCCCAGGTCAAGGGCTCGAGTGGATTGGGGAAATTTACCCAGG AAGTGGAAATTTCTACTACAATGAAAAATTTCAAGGCCGGGTGACCATCACTGC TGATAAAAGCACTTCAACAGCCTATATGGAATTGTCCAGCTTGCGCTCCGAAGAC ACTGCCGTTTATTTCTGCGCCATGCGTAGGTCTTCCTGGGGACAGGGTACACTTG TAACTGTCAGCTCT | 338 |
| | VL | GATGTGGTGATGACTCAGACACCCCTGAGTCTCAGCGTAACACCTGGTCAACCC GCCTCTATTAGTTGTCGAAGCTCTCAAACAATCGTACATAGTAATAGTAAAACCT ATCTCGAATGGTATCTTCAGAAACCAGGGCAGTCTCCTCAACTCCTTATATACAA AGTATCCAACAGGTTTTCCGGTGTACCCGATAGGTTTTCCGGTTCCGGCTCCGGA ACTGACTTTACCCTCAAATAAGTCGAGTGGAGGCTGAGGATGTTGGCGTTTAT TATTGCTTTCAGGGGTCACACGTACCTCTTACCTTCGGCGCAGGCACAAAATTGG AGATTAAA | 354 |
| C3_Hu10 | VH | GAAGTTCAACTGGTCGAGTCTGGAGGAGGCCTCGTGAAGCCGGGCGGTAGTTT GCGCCTCTCTTGTGCCGCCTCAGGGTTTACGTTCTCTAGTTATACTATGAGTTGG GTGCGGCAGGCACCGGGAAAGGGCTGGAATGGGTGGCCTCAATCTCTAGTAG CGGCAGCAATACTTATTATCCTGATAGTGTGAAGGGGAGGTTTACCATCTCACG GGATAACGCTAAGAACAACCTGTATCTTCAAATGAATAGCCTCCGAGCAGAGGA TACAGCACTTTACTACTGCGCTCGCTTTGACTATGGCAGCAGTCTTGATAGTTGG GGGCAGGGCACCTTGCTTACGGTTTCATCC | 370 |
| | VL | GAGATCGTTCTTACCCAATCCCCGGATTTCCTTTCTGTGACCCCCAAAGAAAAG TCACACTCACCTGCCGAGCAAGCCAGTCTATTAGTAACAATTTGCACTGGTATCA GCAGAAGAGTGACCAATCTCCCAAACTCCTTATTAAGTACGCCTCTCAGTCAATA TCCGGCATACCTAGCCGCTTTTCCGGTTCTGGTAGTGGCACCGACTTTACTCTCA CTATCAATTCAGTGGAGGCTGAGGATGCCGCCACGTATTTTTGTCAGCAATCAA AGAGTTGGCCCCGGACATTTGGAGGGGGAACTAAGCTGGAGATTAAG | 386 |
| C3_Hu11 | VH | GAAGTTCAACTGGTCGAGTCTGGAGGAGGCCTCGTGAAGCCGGGCGGTAGTTT GCGCCTCTCTTGTGCCGCCTCAGGGTTTACGTTCTCTAGTTATACTATGAGTTGG GTGCGGCAGGCACCGGGAAAGGGCTGGAATGGGTGGCCTCAATCTCTAGTAG CGGCAGCAATACTTATTATCCTGATAGTGTGAAGGGGAGGTTTACCATCTCACG GGATAACGCTAAGAACAACCTGTATCTTCAAATGAATAGCCTCCGAGCAGAGGA TACAGCACTTTACTACTGCGCTCGCTTTGACTATGGCAGCAGTCTTGATAGTTGG GGGCAGGGCACCTTGCTTACGGTTTCATCC | 402 |
| | VL | GAAATTGTGCTTACCCAGTCCCCAGACTTCCTGTCCGTGACCCCTAAAGAGAAG GTGACACTGACTTGCAGGGCCTCACAATCCATTGGCAATAACCTTCACTGGTATC AGCAGAAGTCCGACCAGTCTCCGAAACTCCTCATCAAGTATGCCAGCCAGTCAA TTAGCGGAATACCGTCTCGGTTTAGCGGATCTGGGTCTGGTACTGACTTCACGCT GACGATCAATAGCGTGGAAGCGGAGGACGCCGCCACCTATTTCTGCCAGCAATC TAAGTCCTGGCCGAGAACGTTCGGAGGCGGTACTAAACTTGAGATCAAG | 418 |
| C21_Hu11 | VH | GAGGTACAGCTCGTCGAAAGTGGCGGCGGTCTTGTCAAGCCGGGAGGAAGTTT GCGCCTGTCCTGTGCAGCATCCGGATTCACGTTTTCTTCTTATACGATGAGTTGG GTCCGGCAGGCACCGGGGAAAGGATTGGAATGGGTTGCGTCTATTAGTAGCTC TGGATCTAACACATACTACCCAGACTCAGTTAAAGGTCGCTTCACGATAAGTCGG GACAACGCTAAAAATAACCTGTATTTGCAAATGAACAGCTTGCGAGCTGAGGAC ACCGCCCTCTACTACTGTGCCCGATTTGATTATGGATCAAGTTTGGATTCATGGG GCCAAGGGACCCTGCTCACAGTAAGCTCT | 434 |
| | VL | GAAATCGTTCTTACTCAGTCCCCGGATTTTTTGAGTGTAACGCCTAAAGAGAAGG TGACCCTGTCCTGCCGCGCTTCCAATCTATATCAAACTATCTTCATTGGTACCAG CAAAAAAGCGACCAGTCCCCGAAACTGCTCATCAAATACGCTAGCCAATCAATA AGCGGCATCCCTAGCAGGTTTTCCGGTAGCGGTAGTGGCACAGACTTCACATTG AGCATAAACAGCGTGGAAGCCGAGGATGCAGCAACATACTTTTGCCAACAGAG CAAGTCCTGGCCGAGGACGTTCGGTGGGGCACCAAATTGGAAATAAAG | 450 |
| C21_Hu21 | VH | GAGGTCCAACTTGTTGAATCCGGTGGAGGGCTGGTGCAGCCTGGTGGATCCCTC CGCCTTTCCTGTGCAGCATCAGGTTTTACTTTTTCCTCATACACCATGTCTTGGGT | 466 |

TABLE G2-continued

Nucleic acid sequences of humanized VH and VL regions.

| Domain | Nucleotide Sequence | SEQ ID NO |
|---|---|---|
|  | TCGCCAGGCTCCAGGGAAAGGATTGGAATGGGTGGCAACTATCAGTAGTAGCG GGGACAATACATACTATCCCGATTCCGTGAAAGGGAGATTTACGATTTCACGCG ACAACAGCAAAAATACCCTTTACCTGCAAATGAGTTCCTTGCGGGCCGAGGACA CTGCCCTCTACTACTGCGCTCGCTTCGATTACGGTTCCAGCCTGGACTCATGGGG TCAAGGGACTACACTGACTGTTTCTTCC |  |
| VL | GAGATCGTGCTCACCCAATCTCCTGACTTCCTTAGCGTTACACCAGGGGAGAAA GTAACTCTTACGTGCCGGGCCTCCCAGAGCATCTCCAATTATTTGCATTGGTACC AGCAAAAGAGTGACCAGAGCCCTAAGCTGCTCATCAAATACGCATCACAGAGTA TTAGCGGCGTTCCCTCACGGTTCTCTGGCTCCGGTTCCGGTACAGACTTCACTTT GACGATTTCAAGTGTAGAGGCCGAGGACTTCGCAACTTACTTTTGTCAGCAAAG CAAATCCTGGCCTCGAACTTTCGGCGGGGGTACAAAACTCGAAATCAAG | 482 |

TABLE H

Nucleic acid sequences of anti-LG-5 VH and VL regions.

| LG-5 | Chain | Nucleotide Sequence | SEQ ID NO |
|---|---|---|---|
| AN01 | VH | GAGGTGCAGCTGCAGCAGAGCGGCCCTGAGCTGGTGAAACCTGGCGCCAGCGT GAAGATGAGCTGCAAGGCCAGCGGCTACACCTTCACCAGCTACAACATCCACTG GGTGAAACAGAAGCCCGGCCAGGGCCTGGAATGGATTGGCTACATCAACCCCT ACAACGACGGCACCAAGTACAGCGAGAAGTTCAAGGGCAAGGCCACCCTGACC AGCGACAGAAGCAGCAGCACCGCCTACATGGAAGTGTCCAGCCTGACCTCCGA GGACAGCGCCGTGTACTACTGCGCCATCTACGGCAACAGCTACTGGGGCCAGG GCAGCACCCTGACCGTGTCCAGC | 250 |
|  | VL | GACATCGTGATGACCCAGGCTGCCCCCAGCATCCCCGTGACACCTGGCGAGTCC GTGTCCATCAGCTGCAGAAGCAGCAAGAGCCTGCTGCACAGCAACGGCAATACC TACCTGTACTGGTTCCTGCAGCGGCCTGGCCAGTCCCCCAGCGGCTGATCTACT ACATGAGCAACCTGGACAGCGGCGTGCCCGACCGGTTTAGCGGCAGAGGCAGC GGCACAGACTTTACCCTGCGGATCAGCCGGGTGGAAGCCGAGGACGTGGGCGT GTACTATTGCATGCAGGGCCTGGAATACCCCTACACCTTTGGAGGCGGCACCAA GCTGGAAATCAAG | 251 |
| C3 | VH | GACGTGATGCTGGTCGAGAGCGGCGGAGATCTGGTCAAACCCGGGGGTTCTCT GAAGCTGAGTTGTGCCGCTTCAGGCTTCACTTTTTCTAGTTACACCATGAGCTGG GTGCGACAGACCCCAGAGAAGCGGCTGGAATGGGTCGCTAGCATCTCAAGCGG CGGAGGGAACACCTACTATCCCGACTCTGTGAAAGGCAGATTCACAATTAGTCG CGATAATGCAAAGAACAATCTGTACCTGCAGATGTCCTCTCTGAGGTCCGAAGA TACTGCCCTGTACTATTGTGCTAGATTTGACTATGGAAGTTCACTGGATTCTTGG GGACAGGGGACCACACTGACAGTGAGCTCC | 252 |
|  | VL | GACATCGTCCTGACCCAGAGTCCTGCCACCCGTGTCTGTGACACCAGGCGATTCTG TCAGTCTGTCATGTAGAGCTAGCCAGTCCATCTCTAACAATCTGCACTGGTACCA GCAGAAGTCACATGAAAGCCCCAGACTGCTGATCAAGTATGCCAGTCAGTCAAT CAGCGGTATTCCTTCCCGCTTCTCCGGCTCTGGAAGTGGGACAGACTTTACTCTG TCCATCAACTCTGTGGAGACAGAAGATTTCGGCATGTATTTTTGTCAGCAGAGCA AGAATTGGCCCAGGACATTTGGCGGAGGGACTAAGCTGGAGATCAAG | 253 |
| C21 | VH | GAAGTGATGCTGGTCGAAAGTGGAGGAGGACTGGTGAAACCAGGTGGAAGCC TGAAGCTGTCCTGTGCCGCTTCTGGCTTCACTTTTTCAAGCTATACCATGAGCTG GGTGCGACAGACACCTGAGAAGCGGCTGGAATGGGTCGCTACAATCTCCTCTG GAGGGGACAACACTTACTATCCAGATAGCGTGAAAGGCAGATTCACTATTTCCC GCGACAATGCAAAGAACAATCTGTACCTGCAGATGAGTTCACTGAGGAGCGAG GATACCGCCCTGTACTATTGCGCTAGATTTGACTATGGAAGCTCCCTGGATTGTT GGGGACAGGGGACCACACTGACCGTGTCTAGT | 254 |
|  | VL | GACATCGTCCTGACTCAGAGCCCTGCCACCCTGTCCGTGACACCAGGCGATTCA GTCAGCCTGTCCTGTAGAGCTTCTCAGAGTATCTCAAACTACCTGCACTGGTATC AGCAGAAGAGTCATGAATCACCCAGACTGCTGATCAAGTACGCCAGCCAGTCCA TCTCTGGGATTCCTAGCCGCTTCAGTGGCTCAGGAAGCGGGACAGACTTTACTCT GAGCATCAATTCCGTGGAGACAGAAGATTTCGGCATGTATTTTTGTCAGCAGTC CAAGTCTTGGCCCAGGACATTTGGCGAGGGACTGAGCTGGAGATCAAG | 255 |
| TLF39 | VH | GAGGTGCAACTGGTGCAGTCTGGAGCAGAGGTGAAAAGCCCGGGGAGTCTCT GAAGATCTCCTGTAAGGGTTCTGGATACAGCTTTACCAGCTACTGGATCGGCTG GGTGCGCCAGATGCCCGGGAAAGGCCTGGAGTGGATGGGGATCATCTATCCTG GTGACTCTGATACCAGATACAGCCCGTCCTTCCAAGGCCAGGTCACCATCTCAGC CGACAAGTCCATCAGCACCGCCTACCTGCAGTGGAGCAGCCTGAAGGCCTCGGA CACCGCCATGTATTACTGTGCGAGACGCGGGTATCGCAGCAGCTGGTACTTTGA CTACTGGGGCCAGGGAACCCTGGTCACCGTCTCCTCA | 256 |

TABLE H-continued

Nucleic acid sequences of anti-LG-5 VH and VL regions.

| LG-5 | Chain | Nucleotide Sequence | SEQ ID NO |
|---|---|---|---|
| | VL | GCCATCCAGATGACCCAGTCTCCATCCTCCCTGTCTGCATCTGTAGGAGACAGAG TCACCATCACTTGCCGGGCAAGTCAGGGCATTAGAAATGATTTAGGCTGGTATC AGCAGAAACCAGGGAAAGCCCCTAAGCTCCTGATCTATGCTGCATCCAGTTTAC AAAGTGGGGTCCCATCAAGGTTCAGCGGCAGTGGATCAGGCACAGATTTCACTT TCACCATCAGCAGCCTGCAGCCTGAAGATTTTGCAACTTATTACTGTCTACAAGA TTACAATTACCCGCTCACTTTCGGCGGAGGGACCAAGGTGGAGATCAAA | 257 |
| TLF86 | VH | GAGGTGCAGCTGGTGGAGTCTGGGGGAGGTGTGGTACGGCCGGGGGGGTCCC TGAGACTCTCCTGTGCAGCCTCTGGATTCACCTTTGATGATTATGGCATGAGCTG GGTCCGCCAAGCTCCAGGGAAGGGGCTGGAGTGGGTCTCTGGTATTAATTGGA ATGGTGGTAGCACAGGTTATGCAGACTCTGTGAAGGGCCGATTCACCATCTCCA GAGACAACGCCAAGAACTCCCTGTATCTGCAAATGAACAGTCTGAGAGCCGAG GACACGGCCTTGTATCACTGTGCGAGAGAAGGGGGGGAGCTATTAATGGACTA TTGGGGCCAGGGAACCCTGGTCACCGTCTCCTCA | 258 |
| | VL | GAAATTGTGTTGACACAGTCTCCAGCCACCCTGTCTTTGTCTCCAGGGGAAAGA GCCACCCTCTCCTGCAGGGCCAGTCAGAGTGTTAGCACCTACTTAGCCTGGTACC AACAGAAACCTGGCCAGGCTCCCAGGCTCCTCATCTATGATGCATCCAACAGGG CCACTGGCATCCCACCCAGGTTCAGTGGCAGTGGGTCTGGGACAGACTTCACTC TCACCATCAGCAGCCTAGAGCCTGAAGATTTTGCAGTTTATTACTGTCAGCAGCG TAGCAACTGGCCTCCTACTTTCGGCGGAGGGACCACGGTGGAGATCAAA | 259 |

TABLE I

Nucleic acid sequences of anti-LG-4/5 VH and VL regions.

| LG-4/5 | Chain | Nucleotide Sequence | SEQ ID NO |
|---|---|---|---|
| CL-40968 | VH | GAAGTTCAATTGTTAGAGTCTGGTGGCGGTCTTGTTCAGCCTGGTGGTTCTTTAC GTCTTTCTTGCGCTGCTTCCGGATTCACTTTCTCTCATTACTCTATGGTTTGGGTTC GCCAAGCTCCTGGTAAAGGTTTGGAGTGGGTTTCTTATATCTATCCTTCTGGTGG CACTTCGTATGCTGACTCCGTTAAAGGTCGCTTCACTATCTCTAGAGACAACTCT AAGAATACTCTCTACTTGCAGATGAACAGCTTAAGGGCTGAGGACACGGCCGTG TATTACTGTGCGAGACATTGGCGGGGGTATAGCAGCAGCTGGTACCACCCGGC GTACTTTGACTACTGGGGCCAGGGCACCCTGGTCACCGTCTCAAGC | 260 |
| | VL | GACATCCAGATGACCCAGTCTCCAGCCACCCTGTCTTTGTCTCCAGGGGAAAGA GCCACCCTCTCCTGCAGGGCCAGTCAGAGTGTTAGCAGCTACTTAGCCTGGTAC CAACAGAAACCTGGCCAGGCTCCCAGGCTCCTCATCTATGATGCATCCAACAGG GCCACTGGCATCCCAGCCAGGTTCAGTGGCAGTGGGTCTGGGACAGACTTCACT CTCACCATCAGCAGCCTAGAGCCTGAAGATTTTGCAGTTTATTACTGTCAGCAGC GTAGCAACTGGCCTCTCACTTTCGGCGGAGGGACCAAGGTGGAGATCAAA | 261 |
| CL-40992 | VH | GAAGTTCAATTGTTAGAGTCTGGTGGCGGTCTTGTTCAGCCTGGTGGTTCTTTAC GTCTTTCTTGCGCTGCTTCCGGATTCACTTTCTCTTGGTACCCTATGATGTGGGTT CGCCAAGCTCCTGGTAAAGGTTTGGAGTGGGTTTCTTCTATCTATCCTTCTGGTG GCACTACTACTTATGCTGACTCCGTTAAAGGTCGCTTCACTATCTCTAGAGACAA CTCTAAGAATACTCTCTACTTGCAGATGAACAGCTTAAGGGCTGAGGACACGGC CGTGTATTACTGTGCGAGGTCGTATTACTATGATAGTAGTGGTTATTACTCACAT GATGCTTTTGATATCTGGGGCCAAGGGACAATGGTCACCGTCTCAAGC | 262 |
| | VL | GACATCCAGATGACCCAGTCTCCATCCTCCCTGTCTGCATCTGTGGGAGACAGA GTCGCCATCACTTGCCGCGCAAGTCAGAGCATCGACACCTATTTAAATTGGTATC AGCAGAAACCAGGGAAAGCCCCTAAACTCCTGATCTATGCTGCATCCAAGTTGG AAGACGGGGTCCCATCAAGATTCAGTGGCAGTGGAACTGGGACAGATTTCACTC TCACCATCAGAAGTCTGCAACCTGAAGATTTTGCAAGTTATTTCTGTCAACAGAG CTACTCTAGTCCAGGGATCACTTTCGGCCCTGGGACCAAGGTGGAGATCAAA | 263 |
| CL-41136 | VH | GAAGTTCAATTGTTAGAGTCTGGTGGCGGTCTTGTTCAGCCTGGTGGTTCTTTAC GTCTTTCTTGCGCTGCTTCCGGATTCACTTTCTCTGATTACGAGATGCATTGGGTT CGCCAAGCTCCTGGTAAAGGTTTGGAGTGGGTTCTTCTATCTGGCCTTCTGGTG GCCTTACTAAGTATGCTGACCCCGTTAAAGGTCGCTTCACTATCTCTAGAGACAA CTCTAAGAATACTCTCTACTTGCAGATGAACAGCTTAAGGGCTGAGGACACGGC CGTGTATTACTGTGCGAGAGATTCCTATTACTATGATAGTAGTGGTGCTCTTGGC TACTGGGGCCAGGGAACCCTGGTCACCGTCTCAAGC | 264 |
| | VL | GACATCCAGATGACCCAGTCTCCTTCCACCCTGTCTGCATCTGTAGGAGACAGAG TCACCATCACTTGCCGGGCCAGTCAGAGTGTTAGTAACTGGTTGGCCTGGTATC AGCAGAAACCAGGGAAAGCCCCTAAGCTCCTGATCTATAAGGCGTCTAGTTTAG AAAGTGGGGTCCCATCGAGGTTCAGCGGCAGTGGATCTGGGACAGAATTCACT CTCACCATCAGCAGCCTGCAGCCTGATGATTTTGCAACTTATTACTGCCTACAGT ATGTGAGTTATCCCCTCACTTTTGGCGGAGGGACCAAGGTGGACATCAAA | 265 |

TABLE I-continued

Nucleic acid sequences of anti-LG-4/5 VH and VL regions.

| LG-4/5 | Chain | Nucleotide Sequence | SEQ ID NO |
|---|---|---|---|
| CL-41400 | VH | GAAGTTCAATTGTTAGAGTCTGGTGGCGGTCTTGTTCAGCCTGGTGGTTCTTTAC<br>GTCTTTCTTGCGCTGCTTCCGGATTCACTTTCTCTTATTACGATATGTATTGGGTT<br>CGCCAAGCTCCTGGTAAAGGTTTGGAGTGGGTTTCTCGTATCTATTCTTCTGGTG<br>GCCATACTTGGTATGCTGACTCCGTTAAAGGTCGCTTCACTATCTCTAGAGACAA<br>CTCTAAGAATACTCTCTACTTGCAGATGAACAGCTTAAGGGCTGAGGACACGGC<br>TGTGTATTACTGTGCGAGGCCCGGGTATAGCAGTGGCTGGTACGATGGCACCTA<br>CTTTGACTACTGGGGCCAGGGAACCCTGGTCACCGTCTCAAGC | 266 |
| | VL | GACATCCAGATGACCCAGTCTCCTTCCACCCTGTCTGCATCTGTTGGCGACAGAG<br>TCACCATTACTTGTCGGGCCAGTCAGAGTATTGATACTTGGCTGGCCTGGTATCG<br>GCAGAAACCAGGGAAAGCCCCTAATGTCGTAATTCATTCCGCGTCTACTTTACAA<br>AGTGGCGTCCCCGCAAGGTTCAGCGGCAGTGGATTTGGGACAGAATGGACTCT<br>CACTATCACCAACCTGCAGCCTGATGATTTTGCCACCTATTATTGCCAACAATATA<br>AGACTTATCCGTTCACTTTTGGCCAGGGGACGAAGCTGGAGATCAAG | 267 |
| CL-41500 | VH | GAAGTTCAATTGTTAGAGTCTGGTGGCGGTCTTGTTCAGCCTGGTGGTTCTTTAC<br>GTCTTTCTTGCGCTGCTTCCGGATTCACTTTCTCTCATTACCAGATGGAGTGGGTT<br>CGCCAAGCTCCTGGTAAAGGTTTGGAGTGGGTTTCTTCTATCTCTCCTTCTGGTG<br>GCTTTACTTCTTATGCTGACTCCGTTAAAGGTCGCTTCACTATCTCTAGAGACAAC<br>TCTAAGAATACTCTCTACTTGCAGATGAACAGCTTAAGGGCTGAGGACACAGCC<br>GTGTATTACTGTACGAGAGAGCCGGGGAGGTTGTGGGCTTTTGATATCTGGGG<br>CCAAGGGACAATGGTCACCGTCTCAAGC | 268 |
| | VL | GACATCCAGATGACCCAGTCTCCATCTTTCGTGTCTGCATCTGTCGGAGACAGAG<br>TCACCATCACTTGCCGGGCGAGTCAGGATATTCGTAATTGGCTAGCCTGGTATCA<br>ACAGGAGTCCGGGAAAGCCCCTCGGCTCCTGATCTCTGCTGCATCCAGTAGGCA<br>CAGTGGCGTCTCATCTAGATTCAGCGGCAGTGGATCTGGGACAGACTTCACCCT<br>CACCATCACCAGTCTGCAGCCTGAAGATTCAGCAACTTATTTTTGTCAACAGGCT<br>GACAGTTCCCCTCGGACGTTCGGCCAAGGGACCAAGGTGGAAATCAAA | 269 |
| TLG3/TLG4 | VH | CAGGTGCAACTGGTGCAGTCTGGGGCTGAGGTGAAGAAGCCTGGGGCCTCAGT<br>GAAGGTCTCCTGCAAGGCTTCTGGATACACCTTCACCGGCTACTATATGCACTGG<br>GTGCGACAGGCCCCTGGACAAGGGCTTGAGTGGATGGGATGGATCAACCCTAA<br>CAGTGGTGGCACAAACTATGCACAGAAGTTTCAGGGCAGGGTCACCATGACCA<br>GGGACACGTCCATCAACACAGCCTACATGGAACTGAGCAGGCTGAGATCTGAC<br>GACACGGCCGTGTATTACTGTGCGGTCTTTGGTTCGGGGAGTTCTTGGGGCCAG<br>GGAACCCTGGTCACCGTCTCCTCA | 270 |
| | VL | GACATCCAGATGACCCAGTCTCCATCCTCACTGTCTGCATCTGTGGGAGACAGA<br>GTCACCATCACTTGTCGGGCGAGTCAGGGTATTAGCAATTCTTTAGCCTGGTTTC<br>AGCAGAAACCAGGGAAAGCCCCTAAGTCCCTGATCTATGCTGCATCCAGTTTGC<br>AAAGTGGGGTCCCATCAAAGTTCAGCGGCAGTGGATCTGGGACAGATTTCACTC<br>TCACCATCAGCAGCCTGCAGCCTGAAGATTTTGCAACTTATTACTGCCAACAATA<br>TAAGAGTTACCCGTACACATTTGGCCAGGGGACCAAGCTGGAGATCAAA | 271 |
| TLG26 | VH | CAGGTGCAGCTGGTGCAGTCTGGGGCTGAGGTGAAGAAGCCTGGGGCCTCAGT<br>GAAGGTCTCCTGCAAGGCTTCTGGAAACACCTTCACCGGCTACTATATACACTGG<br>GTTCGACAGGCCCCTGGACAAGGGCTTGAGTGGATGGGATGGATTAAACCTAG<br>TACTGGTGACACAAACTATGCACAGAATTTTCTGGACAGGGTCACCATGACCAG<br>GGACACGTCCATCAGCACAGCCTACATGGAACTCAGCAGGCTGAGATCTGACGA<br>CACGGCCGTGTATTACTGTGCGGTCTTTGGTTCGGGGAGTTCTTGGGGCCAGGG<br>AACCCTGGTCACCGTCTCCTCA | 272 |
| | VL | GACATCCACATGACCCAGTCTCCATCCTCACTGTCTGCATTTGTAGGAGACAGAG<br>TCACCATCACTTGTCGGGCGAGTCAGGGCATTAGCAATTATTTAGCCTGGTTTCA<br>GCAGAAACCAGGGAAAGCCCCTAAGTCCCTGATCTATGCTGCATCCAGTTTGCA<br>AAGTGGGGTCCCATCAAAGTTCAGCGGCAGTGGATCTGGGACAGATTTCACTCT<br>CACCATCAACAACCTGCAGCCTGAAGATTTTGCAACTTATTACTGCCAACAGTAT<br>AAGACTTACCCGTACACATTTGGCCAGGGGACCAAGCTGGAGATCAAA | 273 |
| TLI-3 | VH | CAGGTGCAGCTGGTGGAGTCTGGGGGAGGCGTGGTCCAGCCTGGGAGGTCCCT<br>GAGACTCTCCTGTGCAGCGTCTGGATTCACCTTCAGTAGCTATGGCATGCACTGG<br>GTCCGCCAGGCTCCAGGCAAGGGGCTGGAGTGGGTGGCAGTTATATGGTATGA<br>TGGAAGTAATAAATACTATGCAGACTCCGTGAAGGGCCGATTCACCATCTCCAG<br>AGACAATTCCAAGAACACGCTGTATCTGCAAATGAACAGTCTGAGAGCCGAGGA<br>CGCGGCTGTGTATTACTGTGCGAGAGAAGGTGGCTGGTACGGCGGGGACTACT<br>ACTACGGTATGGACGTCTGGGGCCAAGGGACCACGGTCACCGTCTCCTCA | 274 |
| | VL | GCCATCCAGTTGACCCAGTCTCCATCCTCCCTGTCTGCATCTGTAGGAGACAGAG<br>TCACCATCACTTGCCGGGCAAGTCAGGGCATTAGCAGTGCTTTAGCCTGGTATC<br>AGCAGAAACCAGGGAAAGCTCCTAAGCTCCTGATCTATGATGCCTCCAGTTTGG<br>AAAGTGGGGTCCCATCAAGGTTCAGCGGCAGTGGATCTGGGACAGATTTCACTC<br>TCACCATCAGCAGCCTGCAGCCTGAAGATTTTGCAACTTATTACTGTCATCAGTTT<br>AATAATTACCCATTCACTTTCGGCCCTGGGACCAAAGTGGATATCAAA | 275 |
| TLI-7 | VH | GAAGTGCAGCTGCTGGAATCTGGCGGCGGACTGGTGCAGCCTGGCGGATCTCT<br>GAGACTGTCCTGTGTGGCCTCCGGCTTCACCTTCTCCAGCTACGCCATGTCCTGG<br>GTGCGACAGGCTCCTGGCAAGGGCCTGGAATGGGTGTCCGGCATCTCTGGCAG<br>GGGCGGCTCTCCTAACTACGCCGACTCTGTGAAGGGCCGGTTCACCATCTCCCG | 276 |

TABLE I-continued

Nucleic acid sequences of anti-LG-4/5 VH and VL regions.

| LG-4/5 | Chain | Nucleotide Sequence | SEQ ID NO |
|---|---|---|---|
| | VL | GGACAACTCCAAGAACACCCTGTACCTCCAGATGAACTCCCTGCGGGCCGAGGA<br>CACCGCCGTGTACTACTGTGCTAAGGACGGCGACGGCTCCGGCCCTCCCTACTA<br>CTTTGATTACTGGGGCCAGGGCACCCTCGTGACCGTGTCATCT<br>GACATCCAGATGACCCAGTCCCCCTCCAGCCTGTCTGCCTCTGTGGGCGACAGA<br>GTGACCATCACCTGTCGGGCCTCCCAGGGCATCTCTTCTTGGCTGGCCTGGTATC<br>AGCAGAAGCCCGAGAAGGCCCCCAAGTCCCTGATCTACGCCGCCAGCTCTCTCC<br>AGTCTGGCGTGCCCTCCAGATTCTCCGGCTCTGGCACCGACTTTACCCT<br>GACCATCAGCTCCCTCCAGCCCGAGGACTTCGCCACCTACTACTGCCAGCAGTAC<br>AACTCCTACCCCTACACCTTCGGCCAGGGCACCAAGCTGGAAATCAAG | 277 |
| TTLK71-4-6 | VH | CAGGTGCAGCTGATGGAGTCTGGGGGAGGCGTGGTCCAGCCTGGGAGGTCCCT<br>GAGACTCTCCTGTGCAGCGTCTGGATTCACCTTCAGTGGCTATGGCATGCACTG<br>GGTCCGCCAGGCTCCAGGGAAGGGGCTGGAGTGGGTGGCAGTTATATGGTCTG<br>ATGGAAGTAATAGATACTATACAGACTCCGTGAAGGGCCGATTCACCATCTCCA<br>GAGACAATTCCAAGAACACGCTGTCTCTGCAAATGAACAGCCTGAGAGCCGAG<br>GACACGGCTGTGTATTACTGTGCGAGAGATAGGGGGATTACTATGGTTCGGGG<br>ACTTATTATAAAATACTACTACTACACGGTTTGGACGTCTGGGGCCAAGGGACC<br>TCGGTCACCGTCTCCTCA | 278 |
| | VL | GAAATTGTGTTGACACAGTCTCCAGCCACCCTGTCTTTGTCTCCAGGGGAAAGA<br>GCCACCCTCTCCTGCAGGGCCAGTCAGAGTGTTAGCAGCTACTTAGCCTGGTAC<br>CAACAGAAACCTGGCCAGGCTCCCAGGCTCCTCATCTATGATGCATCCAACAGG<br>GCCACTGGCATCCCAGCCAGGTTCAGTGGCAGTGGGTCTGGGACAGACTTCACT<br>CTCACCATCAGCAGCCTAGAGCCTGAAGATTTTGCAGTTTATTACTGTCAGCAGC<br>GTAGCAACTGGTGGACGTTCGGCCAAGGGACCAAGGTGGAAATCAAA | 279 |
| TTLK123-3 | VH | CAGGTGCAGCTGGTGGAGTCTGGGGGAGGCGTGGTCCAGCCTGGGAGGTCCCT<br>GAGACTCTCCTGTGCAGCGTCTGGATTCACCTTCAGTAGCTTTGGCATGCACTGG<br>GTCCGCCAGGCTCCAGGCAAGGGGCTGGAGTGGGTGGCAGTTATATACATGA<br>TGGAAGTAATAAATACTATGCAGACTCCGTGAAGGGCCGATTCACCATCTCCAG<br>AGACAATTCCAAGAACACGCTGTATCTGCAAATGAACAGCCTGAGAGCCGAGG<br>ACACGGCTGTGTATTACTGTGCGAGAGATGACAACTGGAACGACGGGGACTTT<br>GACTACTGGGGCCAGGGAACCCTGGTCACCGTCTCCTCA | 280 |
| | VL | GACATCCAGTTGACCCAGTCTCCATCCTTCCTGTCTGCATCTGTAGGAGACAGAG<br>TCACCATCACTTGCCGGGCCAGTCAGGGCATTAGTAGTTATTAGCCTGGTATCA<br>GCAAAAACCAGGGAAAGCCCCTAAGCTCCTGATCTATGCTGCATCCACTTTGCAA<br>AGTGGGGTCCCATCAAGGTTCAGCGGCAGTGGATCTGGGACAGAATTCACTCTC<br>ACAATCAGCAGCCTGCAGCCTGAAGATTTTGCAACTTATTACTGTCAACAGCTTA<br>ATAGTTACCCTCGGACGTTCGGCCAAGGGACCAAGGTGGAAATCAAA | 281 |
| TTLK145-6-3 | VH | GAGGTGCAGCTGTTGGAGTCTGGGGGAGGCTTGGTACAGCCTGGGGAGTCCCT<br>GAGACTCTCCTGTGCAGCCTCTGGATTCACCTTTAACAGATTTGTCATGAGTTGG<br>GTCCGCCAGGCTCCAGGGAAGGGGCTGGAGTGGGTCTCAACTATTAGTGGTAG<br>TGGTGGTAGCACATACTACGCAGACTCCGTGAAGGGCCGGTTCACCATCTCCAG<br>AGACAATTCCAAGAACACGCTGTATCTGCAAATGAACAGCCTGAGAGCCGAGG<br>ACACGGCCGTGTATTACTGTGCGAAAGATTTTACGTATTACTATGGTTCGGGGA<br>ATTATTATAACTGGTTCGACCCCAGGGGCCAGGGAACCCTGGTCACCGTCTCCTCA | 282 |
| | VL | GACATCCAGATGACCCAGTCTCCTTCCACCCTGTCTACATCTGTAGGAGACAGAG<br>TCACCATCACTTGCCGGGCCAGTCAGAGTATTAGTAGCTGTTGGCCTGGTATC<br>AGCAGAAACCAGGGAAAGCCCCTAAGCTCCTGATCTATAAGGCGTCTAGTTTAG<br>AAAGTGGGGTCCCATCAAGGTTCAGCGGCAGTGGATCTGGGACAGAATTCACT<br>CTCACCATCAGCAGCCTGCAGCCTGATGATTTTGCAACTTATTACTGCCAACAGT<br>ATAATAGTTATTCTCGGACGTTCGGCCAAGGGACCAAGGTGGAAATCAAA | 283 |
| TTLK170-2 | VH | CAGGTGCAGCTACAGCAGTGGGGCGCAGGACTGTTGAAGCCTTCGGAGACCCT<br>GTCCCTCACCTGCGCTGTCTATGGTGGGTCCTTTAGTGGTTACTACTGGAGCTGG<br>ATCCGCCAGCCCCCAGGGAAGGGGCTGGAGTGGATTGGGGAAATCAATCATAG<br>TGGAGGCACCAACTACAACCCGTCCCTCAAGAGTCGAGTCACCATATCAGTAGA<br>CACGTCCAAGAACCACTTCTCCCTGAAGCTGAGCTCTGTGACCGCCGCGGACAC<br>GGCTGTGTATTACTGTGCGAGAACTAGTGACTACGATTACTACTACGGTATG<br>GACGTCTGGGGCAAGGGACCACGGTCACCGTCTCCTCA | 284 |
| | VL | CAGCCTGTGCTGACTCAGCCAACTTCCCTCTCAGCATCCTGGAGCATCAGCCA<br>GACTCACCTGCACCTTGCGCAGTGGCATCAATCTTGGTCGCTACAGGATATTCTG<br>GTACCAGCAGAAGCCAGAGAGCCCTCCCCGGTATCTCCTGAGCTACTACTCAGA<br>CTCAAGTAAGCATCAGGGCTCTGGAGTCCCCAGCCGCTTCTCTGGATCCAAAGA<br>TGCTTCGAGCAATGCAGGGATTTTAGTCATCTCTGGGCTCCAGTCTGAGGATGA<br>GGCTGACTATTACTGTATGATTTGGCACAGGAGTGCTTTGTTTATTTTCGGCAGT<br>GGAACCAAGGTCACTGTCCTA | 285 |
| WJL10 | VH | CAGGTTCAGCTACAGCAGTCTGGACCTGAGCTGGTGAAGCCTGGGGCTTCAGTG<br>AAGTTGTCCTGCAAGGCTTCTGGTTACACCTTCACAAGCTACGAGATAAACTGGT<br>TGAAGCAGAGGCCTGGACAGGGACTTGAGTGGATTGGATTGATTTATCCTAGA<br>GATGGAGATACTAAGTACAATGAGAAGTTCAAGGGCAAGGCCACATTGACTGC<br>AGACACATCCTCCAGCACAGCGTACATGGAGCTCCACAGCCTGACATCTGAGGA | 286 |

TABLE I-continued

Nucleic acid sequences of anti-LG-4/5 VH and VL regions.

| LG-4/5 | Chain | Nucleotide Sequence | SEQ ID NO |
|---|---|---|---|
| | | CTCTGCGGTCTATTTCTGTGCAAGACACACCCCAGGGGCTTTCTGGGGCCAAGG GACTCTGGTCACTGTCTCTGCA | |
| | VL | GATGTTGTGATGACCCAAACTCCCCTCTCCCTGCCGGTCAGTCTTGGAGATCAAG CCTCCATCTCTTGCAGATCTAGTCAGAGCCTTGTTCACAGTAATGGAGACACCTA TTTACATTGGTACCTACAGAAGCCAGGCCAGTCTCCAAAGCTCCTGATCTACAA GTTTCCAACCGATTTTCTGGGGTCCCAGACAGGTTCAGTGGCAGTGGATCAGGG ACAGATTTCACACTCAAGATCAGCAGAGTGGAGGCTGAGGATCTGGAAATTTAT TTCTGCTCTCAAAGCACACATGTTCCGTACACGTTCGGAGGGGGGACCAAACTG GAAATAAAA | 287 |
| WJL48 | VH | GACGTGAAGCTGGTGGAGTCTGGGGAAGGCTTAGTGAAGCCCGGAGGGTCCCT GAAACTCTCTTGTGCAGCCTCTGGATTCACTTTCAGTAGGTATGCCATGTCTTGG GTTCGCCAGACTCCAGAAAAGAGGCTGGAATGGGTCGCATATATTAGTAGTGG AGGTGATTACATCCACTATGGAGAAACTGTGAAGGGCCGATTCACCATCTCCAG AGACAATGCCAGGAACACCCTGTACCTGCAAATGAGCAGTCTGAAGTCTGAGGA CACAGCCATGTATTACTGTACAAGAGTTCTCTTTTATTATTACGGCAGTAGCTAC GTCTTTTTTGACTACTGGGGCCAAGGCACCACTCTCACAGTCTCCTCA | 288 |
| | VL | GATATCCAGATGACACAGACTACATCCTCCCTGTCAGTCTCTCTGGGAGACAGA GTCACCATCAGTTGCAGGGCAAGTCAGGACATCAGCAATTTTCTAAACTGGTAT CAGCAGAAACCAGATGGAACTGTTAATCTCCTGATCTACTACACATCAAAATTAC ACTCAGGAGTCCCATCAAGGTTCAGTGGCGGTGGGTCTGGAAGAGATTATTCTC TCACCATTAATAACCTGGAGCAAGAAGATATTGCCTCTTACTTTTGCCAACAGGG TCATACGCTTCCGTATACGTTCGGAGGGGGGACCAAGCTGGAAATAAAA | 289 |

TABLE 12

Amino acid sequences of humanized, multispecific binding proteins.

| Name | Chain | Sequence | SEQ ID NO |
|---|---|---|---|
| 3407 | I | EIVLTQSPDFLSVTPKEKVTLTCRASQSISNNLHWYQQKSDQSPKLLIKYASQSISGIPSR FSGSGSGTDFTLTINSVEAEDAATYFCQQSKSWPRTFGGGTKLEIKDKTHTEIVLTQSP DFLSVTPKEKVTLTCRASQSISNNLHWYQQKSDQSPKLLIKYASQSISGIPSRFSGSGSG TDFTLTINSVEAEDAATYFCQQSKSWPRTFGGGTKLEIKDKTHTRTVAAPSVFIFPPSDE QLKSGTASVVCLLNNFYPREAKVQWKVDNALQSGNSQESVTEQDSKDSTYSLSSTLTL SKADYEKHKVYACEVTHQGLSSPVTKSFNRGEC | 500 |
| | II | EVQLVESGGGLVKPGGSLRLSCAASGFTFSSYTMSWVRQAPGKGLEWVASISSSGSN TYYPDSVKGRFTISRDNAKNNLYLQMNSLRAEDTALYYCARFDYGSSLDSWGQGTLLT VSSDKTHTEVQLVESGGGLVKPGGSLRLSCAASGFTFSSYTMSWVRQAPGKGLEWVA SISSSGSNTYYPDSVKGRFTISRDNAKNNLYLQMNSLRAEDTALYYCARFDYGSSLDSW GQGTLLTVSSDKTHTASTKGPSVFPLAPSSKSTSGGTAALGCLVKDYFPEPVTVSWNSG ALTSGVHTFPAVLQSSGLYSLSSVVTVPSSSLGTQTYICNVNHKPSNTKVDKKVEPKSCD KTHTCPPCPAPELLGGPSVFLFPPKPKDTLYITREPEVTCVVVDVSHEDPEVKFNWYVD GVEVHNAKTKPREEQYNSTYRVVSVLTVLHQDWLNGKEYKCKVSNKALPAPIEKTISK AKGQPREPQVYTLPPCRDELTKNQVSLWCLVKGFYPSDIAVEWESNGQPENNYKTTP PVLDSDGSFFLYSKLTVDKSRWQQGNVFSCSVMHEALHNHYTQKSLSLSPG | 498 |
| | III | QVQLVQSGAEVVKPGSSVKVSCEASGFTFTDSVITWVRQRPGQGLEWIGEIYPGSGN FYYNEKFQGRVTITADKSTSTAYMELSSLRSEDTAVYFCAMRRSSWGQGTLVTVSSAS TKGPSVFPLAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCPAPELLGGP SVFLFPPKPKDTLYITREPEVTCVVVDVSHEDPEVKFNWYVDGVEVHNAKTKPREEQY NNASRVVSVLTVLHQDWLNGKEYKCKVSNKALPAPIEKTISKAKGQPREPQVCTLPPS RDELTKNQVSLSCAVKGFYPSDIAVEWESNGQPENNYKTTPPVLDSDGSFFLVSKLTV DKSRWQQGNVFSCSVMHEALHNRFTQKSLSLSPG | 499 |
| | IV | DVVMTQTPLSLSVTPGQPASISCKSSQTIVHSNSKTYLEWYLQKPGQSPQLLIYKVSSRF SGVPDRFSGSGSGTDFTLKISRVEAEDVGVYYCFQGSHVPLTFGQGTKLEIKRTVAAPS VFIFPPSDEQLKSGTASVVCLLNNFYPREAKVQWKVDNALQSGNSQESVTEQDSKDST YSLSSTLTLSKADYEKHKVYACEVTHQGLSSPVTKSFNRGEC | 501 |
| 3423 | I | EIVLTQSPDFLSVTPKEKVTLSCRASQSISNYLHWYQQKSDQSPKLLIKYASQSISGIPSRF SGSGSGTDFTLSINSVEAEDAATYFCQQSKSWPRTFGGGTKLEIKDKTHTEIVLTQSPD FLSVTPKEKVTLTCRASQSISNNLHWYQQKSDQSPKLLIKYASQSISGIPSRFSGSGSGT DFTLTINSVEAEDAATYFCQQSKSWPRTFGGGTKLEIKDKTHTRTVAAPSVFIFPPSDE QLKSGTASVVCLLNNFYPREAKVQWKVDNALQSGNSQESVTEQDSKDSTYSLSSTLTL SKADYEKHKVYACEVTHQGLSSPVTKSFNRGEC | 504 |
| | II | EVQLVESGGGLVKPGGSLRLSCAASGFTFSSYTMSWVRQAPGKGLEWVASISSSGSN TYYPDSVKGRFTISRDNAKNNLYLQMNSLRAEDTALYYCARFDYGSSLDSWGQGTLLT VSSDKTHTEVQLVESGGGLVKPGGSLRLSCAASGFTFSSYTMSWVRQAPGKGLEWVA SISSSGSNTYYPDSVKGRFTISRDNAKNNLYLQMNSLRAEDTALYYCARFDYGSSLDSW | 502 |

TABLE 12-continued

Amino acid sequences of humanized, multispecific binding proteins.

| Name | Chain | Sequence | SEQ ID NO |
|---|---|---|---|
| | | GQGTLLTVSSDKTHTASTKGPSVFPLAPSSKSTSGGTAALGCLVKDYFPEPVTVSWNSG ALTSGVHTFPAVLQSSGLYSLSSVVTVPSSSLGTQTYICNVNHKPSNTKVDKKVEPKSCD KTHTCPPCPAPELLGGPSVFLFPPKPKDTLYITREPEVTCVVVDVSHEDPEVKFNWYVD GVEVHNAKTKPREEQYNNASRVVSVLTVLHQDWLNGKEYKCKVSNKALPAPIEKTISK AKGQPREPQVYTLPPCRDELTKNQVSLWCLVKGFYPSDIAVEWESNGQPENNYKTTP PVLDSDGSFFLYSKLTVDKSRWQQGNVFSCSVMHEALHNHYTQKSLSLSPG | |
| | III | QVQLVQSGAEVVKPGSSVKVSCEASGFTFTDSVITWVRQRPGQGLEWIGEIYPGSGN FYYNEKFQGRVTITADKSTSTAYMELSSLRSEDTAVYFCAMRSSWGQGTLVTVSSAS TKGPSVFPLAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCPAPELLGGP SVFLFPPKPKDTLYITREPEVTCVVVDVSHEDPEVKFNWYVDGVEVHNAKTKPREEQY NNASRVVSVLTVLHQDWLNGKEYKCKVSNKALPAPIEKTISKAKGQPREPQVCTLPPS RDELTKNQVSLSCAVKGFYPSDIAVEWESNGQPENNYKTTPPVLDSDGSFFLVSKLTV DKSRWQQGNVFSCSVMHEALHNRFTQKSLSLSPG | 503 |
| | IV | DVVMTQTPLSLSVTPGQPASISCKSSQTIVHSNSKTYLEWYLQKPGQSPQLLIYKVSSRF SGVPDRFSGSGSGTDFTLKISRVEAEDVGVYYCFQGSHVPLTFGQGTKLEIKRTVAAPS VFIFPPSDEQLKSGTASVVCLLNNFYPREAKVQWKVDNALQSGNSQESVTEQDSKDST YSLSSTLTLSKADYEKHKVYACEVTHQGLSSPVTKSFNRGEC | 505 |
| 3429 | I | EIVLTQSPDFLSVTPGEKVTLTCRASQSISNYLHWYQQKSDQSPKLLIKYASQSISGVPSR FSGSGSGTDFTLTISSVEAEDFATYFCQQSKSWPRTFGGGTKLEIKDKTHTEIVLTQSPD FLSVTPKEKVTLTCRASQSIGNNLHWYQQKSDQSPKLLIKYASQSISGIPRFSGSGSGT DFTLTINSVEAEDAATYFCQQSKSWPRTFGGGTKLEIKDKTHTRTVAAPSVFIFPPSDE QLKSGTASVVCLLNNFYPREAKVQWKVDNALQSGNSQESVTEQDSKDSTYSLSSTLTL SKADYEKHKVYACEVTHQGLSSPVTKSFNRGEC | 508 |
| | II | EVQLVESGGGLVKPGGSLRLSCAASGFTFSSYTMSWVRQAPGKGLEWVASISSSGSN TYYPDSVKGRFTISRDNAKNNLYLQMNSLRAEDTALYYCARFDYGSSLDSWGQGTLLT VSSDKTHTEVQLVESGGGLVQPGGSLRLSCAASGFTFSSYTMSWVRQAPGKGLEWV ATISSSGDNTYYPDSVKGRFTISRDNSKNTLYLQMSSLRAEDTALYYCARFDYGSSLDS WGQGTTLTVSSDKTHTASTKGPSVFPLAPSSKSTSGGTAALGCLVKDYFPEPVTVSWN SGALTSGVHTFPAVLQSSGLYSLSSVVTVPSSSLGTQTYICNVNHKPSNTKVDKKVEPKS CDKTHTCPPCPAPELLGGPSVFLFPPKPKDTLYITREPEVTCVVVDVSHEDPEVKFNWY VDGVEVHNAKTKPREEQYNNASRVVSVLTVLHQDWLNGKEYKCKVSNKALPAPIEKTI SKAKGQPREPQVYTLPPCRDELTKNQVSLWCLVKGFYPSDIAVEWESNGQPENNYKT TPPVLDSDGSFFLYSKLTVDKSRWQQGNVFSCSVMHEALHNHYTQKSLSLSPG | 506 |
| | III | QVQLVQSGAEVVKPGSSVKVSCEASGFTFTDSVITWVRQRPGQGLEWIGEIYPGSGN FYYNEKFQGRVTITADKSTSTAYMELSSLRSEDTAVYFCAMRSSWGQGTLVTVSSAS TKGPSVFPLAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCPAPELLGGP SVFLFPPKPKDTLYITREPEVTCVVVDVSHEDPEVKFNWYVDGVEVHNAKTKPREEQY NNASRVVSVLTVLHQDWLNGKEYKCKVSNKALPAPIEKTISKAKGQPREPQVCTLPPS RDELTKNQVSLSCAVKGFYPSDIAVEWESNGQPENNYKTTPPVLDSDGSFFLVSKLTV DKSRWQQGNVFSCSVMHEALHNRFTQKSLSLSPG | 507 |
| | IV | DVVMTQTPLSLSVTPGQPASISCKSSQTIVHSNSKTYLEWYLQKPGQSPQLLIYKVSSRF SGVPDRFSGSGSGTDFTLKISRVEAEDVGVYYCFQGSHVPLTFGQGTKLEIKRTVAAPS VFIFPPSDEQLKSGTASVVCLLNNFYPREAKVQWKVDNALQSGNSQESVTEQDSKDST YSLSSTLTLSKADYEKHKVYACEVTHQGLSSPVTKSFNRGEC | 509 |
| 3437 | I | EIVLTQSPDFLSVTPKEKVTLTCRASQSIGNNLHWYQQKSDQSPKLLIKYASQSISGIPSR FSGSGSGTDFTLTINSVEAEDAATYFCQQSKSWPRTFGGGTKLEIKDKTHTEIVLTQSP DFLSVTPKEKVTLSCRASQSISNYLHWYQQKSDQSPKLLIKYASQSISGIPRFSGSGSGT DFTLSINSVEAEDAATYFCQQSKSWPRTFGGGTKLEIKDKTHTRTVAAPSVFIFPPSDE QLKSGTASVVCLLNNFYPREAKVQWKVDNALQSGNSQESVTEQDSKDSTYSLSSTLTL SKADYEKHKVYACEVTHQGLSSPVTKSFNRGEC | 512 |
| | II | EVQLVESGGGLVKPGGSLRLSCAASGFTFSSYTMSWVRQAPGKGLEWVASISSSGSN TYYPDSVKGRFTISRDNAKNNLYLQMNSLRAEDTALYYCARFDYGSSLDSWGQGTLLT VSSDKTHTEVQLVESGGGLVKPGGSLRLSCAASGFTFSSYTMSWVRQAPGKGLEWVA SISSSGSNTYYPDSVKGRFTISRDNAKNNLYLQMNSLRAEDTALYYCARFDYGSSLDSW GQGTLLTVSSDKTHTASTKGPSVFPLAPSSKSTSGGTAALGCLVKDYFPEPVTVSWNSG ALTSGVHTFPAVLQSSGLYSLSSVVTVPSSSLGTQTYICNVNHKPSNTKVDKKVEPKSCD KTHTCPPCPAPELLGGPSVFLFPPKPKDTLYITREPEVTCVVVDVSHEDPEVKFNWYVD GVEVHNAKTKPREEQYNNASRVVSVLTVLHQDWLNGKEYKCKVSNKALPAPIEKTISK AKGQPREPQVYTLPPCRDELTKNQVSLWCLVKGFYPSDIAVEWESNGQPENNYKTTP PVLDSDGSFFLYSKLTVDKSRWQQGNVFSCSVMHEALHNHYTQKSLSLSPG | 510 |
| | III | QVQLVQSGAEVVKPGSSVKVSCEASGFTFTDSVITWVRQRPGQGLEWIGEIYPGSGN FYYNEKFQGRVTITADKSTSTAYMELSSLRSEDTAVYFCAMRSSWGQGTLVTVSSAS TKGPSVFPLAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCPAPELLGGP SVFLFPPKPKDTLYITREPEVTCVVVDVSHEDPEVKFNWYVDGVEVHNAKTKPREEQY NNASRVVSVLTVLHQDWLNGKEYKCKVSNKALPAPIEKTISKAKGQPREPQVCTLPPS RDELTKNQVSLSCAVKGFYPSDIAVEWESNGQPENNYKTTPPVLDSDGSFFLVSKLTV DKSRWQQGNVFSCSVMHEALHNRFTQKSLSLSPG | 511 |
| | IV | DVVMTQTPLSLSVTPGQPASISCKSSQTIVHSNSKTYLEWYLQKPGQSPQLLIYKVSSRF SGVPDRFSGSGSGTDFTLKISRVEAEDVGVYYCFQGSHVPLTFGQGTKLEIKRTVAAPS | 513 |

TABLE 12-continued

Amino acid sequences of humanized, multispecific binding proteins.

| Name | Chain | Sequence | SEQ ID NO |
|---|---|---|---|
| | | VFIFPPSDEQLKSGTASVVCLLNNFYPREAKVQWKVDNALQSGNSQESVTEQDSKDST<br>YSLSSTLTLSKADYEKHKVYACEVTHQGLSSPVTKSFNRGEC | |
| 3439 | I | EIVLTQSPDFLSVTPKEKVTLTCRASQSISNNLHWYQQKSDQSPKLLIKYASQSISGIPSR<br>FSGSGSGTDFTLTINSVEAEDAATYFCQQSKSWPRTFGGGTKLEIKDKTHTEIVLTQSP<br>DFLSVTPGEKVTLTCRASQSISNYLHWYQQKSDQSPKLLIKYASQSISGVPSRFSGSGSG<br>TDFTLTISSVEAEDFATYFCQQSKSWPRTFGGGTKLEIKDKTHTRTVAAPSVFIFPPSDE<br>QLKSGTASVVCLLNNFYPREAKVQWKVDNALQSGNSQESVTEQDSKDSTYSLSSTLTL<br>SKADYEKHKVYACEVTHQGLSSPVTKSFNRGEC | 516 |
| | II | EVQLVESGGGLVQPGGSLRLSCAASGFTFSSYTMSWVRQAPGKGLEWVATISSSGDN<br>TYYPDSVKGRFTISRDNSKNTLYLQMSSLRAEDTALYYCARFDYGSSLDSWGQGTTLTV<br>SSDKTHTEVQLVESGGGLVKPGGSLRLSCAASGFTFSSYTMSWVRQAPGKGLEWVAS<br>ISSSGSNTYYPDSVKGRFTISRDNAKNNLYLQMNSLRAEDTALYYCARFDYGSSLDSW<br>GQGTLLTVSSDKTHTASTKGPSVFPLAPSSKSTGGTAALGCLVKDYFPEPVTVSWNSG<br>ALTSGVHTFPAVLQSSGLYSLSSVVTVPSSSLGTQTYICNVNHKPSNTKVDKKVEPKSCD<br>KTHTCPPCPAPELLGGPSVFLFPPKPKDTLYITREPEVTCVVVDVSHEDPEVKFNWYVD<br>GVEVHNAKTKPREEQYNNASRVVSVLTVLHQDWLNGKEYKCKVSNKALPAPIEKTISK<br>AKGQPREPQVYTLPPCRDELTKNQVSLWCLVKGFYPSDIAVEWESNGQPENNYKTTP<br>PVLDSDGSFFLYSKLTVDKSRWQQGNVFSCSVMHEALHNHYTQKSLSLSPG | 514 |
| | III | QVQLVQSGAEVVKPGSSVKVSCEASGFTFTDSVITWVRQRPGQGLEWIGEIYPGSGN<br>FYYNEKFQGRVTITADKSTSTAYMELSSLRSEDTAVYFCAMRRSSWGQGTLVTVSSAS<br>TKGPSVFPLAPSSKSTSGGTAALGCLVKDYFPEPVTVSWNSGALTSGVHTFPAVLQSSG<br>LYSLSSVVTVPSSSLGTQTYICNVNHKPSNTKVDKKVEPKSCDKTHTCPPCPAPELLGGP<br>SVFLFPPKPKDTLYITREPEVTCVVVDVSHEDPEVKFNWYVDGVEVHNAKTKPREEQY<br>NNASRVVSVLTVLHQDWLNGKEYKCKVSNKALPAPIEKTISKAKGQPREPQVCTLPPS<br>RDELTKNQVSLSCAVKGFYPSDIAVEWESNGQPENNYKTTPPVLDSDGSFFLVSKLTV<br>DKSRWQQGNVFSCSVMHEALHNRFTQKSLSLSPG | 515 |
| | IV | DVVMTQTPLSLSVTPGQPASISCKSSQTIVHSNSKTYLEWYLQKPGQSPQLLIYKVSSRF<br>SGVPDRFSGSGSGTDFTLKISRVEAEDVGVYYCFQGSHVPLTFGQGTKLEIKRTVAAPS<br>VFIFPPSDEQLKSGTASVVCLLNNFYPREAKVQWKVDNALQSGNSQESVTEQDSKDST<br>YSLSSTLTLSKADYEKHKVYACEVTHQGLSSPVTKSFNRGEC | 517 |

TABLE 13

Amino acid sequences of humanized, bispecific binding proteins.

| Name | Chain | Sequence | SEQ ID NO |
|---|---|---|---|
| AS30_Hu6 x<br>C3_Hu10<br>Duobody | HC1 | QVQLVQSGAEVVKPGSSVKVSCEASGFTFTDSVITWVRQRPGQGLEWIGEIYPGSG<br>NFYYNEKFQGRVTITADKSTSTAYMELSSLRSEDTAVYFCAMRRSSWGQGTLVTVS<br>SASTKGPSVFPLAPSSKSTSGGTAALGCLVKDYFPEPVTVSWNSGALTSGVHTFPAV<br>LQSSGLYSLSSVVTVPSSSLGTQTYICNVNHKPSNTKVDKKVEPKSCDKTHTCPPCPA<br>PELLGGPSVFLFPPKPKDTLMISRTPEVTCVVVDVSHEDPEVKFNWYVDGVEVHNA<br>KTKPREEQYNNASRVVSVLTVLHQDWLNGKEYKCKVSNKALPAPIEKTISKAKGQPR<br>EPQVYTLPPSRDELTKNQVSLTCLVKGFYPSDIAVEWESNGQPENNYKTTPPVLDSD<br>GSFFLYSRLTVDKSRWQQGNVFSCSVMHEALHNHYTQKSLSLSPG | 518 |
| | HC2 | EVQLVESGGGLVKPGGSLRLSCAASGFTFSSYTMSWVRQAPGKGLEWVASISSSGS<br>NTYYPDSVKGRFTISRDNAKNNLYLQMNSLRAEDTALYYCARFDYGSSLDSWGQGT<br>LLTVSSASTKGPSVFPLAPSSKSTSGGTAALGCLVKDYFPEPVTVSWNSGALTSGVHT<br>FPAVLQSSGLYSLSSVVTVPSSSLGTQTYICNVNHKPSNTKVDKKVEPKSCDKTHTCP<br>PCPAPELLGGPSVFLFPPKPKDTLMISRTPEVTCVVVDVSHEDPEVKFNWYVDGVEV<br>HNAKTKPREEQYNNSARVVSVLTVLHQDWLNGKEYKCKVSNKALPAPIEKTISKAK<br>GQPREPQVYTLPPSRDELTKNQVSLTCLVKGFYPSDIAVEWESNGQPENNYKTTPP<br>VLDSDGSFLLYSKLTVDKSRWQQGNVFSCSVMHEALHNHYTQKSLSLSPG | 519 |
| | LC1 | DVVMTQTPLSLSVTPGQPASISCKSSQTIVHSNSKTYLEWYLQKPGQSPQLLIYKVSS<br>RFSGVPDRFSGSGSGTDFTLKISRVEAEDVGVYYCFQGSHVPLTFGQGTKLEIKRTVA<br>APSVFIFPPSDEQLKSGTASVVCLLNNFYPREAKVQWKVDNALQSGNSQESVTEQD<br>SKDSTYSLSSTLTLSKADYEKHKVYACEVTHUGLSSPVTKSFNRGEC | 520 |
| | LC2 | EIVLTQSPDFLSVTPKEKVTLTCRASQSISNNLHWYQQKSDQSPKLLIKYASQSISGIPS<br>RFSGSGSGTDFTLTINSVEAEDAATYFCQQSKSWPRTFGGGTKLEIKRTVAAPSVFIF<br>PPSDEQLKSGTASVVCLLNNFYPREAKVQWKVDNALQSGNSQESVTEQDSKDSTYS<br>LSSTLTLSKADYEKHKVYACEVTHQGLSSPVTKSFNRGEC | 521 |
| AS30_Hu6 x<br>C21_Hu11<br>Duetmab | HC1 | QVQLVQSGAEVVKPGSSVKVSCEASGFTFTDSVITWVRQRPGQGLEWIGEIYPGSG<br>NFYYNEKFQGRVTITADKSTSTAYMELSSLRSEDTAVYFCAMRRSSWGQGTLVTVS<br>SASTKGPSVCPLAPSSKSTSGGTAALGCLVKDYFPEPVTVSWNSGALTSGVHTFPAV<br>LQSSGLYSLSSVVTVPSSSLGTQTYICNVNHKPSNTKVDKKVEPKSVDKTHTCPPCPA<br>PE LLGGPSVFLFPPKPKDTLMISRTPEVTCVVVDVSHEDPEVKFNWYVDGVEVHNA<br>KTKPREEQYNNASRVVSVLTVLHQDWLNGKEYKCKVSNKALPAPIEKTISKAKGQPR | 524 |

TABLE 13-continued

Amino acid sequences of humanized, bispecific binding proteins.

| Name | Chain | Sequence | SEQ ID NO |
|---|---|---|---|
| | | EPQVYTLPPCRDELTKNQVSLWCLVKGFYPSDIAVEWESNGQPENNYKTTPPVLDS DGSFFLYSKLTVDKSRWQQGNVFSCSVMHEALHNHYTQKSLSLSPG | |
| | HC2 | EVQLVESGGGLVKPGGSLRLSCAASGFTFSSYTMSWVRQAPGKGLEWVASISSSGS NTYYPDSVKGRFTISRDNAKNNLYLQMNSLRAEDTALYYCARFDYGSSLDSWGQGT LLTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCDKTHTCP PCPAPELLGGPSVFLFPPKPKDTLMISRTPEVTCVVVDVSHEDPEVKFNWYVDGVEV HNAKTKPREEQYNNASRVVSVLTVLHQDWLNGKEYKCKVSNKALPAPIEKTISKAK GQPREPQVCTLPPSRDELTKNQVSLSCAVKGFYPSDIAVEWESNGQPENNYKTTPP VLDSDGSFFLVSKLTVDKSRWQQGNVFSCSVMHEALHNRFTQKSLSLSPG | 525 |
| | LC1 | DVVMTQTPLSLSVTPGQPASISCKSSQTIVHSNSKTYLEWYLQKPGQSPQLLIYKVSS RFSGVPDRFSGSGSGTDFTLKISRVEAEDVGVYYCFQGSHVPLTFGQGTKLEIKRTVA APSVFIFPPCDEQLKSGTASVVCLLNNFYPREAKVQWKVDNALQSGNSQESVTEQD SKDSTYSLSSTLTLSKADYEKHKVYACEVTHUGLSSPVTKSFNRGEV | 526 |
| | LC2 | EIVLTQSPDFLSVTPKEKVTLSCRASQSISNYLHWYQQKSDSPKLLIKYASQSISGIPS RFSGSGSGTDFTLSINSVEAEDAATYFCQQSKSWPRTFGGGTKLEIKRTVAAPSVFIF PPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 527 |
| AS30_Hu6 x C3_Hu10 TBTI | HC | QVQLVQSGAEVVKPGSSVKVSCEASGFTFTDSVITWVRQRPGQGLEWIGEIYPGSG NFYYNEKFQGRVTITADKSTSTAYMELSSLRSEDTAVYFCAMRRSSWGQGTLVTVS SGGGGSGGGGSEVQLVESGGGLVKPGGSLRLSCAASGFTFSSYTMSWVRQAPGKG LEWVASISSSGSNTYYPDSVKGRFTISRDNAKNNLYLQMNSLRAEDTALYYCARFDY GSSLDSWGQGTLLTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTKVDKK VEPKSCDKTHTCPPCPAPELLGGPSVFLFPPKPKDTLMISRTPEVTCVVVDVSHEDPE VKFNWYVDGVEVHNAKTKPREEQYNNASRVVSVLTVLHQDWLNGKEYKCKVSNK ALPAPIEKTISKAKGQPREPQVYTLPPSRDELTKNQVSLTCLVKGFYPSDIAVEWESN GQPENNYKTTPPVLDSDGSFFLYSKLTVDKSRWQQGNVFSCSVMHEALHNHYTQK SLSLSPG | 522 |
| | LC | DVVMTQTPLSLSVTPGQPASISCKSSQTIVHSNSKTYLEWYLQKPGQSPQLLIYKVSS RFSGVPDRFSGSGSGTDFTLKISRVEAEDVGVYYCFQGSHVPLTFGQGTKLEIKGGG GSGGGGSEIVLTQSPDFLSVTPKEKVTLTCRASQSISNNLHWYQQKSDQSPKLLIKYA SQSISGIPSRFSGSGSGTDFTLTINSVEAEDAATYFCQQSKSWPRTFGGGTKLEIKRTV AAPSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC | 523 |
| AS30_Hu6 x C21_Hu11 TBTI | HC | QVQLVQSGAEVVKPGSSVKVSCEASGFTFTDSVITWVRQRPGQGLEWIGEIYPGSG NFYYNEKFQGRVTITADKSTSTAYMELSSLRSEDTAVYFCAMRRSSWGQGTLVTVS SGGGGSGGGGSEVQLVESGGGLVKPGGSLRLSCAASGFTFSSYTMSWVRQAPGKG LEWVASISSSGSNTYYPDSVKGRFTISRDNAKNNLYLQMNSLRAEDTALYYCARFDY GSSLDSWGQGTLLTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTKVDKK VEPKSCDKTHTCPPCPAPELLGGPSVFLFPPKPKDTLMISRTPEVTCVVVDVSHEDPE VKFNWYVDGVEVHNAKTKPREEQYNNASRVVSVLTVLHQDWLNGKEYKCKVSNK ALPAPIEKTISKAKGQPREPQVYTLPPSRDELTKNQVSLTCLVKGFYPSDIAVEWESN GQPENNYKTTPPVLDSDGSFFLYSKLTVDKSRWQQGNVFSCSVMHEALHNHYTQK SLSLSPG | 528 |
| | LC | DVVMTQTPLSLSVTPGQPASISCKSSQTIVHSNSKTYLEWYLQKPGQSPQLLIYKVSS RFSGVPDRFSGSGSGTDFTLKISRVEAEDVGVYYCFQGSHVPLTFGQGTKLEIKGGG GSGGGGSEIVLTQSPDFLSVTPKEKVTLSCRASQSISNYLHWYQQKSDQSPKLLIKYA SQSISGIPSRFSGSGSGTDFTLSINSVEAEDAATYFCQQSKSWPRTFGGGTKLEIKRTV AAPSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC | 529 |
| AS30_Hu9 x C3_Hu11 CODV | HC | QVQLVQSGAEVVKPGSSVKVSCEASGFTFTDSVITWVRQRPGQGLEWIGEIYPGSG NFYYNEKFQGRVTITADKSTSTAYMELSSLRSEDTAVYFCAMRRSSWGQGTLVTVS SSEVQLVESGGGLVKPGGSLRLSCAASGFTFSSYTMSWVRQAPGKGLEWVASISSS GSNTYYPDSVKGRFTISRDNAKNNLYLQMNSLRAEDTALYYCARFDYGSSLDSWGQ GTLLTVSSRTASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSCDK HTCPPCPAPELLGGPSVFLFPPKPKDTLMISRTPEVTCVVVDVSHEDPEVKFNWYVD GVEVHNAKTKPREEQYNNASRVVSVLTVLHQDWLNGKEYKCKVSNKALPAPIEKTI SKAKGQPREPQVYTLPPSRDELTKNQVSLTCLVKGFYPSDIAVEWESNGQPENNYK TTPPVLDSDGSFFLYSKLTVDKSRWQQGNVFSCSVMHEALHNHYTQKSLSLSPG | 530 |
| | LC | EIVLTQSPDFLSVTPKEKVTLTCRASQSIGNNLHWYQQKSDQSPKLLIKYASQSISGIP SRFSGSGSGTDFTLTINSVEAEDAATYFCQQSKSWPRTFGGGTKLEIKGQPKAAPDV VMTQTPLSLSVTPGQPASISCRSSQTIVHSNSKTYLEWYLQKPGQSPQLLIYKVSNRF SGVPDRFSGSGSGTDFTLKISRVEAEDVGVYYCFQGSHVPLTFGAGTKLEIKTKGPSR TVAAPSVFIFPPSDEQLKSGTASVVCLLNNFYPREAKVQWKVDNALQSGNSQESVT EQDSKDSTYSLSSTLTLSKADYEKHKVYACEVTHQGLSSPVTKSFNRGEC | 531 |
| AS30_Hu9 x C21_Hu21 | HC | QVQLVQSGAEVVKPGSSVKVSCEASGFTFTDSVITWVRQRPGQGLEWIGEIYPGSG NFYYNEKFQGRVTITADKSTSTAYMELSSLRSEDTAVYFCAMRRSSWGQGTLVTVS | 532 |

TABLE 13-continued

Amino acid sequences of humanized, bispecific binding proteins.

| Name | Chain | Sequence | SEQ ID NO |
|------|-------|----------|-----------|
| CODV | | SSEVQLVESGGGLVQPGGSLRLSCAASGFTFSSYTMSWVRQAPGKGLEWVATISSS GDNTYYPDSVKGRFTISRDNSKNTLYLQMSSLRAEDTALYYCARFDYGSSLDSWGQ GTTLTVSSRTASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSCDKT HTCPPCPAPELLGGPSVFLFPPKPKDTLMISRTPEVTCVVVDVSHEDPEVKFNWYVD GVEVHNAKTKPREEQYNNASRVVSVLTVLHQDWLNGKEYKCKVSNKALPAPIEKTI SKAKGQPREPQVYTLPPSRDELTKNQVSLTCLVKGFYPSDIAVEWESNGQPENNYK TTPPVLDSGSFFLYSKLTVDKSRWQQGNVFSCSVMHEALHNHYTQKSLSLSPG | |
| | LC | EIVLTQSPDFLSVTPGEKVTLTCRASQSISNYLHWYQQKSDQSPKLLIKYASQSISGVP SRFSGSGSGTDFTLTISSVEAEDFATYFCQQSKSWPRTFGGGTKLEIKGQPKAAPDV VMTQTPLSLSVTPGQPASISCRSSQTIVHSNSKTYLEWYLQKPGQSPQLLIYKVSNRF SGVPDRFSGSGSGTDFTLKISRVEAEDVGVYYCFQGSHVPLTFGAGTKLEIKTKGPSR TVAAPSVFIFPPSDEQLKSGTASVVCLLNNFYPREAKVQWKVDNALQSGNSQESVT EQDSKDSTYSLSSTLTLSKADYEKHKVYACEVTHQGLSSPVTKSFNRG EC | 533 |

TABLE 14

Amino acid and DNA sequences of humanized, multispecific and bispecific binding proteins.

| SEQ ID NO | Binding Protein | Chain | Sequence | DNA/ Protein |
|-----------|-----------------|-------|----------|--------------|
| 306 | AS30SS_Hu6 | VH | VH domain | DNA |
| 307 | AS30SS_Hu6 | VH | FW1 | DNA |
| 308 | AS30SS_Hu6 | VH | CDR-H1 | DNA |
| 309 | AS30SS_Hu6 | VH | FW2 | DNA |
| 310 | AS30SS_Hu6 | VH | CDR-H2 | DNA |
| 311 | AS30SS_Hu6 | VH | FW3 | DNA |
| 312 | AS30SS_Hu6 | VH | CDR-H3 | DNA |
| 313 | AS30SS_Hu6 | VH | FW4 | DNA |
| 314 | AS30SS_Hu6 | VH | VH domain | protein |
| 315 | AS30SS_Hu6 | VH | FW1 | protein |
| 316 | AS30SS_Hu6 | VH | CDR-H1 | protein |
| 317 | AS30SS_Hu6 | VH | FW2 | protein |
| 318 | AS30SS_Hu6 | VH | CDR-H2 | protein |
| 319 | AS30SS_Hu6 | VH | FW3 | protein |
| 320 | AS30SS_Hu6 | VH | CDR-H3 | protein |
| 321 | AS30SS_Hu6 | VH | FW4 | protein |
| 322 | AS30SS_Hu6 | VL | VL domain | DNA |
| 323 | AS30SS_Hu6 | VL | FW1 | DNA |
| 324 | AS30SS_Hu6 | VL | CDR-L1 | DNA |
| 325 | AS30SS_Hu6 | VL | FW2 | DNA |
| 326 | AS30SS_Hu6 | VL | CDR-L2 | DNA |
| 327 | AS30SS_Hu6 | VL | FW3 | DNA |
| 328 | AS30SS_Hu6 | VL | CDR-L3 | DNA |
| 329 | AS30SS_Hu6 | VL | FW4 | DNA |
| 330 | AS30SS_Hu6 | VL | VL domain | protein |
| 331 | AS30SS_Hu6 | VL | FW1 | protein |
| 332 | AS30SS_Hu6 | VL | CDR-L1 | protein |
| 333 | AS30SS_Hu6 | VL | FW2 | protein |
| 334 | AS30SS_Hu6 | VL | CDR-L2 | protein |
| 335 | AS30SS_Hu6 | VL | FW3 | protein |
| 336 | AS30SS_Hu6 | VL | CDR-L3 | protein |
| 337 | AS30SS_Hu6 | VL | FW4 | protein |
| 338 | AS30SS_Hu9 | VH | VH domain | DNA |
| 339 | AS30SS_Hu9 | VH | FW1 | DNA |
| 340 | AS30SS_Hu9 | VH | CDR-H1 | DNA |
| 341 | AS30SS_Hu9 | VH | FW2 | DNA |
| 342 | AS30SS_Hu9 | VH | CDR-H2 | DNA |
| 343 | AS30SS_Hu9 | VH | FW3 | DNA |
| 344 | AS30SS_Hu9 | VH | CDR-H3 | DNA |
| 345 | AS30SS_Hu9 | VH | FW4 | DNA |
| 346 | AS30SS_Hu9 | VH | VH domain | protein |
| 347 | AS30SS_Hu9 | VH | FW1 | protein |
| 348 | AS30SS_Hu9 | VH | CDR-H1 | protein |
| 349 | AS30SS_Hu9 | VH | FW2 | protein |
| 350 | AS30SS_Hu9 | VH | CDR-H2 | protein |
| 351 | AS30SS_Hu9 | VH | FW3 | protein |
| 352 | AS30SS_Hu9 | VH | CDR-H3 | protein |
| 353 | AS30SS_Hu9 | VH | FW4 | protein |
| 354 | AS30SS_Hu9 | VL | VL domain | DNA |
| 355 | AS30SS_Hu9 | VL | FW1 | DNA |
| 356 | AS30SS_Hu9 | VL | CDR-L1 | DNA |
| 357 | AS30SS_Hu9 | VL | FW2 | DNA |
| 358 | AS30SS_Hu9 | VL | CDR-L2 | DNA |
| 359 | AS30SS_Hu9 | VL | FW3 | DNA |
| 360 | AS30SS_Hu9 | VL | CDR-L3 | DNA |
| 361 | AS30SS_Hu9 | VL | FW4 | DNA |
| 362 | AS30SS_Hu9 | VL | VL domain | protein |
| 363 | AS30SS_Hu9 | VL | FW1 | protein |
| 364 | AS30SS_Hu9 | VL | CDR-L1 | protein |
| 365 | AS30SS_Hu9 | VL | FW2 | protein |
| 366 | AS30SS_Hu9 | VL | CDR-L2 | protein |
| 367 | AS30SS_Hu9 | VL | FW3 | protein |
| 368 | AS30SS_Hu9 | VL | CDR-L3 | protein |
| 369 | AS30SS_Hu9 | VL | FW4 | protein |
| 370 | C3_Hu10 | VH | VH domain | DNA |
| 371 | C3_Hu10 | VH | FW1 | DNA |
| 372 | C3_Hu10 | VH | CDR-H1 | DNA |
| 373 | C3_Hu10 | VH | FW2 | DNA |
| 374 | C3_Hu10 | VH | CDR-H2 | DNA |
| 375 | C3_Hu10 | VH | FW3 | DNA |
| 376 | C3_Hu10 | VH | CDR-H3 | DNA |
| 377 | C3_Hu10 | VH | FW4 | DNA |
| 378 | C3_Hu10 | VH | VH domain | protein |
| 379 | C3_Hu10 | VH | FW1 | protein |
| 380 | C3_Hu10 | VH | CDR-H1 | protein |
| 381 | C3_Hu10 | VH | FW2 | protein |
| 382 | C3_Hu10 | VH | CDR-H2 | protein |
| 383 | C3_Hu10 | VH | FW3 | protein |
| 384 | C3_Hu10 | VH | CDR-H3 | protein |
| 385 | C3_Hu10 | VH | FW4 | protein |
| 386 | C3_Hu10 | VL | VL domain | DNA |
| 387 | C3_Hu10 | VL | FW1 | DNA |
| 388 | C3_Hu10 | VL | CDR-L1 | DNA |
| 389 | C3_Hu10 | VL | FW2 | DNA |
| 390 | C3_Hu10 | VL | CDR-L2 | DNA |
| 391 | C3_Hu10 | VL | FW3 | DNA |
| 392 | C3_Hu10 | VL | CDR-L3 | DNA |
| 393 | C3_Hu10 | VL | FW4 | DNA |
| 394 | C3_Hu10 | VL | VL domain | protein |
| 395 | C3_Hu10 | VL | FW1 | protein |
| 396 | C3_Hu10 | VL | CDR-L1 | protein |
| 397 | C3_Hu10 | VL | FW2 | protein |
| 398 | C3_Hu10 | VL | CDR-L2 | protein |
| 399 | C3_Hu10 | VL | FW3 | protein |
| 400 | C3_Hu10 | VL | CDR-L3 | protein |
| 401 | C3_Hu10 | VL | FW4 | protein |

TABLE 14-continued

Amino acid and DNA sequences of humanized, multispecific and bispecific binding proteins.

| SEQ ID NO | Binding Protein | Chain | Sequence | DNA/Protein |
|---|---|---|---|---|
| 402 | C3_Hu11 | VH | VH domain | DNA |
| 403 | C3_Hu11 | VH | FW1 | DNA |
| 404 | C3_Hu11 | VH | CDR-H1 | DNA |
| 405 | C3_Hu11 | VH | FW2 | DNA |
| 406 | C3_Hu11 | VH | CDR-H2 | DNA |
| 407 | C3_Hu11 | VH | FW3 | DNA |
| 408 | C3_Hu11 | VH | CDR-H3 | DNA |
| 409 | C3_Hu11 | VH | FW4 | DNA |
| 410 | C3_Hu11 | VH | VH domain | protein |
| 411 | C3_Hu11 | VH | FW1 | protein |
| 412 | C3_Hu11 | VH | CDR-H1 | protein |
| 413 | C3_Hu11 | VH | FW2 | protein |
| 414 | C3_Hu11 | VH | CDR-H2 | protein |
| 415 | C3_Hu11 | VH | FW3 | protein |
| 416 | C3_Hu11 | VH | CDR-H3 | protein |
| 417 | C3_Hu11 | VH | FW4 | protein |
| 418 | C3_Hu11 | VL | VL domain | DNA |
| 419 | C3_Hu11 | VL | FW1 | DNA |
| 420 | C3_Hu11 | VL | CDR-L1 | DNA |
| 421 | C3_Hu11 | VL | FW2 | DNA |
| 422 | C3_Hu11 | VL | CDR-L2 | DNA |
| 423 | C3_Hu11 | VL | FW3 | DNA |
| 424 | C3_Hu11 | VL | CDR-L3 | DNA |
| 425 | C3_Hu11 | VL | FW4 | DNA |
| 426 | C3_Hu11 | VL | VL domain | protein |
| 427 | C3_Hu11 | VL | FW1 | protein |
| 428 | C3_Hu11 | VL | CDR-L1 | protein |
| 429 | C3_Hu11 | VL | FW2 | protein |
| 430 | C3_Hu11 | VL | CDR-L2 | protein |
| 431 | C3_Hu11 | VL | FW3 | protein |
| 432 | C3_Hu11 | VL | CDR-L3 | protein |
| 433 | C3_Hu11 | VL | FW4 | protein |
| 434 | C21_Hu11 | VH | VH domain | DNA |
| 435 | C21_Hu11 | VH | FW1 | DNA |
| 436 | C21_Hu11 | VH | CDR-H1 | DNA |
| 437 | C21_Hu11 | VH | FW2 | DNA |
| 438 | C21_Hu11 | VH | CDR-H2 | DNA |
| 439 | C21_Hu11 | VH | FW3 | DNA |
| 440 | C21_Hu11 | VH | CDR-H3 | DNA |
| 441 | C21_Hu11 | VH | FW4 | DNA |
| 442 | C21_Hu11 | VH | VH domain | protein |
| 443 | C21_Hu11 | VH | FW1 | protein |
| 444 | C21_Hu11 | VH | CDR-H1 | protein |
| 445 | C21_Hu11 | VH | FW2 | protein |
| 446 | C21_Hu11 | VH | CDR-H2 | protein |
| 447 | C21_Hu11 | VH | FW3 | protein |
| 448 | C21_Hu11 | VH | CDR-H3 | protein |
| 449 | C21_Hu11 | VH | FW4 | protein |
| 450 | C21_Hu11 | VL | VL domain | DNA |
| 451 | C21_Hu11 | VL | FW1 | DNA |
| 452 | C21_Hu11 | VL | CDR-L1 | DNA |
| 453 | C21_Hu11 | VL | FW2 | DNA |
| 454 | C21_Hu11 | VL | CDR-L2 | DNA |
| 455 | C21_Hu11 | VL | FW3 | DNA |
| 456 | C21_Hu11 | VL | CDR-L3 | DNA |
| 457 | C21_Hu11 | VL | FW4 | DNA |
| 458 | C21_Hu11 | VL | VL domain | protein |
| 459 | C21_Hu11 | VL | FW1 | protein |
| 460 | C21_Hu11 | VL | CDR-L1 | protein |
| 461 | C21_Hu11 | VL | FW2 | protein |
| 462 | C21_Hu11 | VL | CDR-L2 | protein |
| 463 | C21_Hu11 | VL | FW3 | protein |
| 464 | C21_Hu11 | VL | CDR-L3 | protein |
| 465 | C21_Hu11 | VL | FW4 | protein |
| 466 | C21_Hu21 | VH | VH domain | DNA |
| 467 | C21_Hu21 | VH | FW1 | DNA |
| 468 | C21_Hu21 | VH | CDR-H1 | DNA |
| 469 | C21_Hu21 | VH | FW2 | DNA |
| 470 | C21_Hu21 | VH | CDR-H2 | DNA |
| 471 | C21_Hu21 | VH | FW3 | DNA |
| 472 | C21_Hu21 | VH | CDR-H3 | DNA |
| 473 | C21_Hu21 | VH | FW4 | DNA |
| 474 | C21_Hu21 | VH | VH domain | protein |
| 475 | C21_Hu21 | VH | FW1 | protein |
| 476 | C21_Hu21 | VH | CDR-H1 | protein |
| 477 | C21_Hu21 | VH | FW2 | protein |
| 478 | C21_Hu21 | VH | CDR-H2 | protein |
| 479 | C21_Hu21 | VH | FW3 | protein |
| 480 | C21_Hu21 | VH | CDR-H3 | protein |
| 481 | C21_Hu21 | VH | FW4 | protein |
| 482 | C21_Hu21 | VL | VL domain | DNA |
| 483 | C21_Hu21 | VL | FW1 | DNA |
| 484 | C21_Hu21 | VL | CDR-L1 | DNA |
| 485 | C21_Hu21 | VL | FW2 | DNA |
| 486 | C21_Hu21 | VL | CDR-L2 | DNA |
| 487 | C21_Hu21 | VL | FW3 | DNA |
| 488 | C21_Hu21 | VL | CDR-L3 | DNA |
| 489 | C21_Hu21 | VL | FW4 | DNA |
| 490 | C21_Hu21 | VL | VL domain | protein |
| 491 | C21_Hu21 | VL | FW1 | protein |
| 492 | C21_Hu21 | VL | CDR-L1 | protein |
| 493 | C21_Hu21 | VL | FW2 | protein |
| 494 | C21_Hu21 | VL | CDR-L2 | protein |
| 495 | C21_Hu21 | VL | FW3 | protein |
| 496 | C21_Hu21 | VL | CDR-L3 | protein |
| 497 | C21_Hu21 | VL | FW4 | protein |
| 498 | Triab 3407 | HC1 | Full chain | protein |
| 499 | Triab 3407 | HC2 | Full chain | protein |
| 500 | Triab 3407 | LC1 | Full chain | protein |
| 501 | Triab 3407 | LC2 | Full chain | protein |
| 502 | Triab 3423 | HC1 | Full chain | protein |
| 503 | Triab 3423 | HC2 | Full chain | protein |
| 504 | Triab 3423 | LC1 | Full chain | protein |
| 505 | Triab 3423 | LC2 | Full chain | protein |
| 506 | Triab 3429 | HC1 | Full chain | protein |
| 507 | Triab 3429 | HC2 | Full chain | protein |
| 508 | Triab 3429 | LC1 | Full chain | protein |
| 509 | Triab 3429 | LC2 | Full chain | protein |
| 510 | Triab 3437 | HC1 | Full chain | protein |
| 511 | Triab 3437 | HC2 | Full chain | protein |
| 512 | Triab 3437 | LC1 | Full chain | protein |
| 513 | Triab 3437 | LC2 | Full chain | protein |
| 514 | Triab 3439 | HC1 | Full chain | protein |
| 515 | Triab 3439 | HC2 | Full chain | protein |
| 516 | Triab 3439 | LC1 | Full chain | protein |
| 517 | Triab 3439 | LC2 | Full chain | protein |
| 518 | AS30_Hu6 × C3_Hu10 duobody | HC1 | Full chain | protein |
| 519 | AS30_Hu6 × C3_Hu10 duobody | HC2 | Full chain | protein |
| 520 | AS30_Hu6 × C3_Hu10 duobody | LC1 | Full chain | protein |
| 521 | AS30_Hu6 × C3_Hu10 duobody | LC2 | Full chain | protein |
| 522 | AS30_Hu6 × C3_Hu10 TBTI | HC | Full chain | protein |
| 523 | AS30_Hu6 × C3_Hu10 TBTI | LC | Full chain | protein |
| 524 | AS30_Hu6 × C21_Hu11 duetmab | HC1 | Full chain | protein |
| 525 | AS30_Hu6 × C21_Hu11 duetmab | HC2 | Full chain | protein |
| 526 | AS30_Hu6 × C21_Hu11 duetmab | LC1 | Full chain | protein |
| 527 | AS30_Hu6 × C21_Hu11 duetmab | LC2 | Full chain | protein |
| 528 | AS30_Hu6 × C21_Hu11 TBTI | HC | Full chain | protein |
| 529 | AS30_Hu6 × C21_Hu11 TBTI | LC | Full chain | protein |
| 530 | AS30_Hu9 × C3_Hu11 CODV | HC | Full chain | protein |
| 531 | AS30_Hu9 × C3_Hu11 CODV | LC | Full chain | protein |
| 532 | AS30_Hu9 × C21_Hu21 CODV | HC | Full chain | protein |
| 533 | AS30_Hu9 × C21_Hu21 CODV | LC | Full chain | protein |

Target Proteins

Provided herein are multispecific binding molecules (e.g., binding proteins) that include a binding domain that binds an extracellular portion of dystroglycan and a binding domain that binds laminin-2. The terms "binds" and "specifically binds" are used interchangeably herein. In some embodiments, a binding domain that "binds" an antigen (e.g., laminin-2 or an extracellular portion of dystroglycan) binds to the antigen with an $K_D$ of less than or equal to about $1\times10^{-6}$ M. In some embodiments, binding affinity (e.g., $K_D$) of the antigen binding domain to the antigen (e.g., an antigen epitope) is assayed using the antigen binding domain in a monovalent antibody or antigen-binding fragment thereof. In some embodiments, binding affinity (e.g., $K_D$) of the antigen binding domain to the antigen (e.g., an antigen epitope) is assayed using the antigen binding domain in a multispecific format of the present disclosure.

As used herein, dystroglycan (DG) refers to the dystrophin-associated protein that acts as a component of the dystrophin complex linking the extracellular matrix (ECM, also known as the basal lamina) to the F-actin-associated cytoskeleton of muscle fibers. Dystroglycan comprises two subunits, alpha dystroglycan and beta dystroglycan, that are post-translationally cleaved and associate non-covalently with each other. In some embodiments, the dystroglycan is human dystroglycan (e.g., a protein encoded by the human DAG1 gene as set forth in NCBI Ref. Seq. Gene ID No. 1605, or a protein corresponding to UniProt Entry Q14118). In some embodiments, the dystroglycan is mouse dystroglycan (e.g., a protein encoded by the mouse Dag1 gene as set forth in NCBI Ref. Seq. Gene ID No. 13138, or a protein corresponding to UniProt Entry Q62165).

In some embodiments, a binding domain of the present disclosure binds alpha-dystroglycan. In some embodiments, a binding domain of the present disclosure binds beta-dystroglycan. In some embodiments, a binding domain of the present disclosure binds a polypeptide comprising the sequence SIVVEWTNN TLPLEPCPKE QIIGLSRRIA DENGKPRPAF SNALEPDFKA LSIAVTGSGS CRHLQFIPVA PPSPGSSAAP ATEVPDRDPE KSSEDD (SEQ ID NO:290). In some embodiments, a binding domain of the present disclosure binds an epitope or region within the sequence SIVVEWTNN TLPLEPCPKE QIIGLSRRIA DENGKPRPAF SNALEPDFKA LSIAVTGSGS CRHLQFIPVA PPSPGSSAAP ATEVPDRDPE KSSEDD (SEQ ID NO:290). In some embodiments, a binding domain of the present disclosure binds a polypeptide comprising the sequence SIVVEWT NNTLPLEPCP KEQIAGLSRR IAEDDGKPRP AFSNALEPDF KATSITVTGS GSCRHLQFIP VVPPRRVPSE APPTEVPDRD PEKSSEDDV (SEQ ID NO:291). In some embodiments, a binding domain of the present disclosure binds an epitope or region within the sequence SIVVEWT NNTLPLEPCP KEQIAGLSRR IAEDDGKPRP AFSNALEPDF KATSITVTGS GSCRHLQFIP VVPPRRVPSE APPTEVPDRD PEKSSEDDV (SEQ ID NO:291). In some embodiments, a binding domain of the present disclosure binds the extracellular portion of human dystroglycan. In some embodiments, a binding domain of the present disclosure binds the extracellular portion of mouse dystroglycan. In some embodiments, a binding domain of the present disclosure binds the extracellular portions of human and mouse dystroglycan.

In some embodiments, a binding domain of the present disclosure binds the extracellular portion of human dystroglycan with an equilibrium dissociation constant ($K_D$) lower than about 1 µM, lower than about 500 nM, lower than about 400 nM, lower than about 300 nM, lower than about 200 nM, lower than about 100 nM, lower than about 50 nM, lower than about 25 nM, lower than about 10 nM, or lower than about 1 nM. In some embodiments, the affinity of binding between a binding domain of the present disclosure and the extracellular portion of human dystroglycan is measured when the binding domain is in a bispecific format, rather than as a monospecific binding domain (such as a monospecific antibody). In some embodiments, an antigen binding site of the present disclosure that binds the extracellular portion of dystroglycan binds the extracellular portion of human dystroglycan with an equilibrium dissociation constant ($K_D$) lower than about 1 µM, lower than about 500 nM, lower than about 400 nM, lower than about 300 nM, lower than about 200 nM, lower than about 100 nM, lower than about 50 nM, lower than about 25 nM, lower than about 10 nM, or lower than about 1 nM when assayed as part of a multispecific binding protein.

As used herein, laminin-2 (also known as merosin) refers to the extracellular basement membrane protein that binds to dystroglycan. Laminin-2 is composed of three subunits: alpha, beta, and gamma. In some embodiments, the laminin-2 is human laminin subunit alpha 2 (e.g., a protein encoded by the human LAMA2 gene as set forth in NCBI Ref. Seq. Gene ID No. 3908, or a protein corresponding to UniProt Entry P24043). In some embodiments, the dystroglycan is mouse laminin subunit alpha 2 (e.g., a protein encoded by the mouse Lama2 gene as set forth in NCBI Ref. Seq. Gene ID No. 16773, or a protein corresponding to UniProt Entry Q60675).

In some embodiments, a binding domain of the present disclosure binds laminin-2. In some embodiments, a binding domain of the present disclosure binds a polypeptide comprising a laminin G-like (LG) domain 4 of laminin-2, a laminin G-like (LG) domain 5 of laminin-2, or both. In some embodiments, a binding domain of the present disclosure binds a polypeptide comprising the sequence VQPQPV PTPAFPFPAP TMVHGPCVAE SEPALLTGSK QFGLSRNSHI AIAFDDTKVK NRLTIELEVR TEAESGLLFY MARINHADFA TVQLRNGFPY FSYDLGSGDT STMIPTKIND GQWHKIKIVR VKQEGILYVD DASSQTISPK KADILDVVGI LYVGGLPINY TTRRIGPVTY SLDGCVRNLH MEQAPVDLDQ PTSSFHVGTC FANAESGTYF DGTGFAKAVG GFKVGLDLLV EFEFRTTRPT GVLLGVSSQK MDGMGIEMID EKLMFHVDNG AGRFTAIYDA GIPGHMCNGQ WHKVTAKKIK NRLELVVDGN QVDAQSPNSA STSADTNDPV FVGGFPGGLN QFGLTTNIRF RGCIRSLKLT KGTGKPLEVN FAKALELRGV QPVSCPTT (SEQ ID NO:300). In some embodiments, a binding domain of the present disclosure binds an epitope or region within the sequence VQPQPV PTPAFPFPAP TMVHGPCVAE SEPALLTGSK QFGLSRNSHI AIAFDDTKVK NRLTIELEVR TEAESGLLFY MARINHADFA TVQLRNGFPY FSYDLGSGDT STMIPTKIND GQWHKIKIVR VKQEGILYVD DASSQTISPK KADILDVVGI LYVGGLPINY TTRRIGPVTY SLDGCVRNLH MEQAPVDLDQ PTSSFHVGTC FANAESGTYF DGTGFAKAVG GFKVGLDLLV EFEFRTTRPT GVLLGVSSQK MDGMGIEMID EKLMFHVDNG AGRFTAIYDA GIPGHMCNGQ WHKVTAKKIK NRLELVVDGN QVDAQSPNSA STSADTNDPV FVGGFPGGLN QFGLTTNIRF RGCIRSLKLT KGTGKPLEVN FAKALELRGV QPVSCPTT (SEQ ID NO:300). In some embodiments, a binding domain of the present disclosure binds a polypeptide comprising the sequence ANAESGTYF DGTGFAKAVG GFKVGLDLLV EFEFRTTRPT GVLLGVSSQK MDGMGIEMID EKLMFHVDNG AGRFTAIYDA GIPGHMCNGQ WHKVTAKKIK NRLELVVDGN QVDAQSPNSA STSADTNDPV FVGGFPGGLN QFGLTTNIRF RGCIRSLKLT KGTGKPLEVN FAKALELRGV QPVSCPTT (SEQ ID NO:292). In some embodiments, a binding domain of the present disclosure binds an epitope or region within the sequence ANAESGTYF DGTGFAKAVG GFKVGLDLLV EFEFRTTRPT GVLLGVSSQK MDGMGIEMID EKLMFHVDNG AGRFTAIYDA GIPGHMCNGQ WHKVTAKKIK NRLELVVDGN QVDAQSPNSA STSADTNDPV FVGGFPGGLN QFGLTTNIRF RGCIRSLKLT KGTGKPLEVN FAKALELRGV QPVSCPTT (SEQ ID NO:292). In some embodiments, a binding domain of the present disclosure binds a polypeptide comprising the sequence Q PEPVPTPAFP TPTPVLTHGP CAAESEPALL IGSKQFGLSR NSHIAIAFDD TKVKNRLTIE LEVRTEAESG LLFYMARINH ADFATVQLRN GLPYFSYDLG SGDTHTMIPT KINDGQWHKI KIMRSKQEGI LYVDGASNRT ISPKKADILD VVGMLYVGGL PINYTTRRIG PVTYSIDGCV RNLHMAEAPA DLEQPTSSFH VGTCFANAQR GTYFDGTGFA KAVGGFKVGL DLLVEFEFRT TTTTGVLLGI SSQKMDGMGI EMIDEKLMFH VDNGAGRFTA VYDAGVPGHL CDGQWHKVTA NKIKHRIELT VDGNQVEAQS PNPASTSADT NDPVFVGGFP DDLKQFGLTT SIPFRGCIRS LKLTKGTGKP LEVNFAKALE LRGVQPVSCP AN (SEQ ID NO:301). In some embodiments, a binding domain of the present disclosure binds an epitope or region within the sequence Q PEPVPTPAFP TPTPVLTHGP CAAESEPALL IGSKQFGLSR NSHIAIAFDD TKVKNRLTIE LEVRTEAESG LLFYMARINH ADFATVQLRN GLPYFSYDLG SGDTHTMIPT KINDGQWHKI KIMRSKQEGI LYVDGASNRT ISPKKADILD VVGMLYVGGL PINYTTRRIG PVTYSIDGCV RNLHMAEAPA DLEQPTSSFH VGTCFANAQR GTYFDGTGFA KAVGGFKVGL DLLVEFEFRT TTTTGVLLGI SSQKMDGMGI EMIDEKLMFH VDNGAGRFTA VYDAGVPGHL CDGQWHKVTA NKIKHRIELT VDGNQVEAQS PNPASTSADT NDPVFVGGFP DDLKQFGLTT SIPFRGCIRS LKLTKGTGKP LEVNFAKALE LRGVQPVSCP AN (SEQ ID NO:301). In some embodiments, a binding domain of the present disclosure binds a polypeptide comprising the sequence ANAQR GTYFDGTGFA KAVGGFKVGL DLLVEFEFRT TTTTGVLLGI SSQKMDGMGI EMIDEKLMFH VDNGAGRFTA VYDAGVPGHL CDGQWHKVTA NKIKHRIELT VDGNQVEAQS PNPASTSADT NDPVFVGGFP DDLKQFGLTT SIPFRGCIRS LKLTKGTGKP LEVNFAKALE LRGVQPVSCP AN (SEQ ID NO:293). In some embodiments, a binding domain of the present disclosure binds an epitope or region within the sequence ANAQR GTYFDGTGFA KAVGGFKVGL DLLVEFEFRT TTTTGVLLGI SSQKMDGMGI EMIDEKLMFH VDNGAGRFTA VYDAGVPGHL CDGQWHKVTA NKIKHRIELT VDGNQVEAQS PNPASTSADT NDPVFVGGFP DDLKQFGLTT SIPFRGCIRS LKLTKGTGKP LEVNFAKALE LRGVQPVSCP AN (SEQ ID NO:293). In some embodiments, a binding domain of the present disclosure binds human laminin-2. In some embodiments, a binding domain of the present disclosure binds mouse laminin-2. In some embodiments, a binding domain of the present disclosure binds human and mouse laminin-2.

In some embodiments, a binding domain of the present disclosure binds human laminin-2 with an equilibrium dissociation constant ($K_D$) lower than about 1 μM, lower than about 500 nM, lower than about 400 nM, lower than about 300 nM, lower than about 200 nM, lower than about 100 nM, lower than about 50 nM, lower than about 25 nM, lower than about 10 nM, or lower than about 1 nM. In some embodiments, the affinity of binding between a binding domain of the present disclosure and human laminin-2 is measured when the binding domain is in a bispecific format, rather than as a monospecific binding domain (such as a monospecific antibody). In some embodiments, an antigen binding site of the present disclosure that binds laminin-2 binds human laminin-2 with an equilibrium dissociation constant ($K_D$) lower than about 1 μM, lower than about 500 nM, lower than about 400 nM, lower than about 300 nM, lower than about 200 nM, lower than about 100 nM, lower than about 50 nM, lower than about 25 nM, lower than about 10 nM, or lower than about 1 nM when assayed as part of a multispecific binding protein.

In some embodiments, a $V_{H1}/V_{L1}$ binding pair of the present disclosure binds the extracellular portion of dystroglycan, and a $V_{H2}/V_{L2}$ binding pair of the present disclosure binds laminin-2. In some embodiments, a $V_{H2}/V_{L2}$ binding pair of the present disclosure binds the extracellular portion of dystroglycan, and a $V_{H1}/V_{L1}$ binding pair of the present disclosure binds laminin-2.

Antibodies

The present disclosure also provides antibodies (e.g., monovalent and/or monoclonal antibodies) comprising 1, 2, 3, 4, 5, or 6 CDR sequences of a binding domain shown in Table A2, D2, or I4, or a VH and/or VL domain sequence of a binding domain shown in Table D2 or I4 or encoded by a polynucleotide sequence shown in Table G2. In some embodiments, the antibody binds an extracellular portion of dystroglycan. In some embodiments, the antibody binds laminin-2. In some embodiments, the antibody comprises (a) an antibody heavy chain comprising a heavy chain variable domain (VH) comprising a CDR-H1 comprising an amino acid sequence selected from the group consisting of SEQ ID NOs:1-8, a CDR-H2 comprising an amino acid sequence selected from the group consisting of SEQ ID NOs:9-17, and a CDR-H3 comprising an amino acid sequence selected from the group consisting of SEQ ID NOs:18-27; and (b) an antibody light chain comprising a light chain variable domain (VL) comprising a CDR-L1 comprising an amino acid sequence selected from the group consisting of SEQ ID NOs:28-37, a CDR-L2 comprising an amino acid sequence selected from the group consisting of SEQ ID NOs:38-42, and a CDR-L3 comprising an amino acid sequence selected from the group consisting of SEQ ID NOs:43-50. In some embodiments, the VH domain comprises an amino acid sequence selected from the group consisting of SEQ ID NOs:170, 172, 174, 176, 178, 180, 182, 184, 186, and 188; and the VL domain comprises an amino acid sequence selected from the group consisting of SEQ ID NOs:171, 173, 175, 177, 179, 181, 183, 185, 187, and 189. In some embodiments, the antibody comprises (a) an antibody heavy chain comprising a heavy chain variable domain (VH) comprising a CDR-H1 comprising the sequence of SEQ ID NO:316, a CDR-H2 comprising the sequence of SEQ ID NO:318, and a CDR-H3 comprising the sequence of SEQ ID NO:320; and (b) an antibody light chain comprising a light chain variable domain (VL) comprising a CDR-L1 comprising the sequence of SEQ ID NO:332, a CDR-L2 comprising the sequence of SEQ ID NO:334, and a CDR-L3 comprising the sequence of SEQ ID NO:336. In some embodiments, the VH domain comprises the amino acid sequence of SEQ ID NO:314, and the VL domain comprises the amino acid sequence of SEQ ID NO:330. In some embodiments, the VH domain comprises the amino acid sequence of SEQ ID NO:346, and the VL domain comprises the amino acid sequence of SEQ ID NO:362. In some embodiments, the antibody comprises (a) an antibody heavy chain comprising a CDR-H1 comprising an amino acid sequence selected from the group consisting of SEQ ID NOs:51-55 and 81-95, a CDR-H2 comprising an amino acid sequence selected from the group consisting of SEQ ID NOs:56-60 and 96-110, and a CDR-H3 comprising an amino acid sequence selected from the group consisting of SEQ ID NOs:61-65 and 111-125; and (b) an antibody light chain comprising a light chain variable domain (VL) comprising a CDR-L1 comprising an amino acid sequence selected from the group consisting of SEQ ID NOs:66-70 and 126-140, a CDR-L2 comprising an amino acid sequence selected from the group consisting of SEQ ID NOs:38, 71-75, and 141-154, and a CDR-L3 comprising an amino acid sequence selected from the group consisting of SEQ ID NOs:76-80 and 155-169. In some embodiments, the VH domain comprises an amino acid sequence selected from the group consisting of SEQ ID NOs:190, 192, 194, 196, 198, 200, 202, 204, 206, 208, 210, 212, 214, 216, 218, 220, 222, 224, 226, and 228; and the VL domain comprises an amino acid sequence selected from the group consisting of SEQ ID NOs: 191, 193, 195, 197, 199, 201, 203, 205, 207, 209, 211, 213, 215, 217, 219, 221, 223, 225, 227, and 229. In some embodiments, the antibody comprises an antibody heavy chain comprising a heavy chain variable domain (VH) comprising a CDR-H1 comprising the sequence of SEQ ID NO:380, a CDR-H2 comprising the sequence of SEQ ID NO:382, and a CDR-H3 comprising the sequence of SEQ ID NO:384, and an antibody light chain comprising a light chain variable domain (VL) comprising a CDR-L1 comprising the sequence of SEQ ID NO:428, a CDR-L2 comprising the sequence of SEQ ID NO:398, and a CDR-L3 comprising the sequence of SEQ ID NO:400. In some embodiments, the antibody comprises an antibody heavy chain comprising a heavy chain variable domain (VH) comprising a CDR-H1 comprising the sequence of SEQ ID NO:380, a CDR-H2 comprising the sequence of SEQ ID NO:382, and a CDR-H3 comprising the sequence of SEQ ID NO:384, and an antibody light chain comprising a light chain variable domain (VL) comprising a CDR-L1 comprising the sequence of SEQ ID NO:428, a CDR-L2 comprising the sequence of SEQ ID NO:398, and a CDR-L3 comprising the sequence of SEQ ID NO:400. In some embodiments, the antibody comprises an antibody heavy chain comprising a heavy chain variable domain (VH) comprising a CDR-H1 comprising the sequence of SEQ ID NO:444, a CDR-H2 comprising the sequence of SEQ ID NO:446, and a CDR-H3 comprising the sequence of SEQ ID NO:448, and an antibody light chain comprising a light chain variable domain (VL) comprising a CDR-L1 comprising the sequence of SEQ ID NO:460, a CDR-L2 comprising the sequence of SEQ ID NO:462, and a CDR-L3 comprising the sequence of SEQ ID NO:464. In some embodiments, the antibody comprises an antibody heavy chain comprising a heavy chain variable domain (VH) comprising a CDR-H1 comprising the sequence of SEQ ID NO:444, a CDR-H2 comprising the sequence of SEQ ID NO:478, and a CDR-H3 comprising the sequence of SEQ ID NO:448, and an antibody light chain comprising a light chain variable domain (VL) comprising a CDR-L1 comprising the sequence of SEQ ID NO:460, a CDR-L2 comprising the sequence of SEQ ID NO:462, and a CDR-L3 comprising the sequence of SEQ ID NO:464. In some embodiments, the VH domain comprises the amino acid sequence of SEQ ID NO:378, and the VL domain comprises the amino acid sequence of SEQ ID NO:394. In some embodiments, the VH domain comprises the amino acid sequence of SEQ ID NO:410, and the VL domain comprises the amino acid sequence of SEQ ID NO:426. In some embodiments, the VH domain comprises the amino acid sequence of SEQ ID NO:442, and the VL domain comprises the amino acid sequence of SEQ ID NO:458. In some embodiments, the VH domain comprises the amino acid sequence of SEQ ID NO:474, and the VL domain comprises the amino acid sequence of SEQ ID NO:490.

Nucleic Acids

Provided herein are isolated nucleic acid molecules comprising a nucleotide sequence encoding any of the multi-specific (e.g., bispecific) binding molecules (e.g., bispecific binding proteins) of the present disclosure.

Standard recombinant DNA methodologies are used to construct the polynucleotides that encode the polypeptides which form the binding proteins, incorporate these polynucleotides into recombinant expression vectors, and introduce such vectors into host cells. See e.g., Sambrook et al., 2001, MOLECULAR CLONING: A LABORATORY MANUAL (Cold Spring Harbor Laboratory Press, 3rd ed.). Enzymatic reactions and purification techniques may be performed according to manufacturer's specifications, as commonly accomplished in the art, or as described herein. Unless specific definitions are provided, the nomenclature utilized in connection with, and the laboratory procedures and techniques of, analytical chemistry, synthetic organic chemistry, and medicinal and pharmaceutical chemistry described herein are those well-known and commonly used in the art. Similarly, conventional techniques may be used for chemical syntheses, chemical analyses, pharmaceutical preparation, formulation, delivery, and treatment of patients.

Other aspects of the present disclosure relate to isolated nucleic acid molecules comprising a nucleotide sequence encoding any of the binding proteins or polypeptide chains thereof described herein. In some embodiments, the isolated nucleic acid is operably linked to a heterologous promoter to direct transcription of the binding protein-coding nucleic acid sequence. A promoter may refer to nucleic acid control sequences which direct transcription of a nucleic acid. A first nucleic acid sequence is operably linked to a second nucleic acid sequence when the first nucleic acid sequence is placed in a functional relationship with the second nucleic acid sequence. For instance, a promoter is operably linked to a coding sequence of a binding protein if the promoter affects the transcription or expression of the coding sequence. Examples of promoters may include, but are not limited to, promoters obtained from the genomes of viruses (such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), and the like), from heterologous eukaryotic promoters (such as the actin promoter, an immunoglobulin promoter, from heat-shock promoters, and the like), the CAG-promoter (Niwa et al., Gene 108(2):193-9, 1991), the phosphoglycerate kinase (PGK)-promoter, a tetracycline-inducible promoter (Masui et al., Nucleic Acids Res. 33:e43, 2005), the lac system, the trp system, the tac system, the trc system, major operator and promoter regions of phage lambda, the promoter for 3-phosphoglycerate kinase, the promoters of yeast acid phosphatase, and the promoter of the yeast alpha-mating factors. Polynucleotides encoding binding proteins of the present disclosure may be under the control of a constitutive promoter, an inducible promoter, or any other suitable promoter described herein or other suitable promoter that will be readily recognized by one skilled in the art.

In some embodiments, the isolated nucleic acid is incorporated into a vector. In some embodiments, the vector is an expression vector. Expression vectors may include one or more regulatory sequences operatively linked to the polynucleotide to be expressed. The term "regulatory sequence" includes promoters, enhancers and other expression control elements (e.g., polyadenylation signals). Examples of suitable enhancers may include, but are not limited to, enhancer sequences from mammalian genes (such as globin, elastase, albumin, α-fetoprotein, insulin and the like), and enhancer sequences from a eukaryotic cell virus (such as SV40 enhancer on the late side of the replication origin (bp 100-270), the cytomegalovirus early promoter enhancer, the polyoma enhancer on the late side of the replication origin, adenovirus enhancers, and the like). Examples of suitable vectors may include, for example, plasmids, cosmids, episomes, transposons, and viral vectors (e.g., adenoviral, vaccinia viral, Sindbis-viral, measles, herpes viral, lentiviral, retroviral, adeno-associated viral vectors, etc.). Expression vectors can be used to transfect host cells, such as, for example, bacterial cells, yeast cells, insect cells, and mammalian cells. Biologically functional viral and plasmid DNA vectors capable of expression and replication in a host are known in the art, and can be used to transfect any cell of interest.

Further provided herein are vector systems comprising multiple vectors, wherein the multiple vectors collectively encode a bispecific binding protein of the present disclosure. For example, in some embodiments, a vector system comprises one or more vectors encoding a first, second, third, and fourth polypeptide chain of a bispecific binding molecule of the present disclosure. In some embodiments, a vector system comprises a first, second, third, and fourth polypeptide chain of a bispecific binding molecule of the present disclosure.

Host Cells and Methods of Producing Binding Proteins

Other aspects of the present disclosure relate to a host cell (e.g., an isolated host cell) comprising one or more isolated polynucleotides, vectors, and/or vector systems described herein. In some embodiments, an isolated host cell of the present disclosure is cultured in vitro. In some embodiments, the host cell is a bacterial cell (e.g., an *E. coli* cell). In some embodiments, the host cell is a yeast cell (e.g., an *S. cerevisiae* cell). In some embodiments, the host cell is an insect cell. Examples of insect host cells may include, for example, *Drosophila* cells (e.g., S2 cells), *Trichoplusia ni* cells (e.g., High Five™ cells), and *Spodoptera frupperda* cells (e.g., Sf21 or Sf9 cells). In some embodiments, the host cell is a mammalian cell. Examples of mammalian host cells may include, for example, human embryonic kidney cells (e.g., 293 or 293 cells subcloned for growth in suspension culture), Expi293™ cells, CHO cells, baby hamster kidney cells (e.g., BHK, ATCC CCL 10), mouse sertoli cells (e.g., TM4 cells), monkey kidney cells (e.g., CV1 ATCC CCL 70), African green monkey kidney cells (e.g., VERO-76, ATCC CRL-1587), human cervical carcinoma cells (e.g., HELA, ATCC CCL 2), canine kidney cells (e.g., MDCK, ATCC CCL 34), buffalo rat liver cells (e.g., BRL 3A, ATCC CRL 1442), human lung cells (e.g., W138, ATCC CCL 75), human liver cells (e.g., Hep G2, HB 8065), mouse mammary tumor cells (e.g., MMT 060562, ATCC CCL51), TRI cells, MRC 5 cells, FS4 cells, a human hepatoma line (e.g., Hep G2), and myeloma cells (e.g., NS0 and Sp2/0 cells).

Other aspects of the present disclosure relate to a method of producing any of the binding proteins described herein. In some embodiments, the method includes a) culturing a host cell (e.g., any of the host cells described herein) comprising an isolated nucleic acid, vector, and/or vector system (e.g., any of the isolated nucleic acids, vectors, and/or vector systems described herein) under conditions such that the host cell expresses the binding molecule; and b) isolating the binding molecule from the host cell.

In some embodiments, multiple host cells can be used to produce components of a bispecific binding molecule (e.g., protein), which are then assembled into the bispecific binding molecule. In some embodiments, provided herein is a method of producing a bispecific binding protein comprising a first binding domain that binds an extracellular portion of dystroglycan and a second binding domain that binds laminin-2, the method comprising: a) culturing a first host cell that comprises a nucleic acid molecule encoding a first polypeptide chain comprising the first binding domain under conditions such that the host cell expresses the first polypeptide chain as part of a first monospecific binding protein with a first CH3 domain; b) culturing a second host cell that comprises a nucleic acid molecule encoding a second polypeptide chain comprising the second binding domain conditions such that the host cell expresses the second polypeptide chain as part of a second monospecific binding protein with a second CH3 domain; c) isolating the first monospecific binding protein from the first host cell; d) isolating the second monospecific binding protein from the second host cell; e) incubating the isolated first and second monospecific binding proteins under reducing conditions sufficient to allow cysteines in the hinge region to undergo disulfide bond isomerization; and f) obtaining the bispecific binding protein, wherein the first and second CH3 domains are different and are such that the heterodimeric interaction between said first and second CH3 domains is stronger than each of the homodimeric interactions of said first and second CH3 domains. For greater description, see, e.g., US PG Pub. No. US2013/0039913 and Labrijn, A. F. et al. (2013) *Proc. Natl. Acad. Sci.* 110:5145-5150.

Methods of culturing host cells under conditions to express a protein are well known to one of ordinary skill in the art. Methods of isolating proteins from cultured host cells are well known to one of ordinary skill in the art, including, for example, by affinity chromatography (e.g., two step affinity chromatography comprising protein A affinity chromatography followed by size exclusion chromatography).

Use for Binding Proteins

Further provided herein are methods for treating or preventing an alpha-dystroglycanopathy in an individual, the method comprising administering to the individual a bispecific binding molecule of the present disclosure. Also provided herein are methods for providing linkage between laminin-2 and an extracellular portion of dystroglycan in an individual, the method comprising administering to the individual a bispecific binding molecule of the present disclosure. Further provided herein are kits comprising a bispecific binding molecule of the present disclosure and instructions for use in treating or preventing an alpha-dystroglycanopathy in an individual. In some embodiments, the individual is a human.

Further provided herein are methods for treating or preventing an alpha-dystroglycanopathy in an individual, the method comprising administering to the individual a multispecific binding molecule of the present disclosure. Also provided herein are methods for providing linkage between laminin-2 and an extracellular portion of dystroglycan in an individual, the method comprising administering to the individual a multispecific binding molecule of the present disclosure. Further provided herein are kits comprising a multispecific binding molecule of the present disclosure and instructions for use in treating or preventing an alpha-dystroglycanopathy in an individual. In some embodiments, the individual is a human.

In some embodiments, the individual has reduced expression of alpha-dystroglycan (e.g., as compared to expression in a control individual, or one lacking a genetic mutation described herein). In some embodiments, expression refers to expression in one or more tissues, e.g., muscle tissue.

In some embodiments, alpha-dystroglycan expressed in the individual has impaired or aberrant O-glycosylation (e.g., as compared to expression in a control individual, or one lacking a genetic mutation described herein).

In some embodiments, the individual has, has been diagnosed with, or has a propensity for developing an alpha-dystroglycanopathy. In some embodiments, the individual has a mutation in a gene selected from the group consisting of: dystroglycan (DAG1), protein O-mannosyltransferase-1 (POMT1), protein O-mannosyltransferase-2 (POMT2), protein O-linked mannose beta1,2-N-acetylglucosylaminyltransferase subunit 1 (POMGNT1), protein O-linked mannose beta1,4-N-acetylglucosylaminyltransferase subunit 2 (POMGNT2), xylosyl- and glucuronyltransferase 1 (LARGE1), xylosyl- and glucuronyltransferase 2 (LARGE2), dolichyl-phosphate mannosyltransferase subunit 1 (DPM1), dolichyl-phosphate mannosyltransferase subunit 2 (DPM2), dolichyl-phosphate mannosyltransferase subunit 3 (DPM3), fukutin, fukutin related protein (FKRP), isprenoid synthase domain containing (ISPD), protein O-mannose kinase (POMK), beta-1,3-N-acetylgalactosaminyltransferase 2 (B3GALNT2), beta-1,4-glucuronyltransferase 1 (B4GAT1), dolichol kinase (DOLK), transmembrane protein 5 (TMEM5), and GDP-mannose pyrophosphorylase B (GMPPB).

In some embodiments, a bispecific binding molecule of the present disclosure is administered by intravenous infusion, intramuscular injection, intraperitoneal injection, or subcutaneous injection.

The binding proteins can be employed in any known assay method, such as competitive binding assays, direct and indirect sandwich assays, and immunoprecipitation assays for the detection and quantitation of one or more target antigens. The binding proteins will bind the one or more target antigens with an affinity that is appropriate for the assay method being employed.

Also provided herein are pharmaceutical compositions comprising a bispecific binding molecule of the present disclosure and an optional pharmaceutically acceptable carrier.

Also provided herein are pharmaceutical compositions comprising a multispecific binding molecule of the present disclosure and an optional pharmaceutically acceptable carrier.

The pharmaceutical composition can contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—e.g., sodium or potassium chloride—or mannitol sorbitol), delivery vehicles, diluents, excipients and/or pharmaceutical adjuvants (see, e.g., REMINGTON'S PHARMACEUTICAL SCIENCES (18th Ed., A. R. Gennaro, ed., Mack Publishing Company 1990), and subsequent editions of the same, incorporated herein by reference for any purpose). Acceptable formulation materials are nontoxic to recipients at the dosages and concentrations employed.

The optimal pharmaceutical composition will be determined by a skilled artisan depending upon, for example, the intended route of administration, delivery format, and desired dosage. Such compositions can influence the physical state, stability, rate of in vivo release, and rate of in vivo clearance of the binding protein.

The primary vehicle or carrier in a pharmaceutical composition can be either aqueous or non-aqueous in nature. For example, a suitable vehicle or carrier for injection can be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which can further include sorbitol or a suitable substitute. In one embodiment of the disclosure, binding protein compositions can be prepared for storage by mixing the selected composition having the desired degree of purity with optional formulation agents in the form of a lyophilized cake or an aqueous solution. Further, the binding protein can be formulated as a lyophilizate using appropriate excipients such as sucrose.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use can be in the form of a pyrogen-free, parenterally acceptable, aqueous solution comprising the desired binding protein in a pharmaceutically acceptable vehicle. A particularly suitable vehicle for parenteral injection is sterile distilled water in which a binding protein is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which can then be delivered via a depot injection. Hyaluronic acid can also be used, and this can have the effect of promoting sustained duration in the circulation. Other suitable means for the introduction of the desired molecule include implantable drug delivery devices.

It is also contemplated that certain formulations can be administered orally. In one embodiment of the disclosure, binding proteins that are administered in this fashion can be formulated with or without those carriers customarily used in the compounding of solid dosage forms such as tablets and capsules. For example, a capsule can be designed to release the active portion of the formulation at the point in the gastrointestinal tract where bioavailability is maximized and pre-systemic degradation is minimized. Additional agents can be included to facilitate absorption of the binding protein. Diluents, flavorings, low melting point waxes, vegetable oils, lubricants, suspending agents, tablet disintegrating agents, and binders can also be employed.

Another pharmaceutical composition can involve an effective quantity of binding proteins in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions of the disclosure will be evident to those skilled in the art, including formulations involving binding proteins in sustained- or controlled-delivery formulations. Techniques for formulating a variety of other sustained- or controlled-delivery means, such as liposome carriers, bio-erodible microparticles or porous beads and depot injections, are also known to those skilled in the art. Additional examples of sustained-release preparations include semipermeable polymer matrices in the form of shaped articles, e.g. films, or microcapsules. Sustained release matrices can include polyesters, hydrogels, polylactides, copolymers of L-glutamic acid and gamma ethyl-L-glutamate, poly(2-hydroxyethyl-methacrylate), ethylene vinyl acetate, or poly-D(−)-3-hydroxybutyric acid. Sustained-release compositions can also include liposomes, which can be prepared by any of several methods known in the art.

Pharmaceutical compositions to be used for in vivo administration typically must be sterile. This can be accomplished by filtration through sterile filtration membranes. Where the composition is lyophilized, sterilization using this method can be conducted either prior to, or following, lyophilization and reconstitution. The composition for parenteral administration can be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it can be stored in sterile vials as a solution, suspension, gel, emulsion, solid, or as a dehydrated or lyophilized powder. Such formulations can be stored either in a ready-to-use form or in a form (e.g., lyophilized) requiring reconstitution prior to administration.

The disclosure also encompasses kits for producing a single-dose administration unit. The kits can each contain both a first container having a dried protein and a second container having an aqueous formulation. Also included within the scope of this disclosure are kits containing single and multi-chambered pre-filled syringes (e.g., liquid syringes and lyosyringes).

The effective amount of a binding protein pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the binding protein is being used, the route of administration, and the size (body weight, body surface, or organ size) and condition (the age and general health) of the patient. Accordingly, the clinician can titer the dosage and modify the route of administration to obtain the optimal therapeutic effect.

Dosing frequency will depend upon the pharmacokinetic parameters of the binding protein in the formulation being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

EXAMPLES

The present disclosure will be more fully understood by reference to the following examples. They should not, however, be construed as limiting the scope of the present disclosure. It is understood that the examples and embodiments described herein are for illustrative purposes only and that various modifications or changes in light thereof will be suggested to persons skilled in the art and are to be included within the spirit and purview of this application and scope of the appended claims.

Example 1

Identification of Anti-Beta-DG ECD, Anti-LG-5, and Anti-LG-4/5 Antibodies

Methods
Protein Expression

To express murine beta-DG extracellular domain (mbeta-DG ECD), a construct was generated that contained an *E. coli* codon-optimized cassette encoding an N-terminal maltose binding protein, TEV cleavage site, mbeta-DG (UniProt Q62165, amino acids 652-746), and a C-terminal HPC4 tag, with pET22b as the parent vector backbone. The construct was transformed into chemically competent Origami B (DE3) pLysS cells (Novagen). Expression was performed at 37° C., with ITPG induction at OD=0.6. Cells were pelleted and resuspended in lysis buffer containing EDTA-free protease inhibitors (Roche) and lysed by sonication. mbeta-DG-HPC4 was purified from clarified cell lysate by processing cell lysate over an amylose resin column (New England Biolabs), cleaving off the maltose binding protein with Turbo TEV protease (Eton Biosciences), processing the digest over an amylose resin and His-Trap FastFlow column (GE Healthcare) to remove undigested fusion protein and cleaved maltose binding protein, and processing the flow through over NETS-activated Sepharose 4 FastFlow resin (GE Healthcare) coupled with mouse anti-HPC4 antibody.

Further purification was carried out on a Superdex 75 size exclusion column (GE Healthcare), and eluate fractions with highly purified mbeta-DG-HPC4 (as determined by running fraction samples on an SDS-PAGE gel and coomassie staining) were collected and pooled.

To express murine or laminin G-like 5 domain (mLG-5 or hLG-5) constructs were generated that contained a mammalian codon-optimized cassette encoding N-terminal Avi and HPC4 tags, and either mLG-5 (see UniProt Q60675, amino acids 2932-3118; SEQ ID NO:292) or hLG-5 (UniProt P24043, amino acids 2936-3122; SEQ ID NO:293). The construct was used to transfect Expi293F cells using Expifectamine reagent (Thermo Fisher). After 7 days expression, soluble biotinylated protein was purified from the supernatant with NHS-activated Sepharose 4 FastFlow resin (GE Healthcare) coupled with mouse anti-HPC4 antibody.

To express murine or human laminin G-like 4 and 5 domains (mLG-4/5 or hLG-4/5), constructs were generated that contained a mammalian codon-optimized cassette encoding an N-terminal mIgG2a fusion partner, TEV cleavage site, an Avi tag, an HPC4 tag, and either mLG-4/5 (UniProt Q60675, amino acids 2725-3118; SEQ ID NO:292) or hLG-4/5 (UniProt P24043, amino acids 2729-3122; SEQ ID NO:293). The constructs were used to transfect Expi293F cells using Expifectamine reagent (Thermo Fisher). After 7 days expression, soluble protein was purified from the supernatant with a HiTrap Mab Select SuRe column (GE Healthcare). mIgG2a was cleaved off the mLG-4/5 protein using Turbo TEV protease (Nacalai USA), and the digest was processed over Mab Select SuRe resin (GE Healthcare) and Ni-NTA resin (Qiagen) to remove mIgG2a and TEV protease from purified mLG-4/5.

Phage Display

Purified mbeta-DG, mLG-5, or mLG-4/5 and hLG-4/5 (e.g., alternating between using mouse and human peptides) was coupled to magnetic tosyl-activated beads (Invitrogen) and used to enrich phage display libraries for mbeta-DG, mLG-5, or mLG-4/5 binders. Antibody phage display libraries were used in mbeta-DG selections, and the Dyax FAB 310 antibody phage display library was used for hLG-4/5 and mLG-4/5 selections. Libraries were first depleted of non-specific binders using uncoated beads and an HPC4-6× His-Avi tagged unrelated protein. Three rounds of selection were then performed on the depleted libraries, using diminishing concentrations of antigen at each round (500 nM antigen at round 1, to 1 nM antigen at round 3). The enriched libraries were plated, individual library clones were picked and cultured in a 96-well format, and phage monoclonal antibodies were produced for each clone for phage ELISA binding assay.

Phage ELISA Binding Assay

Purified antigen (mbeta-DG, mLG-5, hLG-5, mLG-4/5, or hLG-4/5) was coated on Nunc MaxiSorp 96-well ELISA plates (Thermo Scientific) at 1 ug/ml. Phage monoclonal antibodies from the selected library clones were added to each well and positive or negative binding was detected using anti-M13 Europium labelled secondary (GE Healthcare, antibody custom labelled by Perkin Elmer).

Variable Region Sequencing

Bacterial stocks of positive binding clones were PCR amplified and sequenced, and unique variable heavy chain (VH) and variable light chain (VL) sequences were identified.

Results

Several phage library clones with specific binding affinity for beta-DG, LG-5, and LG-4/5 were identified: 10 clones specifically bound beta-DG, and 15 clones specifically bound LG-4/5. Sequencing of these clones revealed that variable heavy and variable light regions of each clone were distinct, as shown in Tables D through I supra (see, e.g., clones B04, B06, CL-40968, CL-40992, CL-41136, CL-41400, and CL-41500). Complementarity-determining regions (CDRs) of these clones are identified in Tables A through C supra.

Example 2

Generation of Hybridomas, Monoclonal Antibodies, and Chimeric Antibodies Targeted Against Beta-DG, LG-5, and LG-4/5

Methods

Cell Line Production

Stable cell lines with either human or murine beta-DG surface expression were created by codon optimizing constructs containing an N-terminal myc tag and the extracellular and endogenous transmembrane domains of beta-DG (mouse UniProt Q62165, amino acids 652-893; human UniProt Q14118, amino acids 654-895). Adherent human embryonic kidney cells (HEK) and adherent Chinese hamster ovarian cells (CHO-K1) were transfected using lipofectamine (Thermo Fisher) and cells were selected with Geneticin (Gibco). Surviving cells were serial diluted for single cell clonality and surface expression of beta-DG was confirmed by anti-myc flow cytometry.

Stable cell lines with either human or murine LG-5 surface expression were created by codon optimizing constructs containing a N-terminal myc tag, a Gly/Ser linker, LG-5 (mouse UniProt Q60675, amino acids 2932-3118; human UniProt P24043, amino acids 2936-3122), and a Tfr1 transmembrane domain for mammalian expression. Adherent Chinese hamster ovarian cells (CHO-K1) were transfected using lipofectamine (Thermo Fisher) and cells were selected with Geneticin (Gibco). Surviving cells were serial diluted for single cell clonality and surface expression of beta-DG was confirmed by anti-myc flow cytometry.

Stable cell lines with either human or murine LG-4/5 surface expression were created by codon optimizing constructs containing a N-terminal myc tag, a Gly/Ser linker, LG-4/5 (mouse UniProt Q60675, amino acids 2725-3118; human UniProt P24043, amino acids 2729-3122), and a Tfr1 transmembrane domain for mammalian expression. Adherent human embryonic kidney cells (HEK) were transfected using lipofectamine (Thermo Fisher) and cells were selected with Geneticin (Gibco). Surviving cells were serial diluted for single cell clonality and surface expression of beta-DG was confirmed by anti-myc flow cytometry.

Mouse Immunization

Balb/c and Trianni mice were immunized with hbeta-DG, hLG-5, or hLG-4/5, then boosted with these proteins 3-4 times every two weeks. For mice immunized with hLG-4/5, mice were additionally boosted 3 times with human merosin every 2 weeks and once with a synthetic peptide that has identical sequence between human and mouse LG-5 (amino acid sequence=GFAKAVGGFKVGLDLLVEFE; SEQ ID NO:295).

Hybridoma Generation

Hybridoma cells were made by fusing mouse myeloma cells (from a Balb/c B-lymphoblast cell line, SP2/0, fused with Sendai virus) that are deficient in adenosine phosphoribosyltransferase (APRT) with spleen cells from the immunized mice. HAT selection (hypoxanthine, azaserine, and thymidine) and serial dilutions were performed to achieve single cell clonality.

ELISA Antibody Binding Assay

For ELISA assays, plates coated in either human beta-DG or LG-4/5 were blocked with 5% fetal bovine serum in PBS, and each well was incubated with a distinct culture supernatant. Plates were washed with PBS, incubated with HRP conjugated anti-mouse Fc secondary antibody, washed again with PBS, and developed for colorimetric measuring.

Fluorescence Activated Cell Sorting (FACS) Antibody Binding Assay

For FACS assays, stable cells with either human or murine beta-DG or LG-4/5 surface expression (see above) were incubated with antibody-containing culture supernatant, washed with PBS, incubated with FITC-conjugated anti-mouse Fc secondary antibody (Thermo Fisher), washed again with PBS, and analyzed on a flow cytometer.

Surface Plasmon Resonance (Biacore) Kinetics Assay

Hybridoma antibodies (contained in culture supernatant)t were further characterized by measuring antibody/antigen binding affinity and on/off-rate by Biacore kinetics assay, as per manufacturer's protocol (GE Healthcare). Antigens used for binding were human or murine beta-DG or LG-4/5.

subcloned into a mammalian expression vector with the constant human kappa chain. Expi293F cells were co-transfected with these constructs using Expifectamine reagent (Thermo Fisher) to express chimeric antibodies. After 7 days expression, antibodies were purified from the supernatant with a HiTrap MabSelect SuRe column (GE). Purified antibodies were rescreened by ELISA, FACS, and Biacore (GE Healthcare) to confirm binding affinity to beta-DG, LG-5, or LG-4/5. To confirm that antibodies bound to their respective antigens in muscle tissue, immunofluorescence staining with unfixed frozen human and mouse muscle tissue sections was performed.

Results

To screen for and select hybridomas that produced antibodies specific to beta-DG, LG-5, or LG-4/5, ELISA, FACS analysis, and Biacore kinetics assay were used to assess antibody binding. ELISA assays showed a range of binding affinities of antibodies to beta-DG, LG-5, or LG-4/5, with several samples giving strong colorimetric signal (exemplary data for three antibodies are provided in Table J below).

TABLE J

Monoclonal antibody anti-LG-5 binding kinetics

| Clone name | Immobilized mAb with hLG-5 in flow | | | Immobilized mAb with mLG-5 in flow | | |
| --- | --- | --- | --- | --- | --- | --- |
| | ka(1/Ms) | kd(1/s) | KD(M) | ka(1/Ms) | kd (1/s) | KD(M) |
| AN01 | 9.90E+04 | 9.15E−04 | 9.24E−09 | nb | nb | nb |
| C3 | 4.88E+05 | 1.30E−03 | 2.66E−09 | 5.19E+05 | 4.29E−03 | 8.27E−09 |
| C21 | 4.67E+05 | 1.31E−03 | 2.80E−09 | 8.13E+05 | 2.53E−03 | 3.04E−09 | nb: no binding.

Monoclonal Antibody Generation

Hybridoma clones were expanded and terminal flasks with ultra-low IgG fetal bovine serum supplement were seeded. After 7 days, supernatant was harvested and monoclonal antibodies were purified using a HiTrap Mab Select SuRe column (GE Healthcare). Resulting antibodies were tested again by ELISA, FACS, and Biacore kinetics assay (GE Healthcare) to confirm antibody binding properties.

Immunofluorescence

Immunofluorescence staining with unfixed frozen human and mouse muscle tissue sections was performed. Muscle tissue sections were stained with purified antibodies against beta-DG or LG-4/5, washed, stained with fluorescently labeled anti-mouse IgG secondary antibody, washed, mounted, and imaged using a fluorescence microscope.

Variable Region Sequencing

Total RNA was isolated from hybridoma cells that produced high affinity antibodies using the RNeasy Mini Kit (Qiagen) and first-strand cDNA was synthesized using the SMARTer RACE cDNA Amplification Kit (Clontech). The VH and VL gene segments were amplified by 5'-Rapid Amplification of cDNA Ends (5'-RACE) PCR using isotype specific primers. Amplified PCR fragments were cloned and sequenced. See, e.g., clones TDG-2, TDI-11, TDI-23, TDI-38, TLF39, TLF86, TLG3/TLG4, TLG26, TLI-3, TLI-7, TTLK71-4-6, TTLK123-3, TTLK145-6-3, TTLK170-2, WJL10, and WJL48.

Chimeric Antibody Production

Figure 3B:
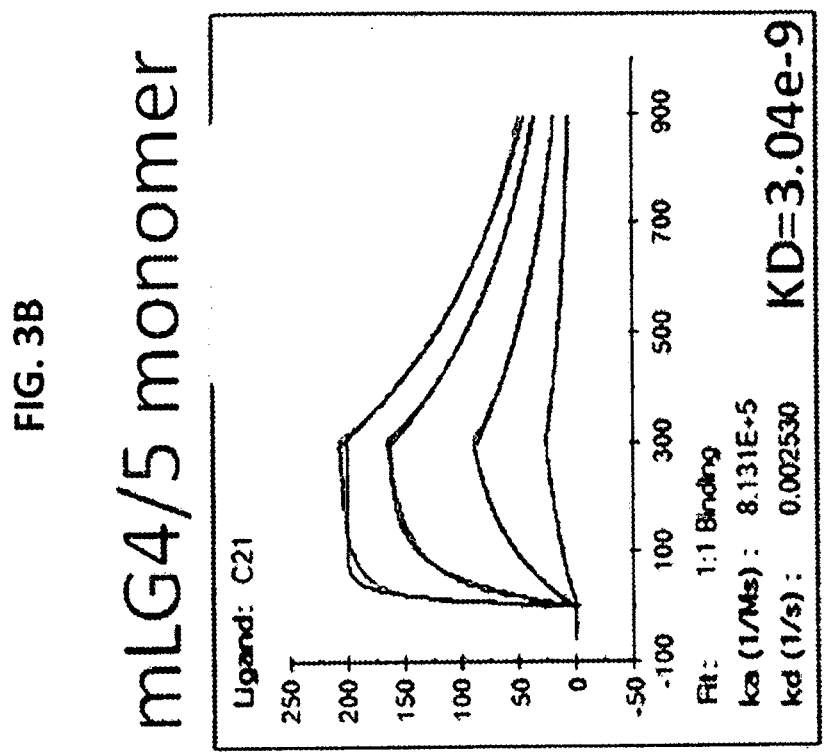
FIGS. 3A and 3B show surface plasmon resonance (Biacore; GE Healthcare) kinetics assay data of the anti-laminin-2 antibody derived from hybridoma clone C21 binding to human (FIG. 3A) and mouse (FIG. 3B) LG-4/5.
Figure 3A:
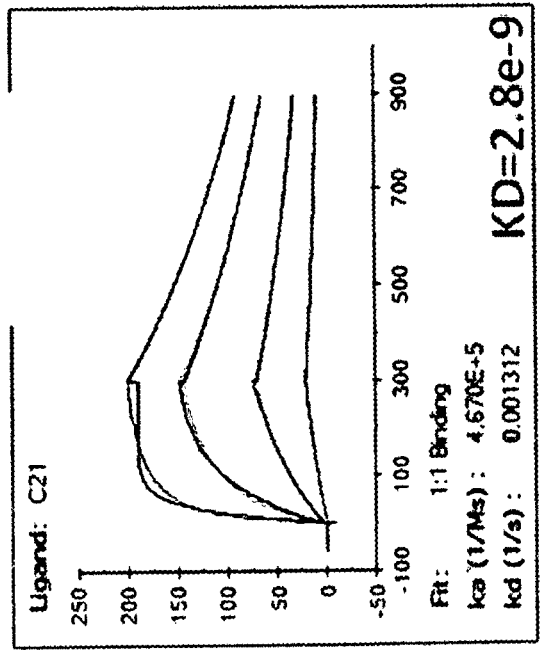
Figure 3C:
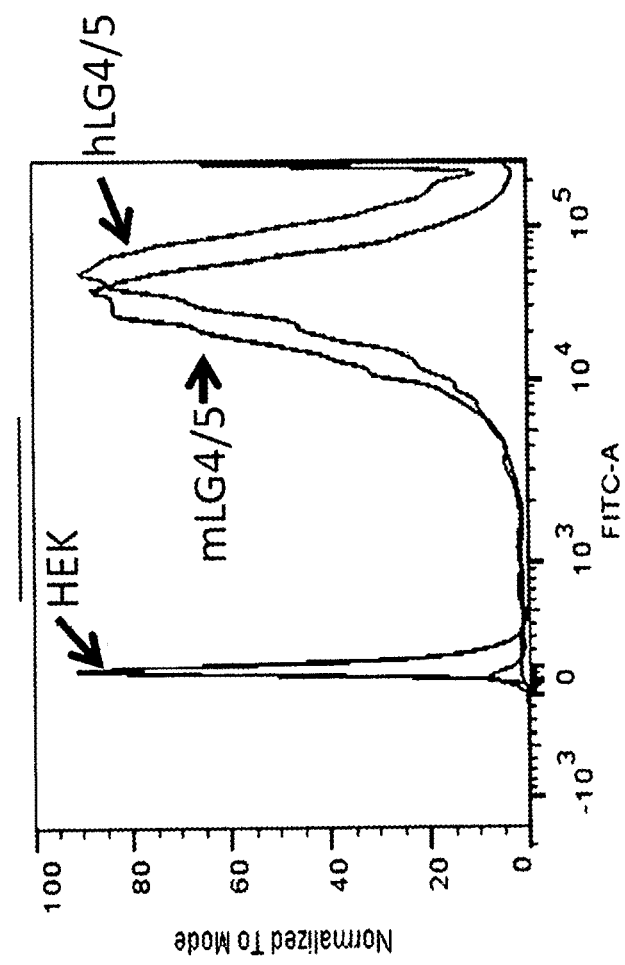
FIG. 3C shows fluorescence activated cell sorting (FACS) analysis of the anti-laminin-2 antibody derived from hybridoma clone C21 binding to human and mouse LG-4/5 expressed on HEK293 cells.
Figure 3D:
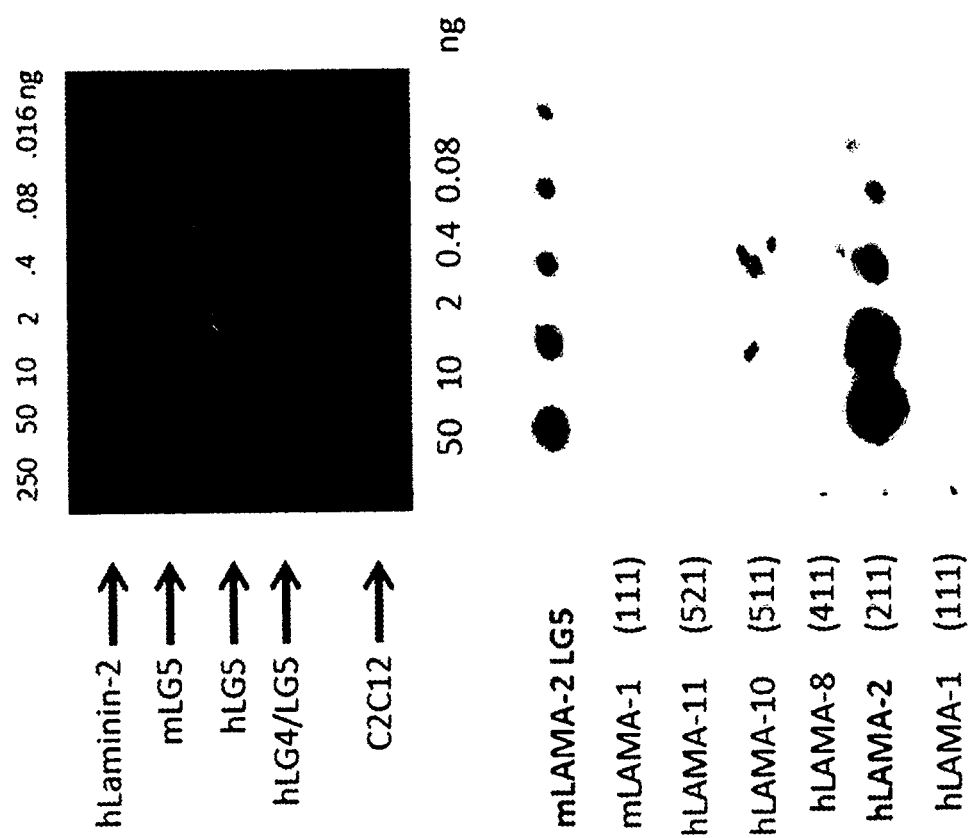
FIG. 3D shows a dot blot with various amounts of recombinant human laminin-2, murine LG-5 (mLG5), human LG-5 (hLG5), and human LG-4/5 (hLG4/LG5) dotted onto nitrocellulose then probed with anti-laminin-2 antibody derived from hybridoma clone C21. The amount of laminin-2 in the C2C12 cell lysate was below the detection limit.
Figure 3F:
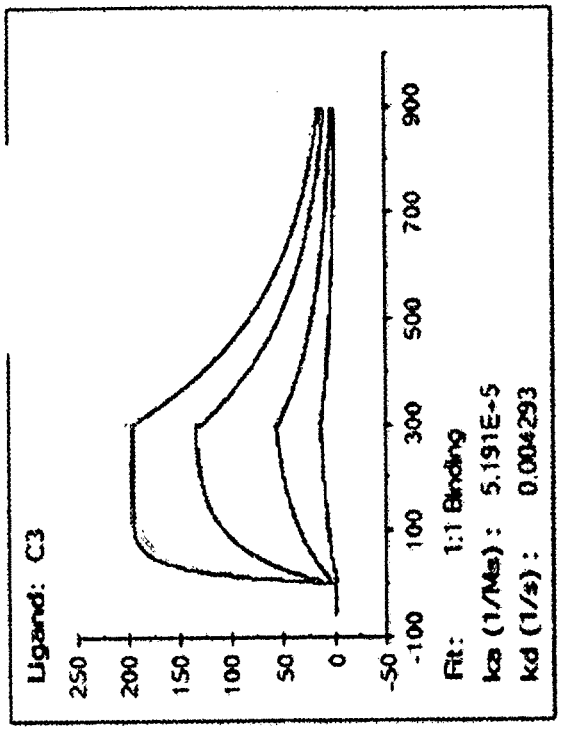
FIGS. 3E and 3F show surface plasmon resonance (Biacore; GE Healthcare) kinetics assay data of the anti-laminin-2 antibody derived from hybridoma clone C3 binding to human (FIG. 3F) and mouse (FIG. 3G) LG-4/5.
Figure 3E:
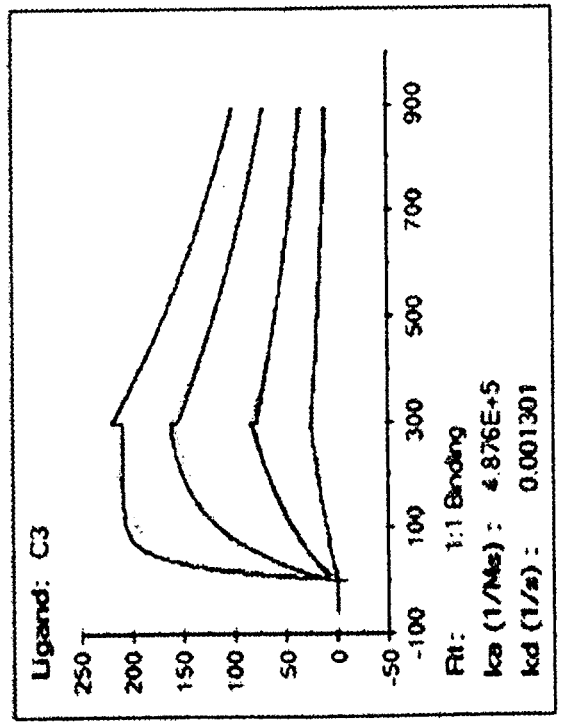
Figure 3G:
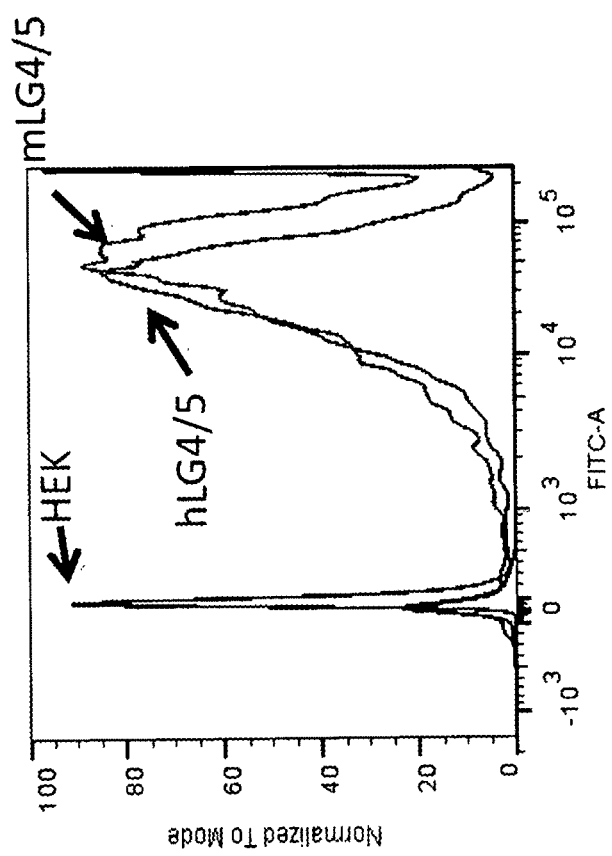
FIG. 3G shows fluorescence activated cell sorting (FACS) analysis of the anti-laminin-2 antibody derived from hybridoma clone C3 binding to human and mouse LG-4/5 expressed on HEK293 cells.

VH and VL sequences generated from 5'-RACE PCR were codon optimized for mammalian expression and synthesized. VH sequences were subcloned into a mammalian expression vector with human IgG1 and VL sequences were Samples giving a strong colorimetric signal were assayed using FACS for binding affinity to cells expressing beta-DG or LG-4/5 on their surface. FACS analysis revealed that antibodies derived from clones C21 and C3 had binding affinity for both murine and human LG-4/5 (FIGS. 3C & 3G, respectively). These antibodies did not bind control cells that lacked surface expression of beta-DG or LG-4/5, as shown by insignificant fluorescence detection.

Figure 3H:
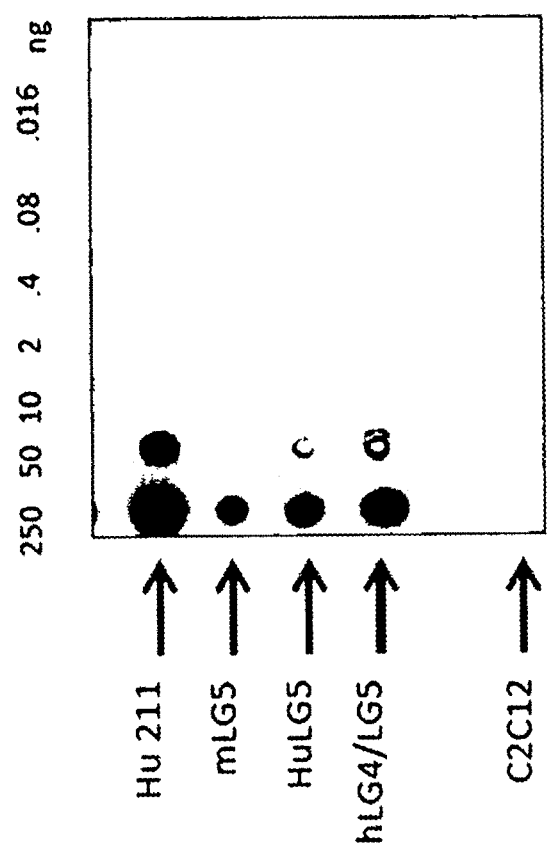
FIG. 3H shows a dot blot with various amounts of recombinant human laminin-2 (Hu 211), murine LG-5 (mLG5), human LG-5 (hLG5), and human LG-4/5 (hLG4/LG5) dotted onto nitrocellulose then probed with anti-laminin-2 antibody derived from hybridoma clone C3. The amount of laminin-2 in the C2C12 cell lysate was below the detection limit.

Various amounts of recombinant human laminin-2 (from Biolamina), murine LG-5, human LG-5, human LG4/5 were dot blotted onto nitrocellulose membrane and probed with anti-laminin-2 antibody. Results indicated that the antibodies recognized Laminin-2 or its fragments containing LG-5 (FIG. 3D, top for C21). To determine the antibody specificity, different laminin isoforms with different alpha chains were dotted onto the blot. Only mLG-5 and human laminin-2 containing alpha-2 were recognized, supporting the antibodies' binding specificity (FIG. 3D, bottom for C21; FIG. 3H for C3).

Figure 3J:
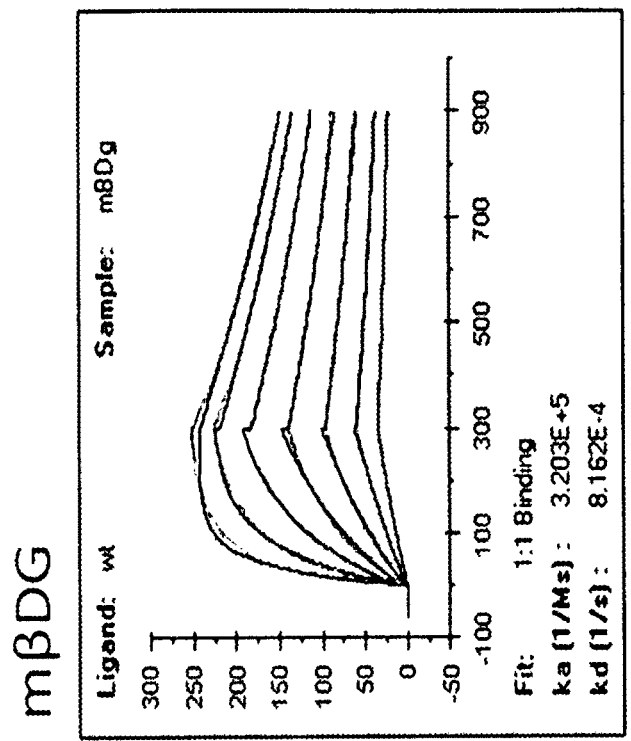
FIGS. 3I and 3J show surface plasmon resonance (Biacore; GE Healthcare) kinetics assay data of the anti-beta-DG antibody derived from hybridoma clone AS30 binding to human (FIG. 3I) and mouse (FIG. 3J) beta-DG.
Figure 3I:
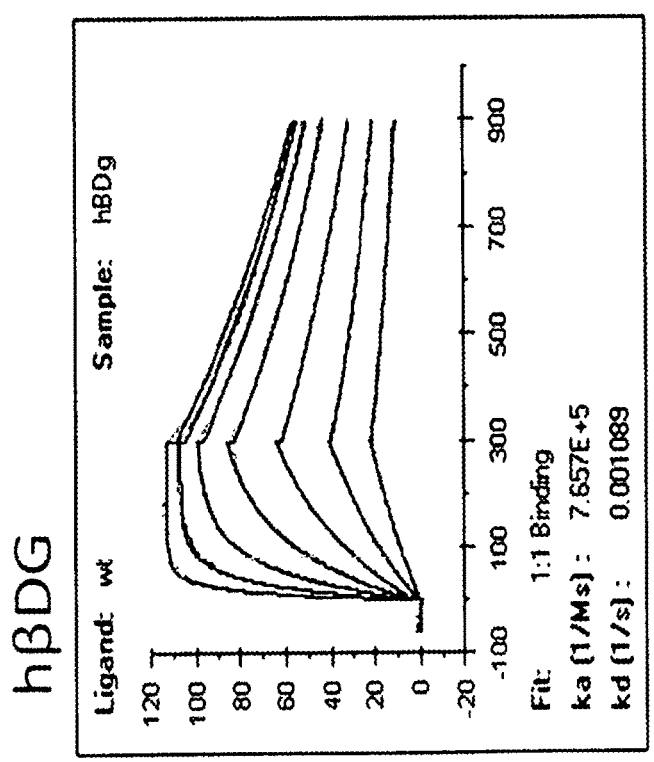

Anti-dystroglycan antibody clones were also characterized. Kinetics revealed that all antibodies tested displayed high affinity to their respective antigens, with most KDs in the $10^{-9}$M range (nanomolar sensitivity), as shown in Table K and FIGS. 3I & 3J (clone AS30) and 3M & 3N (clone AS19). In addition, on and off-rates for tested antibodies were fairly typical for high affinity antibodies, with the exception of anti-beta-DG clone AS19, which had very high on and off rates (Table K).

TABLE K

Monoclonal antibody anti-beta-DG binding kinetics.

| Clone name | Immobilized mAb with hBeta-DG in flow | | | Immobilized mAb with mBeta-DG in flow | | |
|---|---|---|---|---|---|---|
| | ka(1/Ms) | kd(1/s) | KD(M) | ka(1/Ms) | kd(1/s) | KD(M) |
| B06 | 9.68E+05 | 2.16E−03 | 2.36E−09 | 1.43E+04 | 2.32E−03 | 1.62E−07 |
| B04 | 6.20E+04 | 1.60E+03 | 2.57E−09 | 6.20E+04 | 1.60E−03 | 2.57E−08 |
| AS30 | 8.90E+05 | 9.63E−04 | 1.08E−09 | 7.73E+05 | 1.13E−03 | 1.48E−09 |
| AS19 | 4.43E+09 | 1.04E+01 | 2.06E−09 | 2.02E+09 | 9.33E+00 | 3.38E−09 |
| AS55 | 1.47E+05 | 7.27E−04 | 5.00E−09 | 3.04E+05 | 1.36E−03 | 4.47E−09 |

Figure 3L:
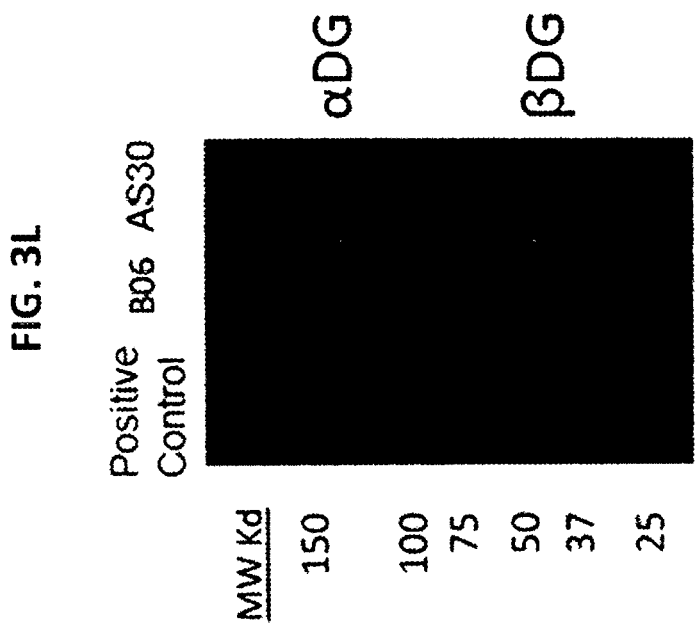
FIG. 3L shows a Western blot of samples generated via immunoprecipitation of beta-DG from C2C12 cell lysates using anti-beta-DG antibody derived from hybridoma clone AS30. The first lane shows the positive control, the second lane shows the immunoprecipitation sample probed with the anti-beta-DG antibody derived from a phage display clone B06 (which has low affinity to βDG and thus minimal pulldown of βDG and alpha-DG), and the third lane shows the immunoprecipitation sample probed with the high affinity anti-beta-DG antibody derived from hybridoma clone AS30 (where abundant βDG and alpha-DG were immunoprecipitated).
Figure 3K:
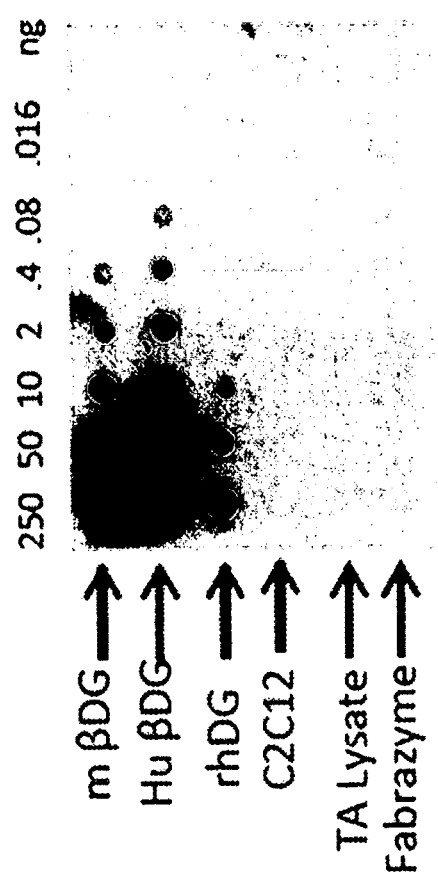
FIG. 3K shows a dot blot with various amounts of recombinant murine beta-DG ECD (m βDG), human beta-DG ECD (Hu βDG), or recombinant dystroglycan (rhDG) dotted onto nitrocellulose then probed with anti-beta-DG antibody derived from hybridoma clone AS30. The amount of βDG in C2C12 cell lysate and tibialis anterior muscle cell lysate (TA lysate) were below the detection limit. Fabrazyme (agalsidase beta, Genzyme) was used as a negative control.
Figure 3N:
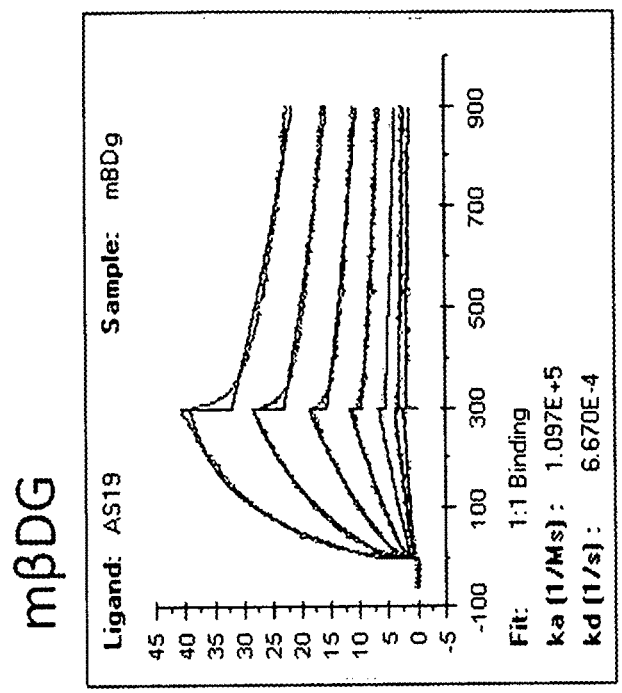
FIGS. 3M and 3N show surface plasmon resonance (Biacore; GE Healthcare) kinetics assay data of the anti-beta-DG antibody derived from hybridoma clone AS19 binding to human (FIG. 3M) and mouse (FIG. 3N) beta-DG.
Figure 3M:
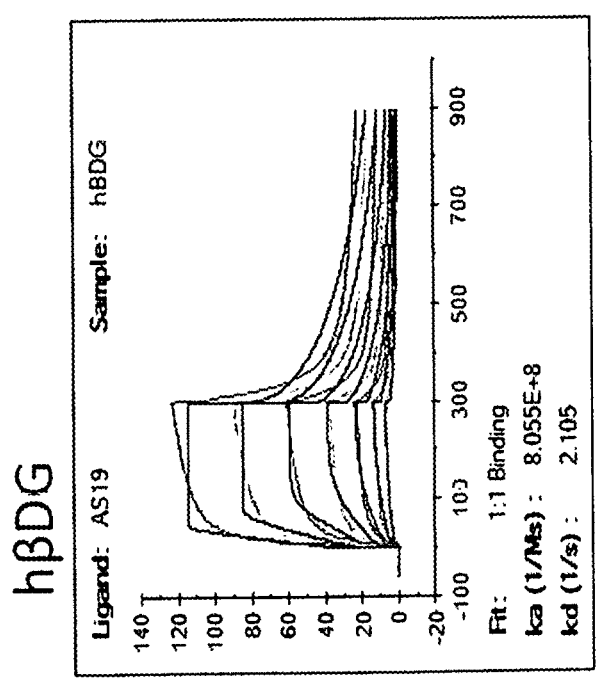
Figure 3O:
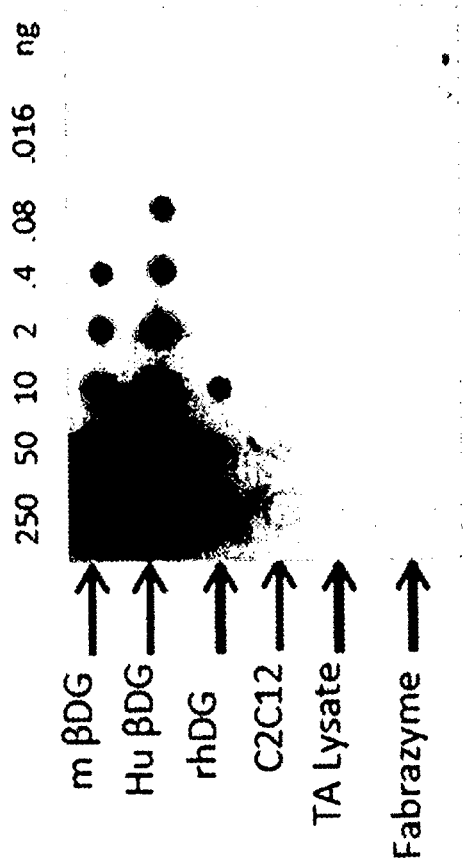
FIG. 3O shows a dot blot with various amounts of recombinant murine beta-DG ECD, human beta-DG ECD, or recombinant dystroglycan dotted onto nitrocellulose then probed with anti-beta-DG antibody derived from hybridoma clone AS19. C2C12 cell lysate, tibialislis anterior muscle cell lysate (TA lysate). Fabrazyme (agalsidase beta, Genzyme) was used as the negative control.

To characterize clones AS30 and AS19, various amount of recombinant mouse or human beta-DG ECD, recombinant dystroglycan (from R&D Systems), C2C12 cell lysate, TA lysate and Fabrazyme as negative control were dot blotted onto nitrocellulose membrane and probed with anti-beta-DG antibody (FIG. 3K for AS30; FIG. 3O for AS19). Results indicate that all proteins containing beta-DG were detected. No signal was detected with C2C12 or TA lysate, probably due to very low amount of beta-DG in these samples. As expected, antibodies also did not detect negative control Fabrazyme.

Figure 3P:
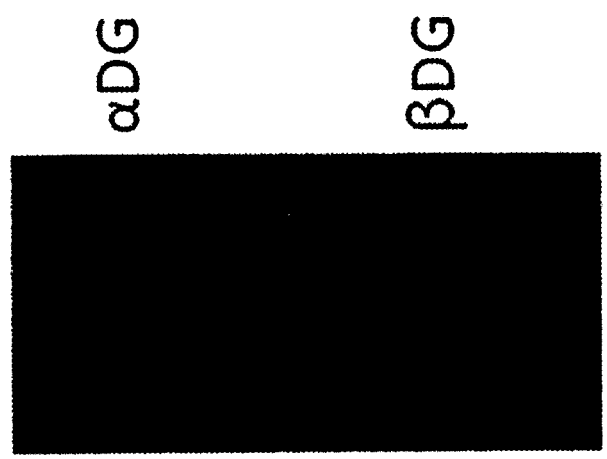
FIG. 3P shows a Western blot of samples generated via immunoprecipitation of beta-DG from C2C12 cell lysates using anti-beta-DG antibody derived from hybridoma clone AS19. The first lane shows the positive control, the second lane shows the immunoprecipitation sample probed with the anti-beta-DG antibody derived from phage display clone B06 (which has low affinity to βDG and thus minimal pulldown of βDG and alpha-DG), and the third lane shows the immunoprecipitation sample probed with the anti-beta-DG antibody derived from hybridoma clone AS19.

Immunoprecipitation of beta-DG from C2C12 cell lysates solubilized under non-denaturing condition was performed with anti-beta-DG clone AS30 or AS19. The beta-DG/antibody complex was captured by protein A beads and run on SDS-PAGE, then reprobed with anti-alpha-DG and anti-beta-DG from R&D Systems. Both alpha-DG and beta-DG were immunoprecipitated, indicating they remain in complex after solubilization, and binding of anti-beta-DG antibody clones did not interfere the binding of alpha-DG to beta-DG (FIG. 3L for AS30; FIG. 3P for AS19).

After hybridoma clones were expanded and monoclonal antibodies purified, antibodies were rescreened by ELISA, FACS, and Biacore to confirm binding affinity. Results were extremely similar to those generated for antibodies from culture supernatant, confirming that the antibodies retained their kinetic characteristics after amplification.

To determine if antibodies could bind to muscle tissue, which contains abundant beta-DG and LG-4/5, immunofluorescence staining was done on mouse and human muscle tissue using purified antibodies. Unfixed tissue was used such that the native antigen conformation was preserved. Characteristic muscle sarcolemma staining was clearly demonstrated for human and mouse tissues, indicating specific LG-4/5 binding for C21 (FIG. 4A) and C3 (FIG. 4B), and specific beta-DG binding for AS30 (FIG. 4C) and AS19 (FIG. 4D). Sections stained with only secondary antibody did not reveal any fluorescent signal.

Example 3

Generation of Bispecific Antibodies Recognizing Beta-DG and the LG-4/5 Domain of the Laminin-2 Alpha Subunit Methods
Tetravalent Bispecific Tandem Ig (TBTI) Antibody Generation VH and VL sequences obtained from generated hybridoma cells were codon-optimized for mammalian expression and synthesized (Genscript). To generate constructs expressing the light chains, one VL sequence specific to beta-DG, a $(G4S)_2$ linker, one VL sequence specific to LG-4/5, and human kappa chain (Genbank Q502W4) or murine kappa chain (Genbank BAB33404) were fused together and cloned into the transient episomal expression vector pXL, an analogue of the pTT vector described by Durocher et al. (Nucl. Acids Res. 2002, 30(2), E9). To generate constructs expressing the heavy chains, one VH sequence specific to beta-DG, a $(G4S)_2$ linker, one VH sequence specific to LG-4/5, and human IgG1 (Genbank Q569F4) or murine IgG1 (GenBank AAA75163.1) were fused together (FIG. 4A) and cloned into expression vector pXL. VH and VL sequences used were obtained from clones AN01, C3, and C21 for LG-4/5-specific binding, and from clone B6, AS19, and AS30 for beta-DG-specific binding.

These constructs were co-transfected into HEK293 Free-Style 293-F or Expi293 cells (Thermo Fisher). After 7 days expression, antibodies were purified from the supernatant with a HiTrap MabSelect™ SuRe™ Protein A column (GE Healthcare).

Crossover Dual Variable Domain Ig (CODVIg) Antibody Generation

VH and VL sequences obtained from generated hybridoma cells were codon-optimized for mammalian expression and synthesized (Genscript). To generate constructs expressing the light chains, one VL sequence specific to LG-4/5, an $L_1$ linker, one VL sequence specific to beta-DG, a $L_2$ linker, and human kappa chain (Genbank Q502W4) or murine kappa chain (Genbank BAB33404) were fused together and cloned into expression vector pXL. To generate constructs expressing the heavy chains, one VH sequence specific to beta-DG, a $L_3$ linker, one VH sequence specific to LG-4/5, a $L_4$ linker, and human IgG1 (Genbank Q569F4) or murine IgG1 (GenBank AAA75163.1) were fused together and cloned into expression vector pXL. Specific combinations of linker sequences used are provided below.

These constructs were co-transfected into HEK293 Free-Style 293-F or Expi293 cells (Thermo Fisher). After 7 days expression, antibodies were purified from the supernatant with a HiTrap MabSelect™ SuRe™ Protein A column (GE Healthcare).

Sequential Biacore Binding Analysis
Parental monoclonal antibodies (AS19, C3 and C21) and three bispecific antibodies (AS19×C3 and AS30×C3 in TBTI, and AS30×C3 in CODVIg) were each immobilized onto individual CM5 Series S Biacore chips (GE Healthcare). Human or murine LG-4/5, followed in sequence by human or murine beta-DG, was flown over each chip and binding was assessed.

Double Deck Sandwich ELISA
96-well plates were coated with 50 ng human LG-4/5 and blocked with 5% fetal bovine serum in PBS. Each well was incubated with 1 μg of the generated bispecific antibodies (murine IgG backbone). After 2 hours, wells were washed with PBS and re-incubated with 16 ng to 1 µg per well of human beta-DG fused to the human hIgG1 Fc antibody region (hbeta-DG-hFc). After 2 hours, wells were washed with PBS, incubated with a HRP conjugated anti-hFc secondary antibody for 45 minutes, washed again with PBS, and developed for colorimetric measuring.

Results

Figure 5B:
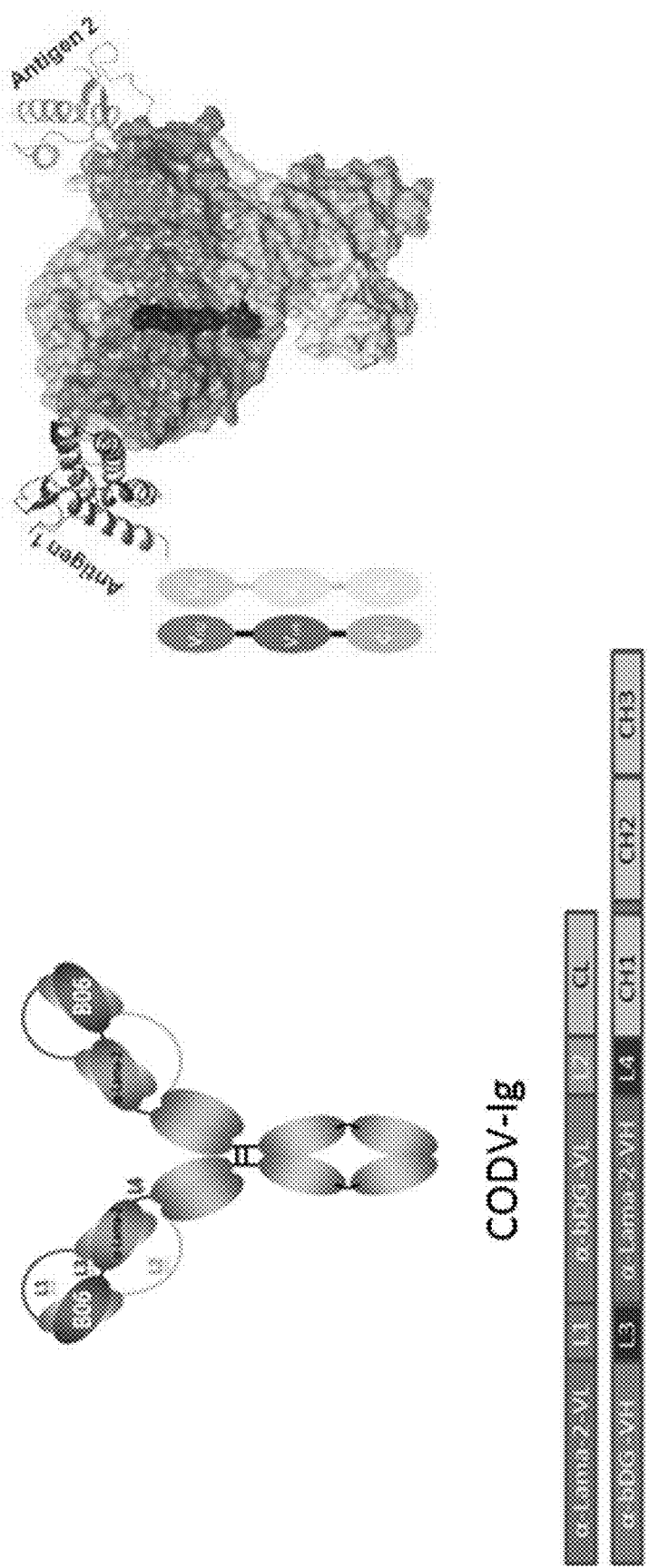
FIG. 5B shows a schematic design for crossover dual variable domain IgG format (CODV) bispecific antibodies that are specific to beta-DG and laminin-2, in accordance with some embodiments.

Antibodies were engineered into multiple bispecific formats including tetravalent bispecific tandem IgG format (TBTI; FIG. 5A) as well as crossover dual variable domain IgG format (CODVIg; FIG. 5B) as described above. To create these formats a light chain and a heavy chain plasmid for each construct was synthesized. One with a variable light chain region of an anti-βDG from the listed monoclonal sequences followed by a linker and then a variable light chain region from an anti-LG4/5 monoclonal followed by an additional linker and then the constant light chain domain. The same principle was used to develop the heavy chain plasmids and then for expression these were co-transfected in mammalian cells. Multiple linker combinations were attempted and both variable region orientations were tested (i.e. having the anti-LG4/5 farther from the constant region rather than anti-βDG variable region and vice versa).

Bispecific antibodies (biAbs) recognizing beta-DG (using clones B06, AS19, and AS30) and LG-4/5 (using clones AN01, C3, and C21) were generated in TBTI or CODVIg format.

Multiple linker combinations were attempted and both variable region orientations were tested (i.e. having the anti-LG4/5 farther from the constant region rather than anti-βDG variable region and vice versa). For TBTI, (T1T2 and T5T6), the linker between the light chain variable regions consisted of 10 residues that were glycine or serine (e.g., GGGGSGGGGS; SEQ ID NO:294) and no linker was used between the second variable region and the constant region. The same linker (10 residues that were glycine or serine) was used between the heavy chain variable regions and no linker was used between the second heavy chain variable and the constant. For CODVIg format, two sets of linker lengths were used: 10-10-0-0 and 7-5-1-2 (# of residues for $L_1$-$L_2$-$L_3$-$L_4$). CODVIg C5C6 linkers consisted of 10 residues that were glycine or serine between variable light chains and 10 residues that were glycine or serine between the second variable region and the light constant region. No linkers were used on the heavy chain. Linker sequences for these combinations are as follows (depicted as $L_1$, $L_2$, $L_3$, $L_4$): GQPKAAP (SEQ ID NO:297), TKGPS (SEQ ID NO:298), S, RT; GGSGSSGSGG (SEQ ID NO:299), GGSGSSGSGG (SEQ ID NO:299), 0,0; and EPKSDKTHTSPPSP (SEQ ID NO:296), GG, EPKSDKTHTSPPSP (SEQ ID NO:296), GG. A list of bispecific antibodies created is provided in Table L below.

TABLE L

CODV and TBTI bispecific antibody configurations tested.

| CODV with 10-10-0-0 linker | CODV with 7-5-1-2 linker | TBTI with (GGGGS)2 Linker |
|---|---|---|
| | anti-laminin-2 (AN01) × anti-beta-DG(clone B04) | anti-laminin-2(AN01) × anti-beta-DG(clone B04) |
| | anti-beta-DG(clone B04) × anti-laminin-2(AN01) | anti-beta-DG(clone B04) × anti-laminin-2(AN01) |
| | anti-laminin-2(AN01) × anti-beta-DG(clone B06) | anti-laminin-2(AN01) × anti-beta-DG(clone B06) |
| | *anti-beta-DG(clone B06) × anti-laminin-2(AN01) = 1331 and 1460 | anti-beta-DG(clone B06) × anti-laminin-2(AN01) |
| anti-beta-DG(AS19) × anti-laminin-2(C3) | anti-beta-DG(AS19) × anti-laminin-2(C3) | *anti-beta-DG(AS19) × anti-laminin-2(C3) = T1T2 |
| anti-laminin-2(C03) × anti-beta-DG(clone AS19) | anti-laminin-2(C03) × anti-beta-DG(clone AS19) | anti-laminin-2(C03) × anti-beta-DG(clone AS19) |
| anti-beta-DG(clone AS19) × anti-laminin-2(C3) | anti-beta-DG(clone AS19) × anti-laminin-2(C3) | anti-beta-DG(clone AS19) × anti-laminin-2(C3) |
| anti-laminin-2(C3) × anti-beta-DG(clone AS19) | anti-laminin-2(C3) × anti-beta-DG(clone AS19) | anti-laminin-2(C3) × anti-beta-DG(clone AS19) |
| anti-beta-DG(AS30) × anti-laminin-2(C3) = C5C6 | anti-beta-DG(AS30) × anti-laminin-2(C3) | anti-beta-DG(AS30) × anti-laminin-2(C3) = T5T6 |
| anti-laminin-2(C03) × anti-beta-DG(clone AS30) | anti-laminin-2(C03) × anti-beta-DG(clone AS30) | anti-laminin-2(C03) × anti-beta-DG(clone AS30) |
| anti-beta-DG(clone AS30) × anti-laminin-2(C21) | anti-beta-DG(clone AS30) × anti-laminin-2(C21) | anti-beta-DG(clone AS30) × anti-laminin-2(C21) |
| anti-laminin-2(C21) × anti-beta-DG(clone AS30) | anti-laminin-2(C21) × anti-beta-DG(clone AS30) | anti-laminin-2(C21) × anti-beta-DG(clone AS30) |

To confirm that biAbs have the capacity to bind LG-4/5 and beta-DG at the same time, sequential Biacore analysis (GE Healthcare) and double deck Sandwich ELISA assays were performed.

Figure 6A:
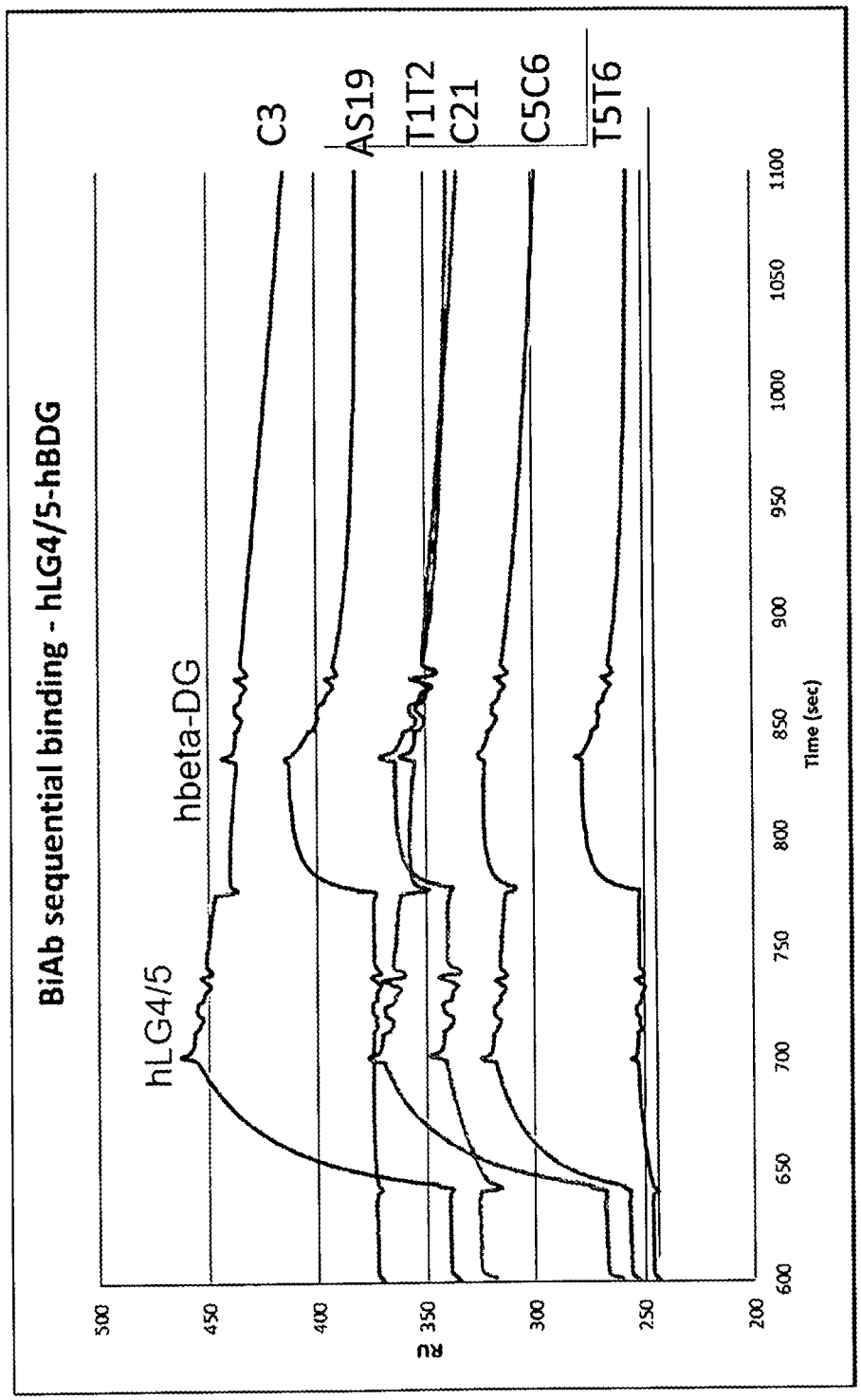
FIGS. 6A and 6B show sequential surface plasmon resonance (Biacore; GE Healthcare) binding analysis data for parent monoclonal antibodies (AS19, C3, and C21) and bispecific antibodies (T1T2, C5C6, and T5T6) for human LG-4/5 and human beta-DG (FIG. 6A) or for murine LG-4/5 and murine beta-DG (FIG. 6B).
Figure 6B:
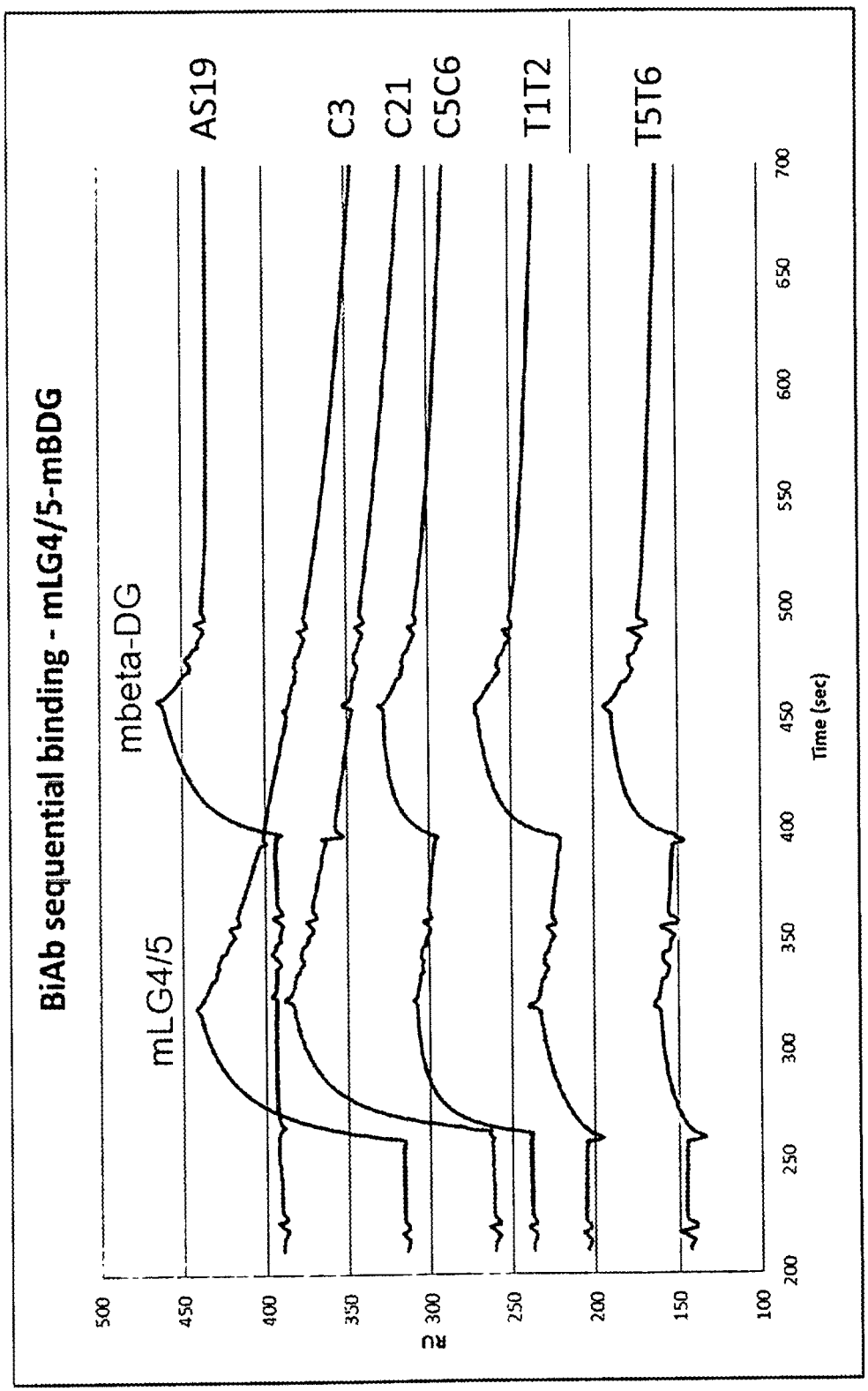

Parental mAbs to LG-4/5 or beta-DG and biAbs of anti-LG4/5 and beta-DG were captured onto biacore chips, and then flowed with human LG4/5 and human beta-DG sequentially to determine their concurrent bindings to both antigens. Sequential Biacore analysis revealed that bispecific antibodies can bind either human ($1^{st}$ peak, FIG. 6A) or murine LG-4/5 ($1^{st}$ peak, FIG. 6B) first, and then further associate with human ($2^{nd}$ peak, FIG. 6A) or murine beta-DG ($2^{nd}$ peak, FIG. 6B). In contrast, parental monoclonal antibodies were only able to bind to one target, either LG-4/5 (C3 and C21 in FIGS. 6A & 6B) or beta-DG (AS19 in FIGS. 6A & 6B).

Figure 7:
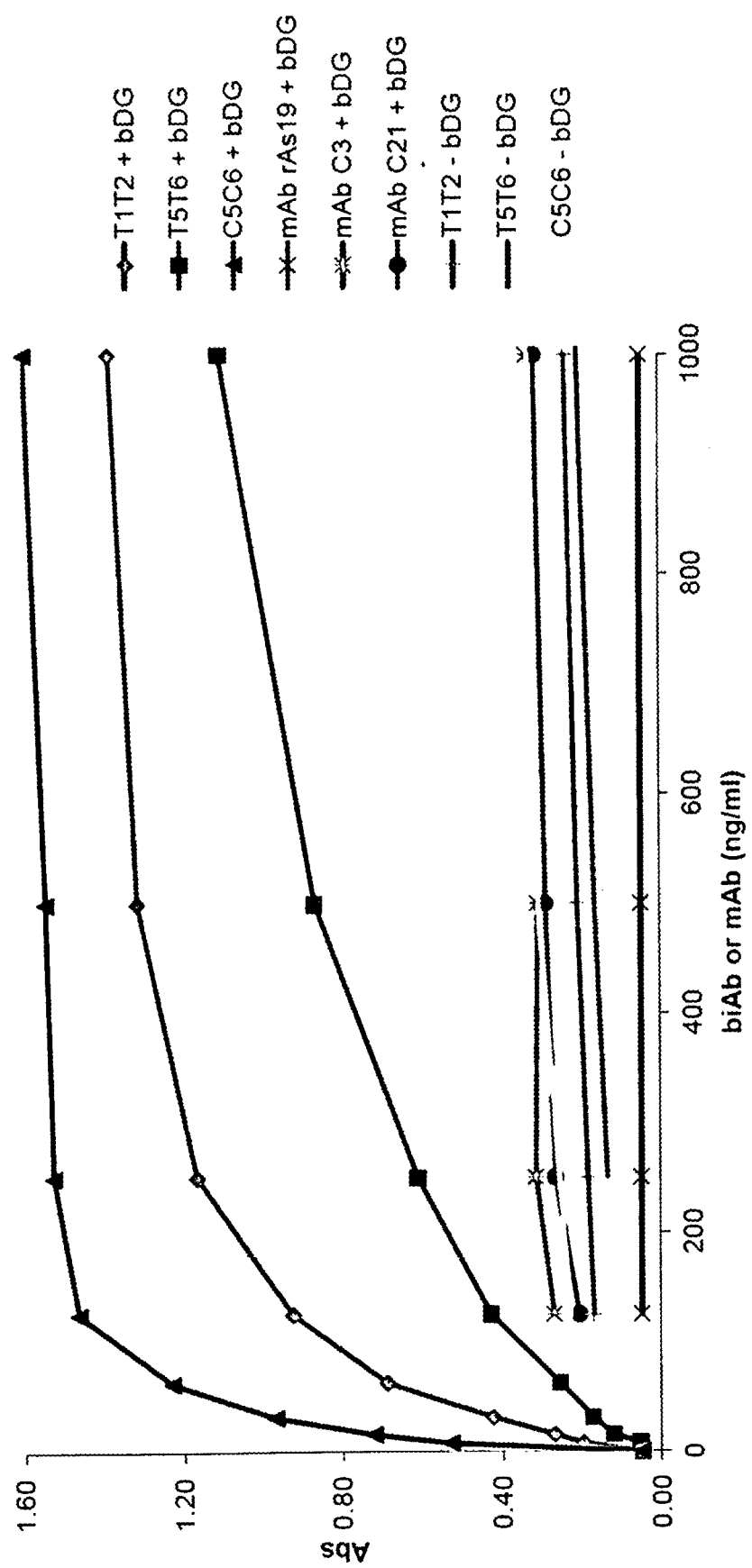
FIG. 7 shows double deck Sandwich ELISA results for the simultaneous binding of LG-4/5 and beta-DG to bispecific antibodies. Parental monoclonal antibodies (AS19, C3, and C21) with beta-DG added and bispecific antibodies (T1T2, C5C6, or T5T6) with or without beta-DG added were assayed for binding. Only bispecific antibodies T1T2, T5T6, and C5C6 showed significant binding to LG-4/5 and beta-DG simultaneously.

Double deck Sandwich ELISA revealed that bispecific antibodies can simultaneously bind hLG-4/5 and hbeta-DG. Colorimetric signals could be detected only when hLG-4/5 and hbeta-DG-hFc were both added in the assay (FIG. 7). No signal was detected when parental monoclonal antibodies were used or when hbeta-DG-hFc was omitted. Three bispecific antibodies (biAbs), T1T2, T5T6, and C5C6, had the anticipated signal indicating simultaneous binding to both targets. The parental anti-LG4/5 or anti-beta-DG mAbs, or biAbs without beta-DG-hFc in the $2^{nd}$ step were all negative in this assay.

Example 4

Intra-Muscular Injection of Bi-Specific Antibodies Into LARGE$^{myd-3J/GrsrJ}$ Mice Methods
LARGE$^{myd-3J/GrsrJ}$ Mouse Model LARGE$^{myd-3J/GrsrJ}$ (stock #008581) mice from Jackson lab is a mouse model of alpha-dystroglycanopathy caused by a mutation in the LARGE gene. The mutation of the LARGE gene maps between D8Mit65 and DMit249, with markers at 44.4 Mb and 83.8 Mb, respectively; the LARGE gene is located at 75.7 Mb. Mice homozygous for the LARGE generally begin to display evidence of muscle degeneration at two to three months of age, although some animals may exhibit symptoms as early as wean age. Inability to splay the hind legs outward when held up by the tail is an initial phenotype and this progresses with age to include swaying gait, then dragging of the hind legs.
Bispecific Antibody Injection A group of 10 LARGE$^{myd-3J/GrsrJ}$ mice were given intramuscular injections into the left and right tibialis anterior (TA) muscles. The left TA received two injections of biAb (T1T2; murine Fc backbone) at 0.7 µg/µl in 500 µl saline per injection. The right TA received two control injections of a 1:1 weight by weight mixture of parental AS19 and C3 antibodies at 0.7 µg/µl in 50 µl saline per injection. The two injections were spaced 3 days apart.
Exercise-Induced Tissue Damage One day after the last intramuscular injection, all mice received intraperitoneal injections (IP) of Evans blue dye (EBD) at 10 mg/ml with 50 µl given per 10 g body weight. One day after IP of EBD, all mice were exercised via a forced treadmill until exhaustion. The animals were euthanized with $CO_2$ according to standard IACUC protocol.
Tissue Preparation and Immunofluorescence Staining After euthanasia, the TA muscles were removed, cut, and placed in optimum cutting temperature compound. The tissue was then rapidly frozen via a 2-methyl butane dry ice bath. The tissue was cryo-sectioned in a cryostat, at a thickness of 10 microns. Four different levels were cut (in triplicate) from the TA, 100 microns apart.

Figure 8A:
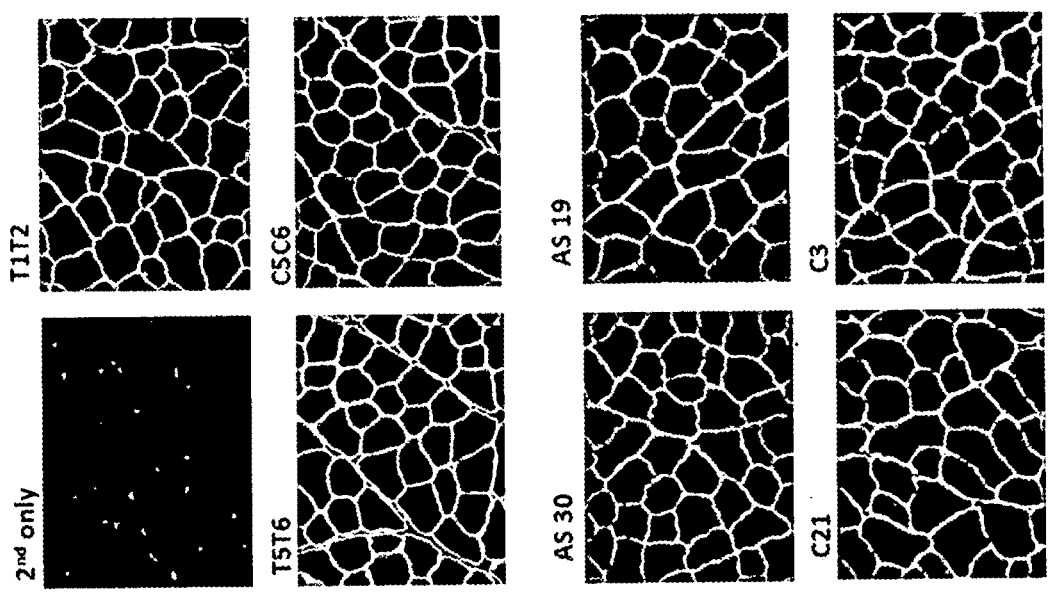
FIGS. 8A and 8B show unfixed frozen sections of wild-type murine muscle tissue (FIG. 8A) or LARGE$^{myd-3J/GrsrJ}$ murine muscle tissue (FIG. 8B) stained with parental monoclonal antibodies (AS19, C3, and C21) or bispecific antibodies (T1T2, C5C6, or T5T6) and detected with fluorescently labeled anti-mouse IgG secondary antibody.
Figure 8B:
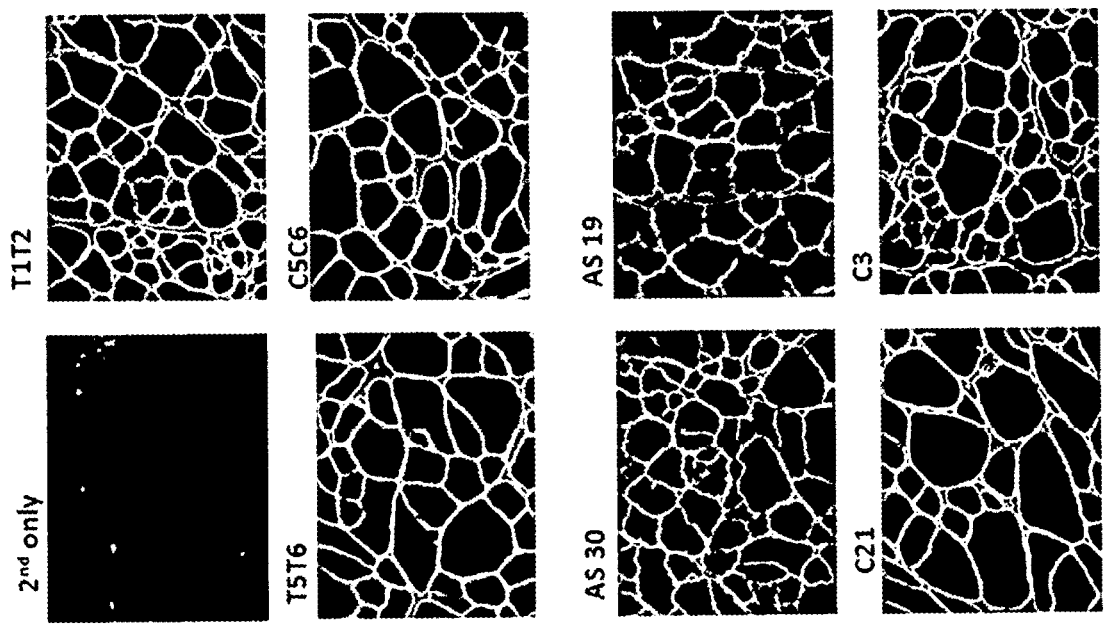

Slide sections were quickly dipped into cold PBS and fixed in ice-cold acetone for 15 minutes. Slides were washed and blocked (2% BSA and 1% normal goat serum in PBS) overnight at 4° C. The next day, slides were incubated with anti-mIgG Alexa Fluor 488 (Invitrogen) at 1:100 dilution for 2 hours (room temperature). Slides were washed and mounted using Vectashield mounting media with DAPI (Vector Labs). Slides were visualized with an inverted microscope (Olympus IX71) utilizing appropriate filter sets.
Evans Blue Dye (EBD) Myofiber Damage Evaluation Tissue sections were processed as above except without immunofluorescence staining. All EBD positive fibers on each section were counted manually for both the left TA (biAb IM) and right TA (monoclonal parent antibody IM).
Results In order to determine whether biAbs are able to bind native antigens in mouse muscle tissues, unfixed frozen sections of wildtype or LARGE$^{myd-3J/GrsrJ}$ mice, which are a murine model for alpha-dystroglycanopathy, were stained with biAbs (T1T2, T5T6, C5C6) or parental mAbs. The results indicated that biAbs were able to bind as well as the monospecific parental mAbs in both wild-type (FIG. 8A) and LARGE$^{myd-3J/GrsrJ}$ (FIG. 8B) mouse muscle tissue sections.

Figure 8C:
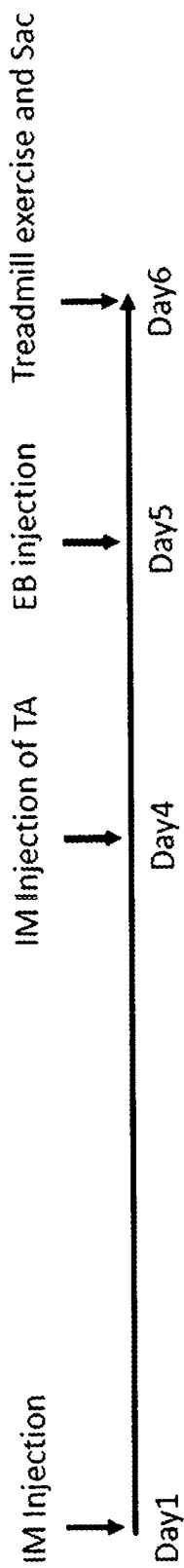
FIG. 8C outlines the bispecific intramuscular injection study plan for testing the effect of bispecific antibodies on exercise-induced muscle damage. Bispecific antibodies were injected intramuscularly into tibialis anterior (TA) muscles of LARGE$^{myd-3J/GrsrJ}$ mice at day 1 and day 4 of the experiment. Evans blue dye (EB) was injected at day 5 to track muscle fiber damage. Mice underwent forced treadmill exercise and were sacrificed on day 6.

Bispecific antibodies were then intramuscularly administered to wildtype or LARGE$^{myd-3J/GrsrJ}$ mice (study outline is shown in FIG. 8C). To assess the effect of bispecific antibodies on exercise-induced tissue damage, immunofluorescence and Evans blue dye myofiber staining was performed on tissue from exercised mice. Immunofluorescence revealed that bispecific antibodies bound well to mouse muscle tissue (left or right tibialis anterior (TA) muscle) and was detectable 2 days after the last antibody injection (FIG. 8E). biAb treated left TAs had significantly fewer EBD positive fibers compared to the right contralateral control TAs (FIG. 8D). Evans blue dye penetrated many muscle fibers of LARGE$^{myd-3J/GrsrJ}$ mouse tissue treated with a mixture of parental antibodies, indicating exercise-induced damage since the dye only penetrates and stains muscle fibers with membrane damage (FIG. 8E). In contrast, Evans blue dye penetrated significantly fewer muscle fibers of LARGE$^{myd-3J/GrsrJ}$ mouse tissue treated with bispecific antibodies (FIG. 8E). This indicates that local injection of bispecific antibodies, but not parental monoclonal antibodies, protected muscle from exercise-induced damage in an in vivo mammalian model for alpha-dystroglycanopathy.

Example 5

Systematic Delivery of Bi-Specific Antibodies Into LARGE$^{myd-3J/GrsrJ}$ Mice Methods
Antibody Delivery For exercise-induced tissue damage testing, four different groups of LARGE$^{myd-3J/GrsrJ}$ mice were intravenously injected with a single dose of parental or bispecific antibody (with murine Fc region) via the lateral tail vein (IV) or intraperitoneally (IP). Each group received one of the following: parental anti-LG-4/5 (clone C3, IV), parental anti-beta-DG (clone AS19, IV), biAb (AS19×C3, IV), and biAb (AS19×C3, IP). One day after the injection, all mice received intraperitoneal injections (IP) of Evans blue dye (EBD) at 10 mg/ml with 50 µl given per 10 g body weight.

For behavioral testing, creatine kinase measurements, and biodistribution immunofluorescence experiments, LARGE$^{myd-3J/GrsrJ}$ mice (aged 11-19 weeks) were randomized into two groups (n=16) before treatment. One group of mice was dosed at 30 mg biAb (T1T2) per kg mouse twice a week for 7 weeks. The second group of mice was dosed with a mixture of parental monoclonal antibodies (AS19 and C3, 15 mg antibody per kg mouse each) twice a week for 7 weeks. To prevent anaphylactic reaction, 5 mg per kg of diphenhydramine was pre-dosed intraperitoneally 10 minutes before administration of antibodies. Wildtype mice were treated with saline as a control.
Exercise-Induced Tissue Damage 1 day after intraperitoneal EBD injection, all mice were exercised via a forced treadmill until exhaustion. The animals were euthanized with $CO_2$ according to the standard IACUC protocol.
Behavioral Testing and Creatine Kinase Measurements For grip strength test, mice were allowed to acclimate to the testing room for 10 min before the test. The grip strength meter (Columbia Instruments, Columbus, Ohio) was mounted horizontally on a stable surface. The test mouse was gently placed on the top of the grid such that both of its front paws and hind paws were allowed to clasp onto the grid. The animal was then gently pulled backwards by its tail until the grip was released. The amount of force generated at the point of release was recorded on the strain gauge (grams). This procedure was performed 3 times for each animal and the grip force value was then calculated as the average of three tests.

For wire hang test, each animal was put on a wire screen, which was gently shifted side to side until the animal grabbed the wire. The wire-screen was then lifted to about 2 feet above a cushion pad and turned upside down. The time (latency) of animal from falling off the wire screen to the cushion pad was recorded, with a maximum cut-off time of 60 seconds. Each animal was tested twice with resting time of at least 5 min between tests.

Creatine kinase (CK) levels were measured at the beginning of the study (prior to bispecific antibody treatment) and at the end of the study (1 hr post-treadmill exercise after 7 weeks of bispecific antibody treatment) via standard colorimetric assay.

Tissue Preparation and Immunofluorescence Staining

For detection of bispecific antibodies in target organs, animals were euthanized 4 days after the last bispecific antibody intramuscular injection. TA muscles were removed, cut and placed in optimum cutting temperature compound. The tissue was then rapidly frozen via a 2-methyl butane dry ice bath. The tissue was cryo-sectioned in a cryostat, at a thickness of 10 microns.

For exercise-induced tissue damage samples, TA muscles were removed, cut and placed in optimum cutting temperature compound after exercise. The tissue was then rapidly frozen via a 2-methyl butane dry ice bath. The tissue was cryo-sectioned in a cryostat, at a thickness of 10 microns. Four different levels were cut (in triplicate) from the TA, 100 microns apart.

For both sets of tissue samples, slides were washed and blocked (2% BSA and 1% normal goat serum in PBS) overnight at 4° C. The next day, slides were incubated with anti-mIgG Alexa Fluor 488 (Invitrogen) at 1:100 dilution for 2 hours (room temperature). Slides were washed and mounted using Vectashield mounting media with DAPI (Vector Labs). Slides were visualized with an inverted microscope (Olympus IX71) utilizing appropriate filter sets.

Evans Blue Dye (EBD) Myofiber Damage Evaluation

Tissue sections were processed as above except without immunofluorescence staining. All EBD positive fibers on each section were counted manually for both the left TA (biAb IM) and right TA (monoclonal parent antibody IM).

Results

Figure 8F:
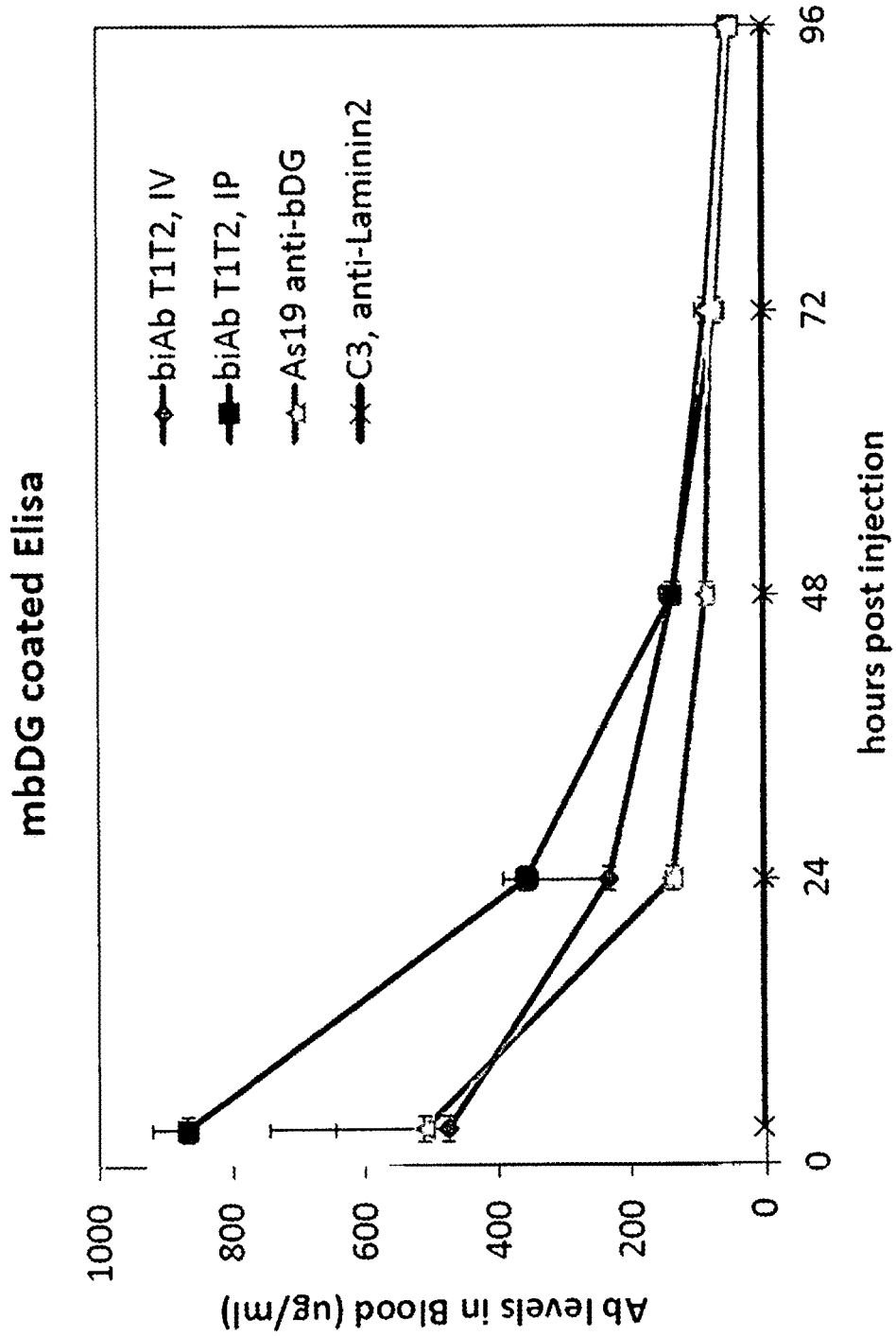
FIG. 8F shows the pharmacokinetics and biodistribution of bispecific antibody T1T2 (administered either by tail vein injection or intraperitoneally) and of parental antibodies derived from hybridoma clones AS19 or C3 after systemic delivery. Bispecific antibodies are still detectable in blood 4 days after dosing.

LARGE$^{myd-3J/GrsrJ}$ mice were dosed with 30 mg/kg of biAb (T1T2) and the parental antibodies as control, either by tail vein injection (IV) or intraperitoneally (IP) for comparison. Blood samples were collected by eye bleeding at 24, 48, 72, and 96 hrs after dosing, and the antibody levels were measured by ELISA coated with beta-DG (FIG. 8F) or LG4/5 (not shown). biAb had similar clearance rate of the parental mAbs. IP dosing resulted in high concentration but the overall pharmacokinetics of the biAb was similar to that dosed by IV. The anti-LG4/5 parental mAb had no signal when beta-DG was used for coating as expected.

Figure 9A:
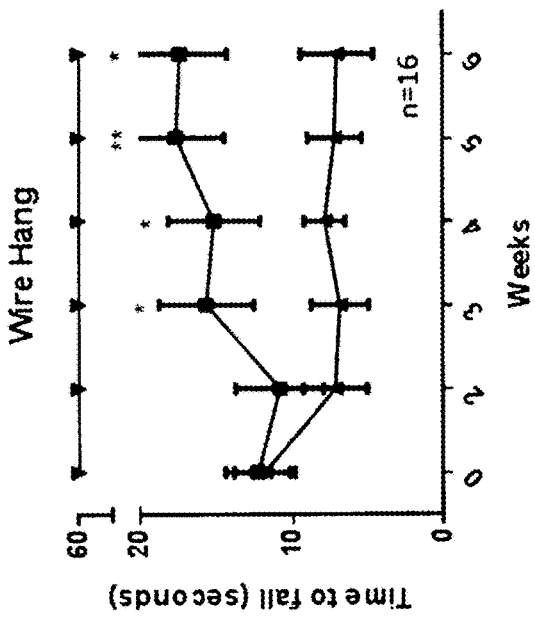
FIGS. 9A to 9C show behavioral testing of wildtype mice (triangles pointing down), LARGE$^{myd-3J/GrsrJ}$ mice treated with control monoclonal parental antibodies (triangles pointing up), and bispecific antibody-treated LARGE$^{myd-3J/GrsrJ}$ mice (squares).
Figure 9B:
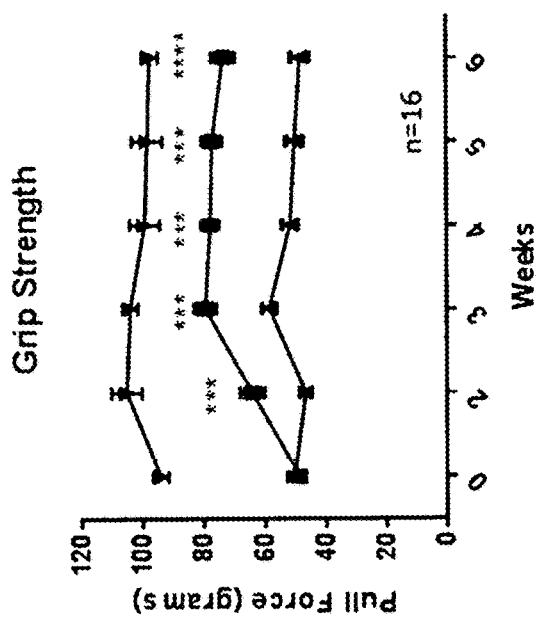
Figure 9C:
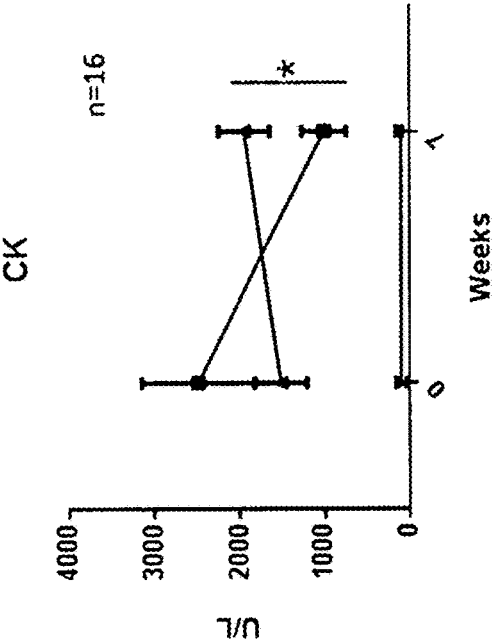

Bispecific antibodies were next administered IV to wild-type or LARGE$^{myd-3J/Grsd}$ mice. Behavioral testing revealed that LARGE$^{myd-3J/GrsrJ}$ mice that were administered bispecific antibodies performed better on the grip strength test and wire hang test (FIGS. 9A & 9B), which are measures of muscle function, than mice treated with monoclonal parental antibodies (FIGS. 9A & 9B). Control wild-type mice treated with saline are also shown in FIGS. 9A & 9B. These data demonstrate that bispecific antibodies improved muscle function. LARGE$^{myd-3J/GrsrJ}$ mice that were administered bispecific antibodies also maintained performance on the treadmill test, whereas LARGE$^{myd-3J/GrsrJ}$ mice treated with control antibody showed performance deterioration (FIG. 9C).

Figure 9D:
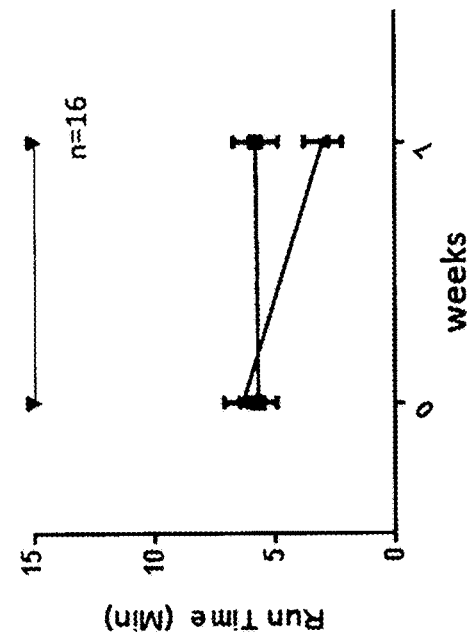
FIG. 9D shows that bispecific antibody-treated LARGE$^{myd-3J/GrsrJ}$ mice have decreased creatine kinase levels compared to untreated LARGE$^{myd-3J/GrsrJ}$ mice, suggesting less muscle damage.

Despite poor performance in the treadmill test, LARGE$^{myd-3J/GrsrJ}$ mice treated with control antibody showed increased CK levels. Significant elevation of serum CK levels indicates acute muscle damage as the result of lacking sarcolemma protection. By the end of the study, creatine kinase levels were significantly lower for LARGE$^{myd-3J/GrsrJ}$ mice treated with bispecific antibodies compared to mice treated with monoclonal parental antibodies (FIG. 9D). Treatment with bispecific antibodies lowered the creatine kinase levels in LARGE$^{myd-3J/GrsrJ}$ mice indicating that bispecific antibodies helped to protect muscles from damage.

Figure 10:
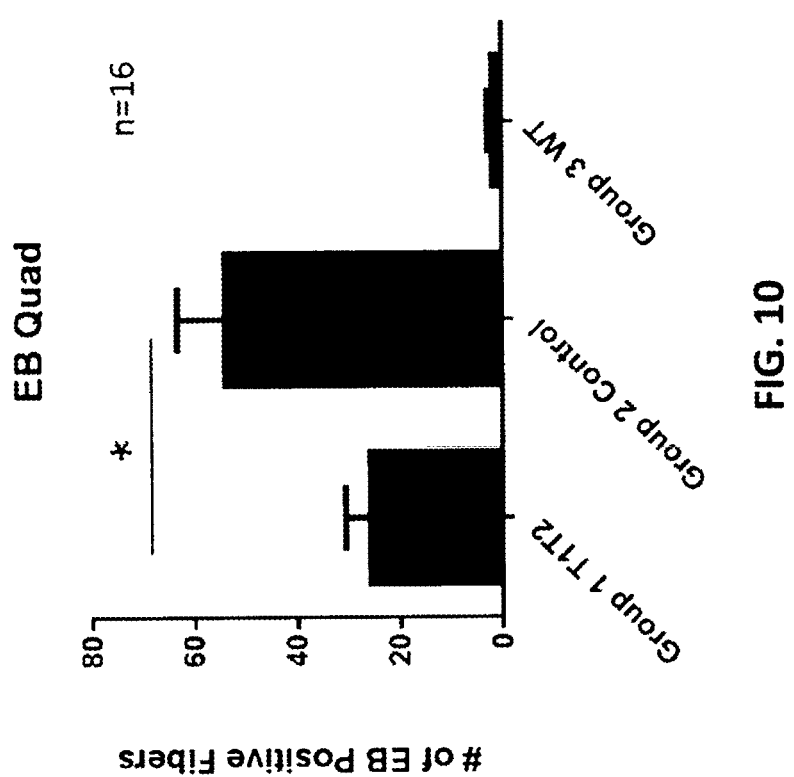
FIG. 10 shows the average number of Evans blue positive (i.e. damaged) muscle fibers in tissue from LARGE$^{myd-3J/GrsrJ}$ mice treated with bispecific antibody T1T2 (group 1 T1T2) versus a mixture of parental monoclonal antibodies AS19 and C3 (group 2 control). Wildtype untreated mice (group 3 WT) were used as a control. Less damage was seen with bispecific antibody T1T2 treatment than with the control parental antibody treatment in LARGE$^{myd-3J/GrsrJ}$ mice.

To assess the effect of bispecific antibodies on exercise-induced tissue damage, Evans blue dye myofiber staining was performed on tissue from exercised mice. Evans blue dye penetrated many muscle fibers of LARGE$^{myd-3J/GrsrJ}$ mouse tissue treated with a mixture of parental antibodies, indicating exercise-induced damage since the dye only penetrates and stains muscle fibers with membrane damage. In contrast, Evans blue dye penetrated significantly fewer muscle fibers of LARGE$^{myd-3J/GrsrJ}$ mouse tissue treated with bispecific antibodies than that of mice treated with parental antibodies (FIG. 10). This indicates that systematic delivery of bispecific antibodies, but not of parental monoclonal antibodies, protected muscle from exercise-induced damage.

For detection of bispecific antibodies in target organs, animals were euthanized 4 days after the last bispecific antibody intramuscular injection and immunofluorescence staining was performed. Staining revealed that even after 4 days, bispecific antibody T1T2 (AS19×C3) administered either by IV or intraperitoneally still specifically bound muscle tissue in the quadriceps, TA, diaphragm, and heart, but did not stain brain tissue, which was used as a negative control (FIG. 11, first and second row). Parental monoclonal antibody AS19 did not stain muscle tissue well (FIG. 11, third row), potentially due to a fast off-rate of the antibody (see Table K). However, parental monoclonal antibody C3 stained muscle tissue well (FIG. 11, fourth row), as is consistent with FIG. 4B.

Figure 12B:
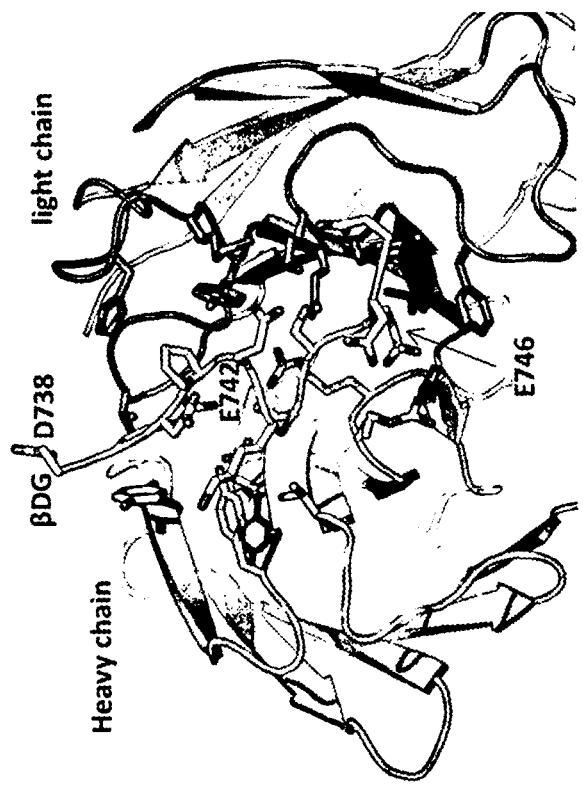
FIG. 12B shows a close up view of the interaction between the CDRs of AS30 Fab and antigen beta-DG. Residues involved in the interaction are shown as sticks; arrows in CDRs indicate orientation from N-terminus to C-terminus.
Figure 12A:
FIG. 12A shows the overall structure of the AS30 Fab bound to antigen human beta-DG, with the antigen shown between the heavy chain and light chain.

The overall structure of the AS30 Fab bound to antigen beta-DG was determined, with the antigen shown between the heavy chain and light chain (FIG. 12A). FIG. 12B shows a close-up view of the CDR regions and the antigen. AS30 Fab and human βDG were mixed at 1:1 molar ratio and incubated on ice for 30 minutes before subjected to SEC Superdex 200 10/300 GL column (GE Healthcare) at 4° C. AS30:βDG complex was crystallized and its structure was determined with molecular replacement and refined to 2.55 Å. AS30 Fab and βDG sequence D$^{738}$RDPEKSSEDD$^{748}$ (SEQ ID NO:302) were visible in the electron density map. The crystal structure shows that AS30 antibody recognizes the linear peptide D$^{738}$RDPEKSSEDD$^{748}$ (SEQ ID NO:302) in βDG.

Figure 12D:
FIG. 12D shows a close up view of the interaction between the CDRs of C21 Fab and antigen laminin-2 LG-5 domain. Residues involved in the interaction are shown as sticks; arrows in CDRs indicate orientation from N-terminus to C-terminus.
Figure 12C:
FIG. 12C shows the overall structure of the C21 Fab bound to antigen human laminin-2 LG-5 domain, with the antigen shown between the heavy chain and light chain.

In addition, the overall structure of the C21 Fab bound to antigen human laminin-2 LG-5 domain was determined, with the antigen shown between the heavy chain and light chain (FIG. 12AC). FIG. 12D shows a close-up view of the CDR regions and the antigen. C21:LG5 complex structure was obtained in a similar fashion as AS30:βDG and was refined to 2.70 Å. C21Fab and human LG5 were both visible in the electrondensity, and C21 recognizes a conformational epitope on LG5.

Example 6

Generation of Trivalent, Multispecific Antibodies Recognizing Beta-DG and Laminin-2

Methods
Antibody Humanization

Humanization of the lead hybridoma antibodies was performed using both CDR grafting and 3D modeling techniques. Methods for antibody humanization are described in Jones et al., Nature 321: 522 (1986); Verhoeyen et al., Science 239: 1534 (1988); Sims et al., J Immunol 151: 2296 (1993); Chothia and Lesk, J Mol Biol 196: 901 (1987); Carter et al., Proc Natl Acad Sci USA 89: 4285 (1992); Presta et al., J Immunol 151: 2623 (1993); U.S. Pat. Nos. 5,589,205; 5,565,332; 6,180,370; 6,632,927; 7,241,877; 7,244,615; 7,244,832; 7,262,050; and U.S. Patent Publication No. 2004/0236078 (filed Apr. 30, 2004).

Antibody Expression and Purification

The aDG trivalent antibodies were constructed by creating mammalian expression vectors with heavy chain constant regions that contain the knob-in-hole, NNAS, YTE, and RF variants and light chain constant regions. DNA variable domains with the desired linkers were synthesized and inserted in the desired heavy or light chain vectors. The configuration of each triAb is shown in Table M (numbering of antigen binding domains according to diagram in FIG. 13, i.e., VH1/VL1 and VH2/VL2 form CODV arm, and VH3/VL3 forms Fab arm). Amino acid sequences of the polypeptide chains of the triabs are provided in Table I2.

TABLE M triAb configurations.

| triAb Name | VH1/VL1 binding domain | VH2/VL2 binding domain | VH3/VL3 binding domain |
|---|---|---|---|
| 3407 | C3_Hu10 | C3_Hu10 | AS30_Hu6 |
| 3423 | C3_Hu10 | C21_Hu11 | AS30_Hu6 |
| 3429 | C3_Hu11 | C21_Hu21 | AS30_Hu6 |
| 3437 | C21_Hu11 | C3_Hu11 | AS30_Hu6 |
| 3439 | C21_Hu21 | C3_Hu10 | AS30_Hu6 |

Trivalent antibodies were produced by transient cotransfection of four plasmids in Expi293F cells with Expifectamine (Thermo Fisher Scientific, A14635). Antibodies were purified with MabSelect SuRe columns (GE Healthcare, 11003494) followed by cation exchange with a HiTrap SP HP columns (GE Healthcare, 17115201). All proteins were then assessed for concentration, purity, and aggregation.

Dual Binding of Antibodies to Human Antigens

Figure 1A:
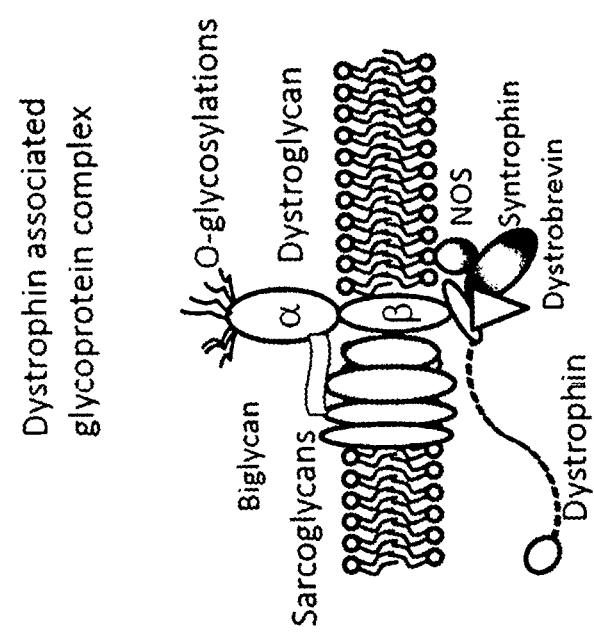

A dual binding sandwich ELISA was performed by coating Thermo Nunc Immobilized SA 96 well plates with either 2 ug/mL of biotinylated N'Avi-HPC4-human LG4/5 or biotinylated human-beta DG-HPC4-Avi-C'. After overnight incubation at 4° C., the plates were blocked with PBS+1% BSA+0.1% Tween for 1 hour at room temperature. After washing (BioTek ELx405 Select CW) with PBS, the trivalent or parental antibodies were added to the plate started at 8 ug/mL and a 2-fold dilution was performed across the plate, antibody was incubated for 1 hour at room temperature. After washing, the second antigen of beta-DG-mFc (FIG. 1A) or LG4/5-mFc was added at 5 ug/mL. Following the second antigen, a secondary antibody of donkey anti-mouse (Jackson ImmunoResearch) at a 1:2,000 dilution was added for 30 minutes. ABTS was resuspended in ABTS buffer (Roche) and added to the wells for detection. Resulting signal was read with the Perkin Elmer EnVision Multimode Plate Reader at 405 nm.

For sequential dual binding of antigens to trivalent antibodies, a Series S Sensor Protein G chip (GE Healthcare, 29179315) was used with a T100 Biacore. This chip was used to immobilize trivalent or parental antibody to the surface (60 seconds with 5 ug/mL of antibody). After capture, 200 nM of LG4/5 was flowed over the chip for 60 seconds followed by 200 nM of beta-DG for 60 seconds. Binding to the trivalent antibody was observed by the change of mass detected on the chip in relative units (RU).

Binding Kinetics Assay

Surface plasmon resonance ("SPR;" T100 Biacore; GE Healthcare) kinetics assay data with the trivalent antibodies was performed by immobilizing the antibodies (10 ug/mL) onto a Sensor S Protein G chip and then flowing serial dilutions of antigen over the chip (LG4/5: 80 nM-1.25 nM, BDG: 5 nM-0.31 nM and 4 nM-0.25 nM). Data was evaluated with a 1:1 binding model using the BIAevaluation software.

Results

Figure 13:
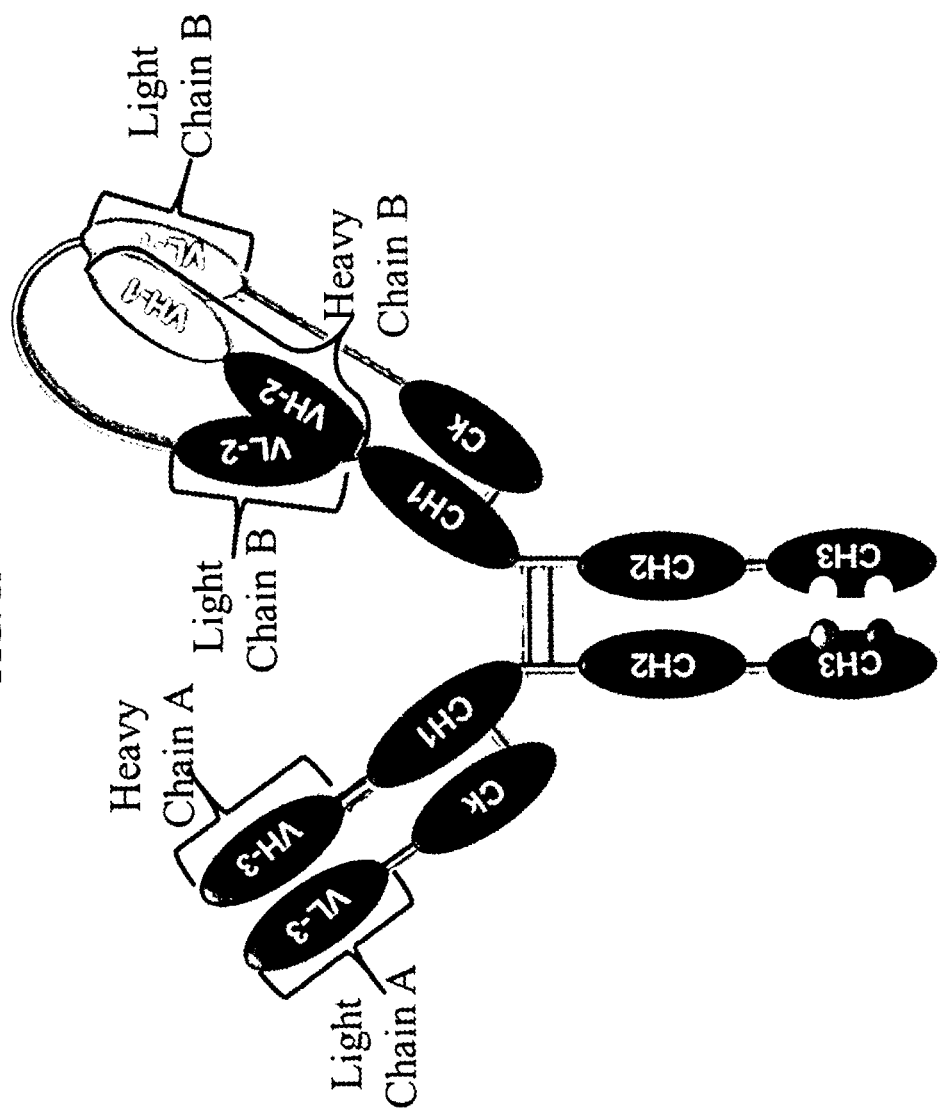
FIG. 13 shows a schematic representation of a trivalent binding protein (triAb) comprising four polypeptide chains that form three antigen binding sites for binding laminin-2 or beta-DG, in accordance with some embodiments.

Trivalent antibodies (triAbs) were generated according to the format shown in FIG. 13. These triAbs had a CODV arm with two distinct anti-laminin-2 antigen binding domains (VH-1/VL-1 and VH-2/VL-2 in FIG. 13) and a Fab arm (VH-3/VL-3 in FIG. 13) with an anti-beta-DG antigen binding domain.

Figure 14A:
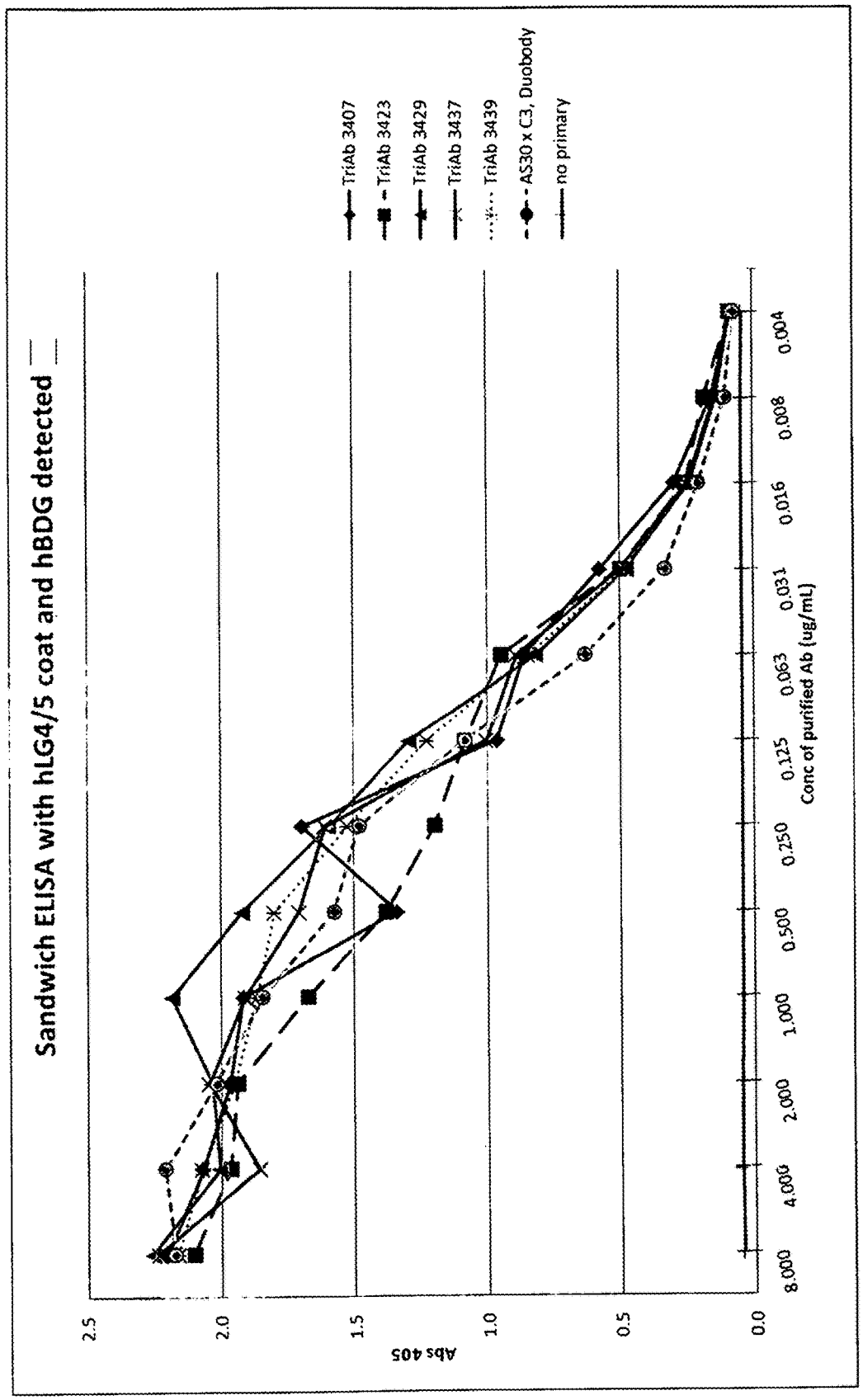
FIGS. 14A & 14B show the results of dual binding sandwich ELISA assays examining triAb binding to human LG4/5 or beta-DG.
Figure 14B:
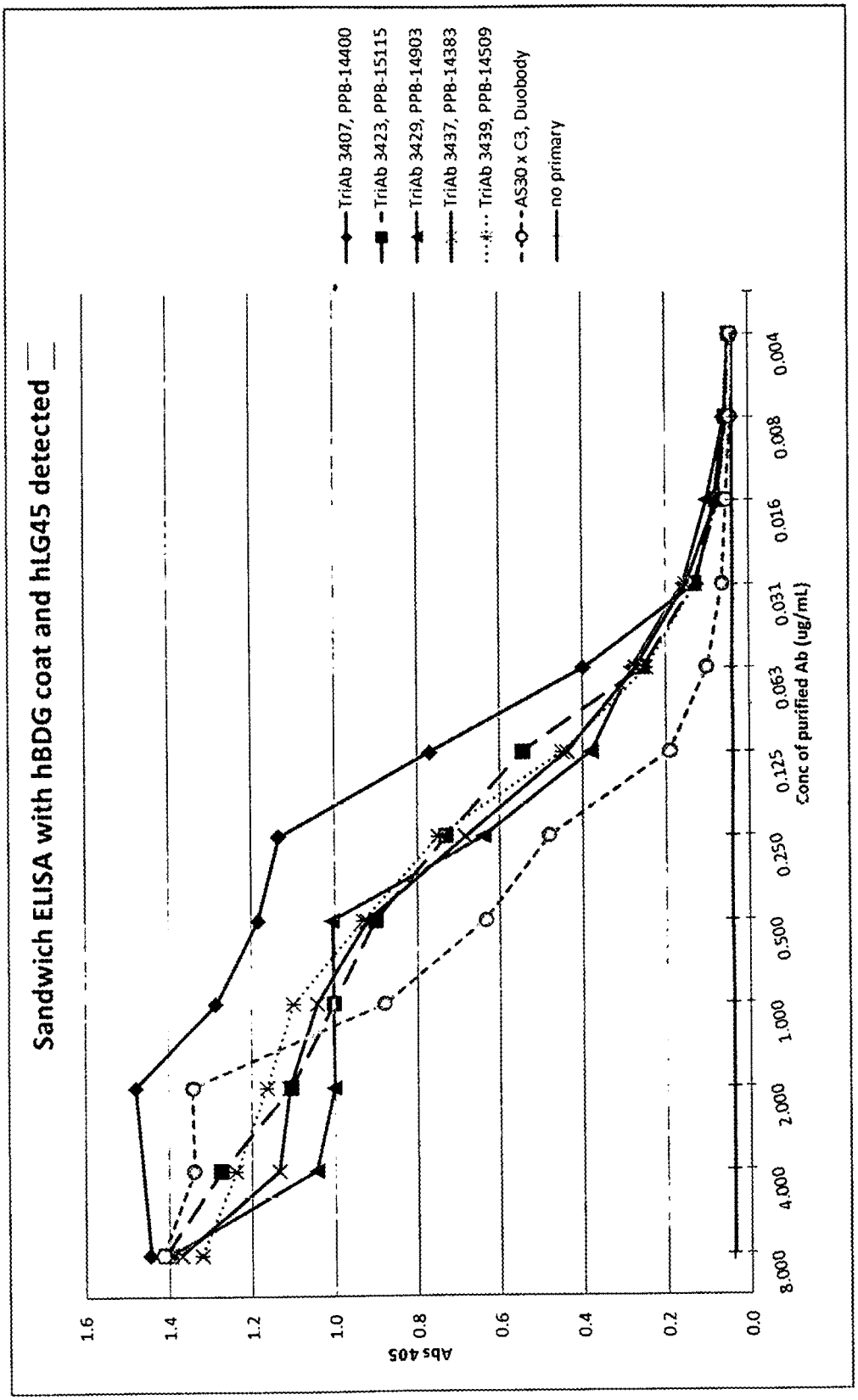
Figure 14C:
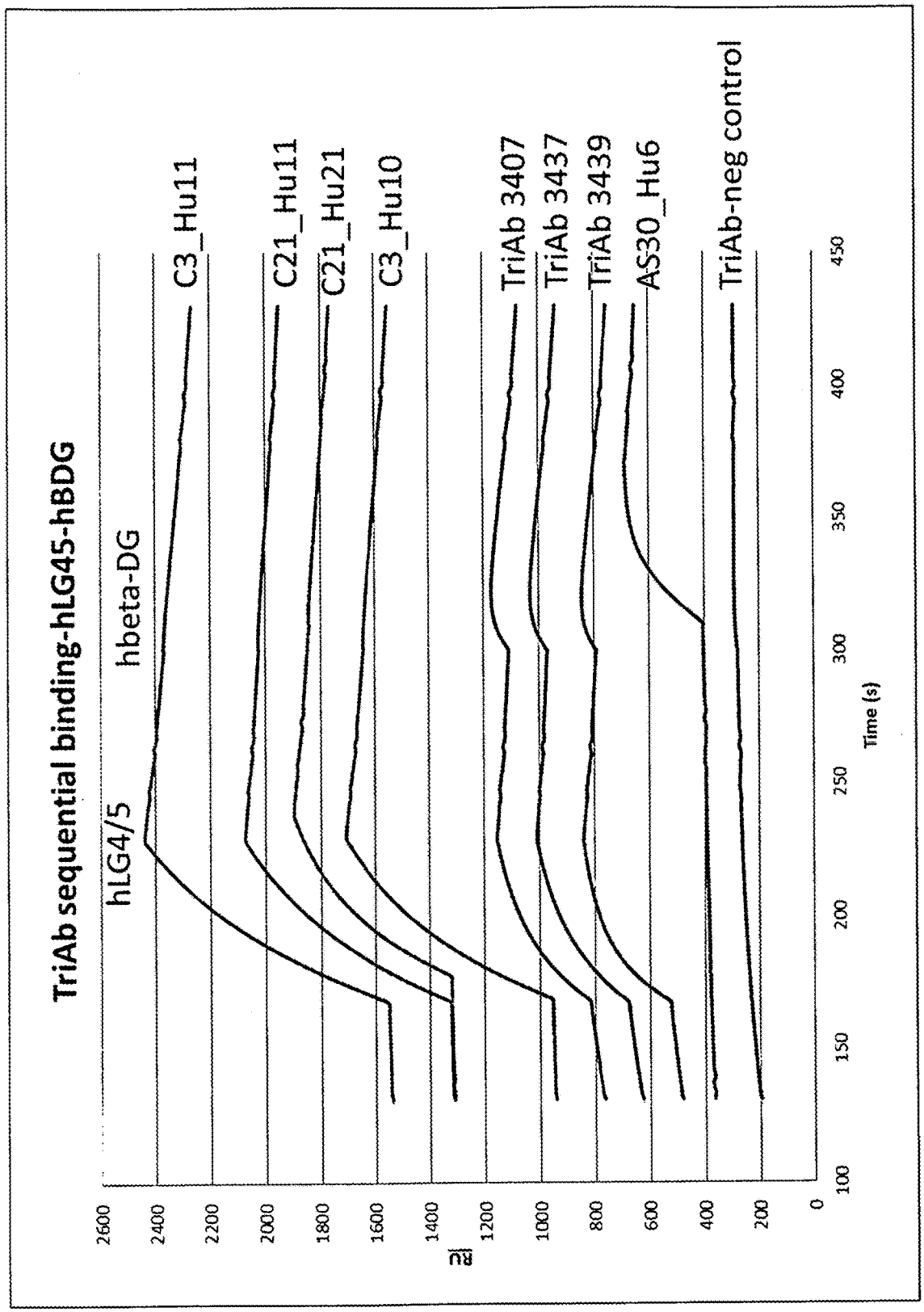
FIG. 14C shows sequential binding of triAb 3407, 3437, or 3439 to human LG4/5, then human beta-DG. In contrast, monovalent anti-LG4/5 antibodies C3_Hu11, C21_Hu11, C21_Hu21, and C3_Hu10 only bound LG4/5, while monovalent anti-beta-DG antibody AS30_Hu6 only bound beta-DG, and negative control triAb showed no binding.

To show binding of the triAbs to both antigens, a dual binding sandwich ELISA was performed as described above using 2 ug/mL of biotinylated N'Avi-HPC4-human LG4/5 (FIG. 14A) or biotinylated human-beta DG-HPC4-Avi-C' (FIG. 14B). In both orientations, all triAbs tested showed simultaneous dual binding.

Figure 1C:
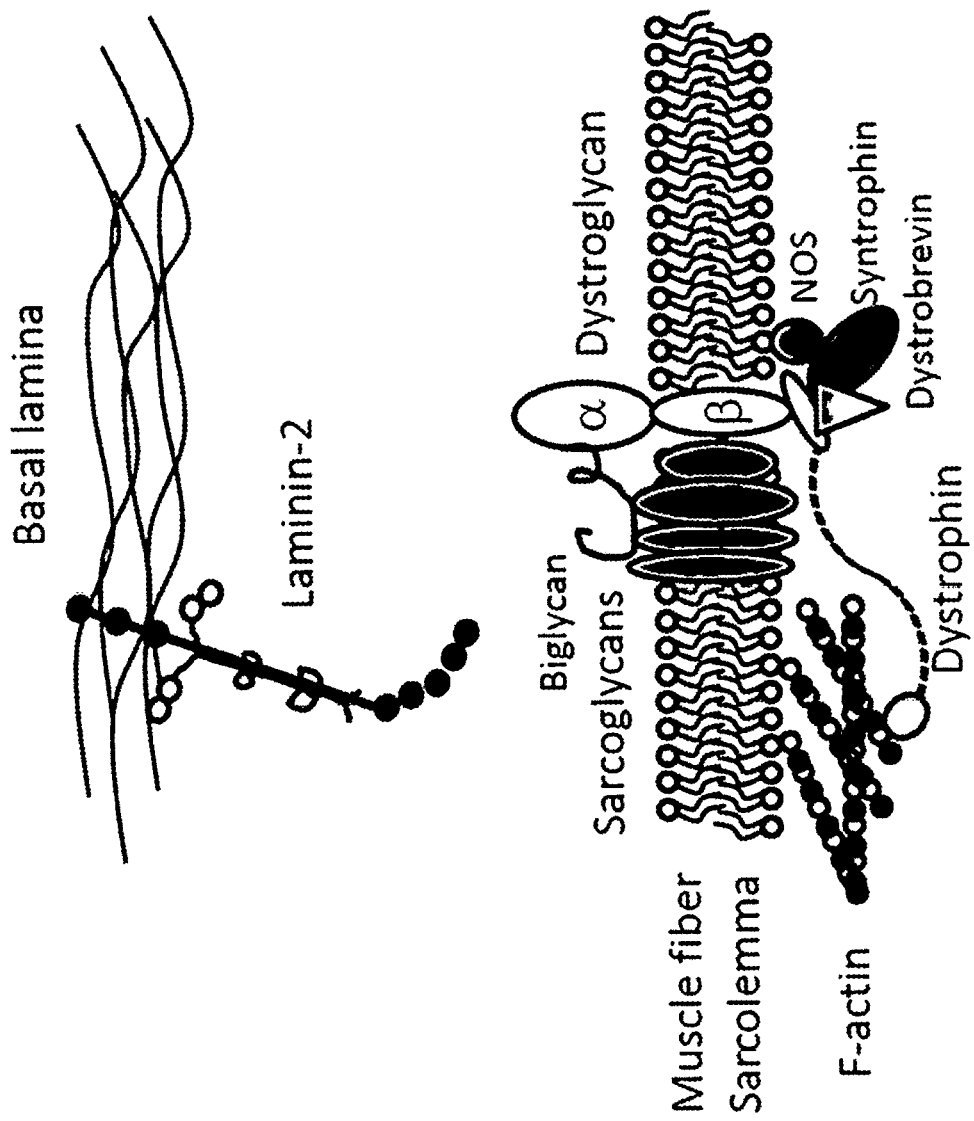
FIG. 1C shows the etiology of alpha-dystroglycanopathy. In the absence of O-linked glycosylation on alpha-dystroglycan, the binding of laminin-2 and alpha-dystroglycan is lost, resulting in the detachment of the basal lamina from the muscle sarcolemma and leading to membrane damage during exercise and muscular dystrophy.
Figure 2A:
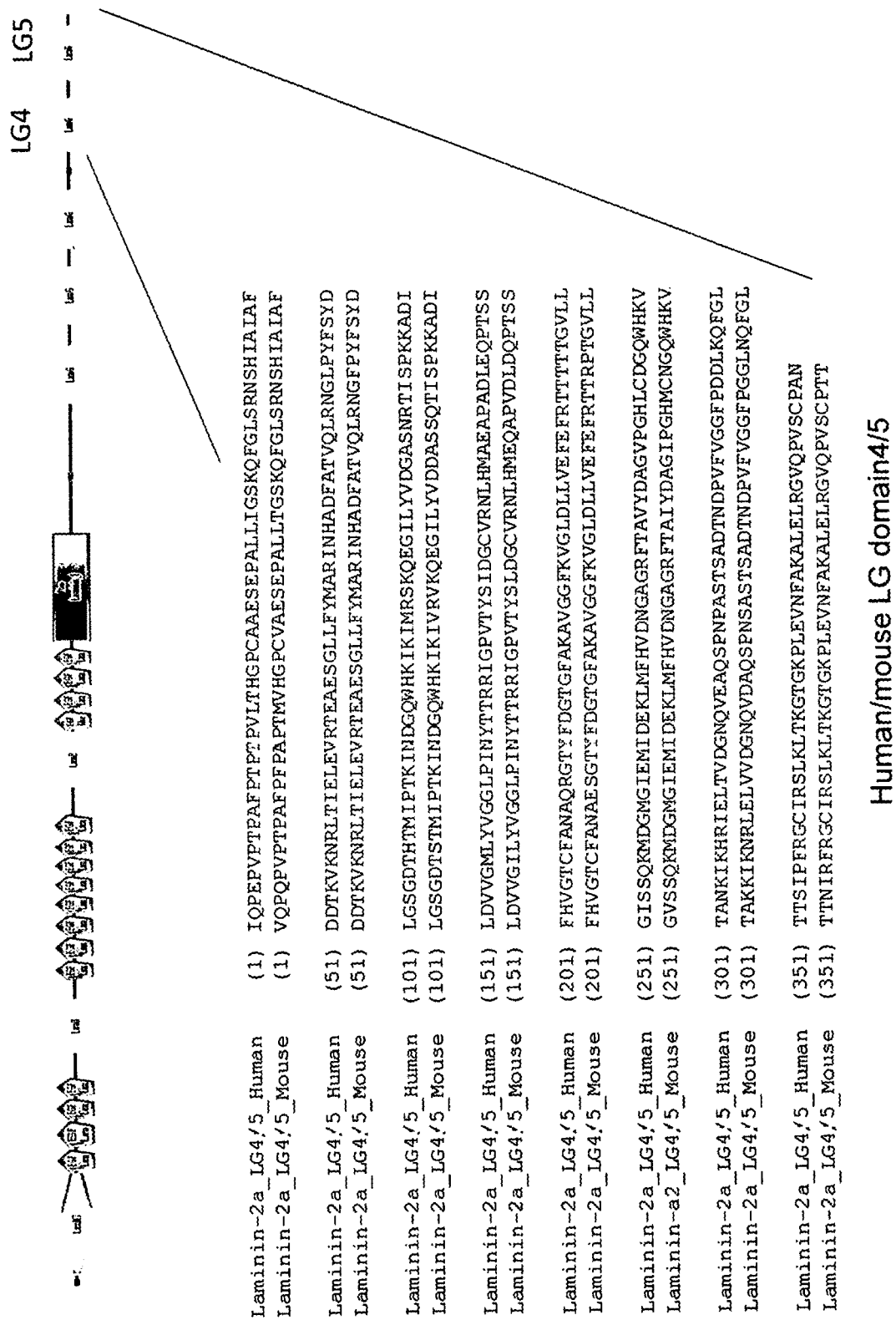
FIG. 2A shows a sequence alignment of human and mouse laminin globular (LG)-4/5 domains. The protein sequences of human and mouse LG-5 have significant homology, with 88% identity. Boxed sequences in the alpha-2 subunits of human and murine laminin-2 were used for protein expression and antibody generation. Shown are SEQ ID NOs:305 (upper) and 300 (lower).
Figure 2B:
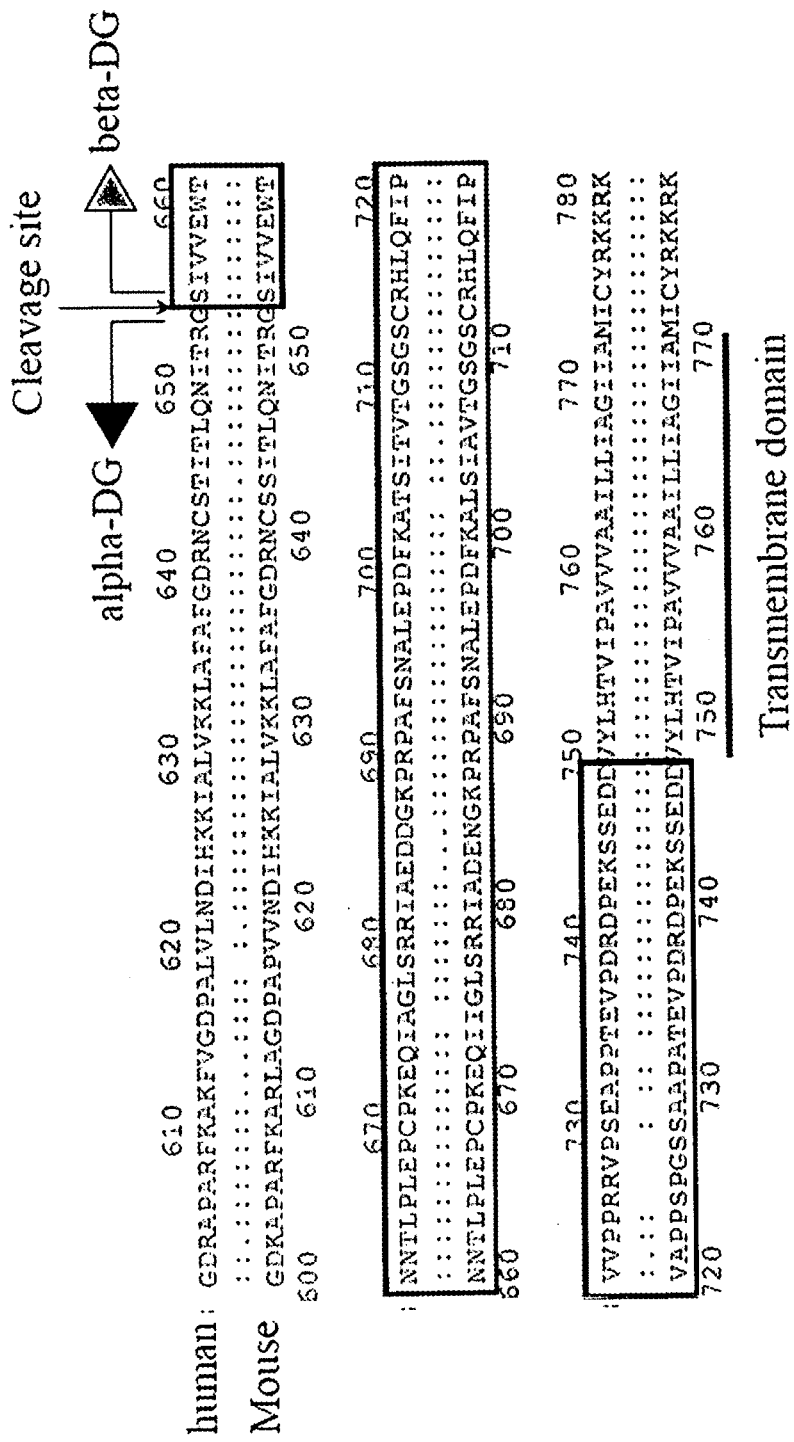
FIG. 2B shows a sequence alignment of human and mouse beta-dystroglycan (DG) extracellular domains. The protein sequences of human and mouse beta-DG extracellular domains have a homolog with 88.4% identity. Boxed sequences in human and murine beta-DGs were used for protein expression and antibody generation. Shown are SEQ ID NOs:303 (upper) and 304 (lower).

Additionally, surface plasmon resonance was performed to show sequential binding of the human laminin-2 and beta-DG antigens (FIG. 1C). The triAbs showed binding to both antigens, while the monoclonal antibodies (humanized C3 and C21 variants for binding laminin-2 and humanized AS30 variant for binding beta-DG) only bound their respective antigen.

SPR was used as described above to analyze the kinetics of triAb binding to laminin-2 (Table N) or beta-DG (Table O).

TABLE N triAb binding to laminin-2 (SPR).

| | ka (1/Ms) | kd (1/s) | KD (M) |
|---|---|---|---|
| 3407 | 1.57E+06 | 3.26E−03 | 2.08E−09 |
| 3423 | 2.70E+06 | 4.33E−03 | 1.60E−09 |
| 3429 | 2.13E+06 | 4.04E−03 | 1.90E−09 |
| 3437 | 2.41E+06 | 4.50E−03 | 1.87E−09 |
| 3439 | 3.07E+06 | 4.00E−03 | 1.30E−09 |
| AS30 Hu6 | 2.54E+06 | 2.02E−03 | 7.96E−10 |

TABLE O triAb binding to beta-DG (SPR).

| | ka (1/Ms) | kd (1/s) | KD (M) |
|---|---|---|---|
| 3407 | 1.70E+05 | 2.53E-03 | 1.49E-08 |
| 3423 | 1.85E+05 | 2.28E-03 | 1.23E-08 |
| 3429 | 1.97E+05 | 2.19E-03 | 1.11E-08 |
| 3437 | 1.70E+05 | 2.31E-03 | 1.36E-08 |
| 3439 | 2.83E+05 | 2.89E-03 | 1.02E-08 |
| C3 Hu11 | 1.19E+05 | 1.17E-03 | 9.83E-09 |
| C21 Hu21 | 1.60E+05 | 1.44E-03 | 8.99E-09 |

As shown in Table N, five triAbs were able to bind human beta-DG with nanomolar affinity ($K_D$ between 1.3-2.1 nM), comparable to that of the humanized AS30 antigen binding domain used in monovalent antibody format (0.8 nM). Similarly, Table O shows that the same triAbs were also able to bind human laminin-2 with nanomolar affinity ($K_D$ between 10.2-14.9 nM), comparable to those of the humanized C3 and C21 antigen binding domains used in monovalent antibody format (9.8 nM and 9.0 nM, respectively).

These data demonstrate that bispecific anti-laminin-2/beta-DG antibodies in the trivalent format illustrated in FIG. 13 were capable of simultaneous dual binding to their targets with similar binding affinity as compared with a traditional monovalent antibody format.

Example 7

Improvement of Muscle Functions of LARGE$^{myd-3J/GrsrJ}$ Mice on Behavioral Tests after Treatment with Trivalent, Multispecific Antibodies Recognizing Beta-DG and Laminin-2

Methods
Antibody Administration

The LARGE/myd-3j mice described in Example 4 (ages at 8-16 weeks) were randomized into five groups based on their hind-leg splay score, wire-hang score, grip-strength and treadmill to ensure these scores were similar among groups (n=11) before treatment. Mice were then dosed at 30 mg/kg twice a week via tail vein injection (Monday and Thursday) with TriAbs (3407, 3437, and 3439) and a control TriAb that recognizes unrelated protein targets as well as a saline group as controls for up to 3.5 weeks with 7 doses. In addition, a wildtype mice group (n=6) was included as benchmarks for behavioral tests. To prevent anaphylactic reaction, 5 mg/kg diphenhydramine was pre-dosed IP 10 min before administration of antibodies. Grip-strength and wire-hang were tested weekly starting at week-2. Wildtype were treated with saline as benchmarks for various behavioral tests.

Behavioral Testing

For the hind-leg splay test, mice were lifted by their tails, and the positions of the hind legs relative to the body were recorded and graded.

The wire-hang test was conducted by placing mice on a wire grid and acclimating for 1 min; then, the wire grid with the mouse grasping on was slowly turned upside down at a defined speed of 2 sec, and the time the mouse held onto the grid was recorded, with a cutoff time of 60 sec. The test was repeated 3 times for each mouse and the results averaged.

Grip strength was evaluated by placing the mice on a Grip Strength Meter (Columbus Instruments), allowing the mouse to grasp the metal grid firmly, and pulling the tail horizontally until the mouse let go; then, the force was recorded. The test was repeated 5 times with a 1 min rest in between. Highest and lowest readings were removed for each mouse and the results were the average of the three remaining readings.

For treadmill run time, mice were placed onto individual lanes of a treadmill equipped with an electric shocking grid (Model 1055SRM Exer-3/6, Columbus Instruments). The animals were acclimated to the treadmill for 5 min, and then the mice were tested with a defined protocol with increasing speed. When a mouse spent more than 3 sec on the shocking grid without being able to run, the shocking grid was turned off and the total run time was recorded.

All behavioral tests were performed while blinded to mouse identity and treatment, with the results unblinded after testing.

Results

The triAbs generated in Example 6 were tested for their effects on muscle function in LARGE/myd-3j mice.

Figure 15:
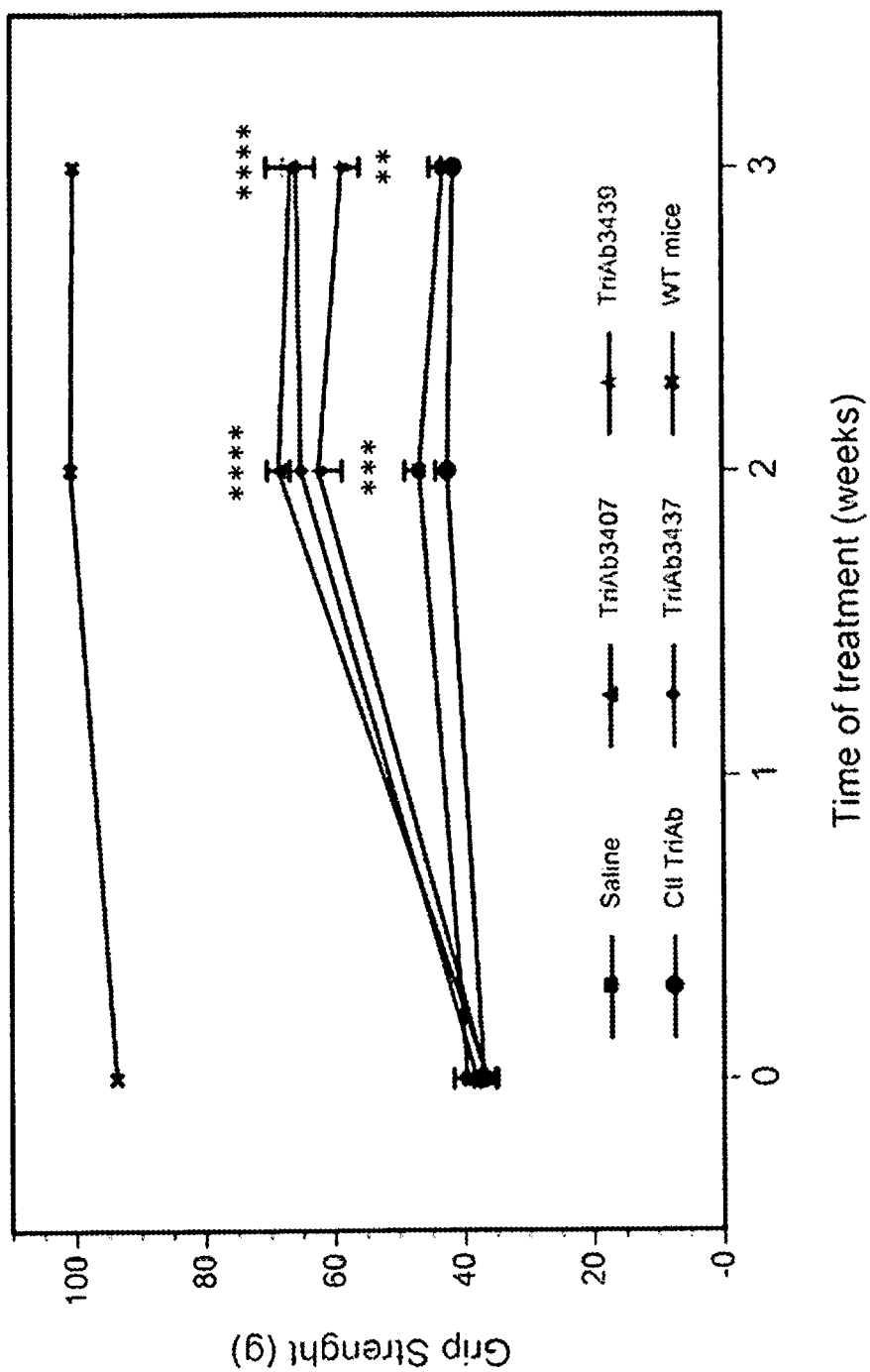
FIG. 15 shows the effects of treatment with triAb 3407, 3437, or 3439 on muscle function in LARGE$^{myd-3J/GrsrJ}$ mice using a grip strength assay. Administration with indicated triAbs was compared with administration of saline or negative control triAb. Performance of wild-type mice in the assay was also measured.
Figure 16:
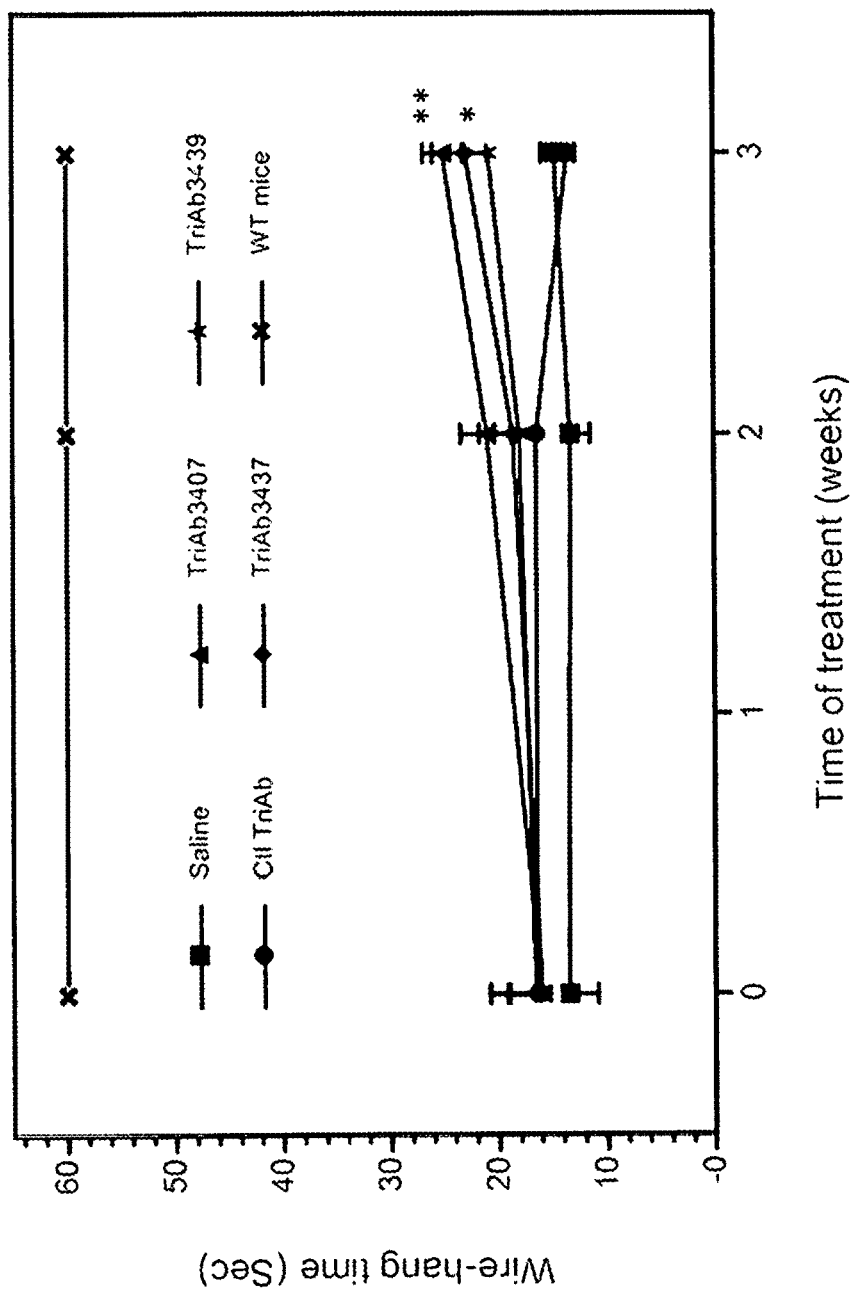
FIG. 16 shows the effects of treatment with triAb 3407, 3437, or 3439 on muscle function in LARGE$^{myd-3J/GrsrJ}$ mice using a wire-hang assay. Administration with indicated triAbs was compared with administration of saline or negative control triAb. Performance of wild-type mice in the assay was also measured.
Figure 17:
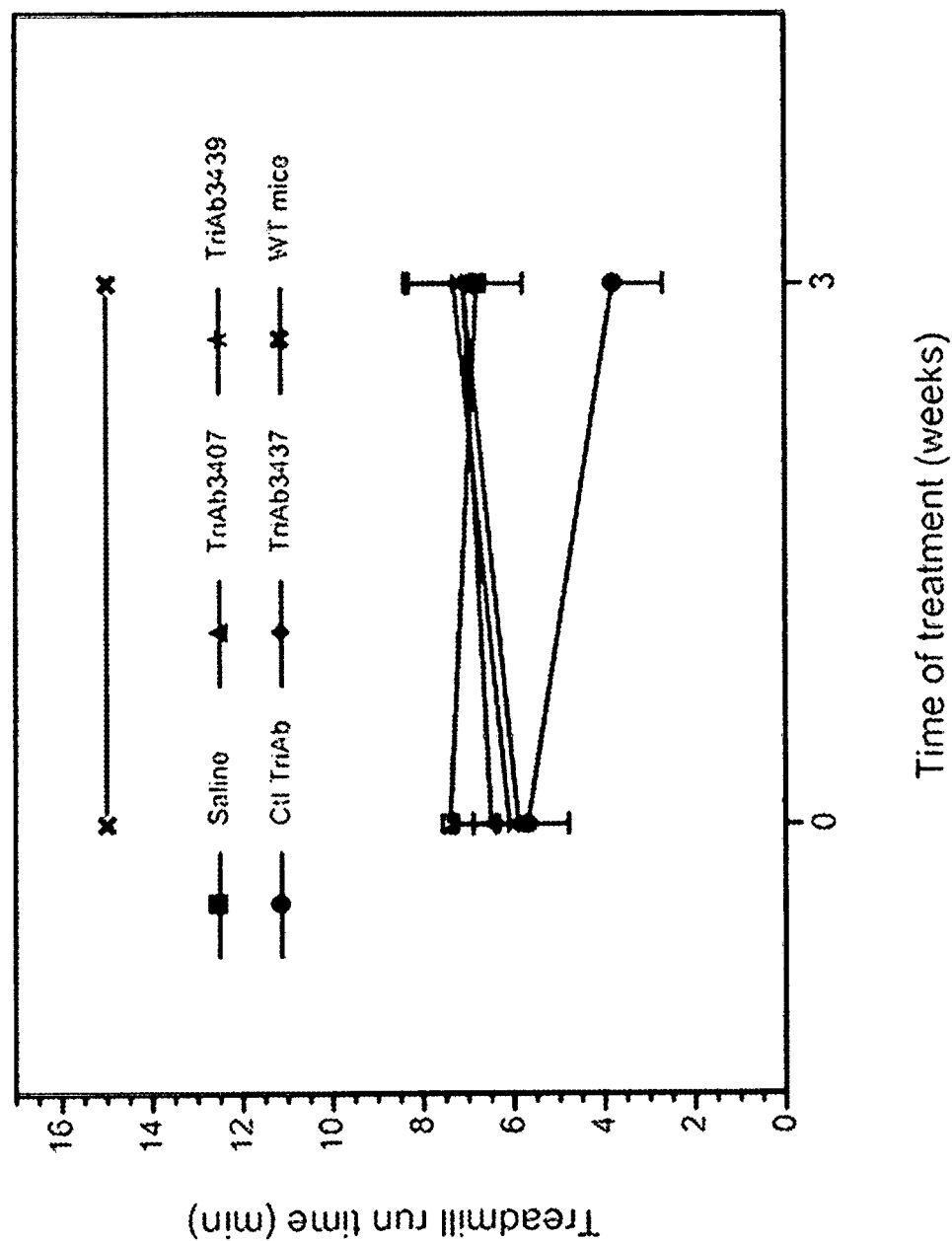
FIG. 17 shows the effects of treatment with triAb 3407, 3437, or 3439 on muscle function in LARGE$^{myd-3J/GrsrJ}$ mice using a treadmill assay. Administration with indicated triAbs was compared with administration of saline or negative control triAb. Performance of wild-type mice in the assay was also measured.

Large/myd-3j mice showed significantly improved performance on grip-strength (FIG. 15) and wire-hang (FIG. 16) after two weeks of treatment with TriAb 3407, 3437, or 3439, as was observed with biAb treatment described previously (see Example 5). Treadmill performance was maintained or slightly improved with TriAbs treatment (FIG. 17), however without statistical significance as compared to controls, which instead demonstrated slight deterioration. Typically, statistically significant improvement on treadmill run time requires longer time of treatment.

Taken together, the results of multiple functional assays demonstrated that treatment with trivalent, bispecific anti-laminin-2/beta-DG antibodies led to improved muscle function in a murine model for alpha-dystroglycanopathy.

While the present disclosure includes various embodiments, it is understood that variations and modifications will occur to those skilled in the art. Therefore, it is intended that the appended claims cover all such equivalent variations that come within the scope of the disclosure. In addition, the section headings used herein are for organizational purposes only and are not to be construed as limiting the subject matter described.

Each embodiment herein described may be combined with any other embodiment or embodiments unless clearly indicated to the contrary. In particular, any feature or embodiment indicated as being preferred or advantageous may be combined with any other feature or features or embodiment or embodiments indicated as being preferred or advantageous, unless clearly indicated to the contrary.

What is claimed is:

1. An isolated nucleic acid molecule comprising a nucleotide sequence encoding a bispecific binding molecule comprising a first binding domain that binds an extracellular portion of dystroglycan and a second binding domain that binds laminin-2, wherein the bispecific binding molecule is a bispecific binding protein comprising one or more polypeptide chains, and wherein the bispecific binding molecule comprises two light chains comprising a structure represented by the formula:

$$V_{L1}\text{-}L_5\text{-}V_{L2}\text{-}L_6\text{-}C_L \quad [III]$$

and two heavy chains comprising a structure represented by the formula:

$$V_{H1}\text{-}L_7\text{-}V_{H2}\text{-}L_8\text{-}C_{H1}\text{-hinge-}C_{H2}\text{-}C_{H3} \quad [IV]$$

wherein:

$V_{L1}$ is a first immunoglobulin light chain variable domain;

$V_{L2}$ is a second immunoglobulin light chain variable domain;

$V_{H1}$ is a first immunoglobulin heavy chain variable domain;

$V_{H2}$ is a second immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_5$, $L_6$, $L_7$, and $L_8$ are amino acid linkers;

wherein the $V_{H1}$ and $V_{L1}$ domains form a $V_{H1}/V_{L1}$ binding pair, and wherein the $V_{H2}$ and $V_{L2}$ domains form a $V_{H2}/V_{L2}$ binding pair, and wherein (a) the $V_{H1}$ domain comprises a CDR-H1 comprising the amino acid sequence of SEQ ID NO:1, a CDR-H2 comprising the amino acid sequence of SEQ ID NO:9, and a CDR-H3 comprising the amino acid sequence of SEQ ID NO:18; the $V_{L1}$ domain comprises a CDR-L1 comprising the amino acid sequence of SEQ ID NO:28, a CDR-L2 comprising the amino acid sequence of SEQ ID NO:38, and a CDR-L3 comprising the amino acid sequence of SEQ ID NO:43; the $V_{H2}$ domain comprises a CDR-H1 comprising the amino acid sequence of SEQ ID NO:52, a CDR-H2 comprising the amino acid sequence of SEQ ID NO:57, and a CDR-H3 comprising the amino acid sequence of SEQ ID NO:62; and the $V_{L2}$ domain comprises a CDR-L1 comprising the amino acid sequence of SEQ ID NO:67, a CDR-L2 comprising the amino acid sequence of SEQ ID NO:72, and a CDR-L3 comprising the amino acid sequence of SEQ ID NO:77; or (b) the $V_{H2}$ domain comprises a CDR-H1 comprising the amino acid sequence of SEQ ID NO:1, a CDR-H2 comprising the amino acid sequence of SEQ ID NO:9, and a CDR-H3 comprising the amino acid sequence of SEQ ID NO:18; the $V_{L2}$ domain comprises a CDR-L1 comprising the amino acid sequence of SEQ ID NO:28, a CDR-L2 comprising the amino acid sequence of SEQ ID NO:38, and a CDR-L3 comprising the amino acid sequence of SEQ ID NO:43; the $V_{H1}$ domain comprises a CDR-H1 comprising the amino acid sequence of SEQ ID NO:52, a CDR-H2 comprising the amino acid sequence of SEQ ID NO:57, and a CDR-H3 comprising the amino acid sequence of SEQ ID NO:62; and the $V_{L1}$ domain comprises a CDR-L1 comprising the amino acid sequence of SEQ ID NO:67, a CDR-L2 comprising the amino acid sequence of SEQ ID NO:72, and a CDR-L3 comprising the amino acid sequence of SEQ ID NO:77.

2. The nucleic acid molecule of claim 1, wherein $L_5$, $L_6$, $L_7$, and $L_8$ are each 0 to 50 amino acid residues in length.

3. The nucleic acid molecule of claim 1, wherein $L_5$, $L_6$, $L_7$, and $L_8$ are each 0 to 25 amino acid residues in length.

4. The nucleic acid molecule of claim 1, wherein $L_5$, $L_6$, $L_7$, and $L_8$ are each 0 to 14 amino acid residues in length.

5. The nucleic acid molecule of claim 1, wherein the $L_5$ and $L_7$ linkers comprise the amino acid sequence of GGGGSGGGGS (SEQ ID NO:294), and wherein the $L_6$ and $L_8$ linkers are each 0 amino acid residues in length.

6. The nucleic acid molecule of claim 1, wherein one or both of the variable domains of the polypeptides of formula III and formula IV are humanized or mouse variable domains.

7. The nucleic acid molecule of claim 1, wherein the $V_{H1}$ domain comprises the amino acid sequence of SEQ ID NO:170.

8. The nucleic acid molecule of claim 1, wherein the $V_{L1}$ domain comprises the amino acid sequence of SEQ ID NO:171.

9. The nucleic acid molecule of claim 1, wherein the $V_{H2}$ domain comprises the amino acid sequence of SEQ ID NO:192.

10. The nucleic acid molecule of claim 1, wherein the $V_{L2}$ domain comprises the amino acid sequence of SEQ ID NO:193.

11. The nucleic acid molecule of claim 1, wherein the $V_{H1}$ domain comprises the amino acid sequence of SEQ ID NO:170, the $V_{L1}$ domain comprises the amino acid sequence of SEQ ID NO:171, the $V_{H2}$ domain comprises the amino acid sequence of SEQ ID NO:192, and the $V_{L2}$ domain comprises the amino acid sequence of SEQ ID NO:193.

12. The nucleic acid molecule of claim 1, wherein the $V_{H1}$ domain comprises the amino acid sequence of SEQ ID NO:192.

13. The nucleic acid molecule of claim 1, wherein the $V_{L1}$ domain comprises the amino acid sequence of SEQ ID NO:193.

14. The nucleic acid molecule of claim 1, wherein the $V_{H2}$ domain comprises the amino acid sequence of SEQ ID NO:170.

15. The nucleic acid molecule of claim 1, wherein the $V_{L2}$ domain comprises the amino acid sequence of SEQ ID NO:171.

16. The nucleic acid molecule of claim 1, wherein the $V_{H1}$ domain comprises the amino acid sequence of SEQ ID NO:192, the $V_{L1}$ domain comprises the amino acid sequence of SEQ ID NO:193, the $V_{H2}$ domain comprises the amino acid sequence of SEQ ID NO:170, and the $V_{L2}$ domain comprises the amino acid sequence of SEQ ID NO:171.

17. An expression vector comprising the nucleic acid molecule of claim 1.

18. An isolated host cell comprising the expression vector of claim 17.

19. An isolated host cell comprising the nucleic acid molecule of claim 1.

20. A method of producing a bispecific binding molecule, the method comprising:

a) culturing the host cell of claim 19 under conditions such that the host cell expresses the bispecific binding molecule; and b) isolating the bispecific binding molecule from the host cell.

21. A vector system comprising one or more vectors encoding two light chains and two heavy chains of a bispecific binding molecule comprising a first binding domain that binds an extracellular portion of dystroglycan and a second binding domain that binds laminin-2, wherein the bispecific binding molecule is a bispecific binding protein comprising one or more polypeptide chains, and wherein the bispecific binding molecule comprises two light chains comprising a structure represented by the formula:

$$V_{L1}\text{-}L_5\text{-}V_{L2}\text{-}L_6\text{-}C_L \quad [III]$$

and two heavy chains comprising a structure represented by the formula:

$$V_{H1}\text{-}L_7\text{-}V_{H2}\text{-}L_8\text{-}C_{H1}\text{-hinge-}C_{H2}\text{-}C_{H3} \quad [IV]$$

wherein:

$V_{L1}$ is a first immunoglobulin light chain variable domain;

$V_{L2}$ is a second immunoglobulin light chain variable domain;

$V_{H1}$ is a first immunoglobulin heavy chain variable domain;

$V_{H2}$ is a second immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_5$, $L_6$, $L_7$, and $L_8$ are amino acid linkers;

wherein the $V_{H1}$ and $V_{L1}$ domains form a $V_{H1}/V_{L1}$ binding pair, and wherein the $V_{H2}$ and $V_{L2}$ domains form a $V_{H2}/V_{L2}$ binding pair, and wherein (a) the $V_{H1}$ domain comprises a CDR-H1 comprising the amino acid sequence of SEQ ID NO:1, a CDR-H2 comprising the amino acid sequence of SEQ ID NO:9, and a CDR-H3 comprising the amino acid sequence of SEQ ID NO:18; the $V_{L1}$ domain comprises a CDR-L1 comprising the amino acid sequence of SEQ ID NO:28, a CDR-L2 comprising the amino acid sequence of SEQ ID NO:38, and a CDR-L3 comprising the amino acid sequence of SEQ ID NO:43; the $V_{H2}$ domain comprises a CDR-H1 comprising the amino acid sequence of SEQ ID NO:52, a CDR-H2 comprising the amino acid sequence of SEQ ID NO:57, and a CDR-H3 comprising the amino acid sequence of SEQ ID NO:62; and the $V_{L2}$ domain comprises a CDR-L1 comprising the amino acid sequence of SEQ ID NO:67, a CDR-L2 comprising the amino acid sequence of SEQ ID NO:72, and a CDR-L3 comprising the amino acid sequence of SEQ ID NO:77; or (b) the $V_{H2}$ domain comprises a CDR-H1 comprising the amino acid sequence of SEQ ID NO:1, a CDR-H2 comprising the amino acid sequence of SEQ ID NO:9, and a CDR-H3 comprising the amino acid sequence of SEQ ID NO:18; the $V_{L2}$ domain comprises a CDR-L1 comprising the amino acid sequence of SEQ ID NO:28, a CDR-L2 comprising the amino acid sequence of SEQ ID NO:38, and a CDR-L3 comprising the amino acid sequence of SEQ ID NO:43; the $V_{H1}$ domain comprises a CDR-H1 comprising the amino acid sequence of SEQ ID NO:52, a CDR-H2 comprising the amino acid sequence of SEQ ID NO:57, and a CDR-H3 comprising the amino acid sequence of SEQ ID NO:62; and the $V_{L1}$ domain comprises a CDR-L1 comprising the amino acid sequence of SEQ ID NO:67, a CDR-L2 comprising the amino acid sequence of SEQ ID NO:72, and a CDR-L3 comprising the amino acid sequence of SEQ ID NO:77.

22. The vector system of claim 21, wherein $L_5$, $L_6$, $L_7$, and $L_8$ are each 0 to 50 amino acid residues in length.

23. The vector system of claim 21, wherein $L_5$, $L_6$, $L_7$, and $L_8$ are each 0 to 25 amino acid residues in length.

24. The vector system of claim 21, wherein $L_5$, $L_6$, $L_7$, and $L_8$ are each 0 to 14 amino acid residues in length.

25. The vector system of claim 21, wherein the $L_5$ and $L_7$ linkers comprise the amino acid sequence of GGGGSGGGGS (SEQ ID NO:294), and wherein the $L_6$ and $L_8$ linkers are each 0 amino acid residues in length.

26. The vector system of claim 21, wherein one or both of the variable domains of the polypeptides of formula III and formula IV are humanized or mouse variable domains.

27. The vector system of claim 21, wherein the $V_{H1}$ domain comprises the amino acid sequence of SEQ ID NO:170.

28. The vector system of claim 21, wherein the $V_{L1}$ domain comprises the amino acid sequence of SEQ ID NO:171.

29. The vector system of claim 21, wherein the $V_{H2}$ domain comprises the amino acid sequence of SEQ ID NO:192.

30. The vector system of claim 21, wherein the $V_{L2}$ domain comprises the amino acid sequence of SEQ ID NO:193.

31. The vector system of claim 21, wherein the $V_{H1}$ domain comprises the amino acid sequence of SEQ ID NO:170, the $V_{L1}$ domain comprises the amino acid sequence of SEQ ID NO:171, the $V_{H2}$ domain comprises the amino acid sequence of SEQ ID NO:192, and the $V_{L2}$ domain comprises the amino acid sequence of SEQ ID NO:193.

32. The vector system of claim 21, wherein the $V_{H1}$ domain comprises the amino acid sequence of SEQ ID NO:192.

33. The vector system of claim 21, wherein the $V_{L1}$ domain comprises the amino acid sequence of SEQ ID NO:193.

34. The vector system of claim 21, wherein the $V_{H2}$ domain comprises the amino acid sequence of SEQ ID NO:170.

35. The vector system of claim 21, wherein the $V_{L2}$ domain comprises the amino acid sequence of SEQ ID NO:171.

36. The vector system of claim 21, wherein the $V_{H1}$ domain comprises the amino acid sequence of SEQ ID NO:192, the $V_{L1}$ domain comprises the amino acid sequence of SEQ ID NO:193, the $V_{H2}$ domain comprises the amino acid sequence of SEQ ID NO:170, and the $V_{L2}$ domain comprises the amino acid sequence of SEQ ID NO:171.

37. An isolated host cell comprising the vector system of claim 21.

38. A method of producing a bispecific binding molecule, the method comprising:
   a) culturing the host cell of claim 37 under conditions such that the host cell expresses the bispecific binding molecule; and
   b) isolating the bispecific binding molecule from the host cell.

\* \* \* \* \*

SEQUENCE LISTING

<160> NUMBER OF SEQ ID NOS: 534

<210> SEQ ID NO 1
<211> LENGTH: 8
<212> TYPE: PRT
<213> ORGANISM: Artificial Sequence

```
<220> FEATURE:
<223> OTHER INFORMATION: Synthetic Construct

<400> SEQUENCE: 1

Gly Phe Thr Phe Thr Asp Ser Val
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic Construct

<400> SEQUENCE: 2

Gly Phe Thr Phe Ser Ser Tyr Ala
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic Construct

<400> SEQUENCE: 3

Gly Tyr Ser Phe Ser Asn Tyr Trp
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Construct

<400> SEQUENCE: 4

Gly Phe Asn Ile Lys Asp Thr Tyr
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic Construct

<400> SEQUENCE: 5

Gly Tyr Thr Phe Thr Thr Tyr Tyr
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Construct

<400> SEQUENCE: 6

Gly Phe Thr Phe Ser Ser Tyr Gly
1               5

<210> SEQ ID NO 7
<211> LENGTH: 8
<212> TYPE: PRT
<213> ORGANISM: Artificial Sequence
<220> FEATURE:
```

```
<223> OTHER INFORMATION: Synthetic Construct

<400> SEQUENCE: 7

Gly Tyr Ser Phe Thr Ser Tyr Trp
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic Construct

<400> SEQUENCE: 8

Gly Tyr Ser Phe Thr Ser Tyr Trp
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic Construct

<400> SEQUENCE: 9

Ile Tyr Pro Gly Ser Gly Ser Ile
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic Construct

<400> SEQUENCE: 10

Ile Tyr Pro Gly Ser Gly Asn Phe
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic Construct

<400> SEQUENCE: 11

Ile Ser Gly Ser Gly Gly Ser Thr
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic Construct

<400> SEQUENCE: 12

Ile Tyr Pro Gly Asp Ser Asp Thr
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic Construct
```

<400> SEQUENCE: 13

Ile Asp Pro Ala Asn Gly Asn Thr
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic Construct

<400> SEQUENCE: 14

Ile Asn Pro Ser Ala Gly Asn Thr
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic Construct

<400> SEQUENCE: 15

Ile Trp Tyr Asp Gly Ser Asn Lys
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic Construct

<400> SEQUENCE: 16

Ile Tyr Pro Gly Asp Ser Asp Thr
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic Construct

<400> SEQUENCE: 17

Ile Tyr Pro Gly Asp Ser Asp Thr
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic Construct

<400> SEQUENCE: 18

Ala Met Arg Arg Ser Tyr
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic Construct

```
<400> SEQUENCE: 19

Ala Met Arg Arg Ser Ser
1               5

<210> SEQ ID NO 20
<211> LENGTH: 18
<212> TYPE: PRT
<213> ORGANISM: Artificial Sequence
<220> FEATURE:
<223> OTHER INFORMATION: Synthetic Construct

<400> SEQUENCE: 20

Ala Arg Leu Gly Tyr Cys Ser Ser Thr Ser Cys Tyr Leu Ser Ala Phe
1               5                   10                  15

Asp Ile

<210> SEQ ID NO 21
<211> LENGTH: 13
<212> TYPE: PRT
<213> ORGANISM: Artificial Sequence
<220> FEATURE:
<223> OTHER INFORMATION: Synthetic Construct

<400> SEQUENCE: 21

Arg Val Ile Ile Asn Gly Thr Thr Ser Gly Phe Asp Tyr
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic Construct

<400> SEQUENCE: 22

Gly Arg Ser Gly Gly Asn Tyr Val Gly Tyr
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic Construct

<400> SEQUENCE: 23

Gly Arg Ser Arg Gly Asn Tyr Phe Asp Tyr
1               5                   10

<210> SEQ ID NO 24
<211> LENGTH: 6
<212> TYPE: PRT
<213> ORGANISM: Artificial Sequence
<220> FEATURE:
<223> OTHER INFORMATION: Synthetic Construct

<400> SEQUENCE: 24

Ala Arg Glu Leu Asp Ile
1               5

<210> SEQ ID NO 25
<211> LENGTH: 13
<212> TYPE: PRT
<213> ORGANISM: Artificial Sequence
<220> FEATURE:
<223> OTHER INFORMATION: Synthetic Construct
```

```
<400> SEQUENCE: 25

Ala Arg Glu Gly Met Val Arg Gly Ala Leu Phe Asp Tyr
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Synthetic Construct

<400> SEQUENCE: 26

Ala Arg Gln Leu Arg Asp Tyr Tyr Gly Met Asp Val
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic Construct

<400> SEQUENCE: 27

Ala Arg Gln Leu Arg Asp Tyr Tyr Ser Met Asp Val
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthetic Construct

<400> SEQUENCE: 28

Gln Ser Ile Val His Ser Asn Gly Asn Thr Tyr
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Synthetic Construct

<400> SEQUENCE: 29

Gln Thr Ile Val His Ser Asn Ser Lys Thr Tyr
1               5                   10

<210> SEQ ID NO 30
<211> LENGTH: 6
<212> TYPE: PRT
<213> ORGANISM: Artificial Sequence
<220> FEATURE:
<223> OTHER INFORMATION: Synthetic Construct

<400> SEQUENCE: 30

Gln Ser Ile Ser Ser Trp
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic Construct
```

```
<400> SEQUENCE: 31

Gln Ser Val Ser Ser Asn
1               5

<210> SEQ ID NO 32
<211> LENGTH: 12
<212> TYPE: PRT
<213> ORGANISM: Artificial Sequence
<220> FEATURE:
<223> OTHER INFORMATION: Synthetic Construct

<400> SEQUENCE: 32

Gln Ser Leu Leu Asp Ser Gly Asn Gln Lys Asn Tyr
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Synthetic Construct

<400> SEQUENCE: 33

Gln Ser Leu Lys Ser Asn Gln Lys Asn Tyr
1               5                   10

<210> SEQ ID NO 34
<211> LENGTH: 6
<212> TYPE: PRT
<213> ORGANISM: Artificial Sequence
<220> FEATURE:
<223> OTHER INFORMATION: Synthetic Construct

<400> SEQUENCE: 34

Gln Asp Ile Arg Asn Asp
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic Construct

<400> SEQUENCE: 35

Gln Ser Val Ser Ser Ser Tyr
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic Construct

<400> SEQUENCE: 36

Gln Thr Ile Ser Ser Asn Tyr
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic Construct

<400> SEQUENCE: 37
```

```
Gln Ser Val Ser Ser Ser Tyr
1               5
```

<210> SEQ ID NO 38
<211> LENGTH: 3
<212> TYPE: PRT
<213> ORGANISM: Artificial Sequence
<220> FEATURE:
<223> OTHER INFORMATION: Synthetic Construct

<400> SEQUENCE: 38

```
Lys Val Ser
1
```

<210> SEQ ID NO 39
<211> LENGTH: 3
<212> TYPE: PRT
<213> ORGANISM: Artificial Sequence
<220> FEATURE:
<223> OTHER INFORMATION: Synthetic Construct

<400> SEQUENCE: 39

```
Asp Ala Ser
1
```

<210> SEQ ID NO 40
<211> LENGTH: 3
<212> TYPE: PRT
<213> ORGANISM: Artificial Sequence
<220> FEATURE:
<223> OTHER INFORMATION: Synthetic Construct

<400> SEQUENCE: 40

```
Gly Ala Ser
1
```

<210> SEQ ID NO 41
<211> LENGTH: 3
<212> TYPE: PRT
<213> ORGANISM: Artificial Sequence
<220> FEATURE:
<223> OTHER INFORMATION: Synthetic Construct

<400> SEQUENCE: 41

```
Trp Ala Ser
1
```

<210> SEQ ID NO 42
<211> LENGTH: 3
<212> TYPE: PRT
<213> ORGANISM: Artificial Sequence
<220> FEATURE:
<223> OTHER INFORMATION: Synthetic Construct

<400> SEQUENCE: 42

```
Ala Ala Ser
1
```

<210> SEQ ID NO 43
<211> LENGTH: 9
<212> TYPE: PRT
<213> ORGANISM: Artificial Sequence
<220> FEATURE:
<223> OTHER INFORMATION: Synthetic Construct

<400> SEQUENCE: 43

```
Phe Gln Gly Ser His Val Pro Leu Thr
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic Construct

<400> SEQUENCE: 44

Gln Gln Tyr Asn Ser Tyr Pro Leu Thr
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic Construct

<400> SEQUENCE: 45

Gln His Tyr Asn Asn Leu Pro Leu Thr
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic Construct

<400> SEQUENCE: 46

Gln Gln Tyr Tyr Thr Tyr Pro Trp Thr
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic Construct

<400> SEQUENCE: 47

Leu Gln Asp Phe Asn Phe Pro Phe Thr
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic Construct

<400> SEQUENCE: 48

Gln Gln Asp Tyr Asn Leu Pro Tyr Thr
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic Construct

<400> SEQUENCE: 49

Gln Gln Asp Tyr Asn Leu Pro Arg Thr
```

```
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic Construct

<400> SEQUENCE: 50

Gln Gln Asp Tyr Asn Leu Pro Arg Thr
1               5

<210> SEQ ID NO 51
<211> LENGTH: 8
<212> TYPE: PRT
<213> ORGANISM: Artificial Sequence
<220> FEATURE:
<223> OTHER INFORMATION: Synthetic Construct

<400> SEQUENCE: 51

Gly Tyr Thr Phe Thr Ser Tyr Asn
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic Construct

<400> SEQUENCE: 52

Gly Phe Thr Phe Ser Ser Tyr Thr
1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic Construct

<400> SEQUENCE: 53

Gly Phe Thr Phe Ser Ser Tyr Thr
1               5

<210> SEQ ID NO 54
<211> LENGTH: 8
<212> TYPE: PRT
<213> ORGANISM: Artificial Sequence
<220> FEATURE:
<223> OTHER INFORMATION: Synthetic Construct

<400> SEQUENCE: 54

Gly Tyr Ser Phe Thr Ser Tyr Trp
1               5

<210> SEQ ID NO 55
<211> LENGTH: 8
<212> TYPE: PRT
<213> ORGANISM: Artificial Sequence
<220> FEATURE:
<223> OTHER INFORMATION: Synthetic Construct

<400> SEQUENCE: 55

Gly Phe Thr Phe Asp Asp Tyr Gly
1               5
```

```
<210> SEQ ID NO 56
<211> LENGTH: 8
<212> TYPE: PRT
<213> ORGANISM: Artificial Sequence
<220> FEATURE:
<223> OTHER INFORMATION: Synthetic Construct

<400> SEQUENCE: 56

Ile Asn Pro Tyr Asn Asp Gly Thr
1               5

<210> SEQ ID NO 57
<211> LENGTH: 8
<212> TYPE: PRT
<213> ORGANISM: Artificial Sequence
<220> FEATURE:
<223> OTHER INFORMATION: Synthetic Construct

<400> SEQUENCE: 57

Ile Ser Ser Gly Gly Gly Asn Thr
1               5

<210> SEQ ID NO 58
<211> LENGTH: 8
<212> TYPE: PRT
<213> ORGANISM: Artificial Sequence
<220> FEATURE:
<223> OTHER INFORMATION: Synthetic Construct

<400> SEQUENCE: 58

Ile Ser Ser Gly Gly Asp Asn Thr
1               5

<210> SEQ ID NO 59
<211> LENGTH: 8
<212> TYPE: PRT
<213> ORGANISM: Artificial Sequence
<220> FEATURE:
<223> OTHER INFORMATION: Synthetic Construct

<400> SEQUENCE: 59

Ile Tyr Pro Gly Asp Ser Asp Thr
1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic Construct

<400> SEQUENCE: 60

Ile Asn Trp Asn Gly Gly Ser Thr
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic Construct

<400> SEQUENCE: 61

Ala Ile Tyr Gly Asn Ser Tyr
1               5
```

<210> SEQ ID NO 62
<211> LENGTH: 11
<212> TYPE: PRT
<213> ORGANISM: Artificial Sequence
<220> FEATURE:
<223> OTHER INFORMATION: Synthetic Construct

<400> SEQUENCE: 62

Ala Arg Phe Asp Tyr Gly Ser Ser Leu Asp Ser
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Synthetic Construct

<400> SEQUENCE: 63

Ala Arg Phe Asp Tyr Gly Ser Ser Leu Asp Cys
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Synthetic Construct

<400> SEQUENCE: 64

Ala Arg Arg Gly Tyr Arg Ser Ser Trp Tyr Phe Asp Tyr
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Synthetic Construct

<400> SEQUENCE: 65

Ala Arg Glu Gly Gly Glu Leu Leu Met Asp Tyr
1               5                   10

<210> SEQ ID NO 66
<211> LENGTH: 11
<212> TYPE: PRT
<213> ORGANISM: Artificial Sequence
<220> FEATURE:
<223> OTHER INFORMATION: Synthetic Construct

<400> SEQUENCE: 66

Lys Ser Leu Leu His Ser Asn Gly Asn Thr Tyr
1               5                   10

<210> SEQ ID NO 67
<211> LENGTH: 6
<212> TYPE: PRT
<213> ORGANISM: Artificial Sequence
<220> FEATURE:
<223> OTHER INFORMATION: Synthetic Construct

<400> SEQUENCE: 67

Gln Ser Ile Ser Asn Asn
1               5

```
<210> SEQ ID NO 68
<211> LENGTH: 6
<212> TYPE: PRT
<213> ORGANISM: Artificial Sequence
<220> FEATURE:
<223> OTHER INFORMATION: Synthetic Construct

<400> SEQUENCE: 68

Gln Ser Ile Ser Asn Tyr
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic Construct

<400> SEQUENCE: 69

Gln Gly Ile Arg Asn Asp
1               5

<210> SEQ ID NO 70
<211> LENGTH: 6
<212> TYPE: PRT
<213> ORGANISM: Artificial Sequence
<220> FEATURE:
<223> OTHER INFORMATION: Synthetic Construct

<400> SEQUENCE: 70

Gln Ser Val Ser Thr Tyr
1               5

<210> SEQ ID NO 71
<211> LENGTH: 3
<212> TYPE: PRT
<213> ORGANISM: Artificial Sequence
<220> FEATURE:
<223> OTHER INFORMATION: Synthetic Construct

<400> SEQUENCE: 71

Tyr Met Ser
1

<210> SEQ ID NO 72
<211> LENGTH: 3
<212> TYPE: PRT
<213> ORGANISM: Artificial Sequence
<220> FEATURE:
<223> OTHER INFORMATION: Synthetic Construct

<400> SEQUENCE: 72

Tyr Ala Ser
1

<210> SEQ ID NO 73
<211> LENGTH: 3
<212> TYPE: PRT
<213> ORGANISM: Artificial Sequence
<220> FEATURE:
<223> OTHER INFORMATION: Synthetic Construct

<400> SEQUENCE: 73

Tyr Ala Ser
1

<210> SEQ ID NO 74
```

```
<211> LENGTH: 3
<212> TYPE: PRT
<213> ORGANISM: Artificial Sequence
<220> FEATURE:
<223> OTHER INFORMATION: Synthetic Construct

<400> SEQUENCE: 74

Ala Ala Ser
1

<210> SEQ ID NO 75
<211> LENGTH: 3
<212> TYPE: PRT
<213> ORGANISM: Artificial Sequence
<220> FEATURE:
<223> OTHER INFORMATION: Synthetic Construct

<400> SEQUENCE: 75

Asp Ala Ser
1

<210> SEQ ID NO 76
<211> LENGTH: 9
<212> TYPE: PRT
<213> ORGANISM: Artificial Sequence
<220> FEATURE:
<223> OTHER INFORMATION: Synthetic Construct

<400> SEQUENCE: 76

Met Gln Gly Leu Glu Tyr Pro Tyr Thr
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic Construct

<400> SEQUENCE: 77

Gln Gln Ser Lys Asn Trp Pro Arg Thr
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic Construct

<400> SEQUENCE: 78

Gln Gln Ser Lys Ser Trp Pro Arg Thr
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic Construct

<400> SEQUENCE: 79

Leu Gln Asp Tyr Asn Tyr Pro Leu Thr
1               5

<210> SEQ ID NO 80
<211> LENGTH: 9
```

```
<212> TYPE: PRT
<213> ORGANISM: Artificial Sequence
<220> FEATURE:
<223> OTHER INFORMATION: Synthetic Construct

<400> SEQUENCE: 80

Gln Gln Arg Ser Asn Trp Pro Pro Thr
1               5

<210> SEQ ID NO 81
<211> LENGTH: 8
<212> TYPE: PRT
<213> ORGANISM: Artificial Sequence
<220> FEATURE:
<223> OTHER INFORMATION: Synthetic Construct

<400> SEQUENCE: 81

Gly Phe Thr Phe Ser His Tyr Ser
1               5

<210> SEQ ID NO 82
<211> LENGTH: 8
<212> TYPE: PRT
<213> ORGANISM: Artificial Sequence
<220> FEATURE:
<223> OTHER INFORMATION: Synthetic Construct

<400> SEQUENCE: 82

Gly Phe Thr Phe Ser Trp Tyr Pro
1               5

<210> SEQ ID NO 83
<211> LENGTH: 8
<212> TYPE: PRT
<213> ORGANISM: Artificial Sequence
<220> FEATURE:
<223> OTHER INFORMATION: Synthetic Construct

<400> SEQUENCE: 83

Gly Phe Thr Phe Ser Asp Tyr Glu
1               5

<210> SEQ ID NO 84
<211> LENGTH: 8
<212> TYPE: PRT
<213> ORGANISM: Artificial Sequence
<220> FEATURE:
<223> OTHER INFORMATION: Synthetic Construct

<400> SEQUENCE: 84

Gly Phe Thr Phe Ser Tyr Tyr Asp
1               5

<210> SEQ ID NO 85
<211> LENGTH: 8
<212> TYPE: PRT
<213> ORGANISM: Artificial Sequence
<220> FEATURE:
<223> OTHER INFORMATION: Synthetic Construct

<400> SEQUENCE: 85

Gly Phe Thr Phe Ser His Tyr Gln
1               5

<210> SEQ ID NO 86
<211> LENGTH: 8
<212> TYPE: PRT
```

```
<213> ORGANISM: Artificial Sequence
<220> FEATURE:
<223> OTHER INFORMATION: Synthetic Construct

<400> SEQUENCE: 86

Gly Tyr Thr Phe Thr Gly Tyr Tyr
1               5

<210> SEQ ID NO 87
<211> LENGTH: 8
<212> TYPE: PRT
<213> ORGANISM: Artificial Sequence
<220> FEATURE:
<223> OTHER INFORMATION: Synthetic Construct

<400> SEQUENCE: 87

Gly Asn Thr Phe Thr Gly Tyr Tyr
1               5

<210> SEQ ID NO 88
<211> LENGTH: 8
<212> TYPE: PRT
<213> ORGANISM: Artificial Sequence
<220> FEATURE:
<223> OTHER INFORMATION: Synthetic Construct

<400> SEQUENCE: 88

Gly Phe Thr Phe Ser Ser Tyr Gly
1               5

<210> SEQ ID NO 89
<211> LENGTH: 8
<212> TYPE: PRT
<213> ORGANISM: Artificial Sequence
<220> FEATURE:
<223> OTHER INFORMATION: Synthetic Construct

<400> SEQUENCE: 89

Gly Phe Thr Phe Ser Ser Tyr Ala
1               5

<210> SEQ ID NO 90
<211> LENGTH: 8
<212> TYPE: PRT
<213> ORGANISM: Artificial Sequence
<220> FEATURE:
<223> OTHER INFORMATION: Synthetic Construct

<400> SEQUENCE: 90

Gly Phe Thr Phe Ser Gly Tyr Gly
1               5

<210> SEQ ID NO 91
<211> LENGTH: 8
<212> TYPE: PRT
<213> ORGANISM: Artificial Sequence
<220> FEATURE:
<223> OTHER INFORMATION: Synthetic Construct

<400> SEQUENCE: 91

Gly Phe Thr Phe Ser Ser Phe Gly
1               5

<210> SEQ ID NO 92
<211> LENGTH: 8
<212> TYPE: PRT
<213> ORGANISM: Artificial Sequence
```

<220> FEATURE:
<223> OTHER INFORMATION: Synthetic Construct

<400> SEQUENCE: 92

Gly Phe Thr Phe Asn Arg Phe Val
1               5

<210> SEQ ID NO 93
<211> LENGTH: 8
<212> TYPE: PRT
<213> ORGANISM: Artificial Sequence
<220> FEATURE:
<223> OTHER INFORMATION: Synthetic Construct

<400> SEQUENCE: 93

Gly Gly Ser Phe Ser Gly Tyr Tyr
1               5

<210> SEQ ID NO 94
<211> LENGTH: 8
<212> TYPE: PRT
<213> ORGANISM: Artificial Sequence
<220> FEATURE:
<223> OTHER INFORMATION: Synthetic Construct

<400> SEQUENCE: 94

Gly Tyr Thr Phe Thr Ser Tyr Glu
1               5

<210> SEQ ID NO 95
<211> LENGTH: 8
<212> TYPE: PRT
<213> ORGANISM: Artificial Sequence
<220> FEATURE:
<223> OTHER INFORMATION: Synthetic Construct

<400> SEQUENCE: 95

Gly Phe Thr Phe Ser Arg Tyr Ala
1               5

<210> SEQ ID NO 96
<211> LENGTH: 7
<212> TYPE: PRT
<213> ORGANISM: Artificial Sequence
<220> FEATURE:
<223> OTHER INFORMATION: Synthetic Construct

<400> SEQUENCE: 96

Ile Tyr Pro Ser Gly Gly Thr
1               5

<210> SEQ ID NO 97
<211> LENGTH: 8
<212> TYPE: PRT
<213> ORGANISM: Artificial Sequence
<220> FEATURE:
<223> OTHER INFORMATION: Synthetic Construct

<400> SEQUENCE: 97

Ile Tyr Pro Ser Gly Gly Thr Thr
1               5

<210> SEQ ID NO 98
<211> LENGTH: 8
<212> TYPE: PRT
<213> ORGANISM: Artificial Sequence
<220> FEATURE:

```
<223> OTHER INFORMATION: Synthetic Construct

<400> SEQUENCE: 98

Ile Trp Pro Ser Gly Gly Leu Thr
1               5

<210> SEQ ID NO 99
<211> LENGTH: 8
<212> TYPE: PRT
<213> ORGANISM: Artificial Sequence
<220> FEATURE:
<223> OTHER INFORMATION: Synthetic Construct

<400> SEQUENCE: 99

Ile Tyr Ser Ser Gly Gly His Thr
1               5

<210> SEQ ID NO 100
<211> LENGTH: 8
<212> TYPE: PRT
<213> ORGANISM: Artificial Sequence
<220> FEATURE:
<223> OTHER INFORMATION: Synthetic Construct

<400> SEQUENCE: 100

Ile Ser Pro Ser Gly Gly Phe Thr
1               5

<210> SEQ ID NO 101
<211> LENGTH: 8
<212> TYPE: PRT
<213> ORGANISM: Artificial Sequence
<220> FEATURE:
<223> OTHER INFORMATION: Synthetic Construct

<400> SEQUENCE: 101

Ile Asn Pro Asn Ser Gly Gly Thr
1               5

<210> SEQ ID NO 102
<211> LENGTH: 8
<212> TYPE: PRT
<213> ORGANISM: Artificial Sequence
<220> FEATURE:
<223> OTHER INFORMATION: Synthetic Construct

<400> SEQUENCE: 102

Ile Lys Pro Ser Thr Gly Asp Thr
1               5

<210> SEQ ID NO 103
<211> LENGTH: 8
<212> TYPE: PRT
<213> ORGANISM: Artificial Sequence
<220> FEATURE:
<223> OTHER INFORMATION: Synthetic Construct

<400> SEQUENCE: 103

Ile Trp Tyr Asp Gly Ser Asn Lys
1               5

<210> SEQ ID NO 104
<211> LENGTH: 8
<212> TYPE: PRT
<213> ORGANISM: Artificial Sequence
<220> FEATURE:
<223> OTHER INFORMATION: Synthetic Construct
```

```
<400> SEQUENCE: 104

Ile Ser Gly Arg Gly Gly Ser Pro
1               5

<210> SEQ ID NO 105
<211> LENGTH: 8
<212> TYPE: PRT
<213> ORGANISM: Artificial Sequence
<220> FEATURE:
<223> OTHER INFORMATION: Synthetic Construct

<400> SEQUENCE: 105

Ile Trp Ser Asp Gly Ser Asn Arg
1               5

<210> SEQ ID NO 106
<211> LENGTH: 8
<212> TYPE: PRT
<213> ORGANISM: Artificial Sequence
<220> FEATURE:
<223> OTHER INFORMATION: Synthetic Construct

<400> SEQUENCE: 106

Ile Tyr Tyr Asp Gly Ser Asn Lys
1               5

<210> SEQ ID NO 107
<211> LENGTH: 8
<212> TYPE: PRT
<213> ORGANISM: Artificial Sequence
<220> FEATURE:
<223> OTHER INFORMATION: Synthetic Construct

<400> SEQUENCE: 107

Ile Ser Gly Ser Gly Gly Ser Thr
1               5

<210> SEQ ID NO 108
<211> LENGTH: 7
<212> TYPE: PRT
<213> ORGANISM: Artificial Sequence
<220> FEATURE:
<223> OTHER INFORMATION: Synthetic Construct

<400> SEQUENCE: 108

Ile Asn His Ser Gly Gly Thr
1               5

<210> SEQ ID NO 109
<211> LENGTH: 8
<212> TYPE: PRT
<213> ORGANISM: Artificial Sequence
<220> FEATURE:
<223> OTHER INFORMATION: Synthetic Construct

<400> SEQUENCE: 109

Ile Tyr Pro Arg Asp Gly Asp Thr
1               5

<210> SEQ ID NO 110
<211> LENGTH: 8
<212> TYPE: PRT
<213> ORGANISM: Artificial Sequence
<220> FEATURE:
<223> OTHER INFORMATION: Synthetic Construct
```

```
<400> SEQUENCE: 110

Ile Ser Ser Gly Gly Asp Tyr Ile
1               5

<210> SEQ ID NO 111
<211> LENGTH: 19
<212> TYPE: PRT
<213> ORGANISM: Artificial Sequence
<220> FEATURE:
<223> OTHER INFORMATION: Synthetic Construct

<400> SEQUENCE: 111

Ala Arg His Trp Arg Gly Tyr Ser Ser Ser Trp Tyr His Pro Ala Tyr
1               5                   10                  15

Phe Asp Tyr

<210> SEQ ID NO 112
<211> LENGTH: 19
<212> TYPE: PRT
<213> ORGANISM: Artificial Sequence
<220> FEATURE:
<223> OTHER INFORMATION: Synthetic Construct

<400> SEQUENCE: 112

Ala Arg Ser Tyr Tyr Tyr Asp Ser Ser Gly Tyr Tyr Ser His Asp Ala
1               5                   10                  15

Phe Asp Ile

<210> SEQ ID NO 113
<211> LENGTH: 15
<212> TYPE: PRT
<213> ORGANISM: Artificial Sequence
<220> FEATURE:
<223> OTHER INFORMATION: Synthetic Construct

<400> SEQUENCE: 113

Ala Arg Asp Ser Tyr Tyr Tyr Asp Ser Ser Gly Ala Leu Gly Tyr
1               5                   10                  15

<210> SEQ ID NO 114
<211> LENGTH: 17
<212> TYPE: PRT
<213> ORGANISM: Artificial Sequence
<220> FEATURE:
<223> OTHER INFORMATION: Synthetic Construct

<400> SEQUENCE: 114

Ala Arg Pro Gly Tyr Ser Ser Gly Trp Tyr Asp Gly Thr Tyr Phe Asp
1               5                   10                  15

Tyr

<210> SEQ ID NO 115
<211> LENGTH: 12
<212> TYPE: PRT
<213> ORGANISM: Artificial Sequence
<220> FEATURE:
<223> OTHER INFORMATION: Synthetic Construct

<400> SEQUENCE: 115

Thr Arg Glu Pro Gly Arg Leu Trp Ala Phe Asp Ile
1               5                   10

<210> SEQ ID NO 116
<211> LENGTH: 8
```

```
<212> TYPE: PRT
<213> ORGANISM: Artificial Sequence
<220> FEATURE:
<223> OTHER INFORMATION: Synthetic Construct

<400> SEQUENCE: 116

Ala Val Phe Gly Ser Gly Ser Ser
1               5

<210> SEQ ID NO 117
<211> LENGTH: 8
<212> TYPE: PRT
<213> ORGANISM: Artificial Sequence
<220> FEATURE:
<223> OTHER INFORMATION: Synthetic Construct

<400> SEQUENCE: 117

Ala Val Phe Gly Ser Gly Ser Ser
1               5

<210> SEQ ID NO 118
<211> LENGTH: 17
<212> TYPE: PRT
<213> ORGANISM: Artificial Sequence
<220> FEATURE:
<223> OTHER INFORMATION: Synthetic Construct

<400> SEQUENCE: 118

Ala Arg Glu Gly Gly Trp Tyr Gly Gly Asp Tyr Tyr Gly Met Asp
1               5                   10                  15

Val

<210> SEQ ID NO 119
<211> LENGTH: 15
<212> TYPE: PRT
<213> ORGANISM: Artificial Sequence
<220> FEATURE:
<223> OTHER INFORMATION: Synthetic Construct

<400> SEQUENCE: 119

Ala Lys Asp Gly Asp Gly Ser Gly Pro Pro Tyr Tyr Phe Asp Tyr
1               5                   10                  15

<210> SEQ ID NO 120
<211> LENGTH: 24
<212> TYPE: PRT
<213> ORGANISM: Artificial Sequence
<220> FEATURE:
<223> OTHER INFORMATION: Synthetic Construct

<400> SEQUENCE: 120

Ala Arg Asp Arg Gly Ile Thr Met Val Arg Gly Leu Ile Ile Lys Tyr
1               5                   10                  15

Tyr Tyr Tyr Tyr Gly Leu Asp Val
                20

<210> SEQ ID NO 121
<211> LENGTH: 13
<212> TYPE: PRT
<213> ORGANISM: Artificial Sequence
<220> FEATURE:
<223> OTHER INFORMATION: Synthetic Construct

<400> SEQUENCE: 121

Ala Arg Asp Asp Asn Trp Asn Asp Gly Asp Phe Asp Tyr
1               5                   10
```

<210> SEQ ID NO 122
<211> LENGTH: 19
<212> TYPE: PRT
<213> ORGANISM: Artificial Sequence
<220> FEATURE:
<223> OTHER INFORMATION: Synthetic Construct

<400> SEQUENCE: 122

Ala Lys Asp Phe Thr Tyr Tyr Tyr Gly Ser Gly Asn Tyr Tyr Asn Trp
1               5                   10                  15

Phe Asp Pro

<210> SEQ ID NO 123
<211> LENGTH: 15
<212> TYPE: PRT
<213> ORGANISM: Artificial Sequence
<220> FEATURE:
<223> OTHER INFORMATION: Synthetic Construct

<400> SEQUENCE: 123

Ala Arg Thr Ser Asp Tyr Asp Tyr Tyr Tyr Gly Met Asp Val
1               5                   10                  15

<210> SEQ ID NO 124
<211> LENGTH: 8
<212> TYPE: PRT
<213> ORGANISM: Artificial Sequence
<220> FEATURE:
<223> OTHER INFORMATION: Synthetic Construct

<400> SEQUENCE: 124

Ala Arg His Thr Pro Gly Ala Phe
1               5

<210> SEQ ID NO 125
<211> LENGTH: 17
<212> TYPE: PRT
<213> ORGANISM: Artificial Sequence
<220> FEATURE:
<223> OTHER INFORMATION: Synthetic Construct

<400> SEQUENCE: 125

Thr Arg Val Leu Phe Tyr Tyr Tyr Gly Ser Ser Tyr Val Phe Phe Asp
1               5                   10                  15

Tyr

<210> SEQ ID NO 126
<211> LENGTH: 6
<212> TYPE: PRT
<213> ORGANISM: Artificial Sequence
<220> FEATURE:
<223> OTHER INFORMATION: Synthetic Construct

<400> SEQUENCE: 126

Gln Ser Val Ser Ser Tyr
1               5

<210> SEQ ID NO 127
<211> LENGTH: 6
<212> TYPE: PRT
<213> ORGANISM: Artificial Sequence
<220> FEATURE:
<223> OTHER INFORMATION: Synthetic Construct

<400> SEQUENCE: 127

```
Gln Ser Ile Asp Thr Tyr
1               5

<210> SEQ ID NO 128
<211> LENGTH: 6
<212> TYPE: PRT
<213> ORGANISM: Artificial Sequence
<220> FEATURE:
<223> OTHER INFORMATION: Synthetic Construct

<400> SEQUENCE: 128

Gln Ser Val Ser Asn Trp
1               5

<210> SEQ ID NO 129
<211> LENGTH: 6
<212> TYPE: PRT
<213> ORGANISM: Artificial Sequence
<220> FEATURE:
<223> OTHER INFORMATION: Synthetic Construct

<400> SEQUENCE: 129

Gln Ser Ile Asp Thr Trp
1               5

<210> SEQ ID NO 130
<211> LENGTH: 6
<212> TYPE: PRT
<213> ORGANISM: Artificial Sequence
<220> FEATURE:
<223> OTHER INFORMATION: Synthetic Construct

<400> SEQUENCE: 130

Gln Asp Ile Arg Asn Trp
1               5

<210> SEQ ID NO 131
<211> LENGTH: 6
<212> TYPE: PRT
<213> ORGANISM: Artificial Sequence
<220> FEATURE:
<223> OTHER INFORMATION: Synthetic Construct

<400> SEQUENCE: 131

Gln Gly Ile Ser Asn Ser
1               5

<210> SEQ ID NO 132
<211> LENGTH: 6
<212> TYPE: PRT
<213> ORGANISM: Artificial Sequence
<220> FEATURE:
<223> OTHER INFORMATION: Synthetic Construct

<400> SEQUENCE: 132

Gln Gly Ile Ser Asn Tyr
1               5

<210> SEQ ID NO 133
<211> LENGTH: 6
<212> TYPE: PRT
<213> ORGANISM: Artificial Sequence
<220> FEATURE:
<223> OTHER INFORMATION: Synthetic Construct

<400> SEQUENCE: 133
```

```
Gln Gly Ile Ser Ser Ala
1               5

<210> SEQ ID NO 134
<211> LENGTH: 6
<212> TYPE: PRT
<213> ORGANISM: Artificial Sequence
<220> FEATURE:
<223> OTHER INFORMATION: Synthetic Construct

<400> SEQUENCE: 134

Gln Gly Ile Ser Ser Trp
1               5

<210> SEQ ID NO 135
<211> LENGTH: 6
<212> TYPE: PRT
<213> ORGANISM: Artificial Sequence
<220> FEATURE:
<223> OTHER INFORMATION: Synthetic Construct

<400> SEQUENCE: 135

Gln Ser Val Ser Ser Tyr
1               5

<210> SEQ ID NO 136
<211> LENGTH: 6
<212> TYPE: PRT
<213> ORGANISM: Artificial Sequence
<220> FEATURE:
<223> OTHER INFORMATION: Synthetic Construct

<400> SEQUENCE: 136

Gln Gly Ile Ser Ser Tyr
1               5

<210> SEQ ID NO 137
<211> LENGTH: 6
<212> TYPE: PRT
<213> ORGANISM: Artificial Sequence
<220> FEATURE:
<223> OTHER INFORMATION: Synthetic Construct

<400> SEQUENCE: 137

Gln Ser Ile Ser Ser Trp
1               5

<210> SEQ ID NO 138
<211> LENGTH: 9
<212> TYPE: PRT
<213> ORGANISM: Artificial Sequence
<220> FEATURE:
<223> OTHER INFORMATION: Synthetic Construct

<400> SEQUENCE: 138

Ser Gly Ile Asn Leu Gly Arg Tyr Arg
1               5

<210> SEQ ID NO 139
<211> LENGTH: 11
<212> TYPE: PRT
<213> ORGANISM: Artificial Sequence
<220> FEATURE:
<223> OTHER INFORMATION: Synthetic Construct

<400> SEQUENCE: 139

Gln Ser Leu Val His Ser Asn Gly Asp Thr Tyr
```

```
                1               5                    10
```

<210> SEQ ID NO 140
<211> LENGTH: 6
<212> TYPE: PRT
<213> ORGANISM: Artificial Sequence
<220> FEATURE:
<223> OTHER INFORMATION: Synthetic Construct

<400> SEQUENCE: 140

Gln Asp Ile Ser Asn Phe
1               5

<210> SEQ ID NO 141
<211> LENGTH: 3
<212> TYPE: PRT
<213> ORGANISM: Artificial Sequence
<220> FEATURE:
<223> OTHER INFORMATION: Synthetic Construct

<400> SEQUENCE: 141

Asp Ala Ser
1

<210> SEQ ID NO 142
<211> LENGTH: 3
<212> TYPE: PRT
<213> ORGANISM: Artificial Sequence
<220> FEATURE:
<223> OTHER INFORMATION: Synthetic Construct

<400> SEQUENCE: 142

Ala Ala Ser
1

<210> SEQ ID NO 143
<211> LENGTH: 3
<212> TYPE: PRT
<213> ORGANISM: Artificial Sequence
<220> FEATURE:
<223> OTHER INFORMATION: Synthetic Construct

<400> SEQUENCE: 143

Lys Ala Ser
1

<210> SEQ ID NO 144
<211> LENGTH: 3
<212> TYPE: PRT
<213> ORGANISM: Artificial Sequence
<220> FEATURE:
<223> OTHER INFORMATION: Synthetic Construct

<400> SEQUENCE: 144

Ser Ala Ser
1

<210> SEQ ID NO 145
<211> LENGTH: 3
<212> TYPE: PRT
<213> ORGANISM: Artificial Sequence
<220> FEATURE:
<223> OTHER INFORMATION: Synthetic Construct

<400> SEQUENCE: 145

Ala Ala Ser
1

```
<210> SEQ ID NO 146
<211> LENGTH: 3
<212> TYPE: PRT
<213> ORGANISM: Artificial Sequence
<220> FEATURE:
<223> OTHER INFORMATION: Synthetic Construct

<400> SEQUENCE: 146

Ala Ala Ser
1

<210> SEQ ID NO 147
<211> LENGTH: 3
<212> TYPE: PRT
<213> ORGANISM: Artificial Sequence
<220> FEATURE:
<223> OTHER INFORMATION: Synthetic Construct

<400> SEQUENCE: 147

Ala Ala Ser
1

<210> SEQ ID NO 148
<211> LENGTH: 3
<212> TYPE: PRT
<213> ORGANISM: Artificial Sequence
<220> FEATURE:
<223> OTHER INFORMATION: Synthetic Construct

<400> SEQUENCE: 148

Asp Ala Ser
1

<210> SEQ ID NO 149
<211> LENGTH: 3
<212> TYPE: PRT
<213> ORGANISM: Artificial Sequence
<220> FEATURE:
<223> OTHER INFORMATION: Synthetic Construct

<400> SEQUENCE: 149

Ala Ala Ser
1

<210> SEQ ID NO 150
<211> LENGTH: 3
<212> TYPE: PRT
<213> ORGANISM: Artificial Sequence
<220> FEATURE:
<223> OTHER INFORMATION: Synthetic Construct

<400> SEQUENCE: 150

Asp Ala Ser
1

<210> SEQ ID NO 151
<211> LENGTH: 3
<212> TYPE: PRT
<213> ORGANISM: Artificial Sequence
<220> FEATURE:
<223> OTHER INFORMATION: Synthetic Construct

<400> SEQUENCE: 151

Ala Ala Ser
1
```

```
<210> SEQ ID NO 152
<211> LENGTH: 3
<212> TYPE: PRT
<213> ORGANISM: Artificial Sequence
<220> FEATURE:
<223> OTHER INFORMATION: Synthetic Construct

<400> SEQUENCE: 152

Lys Ala Ser
1

<210> SEQ ID NO 153
<211> LENGTH: 7
<212> TYPE: PRT
<213> ORGANISM: Artificial Sequence
<220> FEATURE:
<223> OTHER INFORMATION: Synthetic Construct

<400> SEQUENCE: 153

Tyr Tyr Ser Asp Ser Ser Lys
1               5

<210> SEQ ID NO 154
<211> LENGTH: 3
<212> TYPE: PRT
<213> ORGANISM: Artificial Sequence
<220> FEATURE:
<223> OTHER INFORMATION: Synthetic Construct

<400> SEQUENCE: 154

Tyr Thr Ser
1

<210> SEQ ID NO 155
<211> LENGTH: 9
<212> TYPE: PRT
<213> ORGANISM: Artificial Sequence
<220> FEATURE:
<223> OTHER INFORMATION: Synthetic Construct

<400> SEQUENCE: 155

Gln Gln Arg Ser Asn Trp Pro Leu Thr
1               5

<210> SEQ ID NO 156
<211> LENGTH: 10
<212> TYPE: PRT
<213> ORGANISM: Artificial Sequence
<220> FEATURE:
<223> OTHER INFORMATION: Synthetic Construct

<400> SEQUENCE: 156

Gln Gln Ser Tyr Ser Ser Pro Gly Ile Thr
1               5                   10

<210> SEQ ID NO 157
<211> LENGTH: 9
<212> TYPE: PRT
<213> ORGANISM: Artificial Sequence
<220> FEATURE:
<223> OTHER INFORMATION: Synthetic Construct

<400> SEQUENCE: 157

Leu Gln Tyr Val Ser Tyr Pro Leu Thr
1               5
```

```
<210> SEQ ID NO 158
<211> LENGTH: 9
<212> TYPE: PRT
<213> ORGANISM: Artificial Sequence
<220> FEATURE:
<223> OTHER INFORMATION: Synthetic Construct

<400> SEQUENCE: 158

Gln Gln Tyr Lys Thr Tyr Pro Phe Thr
1               5

<210> SEQ ID NO 159
<211> LENGTH: 9
<212> TYPE: PRT
<213> ORGANISM: Artificial Sequence
<220> FEATURE:
<223> OTHER INFORMATION: Synthetic Construct

<400> SEQUENCE: 159

Gln Gln Ala Asp Ser Ser Pro Arg Thr
1               5

<210> SEQ ID NO 160
<211> LENGTH: 9
<212> TYPE: PRT
<213> ORGANISM: Artificial Sequence
<220> FEATURE:
<223> OTHER INFORMATION: Synthetic Construct

<400> SEQUENCE: 160

Gln Gln Tyr Lys Ser Tyr Pro Tyr Thr
1               5

<210> SEQ ID NO 161
<211> LENGTH: 9
<212> TYPE: PRT
<213> ORGANISM: Artificial Sequence
<220> FEATURE:
<223> OTHER INFORMATION: Synthetic Construct

<400> SEQUENCE: 161

Gln Gln Tyr Lys Thr Tyr Pro Tyr Thr
1               5

<210> SEQ ID NO 162
<211> LENGTH: 9
<212> TYPE: PRT
<213> ORGANISM: Artificial Sequence
<220> FEATURE:
<223> OTHER INFORMATION: Synthetic Construct

<400> SEQUENCE: 162

His Gln Phe Asn Asn Tyr Pro Phe Thr
1               5

<210> SEQ ID NO 163
<211> LENGTH: 9
<212> TYPE: PRT
<213> ORGANISM: Artificial Sequence
<220> FEATURE:
<223> OTHER INFORMATION: Synthetic Construct

<400> SEQUENCE: 163

Gln Gln Tyr Asn Ser Tyr Pro Tyr Thr
1               5

<210> SEQ ID NO 164
```

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 164

Gln Gln Arg Ser Asn Trp Trp Thr
1               5

<210> SEQ ID NO 165
<211> LENGTH: 9
<212> TYPE: PRT
<213> ORGANISM: Artificial Sequence
<220> FEATURE:
<223> OTHER INFORMATION: Synthetic Construct

<400> SEQUENCE: 165

Gln Gln Leu Asn Ser Tyr Pro Arg Thr
1               5

<210> SEQ ID NO 166
<211> LENGTH: 9
<212> TYPE: PRT
<213> ORGANISM: Artificial Sequence
<220> FEATURE:
<223> OTHER INFORMATION: Synthetic Construct

<400> SEQUENCE: 166

Gln Gln Tyr Asn Ser Tyr Ser Arg Thr
1               5

<210> SEQ ID NO 167
<211> LENGTH: 10
<212> TYPE: PRT
<213> ORGANISM: Artificial Sequence
<220> FEATURE:
<223> OTHER INFORMATION: Synthetic Construct

<400> SEQUENCE: 167

Met Ile Trp His Arg Ser Ala Leu Phe Ile
1               5                   10

<210> SEQ ID NO 168
<211> LENGTH: 9
<212> TYPE: PRT
<213> ORGANISM: Artificial Sequence
<220> FEATURE:
<223> OTHER INFORMATION: Synthetic Construct

<400> SEQUENCE: 168

Ser Gln Ser Thr His Val Pro Tyr Thr
1               5

<210> SEQ ID NO 169
<211> LENGTH: 9
<212> TYPE: PRT
<213> ORGANISM: Artificial Sequence
<220> FEATURE:
<223> OTHER INFORMATION: Synthetic Construct

<400> SEQUENCE: 169

Gln Gln Gly His Thr Leu Pro Tyr Thr
1               5

<210> SEQ ID NO 170
<211> LENGTH: 113
```

<212> TYPE: PRT
<213> ORGANISM: Artificial Sequence
<220> FEATURE:
<223> OTHER INFORMATION: Synthetic Construct

<400> SEQUENCE: 170

Gln Val Gln Leu Gln Gln Ser Gly Pro Glu Leu Val Lys Pro Gly Ala
1               5                   10                  15

Ser Val Lys Met Ser Cys Lys Ala Ser Gly Phe Thr Phe Thr Asp Ser
            20                  25                  30

Val Ile Ser Trp Val Lys Gln Arg Thr Gly Gln Gly Leu Glu Trp Ile
        35                  40                  45

Gly Glu Ile Tyr Pro Gly Ser Gly Ser Ile Tyr Tyr Asn Glu Lys Phe
    50                  55                  60

Lys Gly Lys Ala Thr Leu Thr Ala Asp Lys Ser Ser Asn Thr Ala Tyr
65                  70                  75                  80

Met Gln Leu Arg Ser Leu Thr Ser Glu Asp Ser Ala Val Tyr Phe Cys
                85                  90                  95

Ala Met Arg Arg Ser Tyr Trp Gly Gln Gly Thr Leu Val Thr Val Ser
            100                 105                 110

Ala

<210> SEQ ID NO 171
<211> LENGTH: 112
<212> TYPE: PRT
<213> ORGANISM: Artificial Sequence
<220> FEATURE:
<223> OTHER INFORMATION: Synthetic Construct

<400> SEQUENCE: 171

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

<210> SEQ ID NO 172
<211> LENGTH: 113
<212> TYPE: PRT
<213> ORGANISM: Artificial Sequence
<220> FEATURE:
<223> OTHER INFORMATION: Synthetic Construct

<400> SEQUENCE: 172

Gln Ile Gln Leu Gln Gln Ser Gly Pro Glu Leu Val Lys Pro Gly Ala
1               5                   10                  15

Ser Val Lys Met Ser Cys Glu Ala Ser Gly Phe Thr Phe Thr Asp Ser
            20                  25                  30

Val Ile Thr Trp Val Lys Gln Arg Pro Gly Gln Gly Leu Glu Trp Ile
        35                  40                  45

```
Gly Glu Ile Tyr Pro Gly Ser Gly Asn Phe Tyr Tyr Asn Glu Lys Phe
            50                  55                  60

Lys Gly Lys Ala Thr Leu Thr Ala Asp Lys Ser Asn Thr Ala Tyr
 65                  70                  75                  80

Met Gln Leu Arg Ser Leu Thr Ser Glu Asp Ser Ala Val Tyr Phe Cys
                85                  90                  95

Ala Met Arg Arg Ser Ser Trp Gly Gln Gly Thr Leu Val Thr Val Ser
                    100                 105                 110

Ala
```

```
<210> SEQ ID NO 173
<211> LENGTH: 112
<212> TYPE: PRT
<213> ORGANISM: Artificial Sequence
<220> FEATURE:
<223> OTHER INFORMATION: Synthetic Construct

<400> SEQUENCE: 173

Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Thr Ile Val His Ser
                20                  25                  30

Asn Ser Lys Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
                100                 105                 110
```

```
<210> SEQ ID NO 174
<211> LENGTH: 125
<212> TYPE: PRT
<213> ORGANISM: Artificial Sequence
<220> FEATURE:
<223> OTHER INFORMATION: Synthetic Construct

<400> SEQUENCE: 174

Gln Val Gln Leu Gln Gln Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Gly Arg Phe Thr Val Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Leu Gly Tyr Cys Ser Ser Thr Ser Cys Tyr Leu Ser Ala Phe
                100                 105                 110

Asp Ile Trp Gly Gln Gly Thr Met Val Thr Val Ser Ser
            115                 120                 125
```

```
<210> SEQ ID NO 175
<211> LENGTH: 107
<212> TYPE: PRT
<213> ORGANISM: Artificial Sequence
<220> FEATURE:
<223> OTHER INFORMATION: Synthetic Construct

<400> SEQUENCE: 175

Glu Ile Val Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 176
<211> LENGTH: 120
<212> TYPE: PRT
<213> ORGANISM: Artificial Sequence
<220> FEATURE:
<223> OTHER INFORMATION: Synthetic Construct

<400> SEQUENCE: 176

Gln Ile Gln Leu Val Gln Ser Gly Ala Glu Val Lys Lys Pro Gly Lys
1               5                   10                  15

Ser Leu Lys Ile Ala Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

His Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Arg Val Ile Ile Asn Gly Thr Thr Ser Gly Phe Asp Tyr Trp Gly Gln
            100                 105                 110

Gly Thr Leu Val Ile Val Ser Ser
        115                 120

<210> SEQ ID NO 177
<211> LENGTH: 107
<212> TYPE: PRT
<213> ORGANISM: Artificial Sequence
<220> FEATURE:
<223> OTHER INFORMATION: Synthetic Construct

<400> SEQUENCE: 177

Glu Thr Thr Leu Thr Gln Ser Pro Ala Thr Leu Ser Val Ser Pro Gly
1               5                   10                  15
```

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Met
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Tyr Asn Asn Leu Pro Leu
                85                  90                  95

Thr Phe Gly Gly Gly Thr Lys Val Asp Leu Lys
            100                 105

<210> SEQ ID NO 178
<211> LENGTH: 117
<212> TYPE: PRT
<213> ORGANISM: Artificial Sequence
<220> FEATURE:
<223> OTHER INFORMATION: Synthetic Construct

<400> SEQUENCE: 178

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Ile Val Tyr
65                  70                  75                  80

Val Gln Phe Ser Ser Leu Thr Ser Glu Asp Thr Ala Val Tyr Tyr Cys
                85                  90                  95

Gly Arg Ser Gly Gly Asn Tyr Val Gly Tyr Trp Gln Gly Thr Thr
            100                 105                 110

Leu Thr Val Ser Ser
        115

<210> SEQ ID NO 179
<211> LENGTH: 113
<212> TYPE: PRT
<213> ORGANISM: Artificial Sequence
<220> FEATURE:
<223> OTHER INFORMATION: Synthetic Construct

<400> SEQUENCE: 179

Asp Ile Val Met Ser Gln Ser Pro Ser Ser Pro Thr Val Ser Val Gly
1               5                   10                  15

Glu Lys Val Thr Met Thr Cys Lys Ser Ser Gln Ser Leu Leu Asp Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Lys Ser Gly Val
    50                  55                  60

Pro Asp Arg Phe Thr Gly Ser Gly Ser Gly Thr Asp Phe Thr Leu Ser
65                  70                  75                  80

Ile Ser Ser Val Lys Ala Glu Asp Leu Ala Val Tyr Tyr Cys Gln Gln
                85                  90                  95

Tyr Tyr Thr Tyr Pro Trp Thr Phe Gly Gly Gly Thr Lys Leu Glu Ile
            100                 105                 110
Lys

<210> SEQ ID NO 180
<211> LENGTH: 117
<212> TYPE: PRT
<213> ORGANISM: Artificial Sequence
<220> FEATURE:
<223> OTHER INFORMATION: Synthetic Construct

<400> SEQUENCE: 180

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Glu Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Gly Arg Ser Arg Gly Asn Tyr Phe Asp Tyr Trp Gly Gln Gly Thr Thr
            100                 105                 110

Leu Thr Val Ser Ser
        115

<210> SEQ ID NO 181
<211> LENGTH: 111
<212> TYPE: PRT
<213> ORGANISM: Artificial Sequence
<220> FEATURE:
<223> OTHER INFORMATION: Synthetic Construct

<400> SEQUENCE: 181

Asp Ile Val Met Ser Gln Pro Pro Ser Ser Leu Ala Val Ser Val Gly
1               5                   10                  15

Glu Lys Val Thr Met Thr Cys Lys Ser Ser Gln Ser Leu Lys Ser Asn
            20                  25                  30

Gln Lys Asn Tyr Leu Ala Trp Tyr Gln Gln Lys Pro Gly Gln Ser Pro
        35                  40                  45

Lys Leu Leu Ile Tyr Trp Ala Ser Thr Arg Glu Ser Gly Val Pro Asp
    50                  55                  60

Arg Phe Thr Gly Ser Gly Ser Gly Thr Asp Phe Thr Leu Thr Ile Ser
65                  70                  75                  80

Ser Val Lys Ala Glu Asp Leu Ala Val Tyr Tyr Cys Gln Gln Tyr Tyr
                85                  90                  95

Thr Tyr Pro Trp Thr Phe Gly Gly Gly Thr Lys Leu Glu Ile Lys
            100                 105                 110

<210> SEQ ID NO 182
<211> LENGTH: 113
<212> TYPE: PRT
<213> ORGANISM: Artificial Sequence
<220> FEATURE:
<223> OTHER INFORMATION: Synthetic Construct

<400> SEQUENCE: 182

Gln Val Gln Leu Val Gln Ser Gly Ala Glu Val Lys Lys Pro Gly Thr
1               5                   10                  15

Ser Val Lys Val Ser Cys Lys Ala Ser Gly Tyr Thr Phe Thr Thr Tyr
            20                  25                  30

Tyr Met His Trp Val Arg Gln Ala Pro Gly Gln Gly Leu Glu Trp Met
        35                  40                  45

Gly Leu Ile Asn Pro Ser Ala Gly Asn Thr Arg Asn Ala Gln Lys Phe
    50                  55                  60

Gln Gly Arg Val Thr Met Thr Arg Asp Thr Ser Thr Asn Thr Val Tyr
65                  70                  75                  80

Met Glu Leu Ser Ser Leu Arg Ser Glu Asp Thr Ala Val Tyr Tyr Cys
                85                  90                  95

Ala Arg Glu Leu Asp Ile Trp Gly Gln Gly Thr Lys Val Thr Val Ser
            100                 105                 110

Ser

<210> SEQ ID NO 183
<211> LENGTH: 107
<212> TYPE: PRT
<213> ORGANISM: Artificial Sequence
<220> FEATURE:
<223> OTHER INFORMATION: Synthetic Construct

<400> SEQUENCE: 183

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Asn Gly Ser Gly Thr Asp Phe Thr Leu Thr Ile Asn Ser Leu Gln Pro
65                  70                  75                  80

Glu Asp Phe Ala Thr Tyr Tyr Cys Leu Gln Asp Phe Asn Phe Pro Phe
                85                  90                  95

Thr Phe Gly Pro Gly Thr Thr Val Asp Ile Asn
            100                 105

<210> SEQ ID NO 184
<211> LENGTH: 120
<212> TYPE: PRT
<213> ORGANISM: Artificial Sequence
<220> FEATURE:
<223> OTHER INFORMATION: Synthetic Construct

<400> SEQUENCE: 184

Gln Val Gln Leu Val Glu Ser Gly Gly Gly Val Val Gln Ser Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Asp Arg Phe Thr Ile Ser Arg Asp Asn Ser Lys Lys Thr Val Tyr

```
                65                  70                  75                  80
Leu Gln Met Asn Ser Leu Arg Ala Glu Asp Thr Ala Val Tyr Tyr Cys
                    85                  90                  95

Ala Arg Glu Gly Met Val Arg Gly Ala Leu Phe Asp Tyr Trp Gly Gln
                100                 105                 110

Gly Thr Leu Val Thr Val Ser Ser
            115                 120

<210> SEQ ID NO 185
<211> LENGTH: 108
<212> TYPE: PRT
<213> ORGANISM: Artificial Sequence
<220> FEATURE:
<223> OTHER INFORMATION: Synthetic Construct

<400> SEQUENCE: 185

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ser Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Pro Asp Leu Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95

Tyr Thr Phe Gly Gln Gly Thr Lys Leu Glu Ile Lys
            100                 105

<210> SEQ ID NO 186
<211> LENGTH: 119
<212> TYPE: PRT
<213> ORGANISM: Artificial Sequence
<220> FEATURE:
<223> OTHER INFORMATION: Synthetic Construct

<400> SEQUENCE: 186

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Val Ile Tyr Pro Gly Asp Ser Asp Thr Arg Tyr Ser Pro Ser Phe
    50                  55                  60

Gln Gly Gln Val Thr Met Ser Ala Asp Lys Ser Ile Ser Thr Ala Tyr
65                  70                  75                  80

Leu Gln Trp Ser Ser Leu Lys Ala Ser Asp Ser Ala Met Tyr Tyr Cys
                85                  90                  95

Ala Arg Gln Leu Arg Asp Tyr Tyr Gly Met Asp Val Trp Gly Gln Gly
            100                 105                 110

Thr Thr Val Thr Val Ser Ser
        115

<210> SEQ ID NO 187
<211> LENGTH: 108
```

```
<212> TYPE: PRT
<213> ORGANISM: Artificial Sequence
<220> FEATURE:
<223> OTHER INFORMATION: Synthetic Construct

<400> SEQUENCE: 187

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Thr Ile Ser Ser Asn
            20                  25                  30

Tyr Phe Ser Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Glu Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95

Arg Thr Phe Gly Gln Gly Thr Lys Val Glu Ile Lys
            100                 105

<210> SEQ ID NO 188
<211> LENGTH: 119
<212> TYPE: PRT
<213> ORGANISM: Artificial Sequence
<220> FEATURE:
<223> OTHER INFORMATION: Synthetic Construct

<400> SEQUENCE: 188

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu His Trp Ser Ser Leu Lys Ala Ser Asp Thr Ala Met Tyr Tyr Cys
                85                  90                  95

Ala Arg Gln Leu Arg Asp Tyr Tyr Ser Met Asp Val Trp Gly Gln Gly
            100                 105                 110

Thr Thr Val Thr Val Ser Ser
        115

<210> SEQ ID NO 189
<211> LENGTH: 108
<212> TYPE: PRT
<213> ORGANISM: Artificial Sequence
<220> FEATURE:
<223> OTHER INFORMATION: Synthetic Construct

<400> SEQUENCE: 189

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ser Trp Tyr Gln Gln Lys Pro Gly Gln Ala Pro Arg Leu Leu
```

```
            35                  40                  45

Ile Tyr Gly Ala Ser Thr Arg Ala Thr Gly Ile Ala Ala Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Val Tyr Tyr Cys Gln Gln Asp Tyr Asn Leu Pro
                     85                  90                  95

Arg Thr Phe Gly Gln Gly Thr Lys Val Glu Ile Lys
                    100                 105

<210> SEQ ID NO 190
<211> LENGTH: 114
<212> TYPE: PRT
<213> ORGANISM: Artificial Sequence
<220> FEATURE:
<223> OTHER INFORMATION: Synthetic Construct

<400> SEQUENCE: 190

Glu Val Gln Leu Gln Gln Ser Gly Pro Glu Leu Val Lys Pro Gly Ala
 1               5                  10                  15

Ser Val Lys Met Ser Cys Lys Ala Ser Gly Tyr Thr Phe Thr Ser Tyr
                20                  25                  30

Asn Ile His Trp Val Lys Gln Lys Pro Gly Gln Gly Leu Glu Trp Ile
            35                  40                  45

Gly Tyr Ile Asn Pro Tyr Asn Asp Gly Thr Lys Tyr Ser Glu Lys Phe
 50                  55                  60

Lys Gly Lys Ala Thr Leu Thr Ser Asp Arg Ser Ser Ser Thr Ala Tyr
 65                  70                  75                  80

Met Glu Val Ser Ser Leu Thr Ser Glu Asp Ser Ala Val Tyr Tyr Cys
                     85                  90                  95

Ala Ile Tyr Gly Asn Ser Tyr Trp Gly Gln Gly Ser Thr Leu Thr Val
                    100                 105                 110

Ser Ser

<210> SEQ ID NO 191
<211> LENGTH: 112
<212> TYPE: PRT
<213> ORGANISM: Artificial Sequence
<220> FEATURE:
<223> OTHER INFORMATION: Synthetic Construct

<400> SEQUENCE: 191

Asp Ile Val Met Thr Gln Ala Ala Pro Ser Ile Pro Val Thr Pro Gly
 1               5                  10                  15

Glu Ser Val Ser Ile Ser Cys Arg Ser Ser Lys Ser Leu Leu His Ser
                20                  25                  30

Asn Gly Asn Thr Tyr Leu Tyr Trp Phe Leu Gln Arg Pro Gly Gln Ser
            35                  40                  45

Pro Gln Arg Leu Ile Tyr Tyr Met Ser Asn Leu Asp Ser Gly Val Pro
 50                  55                  60

Asp Arg Phe Ser Gly Arg Gly Ser Gly Thr Asp Phe Thr Leu Arg Ile
 65                  70                  75                  80

Ser Arg Val Glu Ala Glu Asp Val Gly Val Tyr Tyr Cys Met Gln Gly
                     85                  90                  95

Leu Glu Tyr Pro Tyr Thr Phe Gly Gly Gly Thr Lys Leu Glu Ile Lys
                    100                 105                 110
```

```
<210> SEQ ID NO 192
<211> LENGTH: 118
<212> TYPE: PRT
<213> ORGANISM: Artificial Sequence
<220> FEATURE:
<223> OTHER INFORMATION: Synthetic Construct

<400> SEQUENCE: 192

Asp Val Met Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Ser Ile Ser Ser Gly Gly Gly Asn Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Ala Leu Tyr Tyr Cys
                85                  90                  95

Ala Arg Phe Asp Tyr Gly Ser Ser Leu Asp Ser Trp Gly Gln Gly Thr
            100                 105                 110

Thr Leu Thr Val Ser Ser
        115

<210> SEQ ID NO 193
<211> LENGTH: 107
<212> TYPE: PRT
<213> ORGANISM: Artificial Sequence
<220> FEATURE:
<223> OTHER INFORMATION: Synthetic Construct

<400> SEQUENCE: 193

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Lys Asn Trp Pro Arg
                85                  90                  95

Thr Phe Gly Gly Gly Thr Lys Leu Glu Ile Lys
            100                 105

<210> SEQ ID NO 194
<211> LENGTH: 118
<212> TYPE: PRT
<213> ORGANISM: Artificial Sequence
<220> FEATURE:
<223> OTHER INFORMATION: Synthetic Construct

<400> SEQUENCE: 194

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30
```

Thr Met Ser Trp Val Arg Gln Thr Pro Glu Lys Arg Leu Glu Trp Val
            35                  40                  45

Ala Thr Ile Ser Ser Gly Gly Asp Asn Thr Tyr Tyr Pro Asp Ser Val
 50                  55                  60

Lys Gly Arg Phe Thr Ile Ser Arg Asp Asn Ala Lys Asn Asn Leu Tyr
 65                  70                  75                  80

Leu Gln Met Ser Ser Leu Arg Ser Glu Asp Thr Ala Leu Tyr Tyr Cys
                 85                  90                  95

Ala Arg Phe Asp Tyr Gly Ser Ser Leu Asp Cys Trp Gly Gln Gly Thr
                100                 105                 110

Thr Leu Thr Val Ser Ser
            115

<210> SEQ ID NO 195
<211> LENGTH: 107
<212> TYPE: PRT
<213> ORGANISM: Artificial Sequence
<220> FEATURE:
<223> OTHER INFORMATION: Synthetic Construct

<400> SEQUENCE: 195

Asp Ile Val Leu Thr Gln Ser Pro Ala Thr Leu Ser Val Thr Pro Gly
 1               5                  10                  15

Asp Ser Val Ser Leu Ser Cys Arg Ala Ser Gln Ser Ile Ser Asn Tyr
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
 50                  55                  60

Ser Gly Ser Gly Thr Asp Phe Thr Leu Ser Ile Asn Ser Val Glu Thr
 65                  70                  75                  80

Glu Asp Phe Gly Met Tyr Phe Cys Gln Gln Ser Lys Ser Trp Pro Arg
                 85                  90                  95

Thr Phe Gly Gly Gly Thr Glu Leu Glu Ile Lys
                100                 105

<210> SEQ ID NO 196
<211> LENGTH: 120
<212> TYPE: PRT
<213> ORGANISM: Artificial Sequence
<220> FEATURE:
<223> OTHER INFORMATION: Synthetic Construct

<400> SEQUENCE: 196

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Arg Gly Tyr Arg Ser Ser Trp Tyr Phe Asp Tyr Trp Gly Gln

```
                100               105               110
Gly Thr Leu Val Thr Val Ser Ser
        115                 120
```

<210> SEQ ID NO 197
<211> LENGTH: 107
<212> TYPE: PRT
<213> ORGANISM: Artificial Sequence
<220> FEATURE:
<223> OTHER INFORMATION: Synthetic Construct

<400> SEQUENCE: 197

```
Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Asp Tyr Asn Tyr Pro Leu
                85                  90                  95

Thr Phe Gly Gly Gly Thr Lys Val Glu Ile Lys
            100                 105
```

<210> SEQ ID NO 198
<211> LENGTH: 118
<212> TYPE: PRT
<213> ORGANISM: Artificial Sequence
<220> FEATURE:
<223> OTHER INFORMATION: Synthetic Construct

<400> SEQUENCE: 198

```
Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Glu Gly Gly Glu Leu Leu Met Asp Tyr Trp Gly Gln Gly Thr
            100                 105                 110

Leu Val Thr Val Ser Ser
        115
```

<210> SEQ ID NO 199
<211> LENGTH: 105
<212> TYPE: PRT
<213> ORGANISM: Artificial Sequence
<220> FEATURE:
<223> OTHER INFORMATION: Synthetic Construct

<400> SEQUENCE: 199

-continued

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Thr Tyr
            20                  25                  30

Leu Ala Trp Tyr Gln Gln Lys Pro Gly Gln Ala Pro Arg Leu Leu Ile
        35                  40                  45

Tyr Asp Asn Arg Ala Thr Gly Ile Pro Pro Arg Phe Ser Gly Ser Gly
    50                  55                  60

Ser Gly Thr Asp Phe Thr Leu Thr Ile Ser Ser Leu Glu Pro Glu Asp
65                  70                  75                  80

Phe Ala Val Tyr Tyr Cys Gln Gln Arg Ser Asn Trp Pro Pro Thr Phe
                85                  90                  95

Gly Gly Gly Thr Thr Val Glu Ile Lys
            100                 105

<210> SEQ ID NO 200
<211> LENGTH: 125
<212> TYPE: PRT
<213> ORGANISM: Artificial Sequence
<220> FEATURE:
<223> OTHER INFORMATION: Synthetic Construct

<400> SEQUENCE: 200

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Ser Met Val Trp Val Arg Gln Ala Pro Gly Lys Gly Leu Glu Trp Val
        35                  40                  45

Ser Tyr Ile Tyr Pro Ser Gly Gly Thr Ser Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg His Trp Arg Gly Tyr Ser Ser Ser Trp Tyr His Pro Ala Tyr Phe
            100                 105                 110

Asp Tyr Trp Gly Gln Gly Thr Leu Val Thr Val Ser Ser
        115                 120                 125

<210> SEQ ID NO 201
<211> LENGTH: 105
<212> TYPE: PRT
<213> ORGANISM: Artificial Sequence
<220> FEATURE:
<223> OTHER INFORMATION: Synthetic Construct

<400> SEQUENCE: 201

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Asn Arg Ala Thr Gly Ile Pro Ala Arg Phe Ser Gly Ser Gly
    50                  55                  60

Ser Gly Thr Asp Phe Thr Leu Thr Ile Ser Ser Leu Glu Pro Glu Asp

```
                65                  70                  75                  80
            Phe Ala Val Tyr Tyr Cys Gln Gln Arg Ser Asn Trp Pro Leu Thr Phe
                            85                  90                  95

Gly Gly Gly Thr Lys Val Glu Ile Lys
                        100                 105

<210> SEQ ID NO 202
<211> LENGTH: 126
<212> TYPE: PRT
<213> ORGANISM: Artificial Sequence
<220> FEATURE:
<223> OTHER INFORMATION: Synthetic Construct

<400> SEQUENCE: 202

Glu Val Gln Leu Leu Glu Ser Gly Gly Gly Leu Val Gln Pro Gly Gly
            1               5                   10                  15

Ser Leu Arg Leu Ser Cys Ala Ala Ser Gly Phe Thr Phe Ser Trp Tyr
                        20                  25                  30

Pro Met Met Trp Val Arg Gln Ala Pro Gly Lys Gly Leu Glu Trp Val
                        35                  40                  45

Ser Ser Ile Tyr Pro Ser Gly Gly Thr Thr Thr Tyr Ala Asp Ser Val
                50                  55                  60

Lys Gly Arg Phe Thr Ile Ser Arg Asp Asn Ser Lys Asn Thr Leu Tyr
            65                  70                  75                  80

Leu Gln Met Asn Ser Leu Arg Ala Glu Asp Thr Ala Val Tyr Tyr Cys
                            85                  90                  95

Ala Arg Ser Tyr Tyr Tyr Asp Ser Ser Gly Tyr Tyr Ser His Asp Ala
                        100                 105                 110

Phe Asp Ile Trp Gly Gln Gly Thr Met Val Thr Val Ser Ser
                        115                 120                 125

<210> SEQ ID NO 203
<211> LENGTH: 108
<212> TYPE: PRT
<213> ORGANISM: Artificial Sequence
<220> FEATURE:
<223> OTHER INFORMATION: Synthetic Construct

<400> SEQUENCE: 203

Asp Ile Gln Met Thr Gln Ser Pro Ser Ser Leu Ser Ala Ser Val Gly
            1               5                   10                  15

Asp Arg Val Ala Ile Thr Cys Arg Ala Ser Gln Ser Ile Asp Thr Tyr
                        20                  25                  30

Leu Asn Trp Tyr Gln Gln Lys Pro Gly Lys Ala Pro Lys Leu Leu Ile
                        35                  40                  45

Tyr Ala Ala Ser Lys Leu Glu Asp Gly Val Pro Ser Arg Phe Ser Gly
                50                  55                  60

Ser Gly Thr Gly Thr Asp Phe Thr Leu Thr Ile Arg Ser Leu Gln Pro
            65                  70                  75                  80

Glu Asp Phe Ala Ser Tyr Phe Cys Gln Gln Ser Tyr Ser Ser Pro Gly
                            85                  90                  95

Ile Thr Phe Gly Pro Gly Thr Lys Val Glu Ile Lys
                        100                 105

<210> SEQ ID NO 204
<211> LENGTH: 122
<212> TYPE: PRT
<213> ORGANISM: Artificial Sequence
<220> FEATURE:
```

<223> OTHER INFORMATION: Synthetic Construct

<400> SEQUENCE: 204

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Glu Met His Trp Val Arg Gln Ala Pro Gly Lys Gly Leu Glu Trp Val
        35                  40                  45

Ser Ser Ile Trp Pro Ser Gly Gly Leu Thr Lys Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Tyr Tyr Tyr Asp Ser Ser Gly Ala Leu Gly Tyr Trp
            100                 105                 110

Gly Gln Gly Thr Leu Val Thr Val Ser Ser
        115                 120

<210> SEQ ID NO 205
<211> LENGTH: 107
<212> TYPE: PRT
<213> ORGANISM: Artificial Sequence
<220> FEATURE:
<223> OTHER INFORMATION: Synthetic Construct

<400> SEQUENCE: 205

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Val Ser Asn Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Gln Tyr Val Ser Tyr Pro Leu
                85                  90                  95

Thr Phe Gly Gly Gly Thr Lys Val Asp Ile Lys
            100                 105

<210> SEQ ID NO 206
<211> LENGTH: 124
<212> TYPE: PRT
<213> ORGANISM: Artificial Sequence
<220> FEATURE:
<223> OTHER INFORMATION: Synthetic Construct

<400> SEQUENCE: 206

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Met Tyr Trp Val Arg Gln Ala Pro Gly Lys Gly Leu Glu Trp Val
        35                  40                  45

Ser Arg Ile Tyr Ser Ser Gly Gly His Thr Trp Tyr Ala Asp Ser Val

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Tyr Ser Ser Gly Trp Tyr Asp Gly Thr Tyr Phe Asp
            100                 105                 110

Tyr Trp Gly Gln Gly Thr Leu Val Thr Val Ser Ser
        115                 120

<210> SEQ ID NO 207
<211> LENGTH: 107
<212> TYPE: PRT
<213> ORGANISM: Artificial Sequence
<220> FEATURE:
<223> OTHER INFORMATION: Synthetic Construct

<400> SEQUENCE: 207

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asp Thr Trp
            20                  25                  30

Leu Ala Trp Tyr Arg Gln Lys Pro Gly Lys Ala Pro Asn Val Val Ile
        35                  40                  45

His Ser Ala Ser Thr Leu Gln Ser Gly Val Pro Ala Arg Phe Ser Gly
    50                  55                  60

Ser Gly Phe Gly Thr Glu Trp Thr Leu Thr Ile Thr Asn Leu Gln Pro
65                  70                  75                  80

Asp Asp Phe Ala Thr Tyr Tyr Cys Gln Gln Tyr Lys Thr Tyr Pro Phe
                85                  90                  95

Thr Phe Gly Gln Gly Thr Lys Leu Glu Ile Lys
            100                 105

<210> SEQ ID NO 208
<211> LENGTH: 119
<212> TYPE: PRT
<213> ORGANISM: Artificial Sequence
<220> FEATURE:
<223> OTHER INFORMATION: Synthetic Construct

<400> SEQUENCE: 208

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Gln Met Glu Trp Val Arg Gln Ala Pro Gly Lys Gly Leu Glu Trp Val
        35                  40                  45

Ser Ser Ile Ser Pro Ser Gly Gly Phe Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Glu Pro Gly Arg Leu Trp Ala Phe Asp Ile Trp Gly Gln Gly
            100                 105                 110

Thr Met Val Thr Val Ser Ser
            115

<210> SEQ ID NO 209
<211> LENGTH: 107
<212> TYPE: PRT
<213> ORGANISM: Artificial Sequence
<220> FEATURE:
<223> OTHER INFORMATION: Synthetic Construct

<400> SEQUENCE: 209

```
Asp Ile Gln Met Thr Gln Ser Pro Ser Phe Val Ser Ala Ser Val Gly
1               5                   10                  15

Asp Arg Val Thr Ile Thr Cys Arg Ala Ser Gln Asp Ile Arg Asn Trp
            20                  25                  30

Leu Ala Trp Tyr Gln Gln Glu Ser Gly Lys Ala Pro Arg Leu Leu Ile
        35                  40                  45

Ser Ala Ala Ser Ser Arg His Ser Gly Val Ser Ser Arg Phe Ser Gly
    50                  55                  60

Ser Gly Ser Gly Thr Asp Phe Thr Leu Thr Ile Thr Ser Leu Gln Pro
65                  70                  75                  80

Glu Asp Ser Ala Thr Tyr Phe Cys Gln Gln Ala Asp Ser Ser Pro Arg
                85                  90                  95

Thr Phe Gly Gln Gly Thr Lys Val Glu Ile Lys
            100                 105
```

<210> SEQ ID NO 210
<211> LENGTH: 115
<212> TYPE: PRT
<213> ORGANISM: Artificial Sequence
<220> FEATURE:
<223> OTHER INFORMATION: Synthetic Construct

<400> SEQUENCE: 210

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Val Phe Gly Ser Gly Ser Ser Trp Gly Gln Gly Thr Leu Val Thr
            100                 105                 110

Val Ser Ser
        115
```

<210> SEQ ID NO 211
<211> LENGTH: 107
<212> TYPE: PRT
<213> ORGANISM: Artificial Sequence
<220> FEATURE:
<223> OTHER INFORMATION: Synthetic Construct

<400> SEQUENCE: 211

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Ser
```

```
                 20                  25                  30

Leu Ala Trp Phe Gln Gln Lys Pro Gly Lys Ala Pro Lys Ser Leu Ile
             35                  40                  45

Tyr Ala Ala Ser Ser Leu Gln Ser Gly Val Pro Ser Lys Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Lys Ser Tyr Pro Tyr
                 85                  90                  95

Thr Phe Gly Gln Gly Thr Lys Leu Glu Ile Lys
                100                 105

<210> SEQ ID NO 212
<211> LENGTH: 115
<212> TYPE: PRT
<213> ORGANISM: Artificial Sequence
<220> FEATURE:
<223> OTHER INFORMATION: Synthetic Construct

<400> SEQUENCE: 212

Gln Val Gln Leu Val Gln Ser Gly Ala Glu Val Lys Lys Pro Gly Ala
 1               5                  10                  15

Ser Val Lys Val Ser Cys Lys Ala Ser Gly Asn Thr Phe Thr Gly Tyr
                 20                  25                  30

Tyr Ile His Trp Val Arg Gln Ala Pro Gly Gln Gly Leu Glu Trp Met
             35                  40                  45

Gly Trp Ile Lys Pro Ser Thr Gly Asp Thr Asn Tyr Ala Gln Asn Phe
         50                  55                  60

Leu Asp Arg Val Thr Met Thr Arg Asp Thr Ser Ile Ser Thr Ala Tyr
 65                  70                  75                  80

Met Glu Leu Ser Arg Leu Arg Ser Asp Thr Ala Val Tyr Tyr Cys
                 85                  90                  95

Ala Val Phe Gly Ser Gly Ser Trp Gly Gln Gly Thr Leu Val Thr
                100                 105                 110

Val Ser Ser
        115

<210> SEQ ID NO 213
<211> LENGTH: 107
<212> TYPE: PRT
<213> ORGANISM: Artificial Sequence
<220> FEATURE:
<223> OTHER INFORMATION: Synthetic Construct

<400> SEQUENCE: 213

Asp Ile His Met Thr Gln Ser Pro Ser Ser Leu Ser Ala Phe Val Gly
 1               5                  10                  15

Asp Arg Val Thr Ile Thr Cys Arg Ala Ser Gln Gly Ile Ser Asn Tyr
                 20                  25                  30

Leu Ala Trp Phe Gln Gln Lys Pro Gly Lys Ala Pro Lys Ser Leu Ile
             35                  40                  45

Tyr Ala Ala Ser Ser Leu Gln Ser Gly Val Pro Ser Lys Phe Ser Gly
         50                  55                  60

Ser Gly Ser Gly Thr Asp Phe Thr Leu Thr Ile Asn Asn Leu Gln Pro
 65                  70                  75                  80

Glu Asp Phe Ala Thr Tyr Tyr Cys Gln Gln Tyr Lys Thr Tyr Pro Tyr
                 85                  90                  95
```

Thr Phe Gly Gln Gly Thr Lys Leu Glu Ile Lys
            100                 105

<210> SEQ ID NO 214
<211> LENGTH: 124
<212> TYPE: PRT
<213> ORGANISM: Artificial Sequence
<220> FEATURE:
<223> OTHER INFORMATION: Synthetic Construct

<400> SEQUENCE: 214

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Arg Glu Gly Gly Trp Tyr Gly Gly Asp Tyr Tyr Tyr Gly Met Asp
            100                 105                 110

Val Trp Gly Gln Gly Thr Thr Val Thr Val Ser Ser
        115                 120

<210> SEQ ID NO 215
<211> LENGTH: 105
<212> TYPE: PRT
<213> ORGANISM: Artificial Sequence
<220> FEATURE:
<223> OTHER INFORMATION: Synthetic Construct

<400> SEQUENCE: 215

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Trp Tyr Gln Gln Lys Pro Gly Lys Ala Pro Lys Leu Leu Ile Tyr Asp
        35                  40                  45

Ala Ser Ser Leu Glu Ser Gly Val Pro Ser Arg Phe Ser Gly Ser Gly
    50                  55                  60

Ser Gly Thr Asp Phe Thr Leu Thr Ile Ser Ser Leu Gln Pro Glu Asp
65                  70                  75                  80

Phe Ala Thr Tyr Tyr Cys His Gln Phe Asn Asn Tyr Pro Phe Thr Phe
                85                  90                  95

Gly Pro Gly Thr Lys Val Asp Ile Lys
            100                 105

<210> SEQ ID NO 216
<211> LENGTH: 122
<212> TYPE: PRT
<213> ORGANISM: Artificial Sequence
<220> FEATURE:
<223> OTHER INFORMATION: Synthetic Construct

<400> SEQUENCE: 216

Glu Val Gln Leu Leu Glu Ser Gly Gly Gly Leu Val Gln Pro Gly Gly

```
            1               5                  10                  15
          Ser Leu Arg Leu Ser Cys Val Ala Ser Gly Phe Thr Phe Ser Ser Tyr
                          20                  25                  30

Ala Met Ser Trp Val Arg Gln Ala Pro Gly Lys Gly Leu Glu Trp Val
                          35                  40                  45

Ser Gly Ile Ser Gly Arg Gly Ser Pro Asn Tyr Ala Asp Ser Val
                          50                  55                  60

Lys Gly Arg Phe Thr Ile Ser Arg Asp Asn Ser Lys Asn Thr Leu Tyr
           65                 70                  75                  80

Leu Gln Met Asn Ser Leu Arg Ala Glu Asp Thr Ala Val Tyr Tyr Cys
                          85                  90                  95

Ala Lys Asp Gly Asp Gly Ser Gly Pro Pro Tyr Tyr Phe Asp Tyr Trp
                          100                 105                 110

Gly Gln Gly Thr Leu Val Thr Val Ser Ser
                          115                 120

<210> SEQ ID NO 217
<211> LENGTH: 107
<212> TYPE: PRT
<213> ORGANISM: Artificial Sequence
<220> FEATURE:
<223> OTHER INFORMATION: Synthetic Construct

<400> SEQUENCE: 217

Asp Ile Gln Met Thr Gln Ser Pro Ser Ser Leu Ser Ala Ser Val Gly
           1               5                  10                  15

Asp Arg Val Thr Ile Thr Cys Arg Ala Ser Gln Gly Ile Ser Ser Trp
                          20                  25                  30

Leu Ala Trp Tyr Gln Gln Lys Pro Glu Lys Ala Pro Lys Ser Leu Ile
                          35                  40                  45

Tyr Ala Ala Ser Ser Leu Gln Ser Gly Val Pro Ser Arg Phe Ser Gly
                          50                  55                  60

Ser Gly Ser Gly Thr Asp Phe Thr Leu Thr Ile Ser Ser Leu Gln Pro
           65                 70                  75                  80

Glu Asp Phe Ala Thr Tyr Tyr Cys Gln Gln Tyr Asn Ser Tyr Pro Tyr
                          85                  90                  95

Thr Phe Gly Gln Gly Thr Lys Leu Glu Ile Lys
                          100                 105

<210> SEQ ID NO 218
<211> LENGTH: 131
<212> TYPE: PRT
<213> ORGANISM: Artificial Sequence
<220> FEATURE:
<223> OTHER INFORMATION: Synthetic Construct

<400> SEQUENCE: 218

Gln Val Gln Leu Met Glu Ser Gly Gly Gly Val Val Gln Pro Gly Arg
           1               5                  10                  15

Ser Leu Arg Leu Ser Cys Ala Ala Ser Gly Phe Thr Phe Ser Gly Tyr
                          20                  25                  30

Gly Met His Trp Val Arg Gln Ala Pro Gly Lys Gly Leu Glu Trp Val
                          35                  40                  45

Ala Val Ile Trp Ser Asp Gly Ser Asn Arg Tyr Tyr Thr Asp Ser Val
                          50                  55                  60

Lys Gly Arg Phe Thr Ile Ser Arg Asp Asn Ser Lys Asn Thr Leu Ser
           65                 70                  75                  80
```

Leu Gln Met Asn Ser Leu Arg Ala Glu Asp Thr Ala Val Tyr Tyr Cys
                85                  90                  95

Ala Arg Asp Arg Gly Ile Thr Met Val Arg Gly Leu Ile Ile Lys Tyr
            100                 105                 110

Tyr Tyr Tyr Tyr Gly Leu Asp Val Trp Gly Gln Gly Thr Ser Val Thr
        115                 120                 125

Val Ser Ser
    130

<210> SEQ ID NO 219
<211> LENGTH: 104
<212> TYPE: PRT
<213> ORGANISM: Artificial Sequence
<220> FEATURE:
<223> OTHER INFORMATION: Synthetic Construct

<400> SEQUENCE: 219

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Asn Arg Ala Thr Gly Ile Pro Ala Arg Phe Ser Gly Ser Gly
    50                  55                  60

Ser Gly Thr Asp Phe Thr Leu Thr Ile Ser Ser Leu Glu Pro Glu Asp
65                  70                  75                  80

Phe Ala Val Tyr Tyr Cys Gln Gln Arg Ser Asn Trp Trp Thr Phe Gly
                85                  90                  95

Gln Gly Thr Lys Val Glu Ile Lys
            100

<210> SEQ ID NO 220
<211> LENGTH: 120
<212> TYPE: PRT
<213> ORGANISM: Artificial Sequence
<220> FEATURE:
<223> OTHER INFORMATION: Synthetic Construct

<400> SEQUENCE: 220

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Val Ile Tyr Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Asn Trp Asn Asp Gly Asp Phe Asp Tyr Trp Gly Gln
            100                 105                 110

Gly Thr Leu Val Thr Val Ser Ser
        115                 120

<210> SEQ ID NO 221

<211> LENGTH: 107
<212> TYPE: PRT
<213> ORGANISM: Artificial Sequence
<220> FEATURE:
<223> OTHER INFORMATION: Synthetic Construct

<400> SEQUENCE: 221

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Arg
                85                  90                  95

Thr Phe Gly Gln Gly Thr Lys Val Glu Ile Lys
            100                 105

<210> SEQ ID NO 222
<211> LENGTH: 126
<212> TYPE: PRT
<213> ORGANISM: Artificial Sequence
<220> FEATURE:
<223> OTHER INFORMATION: Synthetic Construct

<400> SEQUENCE: 222

Glu Val Gln Leu Leu Glu Ser Gly Gly Gly Leu Val Gln Pro Gly Glu
1               5                   10                  15

Ser Leu Arg Leu Ser Cys Ala Ala Ser Gly Phe Thr Phe Asn Arg Phe
            20                  25                  30

Val Met Ser Trp Val Arg Gln Ala Pro Gly Lys Gly Leu Glu Trp Val
        35                  40                  45

Ser Thr Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Thr Tyr Tyr Gly Ser Gly Asn Tyr Tyr Asn Trp
            100                 105                 110

Phe Asp Pro Arg Gly Gln Gly Thr Leu Val Thr Val Ser Ser
        115                 120                 125

<210> SEQ ID NO 223
<211> LENGTH: 107
<212> TYPE: PRT
<213> ORGANISM: Artificial Sequence
<220> FEATURE:
<223> OTHER INFORMATION: Synthetic Construct

<400> SEQUENCE: 223

Asp Ile Gln Met Thr Gln Ser Pro Ser Thr Leu Ser Thr Ser Val Gly
1               5                   10                  15

Asp Arg Val Thr Ile Thr Cys Arg Ala Ser Gln Ser Ile Ser Ser Trp
            20                  25                  30

```
Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ser Arg
                 85                  90                  95

Thr Phe Gly Gln Gly Thr Lys Val Glu Ile Lys
                100                 105
```

<210> SEQ ID NO 224
<211> LENGTH: 121
<212> TYPE: PRT
<213> ORGANISM: Artificial Sequence
<220> FEATURE:
<223> OTHER INFORMATION: Synthetic Construct

<400> SEQUENCE: 224

```
Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Gly Thr Asn Tyr Asn Pro Ser Leu Lys
 50                  55                  60

Ser Arg Val Thr Ile Ser Val Asp Thr Ser Lys Asn His Phe Ser Leu
 65                  70                  75                  80

Lys Leu Ser Ser Val Thr Ala Ala Asp Thr Ala Val Tyr Tyr Cys Ala
                 85                  90                  95

Arg Thr Ser Asp Tyr Asp Tyr Tyr Tyr Gly Met Asp Val Trp Gly
                100                 105                 110

Gln Gly Thr Thr Val Thr Val Ser Ser
            115                 120
```

<210> SEQ ID NO 225
<211> LENGTH: 114
<212> TYPE: PRT
<213> ORGANISM: Artificial Sequence
<220> FEATURE:
<223> OTHER INFORMATION: Synthetic Construct

<400> SEQUENCE: 225

```
Gln Pro Val Leu Thr Gln Pro Thr Ser Leu Ser Asp Gly Ala Ser Ala
 1               5                  10                  15

Arg Leu Thr Cys Thr Leu Arg Ser Gly Ile Asn Leu Gly Arg Tyr Arg
            20                  25                  30

Ile Phe Trp Tyr Gln Gln Lys Pro Glu Ser Pro Pro Arg Tyr Leu Leu
        35                  40                  45

Ser Tyr Tyr Ser Asp Ser Ser Lys His Gln Gly Ser Gly Val Pro Ser
 50                  55                  60

Arg Phe Ser Gly Ser Lys Asp Ala Ser Ser Asn Ala Gly Ile Leu Val
 65                  70                  75                  80

Ile Ser Gly Leu Gln Ser Glu Asp Glu Ala Asp Tyr Tyr Cys Met Ile
                 85                  90                  95

Trp His Arg Ser Ala Leu Phe Ile Phe Gly Ser Gly Thr Lys Val Thr
                100                 105                 110
```

<210> SEQ ID NO 226
<211> LENGTH: 115
<212> TYPE: PRT
<213> ORGANISM: Artificial Sequence
<220> FEATURE:
<223> OTHER INFORMATION: Synthetic Construct

<400> SEQUENCE: 226

```
Gln Val Gln Leu Gln Gln Ser Gly Pro Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Glu Ile Asn Trp Leu Lys Gln Arg Pro Gly Gln Gly Leu Glu Trp Ile
        35                  40                  45

Gly Leu Ile Tyr Pro Arg Asp Gly Asp Thr Lys Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Glu Leu His Ser Leu Thr Ser Glu Asp Ser Ala Val Tyr Phe Cys
                85                  90                  95

Ala Arg His Thr Pro Gly Ala Phe Trp Gly Gln Gly Thr Leu Val Thr
            100                 105                 110

Val Ser Ala
        115
```

<210> SEQ ID NO 227
<211> LENGTH: 112
<212> TYPE: PRT
<213> ORGANISM: Artificial Sequence
<220> FEATURE:
<223> OTHER INFORMATION: Synthetic Construct

<400> SEQUENCE: 227

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asp Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Glu Ile Tyr Phe Cys Ser Gln Ser
                85                  90                  95

Thr His Val Pro Tyr Thr Phe Gly Gly Gly Thr Lys Leu Glu Ile Lys
            100                 105                 110
```

<210> SEQ ID NO 228
<211> LENGTH: 124
<212> TYPE: PRT
<213> ORGANISM: Artificial Sequence
<220> FEATURE:
<223> OTHER INFORMATION: Synthetic Construct

<400> SEQUENCE: 228

```
Asp Val Lys Leu Val Glu Ser Gly Glu Gly Leu Val Lys Pro Gly Gly
```

```
              1               5                   10                  15
Ser Leu Lys Leu Ser Cys Ala Ala Ser Gly Phe Thr Phe Ser Arg Tyr
             20                  25                  30

Ala Met Ser Trp Val Arg Gln Thr Pro Glu Lys Arg Leu Glu Trp Val
             35                  40                  45

Ala Tyr Ile Ser Ser Gly Gly Asp Tyr Ile His Tyr Gly Glu Thr Val
             50                  55                  60

Lys Gly Arg Phe Thr Ile Ser Arg Asp Asn Ala Arg Asn Thr Leu Tyr
 65                  70                  75                  80

Leu Gln Met Ser Ser Leu Lys Ser Glu Asp Thr Ala Met Tyr Tyr Cys
                 85                  90                  95

Thr Arg Val Leu Phe Tyr Tyr Tyr Gly Ser Ser Tyr Val Phe Phe Asp
                100                 105                 110

Tyr Trp Gly Gln Gly Thr Thr Leu Thr Val Ser Ser
             115                 120

<210> SEQ ID NO 229
<211> LENGTH: 107
<212> TYPE: PRT
<213> ORGANISM: Artificial Sequence
<220> FEATURE:
<223> OTHER INFORMATION: Synthetic Construct

<400> SEQUENCE: 229

Asp Ile Gln Met Thr Gln Thr Thr Ser Ser Leu Ser Val Ser Leu Gly
 1               5                   10                  15

Asp Arg Val Thr Ile Ser Cys Arg Ala Ser Gln Asp Ile Ser Asn Phe
             20                  25                  30

Leu Asn Trp Tyr Gln Gln Lys Pro Asp Gly Thr Val Asn Leu Leu Ile
             35                  40                  45

Tyr Tyr Thr Ser Lys Leu His Ser Gly Val Pro Ser Arg Phe Ser Gly
         50                  55                  60

Gly Gly Ser Gly Arg Asp Tyr Ser Leu Thr Ile Asn Asn Leu Glu Gln
 65                  70                  75                  80

Glu Asp Ile Ala Ser Tyr Phe Cys Gln Gln Gly His Thr Leu Pro Tyr
                 85                  90                  95

Thr Phe Gly Gly Gly Thr Lys Leu Glu Ile Lys
                100                 105

<210> SEQ ID NO 230
<211> LENGTH: 339
<212> TYPE: DNA
<213> ORGANISM: Artificial Sequence
<220> FEATURE:
<223> OTHER INFORMATION: Synthetic Construct

<400> SEQUENCE: 230
caggtgcagc tgcagcagag cggtcccgag ctggtgaaac ctggcgcatc agtcaaaatg      60
agctgcaagg cctccggctt cacttttacc gactcagtga tcagctgggt caagcagcga     120
accggtcagg gactggagtg gatcggagaa atctaccctg gatctgggag tatctactat     180
aacgagaagt tcaagggaa ggcaacactg actgccgaca aaagctccaa tacagcctat     240
atgcagctgc gatccctgac ttctgaagat agcgccgtgt acttttgcgc aatgcggagg     300
tcctattggg gtcagggcac cctggtgaca gtctctgct                            339

<210> SEQ ID NO 231
<211> LENGTH: 336
```

```
<212> TYPE: DNA
<213> ORGANISM: Artificial Sequence
<220> FEATURE:
<223> OTHER INFORMATION: Synthetic Construct

<400> SEQUENCE: 231
gacgtgctga tgacccagac acccctgagt ctgcctgtct cactgggaga tcaggcttct    60
atcagttgcc gaagctccca gagcatcgtg cattccaacg gaaataccta cctggagtgg   120
tatctgcaga agccagggca gtcccccaag ctgctgatct acaaagtgtc taaccggttc   180
agtggcgtcc cagacaggtt ttcaggtagc ggctccggaa ctgatttcac cctgaaaatt   240
tcccgggtgg aggcagaaga cctgggtgtc tactattgct ccagggcag ccatgtgccc    300 ctgactttg gggccggtac aagctggag ctgaaa                               336

<210> SEQ ID NO 232
<211> LENGTH: 339
<212> TYPE: DNA
<213> ORGANISM: Artificial Sequence
<220> FEATURE:
<223> OTHER INFORMATION: Synthetic Construct

<400> SEQUENCE: 232
cagatccagc tgcagcagtc cggtcccgag ctggtgaaac ctggcgcatc tgtcaagatg    60
agttgcgaag cctcaggctt cactttttacc gactccgtga ttacctgggt caaacagcgc  120
ccaggccagg gactggagtg gatcggagaa atctaccccg gatctgggaa cttctactat   180
aatgagaagt ttaaagggaa ggcaacactg actgccgaca gagctccaa caccgcctac    240 atgcagctgc gatcactgac aagcgaagat agcgccgtgt acttctgcgc aatgcggagg   300
tctagttggg gtcagggcac cctggtgaca gtctctgct                         339

<210> SEQ ID NO 233
<211> LENGTH: 336
<212> TYPE: DNA
<213> ORGANISM: Artificial Sequence
<220> FEATURE:
<223> OTHER INFORMATION: Synthetic Construct

<400> SEQUENCE: 233
gacgtgctga tgacccagac acccctgtct ctgcctgtca gtctgggaga tcaggcttct    60
atcagttgcc gaagctccca gaccatcgtg cattcaaaca gcaagacata cctggagtgg   120
tatctgcaga aaccaggcca gtcccccaag ctgctgatct acaaagtgtc aaatcggttc   180
tctggagtcc cagacaggtt ttccggttct ggcagtggaa ctgatttcac cctgaagatt   240
tctcgggtgg aggcagaaga cctgggtgtc tactattgct ccaggggag ccatgtgccc    300 ctgactttg gggccggtac aagctggag ctgaaa                               336

<210> SEQ ID NO 234
<211> LENGTH: 375
<212> TYPE: DNA
<213> ORGANISM: Artificial Sequence
<220> FEATURE:
<223> OTHER INFORMATION: Synthetic Construct

<400> SEQUENCE: 234
caggtgcagc tgcagcagtc gggggagggc ttggtacagc ctgggggtc cctgagactc    60 tcctgtgcag cctctggatt cacctttagc agctatgcca tgagctgggt ccgccaggct  120
ccagggaagg ggctggagtg ggtctcagct attagtggta gtggtggtag cacatactac   180
```

```
gcagactccg tgaagggccg gttcaccgtc tccagagaca attccaagaa cacgctgtat    240
ctgcaaatga acagcctgag agccgaggac acggccgtat attactgtgc gaggctagga    300
tattgtagta gtaccagctg ctatttgtct gcttttgata tctggggcca agggacaatg    360
gtcaccgtct cttca                                                     375

<210> SEQ ID NO 235
<211> LENGTH: 321
<212> TYPE: DNA
<213> ORGANISM: Artificial Sequence
<220> FEATURE:
<223> OTHER INFORMATION: Synthetic Construct

<400> SEQUENCE: 235
gaaattgtgt tgacacagtc tccttccacc ctgtctgcat ctgtaggaga cagagtcacc     60
atcacttgcc gggccagtca gagtattagt agctggttgg cctggtatca gcagaaacca    120
gggaaagccc ctaagctcct gatctatgat gcctccagtt tggaaagtgg ggtcccatca    180
aggttcagcg gcagtggatc tgggacagaa ttcactctca ccatcagcag cctgcagcct    240
gatgattttg caacttatta ctgccaacag tataatagtt acccgctcac tttcggcgga    300
gggaccaagg tggagatcaa a                                              321

<210> SEQ ID NO 236
<211> LENGTH: 366
<212> TYPE: DNA
<213> ORGANISM: Artificial Sequence
<220> FEATURE:
<223> OTHER INFORMATION: Synthetic Construct

<400> SEQUENCE: 236
cagatccagc tggtgcagtc tggcgccgaa gtgaagaagc ctggcaagag cctgaagatc     60
gcctgcaagg gctccggcta cagcttcagc aactactgga tcggctgggt gcgccagatg    120
cctggaaaag gactggaatg gatgggcatt atctaccctg cgacagcga cacccggtac    180 agccccagct ccacggccaa ggtgacaatc agcgccgaca agagcatctc caccgcctac    240
ctgcagtggt cctcccctgaa ggccagcgac accgccatgt actattgtgc cagaggcgtg    300
atcatcaacg gcaccaccag cggcttcgac tattgggac agggcaccct ggtgatcgtg    360
tcctcc                                                               366

<210> SEQ ID NO 237
<211> LENGTH: 321
<212> TYPE: DNA
<213> ORGANISM: Artificial Sequence
<220> FEATURE:
<223> OTHER INFORMATION: Synthetic Construct

<400> SEQUENCE: 237
gagacaaccc tgacccagag ccccgccacc ctgtccgtgt ctccaggcga gagagccacc     60
ctgagctgca gagccagcca gagcgtgtcc agcaacctgg cctggtatca gcagaagccc    120
ggccaggccc ccagactgct gatgtacggc gccagcacca gagccaccgg catccctgcc    180
agattcagcg gcagcggctc cggcaccgag ttcaccctga ccatcagcag cctgcagagc    240
gaggacttcg ccgtgtacta ctgccagcac tacaacaacc tgcccctgac cttcggcgga    300
ggcaccaagg tggacctgaa g                                              321

<210> SEQ ID NO 238
<211> LENGTH: 351
```

<212> TYPE: DNA
<213> ORGANISM: Artificial Sequence
<220> FEATURE:
<223> OTHER INFORMATION: Synthetic Construct

<400> SEQUENCE: 238

```
gaagtccaac tccaacagtc tggggcagaa cttgtcaaac ctggggcttc agtaaaattg      60
agttgcacag caagtggctt taacatcaaa gacacatata ttcattgggt gaagcaacga     120
ccagaacaag gcttggagtg gatcggtagg attgaccctg caaacgggaa tacaaaatat     180
gaccctaaat tccagggaaa ggctacaata acagcagaca ccagcagtaa cattgtctat     240
gtgcaattta gctctcttac ctctgaggac actgctgtct attattgcgg acgtagtggc     300
gggaattatg tgggttattg gggccagggg acaacactca ccgtatcctc t              351
```

<210> SEQ ID NO 239
<211> LENGTH: 339
<212> TYPE: DNA
<213> ORGANISM: Artificial Sequence
<220> FEATURE:
<223> OTHER INFORMATION: Synthetic Construct

<400> SEQUENCE: 239

```
gatatagtaa tgtcccagtc tccttcatca cctactgtgt cagttggaga aaaagtcacc      60
atgacctgta gtcctcaca gtccctcttg gacagcggga atcagaaaaa ttatctcgca     120
tggtatcagc aaaagccagg gcagtcccct aagctgttga tctattgggc aagtacaagg     180
aaaagtggcg tgcctgatag attcacaggg agcggcagcg ggacagactt cactttgagc     240
atctcttcag taaaagccga agacctggca gtgtactact gtcagcaata ttatacctac     300
ccttggactt ttggtggcgg gaccaaactg gaaataaaa                            339
```

<210> SEQ ID NO 240
<211> LENGTH: 351
<212> TYPE: DNA
<213> ORGANISM: Artificial Sequence
<220> FEATURE:
<223> OTHER INFORMATION: Synthetic Construct

<400> SEQUENCE: 240

```
gaggttcaac ttcagcaatc aggggctgag cttgtaaaac ctggagcctc tgtaaaactc      60
tcttgtaccg cctccgggtt caacataaaa gatacatata tgcactgggt aaaggagcgg     120
cccgaacagg gactcgaatg gatcgggagg attgacccag ctaacggaaa taccaagtat     180
gatccaaaat ttcaggggaa agctacaata accgccgata cttctagtaa tacagcatat     240
cttcagctca gcagcttgac aagcgaagat accgcagttt actactgcgg tcgatcccga     300
gggaattatt ttgactactg gggccagggt actactctca cagtaagtag c              351
```

<210> SEQ ID NO 241
<211> LENGTH: 339
<212> TYPE: DNA
<213> ORGANISM: Artificial Sequence
<220> FEATURE:
<223> OTHER INFORMATION: Synthetic Construct

<400> SEQUENCE: 241

```
gacatagtaa tgagccagcc acctagttca cttgccgtaa gtgtgggtga aaggtgact       60
atgacctgta aaagtagtca gagcctcctt tactcatcaa atcagaagaa ttacttggcc     120
tggtatcaac agaaacctgg acaaagcccc aaactcctca tactgggc ctctacccga       180
```

```
gagtccggcg taccagatcg gtttaccggt tctggatcag gtacagactt tacacttacc    240
atctcttcag tgaaggctga ggacttggcc gtgtattatt gtcaacaata ttatacatat    300
ccttggactt ttggcggagg gacaaagctc gaaataaag                           339
```

<210> SEQ ID NO 242
<211> LENGTH: 339
<212> TYPE: DNA
<213> ORGANISM: Artificial Sequence
<220> FEATURE:
<223> OTHER INFORMATION: Synthetic Construct

<400> SEQUENCE: 242

```
caggtgcagc tggtgcagtc tggcgccgaa gtgaagaaac ccggcacctc cgtgaaggtg     60
tcctgcaagg cttccggcta cacctttacc acctactaca tgcactgggt gcgacaggcc    120
cctggacagg gcctggaatg gatgggcctg atcaacccct tccgccggca caccagaaac    180
gcccagaaat ccagggcag agtgaccatg acccgggaca cctccaccaa caccgtgtac    240
atggaactgt cctccctgcg gagcgaggac accgccgtgt actactgtgc cagagagctg    300
gacatctggg gccagggcac caaagtgacc gtgtcctct                           339
```

<210> SEQ ID NO 243
<211> LENGTH: 321
<212> TYPE: DNA
<213> ORGANISM: Artificial Sequence
<220> FEATURE:
<223> OTHER INFORMATION: Synthetic Construct

<400> SEQUENCE: 243

```
gccatccaga tgacccagtc ccccagctcc ctgtctgcct ctgtgggcga cagagtgacc     60
atcacctgtc gggcctctca ggacatccgg aacgacctgg gctggtatca gcagaagcct    120
ggcaaggccc ccaagctgct gatctacgcc gcttccagtc tccagtccgg cgtgccctcc    180
agattctccg gcaatggctc tggcaccgac ttcaccctga ccatcaactc cctccagccc    240
gaggacttcg ccacctacta ctgtctccaa gacttcaact tccccttcac cttcggccct    300
ggcaccaccg tggacatcaa c                                              321
```

<210> SEQ ID NO 244
<211> LENGTH: 360
<212> TYPE: DNA
<213> ORGANISM: Artificial Sequence
<220> FEATURE:
<223> OTHER INFORMATION: Synthetic Construct

<400> SEQUENCE: 244

```
caggtgcagc tggtggagtc tgggggaggc gtggtccagt ctggggaggtc cctgagactc     60 tcctgtgcag cgtctggatt cacctccagt agttatggca tgcactgggt ccgccaggct    120
ccaggcaagg ggctggagtg ggtggcagtt atatggtatg atggaagtaa taaatactat    180
gcagactccg tgaaggaccg attcaccatc tccagagaca attccaagaa acgggtgtat    240
ctgcaaatga acagtctgag agccgaggac acggctgttt attactgtgc gagagaaggg    300
atggttcggg gagcccctct tgactactgg ggtcagggaa ccctggtcac cgtctcctca    360
```

<210> SEQ ID NO 245
<211> LENGTH: 324
<212> TYPE: DNA
<213> ORGANISM: Artificial Sequence
<220> FEATURE:
<223> OTHER INFORMATION: Synthetic Construct

<400> SEQUENCE: 245

| gaaattgtaa tgacacagtc tccagccacc ctgtctttgt ctccagggga aagagccacc | 60 |
| --- | --- |
| ctctcctgca gggccagtca gagtgttagc agcagctact tatcctggta ccaacagaaa | 120 |
| cctgggcagg ctcccaggct cctcatctat ggtgcatcca ccagggccac tggcatccca | 180 |
| gccaggttca gtggcagtgg gtctgggcca gacctcactc tcaccatcag cagcctgcag | 240 |
| cctgaagatt ttgcagttta ttactgtcag caggattata acttaccgta cacttttggc | 300 |
| caggggacca agctggagat caaa | 324 |

<210> SEQ ID NO 246
<211> LENGTH: 357
<212> TYPE: DNA
<213> ORGANISM: Artificial Sequence
<220> FEATURE:
<223> OTHER INFORMATION: Synthetic Construct

<400> SEQUENCE: 246

| gaggtgcagc tggtgcagtc tggagcagag gtgaaaaagc ccggggagtc tctgaagatc | 60 |
| --- | --- |
| tcctgtaagg gttctggata cagtttttact agttactgga tcggctgggt gcgccagatg | 120 |
| cccgggaaag gcctggagtg gatgggagtc atctatcctg gtgactctga taccagatat | 180 |
| agcccgtcct tccaaggcca ggtcaccatg tcagccgaca gtccatcag taccgcctac | 240 |
| ctgcagtgga gcagcctgaa ggcctcggac agcgccatgt attactgtgc gagacagcta | 300 |
| cgagactact acggtatgga cgtctggggc caagggacca cggtcaccgt ctcctca | 357 |

<210> SEQ ID NO 247
<211> LENGTH: 324
<212> TYPE: DNA
<213> ORGANISM: Artificial Sequence
<220> FEATURE:
<223> OTHER INFORMATION: Synthetic Construct

<400> SEQUENCE: 247

| gaaattgtaa tgacacagtc tccagccacc ctgtctttgt ctccagggga aagagccacc | 60 |
| --- | --- |
| ctctcctgca gggccagtca gactatcagc agcaactact tttcctggta ccagcagaaa | 120 |
| cctgggcagg ctcccaggct cctcatctat ggtgcatcca ccagggccac tggcattcca | 180 |
| gccaggttca gtggcagtgg gtctgagaca gacttcactc tcaccatcag cagcctgcag | 240 |
| cctgaagatt ttgcagttta ttactgtcag caggattata acttacctcg gacgttcggc | 300 |
| caagggacca aggtggaaat caaa | 324 |

<210> SEQ ID NO 248
<211> LENGTH: 357
<212> TYPE: DNA
<213> ORGANISM: Artificial Sequence
<220> FEATURE:
<223> OTHER INFORMATION: Synthetic Construct

<400> SEQUENCE: 248

| gaggtgcagc tggtgcagtc tggagcagag gtgaaaaagc ccggggagtc tctgaagatc | 60 |
| --- | --- |
| tcctgtaagg gttctggata cagctttacc agctactgga tcggctgggt gcgccagatg | 120 |
| cccgggaaag gcctggagtg gatgggatc atctatcctg gtgactctga taccagatac | 180 |
| agcccgtcct tccaaggcca ggtcaccatc tcagccgaca gtccatcag caccgcctac | 240 |
| ctgcactgga gcagcctgaa ggcctcggac accgccatgt attactgtgc gagacagcta | 300 | cgagactact acagtatgga cgtctggggc caagggacca cggtcaccgt ctcctca    357

<210> SEQ ID NO 249
<211> LENGTH: 324
<212> TYPE: DNA
<213> ORGANISM: Artificial Sequence
<220> FEATURE:
<223> OTHER INFORMATION: Synthetic Construct

<400> SEQUENCE: 249
gaaattgtaa tgacacagtc tccagccacc ctgtctttgt ctccagggga aagagccacc    60
ctctcctgca gggccagtca gagtgttagc agcagctact tatcctggta ccagcagaaa   120
cctgggcagg ctcccaggct cctcatctat ggtgcatcca ccagggccac tggcattgca   180
gccaggttca gtggcagtgg gtctgggaca gacttcactc tcaccatcag cagcctgcag   240
cctgaagatt ttgcagttta ttactgtcag caggattata acttacctcg gacgttcggc   300
caagggacca aggtggaaat caaa                                           324

<210> SEQ ID NO 250
<211> LENGTH: 342
<212> TYPE: DNA
<213> ORGANISM: Artificial Sequence
<220> FEATURE:
<223> OTHER INFORMATION: Synthetic Construct

<400> SEQUENCE: 250
gaggtgcagc tgcagcagag cggccctgag ctggtgaaac ctggcgccag cgtgaagatg    60
agctgcaagg ccagcggcta caccttcacc agctacaaca tccactgggt gaaacagaag   120
cccggccagg gcctggaatg gattggctac atcaacccct acaacgacgg caccaagtac   180
agcgagaagt tcaagggcaa ggccaccctg accagcgaca aagcagcag caccgcctac   240
atggaagtgt ccagcctgac ctccgaggac agcgccgtgt actactgcgc catctacggc   300
aacagctact ggggccaggg cagcaccctg accgtgtcca gc                      342

<210> SEQ ID NO 251
<211> LENGTH: 336
<212> TYPE: DNA
<213> ORGANISM: Artificial Sequence
<220> FEATURE:
<223> OTHER INFORMATION: Synthetic Construct

<400> SEQUENCE: 251
gacatcgtga tgacccaggc tgcccccagc atcccgtga cacctggcga gtccgtgtcc    60
atcagctgca aagcagcaa gagcctgctg cacagcaacg gcaataccta cctgtactgg   120
ttcctgcagc ggcctggcca gtcccccag cggctgatct actacatgag caacctggac   180
agcggcgtgc ccgaccggtt tagcggcaga ggcagcggca cagactttac cctgcggatc   240
agccgggtgg aagccgagga cgtgggcgtg tactattgca tgcagggcct ggaatacccc   300
tacacctttg gaggcggcac caagctggaa atcaag                              336

<210> SEQ ID NO 252
<211> LENGTH: 354
<212> TYPE: DNA
<213> ORGANISM: Artificial Sequence
<220> FEATURE:
<223> OTHER INFORMATION: Synthetic Construct

<400> SEQUENCE: 252
gacgtgatgc tggtcgagag cggcggagat ctggtcaaac ccgggggttc tctgaagctg    60

```
agttgtgccg cttcaggctt cacttttcct agttacacca tgagctgggt gcgacagacc    120
ccagagaagc ggctggaatg ggtcgctagc atctcaagcg gcggagggaa cacctactat    180
cccgactctg tgaaaggcag attcacaatt agtcgcgata atgcaaagaa caatctgtac    240
ctgcagatgt cctctctgag gtccgaagat actgccctgt actattgtgc tagatttgac    300
tatggaagtt cactggattc ttggggacag ggaccacac tgacagtgag ctcc           354

<210> SEQ ID NO 253
<211> LENGTH: 321
<212> TYPE: DNA
<213> ORGANISM: Artificial Sequence
<220> FEATURE:
<223> OTHER INFORMATION: Synthetic Construct

<400> SEQUENCE: 253
gacatcgtcc tgacccagag tcctgccacc ctgtctgtga caccaggcga ttctgtcagt     60
ctgtcatgta gagctagcca gtccatctct aacaatctgc actggtacca gcagaagtca    120
catgaaagcc ccagactgct gatcaagtat gccagtcagt caatcagcgg tattccttcc    180
cgcttctccg gctctggaag tgggacagac tttactctgt ccatcaactc tgtggagaca    240
gaagatttcg gcatgtattt tgtcagcag agcaagaatt ggcccaggac atttggcgga    300
gggactaagc tggagatcaa g                                              321

<210> SEQ ID NO 254
<211> LENGTH: 354
<212> TYPE: DNA
<213> ORGANISM: Artificial Sequence
<220> FEATURE:
<223> OTHER INFORMATION: Synthetic Construct

<400> SEQUENCE: 254
gaagtgatgc tggtcgaaag tggaggagga ctggtgaaac caggtggaag cctgaagctg     60
tcctgtgccg cttctggctt cacttttca agctatacca tgagctgggt gcgacagaca    120
cctgagaagc ggctggaatg ggtcgctaca atctcctctg gagggacaa cacttactat    180 ccagatagcg tgaaaggcag attcactatt tcccgcgaca atgcaaagaa caatctgtac    240
ctgcagatga gttcactgag gagcgaggat accgccctgt actattgcgc tagatttgac    300
tatggaagct ccctggattg ttggggacag ggaccacac tgaccgtgtc tagt           354

<210> SEQ ID NO 255
<211> LENGTH: 321
<212> TYPE: DNA
<213> ORGANISM: Artificial Sequence
<220> FEATURE:
<223> OTHER INFORMATION: Synthetic Construct

<400> SEQUENCE: 255
gacatcgtcc tgactcagag ccctgccacc ctgtccgtga caccaggcga ttcagtcagc     60
ctgtcctgta gacttctca gagtatctca aactacctgc actggtatca gcagaagagt    120
catgaatcac ccagactgct gatcaagtac gccagccagt ccatctctgg gattcctagc    180
cgcttcagtg gctcaggaag cgggacagac tttactctga gcatcaattc cgtggagaca    240
gaagatttcg gcatgtattt tgtcagcag tccaagtctt ggcccaggac atttggcgga    300
gggactgagc tggagatcaa g                                              321

<210> SEQ ID NO 256
```

```
<211> LENGTH: 360
<212> TYPE: DNA
<213> ORGANISM: Artificial Sequence
<220> FEATURE:
<223> OTHER INFORMATION: Synthetic Construct

<400> SEQUENCE: 256
gaggtgcaac tggtgcagtc tggagcagag gtgaaaaagc ccggggagtc tctgaagatc    60
tcctgtaagg gttctggata cagctttacc agctactgga tcggctgggt gcgccagatg   120
cccgggaaag gcctggagtg gatggggatc atctatcctg gtgactctga taccagatac   180
agcccgtcct tccaaggcca ggtcaccatc tcagccgaca gtccatcag caccgcctac    240 ctgcagtgga gcagcctgaa ggcctcggac accgccatgt attactgtgc gagacgcggg   300
tatcgcagca gctggtactt tgactactgg ggccagggaa ccctggtcac cgtctcctca   360

<210> SEQ ID NO 257
<211> LENGTH: 321
<212> TYPE: DNA
<213> ORGANISM: Artificial Sequence
<220> FEATURE:
<223> OTHER INFORMATION: Synthetic Construct

<400> SEQUENCE: 257
gccatccaga tgacccagtc tccatcctcc ctgtctgcat ctgtaggaga cagagtcacc    60
atcacttgcc gggcaagtca gggcattaga aatgatttag ctggtatca gcagaaacca   120 gggaaagccc ctaagctcct gatctatgct gcatccagtt tacaaagtgg ggtcccatca   180
aggttcagcg gcagtggatc aggcacagat ttcactttca ccatcagcag cctgcagcct   240
gaagattttg caacttatta ctgtctacaa gattacaatt acccgctcac tttcggcgga   300
gggaccaagg tggagatcaa a                                              321

<210> SEQ ID NO 258
<211> LENGTH: 354
<212> TYPE: DNA
<213> ORGANISM: Artificial Sequence
<220> FEATURE:
<223> OTHER INFORMATION: Synthetic Construct

<400> SEQUENCE: 258
gaggtgcagc tggtggagtc tgggggaggt gtggtacggc cggggggtc cctgagactc    60 tcctgtgcag cctctggatt cacctttgat gattatggca tgagctgggt ccgccaagct   120
ccagggaagg gctggagtg gtctctggt attaattgga atggtggtag cacaggttat    180
gcagactctg tgaagggccg attcaccatc tccagagaca cgccaagaa ctccctgtat    240 ctgcaaatga acagtctgag agccgaggac acggccttgt atcactgtgc gagagaaggg   300
ggggagctat taatggacta ttgggggccag ggaaccctgg tcaccgtctc ctca         354

<210> SEQ ID NO 259
<211> LENGTH: 321
<212> TYPE: DNA
<213> ORGANISM: Artificial Sequence
<220> FEATURE:
<223> OTHER INFORMATION: Synthetic Construct

<400> SEQUENCE: 259
gaaattgtgt tgacacagtc tccagccacc ctgtctttgt ctccagggga aagagccacc    60
ctctcctgca gggccagtca gagtgttagc acctacttag cctggtacca acagaaacct   120
ggccaggctc ccaggctcct catctatgat gcatccaaca gggccactgg catcccaccc   180
```
aggttcagtg gcagtgggtc tgggacagac ttcactctca ccatcagcag cctagagcct    240
gaagattttg cagtttatta ctgtcagcag cgtagcaact ggcctcctac tttcggcgga    300
gggaccacgg tggagatcaa a    321

<210> SEQ ID NO 260
<211> LENGTH: 375
<212> TYPE: DNA
<213> ORGANISM: Artificial Sequence
<220> FEATURE:
<223> OTHER INFORMATION: Synthetic Construct

<400> SEQUENCE: 260
gaagttcaat tgttagagtc tggtggcggt cttgttcagc ctggtggttc tttacgtctt    60
tcttgcgctg cttccggatt cactttctct cattactcta tggtttgggt tcgccaagct    120
cctggtaaag gtttggagtg ggtttcttat atctatcctt ctggtggcac ttcgtatgct    180
gactccgtta aaggtcgctt cactatctct agagacaact ctaagaatac tctctacttg    240
cagatgaaca gcttaagggc tgaggacacg ccgtgtatt actgtgcgag acattggcgg    300
gggtatagca gcagctggta ccaccggcg tactttgact actggggcca ggcaccctg    360 gtcaccgtct caagc    375

<210> SEQ ID NO 261
<211> LENGTH: 321
<212> TYPE: DNA
<213> ORGANISM: Artificial Sequence
<220> FEATURE:
<223> OTHER INFORMATION: Synthetic Construct

<400> SEQUENCE: 261
gacatccaga tgacccagtc tccagccacc ctgtctttgt ctccagggga aagagccacc    60
ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggcctctcac tttcggcgga    300
gggaccaagg tggagatcaa a    321

<210> SEQ ID NO 262
<211> LENGTH: 378
<212> TYPE: DNA
<213> ORGANISM: Artificial Sequence
<220> FEATURE:
<223> OTHER INFORMATION: Synthetic Construct

<400> SEQUENCE: 262
gaagttcaat tgttagagtc tggtggcggt cttgttcagc ctggtggttc tttacgtctt    60
tcttgcgctg cttccggatt cactttctct tggtaccta tgatgtgggt tcgccaagct    120
cctggtaaag gtttggagtg ggtttcttct atctatcctt ctggtggcac tactacttat    180
gctgactccg ttaaaggtcg cttcactatc tctagagaca actctaagaa tactctctac    240
ttgcagatga acagcttaag ggctgaggac acggccgtgt attactgtgc gaggtcgtat    300
tactatgata gtagtggtta ttactcacat gatgcttttg atatctgggg ccaagggaca    360
atggtcaccg tctcaagc    378

<210> SEQ ID NO 263

```
<211> LENGTH: 324
<212> TYPE: DNA
<213> ORGANISM: Artificial Sequence
<220> FEATURE:
<223> OTHER INFORMATION: Synthetic Construct

<400> SEQUENCE: 263
gacatccaga tgacccagtc tccatcctcc ctgtctgcat ctgtgggaga cagagtcgcc    60
atcacttgcc gcgcaagtca gagcatcgac acctatttaa attggtatca gcagaaacca   120
gggaaagccc ctaaactcct gatctatgct gcatccaagt tggaagacgg ggtcccatca   180
agattcagtg gcagtggaac tgggacagat ttcactctca ccatcagaag tctgcaacct   240
gaagattttg caagttattt ctgtcaacag agctactcta gtccagggat cactttcggc   300
cctgggacca aggtggagat caaa                                          324

<210> SEQ ID NO 264
<211> LENGTH: 366
<212> TYPE: DNA
<213> ORGANISM: Artificial Sequence
<220> FEATURE:
<223> OTHER INFORMATION: Synthetic Construct

<400> SEQUENCE: 264
gaagttcaat tgttagagtc tggtggcggt cttgttcagc ctggtggttc tttacgtctt    60
tcttgcgctg cttccggatt cactttctct gattacgaga tgcattgggt tcgccaagct   120
cctggtaaag gtttggagtg ggtttcttct atctggcctt ctggtggcct tactaagtat   180
gctgaccccg ttaaaggtcg cttcactatc tctagagaca actctaagaa tactctctac   240
ttgcagatga acagcttaag ggctgaggac acggccgtgt attactgtgc gagagattcc   300
tattactatg atagtagtgg tgctcttggc tactggggcc agggaaccct ggtcaccgtc   360
tcaagc                                                              366

<210> SEQ ID NO 265
<211> LENGTH: 321
<212> TYPE: DNA
<213> ORGANISM: Artificial Sequence
<220> FEATURE:
<223> OTHER INFORMATION: Synthetic Construct

<400> SEQUENCE: 265
gacatccaga tgacccagtc tccttccacc ctgtctgcat ctgtaggaga cagagtcacc    60
atcacttgcc gggccagtca gagtgttagt aactggttgg cctggtatca gcagaaacca   120
gggaaagccc ctaagctcct gatctataag gcgtctagtt tagaaagtgg ggtcccatcg   180
aggttcagcg gcagtggatc tgggacagaa ttcactctca ccatcagcag cctgcagcct   240
gatgattttg caacttatta ctgcctacag tatgtgagtt atcccctcac ttttggcgga   300
gggaccaagg tggacatcaa a                                             321

<210> SEQ ID NO 266
<211> LENGTH: 372
<212> TYPE: DNA
<213> ORGANISM: Artificial Sequence
<220> FEATURE:
<223> OTHER INFORMATION: Synthetic Construct

<400> SEQUENCE: 266
gaagttcaat tgttagagtc tggtggcggt cttgttcagc ctggtggttc tttacgtctt    60
tcttgcgctg cttccggatt cactttctct tattacgata tgtattgggt tcgccaagct   120
```

```
cctggtaaag gtttggagtg ggtttctcgt atctattctt ctggtggcca tacttggtat      180
gctgactccg ttaaaggtcg cttcactatc tctagagaca actctaagaa tactctctac      240
ttgcagatga acagcttaag ggctgaggac acggctgtgt attactgtgc gaggcccggg      300
tatagcagtg gctggtacga tggcacctac tttgactact ggggccaggg aaccctggtc      360
accgtctcaa gc                                                          372
```

<210> SEQ ID NO 267
<211> LENGTH: 321
<212> TYPE: DNA
<213> ORGANISM: Artificial Sequence
<220> FEATURE:
<223> OTHER INFORMATION: Synthetic Construct

<400> SEQUENCE: 267

```
gacatccaga tgacccagtc tccttccacc ctgtctgcat ctgttggcga cagagtcacc      60
attacttgtc gggccagtca gagtattgat acttggctgg cctggtatcg cagaaaacca     120
gggaaagccc ctaatgtcgt aattcattcc gcgtctactt tacaaagtgg cgtccccgca     180
aggttcagcg gcagtggatt tgggacagaa tggactctca ctatcaccaa cctgcagcct     240
gatgattttg ccacctatta ttgccaacaa tataagactt atccgttcac ttttggccag     300
gggacgaagc tggagatcaa g                                               321
```

<210> SEQ ID NO 268
<211> LENGTH: 357
<212> TYPE: DNA
<213> ORGANISM: Artificial Sequence
<220> FEATURE:
<223> OTHER INFORMATION: Synthetic Construct

<400> SEQUENCE: 268

```
gaagttcaat tgttagagtc tggtggcggt cttgttcagc ctggtggttc tttacgtctt      60
tcttgcgctg cttccggatt cactttctct cattaccaga tggagtgggt tcgccaagct     120
cctggtaaag gtttggagtg ggtttcttct atctctcctt ctggtggctt tacttcttat     180
gctgactccg ttaaaggtcg cttcactatc tctagagaca actctaagaa tactctctac     240
ttgcagatga acagcttaag ggctgaggac acagccgtgt attactgtac gagagagccg     300 ggggaggttgt gggcttttga tatctggggc caagggacaa tggtcaccgt ctcaagc       357
```

<210> SEQ ID NO 269
<211> LENGTH: 321
<212> TYPE: DNA
<213> ORGANISM: Artificial Sequence
<220> FEATURE:
<223> OTHER INFORMATION: Synthetic Construct

<400> SEQUENCE: 269

```
gacatccaga tgacccagtc tccatctttc gtgtctgcat ctgtcggaga cagagtcacc      60
atcacttgcc gggcgagtca ggatattcgt aattggctag cctggtatca acaggagtcc     120
gggaaagccc ctcggctcct gatctctgct gcatccagta ggcacagtgg cgtctcatct     180
agattcagcg gcagtggatc tgggacagac ttcaccctca ccatcaccag tctgcagcct     240
gaagattcag caacttattt ttgtcaacag gctgacagtt cccctcggac gttcggccaa     300
gggaccaagg tggaaatcaa a                                               321
```

<210> SEQ ID NO 270

```
<211> LENGTH: 345
<212> TYPE: DNA
<213> ORGANISM: Artificial Sequence
<220> FEATURE:
<223> OTHER INFORMATION: Synthetic Construct

<400> SEQUENCE: 270
caggtgcaac tggtgcagtc tggggctgag gtgaagaagc ctggggcctc agtgaaggtc      60
tcctgcaagg cttctggata caccttcacc ggctactata tgcactgggt gcgacaggcc     120
cctggacaag ggcttgagtg gatgggatgg atcaaccctg acagtggtgg cacaaactat     180
gcacagaagt ttcagggcag ggtcaccatg accaggggaca cgtccatcaa cacagcctac     240
atggaactga gcaggctgag atctgacgac acggccgtgt attactgtgc ggtctttggt     300
tcggggagtt cttggggcca gggaaccctg gtcaccgtct cctca                    345

<210> SEQ ID NO 271
<211> LENGTH: 321
<212> TYPE: DNA
<213> ORGANISM: Artificial Sequence
<220> FEATURE:
<223> OTHER INFORMATION: Synthetic Construct

<400> SEQUENCE: 271
gacatccaga tgacccagtc tccatcctca ctgtctgcat ctgtgggaga cagagtcacc      60
atcacttgtc gggcgagtca gggtattagc aattctttag cctggtttca gcagaaacca     120
gggaaagccc ctaagtccct gatctatgct gcatccagtt tgcaaagtgg ggtcccatca     180
aagttcagcg gcagtggatc tgggacagat ttcactctca ccatcagcag cctgcagcct     240
gaagattttg caacttatta ctgccaacaa tataagagtt acccgtacac atttggccag     300
gggaccaagc tggagatcaa a                                              321

<210> SEQ ID NO 272
<211> LENGTH: 345
<212> TYPE: DNA
<213> ORGANISM: Artificial Sequence
<220> FEATURE:
<223> OTHER INFORMATION: Synthetic Construct

<400> SEQUENCE: 272
caggtgcagc tggtgcagtc tggggctgag gtgaagaagc ctggggcctc agtgaaggtc      60
tcctgcaagg cttctggaaa caccttcacc ggctactata tacactgggt tcgacaggcc     120
cctggacaag ggcttgagtg gatgggatgg attaaaccta gtactggtga cacaaactat     180
gcacagaatt ttctggacag ggtcaccatg accagggaca cgtccatcag cacagcctac     240
atggaactca gcaggctgag atctgacgac acggccgtgt attactgtgc ggtctttggt     300
tcggggagtt cttggggcca gggaaccctg gtcaccgtct cctca                    345

<210> SEQ ID NO 273
<211> LENGTH: 321
<212> TYPE: DNA
<213> ORGANISM: Artificial Sequence
<220> FEATURE:
<223> OTHER INFORMATION: Synthetic Construct

<400> SEQUENCE: 273
gacatccaca tgacccagtc tccatcctca ctgtctgcat ttgtaggaga cagagtcacc      60
atcacttgtc gggcgagtca ggcattagc aattatttag cctggtttca gcagaaacca     120
gggaaagccc ctaagtccct gatctatgct gcatccagtt tgcaaagtgg ggtcccatca     180
```

```
aagttcagcg gcagtggatc tgggacagat ttcactctca ccatcaacaa cctgcagcct    240
gaagattttg caacttatta ctgccaacag tataagactt acccgtacac atttggccag    300
gggaccaagc tggagatcaa a                                              321
```

<210> SEQ ID NO 274
<211> LENGTH: 372
<212> TYPE: DNA
<213> ORGANISM: Artificial Sequence
<220> FEATURE:
<223> OTHER INFORMATION: Synthetic Construct

<400> SEQUENCE: 274

```
caggtgcagc tggtggagtc tgggggaggc gtggtccagc ctgggaggtc cctgagactc     60
tcctgtgcag cgtctggatt caccttcagt agctatggca tgcactgggt ccgccaggct    120
ccaggcaagg ggctggagtg ggtggcagtt atatggtatg atggaagtaa taaatactat    180
gcagactccg tgaagggccg attcaccatc tccagagaca attccaagaa cacgctgtat    240
ctgcaaatga acagtctgag agccgaggac gcggctgtgt attactgtgc gagagaaggt    300
ggctggtacg gcggggacta ctactacggt atggacgtct ggggccaagg gaccacggtc    360
accgtctcct ca                                                        372
```

<210> SEQ ID NO 275
<211> LENGTH: 321
<212> TYPE: DNA
<213> ORGANISM: Artificial Sequence
<220> FEATURE:
<223> OTHER INFORMATION: Synthetic Construct

<400> SEQUENCE: 275

```
gccatccagt tgacccagtc tccatcctcc ctgtctgcat ctgtaggaga cagagtcacc     60
atcacttgcc gggcaagtca gggcattagc agtgctttag cctggtatca gcagaaacca    120
gggaaagctc ctaagctcct gatctatgat gcctccagtt tggaaagtgg ggtcccatca    180
aggttcagcg gcagtggatc tgggacagat ttcactctca ccatcagcag cctgcagcct    240
gaagattttg caacttatta ctgtcatcag tttaataatt acccattcac tttcggccct    300
gggaccaaag tggatatcaa a                                              321
```

<210> SEQ ID NO 276
<211> LENGTH: 366
<212> TYPE: DNA
<213> ORGANISM: Artificial Sequence
<220> FEATURE:
<223> OTHER INFORMATION: Synthetic Construct

<400> SEQUENCE: 276

```
gaagtgcagc tgctggaatc tggcggcgga ctggtgcagc ctggcggatc tctgagactg     60
tcctgtgtgg cctccggctt caccttctcc agctacgcca tgtcctgggt gcgacaggct    120
cctggcaagg gcctggaatg ggtgtccggc atctctggca ggggcggctc tcctaactac    180
gccgactctg tgaagggccg gttcaccatc tcccgggaca actccaagaa cacactgtac    240
ctccagatga actccctgcg ggccgaggac accgccgtgt actactgtgc taaggacggc    300
gacggctccg gccctcccta ctactttgat tactggggcc agggcaccct cgtgaccgtg    360
tcatct                                                               366
```

<210> SEQ ID NO 277

```
<211> LENGTH: 321
<212> TYPE: DNA
<213> ORGANISM: Artificial Sequence
<220> FEATURE:
<223> OTHER INFORMATION: Synthetic Construct

<400> SEQUENCE: 277
gacatccaga tgacccagtc cccctccagc ctgtctgcct ctgtgggcga cagagtgacc      60
atcacctgtc gggcctccca gggcatctct tcttggctgg cctggtatca gcagaagccc    120
gagaaggccc ccaagtccct gatctacgcc gccagctctc tccagtctgg cgtgccctcc    180
agattctccg gctctggctc tggcaccgac tttacccctga ccatcagctc cctccagccc    240
gaggacttcg ccacctacta ctgccagcag tacaactcct accctacac cttcggccag      300 ggcaccaagc tggaaatcaa g                                                321

<210> SEQ ID NO 278
<211> LENGTH: 393
<212> TYPE: DNA
<213> ORGANISM: Artificial Sequence
<220> FEATURE:
<223> OTHER INFORMATION: Synthetic Construct

<400> SEQUENCE: 278
caggtgcagc tgatggagtc tggggggaggc gtggtccagc ctgggaggtc cctgagactc     60
tcctgtgcag cgtctggatt caccttcagt ggctatggca tgcactgggt ccgccaggct    120
ccagggaagg gctggagtg gtggcagtt atatggtctg atggaagtaa tagatactat       180
acagactccg tgaagggccg attcaccatc tccagagaca attccaagaa cacgctgtct    240
ctgcaaatga acagcctgag agccgaggac acggctgtgt attactgtgc gagagatagg    300
gggattacta tggttcgggg acttattata aatactact actactacgg tttggacgtc    360
tggggccaag ggacctcggt caccgtctcc tca                                  393

<210> SEQ ID NO 279
<211> LENGTH: 318
<212> TYPE: DNA
<213> ORGANISM: Artificial Sequence
<220> FEATURE:
<223> OTHER INFORMATION: Synthetic Construct

<400> SEQUENCE: 279
gaaattgtgt tgacacagtc tccagccacc ctgtctttgt ctccagggga aagagccacc     60
ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggtggacgtt cggccaaggg    300
accaaggtgg aaatcaaa                                                   318

<210> SEQ ID NO 280
<211> LENGTH: 360
<212> TYPE: DNA
<213> ORGANISM: Artificial Sequence
<220> FEATURE:
<223> OTHER INFORMATION: Synthetic Construct

<400> SEQUENCE: 280
caggtgcagc tggtggagtc tgggggaggc gtggtccagc ctgggaggtc cctgagactc     60
tcctgtgcag cgtctggatt caccttcagt agctttggca tgcactgggt ccgccaggct    120
```

```
ccaggcaagg ggctggagtg ggtggcagtt atatactatg atggaagtaa taaatactat    180
gcagactccg tgaagggccg attcaccatc tccagagaca attccaagaa cacgctgtat    240
ctgcaaatga acagcctgag agccgaggac acggctgtgt attactgtgc gagagatgac    300
aactggaacg acggggactt tgactactgg ggccagggaa ccctggtcac cgtctcctca    360

<210> SEQ ID NO 281
<211> LENGTH: 321
<212> TYPE: DNA
<213> ORGANISM: Artificial Sequence
<220> FEATURE:
<223> OTHER INFORMATION: Synthetic Construct

<400> SEQUENCE: 281
gacatccagt tgacccagtc tccatccttc ctgtctgcat ctgtaggaga cagagtcacc     60
atcacttgcc gggccagtca gggcattagt agttatttag cctggtatca gcaaaaacca    120
gggaaagccc ctaagctcct gatctatgct gcatccactt tgcaaagtgg ggtcccatca    180
aggttcagcg gcagtggatc tgggacagaa ttcactctca caatcagcag cctgcagcct    240
gaagattttg caacttatta ctgtcaacag cttaatagtt accctcggac gttcggccaa    300
gggaccaagg tggaaatcaa a                                              321

<210> SEQ ID NO 282
<211> LENGTH: 378
<212> TYPE: DNA
<213> ORGANISM: Artificial Sequence
<220> FEATURE:
<223> OTHER INFORMATION: Synthetic Construct

<400> SEQUENCE: 282
gaggtgcagc tgttggagtc tgggggaggc ttggtacagc ctggggagtc cctgagactc     60
tcctgtgcag cctctggatt cacctttaac agatttgtca tgagttgggt ccgccaggct    120
ccagggaagg ggctggagtg ggtctcaact attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gaaagatttt    300
acgtattact atggttcggg gaattattat aactggttcg accccagggg ccagggaacc    360
ctggtcaccg tctcctca                                                  378

<210> SEQ ID NO 283
<211> LENGTH: 321
<212> TYPE: DNA
<213> ORGANISM: Artificial Sequence
<220> FEATURE:
<223> OTHER INFORMATION: Synthetic Construct

<400> SEQUENCE: 283
gacatccaga tgacccagtc tccttccacc ctgtctacat ctgtaggaga cagagtcacc     60
atcacttgcc gggccagtca gagtattagt agctggttgg cctggtatca gcagaaacca    120
gggaaagccc ctaagctcct gatctataag cgtctagtt tagaaagtgg ggtcccatca    180
aggttcagcg gcagtggatc tgggacagaa ttcactctca ccatcagcag cctgcagcct    240
gatgattttg caacttatta ctgccaacag tataatagtt attctcggac gttcggccaa    300
gggaccaagg tggaaatcaa a                                              321

<210> SEQ ID NO 284
```

<211> LENGTH: 363
<212> TYPE: DNA
<213> ORGANISM: Artificial Sequence
<220> FEATURE:
<223> OTHER INFORMATION: Synthetic Construct

<400> SEQUENCE: 284

| | | |
|---|---|---|
| caggtgcagc tacagcagtg gggcgcagga ctgttgaagc cttcggagac cctgtccctc | 60 |
| acctgcgctg tctatggtgg gtcctttagt ggttactact ggagctggat ccgccagccc | 120 |
| ccagggaagg ggctggagtg gattggggaa atcaatcata gtggaggcac caactacaac | 180 |
| ccgtccctca agagtcgagt caccatatca gtagacacgt ccaagaacca cttctccctg | 240 |
| aagctgagct ctgtgaccgc cgcggacacg gctgtgtatt actgtgcgag aactagtgac | 300 |
| tacgattact actactacgg tatggacgtc tggggccaag gaccacggt caccgtctcc | 360 |
| tca | 363 |

<210> SEQ ID NO 285
<211> LENGTH: 348
<212> TYPE: DNA
<213> ORGANISM: Artificial Sequence
<220> FEATURE:
<223> OTHER INFORMATION: Synthetic Construct

<400> SEQUENCE: 285

| | | |
|---|---|---|
| cagcctgtgc tgactcagcc aacttccctc tcagcatctc ctggagcatc agccagactc | 60 |
| acctgcacct tgcgcagtgg catcaatctt ggtcgctaca ggatattctg gtaccagcag | 120 |
| aagccagaga gccctccccg gtatctcctg agctactact cagactcaag taagcatcag | 180 |
| ggctctggag tccccagccg cttctctgga tccaaagatg cttcgagcaa tgcagggatt | 240 |
| ttagtcatct ctgggctcca gtctgaggat gaggctgact attactgtat gatttggcac | 300 |
| aggagtgctt tgtttatttt cggcagtgga accaaggtca ctgtccta | 348 |

<210> SEQ ID NO 286
<211> LENGTH: 345
<212> TYPE: DNA
<213> ORGANISM: Artificial Sequence
<220> FEATURE:
<223> OTHER INFORMATION: Synthetic Construct

<400> SEQUENCE: 286

| | | |
|---|---|---|
| caggttcagc tacagcagtc tggacctgag ctggtgaagc ctggggcttc agtgaagttg | 60 |
| tcctgcaagg cttctggtta caccttcaca agctacgaga taaactggtt gaagcagagg | 120 |
| cctggacagg gacttgagtg gattggattg atttatccta gagatggaga tactaagtac | 180 |
| aatgagaagt tcaagggcaa ggccacattg actgcagaca catcctccag cacagcgtac | 240 |
| atggagctcc acagcctgac atctgaggac tctgcggtct atttctgtgc aagacacacc | 300 |
| ccaggggctt tctggggcca agggactctg gtcactgtct ctgca | 345 |

<210> SEQ ID NO 287
<211> LENGTH: 336
<212> TYPE: DNA
<213> ORGANISM: Artificial Sequence
<220> FEATURE:
<223> OTHER INFORMATION: Synthetic Construct

<400> SEQUENCE: 287

| | | |
|---|---|---|
| gatgttgtga tgacccaaac tcccctctcc ctgccggtca gtcttggaga tcaagcctcc | 60 |
| atctcttgca gatctagtca gagccttgtt cacagtaatg gagacaccta tttacattgg | 120 |

```
tacctacaga agccaggcca gtctccaaag ctcctgatct acaaagtttc aaccgattt    180 tctggggtcc cagacaggtt cagtggcagt ggatcaggga cagatttcac actcaagatc    240
agcagagtgg aggctgagga tctggaaatt tatttctgct ctcaaagcac acatgttccg    300
tacacgttcg gaggggggac caaactggaa ataaaa                               336
```

<210> SEQ ID NO 288
<211> LENGTH: 372
<212> TYPE: DNA
<213> ORGANISM: Artificial Sequence
<220> FEATURE:
<223> OTHER INFORMATION: Synthetic Construct

<400> SEQUENCE: 288

```
gacgtgaagc tggtggagtc tggggaaggc ttagtgaagc ccggagggtc cctgaaactc    60
tcttgtgcag cctctggatt cactttcagt aggtatgcca tgtcttgggt tcgccagact   120
ccagaaaaga ggctggaatg ggtcgcatat attagtagtg aggtgatta catccactat    180 ggagaaactg tgaagggccg attcaccatc tccagagaca atgccaggaa caccctgtac    240
ctgcaaatga gcagtctgaa gtctgaggac acagccatgt attactgtac aagagttctc    300
ttttattatt acggcagtag ctacgtcttt tttgactact ggggccaagg caccactctc    360
acagtctcct ca                                                         372
```

<210> SEQ ID NO 289
<211> LENGTH: 321
<212> TYPE: DNA
<213> ORGANISM: Artificial Sequence
<220> FEATURE:
<223> OTHER INFORMATION: Synthetic Construct

<400> SEQUENCE: 289

```
gatatccaga tgacacagac tacatcctcc ctgtcagtct ctctgggaga cagagtcacc    60
atcagttgca gggcaagtca ggacatcagc aattttctaa actggtatca gcagaaacca    120
gatggaactg ttaatctcct gatctactac acatcaaaat tacactcagg agtcccatca    180
aggttcagtg gcggtgggtc tggaagagat tattctctca ccattaataa cctggagcaa    240
gaagatattg cctcttactt ttgccaacag ggtcatacgc ttccgtatac gttcggaggg    300
gggaccaagc tggaaataaa a                                               321
```

<210> SEQ ID NO 290
<211> LENGTH: 95
<212> TYPE: PRT
<213> ORGANISM: Artificial Sequence
<220> FEATURE:
<223> OTHER INFORMATION: Synthetic Construct

<400> SEQUENCE: 290

```
Ser Ile Val Val Glu Trp Thr Asn Asn Thr Leu Pro Leu Glu Pro Cys
  1               5                  10                  15

Pro Lys Glu Gln Ile Ile Gly Leu Ser Arg Arg Ile Ala Asp Glu Asn
                 20                  25                  30

Gly Lys Pro Arg Pro Ala Phe Ser Asn Ala Leu Glu Pro Asp Phe Lys
             35                  40                  45

Ala Leu Ser Ile Ala Val Thr Gly Ser Gly Ser Cys Arg His Leu Gln
         50                  55                  60

Phe Ile Pro Val Ala Pro Pro Ser Pro Gly Ser Ser Ala Ala Pro Ala
 65                  70                  75                  80
```

Thr Glu Val Pro Asp Arg Asp Pro Glu Lys Ser Ser Glu Asp Asp
            85                  90                  95

<210> SEQ ID NO 291
<211> LENGTH: 96
<212> TYPE: PRT
<213> ORGANISM: Artificial Sequence
<220> FEATURE:
<223> OTHER INFORMATION: Synthetic Construct

<400> SEQUENCE: 291

Ser Ile Val Val Glu Trp Thr Asn Asn Thr Leu Pro Leu Glu Pro Cys
1               5                   10                  15

Pro Lys Glu Gln Ile Ala Gly Leu Ser Arg Arg Ile Ala Glu Asp Asp
            20                  25                  30

Gly Lys Pro Arg Pro Ala Phe Ser Asn Ala Leu Glu Pro Asp Phe Lys
        35                  40                  45

Ala Thr Ser Ile Thr Val Thr Gly Ser Gly Ser Cys Arg His Leu Gln
    50                  55                  60

Phe Ile Pro Val Val Pro Pro Arg Arg Val Pro Ser Glu Ala Pro Pro
65                  70                  75                  80

Thr Glu Val Pro Asp Arg Asp Pro Glu Lys Ser Ser Glu Asp Asp Val
                85                  90                  95

<210> SEQ ID NO 292
<211> LENGTH: 183
<212> TYPE: PRT
<213> ORGANISM: Artificial Sequence
<220> FEATURE:
<223> OTHER INFORMATION: Synthetic Construct

<400> SEQUENCE: 292

Ala Asn Ala Glu Ser Gly Thr Tyr Phe Asp Gly Thr Gly Phe Ala Lys
1               5                   10                  15

Ala Val Gly Gly Phe Lys Val Gly Leu Asp Leu Leu Val Glu Phe Glu
            20                  25                  30

Phe Arg Thr Trp Thr Gly Val Leu Leu Gly Val Ser Ser Gln Lys Met
        35                  40                  45

Asp Gly Met Gly Ile Glu Met Ile Asp Glu Lys Leu Met Phe His Val
    50                  55                  60

Asp Asn Gly Ala Gly Arg Phe Thr Ala Ile Tyr Asp Ala Gly Ile Pro
65                  70                  75                  80

Gly His Met Cys Asn Gly Gln Trp His Lys Val Thr Ala Lys Lys Ile
                85                  90                  95

Lys Asn Arg Leu Glu Leu Val Val Asp Gly Asn Gln Val Asp Ala Gln
            100                 105                 110

Ser Pro Asn Ser Ala Ser Thr Ser Ala Asp Thr Asn Asp Pro Val Phe
        115                 120                 125

Val Gly Gly Phe Pro Gly Gln Gln Phe Gly Leu Thr Thr Asn Ile Arg
    130                 135                 140

Phe Arg Gly Cys Ile Arg Ser Leu Lys Leu Thr Lys Gly Thr Gly Lys
145                 150                 155                 160

Pro Leu Glu Val Asn Phe Ala Lys Ala Leu Glu Leu Arg Gly Val Gln
                165                 170                 175

Pro Val Ser Cys Pro Thr Thr
            180

```
<210> SEQ ID NO 293
<211> LENGTH: 187
<212> TYPE: PRT
<213> ORGANISM: Artificial Sequence
<220> FEATURE:
<223> OTHER INFORMATION: Synthetic Construct

<400> SEQUENCE: 293

Ala Asn Ala Gln Arg Gly Thr Tyr Phe Asp Gly Thr Gly Phe Ala Lys
1               5                   10                  15

Ala Val Gly Gly Phe Lys Val Gly Leu Asp Leu Leu Val Glu Phe Glu
            20                  25                  30

Phe Arg Thr Thr Thr Thr Thr Gly Val Leu Leu Gly Ile Ser Ser Gln
        35                  40                  45

Lys Met Asp Gly Met Gly Ile Glu Met Ile Asp Glu Lys Leu Met Phe
    50                  55                  60

His Val Asp Asn Gly Ala Gly Arg Phe Thr Ala Val Tyr Asp Ala Gly
65                  70                  75                  80

Val Pro Gly His Leu Cys Asp Gly Gln Trp His Lys Val Thr Ala Asn
                85                  90                  95

Lys Ile Lys His Arg Ile Glu Leu Thr Val Asp Gly Asn Gln Val Glu
            100                 105                 110

Ala Gln Ser Pro Asn Pro Ala Ser Thr Ser Ala Asp Thr Asn Asp Pro
        115                 120                 125

Val Phe Val Gly Gly Phe Pro Asp Asp Leu Lys Gln Phe Gly Leu Thr
    130                 135                 140

Thr Ser Ile Pro Phe Arg Gly Cys Ile Arg Ser Leu Lys Leu Thr Lys
145                 150                 155                 160

Gly Thr Gly Lys Pro Leu Glu Val Asn Phe Ala Lys Ala Leu Glu Leu
                165                 170                 175

Arg Gly Val Gln Pro Val Ser Cys Pro Ala Asn
            180                 185

<210> SEQ ID NO 294
<211> LENGTH: 10
<212> TYPE: PRT
<213> ORGANISM: Artificial Sequence
<220> FEATURE:
<223> OTHER INFORMATION: Synthetic Construct

<400> SEQUENCE: 294

Gly Gly Gly Gly Ser Gly Gly Gly Gly Ser
1               5                   10

<210> SEQ ID NO 295
<211> LENGTH: 20
<212> TYPE: PRT
<213> ORGANISM: Artificial Sequence
<220> FEATURE:
<223> OTHER INFORMATION: Synthetic Construct

<400> SEQUENCE: 295

Gly Phe Ala Lys Ala Val Gly Gly Phe Lys Val Gly Leu Asp Leu Leu
1               5                   10                  15

Val Glu Phe Glu
            20

<210> SEQ ID NO 296
<211> LENGTH: 14
<212> TYPE: PRT
<213> ORGANISM: Artificial Sequence
```

```
<220> FEATURE:
<223> OTHER INFORMATION: Synthetic Construct

<400> SEQUENCE: 296

Glu Pro Lys Ser Asp Lys Thr His Thr Ser Pro Pro Ser Pro
1               5                   10

<210> SEQ ID NO 297
<211> LENGTH: 7
<212> TYPE: PRT
<213> ORGANISM: Artificial Sequence
<220> FEATURE:
<223> OTHER INFORMATION: Synthetic Construct

<400> SEQUENCE: 297

Gly Gln Pro Lys Ala Ala Pro
1               5

<210> SEQ ID NO 298
<211> LENGTH: 5
<212> TYPE: PRT
<213> ORGANISM: Artificial Sequence
<220> FEATURE:
<223> OTHER INFORMATION: Synthetic Construct

<400> SEQUENCE: 298

Thr Lys Gly Pro Ser
1               5

<210> SEQ ID NO 299
<211> LENGTH: 10
<212> TYPE: PRT
<213> ORGANISM: Artificial Sequence
<220> FEATURE:
<223> OTHER INFORMATION: Synthetic Construct

<400> SEQUENCE: 299

Gly Gly Ser Gly Ser Ser Gly Ser Gly Gly
1               5                   10

<210> SEQ ID NO 300
<211> LENGTH: 390
<212> TYPE: PRT
<213> ORGANISM: Artificial Sequence
<220> FEATURE:
<223> OTHER INFORMATION: Synthetic Construct

<400> SEQUENCE: 300

Val Gln Pro Gln Pro Val Pro Thr Pro Ala Phe Pro Phe Pro Ala Pro
1               5                   10                  15

Thr Met Val His Gly Pro Cys Val Ala Glu Ser Glu Pro Ala Leu Leu
                20                  25                  30

Thr Gly Ser Lys Gln Phe Gly Leu Ser Arg Asn Ser His Ile Ala Ile
            35                  40                  45

Ala Phe Asp Asp Thr Lys Val Lys Asn Arg Leu Thr Ile Glu Leu Glu
        50                  55                  60

Val Arg Thr Glu Ala Glu Ser Gly Leu Leu Phe Tyr Met Ala Arg Ile
65                  70                  75                  80

Asn His Ala Asp Phe Ala Thr Val Gln Leu Arg Asn Gly Phe Pro Tyr
                85                  90                  95

Phe Ser Tyr Asp Leu Gly Ser Gly Asp Thr Ser Thr Met Ile Pro Thr
            100                 105                 110

Lys Ile Asn Asp Gly Gln Trp His Lys Ile Lys Ile Val Arg Val Lys
```

115                 120                 125
Gln Glu Gly Ile Leu Tyr Val Asp Asp Ala Ser Ser Gln Thr Ile Ser
            130                 135                 140

Pro Lys Lys Ala Asp Ile Leu Asp Val Val Gly Ile Leu Tyr Val Gly
145                 150                 155                 160

Gly Leu Pro Ile Asn Tyr Thr Thr Arg Arg Ile Gly Pro Val Thr Tyr
                165                 170                 175

Ser Leu Asp Gly Cys Val Arg Asn Leu His Met Glu Gln Ala Pro Val
            180                 185                 190

Asp Leu Asp Gln Pro Thr Ser Ser Phe His Val Gly Thr Cys Phe Ala
            195                 200                 205

Asn Ala Glu Ser Gly Thr Tyr Phe Asp Gly Thr Gly Phe Ala Lys Ala
        210                 215                 220

Val Gly Gly Phe Lys Val Gly Leu Asp Leu Leu Val Glu Phe Glu Phe
225                 230                 235                 240

Arg Thr Trp Thr Gly Val Leu Leu Gly Val Ser Ser Gln Lys Met Asp
                245                 250                 255

Gly Met Gly Ile Glu Met Ile Asp Glu Lys Leu Met Phe His Val Asp
            260                 265                 270

Asn Gly Ala Gly Arg Phe Thr Ala Ile Tyr Asp Ala Gly Ile Pro Gly
        275                 280                 285

His Met Cys Asn Gly Gln Trp His Lys Val Thr Ala Lys Ile Lys
            290                 295                 300

Asn Arg Leu Glu Leu Val Val Asp Gly Asn Gln Val Asp Ala Gln Ser
305                 310                 315                 320

Pro Asn Ser Ala Ser Thr Ser Ala Asp Thr Asn Asp Pro Val Phe Val
                325                 330                 335

Gly Gly Phe Pro Gly Gln Gln Phe Gly Leu Thr Thr Asn Ile Arg Phe
            340                 345                 350

Arg Gly Cys Ile Arg Ser Leu Lys Leu Thr Lys Gly Thr Gly Lys Pro
        355                 360                 365

Leu Glu Val Asn Phe Ala Lys Ala Leu Glu Leu Arg Gly Val Gln Pro
    370                 375                 380

Val Ser Cys Pro Thr Thr
385                 390

<210> SEQ ID NO 301
<211> LENGTH: 391
<212> TYPE: PRT
<213> ORGANISM: Artificial Sequence
<220> FEATURE:
<223> OTHER INFORMATION: Synthetic Construct

<400> SEQUENCE: 301

Gln Pro Glu Pro Val Pro Thr Pro Ala Phe Pro Thr Pro Thr Pro Val
1               5                   10                  15

Leu Thr His Gly Pro Cys Ala Ala Glu Ser Glu Pro Ala Leu Leu Ile
            20                  25                  30

Gly Ser Lys Gln Phe Gly Leu Ser Arg Asn Ser His Ile Ala Ile Ala
        35                  40                  45

Phe Asp Asp Thr Lys Val Lys Asn Arg Leu Thr Ile Glu Leu Glu Val
    50                  55                  60

Arg Thr Glu Ala Glu Ser Gly Leu Leu Phe Tyr Met Ala Arg Ile Asn
65                  70                  75                  80

His Ala Asp Phe Ala Thr Val Gln Leu Arg Asn Gly Leu Pro Tyr Phe

```
                     85                  90                  95
Ser Tyr Asp Leu Gly Ser Gly Asp Thr His Thr Met Ile Pro Thr Lys
                100                 105                 110

Ile Asn Asp Gly Gln Trp His Lys Ile Lys Ile Met Arg Ser Lys Gln
            115                 120                 125

Glu Gly Ile Leu Tyr Val Asp Gly Asn Arg Thr Ile Ser Pro Lys Lys
        130                 135                 140

Ala Asp Ile Leu Asp Val Val Gly Met Leu Tyr Val Gly Gly Leu Pro
145                 150                 155                 160

Ile Asn Tyr Thr Thr Arg Arg Ile Gly Pro Val Thr Tyr Ser Ile Asp
                165                 170                 175

Gly Cys Val Arg Asn Leu His Met Ala Glu Ala Pro Ala Asp Leu Glu
            180                 185                 190

Gln Pro Thr Ser Ser Phe His Val Gly Thr Cys Phe Ala Asn Ala Gln
        195                 200                 205

Arg Gly Thr Tyr Phe Asp Gly Thr Gly Phe Ala Lys Ala Val Gly Gly
    210                 215                 220

Phe Lys Val Gly Leu Asp Leu Leu Val Glu Phe Glu Phe Arg Thr Thr
225                 230                 235                 240

Thr Thr Thr Gly Val Leu Leu Gly Ile Ser Ser Gln Lys Met Asp Gly
                245                 250                 255

Met Gly Ile Glu Met Ile Asp Glu Lys Leu Met Phe His Val Asp Asn
            260                 265                 270

Gly Ala Gly Arg Phe Thr Ala Val Tyr Asp Ala Gly Val Pro Gly His
        275                 280                 285

Leu Cys Asp Gly Gln Trp His Lys Val Thr Ala Asn Lys Ile Lys His
    290                 295                 300

Arg Ile Glu Leu Thr Val Asp Gly Asn Gln Val Glu Ala Gln Ser Pro
305                 310                 315                 320

Asn Pro Ala Ser Thr Ser Ala Asp Thr Asn Asp Pro Val Phe Val Gly
                325                 330                 335

Gly Phe Pro Asp Asp Leu Lys Gln Phe Gly Leu Thr Thr Ser Ile Pro
            340                 345                 350

Phe Arg Gly Cys Ile Arg Ser Leu Lys Leu Thr Lys Gly Thr Gly Lys
        355                 360                 365

Pro Leu Glu Val Asn Phe Ala Lys Ala Leu Glu Leu Arg Gly Val Gln
    370                 375                 380

Pro Val Ser Cys Pro Ala Asn
385                 390

<210> SEQ ID NO 302
<211> LENGTH: 11
<212> TYPE: PRT
<213> ORGANISM: Artificial Sequence
<220> FEATURE:
<223> OTHER INFORMATION: Synthetic Construct

<400> SEQUENCE: 302

Asp Arg Asp Pro Glu Lys Ser Ser Glu Asp Asp
1               5                   10

<210> SEQ ID NO 303
<211> LENGTH: 180
<212> TYPE: PRT
<213> ORGANISM: Artificial Sequence
<220> FEATURE:
<223> OTHER INFORMATION: Synthetic Construct
```

<400> SEQUENCE: 303

Gly Asp Arg Ala Pro Ala Arg Phe Lys Ala Lys Phe Val Gly Asp Pro
1               5                   10                  15

Ala Leu Val Leu Asn Asp Ile His Lys Lys Ile Ala Leu Val Lys Lys
            20                  25                  30

Leu Ala Phe Ala Phe Gly Asp Arg Asn Cys Ser Thr Ile Thr Leu Gln
        35                  40                  45

Asn Ile Thr Arg Gly Ser Ile Val Val Glu Trp Thr Asn Asn Thr Leu
    50                  55                  60

Pro Leu Glu Pro Cys Pro Lys Glu Gln Ile Ala Gly Leu Ser Arg Arg
65              70                  75                  80

Ile Ala Glu Asp Asp Gly Lys Pro Arg Pro Ala Phe Ser Asn Ala Leu
            85                  90                  95

Glu Pro Asp Phe Lys Ala Thr Ser Ile Thr Val Thr Gly Ser Gly Ser
            100                 105                 110

Cys Arg His Leu Gln Phe Ile Pro Val Val Pro Arg Arg Val Pro
            115                 120                 125

Ser Glu Ala Pro Pro Thr Glu Val Pro Asp Arg Asp Pro Glu Lys Ser
    130                 135                 140

Ser Glu Asp Asp Val Tyr Leu His Thr Val Ile Pro Ala Val Val Val
145                 150                 155                 160

Ala Ala Ile Leu Leu Ile Ala Gly Ile Ile Ala Met Ile Cys Tyr Arg
            165                 170                 175

Lys Lys Arg Lys
            180

<210> SEQ ID NO 304
<211> LENGTH: 180
<212> TYPE: PRT
<213> ORGANISM: Artificial Sequence
<220> FEATURE:
<223> OTHER INFORMATION: Synthetic Construct

<400> SEQUENCE: 304

Gly Asp Lys Ala Pro Ala Arg Phe Lys Ala Arg Leu Ala Gly Asp Pro
1               5                   10                  15

Ala Pro Val Val Asn Asp Ile His Lys Lys Ile Ala Leu Val Lys Lys
            20                  25                  30

Leu Ala Phe Ala Phe Gly Asp Arg Asn Cys Ser Ser Ile Thr Leu Gln
        35                  40                  45

Asn Ile Thr Arg Gly Ser Ile Val Val Glu Trp Thr Asn Asn Thr Leu
    50                  55                  60

Pro Leu Glu Pro Cys Pro Lys Glu Gln Ile Ile Gly Leu Ser Arg Arg
65              70                  75                  80

Ile Ala Asp Glu Asn Gly Lys Pro Arg Pro Ala Phe Ser Asn Ala Leu
            85                  90                  95

Glu Pro Asp Phe Lys Ala Leu Ser Ile Ala Val Thr Gly Ser Gly Ser
            100                 105                 110

Cys Arg His Leu Gln Phe Ile Pro Val Ala Pro Pro Ser Pro Gly Ser
            115                 120                 125

Ser Ala Ala Pro Ala Thr Glu Val Pro Asp Arg Asp Pro Glu Lys Ser
    130                 135                 140

Ser Glu Asp Asp Val Tyr Leu His Thr Val Ile Pro Ala Val Val Val
145                 150                 155                 160

```
Ala Ala Ile Leu Leu Ile Ala Gly Ile Ile Ala Met Ile Cys Tyr Arg
            165                 170                 175

Lys Lys Arg Lys
        180

<210> SEQ ID NO 305
<211> LENGTH: 392
<212> TYPE: PRT
<213> ORGANISM: Artificial Sequence
<220> FEATURE:
<223> OTHER INFORMATION: Synthetic Construct

<400> SEQUENCE: 305

Ile Gln Pro Glu Pro Val Pro Thr Pro Ala Phe Pro Thr Pro Thr Pro
1               5                   10                  15

Val Leu Thr His Gly Pro Cys Ala Ala Glu Ser Glu Pro Ala Leu Leu
            20                  25                  30

Ile Gly Ser Lys Gln Phe Gly Leu Ser Arg Asn Ser His Ile Ala Ile
        35                  40                  45

Ala Phe Asp Asp Thr Lys Val Lys Asn Arg Leu Thr Ile Glu Leu Glu
    50                  55                  60

Val Arg Thr Glu Ala Glu Ser Gly Leu Leu Phe Tyr Met Ala Arg Ile
65                  70                  75                  80

Asn His Ala Asp Phe Ala Thr Val Gln Leu Arg Asn Gly Leu Pro Tyr
                85                  90                  95

Phe Ser Tyr Asp Leu Gly Ser Gly Asp Thr His Thr Met Ile Pro Thr
            100                 105                 110

Lys Ile Asn Asp Gly Gln Trp His Lys Ile Lys Ile Met Arg Ser Lys
        115                 120                 125

Gln Glu Gly Ile Leu Tyr Val Asp Gly Asn Arg Thr Ile Ser Pro Lys
    130                 135                 140

Lys Ala Asp Ile Leu Asp Val Val Gly Met Leu Tyr Val Gly Gly Leu
145                 150                 155                 160

Pro Ile Asn Tyr Thr Thr Arg Arg Ile Gly Pro Val Thr Tyr Ser Ile
                165                 170                 175

Asp Gly Cys Val Arg Asn Leu His Met Ala Glu Ala Pro Ala Asp Leu
            180                 185                 190

Glu Gln Pro Thr Ser Ser Phe His Val Gly Thr Cys Phe Ala Asn Ala
        195                 200                 205

Gln Arg Gly Thr Tyr Phe Asp Gly Thr Gly Phe Ala Lys Ala Val Gly
    210                 215                 220

Gly Phe Lys Val Gly Leu Asp Leu Leu Val Glu Phe Glu Phe Arg Thr
225                 230                 235                 240

Thr Thr Thr Thr Gly Val Leu Leu Gly Ile Ser Ser Gln Lys Met Asp
                245                 250                 255

Gly Met Gly Ile Glu Met Ile Asp Glu Lys Leu Met Phe His Val Asp
            260                 265                 270

Asn Gly Ala Gly Arg Phe Thr Ala Val Tyr Asp Ala Gly Val Pro Gly
        275                 280                 285

His Leu Cys Asp Gly Gln Trp His Lys Val Thr Ala Asn Lys Ile Lys
    290                 295                 300

His Arg Ile Glu Leu Thr Val Asp Gly Asn Gln Val Glu Ala Gln Ser
305                 310                 315                 320

Pro Asn Pro Ala Ser Thr Ser Ala Asp Thr Asn Asp Pro Val Phe Val
                325                 330                 335
```

Gly Gly Phe Pro Asp Asp Leu Lys Gln Phe Gly Leu Thr Thr Ser Ile
            340                 345                 350

Pro Phe Arg Gly Cys Ile Arg Ser Leu Lys Leu Thr Lys Gly Thr Gly
        355                 360                 365

Lys Pro Leu Glu Val Asn Phe Ala Lys Ala Leu Glu Leu Arg Gly Val
    370                 375                 380

Gln Pro Val Ser Cys Pro Ala Asn
385                 390

```
<210> SEQ ID NO 306
<211> LENGTH: 339
<212> TYPE: DNA
<213> ORGANISM: Artificial Sequence
<220> FEATURE:
<223> OTHER INFORMATION: Synthetic Construct

<400> SEQUENCE: 306
caagtacaac tggttcaatc aggcgcagaa gtcgtaaaac ctggttccag cgtaaaagtc    60
agttgtgagg ctagtggatt caccttcacc gatagcgtta ttacatgggt tcgtcagcgc   120
ccaggtcaag gctcgagtg gattggggaa atttacccag aagtggaaa tttctactac     180 aatgaaaaat ttcaaggccg ggtgaccatc actgctgata aaagcacttc aacagcctat   240
atggaattgt ccagcttgcg ctccgaagac actgccgttt atttctgcgc catgcgtagg   300
tcttcctggg gacagggtac acttgtaact gtcagctct                          339

<210> SEQ ID NO 307
<211> LENGTH: 75
<212> TYPE: DNA
<213> ORGANISM: Artificial Sequence
<220> FEATURE:
<223> OTHER INFORMATION: Synthetic Construct

<400> SEQUENCE: 307
caagtacaac tggttcaatc aggcgcagaa gtcgtaaaac ctggttccag cgtaaaagtc    60
agttgtgagg ctagt                                                    75

<210> SEQ ID NO 308
<211> LENGTH: 24
<212> TYPE: DNA
<213> ORGANISM: Artificial Sequence
<220> FEATURE:
<223> OTHER INFORMATION: Synthetic Construct

<400> SEQUENCE: 308
ggattcacct tcaccgatag cgtt                                          24

<210> SEQ ID NO 309
<211> LENGTH: 51
<212> TYPE: DNA
<213> ORGANISM: Artificial Sequence
<220> FEATURE:
<223> OTHER INFORMATION: Synthetic Construct

<400> SEQUENCE: 309
attacatggg ttcgtcagcg cccaggtcaa gggctcgagt ggattgggga a             51

<210> SEQ ID NO 310
<211> LENGTH: 24
<212> TYPE: DNA
<213> ORGANISM: Artificial Sequence
<220> FEATURE:
<223> OTHER INFORMATION: Synthetic Construct
```

<400> SEQUENCE: 310
atttacccag gaagtggaaa tttc    24

<210> SEQ ID NO 311
<211> LENGTH: 114
<212> TYPE: DNA
<213> ORGANISM: Artificial Sequence
<220> FEATURE:
<223> OTHER INFORMATION: Synthetic Construct

<400> SEQUENCE: 311
tactacaatg aaaaatttca aggccgggtg accatcactg ctgataaaag cacttcaaca    60
gcctatatgg aattgtccag cttgcgctcc gaagacactg ccgtttattt ctgc    114

<210> SEQ ID NO 312
<211> LENGTH: 18
<212> TYPE: DNA
<213> ORGANISM: Artificial Sequence
<220> FEATURE:
<223> OTHER INFORMATION: Synthetic Construct

<400> SEQUENCE: 312
gccatgcgta ggtcttcc    18

<210> SEQ ID NO 313
<211> LENGTH: 33
<212> TYPE: DNA
<213> ORGANISM: Artificial Sequence
<220> FEATURE:
<223> OTHER INFORMATION: Synthetic Construct

<400> SEQUENCE: 313
tggggacagg gtacacttgt aactgtcagc tct    33

<210> SEQ ID NO 314
<211> LENGTH: 113
<212> TYPE: PRT
<213> ORGANISM: Artificial Sequence
<220> FEATURE:
<223> OTHER INFORMATION: Synthetic Construct

<400> SEQUENCE: 314

Gln Val Gln Leu Val Gln Ser Gly Ala Glu Val Val Lys Pro Gly Ser
1               5                   10                  15

Ser Val Lys Val Ser Cys Glu Ala Ser Gly Phe Thr Phe Thr Asp Ser
            20                  25                  30

Val Ile Thr Trp Val Arg Gln Arg Pro Gly Gln Gly Leu Glu Trp Ile
        35                  40                  45

Gly Glu Ile Tyr Pro Gly Ser Gly Asn Phe Tyr Asn Glu Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Met Arg Arg Ser Ser Trp Gly Gln Gly Thr Leu Val Thr Val Ser
            100                 105                 110

Ser

<210> SEQ ID NO 315
<211> LENGTH: 25

<212> TYPE: PRT
<213> ORGANISM: Artificial Sequence
<220> FEATURE:
<223> OTHER INFORMATION: Synthetic Construct

<400> SEQUENCE: 315

Gln Val Gln Leu Val Gln Ser Gly Ala Glu Val Val Lys Pro Gly Ser
1               5                   10                  15

Ser Val Lys Val Ser Cys Glu Ala Ser
            20                  25

<210> SEQ ID NO 316
<211> LENGTH: 8
<212> TYPE: PRT
<213> ORGANISM: Artificial Sequence
<220> FEATURE:
<223> OTHER INFORMATION: Synthetic Construct

<400> SEQUENCE: 316

Gly Phe Thr Phe Thr Asp Ser Val
1               5

<210> SEQ ID NO 317
<211> LENGTH: 17
<212> TYPE: PRT
<213> ORGANISM: Artificial Sequence
<220> FEATURE:
<223> OTHER INFORMATION: Synthetic Construct

<400> SEQUENCE: 317

Ile Thr Trp Val Arg Gln Arg Pro Gly Gln Gly Leu Glu Trp Ile Gly
1               5                   10                  15

Glu

<210> SEQ ID NO 318
<211> LENGTH: 8
<212> TYPE: PRT
<213> ORGANISM: Artificial Sequence
<220> FEATURE:
<223> OTHER INFORMATION: Synthetic Construct

<400> SEQUENCE: 318

Ile Tyr Pro Gly Ser Gly Asn Phe
1               5

<210> SEQ ID NO 319
<211> LENGTH: 38
<212> TYPE: PRT
<213> ORGANISM: Artificial Sequence
<220> FEATURE:
<223> OTHER INFORMATION: Synthetic Construct

<400> SEQUENCE: 319

Tyr Tyr Asn Glu Lys Phe Gln Gly Arg Val Thr Ile Thr Ala Asp Lys
1               5                   10                  15

Ser Thr Ser Thr Ala Tyr Met Glu Leu Ser Ser Leu Arg Ser Glu Asp
            20                  25                  30

Thr Ala Val Tyr Phe Cys
        35

<210> SEQ ID NO 320
<211> LENGTH: 6
<212> TYPE: PRT
<213> ORGANISM: Artificial Sequence
<220> FEATURE:

<223> OTHER INFORMATION: Synthetic Construct

<400> SEQUENCE: 320

Ala Met Arg Arg Ser Ser
1               5

<210> SEQ ID NO 321
<211> LENGTH: 11
<212> TYPE: PRT
<213> ORGANISM: Artificial Sequence
<220> FEATURE:
<223> OTHER INFORMATION: Synthetic Construct

<400> SEQUENCE: 321

Trp Gly Gln Gly Thr Leu Val Thr Val Ser Ser
1               5                   10

<210> SEQ ID NO 322
<211> LENGTH: 336
<212> TYPE: DNA
<213> ORGANISM: Artificial Sequence
<220> FEATURE:
<223> OTHER INFORMATION: Synthetic Construct

<400> SEQUENCE: 322
gacgtcgtaa tgactcaaac acccctctct ctttctgtta ccccccggaca gcctgcttca     60 atcagttgta aatcatccca aaccatagtt cattctaata gtaaaactta cctcgaatgg    120
tatctccaaa aacctggtca gtcaccacag ctccttattt acaaggttag ttccagattc    180
tctggcgtcc ctgaccgctt ctctggctcc ggttcaggca ccgactttac tctgaaaatc    240
tcacgggttg aagctgaaga tgttggagtg tactactgct ccagggttc tcacgtccca     300 ttgacctttg gacagggaac taagctcgaa ataaaa                              336

<210> SEQ ID NO 323
<211> LENGTH: 78
<212> TYPE: DNA
<213> ORGANISM: Artificial Sequence
<220> FEATURE:
<223> OTHER INFORMATION: Synthetic Construct

<400> SEQUENCE: 323
gacgtcgtaa tgactcaaac acccctctct ctttctgtta ccccccggaca gcctgcttca     60 atcagttgta aatcatcc                                                   78

<210> SEQ ID NO 324
<211> LENGTH: 33
<212> TYPE: DNA
<213> ORGANISM: Artificial Sequence
<220> FEATURE:
<223> OTHER INFORMATION: Synthetic Construct

<400> SEQUENCE: 324
caaaccatag ttcattctaa tagtaaaact tac                                  33

<210> SEQ ID NO 325
<211> LENGTH: 51
<212> TYPE: DNA
<213> ORGANISM: Artificial Sequence
<220> FEATURE:
<223> OTHER INFORMATION: Synthetic Construct

<400> SEQUENCE: 325
ctcgaatggt atctccaaaa acctggtcag tcaccacagc tccttattta c             51

<210> SEQ ID NO 326
<211> LENGTH: 9
<212> TYPE: DNA
<213> ORGANISM: Artificial Sequence
<220> FEATURE:
<223> OTHER INFORMATION: Synthetic Construct

<400> SEQUENCE: 326 aaggttagt                                                                 9

<210> SEQ ID NO 327
<211> LENGTH: 108
<212> TYPE: DNA
<213> ORGANISM: Artificial Sequence
<220> FEATURE:
<223> OTHER INFORMATION: Synthetic Construct

<400> SEQUENCE: 327
tccagattct ctggcgtccc tgaccgcttc tctggctccg gttcaggcac cgactttact        60
ctgaaaatct cacgggttga agctgaagat gttggagtgt actactgc                    108

<210> SEQ ID NO 328
<211> LENGTH: 27
<212> TYPE: DNA
<213> ORGANISM: Artificial Sequence
<220> FEATURE:
<223> OTHER INFORMATION: Synthetic Construct

<400> SEQUENCE: 328
ttccagggtt ctcacgtccc attgacc                                            27

<210> SEQ ID NO 329
<211> LENGTH: 30
<212> TYPE: DNA
<213> ORGANISM: Artificial Sequence
<220> FEATURE:
<223> OTHER INFORMATION: Synthetic Construct

<400> SEQUENCE: 329
tttggacagg gaactaagct cgaaataaaa                                         30

<210> SEQ ID NO 330
<211> LENGTH: 112
<212> TYPE: PRT
<213> ORGANISM: Artificial Sequence
<220> FEATURE:
<223> OTHER INFORMATION: Synthetic Construct

<400> SEQUENCE: 330

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Thr Ile Val His Ser
            20                  25                  30

Asn Ser Lys Thr Tyr Leu Glu Trp Tyr Leu Gln Lys Pro Gly Gln Ser
        35                  40                  45

Pro Gln Leu Leu Ile Tyr Lys Val Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

```
Ser His Val Pro Leu Thr Phe Gly Gln Gly Thr Lys Leu Glu Ile Lys
                100                 105                 110
```

<210> SEQ ID NO 331
<211> LENGTH: 26
<212> TYPE: PRT
<213> ORGANISM: Artificial Sequence
<220> FEATURE:
<223> OTHER INFORMATION: Synthetic Construct

<400> SEQUENCE: 331

```
Asp Val Val Met Thr Gln Thr Pro Leu Ser Leu Ser Val Thr Pro Gly
1               5                   10                  15

Gln Pro Ala Ser Ile Ser Cys Lys Ser Ser
            20                  25
```

<210> SEQ ID NO 332
<211> LENGTH: 11
<212> TYPE: PRT
<213> ORGANISM: Artificial Sequence
<220> FEATURE:
<223> OTHER INFORMATION: Synthetic Construct

<400> SEQUENCE: 332

```
Gln Thr Ile Val His Ser Asn Ser Lys Thr Tyr
1               5                   10
```

<210> SEQ ID NO 333
<211> LENGTH: 17
<212> TYPE: PRT
<213> ORGANISM: Artificial Sequence
<220> FEATURE:
<223> OTHER INFORMATION: Synthetic Construct

<400> SEQUENCE: 333

```
Leu Glu Trp Tyr Leu Gln Lys Pro Gly Gln Ser Pro Gln Leu Leu Ile
1               5                   10                  15

Tyr
```

<210> SEQ ID NO 334
<211> LENGTH: 3
<212> TYPE: PRT
<213> ORGANISM: Artificial Sequence
<220> FEATURE:
<223> OTHER INFORMATION: Synthetic Construct

<400> SEQUENCE: 334

```
Lys Val Ser
1
```

<210> SEQ ID NO 335
<211> LENGTH: 36
<212> TYPE: PRT
<213> ORGANISM: Artificial Sequence
<220> FEATURE:
<223> OTHER INFORMATION: Synthetic Construct

<400> SEQUENCE: 335

```
Ser Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Val Gly
            20                  25                  30

Val Tyr Tyr Cys
            35
```

<210> SEQ ID NO 336
<211> LENGTH: 9
<212> TYPE: PRT
<213> ORGANISM: Artificial Sequence
<220> FEATURE:
<223> OTHER INFORMATION: Synthetic Construct

<400> SEQUENCE: 336

Phe Gln Gly Ser His Val Pro Leu Thr
1               5

<210> SEQ ID NO 337
<211> LENGTH: 10
<212> TYPE: PRT
<213> ORGANISM: Artificial Sequence
<220> FEATURE:
<223> OTHER INFORMATION: Synthetic Construct

<400> SEQUENCE: 337

Phe Gly Gln Gly Thr Lys Leu Glu Ile Lys
1               5                   10

<210> SEQ ID NO 338
<211> LENGTH: 339
<212> TYPE: DNA
<213> ORGANISM: Artificial Sequence
<220> FEATURE:
<223> OTHER INFORMATION: Synthetic Construct

<400> SEQUENCE: 338
caagtacaac tggttcaatc aggcgcagaa gtcgtaaaac ctggttccag cgtaaaagtc        60
agttgtgagg ctagtggatt caccttcacc gatagcgtta ttacatgggt tcgtcagcgc       120
ccaggtcaag gctcgagtg gattggggaa atttacccag gaagtggaaa tttctactac        180
aatgaaaaat ttcaaggccg ggtgaccatc actgctgata aaagcacttc aacagcctat       240
atggaattgt ccagcttgcg ctccgaagac actgccgttt atttctgcgc catgcgtagg       300
tcttcctggg gacagggtac acttgtaact gtcagctct                              339

<210> SEQ ID NO 339
<211> LENGTH: 75
<212> TYPE: DNA
<213> ORGANISM: Artificial Sequence
<220> FEATURE:
<223> OTHER INFORMATION: Synthetic Construct

<400> SEQUENCE: 339
caagtacaac tggttcaatc aggcgcagaa gtcgtaaaac ctggttccag cgtaaaagtc        60
agttgtgagg ctagt                                                         75

<210> SEQ ID NO 340
<211> LENGTH: 24
<212> TYPE: DNA
<213> ORGANISM: Artificial Sequence
<220> FEATURE:
<223> OTHER INFORMATION: Synthetic Construct

<400> SEQUENCE: 340
ggattcacct tcaccgatag cgtt                                               24

<210> SEQ ID NO 341
<211> LENGTH: 51
<212> TYPE: DNA
<213> ORGANISM: Artificial Sequence -continued
<220> FEATURE:
<223> OTHER INFORMATION: Synthetic Construct

<400> SEQUENCE: 341
attacatggg ttcgtcagcg cccaggtcaa gggctcgagt ggattgggga a    51

<210> SEQ ID NO 342
<211> LENGTH: 24
<212> TYPE: DNA
<213> ORGANISM: Artificial Sequence
<220> FEATURE:
<223> OTHER INFORMATION: Synthetic Construct

<400> SEQUENCE: 342
atttacccag gaagtggaaa tttc    24

<210> SEQ ID NO 343
<211> LENGTH: 114
<212> TYPE: DNA
<213> ORGANISM: Artificial Sequence
<220> FEATURE:
<223> OTHER INFORMATION: Synthetic Construct

<400> SEQUENCE: 343
tactacaatg aaaaatttca aggccgggtg accatcactg ctgataaaag cacttcaaca    60
gcctatatgg aattgtccag cttgcgctcc gaagacactg ccgtttattt ctgc    114

<210> SEQ ID NO 344
<211> LENGTH: 18
<212> TYPE: DNA
<213> ORGANISM: Artificial Sequence
<220> FEATURE:
<223> OTHER INFORMATION: Synthetic Construct

<400> SEQUENCE: 344
gccatgcgta ggtcttcc    18

<210> SEQ ID NO 345
<211> LENGTH: 33
<212> TYPE: DNA
<213> ORGANISM: Artificial Sequence
<220> FEATURE:
<223> OTHER INFORMATION: Synthetic Construct

<400> SEQUENCE: 345
tggggacagg gtacacttgt aactgtcagc tct    33

<210> SEQ ID NO 346
<211> LENGTH: 113
<212> TYPE: PRT
<213> ORGANISM: Artificial Sequence
<220> FEATURE:
<223> OTHER INFORMATION: Synthetic Construct

<400> SEQUENCE: 346

Gln Val Gln Leu Val Gln Ser Gly Ala Glu Val Val Lys Pro Gly Ser
1               5                   10                  15

Ser Val Lys Val Ser Cys Glu Ala Ser Gly Phe Thr Phe Thr Asp Ser
            20                  25                  30

Val Ile Thr Trp Val Arg Gln Arg Pro Gly Gln Gly Leu Glu Trp Ile
        35                  40                  45

Gly Glu Ile Tyr Pro Gly Ser Gly Asn Phe Tyr Tyr Asn Glu Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Met Arg Arg Ser Ser Trp Gly Gln Gly Thr Leu Val Thr Val Ser
            100                 105                 110

Ser

<210> SEQ ID NO 347
<211> LENGTH: 25
<212> TYPE: PRT
<213> ORGANISM: Artificial Sequence
<220> FEATURE:
<223> OTHER INFORMATION: Synthetic Construct

<400> SEQUENCE: 347

Gln Val Gln Leu Val Gln Ser Gly Ala Glu Val Val Lys Pro Gly Ser
1               5                   10                  15

Ser Val Lys Val Ser Cys Glu Ala Ser
            20                  25

<210> SEQ ID NO 348
<211> LENGTH: 8
<212> TYPE: PRT
<213> ORGANISM: Artificial Sequence
<220> FEATURE:
<223> OTHER INFORMATION: Synthetic Construct

<400> SEQUENCE: 348

Gly Phe Thr Phe Thr Asp Ser Val
1               5

<210> SEQ ID NO 349
<211> LENGTH: 17
<212> TYPE: PRT
<213> ORGANISM: Artificial Sequence
<220> FEATURE:
<223> OTHER INFORMATION: Synthetic Construct

<400> SEQUENCE: 349

Ile Thr Trp Val Arg Gln Arg Pro Gly Gln Gly Leu Glu Trp Ile Gly
1               5                   10                  15

Glu

<210> SEQ ID NO 350
<211> LENGTH: 8
<212> TYPE: PRT
<213> ORGANISM: Artificial Sequence
<220> FEATURE:
<223> OTHER INFORMATION: Synthetic Construct

<400> SEQUENCE: 350

Ile Tyr Pro Gly Ser Gly Asn Phe
1               5

<210> SEQ ID NO 351
<211> LENGTH: 38
<212> TYPE: PRT
<213> ORGANISM: Artificial Sequence
<220> FEATURE:
<223> OTHER INFORMATION: Synthetic Construct

<400> SEQUENCE: 351

Tyr Tyr Asn Glu Lys Phe Gln Gly Arg Val Thr Ile Thr Ala Asp Lys

```
                1               5                  10                 15
Ser Thr Ser Thr Ala Tyr Met Glu Leu Ser Ser Leu Arg Ser Glu Asp
                20                 25                 30
Thr Ala Val Tyr Phe Cys
        35
```

<210> SEQ ID NO 352
<211> LENGTH: 6
<212> TYPE: PRT
<213> ORGANISM: Artificial Sequence
<220> FEATURE:
<223> OTHER INFORMATION: Synthetic Construct

<400> SEQUENCE: 352

```
Ala Met Arg Arg Ser Ser
1               5
```

<210> SEQ ID NO 353
<211> LENGTH: 11
<212> TYPE: PRT
<213> ORGANISM: Artificial Sequence
<220> FEATURE:
<223> OTHER INFORMATION: Synthetic Construct

<400> SEQUENCE: 353

```
Trp Gly Gln Gly Thr Leu Val Thr Val Ser Ser
1               5                   10
```

<210> SEQ ID NO 354
<211> LENGTH: 336
<212> TYPE: DNA
<213> ORGANISM: Artificial Sequence
<220> FEATURE:
<223> OTHER INFORMATION: Synthetic Construct

<400> SEQUENCE: 354

| | |
|---|---|
| gatgtggtga tgactcagac acccctgagt ctcagcgtaa cacctggtca acccgcctct | 60 |
| attagttgtc gaagctctca acaatcgta catagtaata gtaaaaccta tctcgaatgg | 120 |
| tatcttcaga aaccagggca gtctcctcaa ctccttatat acaaagtatc caacaggttt | 180 |
| tccggtgtac ccgataggtt ttccggttcc ggctccggaa ctgactttac cctcaaaata | 240 |
| agtcgagtgg aggctgagga tgttggcgtt tattattgct ttcagggtc acacgtacct | 300 |
| cttaccttcg gcgcaggcac aaaattggag attaaa | 336 |

<210> SEQ ID NO 355
<211> LENGTH: 78
<212> TYPE: DNA
<213> ORGANISM: Artificial Sequence
<220> FEATURE:
<223> OTHER INFORMATION: Synthetic Construct

<400> SEQUENCE: 355

| | |
|---|---|
| gatgtggtga tgactcagac acccctgagt ctcagcgtaa cacctggtca acccgcctct | 60 |
| attagttgtc gaagctct | 78 |

<210> SEQ ID NO 356
<211> LENGTH: 33
<212> TYPE: DNA
<213> ORGANISM: Artificial Sequence
<220> FEATURE:
<223> OTHER INFORMATION: Synthetic Construct

<400> SEQUENCE: 356

```
caaacaatcg tacatagtaa tagtaaaacc tat                                    33

<210> SEQ ID NO 357
<211> LENGTH: 51
<212> TYPE: DNA
<213> ORGANISM: Artificial Sequence
<220> FEATURE:
<223> OTHER INFORMATION: Synthetic Construct

<400> SEQUENCE: 357
ctcgaatggt atcttcagaa accagggcag tctcctcaac tccttatata c               51

<210> SEQ ID NO 358
<211> LENGTH: 9
<212> TYPE: DNA
<213> ORGANISM: Artificial Sequence
<220> FEATURE:
<223> OTHER INFORMATION: Synthetic Construct

<400> SEQUENCE: 358 aaagtatcc                                                              9

<210> SEQ ID NO 359
<211> LENGTH: 108
<212> TYPE: DNA
<213> ORGANISM: Artificial Sequence
<220> FEATURE:
<223> OTHER INFORMATION: Synthetic Construct

<400> SEQUENCE: 359
aacaggtttt ccggtgtacc cgataggttt tccggttccg gctccggaac tgactttacc      60
ctcaaaataa gtcgagtgga ggctgaggat gttggcgttt attattgc                   108

<210> SEQ ID NO 360
<211> LENGTH: 27
<212> TYPE: DNA
<213> ORGANISM: Artificial Sequence
<220> FEATURE:
<223> OTHER INFORMATION: Synthetic Construct

<400> SEQUENCE: 360
tttcaggggt cacacgtacc tcttacc                                          27

<210> SEQ ID NO 361
<211> LENGTH: 30
<212> TYPE: DNA
<213> ORGANISM: Artificial Sequence
<220> FEATURE:
<223> OTHER INFORMATION: Synthetic Construct

<400> SEQUENCE: 361
ttcggcgcag gcacaaaatt ggagattaaa                                       30

<210> SEQ ID NO 362
<211> LENGTH: 112
<212> TYPE: PRT
<213> ORGANISM: Artificial Sequence
<220> FEATURE:
<223> OTHER INFORMATION: Synthetic Construct

<400> SEQUENCE: 362

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Thr Ile Val His Ser
```

```
                20                  25                  30

Asn Ser Lys Thr Tyr Leu Glu Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Ala Gly Thr Lys Leu Glu Ile Lys
            100                 105                 110
```

<210> SEQ ID NO 363
<211> LENGTH: 26
<212> TYPE: PRT
<213> ORGANISM: Artificial Sequence
<220> FEATURE:
<223> OTHER INFORMATION: Synthetic Construct

<400> SEQUENCE: 363

```
Asp Val Val Met Thr Gln Thr Pro Leu Ser Leu Ser Val Thr Pro Gly
1               5                   10                  15

Gln Pro Ala Ser Ile Ser Cys Arg Ser Ser
            20                  25
```

<210> SEQ ID NO 364
<211> LENGTH: 11
<212> TYPE: PRT
<213> ORGANISM: Artificial Sequence
<220> FEATURE:
<223> OTHER INFORMATION: Synthetic Construct

<400> SEQUENCE: 364

```
Gln Thr Ile Val His Ser Asn Ser Lys Thr Tyr
1               5                   10
```

<210> SEQ ID NO 365
<211> LENGTH: 17
<212> TYPE: PRT
<213> ORGANISM: Artificial Sequence
<220> FEATURE:
<223> OTHER INFORMATION: Synthetic Construct

<400> SEQUENCE: 365

```
Leu Glu Trp Tyr Leu Gln Lys Pro Gly Gln Ser Pro Gln Leu Leu Ile
1               5                   10                  15

Tyr
```

<210> SEQ ID NO 366
<211> LENGTH: 3
<212> TYPE: PRT
<213> ORGANISM: Artificial Sequence
<220> FEATURE:
<223> OTHER INFORMATION: Synthetic Construct

<400> SEQUENCE: 366

```
Lys Val Ser
1
```

<210> SEQ ID NO 367
<211> LENGTH: 36
<212> TYPE: PRT
<213> ORGANISM: Artificial Sequence
<220> FEATURE:
<223> OTHER INFORMATION: Synthetic Construct

<400> SEQUENCE: 367

Asn Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Val Gly
            20                  25                  30

Val Tyr Tyr Cys
        35

<210> SEQ ID NO 368
<211> LENGTH: 9
<212> TYPE: PRT
<213> ORGANISM: Artificial Sequence
<220> FEATURE:
<223> OTHER INFORMATION: Synthetic Construct

<400> SEQUENCE: 368

Phe Gln Gly Ser His Val Pro Leu Thr
1               5

<210> SEQ ID NO 369
<211> LENGTH: 10
<212> TYPE: PRT
<213> ORGANISM: Artificial Sequence
<220> FEATURE:
<223> OTHER INFORMATION: Synthetic Construct

<400> SEQUENCE: 369

Phe Gly Ala Gly Thr Lys Leu Glu Ile Lys
1               5                   10

<210> SEQ ID NO 370
<211> LENGTH: 354
<212> TYPE: DNA
<213> ORGANISM: Artificial Sequence
<220> FEATURE:
<223> OTHER INFORMATION: Synthetic Construct

<400> SEQUENCE: 370
gaagttcaac tggtcgagtc tggaggaggc ctcgtgaagc cgggcggtag tttgcgcctc    60
tcttgtgccg cctcagggtt tacgttctct agttatacta tgagttgggt gcggcaggca   120
ccgggaaaag ggctggaatg ggtggcctca atctctagta gcggcagcaa tacttattat   180
cctgatagtg tgaaggggag gtttaccatc tcacgggata cgctaagaa caacctgtat    240 cttcaaatga atagcctccg agcagaggat acagcacttt actactgcgc tcgctttgac   300
tatggcagca gtcttgatag ttgggggcag ggcaccttgc ttacggtttc atcc          354

<210> SEQ ID NO 371
<211> LENGTH: 75
<212> TYPE: DNA
<213> ORGANISM: Artificial Sequence
<220> FEATURE:
<223> OTHER INFORMATION: Synthetic Construct

<400> SEQUENCE: 371
gaagttcaac tggtcgagtc tggaggaggc ctcgtgaagc cgggcggtag tttgcgcctc    60
tcttgtgccg cctca                                                    75

<210> SEQ ID NO 372
<211> LENGTH: 24

<212> TYPE: DNA
<213> ORGANISM: Artificial Sequence
<220> FEATURE:
<223> OTHER INFORMATION: Synthetic Construct

<400> SEQUENCE: 372
gggtttacgt tctctagtta tact                                    24

<210> SEQ ID NO 373
<211> LENGTH: 51
<212> TYPE: DNA
<213> ORGANISM: Artificial Sequence
<220> FEATURE:
<223> OTHER INFORMATION: Synthetic Construct

<400> SEQUENCE: 373
atgagttggg tgcggcaggc accgggaaaa gggctggaat gggtggcctc a       51

<210> SEQ ID NO 374
<211> LENGTH: 24
<212> TYPE: DNA
<213> ORGANISM: Artificial Sequence
<220> FEATURE:
<223> OTHER INFORMATION: Synthetic Construct

<400> SEQUENCE: 374
atctctagta gcggcagcaa tact                                    24

<210> SEQ ID NO 375
<211> LENGTH: 114
<212> TYPE: DNA
<213> ORGANISM: Artificial Sequence
<220> FEATURE:
<223> OTHER INFORMATION: Synthetic Construct

<400> SEQUENCE: 375
tattatcctg atagtgtgaa ggggaggttt accatctcac gggataacgc taagaacaac    60
ctgtatcttc aaatgaatag cctccgagca gaggatacag cactttacta ctgc         114

<210> SEQ ID NO 376
<211> LENGTH: 33
<212> TYPE: DNA
<213> ORGANISM: Artificial Sequence
<220> FEATURE:
<223> OTHER INFORMATION: Synthetic Construct

<400> SEQUENCE: 376
gctcgctttg actatggcag cagtcttgat agt                          33

<210> SEQ ID NO 377
<211> LENGTH: 33
<212> TYPE: DNA
<213> ORGANISM: Artificial Sequence
<220> FEATURE:
<223> OTHER INFORMATION: Synthetic Construct

<400> SEQUENCE: 377
tgggggcagg gcaccttgct tacggtttca tcc                          33

<210> SEQ ID NO 378
<211> LENGTH: 118
<212> TYPE: PRT
<213> ORGANISM: Artificial Sequence
<220> FEATURE:
<223> OTHER INFORMATION: Synthetic Construct

<400> SEQUENCE: 378

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Ser Ile Ser Ser Gly Ser Asn Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Asn Ser Leu Arg Ala Glu Asp Thr Ala Leu Tyr Tyr Cys
                85                  90                  95

Ala Arg Phe Asp Tyr Gly Ser Ser Leu Asp Ser Trp Gly Gln Gly Thr
            100                 105                 110

Leu Leu Thr Val Ser Ser
        115
```

<210> SEQ ID NO 379
<211> LENGTH: 25
<212> TYPE: PRT
<213> ORGANISM: Artificial Sequence
<220> FEATURE:
<223> OTHER INFORMATION: Synthetic Construct

<400> SEQUENCE: 379

```
Glu Val Gln Leu Val Glu Ser Gly Gly Gly Leu Val Lys Pro Gly Gly
1               5                   10                  15

Ser Leu Arg Leu Ser Cys Ala Ala Ser
            20                  25
```

<210> SEQ ID NO 380
<211> LENGTH: 8
<212> TYPE: PRT
<213> ORGANISM: Artificial Sequence
<220> FEATURE:
<223> OTHER INFORMATION: Synthetic Construct

<400> SEQUENCE: 380

```
Gly Phe Thr Phe Ser Ser Tyr Thr
1               5
```

<210> SEQ ID NO 381
<211> LENGTH: 17
<212> TYPE: PRT
<213> ORGANISM: Artificial Sequence
<220> FEATURE:
<223> OTHER INFORMATION: Synthetic Construct

<400> SEQUENCE: 381

```
Met Ser Trp Val Arg Gln Ala Pro Gly Lys Gly Leu Glu Trp Val Ala
1               5                   10                  15

Ser
```

<210> SEQ ID NO 382
<211> LENGTH: 8
<212> TYPE: PRT
<213> ORGANISM: Artificial Sequence
<220> FEATURE:
<223> OTHER INFORMATION: Synthetic Construct

<400> SEQUENCE: 382

```
Ile Ser Ser Ser Gly Ser Asn Thr
1               5
```

<210> SEQ ID NO 383
<211> LENGTH: 38
<212> TYPE: PRT
<213> ORGANISM: Artificial Sequence
<220> FEATURE:
<223> OTHER INFORMATION: Synthetic Construct
<400> SEQUENCE: 383

```
Tyr Tyr Pro Asp Ser Val Lys Gly Arg Phe Thr Ile Ser Arg Asp Asn
1               5                   10                  15

Ala Lys Asn Asn Leu Tyr Leu Gln Met Asn Ser Leu Arg Ala Glu Asp
            20                  25                  30

Thr Ala Leu Tyr Tyr Cys
        35
```

<210> SEQ ID NO 384
<211> LENGTH: 11
<212> TYPE: PRT
<213> ORGANISM: Artificial Sequence
<220> FEATURE:
<223> OTHER INFORMATION: Synthetic Construct
<400> SEQUENCE: 384

```
Ala Arg Phe Asp Tyr Gly Ser Ser Leu Asp Ser
1               5                   10
```

<210> SEQ ID NO 385
<211> LENGTH: 11
<212> TYPE: PRT
<213> ORGANISM: Artificial Sequence
<220> FEATURE:
<223> OTHER INFORMATION: Synthetic Construct
<400> SEQUENCE: 385

```
Trp Gly Gln Gly Thr Leu Leu Thr Val Ser Ser
1               5                   10
```

<210> SEQ ID NO 386
<211> LENGTH: 321
<212> TYPE: DNA
<213> ORGANISM: Artificial Sequence
<220> FEATURE:
<223> OTHER INFORMATION: Synthetic Construct
<400> SEQUENCE: 386

```
gagatcgttc ttacccaatc cccggatttc ctttctgtga cccccaaaga aaaagtcaca      60
ctcacctgcc gagcaagcca gtctattagt aacaatttgc actggtatca gcagaagagt     120
gaccaatctc ccaaactcct tattaagtac gcctctcagt caatatccgg catacctagc     180
cgcttttccg gttctggtag tggcaccgac tttactctca ctatcaattc agtggaggct     240
gaggatgccg ccacgtattt ttgtcagcaa tcaaagagtt ggccccggac atttggaggg     300
ggaactaagc tggagattaa g                                              321
```

<210> SEQ ID NO 387
<211> LENGTH: 78
<212> TYPE: DNA
<213> ORGANISM: Artificial Sequence
<220> FEATURE:
<223> OTHER INFORMATION: Synthetic Construct

<400> SEQUENCE: 387
gagatcgttc ttacccaatc cccggatttc ctttctgtga cccccaaaga aaaagtcaca    60
ctcacctgcc gagcaagc                                                  78

<210> SEQ ID NO 388
<211> LENGTH: 18
<212> TYPE: DNA
<213> ORGANISM: Artificial Sequence
<220> FEATURE:
<223> OTHER INFORMATION: Synthetic Construct

<400> SEQUENCE: 388
cagtctatta gtaacaat                                                  18

<210> SEQ ID NO 389
<211> LENGTH: 51
<212> TYPE: DNA
<213> ORGANISM: Artificial Sequence
<220> FEATURE:
<223> OTHER INFORMATION: Synthetic Construct

<400> SEQUENCE: 389
ttgcactggt atcagcagaa gagtgaccaa tctcccaaac tccttattaa g              51

<210> SEQ ID NO 390
<211> LENGTH: 9
<212> TYPE: DNA
<213> ORGANISM: Artificial Sequence
<220> FEATURE:
<223> OTHER INFORMATION: Synthetic Construct

<400> SEQUENCE: 390 tacgcctct                                                             9

<210> SEQ ID NO 391
<211> LENGTH: 108
<212> TYPE: DNA
<213> ORGANISM: Artificial Sequence
<220> FEATURE:
<223> OTHER INFORMATION: Synthetic Construct

<400> SEQUENCE: 391
cagtcaatat ccggcatacc tagccgcttt tccggttctg gtagtggcac cgactttact    60
ctcactatca attcagtgga ggctgaggat gccgccacgt attttgt                  108

<210> SEQ ID NO 392
<211> LENGTH: 27
<212> TYPE: DNA
<213> ORGANISM: Artificial Sequence
<220> FEATURE:
<223> OTHER INFORMATION: Synthetic Construct

<400> SEQUENCE: 392
cagcaatcaa agagttggcc ccggaca                                        27

<210> SEQ ID NO 393
<211> LENGTH: 30
<212> TYPE: DNA
<213> ORGANISM: Artificial Sequence
<220> FEATURE:
<223> OTHER INFORMATION: Synthetic Construct

<400> SEQUENCE: 393
tttggagggg gaactaagct ggagattaag                                     30

-continued

<210> SEQ ID NO 394
<211> LENGTH: 107
<212> TYPE: PRT
<213> ORGANISM: Artificial Sequence
<220> FEATURE:
<223> OTHER INFORMATION: Synthetic Construct

<400> SEQUENCE: 394

Glu Ile Val Leu Thr Gln Ser Pro Asp Phe Leu Ser Val Thr Pro Lys
1               5                   10                  15

Glu Lys Val Thr Leu Thr Cys Arg Ala Ser Gln Ser Ile Ser Asn Asn
            20                  25                  30

Leu His Trp Tyr Gln Gln Lys Ser Asp Gln Ser Pro Lys Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Thr Ile Asn Ser Val Glu Ala
65                  70                  75                  80

Glu Asp Ala Ala Thr Tyr Phe Cys Gln Gln Ser Lys Ser Trp Pro Arg
                85                  90                  95

Thr Phe Gly Gly Gly Thr Lys Leu Glu Ile Lys
            100                 105

<210> SEQ ID NO 395
<211> LENGTH: 26
<212> TYPE: PRT
<213> ORGANISM: Artificial Sequence
<220> FEATURE:
<223> OTHER INFORMATION: Synthetic Construct

<400> SEQUENCE: 395

Glu Ile Val Leu Thr Gln Ser Pro Asp Phe Leu Ser Val Thr Pro Lys
1               5                   10                  15

Glu Lys Val Thr Leu Thr Cys Arg Ala Ser
            20                  25

<210> SEQ ID NO 396
<211> LENGTH: 6
<212> TYPE: PRT
<213> ORGANISM: Artificial Sequence
<220> FEATURE:
<223> OTHER INFORMATION: Synthetic Construct

<400> SEQUENCE: 396

Gln Ser Ile Ser Asn Asn
1               5

<210> SEQ ID NO 397
<211> LENGTH: 17
<212> TYPE: PRT
<213> ORGANISM: Artificial Sequence
<220> FEATURE:
<223> OTHER INFORMATION: Synthetic Construct

<400> SEQUENCE: 397

Leu His Trp Tyr Gln Gln Lys Ser Asp Gln Ser Pro Lys Leu Leu Ile
1               5                   10                  15

Lys

<210> SEQ ID NO 398
<211> LENGTH: 3

<212> TYPE: PRT
<213> ORGANISM: Artificial Sequence
<220> FEATURE:
<223> OTHER INFORMATION: Synthetic Construct

<400> SEQUENCE: 398

Tyr Ala Ser
1

<210> SEQ ID NO 399
<211> LENGTH: 36
<212> TYPE: PRT
<213> ORGANISM: Artificial Sequence
<220> FEATURE:
<223> OTHER INFORMATION: Synthetic Construct

<400> SEQUENCE: 399

Gln Ser Ile Ser Gly Ile Pro Ser Arg Phe Ser Gly Ser Gly Ser Gly
1               5                   10                  15

Thr Asp Phe Thr Leu Thr Ile Asn Ser Val Glu Ala Glu Asp Ala Ala
            20                  25                  30

Thr Tyr Phe Cys
        35

<210> SEQ ID NO 400
<211> LENGTH: 9
<212> TYPE: PRT
<213> ORGANISM: Artificial Sequence
<220> FEATURE:
<223> OTHER INFORMATION: Synthetic Construct

<400> SEQUENCE: 400

Gln Gln Ser Lys Ser Trp Pro Arg Thr
1               5

<210> SEQ ID NO 401
<211> LENGTH: 10
<212> TYPE: PRT
<213> ORGANISM: Artificial Sequence
<220> FEATURE:
<223> OTHER INFORMATION: Synthetic Construct

<400> SEQUENCE: 401

Phe Gly Gly Gly Thr Lys Leu Glu Ile Lys
1               5                   10

<210> SEQ ID NO 402
<211> LENGTH: 354
<212> TYPE: DNA
<213> ORGANISM: Artificial Sequence
<220> FEATURE:
<223> OTHER INFORMATION: Synthetic Construct

<400> SEQUENCE: 402
gaagttcaac tggtcgagtc tggaggaggc ctcgtgaagc cgggcggtag tttgcgcctc      60
tcttgtgccg cctcagggtt tacgttctct agttatacta tgagttgggt gcggcaggca     120
ccgggaaaag ggctggaatg ggtggcctca atctctagta gcggcagcaa tacttattat     180
cctgatagtg tgaaggggag gtttaccatc tcacgggata cgctaagaa caacctgtat      240
cttcaaatga atagcctccg agcagaggat acagcacttt actactgcgc tcgctttgac     300
tatggcagca gtcttgatag ttggggggcag ggcaccttgc ttacggtttc atcc           354

<210> SEQ ID NO 403

```
<211> LENGTH: 75
<212> TYPE: DNA
<213> ORGANISM: Artificial Sequence
<220> FEATURE:
<223> OTHER INFORMATION: Synthetic Construct

<400> SEQUENCE: 403
gaagttcaac tggtcgagtc tggaggaggc ctcgtgaagc cgggcggtag tttgcgcctc    60
tcttgtgccg cctca                                                    75

<210> SEQ ID NO 404
<211> LENGTH: 24
<212> TYPE: DNA
<213> ORGANISM: Artificial Sequence
<220> FEATURE:
<223> OTHER INFORMATION: Synthetic Construct

<400> SEQUENCE: 404
gggtttacgt tctctagtta tact                                          24

<210> SEQ ID NO 405
<211> LENGTH: 51
<212> TYPE: DNA
<213> ORGANISM: Artificial Sequence
<220> FEATURE:
<223> OTHER INFORMATION: Synthetic Construct

<400> SEQUENCE: 405
atgagttggg tgcggcaggc accgggaaaa gggctggaat gggtggcctc a             51

<210> SEQ ID NO 406
<211> LENGTH: 24
<212> TYPE: DNA
<213> ORGANISM: Artificial Sequence
<220> FEATURE:
<223> OTHER INFORMATION: Synthetic Construct

<400> SEQUENCE: 406
atctctagta gcggcagcaa tact                                          24

<210> SEQ ID NO 407
<211> LENGTH: 114
<212> TYPE: DNA
<213> ORGANISM: Artificial Sequence
<220> FEATURE:
<223> OTHER INFORMATION: Synthetic Construct

<400> SEQUENCE: 407
tattatcctg atagtgtgaa ggggaggttt accatctcac gggataacgc taagaacaac    60
ctgtatcttc aaatgaatag cctccgagca gaggatacag cactttacta ctgc         114

<210> SEQ ID NO 408
<211> LENGTH: 33
<212> TYPE: DNA
<213> ORGANISM: Artificial Sequence
<220> FEATURE:
<223> OTHER INFORMATION: Synthetic Construct

<400> SEQUENCE: 408
gctcgctttg actatggcag cagtcttgat agt                                33

<210> SEQ ID NO 409
<211> LENGTH: 33
<212> TYPE: DNA
<213> ORGANISM: Artificial Sequence
```

<220> FEATURE:
<223> OTHER INFORMATION: Synthetic Construct

<400> SEQUENCE: 409
tgggggcagg gcaccttgct tacggtttca tcc                33

<210> SEQ ID NO 410
<211> LENGTH: 118
<212> TYPE: PRT
<213> ORGANISM: Artificial Sequence
<220> FEATURE:
<223> OTHER INFORMATION: Synthetic Construct

<400> SEQUENCE: 410

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Ser Ile Ser Ser Ser Gly Ser Asn Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Asn Ser Leu Arg Ala Glu Asp Thr Ala Leu Tyr Tyr Cys
                85                  90                  95

Ala Arg Phe Asp Tyr Gly Ser Ser Leu Asp Ser Trp Gly Gln Gly Thr
            100                 105                 110

Leu Leu Thr Val Ser Ser
        115

<210> SEQ ID NO 411
<211> LENGTH: 25
<212> TYPE: PRT
<213> ORGANISM: Artificial Sequence
<220> FEATURE:
<223> OTHER INFORMATION: Synthetic Construct

<400> SEQUENCE: 411

Glu Val Gln Leu Val Glu Ser Gly Gly Gly Leu Val Lys Pro Gly Gly
1               5                   10                  15

Ser Leu Arg Leu Ser Cys Ala Ala Ser
            20                  25

<210> SEQ ID NO 412
<211> LENGTH: 8
<212> TYPE: PRT
<213> ORGANISM: Artificial Sequence
<220> FEATURE:
<223> OTHER INFORMATION: Synthetic Construct

<400> SEQUENCE: 412

Gly Phe Thr Phe Ser Ser Tyr Thr
1               5

<210> SEQ ID NO 413
<211> LENGTH: 17
<212> TYPE: PRT
<213> ORGANISM: Artificial Sequence
<220> FEATURE:
<223> OTHER INFORMATION: Synthetic Construct

<400> SEQUENCE: 413

Met Ser Trp Val Arg Gln Ala Pro Gly Lys Gly Leu Glu Trp Val Ala
1               5                   10                  15

Ser

<210> SEQ ID NO 414
<211> LENGTH: 8
<212> TYPE: PRT
<213> ORGANISM: Artificial Sequence
<220> FEATURE:
<223> OTHER INFORMATION: Synthetic Construct

<400> SEQUENCE: 414

Ile Ser Ser Ser Gly Ser Asn Thr
1               5

<210> SEQ ID NO 415
<211> LENGTH: 38
<212> TYPE: PRT
<213> ORGANISM: Artificial Sequence
<220> FEATURE:
<223> OTHER INFORMATION: Synthetic Construct

<400> SEQUENCE: 415

Tyr Tyr Pro Asp Ser Val Lys Gly Arg Phe Thr Ile Ser Arg Asp Asn
1               5                   10                  15

Ala Lys Asn Asn Leu Tyr Leu Gln Met Asn Ser Leu Arg Ala Glu Asp
            20                  25                  30

Thr Ala Leu Tyr Tyr Cys
        35

<210> SEQ ID NO 416
<211> LENGTH: 11
<212> TYPE: PRT
<213> ORGANISM: Artificial Sequence
<220> FEATURE:
<223> OTHER INFORMATION: Synthetic Construct

<400> SEQUENCE: 416

Ala Arg Phe Asp Tyr Gly Ser Ser Leu Asp Ser
1               5                   10

<210> SEQ ID NO 417
<211> LENGTH: 11
<212> TYPE: PRT
<213> ORGANISM: Artificial Sequence
<220> FEATURE:
<223> OTHER INFORMATION: Synthetic Construct

<400> SEQUENCE: 417

Trp Gly Gln Gly Thr Leu Leu Thr Val Ser Ser
1               5                   10

<210> SEQ ID NO 418
<211> LENGTH: 321
<212> TYPE: DNA
<213> ORGANISM: Artificial Sequence
<220> FEATURE:
<223> OTHER INFORMATION: Synthetic Construct

<400> SEQUENCE: 418
gaaattgtgc ttacccagtc cccagacttc ctgtccgtga cccctaaaga gaaggtgaca      60
ctgacttgca gggcctcaca atccattggc aataaccttc actggtatca gcagaagtcc     120
gaccagtctc cgaaactcct catcaagtat gccagccagt caattagcgg aataccgtct     180
cggtttagcg gatctgggtc tggtactgac ttcacgctga cgatcaatag cgtggaagcg    240
gaggacgccg ccacctattt ctgccagcaa tctaagtcct ggccgagaac gttcggaggc    300
ggtactaaac ttgagatcaa g                                              321

<210> SEQ ID NO 419
<211> LENGTH: 78
<212> TYPE: DNA
<213> ORGANISM: Artificial Sequence
<220> FEATURE:
<223> OTHER INFORMATION: Synthetic Construct

<400> SEQUENCE: 419
gaaattgtgc ttacccagtc cccagacttc ctgtccgtga cccctaaaga gaaggtgaca    60
ctgacttgca gggcctca                                                  78

<210> SEQ ID NO 420
<211> LENGTH: 18
<212> TYPE: DNA
<213> ORGANISM: Artificial Sequence
<220> FEATURE:
<223> OTHER INFORMATION: Synthetic Construct

<400> SEQUENCE: 420
caatccattg gcaataac                                                  18

<210> SEQ ID NO 421
<211> LENGTH: 51
<212> TYPE: DNA
<213> ORGANISM: Artificial Sequence
<220> FEATURE:
<223> OTHER INFORMATION: Synthetic Construct

<400> SEQUENCE: 421
cttcactggt atcagcagaa gtccgaccag tctccgaaac tcctcatcaa g             51

<210> SEQ ID NO 422
<211> LENGTH: 9
<212> TYPE: DNA
<213> ORGANISM: Artificial Sequence
<220> FEATURE:
<223> OTHER INFORMATION: Synthetic Construct

<400> SEQUENCE: 422 tatgccagc                                                            9

<210> SEQ ID NO 423
<211> LENGTH: 108
<212> TYPE: DNA
<213> ORGANISM: Artificial Sequence
<220> FEATURE:
<223> OTHER INFORMATION: Synthetic Construct

<400> SEQUENCE: 423
cagtcaatta gcggaatacc gtctcggttt agcggatctg ggtctggtac tgacttcacg    60
ctgacgatca atagcgtgga agcggaggac gccgccacct atttctgc                 108

<210> SEQ ID NO 424
<211> LENGTH: 27
<212> TYPE: DNA
<213> ORGANISM: Artificial Sequence
<220> FEATURE:
<223> OTHER INFORMATION: Synthetic Construct

<400> SEQUENCE: 424
cagcaatcta agtcctggcc gagaacg　　　　　　　　　　　　　　　　　　　27

<210> SEQ ID NO 425
<211> LENGTH: 30
<212> TYPE: DNA
<213> ORGANISM: Artificial Sequence
<220> FEATURE:
<223> OTHER INFORMATION: Synthetic Construct

<400> SEQUENCE: 425
ttcggaggcg gtactaaact tgagatcaag　　　　　　　　　　　　　　　　30

<210> SEQ ID NO 426
<211> LENGTH: 107
<212> TYPE: PRT
<213> ORGANISM: Artificial Sequence
<220> FEATURE:
<223> OTHER INFORMATION: Synthetic Construct

<400> SEQUENCE: 426

Glu Ile Val Leu Thr Gln Ser Pro Asp Phe Leu Ser Val Thr Pro Lys
1               5                   10                  15

Glu Lys Val Thr Leu Thr Cys Arg Ala Ser Gln Ser Ile Gly Asn Asn
            20                  25                  30

Leu His Trp Tyr Gln Gln Lys Ser Asp Gln Ser Pro Lys Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Thr Ile Asn Ser Val Glu Ala
65                  70                  75                  80

Glu Asp Ala Ala Thr Tyr Phe Cys Gln Gln Ser Lys Ser Trp Pro Arg
                85                  90                  95

Thr Phe Gly Gly Gly Thr Lys Leu Glu Ile Lys
            100                 105

<210> SEQ ID NO 427
<211> LENGTH: 26
<212> TYPE: PRT
<213> ORGANISM: Artificial Sequence
<220> FEATURE:
<223> OTHER INFORMATION: Synthetic Construct

<400> SEQUENCE: 427

Glu Ile Val Leu Thr Gln Ser Pro Asp Phe Leu Ser Val Thr Pro Lys
1               5                   10                  15

Glu Lys Val Thr Leu Thr Cys Arg Ala Ser
            20                  25

<210> SEQ ID NO 428
<211> LENGTH: 6
<212> TYPE: PRT
<213> ORGANISM: Artificial Sequence
<220> FEATURE:
<223> OTHER INFORMATION: Synthetic Construct

<400> SEQUENCE: 428

Gln Ser Ile Gly Asn Asn
1               5

<210> SEQ ID NO 429
<211> LENGTH: 17

```
<212> TYPE: PRT
<213> ORGANISM: Artificial Sequence
<220> FEATURE:
<223> OTHER INFORMATION: Synthetic Construct

<400> SEQUENCE: 429

Leu His Trp Tyr Gln Gln Lys Ser Asp Gln Ser Pro Lys Leu Leu Ile
1               5                   10                  15

Lys

<210> SEQ ID NO 430
<211> LENGTH: 3
<212> TYPE: PRT
<213> ORGANISM: Artificial Sequence
<220> FEATURE:
<223> OTHER INFORMATION: Synthetic Construct

<400> SEQUENCE: 430

Tyr Ala Ser
1

<210> SEQ ID NO 431
<211> LENGTH: 36
<212> TYPE: PRT
<213> ORGANISM: Artificial Sequence
<220> FEATURE:
<223> OTHER INFORMATION: Synthetic Construct

<400> SEQUENCE: 431

Gln Ser Ile Ser Gly Ile Pro Ser Arg Phe Ser Gly Ser Gly Ser Gly
1               5                   10                  15

Thr Asp Phe Thr Leu Thr Ile Asn Ser Val Glu Ala Glu Asp Ala Ala
            20                  25                  30

Thr Tyr Phe Cys
        35

<210> SEQ ID NO 432
<211> LENGTH: 9
<212> TYPE: PRT
<213> ORGANISM: Artificial Sequence
<220> FEATURE:
<223> OTHER INFORMATION: Synthetic Construct

<400> SEQUENCE: 432

Gln Gln Ser Lys Ser Trp Pro Arg Thr
1               5

<210> SEQ ID NO 433
<211> LENGTH: 10
<212> TYPE: PRT
<213> ORGANISM: Artificial Sequence
<220> FEATURE:
<223> OTHER INFORMATION: Synthetic Construct

<400> SEQUENCE: 433

Phe Gly Gly Gly Thr Lys Leu Glu Ile Lys
1               5                   10

<210> SEQ ID NO 434
<211> LENGTH: 354
<212> TYPE: DNA
<213> ORGANISM: Artificial Sequence
<220> FEATURE:
<223> OTHER INFORMATION: Synthetic Construct

<400> SEQUENCE: 434
```

```
gaggtacagc tcgtcgaaag tggcggcggt cttgtcaagc cgggaggaag tttgcgcctg    60
tcctgtgcag catccggatt cacgttttct tcttatacga tgagttgggt ccggcaggca   120
ccggggaaag gattggaatg ggttgcgtct attagtagct ctggatctaa cacatactac   180
ccagactcag ttaaaggtcg cttcacgata agtcgggaca acgctaaaaa taacctgtat   240
ttgcaaatga acagcttgcg agctgaggac accgccctct actactgtgc ccgatttgat   300
tatggatcaa gtttggattc atggggccaa gggaccctgc tcacagtaag ctct         354
```

<210> SEQ ID NO 435
<211> LENGTH: 75
<212> TYPE: DNA
<213> ORGANISM: Artificial Sequence
<220> FEATURE:
<223> OTHER INFORMATION: Synthetic Construct

<400> SEQUENCE: 435

```
gaggtacagc tcgtcgaaag tggcggcggt cttgtcaagc cgggaggaag tttgcgcctg    60
tcctgtgcag catcc                                                     75
```

<210> SEQ ID NO 436
<211> LENGTH: 24
<212> TYPE: DNA
<213> ORGANISM: Artificial Sequence
<220> FEATURE:
<223> OTHER INFORMATION: Synthetic Construct

<400> SEQUENCE: 436

```
ggattcacgt tttcttctta tacg                                           24
```

<210> SEQ ID NO 437
<211> LENGTH: 51
<212> TYPE: DNA
<213> ORGANISM: Artificial Sequence
<220> FEATURE:
<223> OTHER INFORMATION: Synthetic Construct

<400> SEQUENCE: 437

```
atgagttggg tccggcaggc accggggaaa ggattggaat gggttgcgtc t             51
```

<210> SEQ ID NO 438
<211> LENGTH: 24
<212> TYPE: DNA
<213> ORGANISM: Artificial Sequence
<220> FEATURE:
<223> OTHER INFORMATION: Synthetic Construct

<400> SEQUENCE: 438

```
attagtagct ctggatctaa caca                                           24
```

<210> SEQ ID NO 439
<211> LENGTH: 114
<212> TYPE: DNA
<213> ORGANISM: Artificial Sequence
<220> FEATURE:
<223> OTHER INFORMATION: Synthetic Construct

<400> SEQUENCE: 439

```
tactacccag actcagttaa aggtcgcttc acgataagtc gggacaacgc taaaataac    60 ctgtatttgc aaatgaacag cttgcgagct gaggacaccg ccctctacta ctgt        114
```

<210> SEQ ID NO 440

```
<211> LENGTH: 33
<212> TYPE: DNA
<213> ORGANISM: Artificial Sequence
<220> FEATURE:
<223> OTHER INFORMATION: Synthetic Construct

<400> SEQUENCE: 440
gcccgatttg attatggatc aagtttggat tca                                    33

<210> SEQ ID NO 441
<211> LENGTH: 33
<212> TYPE: DNA
<213> ORGANISM: Artificial Sequence
<220> FEATURE:
<223> OTHER INFORMATION: Synthetic Construct

<400> SEQUENCE: 441
tggggccaag ggaccctgct cacagtaagc tct                                    33

<210> SEQ ID NO 442
<211> LENGTH: 118
<212> TYPE: PRT
<213> ORGANISM: Artificial Sequence
<220> FEATURE:
<223> OTHER INFORMATION: Synthetic Construct

<400> SEQUENCE: 442

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Ser Ile Ser Ser Gly Ser Asn Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Asn Ser Leu Arg Ala Glu Asp Thr Ala Leu Tyr Tyr Cys
                85                  90                  95

Ala Arg Phe Asp Tyr Gly Ser Ser Leu Asp Ser Trp Gly Gln Gly Thr
            100                 105                 110

Leu Leu Thr Val Ser Ser
        115

<210> SEQ ID NO 443
<211> LENGTH: 25
<212> TYPE: PRT
<213> ORGANISM: Artificial Sequence
<220> FEATURE:
<223> OTHER INFORMATION: Synthetic Construct

<400> SEQUENCE: 443

Glu Val Gln Leu Val Glu Ser Gly Gly Gly Leu Val Lys Pro Gly Gly
1               5                   10                  15

Ser Leu Arg Leu Ser Cys Ala Ala Ser
            20                  25

<210> SEQ ID NO 444
<211> LENGTH: 8
<212> TYPE: PRT
<213> ORGANISM: Artificial Sequence
<220> FEATURE:
<223> OTHER INFORMATION: Synthetic Construct
```

```
<400> SEQUENCE: 444

Gly Phe Thr Phe Ser Ser Tyr Thr
1               5

<210> SEQ ID NO 445
<211> LENGTH: 17
<212> TYPE: PRT
<213> ORGANISM: Artificial Sequence
<220> FEATURE:
<223> OTHER INFORMATION: Synthetic Construct

<400> SEQUENCE: 445

Met Ser Trp Val Arg Gln Ala Pro Gly Lys Gly Leu Glu Trp Val Ala
1               5                   10                  15
Ser

<210> SEQ ID NO 446
<211> LENGTH: 8
<212> TYPE: PRT
<213> ORGANISM: Artificial Sequence
<220> FEATURE:
<223> OTHER INFORMATION: Synthetic Construct

<400> SEQUENCE: 446

Ile Ser Ser Ser Gly Ser Asn Thr
1               5

<210> SEQ ID NO 447
<211> LENGTH: 38
<212> TYPE: PRT
<213> ORGANISM: Artificial Sequence
<220> FEATURE:
<223> OTHER INFORMATION: Synthetic Construct

<400> SEQUENCE: 447

Tyr Tyr Pro Asp Ser Val Lys Gly Arg Phe Thr Ile Ser Arg Asp Asn
1               5                   10                  15

Ala Lys Asn Asn Leu Tyr Leu Gln Met Asn Ser Leu Arg Ala Glu Asp
            20                  25                  30

Thr Ala Leu Tyr Tyr Cys
        35

<210> SEQ ID NO 448
<211> LENGTH: 11
<212> TYPE: PRT
<213> ORGANISM: Artificial Sequence
<220> FEATURE:
<223> OTHER INFORMATION: Synthetic Construct

<400> SEQUENCE: 448

Ala Arg Phe Asp Tyr Gly Ser Ser Leu Asp Ser
1               5                   10

<210> SEQ ID NO 449
<211> LENGTH: 11
<212> TYPE: PRT
<213> ORGANISM: Artificial Sequence
<220> FEATURE:
<223> OTHER INFORMATION: Synthetic Construct

<400> SEQUENCE: 449

Trp Gly Gln Gly Thr Leu Leu Thr Val Ser Ser
1               5                   10
```

<210> SEQ ID NO 450
<211> LENGTH: 321
<212> TYPE: DNA
<213> ORGANISM: Artificial Sequence
<220> FEATURE:
<223> OTHER INFORMATION: Synthetic Construct

<400> SEQUENCE: 450

```
gaaatcgttc ttactcagtc cccggatttt tgagtgtaa cgcctaaaga gaaggtgacc    60
ctgtcctgcc gcgcttccca atctatatca aactatcttc attggtacca gcaaaaaagc   120
gaccagtccc cgaaactgct catcaaatac gctagccaat caataagcgg catccctagc   180
aggttttccg gtagcggtag tggcacagac ttcacattga gcataaacag cgtggaagcc   240
gaggatgcag caacatactt ttgccaacag agcaagtcct ggccgaggac gttcggtggg   300
ggcaccaaat tggaaataaa g                                             321
```

<210> SEQ ID NO 451
<211> LENGTH: 78
<212> TYPE: DNA
<213> ORGANISM: Artificial Sequence
<220> FEATURE:
<223> OTHER INFORMATION: Synthetic Construct

<400> SEQUENCE: 451

```
gaaatcgttc ttactcagtc cccggatttt tgagtgtaa cgcctaaaga gaaggtgacc    60
ctgtcctgcc gcgcttcc                                                  78
```

<210> SEQ ID NO 452
<211> LENGTH: 18
<212> TYPE: DNA
<213> ORGANISM: Artificial Sequence
<220> FEATURE:
<223> OTHER INFORMATION: Synthetic Construct

<400> SEQUENCE: 452

```
caatctatat caaactat                                                  18
```

<210> SEQ ID NO 453
<211> LENGTH: 51
<212> TYPE: DNA
<213> ORGANISM: Artificial Sequence
<220> FEATURE:
<223> OTHER INFORMATION: Synthetic Construct

<400> SEQUENCE: 453

```
cttcattggt accagcaaaa aagcgaccag tccccgaaac tgctcatcaa a             51
```

<210> SEQ ID NO 454
<211> LENGTH: 9
<212> TYPE: DNA
<213> ORGANISM: Artificial Sequence
<220> FEATURE:
<223> OTHER INFORMATION: Synthetic Construct

<400> SEQUENCE: 454

```
tacgctagc                                                             9
```

<210> SEQ ID NO 455
<211> LENGTH: 108
<212> TYPE: DNA
<213> ORGANISM: Artificial Sequence
<220> FEATURE:
<223> OTHER INFORMATION: Synthetic Construct

<400> SEQUENCE: 455
caatcaataa gcggcatccc tagcaggttt tccggtagcg gtagtggcac agacttcaca    60
ttgagcataa acagcgtgga agccgaggat gcagcaacat acttttgc    108

<210> SEQ ID NO 456
<211> LENGTH: 27
<212> TYPE: DNA
<213> ORGANISM: Artificial Sequence
<220> FEATURE:
<223> OTHER INFORMATION: Synthetic Construct

<400> SEQUENCE: 456
caacagagca agtcctggcc gaggacg    27

<210> SEQ ID NO 457
<211> LENGTH: 30
<212> TYPE: DNA
<213> ORGANISM: Artificial Sequence
<220> FEATURE:
<223> OTHER INFORMATION: Synthetic Construct

<400> SEQUENCE: 457
ttcggtgggg gcaccaaatt ggaaataaag    30

<210> SEQ ID NO 458
<211> LENGTH: 107
<212> TYPE: PRT
<213> ORGANISM: Artificial Sequence
<220> FEATURE:
<223> OTHER INFORMATION: Synthetic Construct

<400> SEQUENCE: 458

Glu Ile Val Leu Thr Gln Ser Pro Asp Phe Leu Ser Val Thr Pro Lys
1               5                   10                  15

Glu Lys Val Thr Leu Ser Cys Arg Ala Ser Gln Ser Ile Ser Asn Tyr
            20                  25                  30

Leu His Trp Tyr Gln Gln Lys Ser Asp Gln Ser Pro Lys Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Ala
65                  70                  75                  80

Glu Asp Ala Ala Thr Tyr Phe Cys Gln Gln Ser Lys Ser Trp Pro Arg
                85                  90                  95

Thr Phe Gly Gly Gly Thr Lys Leu Glu Ile Lys
            100                 105

<210> SEQ ID NO 459
<211> LENGTH: 26
<212> TYPE: PRT
<213> ORGANISM: Artificial Sequence
<220> FEATURE:
<223> OTHER INFORMATION: Synthetic Construct

<400> SEQUENCE: 459

Glu Ile Val Leu Thr Gln Ser Pro Asp Phe Leu Ser Val Thr Pro Lys
1               5                   10                  15

Glu Lys Val Thr Leu Ser Cys Arg Ala Ser
            20                  25

```
<210> SEQ ID NO 460
<211> LENGTH: 6
<212> TYPE: PRT
<213> ORGANISM: Artificial Sequence
<220> FEATURE:
<223> OTHER INFORMATION: Synthetic Construct

<400> SEQUENCE: 460

Gln Ser Ile Ser Asn Tyr
1               5

<210> SEQ ID NO 461
<211> LENGTH: 17
<212> TYPE: PRT
<213> ORGANISM: Artificial Sequence
<220> FEATURE:
<223> OTHER INFORMATION: Synthetic Construct

<400> SEQUENCE: 461

Leu His Trp Tyr Gln Gln Lys Ser Asp Gln Ser Pro Lys Leu Leu Ile
1               5                   10                  15

Lys

<210> SEQ ID NO 462
<211> LENGTH: 3
<212> TYPE: PRT
<213> ORGANISM: Artificial Sequence
<220> FEATURE:
<223> OTHER INFORMATION: Synthetic Construct

<400> SEQUENCE: 462

Tyr Ala Ser
1

<210> SEQ ID NO 463
<211> LENGTH: 36
<212> TYPE: PRT
<213> ORGANISM: Artificial Sequence
<220> FEATURE:
<223> OTHER INFORMATION: Synthetic Construct

<400> SEQUENCE: 463

Gln Ser Ile Ser Gly Ile Pro Ser Arg Phe Ser Gly Ser Gly Ser Gly
1               5                   10                  15

Thr Asp Phe Thr Leu Ser Ile Asn Ser Val Glu Ala Glu Asp Ala Ala
            20                  25                  30

Thr Tyr Phe Cys
        35

<210> SEQ ID NO 464
<211> LENGTH: 9
<212> TYPE: PRT
<213> ORGANISM: Artificial Sequence
<220> FEATURE:
<223> OTHER INFORMATION: Synthetic Construct

<400> SEQUENCE: 464

Gln Gln Ser Lys Ser Trp Pro Arg Thr
1               5

<210> SEQ ID NO 465
<211> LENGTH: 10
<212> TYPE: PRT
<213> ORGANISM: Artificial Sequence
<220> FEATURE:
<223> OTHER INFORMATION: Synthetic Construct
```

<400> SEQUENCE: 465

Phe Gly Gly Gly Thr Lys Leu Glu Ile Lys
1               5                   10

<210> SEQ ID NO 466
<211> LENGTH: 354
<212> TYPE: DNA
<213> ORGANISM: Artificial Sequence
<220> FEATURE:
<223> OTHER INFORMATION: Synthetic Construct

<400> SEQUENCE: 466
gaggtccaac ttgttgaatc cggtggaggg ctggtgcagc ctggtggatc cctccgcctt    60
tcctgtgcag catcaggttt tacttttccc tcatacacca tgtcttgggt tcgccaggct   120
ccagggaaag gattggaatg ggtggcaact atcagtagta gcggggacaa tacatactat   180
cccgattccg tgaaagggag atttacgatt tcacgcgaca acagcaaaaa tacccttac   240 ctgcaaatga gttccttgcg ggccgaggac actgccctct actactgcgc tcgcttcgat   300
tacggttcca gcctggactc atggggtcaa ggactacac tgactgtttc ttcc           354

<210> SEQ ID NO 467
<211> LENGTH: 75
<212> TYPE: DNA
<213> ORGANISM: Artificial Sequence
<220> FEATURE:
<223> OTHER INFORMATION: Synthetic Construct

<400> SEQUENCE: 467
gaggtccaac ttgttgaatc cggtggaggg ctggtgcagc ctggtggatc cctccgcctt    60
tcctgtgcag catca                                                     75

<210> SEQ ID NO 468
<211> LENGTH: 24
<212> TYPE: DNA
<213> ORGANISM: Artificial Sequence
<220> FEATURE:
<223> OTHER INFORMATION: Synthetic Construct

<400> SEQUENCE: 468
ggttttactt tttcctcata cacc                                           24

<210> SEQ ID NO 469
<211> LENGTH: 51
<212> TYPE: DNA
<213> ORGANISM: Artificial Sequence
<220> FEATURE:
<223> OTHER INFORMATION: Synthetic Construct

<400> SEQUENCE: 469
atgtcttggg ttcgccaggc tccagggaaa ggattggaat gggtggcaac t              51

<210> SEQ ID NO 470
<211> LENGTH: 24
<212> TYPE: DNA
<213> ORGANISM: Artificial Sequence
<220> FEATURE:
<223> OTHER INFORMATION: Synthetic Construct

<400> SEQUENCE: 470
atcagtagta gcggggacaa taca                                           24

<210> SEQ ID NO 471
<211> LENGTH: 114
<212> TYPE: DNA
<213> ORGANISM: Artificial Sequence
<220> FEATURE:
<223> OTHER INFORMATION: Synthetic Construct

<400> SEQUENCE: 471

```
tactatcccg attccgtgaa agggagattt acgatttcac gcgacaacag caaaaatacc    60
ctttacctgc aaatgagttc cttgcgggcc gaggacactg ccctctacta ctgc         114
```

<210> SEQ ID NO 472
<211> LENGTH: 33
<212> TYPE: DNA
<213> ORGANISM: Artificial Sequence
<220> FEATURE:
<223> OTHER INFORMATION: Synthetic Construct

<400> SEQUENCE: 472

```
gctcgcttcg attacggttc cagcctggac tca                                 33
```

<210> SEQ ID NO 473
<211> LENGTH: 33
<212> TYPE: DNA
<213> ORGANISM: Artificial Sequence
<220> FEATURE:
<223> OTHER INFORMATION: Synthetic Construct

<400> SEQUENCE: 473

```
tggggtcaag ggactacact gactgtttct tcc                                 33
```

<210> SEQ ID NO 474
<211> LENGTH: 118
<212> TYPE: PRT
<213> ORGANISM: Artificial Sequence
<220> FEATURE:
<223> OTHER INFORMATION: Synthetic Construct

<400> SEQUENCE: 474

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Ser Ser Gly Asp Asn Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Leu Tyr Tyr Cys
                85                  90                  95

Ala Arg Phe Asp Tyr Gly Ser Ser Leu Asp Ser Trp Gly Gln Gly Thr
            100                 105                 110

Thr Leu Thr Val Ser Ser
        115

<210> SEQ ID NO 475
<211> LENGTH: 25
<212> TYPE: PRT
<213> ORGANISM: Artificial Sequence
<220> FEATURE:
<223> OTHER INFORMATION: Synthetic Construct

```
<400> SEQUENCE: 475

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 476
<211> LENGTH: 8
<212> TYPE: PRT
<213> ORGANISM: Artificial Sequence
<220> FEATURE:
<223> OTHER INFORMATION: Synthetic Construct

<400> SEQUENCE: 476

Gly Phe Thr Phe Ser Ser Tyr Thr
1               5

<210> SEQ ID NO 477
<211> LENGTH: 17
<212> TYPE: PRT
<213> ORGANISM: Artificial Sequence
<220> FEATURE:
<223> OTHER INFORMATION: Synthetic Construct

<400> SEQUENCE: 477

Met Ser Trp Val Arg Gln Ala Pro Gly Lys Gly Leu Glu Trp Val Ala
1               5                   10                  15

Thr

<210> SEQ ID NO 478
<211> LENGTH: 8
<212> TYPE: PRT
<213> ORGANISM: Artificial Sequence
<220> FEATURE:
<223> OTHER INFORMATION: Synthetic Construct

<400> SEQUENCE: 478

Ile Ser Ser Ser Gly Asp Asn Thr
1               5

<210> SEQ ID NO 479
<211> LENGTH: 38
<212> TYPE: PRT
<213> ORGANISM: Artificial Sequence
<220> FEATURE:
<223> OTHER INFORMATION: Synthetic Construct

<400> SEQUENCE: 479

Tyr Tyr Pro Asp Ser Val Lys Gly Arg Phe Thr Ile Ser Arg Asp Asn
1               5                   10                  15

Ser Lys Asn Thr Leu Tyr Leu Gln Met Ser Ser Leu Arg Ala Glu Asp
            20                  25                  30

Thr Ala Leu Tyr Tyr Cys
        35

<210> SEQ ID NO 480
<211> LENGTH: 11
<212> TYPE: PRT
<213> ORGANISM: Artificial Sequence
<220> FEATURE:
<223> OTHER INFORMATION: Synthetic Construct

<400> SEQUENCE: 480

Ala Arg Phe Asp Tyr Gly Ser Ser Leu Asp Ser
```

<210> SEQ ID NO 481
<211> LENGTH: 11
<212> TYPE: PRT
<213> ORGANISM: Artificial Sequence
<220> FEATURE:
<223> OTHER INFORMATION: Synthetic Construct

<400> SEQUENCE: 481

Trp Gly Gln Gly Thr Thr Leu Thr Val Ser Ser
1               5                   10

<210> SEQ ID NO 482
<211> LENGTH: 321
<212> TYPE: DNA
<213> ORGANISM: Artificial Sequence
<220> FEATURE:
<223> OTHER INFORMATION: Synthetic Construct

<400> SEQUENCE: 482
gagatcgtgc tcacccaatc tcctgacttc cttagcgtta caccagggga gaaagtaact      60
cttacgtgcc gggcctccca gagcatctcc aattatttgc attggtacca gcaaaagagt     120
gaccagagcc ctaagctgct catcaaatac gcatcacaga gtattagcgg cgttccctca     180
cggttctctg gctccggttc cggtacagac ttcactttga cgatttcaag tgtagaggcc     240
gaggacttcg caacttactt tgtcagcaa agcaaatcct ggcctcgaac tttcggcggg     300
ggtacaaaac tcgaaatcaa g                                              321

<210> SEQ ID NO 483
<211> LENGTH: 78
<212> TYPE: DNA
<213> ORGANISM: Artificial Sequence
<220> FEATURE:
<223> OTHER INFORMATION: Synthetic Construct

<400> SEQUENCE: 483
gagatcgtgc tcacccaatc tcctgacttc cttagcgtta caccagggga gaaagtaact      60
cttacgtgcc gggcctcc                                                   78

<210> SEQ ID NO 484
<211> LENGTH: 18
<212> TYPE: DNA
<213> ORGANISM: Artificial Sequence
<220> FEATURE:
<223> OTHER INFORMATION: Synthetic Construct

<400> SEQUENCE: 484
cagagcatct ccaattat                                                   18

<210> SEQ ID NO 485
<211> LENGTH: 51
<212> TYPE: DNA
<213> ORGANISM: Artificial Sequence
<220> FEATURE:
<223> OTHER INFORMATION: Synthetic Construct

<400> SEQUENCE: 485
ttgcattggt accagcaaaa gagtgaccag agccctaagc tgctcatcaa a              51

<210> SEQ ID NO 486
<211> LENGTH: 9
<212> TYPE: DNA

```
<213> ORGANISM: Artificial Sequence
<220> FEATURE:
<223> OTHER INFORMATION: Synthetic Construct

<400> SEQUENCE: 486 tacgcatca                                                                 9

<210> SEQ ID NO 487
<211> LENGTH: 108
<212> TYPE: DNA
<213> ORGANISM: Artificial Sequence
<220> FEATURE:
<223> OTHER INFORMATION: Synthetic Construct

<400> SEQUENCE: 487
cagagtatta gcggcgttcc ctcacggttc tctggctccg gttccggtac agacttcact      60
ttgacgattt caagtgtaga ggccgaggac ttcgcaactt acttttgt                  108

<210> SEQ ID NO 488
<211> LENGTH: 27
<212> TYPE: DNA
<213> ORGANISM: Artificial Sequence
<220> FEATURE:
<223> OTHER INFORMATION: Synthetic Construct

<400> SEQUENCE: 488
cagcaaagca atcctggcc tcgaact                                             27

<210> SEQ ID NO 489
<211> LENGTH: 30
<212> TYPE: DNA
<213> ORGANISM: Artificial Sequence
<220> FEATURE:
<223> OTHER INFORMATION: Synthetic Construct

<400> SEQUENCE: 489
ttcggcgggg gtacaaaact cgaaatcaag                                         30

<210> SEQ ID NO 490
<211> LENGTH: 107
<212> TYPE: PRT
<213> ORGANISM: Artificial Sequence
<220> FEATURE:
<223> OTHER INFORMATION: Synthetic Construct

<400> SEQUENCE: 490

Glu Ile Val Leu Thr Gln Ser Pro Asp Phe Leu Ser Val Thr Pro Gly
1               5                   10                  15

Glu Lys Val Thr Leu Thr Cys Arg Ala Ser Gln Ser Ile Ser Asn Tyr
            20                  25                  30

Leu His Trp Tyr Gln Gln Lys Ser Asp Gln Ser Pro Lys Leu Leu Ile
        35                  40                  45

Lys Tyr Ala Ser Gln Ser Ile Ser Gly Val Pro Ser Arg Phe Ser Gly
    50                  55                  60

Ser Gly Ser Gly Thr Asp Phe Thr Leu Thr Ile Ser Ser Val Glu Ala
65                  70                  75                  80

Glu Asp Phe Ala Thr Tyr Phe Cys Gln Gln Ser Lys Ser Trp Pro Arg
                85                  90                  95

Thr Phe Gly Gly Gly Thr Lys Leu Glu Ile Lys
            100                 105

<210> SEQ ID NO 491
```

```
<211> LENGTH: 26
<212> TYPE: PRT
<213> ORGANISM: Artificial Sequence
<220> FEATURE:
<223> OTHER INFORMATION: Synthetic Construct

<400> SEQUENCE: 491

Glu Ile Val Leu Thr Gln Ser Pro Asp Phe Leu Ser Val Thr Pro Gly
1               5                   10                  15

Glu Lys Val Thr Leu Thr Cys Arg Ala Ser
            20                  25

<210> SEQ ID NO 492
<211> LENGTH: 6
<212> TYPE: PRT
<213> ORGANISM: Artificial Sequence
<220> FEATURE:
<223> OTHER INFORMATION: Synthetic Construct

<400> SEQUENCE: 492

Gln Ser Ile Ser Asn Tyr
1               5

<210> SEQ ID NO 493
<211> LENGTH: 17
<212> TYPE: PRT
<213> ORGANISM: Artificial Sequence
<220> FEATURE:
<223> OTHER INFORMATION: Synthetic Construct

<400> SEQUENCE: 493

Leu His Trp Tyr Gln Gln Lys Ser Asp Gln Ser Pro Lys Leu Leu Ile
1               5                   10                  15

Lys

<210> SEQ ID NO 494
<211> LENGTH: 3
<212> TYPE: PRT
<213> ORGANISM: Artificial Sequence
<220> FEATURE:
<223> OTHER INFORMATION: Synthetic Construct

<400> SEQUENCE: 494

Tyr Ala Ser
1

<210> SEQ ID NO 495
<211> LENGTH: 36
<212> TYPE: PRT
<213> ORGANISM: Artificial Sequence
<220> FEATURE:
<223> OTHER INFORMATION: Synthetic Construct

<400> SEQUENCE: 495

Gln Ser Ile Ser Gly Val Pro Ser Arg Phe Ser Gly Ser Gly Ser Gly
1               5                   10                  15

Thr Asp Phe Thr Leu Thr Ile Ser Ser Val Glu Ala Glu Asp Phe Ala
            20                  25                  30

Thr Tyr Phe Cys
        35

<210> SEQ ID NO 496
<211> LENGTH: 9
<212> TYPE: PRT
<213> ORGANISM: Artificial Sequence
```

```
<220> FEATURE:
<223> OTHER INFORMATION: Synthetic Construct

<400> SEQUENCE: 496

Gln Gln Ser Lys Ser Trp Pro Arg Thr
1               5

<210> SEQ ID NO 497
<211> LENGTH: 10
<212> TYPE: PRT
<213> ORGANISM: Artificial Sequence
<220> FEATURE:
<223> OTHER INFORMATION: Synthetic Construct

<400> SEQUENCE: 497

Phe Gly Gly Gly Thr Lys Leu Glu Ile Lys
1               5                   10

<210> SEQ ID NO 498
<211> LENGTH: 571
<212> TYPE: PRT
<213> ORGANISM: Artificial Sequence
<220> FEATURE:
<223> OTHER INFORMATION: Synthetic Construct

<400> SEQUENCE: 498

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Thr Met Ser Trp Val Arg Gln Ala Pro Gly Lys Gly Leu Glu Trp Val
            35                  40                  45

Ala Ser Ile Ser Ser Ser Gly Ser Asn Thr Tyr Tyr Pro Asp Ser Val
        50                  55                  60

Lys Gly Arg Phe Thr Ile Ser Arg Asp Asn Ala Lys Asn Asn Leu Tyr
65                  70                  75                  80

Leu Gln Met Asn Ser Leu Arg Ala Glu Asp Thr Ala Leu Tyr Tyr Cys
                85                  90                  95

Ala Arg Phe Asp Tyr Gly Ser Ser Leu Asp Ser Trp Gly Gln Gly Thr
            100                 105                 110

Leu Leu Thr Val Ser Ser Asp Lys Thr His Thr Glu Val Gln Leu Val
        115                 120                 125

Glu Ser Gly Gly Gly Leu Val Lys Pro Gly Gly Ser Leu Arg Leu Ser
    130                 135                 140

Cys Ala Ala Ser Gly Phe Thr Phe Ser Ser Tyr Thr Met Ser Trp Val
145                 150                 155                 160

Arg Gln Ala Pro Gly Lys Gly Leu Glu Trp Val Ala Ser Ile Ser Ser
                165                 170                 175

Ser Gly Ser Asn Thr Tyr Tyr Pro Asp Ser Val Lys Gly Arg Phe Thr
            180                 185                 190

Ile Ser Arg Asp Asn Ala Lys Asn Asn Leu Tyr Leu Gln Met Asn Ser
        195                 200                 205

Leu Arg Ala Glu Asp Thr Ala Leu Tyr Tyr Cys Ala Arg Phe Asp Tyr
    210                 215                 220

Gly Ser Ser Leu Asp Ser Trp Gly Gln Gly Thr Leu Leu Thr Val Ser
225                 230                 235                 240

Ser Asp Lys Thr His Thr Ala Ser Thr Lys Gly Pro Ser Val Phe Pro
                245                 250                 255
```

```
Leu Ala Pro Ser Ser Lys Ser Thr Ser Gly Gly Thr Ala Ala Leu Gly
            260                 265                 270

Cys Leu Val Lys Asp Tyr Phe Pro Glu Pro Val Thr Val Ser Trp Asn
            275                 280                 285

Ser Gly Ala Leu Thr Ser Gly Val His Thr Phe Pro Ala Val Leu Gln
            290                 295                 300

Ser Ser Gly Ser Leu Ser Ser Val Val Thr Val Pro Ser Ser Ser Leu
305                 310                 315                 320

Gly Thr Gln Thr Tyr Ile Cys Asn Val Asn His Lys Pro Ser Asn Thr
            325                 330                 335

Lys Val Asp Lys Lys Val Glu Pro Lys Ser Cys Asp Lys Thr His Thr
            340                 345                 350

Cys Pro Pro Cys Pro Ala Pro Glu Leu Leu Gly Gly Pro Ser Val Phe
            355                 360                 365

Leu Phe Pro Pro Lys Pro Lys Asp Thr Leu Tyr Ile Thr Arg Glu Pro
            370                 375                 380

Glu Val Thr Cys Val Val Val Asp Val Ser His Glu Asp Pro Glu Val
385                 390                 395                 400

Lys Phe Asn Trp Tyr Val Asp Gly Val Glu Val His Asn Ala Lys Thr
            405                 410                 415

Lys Pro Arg Glu Glu Gln Tyr Asn Asn Ala Ser Arg Val Val Ser Val
            420                 425                 430

Leu Thr Val Leu His Gln Asp Trp Leu Asn Gly Lys Glu Tyr Lys Cys
            435                 440                 445

Lys Val Ser Asn Lys Ala Leu Pro Ala Pro Ile Glu Lys Thr Ile Ser
450                 455                 460

Lys Ala Lys Gly Gln Pro Arg Glu Pro Gln Val Tyr Thr Leu Pro Pro
465                 470                 475                 480

Cys Arg Asp Glu Leu Thr Lys Asn Gln Val Ser Leu Trp Cys Leu Val
            485                 490                 495

Lys Gly Phe Tyr Pro Ser Asp Ile Ala Val Glu Trp Glu Ser Asn Gly
            500                 505                 510

Gln Pro Glu Asn Asn Tyr Lys Thr Thr Pro Pro Val Leu Asp Ser Asp
            515                 520                 525

Gly Ser Phe Phe Lys Lys Leu Thr Val Asp Lys Ser Arg Trp Gln Gln
            530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly
            565                 570

<210> SEQ ID NO 499
<211> LENGTH: 440
<212> TYPE: PRT
<213> ORGANISM: Artificial Sequence
<220> FEATURE:
<223> OTHER INFORMATION: Synthetic Construct

<400> SEQUENCE: 499

Gln Val Gln Leu Val Gln Ser Gly Ala Glu Val Val Lys Pro Gly Ser
1               5                   10                  15

Ser Val Lys Val Ser Cys Glu Ala Ser Gly Phe Thr Phe Thr Asp Ser
            20                  25                  30

Val Ile Thr Trp Val Arg Gln Arg Pro Gly Gln Gly Leu Glu Trp Ile
            35                  40                  45
```

Gly Glu Ile Tyr Pro Gly Ser Gly Asn Phe Tyr Tyr Asn Glu Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Phe Cys
                 85                  90                  95

Ala Met Arg Arg Ser Ser Trp Gly Gln Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys Asp Lys Thr His Thr Cys Pro Pro Cys Pro
210                 215                 220

Ala Pro Glu Leu Leu Gly Gly Pro Ser Val Phe Leu Phe Pro Pro Lys
225                 230                 235                 240

Pro Lys Asp Thr Leu Tyr Ile Thr Arg Glu Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Asn Ala Ser Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Cys Thr Leu Pro Pro Ser Arg Asp Glu Leu
            340                 345                 350

Thr Lys Asn Gln Val Ser Leu Ser Cys Ala Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Val Ser Lys Leu Thr Val Asp Lys Ser Arg Trp Gln Gln Gly Asn Val
                405                 410                 415

Phe Ser Cys Ser Val Met His Glu Ala Leu His Asn Arg Phe Thr Gln
            420                 425                 430

Lys Ser Leu Ser Leu Ser Pro Gly
        435                 440

<210> SEQ ID NO 500
<211> LENGTH: 331
<212> TYPE: PRT

<213> ORGANISM: Artificial Sequence
<220> FEATURE:
<223> OTHER INFORMATION: Synthetic Construct

<400> SEQUENCE: 500

```
Glu Ile Val Leu Thr Gln Ser Pro Asp Phe Leu Ser Val Thr Pro Lys
1               5                   10                  15

Glu Lys Val Thr Leu Thr Cys Arg Ala Ser Gln Ser Ile Ser Asn Asn
            20                  25                  30

Leu His Trp Tyr Gln Gln Lys Ser Asp Gln Ser Pro Lys Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Thr Ile Asn Ser Val Glu Ala
65                  70                  75                  80

Glu Asp Ala Ala Thr Tyr Phe Cys Gln Gln Ser Lys Ser Trp Pro Arg
                85                  90                  95

Thr Phe Gly Gly Gly Thr Lys Leu Glu Ile Lys Asp Lys Thr His Thr
            100                 105                 110

Glu Ile Val Leu Thr Gln Ser Pro Asp Phe Leu Ser Val Thr Pro Lys
        115                 120                 125

Glu Lys Val Thr Leu Thr Cys Arg Ala Ser Gln Ser Ile Ser Asn Asn
    130                 135                 140

Leu His Trp Tyr Gln Gln Lys Ser Asp Gln Ser Pro Lys Leu Leu Ile
145                 150                 155                 160

Lys Tyr Ala Ser Gln Ser Ile Ser Gly Ile Pro Ser Arg Phe Ser Gly
                165                 170                 175

Ser Gly Ser Gly Thr Asp Phe Thr Leu Thr Ile Asn Ser Val Glu Ala
            180                 185                 190

Glu Asp Ala Ala Thr Tyr Phe Cys Gln Gln Ser Lys Ser Trp Pro Arg
        195                 200                 205

Thr Phe Gly Gly Gly Thr Lys Leu Glu Ile Lys Asp Lys Thr His Thr
    210                 215                 220

Arg Thr Val Ala Ala Pro Ser Val Phe Ile Phe Pro Pro Ser Asp Glu
225                 230                 235                 240

Gln Leu Lys Ser Gly Thr Ala Ser Val Val Cys Leu Leu Asn Asn Phe
                245                 250                 255

Tyr Pro Arg Glu Ala Lys Val Gln Trp Lys Val Asp Asn Ala Leu Gln
            260                 265                 270

Ser Gly Asn Ser Gln Glu Ser Val Thr Glu Gln Asp Ser Lys Asp Ser
        275                 280                 285

Thr Tyr Ser Leu Ser Ser Thr Leu Thr Leu Ser Lys Ala Asp Tyr Glu
    290                 295                 300

Lys His Lys Val Tyr Ala Cys Glu Val Thr His Gln Gly Leu Ser Ser
305                 310                 315                 320

Pro Val Thr Lys Ser Phe Asn Arg Gly Glu Cys
                325                 330
```

<210> SEQ ID NO 501
<211> LENGTH: 219
<212> TYPE: PRT
<213> ORGANISM: Artificial Sequence
<220> FEATURE:
<223> OTHER INFORMATION: Synthetic Construct

<400> SEQUENCE: 501

```
Asp Val Val Met Thr Gln Thr Pro Leu Ser Leu Ser Val Thr Pro Gly
1               5                   10                  15

Gln Pro Ala Ser Ile Ser Cys Lys Ser Ser Gln Thr Ile Val His Ser
            20                  25                  30

Asn Ser Lys Thr Tyr Leu Glu Trp Tyr Leu Gln Lys Pro Gly Gln Ser
        35                  40                  45

Pro Gln Leu Leu Ile Tyr Lys Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 502
<211> LENGTH: 571
<212> TYPE: PRT
<213> ORGANISM: Artificial Sequence
<220> FEATURE:
<223> OTHER INFORMATION: Synthetic Construct

<400> SEQUENCE: 502

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Ser Ile Ser Ser Ser Gly Ser Asn Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Asn Ser Leu Arg Ala Glu Asp Thr Ala Leu Tyr Tyr Cys
                85                  90                  95

Ala Arg Phe Asp Tyr Gly Ser Ser Leu Asp Ser Trp Gly Gln Gly Thr
            100                 105                 110

Leu Leu Thr Val Ser Ser Asp Lys Thr His Thr Glu Val Gln Leu Val
        115                 120                 125

Glu Ser Gly Gly Gly Leu Val Lys Pro Gly Gly Ser Leu Arg Leu Ser
    130                 135                 140
```

```
Cys Ala Ala Ser Gly Phe Thr Phe Ser Ser Tyr Thr Met Ser Trp Val
145                 150                 155                 160

Arg Gln Ala Pro Gly Lys Gly Leu Glu Trp Val Ala Ser Ile Ser Ser
            165                 170                 175

Ser Gly Ser Asn Thr Tyr Tyr Pro Asp Ser Val Lys Gly Arg Phe Thr
            180                 185                 190

Ile Ser Arg Asp Asn Ala Lys Asn Asn Leu Tyr Leu Gln Met Asn Ser
        195                 200                 205

Leu Arg Ala Glu Asp Thr Ala Leu Tyr Tyr Cys Ala Arg Phe Asp Tyr
    210                 215                 220

Gly Ser Ser Leu Asp Ser Trp Gly Gln Gly Thr Leu Leu Thr Val Ser
225                 230                 235                 240

Ser Asp Lys Thr His Thr Ala Ser Thr Lys Gly Pro Ser Val Phe Pro
            245                 250                 255

Leu Ala Pro Ser Ser Lys Ser Thr Ser Gly Gly Thr Ala Ala Leu Gly
            260                 265                 270

Cys Leu Val Lys Asp Tyr Phe Pro Glu Pro Val Thr Val Ser Trp Asn
        275                 280                 285

Ser Gly Ala Leu Thr Ser Gly Val His Thr Phe Pro Ala Val Leu Gln
290                 295                 300

Ser Ser Gly Ser Leu Ser Ser Val Val Thr Val Pro Ser Ser Ser Leu
305                 310                 315                 320

Gly Thr Gln Thr Tyr Ile Cys Asn Val Asn His Lys Pro Ser Asn Thr
            325                 330                 335

Lys Val Asp Lys Lys Val Glu Pro Lys Ser Cys Asp Lys Thr His Thr
            340                 345                 350

Cys Pro Pro Cys Pro Ala Pro Glu Leu Leu Gly Gly Pro Ser Val Phe
        355                 360                 365

Leu Phe Pro Pro Lys Pro Lys Asp Thr Leu Tyr Ile Thr Arg Glu Pro
    370                 375                 380

Glu Val Thr Cys Val Val Val Asp Val Ser His Glu Asp Pro Glu Val
385                 390                 395                 400

Lys Phe Asn Trp Tyr Val Asp Gly Val Glu Val His Asn Ala Lys Thr
            405                 410                 415

Lys Pro Arg Glu Glu Gln Tyr Asn Asn Ala Ser Arg Val Val Ser Val
            420                 425                 430

Leu Thr Val Leu His Gln Asp Trp Leu Asn Gly Lys Glu Tyr Lys Cys
        435                 440                 445

Lys Val Ser Asn Lys Ala Leu Pro Ala Pro Ile Glu Lys Thr Ile Ser
    450                 455                 460

Lys Ala Lys Gly Gln Pro Arg Glu Pro Gln Val Tyr Thr Leu Pro Pro
465                 470                 475                 480

Cys Arg Asp Glu Leu Thr Lys Asn Gln Val Ser Leu Trp Cys Leu Val
            485                 490                 495

Lys Gly Phe Tyr Pro Ser Asp Ile Ala Val Glu Trp Glu Ser Asn Gly
            500                 505                 510

Gln Pro Glu Asn Asn Tyr Lys Thr Thr Pro Pro Val Leu Asp Ser Asp
        515                 520                 525

Gly Ser Phe Phe Lys Lys Leu Thr Val Asp Lys Ser Arg Trp Gln Gln
    530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly
```

<210> SEQ ID NO 503
<211> LENGTH: 440
<212> TYPE: PRT
<213> ORGANISM: Artificial Sequence
<220> FEATURE:
<223> OTHER INFORMATION: Synthetic Construct

<400> SEQUENCE: 503

```
Gln Val Gln Leu Val Gln Ser Gly Ala Glu Val Val Lys Pro Gly Ser
1               5                   10                  15

Ser Val Lys Val Ser Cys Glu Ala Ser Gly Phe Thr Phe Thr Asp Ser
            20                  25                  30

Val Ile Thr Trp Val Arg Gln Arg Pro Gly Gln Gly Leu Glu Trp Ile
        35                  40                  45

Gly Glu Ile Tyr Pro Gly Ser Gly Asn Phe Tyr Asn Glu Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Met Arg Arg Ser Ser Trp Gly Gln Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys Asp Lys Thr His Thr Cys Pro Pro Cys Pro
210                 215                 220

Ala Pro Glu Leu Leu Gly Gly Pro Ser Val Phe Leu Phe Pro Pro Lys
225                 230                 235                 240

Pro Lys Asp Thr Leu Tyr Ile Thr Arg Glu Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Asn Ala Ser Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Cys Thr Leu Pro Pro Ser Arg Asp Glu Leu
            340                 345                 350

Thr Lys Asn Gln Val Ser Leu Ser Cys Ala Val Lys Gly Phe Tyr Pro
```

```
              355                 360                 365

Ser Asp Ile Ala Val Glu Trp Glu Ser Asn Gly Gln Pro Glu Asn Asn
        370                 375                 380

Tyr Lys Thr Thr Pro Pro Val Leu Asp Ser Asp Gly Ser Phe Phe Leu
385                 390                 395                 400

Val Ser Lys Leu Thr Val Asp Lys Ser Arg Trp Gln Gln Gly Asn Val
                405                 410                 415

Phe Ser Cys Ser Val Met His Glu Ala Leu His Asn Arg Phe Thr Gln
            420                 425                 430

Lys Ser Leu Ser Leu Ser Pro Gly
        435                 440

<210> SEQ ID NO 504
<211> LENGTH: 331
<212> TYPE: PRT
<213> ORGANISM: Artificial Sequence
<220> FEATURE:
<223> OTHER INFORMATION: Synthetic Construct

<400> SEQUENCE: 504

Glu Ile Val Leu Thr Gln Ser Pro Asp Phe Leu Ser Val Thr Pro Lys
1               5                   10                  15

Glu Lys Val Thr Leu Ser Cys Arg Ala Ser Gln Ser Ile Ser Asn Tyr
            20                  25                  30

Leu His Trp Tyr Gln Gln Lys Ser Asp Gln Ser Pro Lys Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Ala
65                  70                  75                  80

Glu Asp Ala Ala Thr Tyr Phe Cys Gln Gln Ser Lys Ser Trp Pro Arg
                85                  90                  95

Thr Phe Gly Gly Gly Thr Lys Leu Glu Ile Lys Asp Lys Thr His Thr
            100                 105                 110

Glu Ile Val Leu Thr Gln Ser Pro Asp Phe Leu Ser Val Thr Pro Lys
        115                 120                 125

Glu Lys Val Thr Leu Thr Cys Arg Ala Ser Gln Ser Ile Ser Asn Asn
    130                 135                 140

Leu His Trp Tyr Gln Gln Lys Ser Asp Gln Ser Pro Lys Leu Leu Ile
145                 150                 155                 160

Lys Tyr Ala Ser Gln Ser Ile Ser Gly Ile Pro Ser Arg Phe Ser Gly
                165                 170                 175

Ser Gly Ser Gly Thr Asp Phe Thr Leu Thr Ile Asn Ser Val Glu Ala
            180                 185                 190

Glu Asp Ala Ala Thr Tyr Phe Cys Gln Gln Ser Lys Ser Trp Pro Arg
        195                 200                 205

Thr Phe Gly Gly Gly Thr Lys Leu Glu Ile Lys Asp Lys Thr His Thr
    210                 215                 220

Arg Thr Val Ala Ala Pro Ser Val Phe Ile Phe Pro Pro Ser Asp Glu
225                 230                 235                 240

Gln Leu Lys Ser Gly Thr Ala Ser Val Val Cys Leu Leu Asn Asn Phe
                245                 250                 255

Tyr Pro Arg Glu Ala Lys Val Gln Trp Lys Val Asp Asn Ala Leu Gln
            260                 265                 270

Ser Gly Asn Ser Gln Glu Ser Val Thr Glu Gln Asp Ser Lys Asp Ser
```

```
                    275                 280                 285
Thr Tyr Ser Leu Ser Ser Thr Leu Thr Leu Ser Lys Ala Asp Tyr Glu
    290                 295                 300

Lys His Lys Val Tyr Ala Cys Glu Val Thr His Gln Gly Leu Ser Ser
305                 310                 315                 320

Pro Val Thr Lys Ser Phe Asn Arg Gly Glu Cys
                325                 330

<210> SEQ ID NO 505
<211> LENGTH: 219
<212> TYPE: PRT
<213> ORGANISM: Artificial Sequence
<220> FEATURE:
<223> OTHER INFORMATION: Synthetic Construct

<400> SEQUENCE: 505

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Thr Ile Val His Ser
                20                  25                  30

Asn Ser Lys Thr Tyr Leu Glu Trp Tyr Leu Gln Lys Pro Gly Gln Ser
            35                  40                  45

Pro Gln Leu Leu Ile Tyr Lys Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 506
<211> LENGTH: 571
<212> TYPE: PRT
<213> ORGANISM: Artificial Sequence
<220> FEATURE:
<223> OTHER INFORMATION: Synthetic Construct

<400> SEQUENCE: 506

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30
```

```
Thr Met Ser Trp Val Arg Gln Ala Pro Gly Lys Gly Leu Glu Trp Val
        35                  40                  45

Ala Ser Ile Ser Ser Gly Ser Asn Thr Tyr Tyr Pro Asp Ser Val
 50                  55                  60

Lys Gly Arg Phe Thr Ile Ser Arg Asp Asn Ala Lys Asn Asn Leu Tyr
 65                  70                  75                  80

Leu Gln Met Asn Ser Leu Arg Ala Glu Asp Thr Ala Leu Tyr Tyr Cys
                 85                  90                  95

Ala Arg Phe Asp Tyr Gly Ser Ser Leu Asp Ser Trp Gly Gln Gly Thr
                100                 105                 110

Leu Leu Thr Val Ser Ser Asp Lys Thr His Thr Glu Val Gln Leu Val
                115                 120                 125

Glu Ser Gly Gly Gly Leu Val Gln Pro Gly Gly Ser Leu Arg Leu Ser
130                 135                 140

Cys Ala Ala Ser Gly Phe Thr Phe Ser Ser Tyr Thr Met Ser Trp Val
145                 150                 155                 160

Arg Gln Ala Pro Gly Lys Gly Leu Glu Trp Val Ala Thr Ile Ser Ser
                165                 170                 175

Ser Gly Asp Asn Thr Tyr Tyr Pro Asp Ser Val Lys Gly Arg Phe Thr
                180                 185                 190

Ile Ser Arg Asp Asn Ser Lys Asn Thr Leu Tyr Leu Gln Met Ser Ser
                195                 200                 205

Leu Arg Ala Glu Asp Thr Ala Leu Tyr Tyr Cys Ala Arg Phe Asp Tyr
                210                 215                 220

Gly Ser Ser Leu Asp Ser Trp Gly Gln Gly Thr Thr Leu Thr Val Ser
225                 230                 235                 240

Ser Asp Lys Thr His Thr Ala Ser Thr Lys Gly Pro Ser Val Phe Pro
                245                 250                 255

Leu Ala Pro Ser Ser Lys Ser Thr Ser Gly Gly Thr Ala Ala Leu Gly
                260                 265                 270

Cys Leu Val Lys Asp Tyr Phe Pro Glu Pro Val Thr Val Ser Trp Asn
                275                 280                 285

Ser Gly Ala Leu Thr Ser Gly Val His Thr Phe Pro Ala Val Leu Gln
290                 295                 300

Ser Ser Gly Ser Leu Ser Ser Val Val Thr Val Pro Ser Ser Ser Leu
305                 310                 315                 320

Gly Thr Gln Thr Tyr Ile Cys Asn Val Asn His Lys Pro Ser Asn Thr
                325                 330                 335

Lys Val Asp Lys Lys Val Glu Pro Lys Ser Cys Asp Lys Thr His Thr
                340                 345                 350

Cys Pro Pro Cys Pro Ala Pro Glu Leu Leu Gly Gly Pro Ser Val Phe
                355                 360                 365

Leu Phe Pro Pro Lys Pro Lys Asp Thr Leu Tyr Ile Thr Arg Glu Pro
                370                 375                 380

Glu Val Thr Cys Val Val Val Asp Val Ser His Glu Asp Pro Glu Val
385                 390                 395                 400

Lys Phe Asn Trp Tyr Val Asp Gly Val Glu Val His Asn Ala Lys Thr
                405                 410                 415

Lys Pro Arg Glu Glu Gln Tyr Asn Asn Ala Ser Arg Val Val Ser Val
                420                 425                 430

Leu Thr Val Leu His Gln Asp Trp Leu Asn Gly Lys Glu Tyr Lys Cys
                435                 440                 445

Lys Val Ser Asn Lys Ala Leu Pro Ala Pro Ile Glu Lys Thr Ile Ser
```

```
                    450                 455                 460
Lys Ala Lys Gly Gln Pro Arg Glu Pro Gln Val Tyr Thr Leu Pro Pro
465                 470                 475                 480

Cys Arg Asp Glu Leu Thr Lys Asn Gln Val Ser Leu Trp Cys Leu Val
                485                 490                 495

Lys Gly Phe Tyr Pro Ser Asp Ile Ala Val Glu Trp Glu Ser Asn Gly
            500                 505                 510

Gln Pro Glu Asn Asn Tyr Lys Thr Thr Pro Pro Val Leu Asp Ser Asp
            515                 520                 525

Gly Ser Phe Phe Lys Leu Thr Val Asp Lys Ser Arg Trp Gln Gln
            530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly
                565                 570

<210> SEQ ID NO 507
<211> LENGTH: 440
<212> TYPE: PRT
<213> ORGANISM: Artificial Sequence
<220> FEATURE:
<223> OTHER INFORMATION: Synthetic Construct

<400> SEQUENCE: 507

Gln Val Gln Leu Val Gln Ser Gly Ala Glu Val Val Lys Pro Gly Ser
1               5                   10                  15

Ser Val Lys Val Ser Cys Glu Ala Ser Gly Phe Thr Phe Thr Asp Ser
            20                  25                  30

Val Ile Thr Trp Val Arg Gln Arg Pro Gly Gln Gly Leu Glu Trp Ile
        35                  40                  45

Gly Glu Ile Tyr Pro Gly Ser Gly Asn Phe Tyr Tyr Asn Glu Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Met Arg Arg Ser Ser Trp Gly Gln Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Ser Leu
                165                 170                 175

Ser Ser Val Val Thr Val Pro Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Tyr Ile Thr Arg Glu Pro Glu Val Thr Cys Val
```

```
                        245                 250                 255
Val Val Asp Val Ser His Glu Asp Pro Glu Val Lys Phe Asn Trp Tyr
                260                 265                 270

Val Asp Gly Val Glu Val His Asn Ala Lys Thr Lys Pro Arg Glu Glu
            275                 280                 285

Gln Tyr Asn Asn Ala Ser Arg Val Val Ser Val Leu Thr Val Leu His
        290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Cys Thr Leu Pro Pro Ser Arg Asp Glu Leu
            340                 345                 350

Thr Lys Asn Gln Val Ser Leu Ser Cys Ala Val Lys Gly Phe Tyr Pro
        355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Val Ser Lys Leu Thr Val Asp Lys Ser Arg Trp Gln Gln Gly Asn Val
                405                 410                 415

Phe Ser Cys Ser Val Met His Glu Ala Leu His Asn Arg Phe Thr Gln
            420                 425                 430

Lys Ser Leu Ser Leu Ser Pro Gly
        435                 440

<210> SEQ ID NO 508
<211> LENGTH: 331
<212> TYPE: PRT
<213> ORGANISM: Artificial Sequence
<220> FEATURE:
<223> OTHER INFORMATION: Synthetic Construct

<400> SEQUENCE: 508

Glu Ile Val Leu Thr Gln Ser Pro Asp Phe Leu Ser Val Thr Pro Gly
1               5                   10                  15

Glu Lys Val Thr Leu Thr Cys Arg Ala Ser Gln Ser Ile Ser Asn Tyr
                20                  25                  30

Leu His Trp Tyr Gln Gln Lys Ser Asp Gln Ser Pro Lys Leu Leu Ile
            35                  40                  45

Lys Tyr Ala Ser Gln Ser Ile Ser Gly Val Pro Ser Arg Phe Ser Gly
        50                  55                  60

Ser Gly Ser Gly Thr Asp Phe Thr Leu Thr Ile Ser Ser Val Glu Ala
65                  70                  75                  80

Glu Asp Phe Ala Thr Tyr Phe Cys Gln Gln Ser Lys Ser Trp Pro Arg
                85                  90                  95

Thr Phe Gly Gly Gly Thr Lys Leu Glu Ile Lys Asp Lys Thr His Thr
            100                 105                 110

Glu Ile Val Leu Thr Gln Ser Pro Asp Phe Leu Ser Val Thr Pro Lys
        115                 120                 125

Glu Lys Val Thr Leu Thr Cys Arg Ala Ser Gln Ser Ile Gly Asn Asn
            130                 135                 140

Leu His Trp Tyr Gln Gln Lys Ser Asp Gln Ser Pro Lys Leu Leu Ile
145                 150                 155                 160

Lys Tyr Ala Ser Gln Ser Ile Ser Gly Ile Pro Ser Arg Phe Ser Gly
```

```
                    165                 170                 175
Ser Gly Ser Gly Thr Asp Phe Thr Leu Thr Ile Asn Ser Val Glu Ala
                180                 185                 190

Glu Asp Ala Ala Thr Tyr Phe Cys Gln Gln Ser Lys Ser Trp Pro Arg
            195                 200                 205

Thr Phe Gly Gly Gly Thr Lys Leu Glu Ile Lys Asp Lys Thr His Thr
        210                 215                 220

Arg Thr Val Ala Ala Pro Ser Val Phe Ile Phe Pro Pro Ser Asp Glu
225                 230                 235                 240

Gln Leu Lys Ser Gly Thr Ala Ser Val Val Cys Leu Leu Asn Asn Phe
                245                 250                 255

Tyr Pro Arg Glu Ala Lys Val Gln Trp Lys Val Asp Asn Ala Leu Gln
            260                 265                 270

Ser Gly Asn Ser Gln Glu Ser Val Thr Glu Gln Asp Ser Lys Asp Ser
        275                 280                 285

Thr Tyr Ser Leu Ser Ser Thr Leu Thr Leu Ser Lys Ala Asp Tyr Glu
    290                 295                 300

Lys His Lys Val Tyr Ala Cys Glu Val Thr His Gln Gly Leu Ser Ser
305                 310                 315                 320

Pro Val Thr Lys Ser Phe Asn Arg Gly Glu Cys
                325                 330

<210> SEQ ID NO 509
<211> LENGTH: 219
<212> TYPE: PRT
<213> ORGANISM: Artificial Sequence
<220> FEATURE:
<223> OTHER INFORMATION: Synthetic Construct

<400> SEQUENCE: 509

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Thr Ile Val His Ser
            20                  25                  30

Asn Ser Lys Thr Tyr Leu Glu Trp Tyr Leu Gln Lys Pro Gly Gln Ser
        35                  40                  45

Pro Gln Leu Leu Ile Tyr Lys Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
```

```
            195                 200                 205
Pro Val Thr Lys Ser Phe Asn Arg Gly Glu Cys
    210                 215

<210> SEQ ID NO 510
<211> LENGTH: 571
<212> TYPE: PRT
<213> ORGANISM: Artificial Sequence
<220> FEATURE:
<223> OTHER INFORMATION: Synthetic Construct

<400> SEQUENCE: 510

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Ser Ile Ser Ser Gly Ser Asn Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Asn Ser Leu Arg Ala Glu Asp Thr Ala Leu Tyr Tyr Cys
                85                  90                  95

Ala Arg Phe Asp Tyr Gly Ser Ser Leu Asp Ser Trp Gly Gln Gly Thr
            100                 105                 110

Leu Leu Thr Val Ser Ser Asp Lys Thr His Thr Glu Val Gln Leu Val
        115                 120                 125

Glu Ser Gly Gly Gly Leu Val Lys Pro Gly Gly Ser Leu Arg Leu Ser
    130                 135                 140

Cys Ala Ala Ser Gly Phe Thr Phe Ser Ser Tyr Thr Met Ser Trp Val
145                 150                 155                 160

Arg Gln Ala Pro Gly Lys Gly Leu Glu Trp Val Ala Ser Ile Ser Ser
                165                 170                 175

Ser Gly Ser Asn Thr Tyr Tyr Pro Asp Ser Val Lys Gly Arg Phe Thr
            180                 185                 190

Ile Ser Arg Asp Asn Ala Lys Asn Asn Leu Tyr Leu Gln Met Asn Ser
        195                 200                 205

Leu Arg Ala Glu Asp Thr Ala Leu Tyr Tyr Cys Ala Arg Phe Asp Tyr
    210                 215                 220

Gly Ser Ser Leu Asp Ser Trp Gly Gln Gly Thr Leu Leu Thr Val Ser
225                 230                 235                 240

Ser Asp Lys Thr His Thr Ala Ser Thr Lys Gly Pro Ser Val Phe Pro
                245                 250                 255

Leu Ala Pro Ser Ser Lys Ser Thr Ser Gly Gly Thr Ala Ala Leu Gly
            260                 265                 270

Cys Leu Val Lys Asp Tyr Phe Pro Glu Pro Val Thr Val Ser Trp Asn
        275                 280                 285

Ser Gly Ala Leu Thr Ser Gly Val His Thr Phe Pro Ala Val Leu Gln
    290                 295                 300

Ser Ser Gly Ser Leu Ser Ser Val Val Thr Val Pro Ser Ser Ser Leu
305                 310                 315                 320

Gly Thr Gln Thr Tyr Ile Cys Asn Val Asn His Lys Pro Ser Asn Thr
                325                 330                 335

Lys Val Asp Lys Lys Val Glu Pro Lys Ser Cys Asp Lys Thr His Thr
```

```
                340              345              350
Cys Pro Pro Cys Pro Ala Pro Glu Leu Leu Gly Gly Pro Ser Val Phe
            355              360              365
Leu Phe Pro Pro Lys Pro Lys Asp Thr Leu Tyr Ile Thr Arg Glu Pro
        370              375              380
Glu Val Thr Cys Val Val Val Asp Val Ser His Glu Asp Pro Glu Val
385              390              395              400
Lys Phe Asn Trp Tyr Val Asp Gly Val Glu Val His Asn Ala Lys Thr
                405              410              415
Lys Pro Arg Glu Glu Gln Tyr Asn Asn Ala Ser Arg Val Val Ser Val
            420              425              430
Leu Thr Val Leu His Gln Asp Trp Leu Asn Gly Lys Glu Tyr Lys Cys
        435              440              445
Lys Val Ser Asn Lys Ala Leu Pro Ala Pro Ile Glu Lys Thr Ile Ser
450              455              460
Lys Ala Lys Gly Gln Pro Arg Glu Pro Gln Val Tyr Thr Leu Pro Pro
465              470              475              480
Cys Arg Asp Glu Leu Thr Lys Asn Gln Val Ser Leu Trp Cys Leu Val
                485              490              495
Lys Gly Phe Tyr Pro Ser Asp Ile Ala Val Glu Trp Glu Ser Asn Gly
            500              505              510
Gln Pro Glu Asn Asn Tyr Lys Thr Thr Pro Pro Val Leu Asp Ser Asp
        515              520              525
Gly Ser Phe Phe Lys Lys Leu Thr Val Asp Lys Ser Arg Trp Gln Gln
    530              535              540
Gly Asn Val Phe Ser Cys Ser Val Met His Glu Ala Leu His Asn His
545              550              555              560
Tyr Thr Gln Lys Ser Leu Ser Leu Ser Pro Gly
                565              570

<210> SEQ ID NO 511
<211> LENGTH: 440
<212> TYPE: PRT
<213> ORGANISM: Artificial Sequence
<220> FEATURE:
<223> OTHER INFORMATION: Synthetic Construct

<400> SEQUENCE: 511

Gln Val Gln Leu Val Gln Ser Gly Ala Glu Val Val Lys Pro Gly Ser
1               5                   10                  15
Ser Val Lys Val Ser Cys Glu Ala Ser Gly Phe Thr Phe Thr Asp Ser
            20                  25                  30
Val Ile Thr Trp Val Arg Gln Arg Pro Gly Gln Gly Leu Glu Trp Ile
        35                  40                  45
Gly Glu Ile Tyr Pro Gly Ser Gly Asn Phe Tyr Tyr Asn Glu Lys Phe
    50                  55                  60
Gln Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Phe Cys
                85                  90                  95
Ala Met Arg Arg Ser Ser Trp Gly Gln Gly Thr Leu Val Thr Val Ser
            100                 105                 110
Ser Ala Ser Thr Lys Gly Pro Ser Val Phe Pro Leu Ala Pro Ser Ser
        115                 120                 125
Lys Ser Thr Ser Gly Gly Thr Ala Ala Leu Gly Cys Leu Val Lys Asp
```

```
            130                 135                 140
Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Ser Leu
                165                 170                 175

Ser Ser Val Val Thr Val Pro Ser Ser Leu Gly Thr Gln Thr Tyr
                180                 185                 190

Ile Cys Asn Val Asn His Lys Pro Ser Asn Thr Lys Val Asp Lys Lys
                195                 200                 205

Val Glu Pro Lys Ser Cys Asp Lys Thr His Thr Cys Pro Pro Cys Pro
210                 215                 220

Ala Pro Glu Leu Leu Gly Gly Pro Ser Val Phe Leu Phe Pro Pro Lys
225                 230                 235                 240

Pro Lys Asp Thr Leu Tyr Ile Thr Arg Glu Pro Glu Val Thr Cys Val
                245                 250                 255

Val Val Asp Val Ser His Glu Asp Pro Glu Val Lys Phe Asn Trp Tyr
                260                 265                 270

Val Asp Gly Val Glu Val His Asn Ala Lys Thr Lys Pro Arg Glu Glu
                275                 280                 285

Gln Tyr Asn Asn Ala Ser Arg Val Val Ser Val Leu Thr Val Leu His
290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Cys Thr Leu Pro Pro Ser Arg Asp Glu Leu
                340                 345                 350

Thr Lys Asn Gln Val Ser Leu Ser Cys Ala Val Lys Gly Phe Tyr Pro
                355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Val Ser Lys Leu Thr Val Asp Lys Ser Arg Trp Gln Gln Gly Asn Val
                405                 410                 415

Phe Ser Cys Ser Val Met His Glu Ala Leu His Asn Arg Phe Thr Gln
                420                 425                 430

Lys Ser Leu Ser Leu Ser Pro Gly
                435                 440

<210> SEQ ID NO 512
<211> LENGTH: 331
<212> TYPE: PRT
<213> ORGANISM: Artificial Sequence
<220> FEATURE:
<223> OTHER INFORMATION: Synthetic Construct

<400> SEQUENCE: 512

Glu Ile Val Leu Thr Gln Ser Pro Asp Phe Leu Ser Val Thr Pro Lys
1               5                   10                  15

Glu Lys Val Thr Leu Thr Cys Arg Ala Ser Gln Ser Ile Gly Asn Asn
                20                  25                  30

Leu His Trp Tyr Gln Gln Lys Ser Asp Gln Ser Pro Lys Leu Leu Ile
            35                  40                  45

Lys Tyr Ala Ser Gln Ser Ile Ser Gly Ile Pro Ser Arg Phe Ser Gly
```

```
                50                  55                  60
Ser Gly Ser Gly Thr Asp Phe Thr Leu Thr Ile Asn Ser Val Glu Ala
 65                  70                  75                  80

Glu Asp Ala Ala Thr Tyr Phe Cys Gln Gln Ser Lys Ser Trp Pro Arg
                 85                  90                  95

Thr Phe Gly Gly Gly Thr Lys Leu Glu Ile Lys Asp Lys Thr His Thr
                100                 105                 110

Glu Ile Val Leu Thr Gln Ser Pro Asp Phe Leu Ser Val Thr Pro Lys
                115                 120                 125

Glu Lys Val Thr Leu Ser Cys Arg Ala Ser Gln Ser Ile Ser Asn Tyr
                130                 135                 140

Leu His Trp Tyr Gln Gln Lys Ser Asp Gln Ser Pro Lys Leu Leu Ile
145                 150                 155                 160

Lys Tyr Ala Ser Gln Ser Ile Ser Gly Ile Pro Ser Arg Phe Ser Gly
                165                 170                 175

Ser Gly Ser Gly Thr Asp Phe Thr Leu Ser Ile Asn Ser Val Glu Ala
                180                 185                 190

Glu Asp Ala Ala Thr Tyr Phe Cys Gln Gln Ser Lys Ser Trp Pro Arg
                195                 200                 205

Thr Phe Gly Gly Gly Thr Lys Leu Glu Ile Lys Asp Lys Thr His Thr
                210                 215                 220

Arg Thr Val Ala Ala Pro Ser Val Phe Ile Phe Pro Pro Ser Asp Glu
225                 230                 235                 240

Gln Leu Lys Ser Gly Thr Ala Ser Val Val Cys Leu Leu Asn Asn Phe
                245                 250                 255

Tyr Pro Arg Glu Ala Lys Val Gln Trp Lys Val Asp Asn Ala Leu Gln
                260                 265                 270

Ser Gly Asn Ser Gln Glu Ser Val Thr Glu Gln Asp Ser Lys Asp Ser
                275                 280                 285

Thr Tyr Ser Leu Ser Ser Thr Leu Thr Leu Ser Lys Ala Asp Tyr Glu
                290                 295                 300

Lys His Lys Val Tyr Ala Cys Glu Val Thr His Gln Gly Leu Ser Ser
305                 310                 315                 320

Pro Val Thr Lys Ser Phe Asn Arg Gly Glu Cys
                325                 330

<210> SEQ ID NO 513
<211> LENGTH: 219
<212> TYPE: PRT
<213> ORGANISM: Artificial Sequence
<220> FEATURE:
<223> OTHER INFORMATION: Synthetic Construct

<400> SEQUENCE: 513

Asp Val Val Met Thr Gln Thr Pro Leu Ser Leu Ser Val Thr Pro Gly
 1               5                  10                  15

Gln Pro Ala Ser Ile Ser Cys Lys Ser Ser Gln Thr Ile Val His Ser
                 20                  25                  30

Asn Ser Lys Thr Tyr Leu Glu Trp Tyr Leu Gln Lys Pro Gly Gln Ser
             35                  40                  45

Pro Gln Leu Leu Ile Tyr Lys Val Ser Ser Arg Phe Ser Gly Val Pro
             50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
```

```
                  85                  90                  95
Ser His Val Pro Leu Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
                210                 215

<210> SEQ ID NO 514
<211> LENGTH: 571
<212> TYPE: PRT
<213> ORGANISM: Artificial Sequence
<220> FEATURE:
<223> OTHER INFORMATION: Synthetic Construct

<400> SEQUENCE: 514

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Thr Met Ser Trp Val Arg Gln Ala Pro Gly Lys Gly Leu Glu Trp Val
            35                  40                  45

Ala Thr Ile Ser Ser Gly Asp Asn Thr Tyr Tyr Pro Asp Ser Val
50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Leu Tyr Tyr Cys
                85                  90                  95

Ala Arg Phe Asp Tyr Gly Ser Ser Leu Asp Ser Trp Gly Gln Gly Thr
                100                 105                 110

Thr Leu Thr Val Ser Ser Asp Lys Thr His Thr Glu Val Gln Leu Val
                115                 120                 125

Glu Ser Gly Gly Gly Leu Val Lys Pro Gly Gly Ser Leu Arg Leu Ser
130                 135                 140

Cys Ala Ala Ser Gly Phe Thr Phe Ser Ser Tyr Thr Met Ser Trp Val
145                 150                 155                 160

Arg Gln Ala Pro Gly Lys Gly Leu Glu Trp Val Ala Ser Ile Ser Ser
                165                 170                 175

Ser Gly Ser Asn Thr Tyr Tyr Pro Asp Ser Val Lys Gly Arg Phe Thr
                180                 185                 190

Ile Ser Arg Asp Asn Ala Lys Asn Asn Leu Tyr Leu Gln Met Asn Ser
                195                 200                 205

Leu Arg Ala Glu Asp Thr Ala Leu Tyr Tyr Cys Ala Arg Phe Asp Tyr
                210                 215                 220

Gly Ser Ser Leu Asp Ser Trp Gly Gln Gly Thr Leu Leu Thr Val Ser
```

```
            225                 230                 235                 240
Ser Asp Lys Thr His Thr Ala Ser Thr Lys Gly Pro Ser Val Phe Pro
                245                 250                 255

Leu Ala Pro Ser Ser Lys Ser Thr Ser Gly Gly Thr Ala Ala Leu Gly
                260                 265                 270

Cys Leu Val Lys Asp Tyr Phe Pro Glu Pro Val Thr Val Ser Trp Asn
                275                 280                 285

Ser Gly Ala Leu Thr Ser Gly Val His Thr Phe Pro Ala Val Leu Gln
            290                 295                 300

Ser Ser Gly Ser Leu Ser Ser Val Val Thr Val Pro Ser Ser Ser Leu
305                 310                 315                 320

Gly Thr Gln Thr Tyr Ile Cys Asn Val Asn His Lys Pro Ser Asn Thr
                325                 330                 335

Lys Val Asp Lys Lys Val Glu Pro Lys Ser Cys Asp Lys Thr His Thr
                340                 345                 350

Cys Pro Pro Cys Pro Ala Pro Glu Leu Leu Gly Gly Pro Ser Val Phe
                355                 360                 365

Leu Phe Pro Pro Lys Pro Lys Asp Thr Leu Tyr Ile Thr Arg Glu Pro
            370                 375                 380

Glu Val Thr Cys Val Val Val Asp Val Ser His Glu Asp Pro Glu Val
385                 390                 395                 400

Lys Phe Asn Trp Tyr Val Asp Gly Val Glu Val His Asn Ala Lys Thr
                405                 410                 415

Lys Pro Arg Glu Glu Gln Tyr Asn Asn Ala Ser Arg Val Val Ser Val
                420                 425                 430

Leu Thr Val Leu His Gln Asp Trp Leu Asn Gly Lys Glu Tyr Lys Cys
            435                 440                 445

Lys Val Ser Asn Lys Ala Leu Pro Ala Pro Ile Glu Lys Thr Ile Ser
                450                 455                 460

Lys Ala Lys Gly Gln Pro Arg Glu Pro Gln Val Tyr Thr Leu Pro Pro
465                 470                 475                 480

Cys Arg Asp Glu Leu Thr Lys Asn Gln Val Ser Leu Trp Cys Leu Val
                485                 490                 495

Lys Gly Phe Tyr Pro Ser Asp Ile Ala Val Glu Trp Glu Ser Asn Gly
                500                 505                 510

Gln Pro Glu Asn Asn Tyr Lys Thr Thr Pro Pro Val Leu Asp Ser Asp
            515                 520                 525

Gly Ser Phe Phe Lys Leu Thr Val Asp Lys Ser Arg Trp Gln Gln
530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly
                565                 570

<210> SEQ ID NO 515
<211> LENGTH: 440
<212> TYPE: PRT
<213> ORGANISM: Artificial Sequence
<220> FEATURE:
<223> OTHER INFORMATION: Synthetic Construct

<400> SEQUENCE: 515

Gln Val Gln Leu Val Gln Ser Gly Ala Glu Val Val Lys Pro Gly Ser
1               5                   10                  15

Ser Val Lys Val Ser Cys Glu Ala Ser Gly Phe Thr Phe Thr Asp Ser
```

```
            20                  25                  30
Val Ile Thr Trp Val Arg Gln Arg Pro Gly Gln Gly Leu Glu Trp Ile
            35                  40                  45
Gly Glu Ile Tyr Pro Gly Ser Gly Asn Phe Tyr Tyr Asn Glu Lys Phe
            50                  55                  60
Gln Gly Arg Val Thr Ile Thr Ala Asp Lys Ser Thr Ser Thr Ala Tyr
 65                  70                  75                  80
Met Glu Leu Ser Ser Leu Arg Ser Glu Asp Thr Ala Val Tyr Phe Cys
                85                  90                  95
Ala Met Arg Arg Ser Ser Trp Gly Gln Gly Thr Leu Val Thr Val Ser
                100                 105                 110
Ser Ala Ser Thr Lys Gly Pro Ser Val Phe Pro Leu Ala Pro Ser Ser
            115                 120                 125
Lys Ser Thr Ser Gly Gly Thr Ala Ala Leu Gly Cys Leu Val Lys Asp
            130                 135                 140
Tyr Phe Pro Glu Pro Val Thr Val Ser Trp Asn Ser Gly Ala Leu Thr
145                 150                 155                 160
Ser Gly Val His Thr Phe Pro Ala Val Leu Gln Ser Ser Gly Ser Leu
                165                 170                 175
Ser Ser Val Val Thr Val Pro Ser Ser Ser Leu Gly Thr Gln Thr Tyr
                180                 185                 190
Ile Cys Asn Val Asn His Lys Pro Ser Asn Thr Lys Val Asp Lys Lys
            195                 200                 205
Val Glu Pro Lys Ser Cys Asp Lys Thr His Thr Cys Pro Pro Cys Pro
            210                 215                 220
Ala Pro Glu Leu Leu Gly Gly Pro Ser Val Phe Leu Phe Pro Pro Lys
225                 230                 235                 240
Pro Lys Asp Thr Leu Tyr Ile Thr Arg Glu Pro Glu Val Thr Cys Val
                245                 250                 255
Val Val Asp Val Ser His Glu Asp Pro Glu Val Lys Phe Asn Trp Tyr
                260                 265                 270
Val Asp Gly Val Glu Val His Asn Ala Lys Thr Lys Pro Arg Glu Glu
            275                 280                 285
Gln Tyr Asn Asn Ala Ser Arg Val Val Ser Val Leu Thr Val Leu His
            290                 295                 300
Gln Asp Trp Leu Asn Gly Lys Glu Tyr Lys Cys Lys Val Ser Asn Lys
305                 310                 315                 320
Ala Leu Pro Ala Pro Ile Glu Lys Thr Ile Ser Lys Ala Lys Gly Gln
                325                 330                 335
Pro Arg Glu Pro Gln Val Cys Thr Leu Pro Pro Ser Arg Asp Glu Leu
                340                 345                 350
Thr Lys Asn Gln Val Ser Leu Ser Cys Ala Val Lys Gly Phe Tyr Pro
            355                 360                 365
Ser Asp Ile Ala Val Glu Trp Glu Ser Asn Gly Gln Pro Glu Asn Asn
            370                 375                 380
Tyr Lys Thr Thr Pro Pro Val Leu Asp Ser Asp Gly Ser Phe Phe Leu
385                 390                 395                 400
Val Ser Lys Leu Thr Val Asp Lys Ser Arg Trp Gln Gln Gly Asn Val
                405                 410                 415
Phe Ser Cys Ser Val Met His Glu Ala Leu His Asn Arg Phe Thr Gln
            420                 425                 430
Lys Ser Leu Ser Leu Ser Pro Gly
            435                 440
```

<210> SEQ ID NO 516
<211> LENGTH: 331
<212> TYPE: PRT
<213> ORGANISM: Artificial Sequence
<220> FEATURE:
<223> OTHER INFORMATION: Synthetic Construct

<400> SEQUENCE: 516

Glu Ile Val Leu Thr Gln Ser Pro Asp Phe Leu Ser Val Thr Pro Lys
1               5                   10                  15

Glu Lys Val Thr Leu Thr Cys Arg Ala Ser Gln Ser Ile Ser Asn Asn
            20                  25                  30

Leu His Trp Tyr Gln Gln Lys Ser Asp Gln Ser Pro Lys Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Thr Ile Asn Ser Val Glu Ala
65                  70                  75                  80

Glu Asp Ala Ala Thr Tyr Phe Cys Gln Gln Ser Lys Ser Trp Pro Arg
                85                  90                  95

Thr Phe Gly Gly Gly Thr Lys Leu Glu Ile Lys Asp Lys Thr His Thr
            100                 105                 110

Glu Ile Val Leu Thr Gln Ser Pro Asp Phe Leu Ser Val Thr Pro Gly
        115                 120                 125

Glu Lys Val Thr Leu Thr Cys Arg Ala Ser Gln Ser Ile Ser Asn Tyr
    130                 135                 140

Leu His Trp Tyr Gln Gln Lys Ser Asp Gln Ser Pro Lys Leu Leu Ile
145                 150                 155                 160

Lys Tyr Ala Ser Gln Ser Ile Ser Gly Val Pro Ser Arg Phe Ser Gly
                165                 170                 175

Ser Gly Ser Gly Thr Asp Phe Thr Leu Thr Ile Ser Ser Val Glu Ala
            180                 185                 190

Glu Asp Phe Ala Thr Tyr Phe Cys Gln Gln Ser Lys Ser Trp Pro Arg
        195                 200                 205

Thr Phe Gly Gly Gly Thr Lys Leu Glu Ile Lys Asp Lys Thr His Thr
    210                 215                 220

Arg Thr Val Ala Ala Pro Ser Val Phe Ile Phe Pro Pro Ser Asp Glu
225                 230                 235                 240

Gln Leu Lys Ser Gly Thr Ala Ser Val Val Cys Leu Leu Asn Asn Phe
                245                 250                 255

Tyr Pro Arg Glu Ala Lys Val Gln Trp Lys Val Asp Asn Ala Leu Gln
            260                 265                 270

Ser Gly Asn Ser Gln Glu Ser Val Thr Glu Gln Asp Ser Lys Asp Ser
        275                 280                 285

Thr Tyr Ser Leu Ser Ser Thr Leu Thr Leu Ser Lys Ala Asp Tyr Glu
    290                 295                 300

Lys His Lys Val Tyr Ala Cys Glu Val Thr His Gln Gly Leu Ser Ser
305                 310                 315                 320

Pro Val Thr Lys Ser Phe Asn Arg Gly Glu Cys
                325                 330

<210> SEQ ID NO 517
<211> LENGTH: 219
<212> TYPE: PRT
<213> ORGANISM: Artificial Sequence
<220> FEATURE:
<223> OTHER INFORMATION: Synthetic Construct

<400> SEQUENCE: 517

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Thr Ile Val His Ser
            20                  25                  30

Asn Ser Lys Thr Tyr Leu Glu Trp Tyr Leu Gln Lys Pro Gly Gln Ser
        35                  40                  45

Pro Gln Leu Leu Ile Tyr Lys Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 518
<211> LENGTH: 438
<212> TYPE: PRT
<213> ORGANISM: Artificial Sequence
<220> FEATURE:
<223> OTHER INFORMATION: Synthetic Construct

<400> SEQUENCE: 518

Gln Val Gln Leu Val Gln Ser Gly Ala Glu Val Val Lys Pro Gly Ser
1               5                   10                  15

Ser Val Lys Val Ser Cys Glu Ala Ser Gly Phe Thr Phe Thr Asp Ser
            20                  25                  30

Val Ile Thr Trp Val Arg Gln Arg Pro Gly Gln Gly Leu Glu Trp Ile
        35                  40                  45

Gly Glu Ile Tyr Pro Gly Ser Gly Asn Phe Tyr Tyr Asn Glu Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Met Arg Arg Ser Ser Trp Gly Gln Gly Thr Leu Val Thr Val Ser
            100                 105                 110

Ser Ala Ser Thr Lys Gly Pro Ser Val Phe Pro Leu Ala Pro Ser Ser

```
                115                 120                 125
Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys Asp Lys Thr His Thr Cys Pro Pro Cys Pro
210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Asn Ala Ser Arg Val Val Ser Val Leu Thr Val Leu His
290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Asp Glu Leu
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Lys
385                 390                 395                 400

Arg Leu Thr Val Asp Lys Ser Arg Trp Gln Gln Gly Asn Val Phe Ser
                405                 410                 415

Cys Ser Val Met His Glu Ala Leu His Asn His Tyr Thr Gln Lys Ser
            420                 425                 430

Leu Ser Leu Ser Pro Gly
            435

<210> SEQ ID NO 519
<211> LENGTH: 443
<212> TYPE: PRT
<213> ORGANISM: Artificial Sequence
<220> FEATURE:
<223> OTHER INFORMATION: Synthetic Construct

<400> SEQUENCE: 519

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
```

```
                35                  40                  45
Ala Ser Ile Ser Ser Gly Ser Asn Thr Tyr Tyr Pro Asp Ser Val
 50                  55                  60

Lys Gly Arg Phe Thr Ile Ser Arg Asp Asn Ala Lys Asn Asn Leu Tyr
 65                  70                  75                  80

Leu Gln Met Asn Ser Leu Arg Ala Glu Asp Thr Ala Leu Tyr Tyr Cys
                 85                  90                  95

Ala Arg Phe Asp Tyr Gly Ser Ser Leu Asp Ser Trp Gly Gln Gly Thr
                100                 105                 110

Leu Leu Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
                130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Asn Asn Ser Ala Arg Val Val Ser Val
                290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Leu Lys Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly
                435                 440

<210> SEQ ID NO 520
```

```
<211> LENGTH: 219
<212> TYPE: PRT
<213> ORGANISM: Artificial Sequence
<220> FEATURE:
<223> OTHER INFORMATION: Synthetic Construct

<400> SEQUENCE: 520

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Thr Ile Val His Ser
            20                  25                  30

Asn Ser Lys Thr Tyr Leu Glu Trp Tyr Leu Gln Lys Pro Gly Gln Ser
        35                  40                  45

Pro Gln Leu Leu Ile Tyr Lys Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gly
                85                  90                  95

Ser His Val Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 521
<211> LENGTH: 214
<212> TYPE: PRT
<213> ORGANISM: Artificial Sequence
<220> FEATURE:
<223> OTHER INFORMATION: Synthetic Construct

<400> SEQUENCE: 521

Glu Ile Val Leu Thr Gln Ser Pro Asp Phe Leu Ser Val Thr Pro Lys
1               5                   10                  15

Glu Lys Val Thr Leu Thr Cys Arg Ala Ser Gln Ser Ile Ser Asn Asn
            20                  25                  30

Leu His Trp Tyr Gln Gln Lys Ser Asp Gln Ser Pro Lys Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Thr Ile Asn Ser Val Glu Ala
65                  70                  75                  80

Glu Asp Ala Ala Thr Tyr Phe Cys Gln Gln Ser Lys Ser Trp Pro Arg
                85                  90                  95

Thr Phe Gly Gly Gly Thr Lys Leu Glu Ile Lys Arg Thr Val Ala Ala
```

```
                100             105                 110
Pro Ser Val Phe Ile Phe Pro Ser Asp Glu Gln Leu Lys Ser Gly
        115                 120             125

Thr Ala Ser Val Val Cys Leu Leu Asn Asn Phe Tyr Pro Arg Glu Ala
        130                 135             140

Lys Val Gln Trp Lys Val Asp Asn Ala Leu Gln Ser Gly Asn Ser Gln
145                 150             155                 160

Glu Ser Val Thr Glu Gln Asp Ser Lys Asp Ser Thr Tyr Ser Leu Ser
                165                 170             175

Ser Thr Leu Thr Leu Ser Lys Ala Asp Tyr Glu Lys His Lys Val Tyr
            180                 185             190

Ala Cys Glu Val Thr His Gln Gly Leu Ser Ser Pro Val Thr Lys Ser
        195                 200             205

Phe Asn Arg Gly Glu Cys
        210

<210> SEQ ID NO 522
<211> LENGTH: 566
<212> TYPE: PRT
<213> ORGANISM: Artificial Sequence
<220> FEATURE:
<223> OTHER INFORMATION: Synthetic Construct

<400> SEQUENCE: 522

Gln Val Gln Leu Val Gln Ser Gly Ala Glu Val Val Lys Pro Gly Ser
1               5                   10                  15

Ser Val Lys Val Ser Cys Glu Ala Ser Gly Phe Thr Phe Thr Asp Ser
            20                  25                  30

Val Ile Thr Trp Val Arg Gln Arg Pro Gly Gln Gly Leu Glu Trp Ile
        35                  40                  45

Gly Glu Ile Tyr Pro Gly Ser Gly Asn Phe Tyr Tyr Asn Glu Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Met Arg Arg Ser Ser Trp Gly Gln Gly Thr Leu Val Thr Val Ser
            100                 105                 110

Ser Gly Gly Gly Gly Ser Gly Gly Gly Ser Glu Val Gln Leu Val
        115                 120                 125

Glu Ser Gly Gly Gly Leu Val Lys Pro Gly Gly Ser Leu Arg Leu Ser
    130                 135                 140

Cys Ala Ala Ser Gly Phe Thr Phe Ser Ser Tyr Thr Met Ser Trp Val
145                 150                 155                 160

Arg Gln Ala Pro Gly Lys Gly Leu Glu Trp Val Ala Ser Ile Ser Ser
                165                 170                 175

Ser Gly Ser Asn Thr Tyr Tyr Pro Asp Ser Val Lys Gly Arg Phe Thr
            180                 185                 190

Ile Ser Arg Asp Asn Ala Lys Asn Asn Leu Tyr Leu Gln Met Asn Ser
        195                 200                 205

Leu Arg Ala Glu Asp Thr Ala Leu Tyr Tyr Cys Ala Arg Phe Asp Tyr
    210                 215                 220

Gly Ser Ser Leu Asp Ser Trp Gly Gln Gly Thr Leu Leu Thr Val Ser
225                 230                 235                 240

Ser Ala Ser Thr Lys Gly Pro Ser Val Phe Pro Leu Ala Pro Ser Ser
```

```
            245                 250                 255
Lys Ser Thr Ser Gly Thr Ala Ala Leu Gly Cys Leu Val Lys Asp
            260                 265                 270

Tyr Phe Pro Glu Pro Val Thr Val Ser Trp Asn Ser Gly Ala Leu Thr
            275                 280                 285

Ser Gly Val His Thr Phe Pro Ala Val Leu Gln Ser Ser Gly Ser Leu
            290                 295                 300

Ser Ser Val Val Thr Val Pro Ser Ser Leu Gly Thr Gln Thr Tyr
305                 310                 315                 320

Ile Cys Asn Val Asn His Lys Pro Ser Asn Thr Lys Val Asp Lys Lys
                    325                 330                 335

Val Glu Pro Lys Ser Cys Asp Lys Thr His Thr Cys Pro Pro Cys Pro
            340                 345                 350

Ala Pro Glu Leu Leu Gly Gly Pro Ser Val Phe Leu Phe Pro Pro Lys
            355                 360                 365

Pro Lys Asp Thr Leu Met Ile Ser Arg Thr Pro Glu Val Thr Cys Val
            370                 375                 380

Val Val Asp Val Ser His Glu Asp Pro Glu Val Lys Phe Asn Trp Tyr
385                 390                 395                 400

Val Asp Gly Val Glu Val His Asn Ala Lys Thr Lys Pro Arg Glu Glu
                    405                 410                 415

Gln Tyr Asn Asn Ala Ser Arg Val Val Ser Val Leu Thr Val Leu His
                    420                 425                 430

Gln Asp Trp Leu Asn Gly Lys Glu Tyr Lys Cys Lys Val Ser Asn Lys
            435                 440                 445

Ala Leu Pro Ala Pro Ile Glu Lys Thr Ile Ser Lys Ala Lys Gly Gln
450                 455                 460

Pro Arg Glu Pro Gln Val Tyr Thr Leu Pro Pro Ser Arg Asp Glu Leu
465                 470                 475                 480

Thr Lys Asn Gln Val Ser Leu Thr Cys Leu Val Lys Gly Phe Tyr Pro
                    485                 490                 495

Ser Asp Ile Ala Val Glu Trp Glu Ser Asn Gly Gln Pro Glu Asn Asn
            500                 505                 510

Tyr Lys Thr Thr Pro Pro Val Leu Asp Ser Asp Gly Ser Phe Phe Lys
            515                 520                 525

Lys Leu Thr Val Asp Lys Ser Arg Trp Gln Gln Gly Asn Val Phe Ser
            530                 535                 540

Cys Ser Val Met His Glu Ala Leu His Asn His Tyr Thr Gln Lys Ser
545                 550                 555                 560

Leu Ser Leu Ser Pro Gly
                565

<210> SEQ ID NO 523
<211> LENGTH: 336
<212> TYPE: PRT
<213> ORGANISM: Artificial Sequence
<220> FEATURE:
<223> OTHER INFORMATION: Synthetic Construct

<400> SEQUENCE: 523

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Thr Ile Val His Ser
            20                  25                  30

Asn Ser Lys Thr Tyr Leu Glu Trp Tyr Leu Gln Lys Pro Gly Gln Ser
```

```
            35                  40                  45
Pro Gln Leu Leu Ile Tyr Lys Val Ser Ser Arg Phe Ser Gly Val Pro
            50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
               100                 105                 110

Gly Gly Gly Gly Ser Gly Gly Gly Ser Glu Ile Val Leu Thr Gln
               115                 120                 125

Ser Pro Asp Phe Leu Ser Val Thr Pro Lys Glu Lys Val Thr Leu Thr
               130                 135                 140

Cys Arg Ala Ser Gln Ser Ile Ser Asn Asn Leu His Trp Tyr Gln Gln
145                 150                 155                 160

Lys Ser Asp Gln Ser Pro Lys Leu Leu Ile Lys Tyr Ala Ser Gln Ser
                165                 170                 175

Ile Ser Gly Ile Pro Ser Arg Phe Ser Gly Ser Gly Ser Gly Thr Asp
                180                 185                 190

Phe Thr Leu Thr Ile Asn Ser Val Glu Ala Glu Asp Ala Ala Thr Tyr
                195                 200                 205

Phe Cys Gln Gln Ser Lys Ser Trp Pro Arg Thr Phe Gly Gly Gly Thr
                210                 215                 220

Lys Leu Glu Ile Lys Arg Thr Val Ala Ala Pro Ser Val Phe Ile Phe
225                 230                 235                 240

Pro Pro Ser Asp Glu Gln Leu Lys Ser Gly Thr Ala Ser Val Val Cys
                245                 250                 255

Leu Leu Asn Asn Phe Tyr Pro Arg Glu Ala Lys Val Gln Trp Lys Val
                260                 265                 270

Asp Asn Ala Leu Gln Ser Gly Asn Ser Gln Glu Ser Val Thr Glu Gln
                275                 280                 285

Asp Ser Lys Asp Ser Thr Tyr Ser Leu Ser Ser Thr Leu Thr Leu Ser
                290                 295                 300

Lys Ala Asp Tyr Glu Lys His Lys Val Tyr Ala Cys Glu Val Thr His
305                 310                 315                 320

Gln Gly Leu Ser Ser Pro Val Thr Lys Ser Phe Asn Arg Gly Glu Cys
                325                 330                 335

<210> SEQ ID NO 524
<211> LENGTH: 438
<212> TYPE: PRT
<213> ORGANISM: Artificial Sequence
<220> FEATURE:
<223> OTHER INFORMATION: Synthetic Construct

<400> SEQUENCE: 524

Gln Val Gln Leu Val Gln Ser Gly Ala Glu Val Val Lys Pro Gly Ser
1               5                  10                  15

Ser Val Lys Val Ser Cys Glu Ala Ser Gly Phe Thr Phe Thr Asp Ser
                20                  25                  30

Val Ile Thr Trp Val Arg Gln Arg Pro Gly Gln Gly Leu Glu Trp Ile
                35                  40                  45

Gly Glu Ile Tyr Pro Gly Ser Gly Asn Phe Tyr Tyr Asn Glu Lys Phe
                50                  55                  60

Gln Gly Arg Val Thr Ile Thr Ala Asp Lys Ser Thr Ser Thr Ala Tyr
```

```
            65                  70                  75                  80
Met Glu Leu Ser Ser Leu Arg Ser Glu Asp Thr Ala Val Tyr Phe Cys
                85                  90                  95

Ala Met Arg Arg Ser Ser Trp Gly Gln Gly Thr Leu Val Thr Val Ser
            100                 105                 110

Ser Ala Ser Thr Lys Gly Pro Ser Val Cys Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Ser Leu
                165                 170                 175

Ser Ser Val Val Thr Val Pro Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Val Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Asn Ala Ser Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Cys Arg Asp Glu Leu
            340                 345                 350

Thr Lys Asn Gln Val Ser Leu Trp Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Lys
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Asn His Tyr Thr Gln Lys Ser
            420                 425                 430

Leu Ser Leu Ser Pro Gly
        435

<210> SEQ ID NO 525
<211> LENGTH: 445
<212> TYPE: PRT
<213> ORGANISM: Artificial Sequence
<220> FEATURE:
<223> OTHER INFORMATION: Synthetic Construct
```

```
<400> SEQUENCE: 525

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Ser Ile Ser Ser Ser Gly Ser Asn Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Asn Ser Leu Arg Ala Glu Asp Thr Ala Leu Tyr Tyr Cys
                85                  90                  95

Ala Arg Phe Asp Tyr Gly Ser Ser Leu Asp Ser Trp Gly Gln Gly Thr
            100                 105                 110

Leu Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Asn Ala Ser Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Cys Thr Leu Pro Pro
            340                 345                 350

Ser Arg Asp Glu Leu Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415
```

```
Gln Gln Gly Asn Val Phe Ser Cys Ser Val Met His Glu Ala Leu His
            420                 425                 430

Asn Arg Phe Thr Gln Lys Ser Leu Ser Leu Ser Pro Gly
            435                 440                 445

<210> SEQ ID NO 526
<211> LENGTH: 219
<212> TYPE: PRT
<213> ORGANISM: Artificial Sequence
<220> FEATURE:
<223> OTHER INFORMATION: Synthetic Construct

<400> SEQUENCE: 526

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Thr Ile Val His Ser
            20                  25                  30

Asn Ser Lys Thr Tyr Leu Glu Trp Tyr Leu Gln Lys Pro Gly Gln Ser
        35                  40                  45

Pro Gln Leu Leu Ile Tyr Lys Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110

Arg Thr Val Ala Ala Pro Ser Val Phe Ile Phe Pro Pro Cys Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Val
    210                 215

<210> SEQ ID NO 527
<211> LENGTH: 214
<212> TYPE: PRT
<213> ORGANISM: Artificial Sequence
<220> FEATURE:
<223> OTHER INFORMATION: Synthetic Construct

<400> SEQUENCE: 527

Glu Ile Val Leu Thr Gln Ser Pro Asp Phe Leu Ser Val Thr Pro Lys
1               5                   10                  15

Glu Lys Val Thr Leu Ser Cys Arg Ala Ser Gln Ser Ile Ser Asn Tyr
            20                  25                  30

Leu His Trp Tyr Gln Gln Lys Ser Asp Gln Ser Pro Lys Leu Leu Ile
        35                  40                  45

Lys Tyr Ala Ser Gln Ser Ile Ser Gly Ile Pro Ser Arg Phe Ser Gly
```

```
              50                  55                  60
Ser Gly Ser Gly Thr Asp Phe Thr Leu Ser Ile Asn Ser Val Glu Ala
 65                  70                  75                  80

Glu Asp Ala Ala Thr Tyr Phe Cys Gln Gln Ser Lys Ser Trp Pro Arg
                     85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 528
<211> LENGTH: 566
<212> TYPE: PRT
<213> ORGANISM: Artificial Sequence
<220> FEATURE:
<223> OTHER INFORMATION: Synthetic Construct

<400> SEQUENCE: 528

Gln Val Gln Leu Val Gln Ser Gly Ala Glu Val Val Lys Pro Gly Ser
  1               5                  10                  15

Ser Val Lys Val Ser Cys Glu Ala Ser Gly Phe Thr Phe Thr Asp Ser
                 20                  25                  30

Val Ile Thr Trp Val Arg Gln Arg Pro Gly Gln Gly Leu Glu Trp Ile
             35                  40                  45

Gly Glu Ile Tyr Pro Gly Ser Gly Asn Phe Tyr Tyr Asn Glu Lys Phe
         50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Phe Cys
                 85                  90                  95

Ala Met Arg Arg Ser Ser Trp Gly Gln Gly Thr Leu Val Thr Val Ser
                100                 105                 110

Ser Gly Gly Gly Gly Ser Gly Gly Gly Ser Glu Val Gln Leu Val
            115                 120                 125

Glu Ser Gly Gly Gly Leu Val Lys Pro Gly Gly Ser Leu Arg Leu Ser
            130                 135                 140

Cys Ala Ala Ser Gly Phe Thr Phe Ser Ser Tyr Thr Met Ser Trp Val
145                 150                 155                 160

Arg Gln Ala Pro Gly Lys Gly Leu Glu Trp Val Ala Ser Ile Ser Ser
                165                 170                 175

Ser Gly Ser Asn Thr Tyr Tyr Pro Asp Ser Val Lys Gly Arg Phe Thr
                180                 185                 190

Ile Ser Arg Asp Asn Ala Lys Asn Asn Leu Tyr Leu Gln Met Asn Ser
```

195                 200                 205
Leu Arg Ala Glu Asp Thr Ala Leu Tyr Tyr Cys Ala Arg Phe Asp Tyr
210                 215                 220
Gly Ser Ser Leu Asp Ser Trp Gly Gln Gly Thr Leu Leu Thr Val Ser
225                 230                 235                 240
Ser Ala Ser Thr Lys Gly Pro Ser Val Phe Pro Leu Ala Pro Ser Ser
            245                 250                 255
Lys Ser Thr Ser Gly Gly Thr Ala Ala Leu Gly Cys Leu Val Lys Asp
                260                 265                 270
Tyr Phe Pro Glu Pro Val Thr Val Ser Trp Asn Ser Gly Ala Leu Thr
            275                 280                 285
Ser Gly Val His Thr Phe Pro Ala Val Leu Gln Ser Ser Gly Ser Leu
        290                 295                 300
Ser Ser Val Val Thr Val Pro Ser Ser Ser Leu Gly Thr Gln Thr Tyr
305                 310                 315                 320
Ile Cys Asn Val Asn His Lys Pro Ser Asn Thr Lys Val Asp Lys Lys
                325                 330                 335
Val Glu Pro Lys Ser Cys Asp Lys Thr His Thr Cys Pro Pro Cys Pro
            340                 345                 350
Ala Pro Glu Leu Leu Gly Gly Pro Ser Val Phe Leu Phe Pro Pro Lys
        355                 360                 365
Pro Lys Asp Thr Leu Met Ile Ser Arg Thr Pro Glu Val Thr Cys Val
370                 375                 380
Val Val Asp Val Ser His Glu Asp Pro Glu Val Lys Phe Asn Trp Tyr
385                 390                 395                 400
Val Asp Gly Val Glu Val His Asn Ala Lys Thr Lys Pro Arg Glu Glu
                405                 410                 415
Gln Tyr Asn Ser Thr Tyr Arg Val Val Ser Val Leu Thr Val Leu His
            420                 425                 430
Gln Asp Trp Leu Asn Gly Lys Glu Tyr Lys Cys Lys Val Ser Asn Lys
        435                 440                 445
Ala Leu Pro Ala Pro Ile Glu Lys Thr Ile Ser Lys Ala Lys Gly Gln
    450                 455                 460
Pro Arg Glu Pro Gln Val Tyr Thr Leu Pro Pro Ser Arg Asp Glu Leu
465                 470                 475                 480
Thr Lys Asn Gln Val Ser Leu Thr Cys Leu Val Lys Gly Phe Tyr Pro
                485                 490                 495
Ser Asp Ile Ala Val Glu Trp Glu Ser Asn Gly Gln Pro Glu Asn Asn
            500                 505                 510
Tyr Lys Thr Thr Pro Pro Val Leu Asp Ser Asp Gly Ser Phe Phe Lys
        515                 520                 525
Lys Leu Thr Val Asp Lys Ser Arg Trp Gln Gln Gly Asn Val Phe Ser
    530                 535                 540
Cys Ser Val Met His Glu Ala Leu His Asn His Tyr Thr Gln Lys Ser
545                 550                 555                 560
Leu Ser Leu Ser Pro Gly
                565

<210> SEQ ID NO 529
<211> LENGTH: 336
<212> TYPE: PRT
<213> ORGANISM: Artificial Sequence
<220> FEATURE:
<223> OTHER INFORMATION: Synthetic Construct

```
<400> SEQUENCE: 529

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Thr Ile Val His Ser
            20                  25                  30

Asn Ser Lys Thr Tyr Leu Glu Trp Tyr Leu Gln Lys Pro Gly Gln Ser
        35                  40                  45

Pro Gln Leu Leu Ile Tyr Lys Val Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110

Gly Gly Gly Gly Ser Gly Gly Gly Gly Ser Glu Ile Val Leu Thr Gln
        115                 120                 125

Ser Pro Asp Phe Leu Ser Val Thr Pro Lys Glu Lys Val Thr Leu Ser
    130                 135                 140

Cys Arg Ala Ser Gln Ser Ile Ser Asn Tyr Leu His Trp Tyr Gln Gln
145                 150                 155                 160

Lys Ser Asp Gln Ser Pro Lys Leu Leu Ile Lys Tyr Ala Ser Gln Ser
                165                 170                 175

Ile Ser Gly Ile Pro Ser Arg Phe Ser Gly Ser Gly Ser Gly Thr Asp
            180                 185                 190

Phe Thr Leu Ser Ile Asn Ser Val Glu Ala Glu Asp Ala Ala Thr Tyr
        195                 200                 205

Phe Cys Gln Gln Ser Lys Ser Trp Pro Arg Thr Phe Gly Gly Gly Thr
    210                 215                 220

Lys Leu Glu Ile Lys Arg Thr Val Ala Ala Pro Ser Val Phe Ile Phe
225                 230                 235                 240

Pro Pro Ser Asp Glu Gln Leu Lys Ser Gly Thr Ala Ser Val Val Cys
                245                 250                 255

Leu Leu Asn Asn Phe Tyr Pro Arg Glu Ala Lys Val Gln Trp Lys Val
            260                 265                 270

Asp Asn Ala Leu Gln Ser Gly Asn Ser Gln Glu Ser Val Thr Glu Gln
        275                 280                 285

Asp Ser Lys Asp Ser Thr Tyr Ser Leu Ser Ser Thr Leu Thr Leu Ser
    290                 295                 300

Lys Ala Asp Tyr Glu Lys His Lys Val Tyr Ala Cys Glu Val Thr His
305                 310                 315                 320

Gln Gly Leu Ser Ser Pro Val Thr Lys Ser Phe Asn Arg Gly Glu Cys
                325                 330                 335

<210> SEQ ID NO 530
<211> LENGTH: 559
<212> TYPE: PRT
<213> ORGANISM: Artificial Sequence
<220> FEATURE:
<223> OTHER INFORMATION: Synthetic Construct

<400> SEQUENCE: 530

Gln Val Gln Leu Val Gln Ser Gly Ala Glu Val Val Lys Pro Gly Ser
1               5                   10                  15

Ser Val Lys Val Ser Cys Glu Ala Ser Gly Phe Thr Phe Thr Asp Ser
```

-continued

```
                20                  25                  30
Val Ile Thr Trp Val Arg Gln Arg Pro Gly Gln Gly Leu Glu Trp Ile
            35                  40                  45
Gly Glu Ile Tyr Pro Gly Ser Gly Asn Phe Tyr Tyr Asn Glu Lys Phe
 50                  55                  60
Gln Gly Arg Val Thr Ile Thr Ala Asp Lys Ser Thr Ser Thr Ala Tyr
 65                  70                  75                  80
Met Glu Leu Ser Ser Leu Arg Ser Glu Asp Thr Ala Val Tyr Phe Cys
                85                  90                  95
Ala Met Arg Arg Ser Ser Trp Gly Gln Gly Thr Leu Val Thr Val Ser
            100                 105                 110
Ser Ser Glu Val Gln Leu Val Glu Ser Gly Gly Gly Leu Val Lys Pro
        115                 120                 125
Gly Gly Ser Leu Arg Leu Ser Cys Ala Ala Ser Gly Phe Thr Phe Ser
    130                 135                 140
Ser Tyr Thr Met Ser Trp Val Arg Gln Ala Pro Gly Lys Gly Leu Glu
145                 150                 155                 160
Trp Val Ala Ser Ile Ser Ser Gly Ser Asn Thr Tyr Tyr Pro Asp
                165                 170                 175
Ser Val Lys Gly Arg Phe Thr Ile Ser Arg Asp Asn Ala Lys Asn Asn
            180                 185                 190
Leu Tyr Leu Gln Met Asn Ser Leu Arg Ala Glu Asp Thr Ala Leu Tyr
        195                 200                 205
Tyr Cys Ala Arg Phe Asp Tyr Gly Ser Ser Leu Asp Ser Trp Gly Gln
    210                 215                 220
Gly Thr Leu Leu Thr Val Ser Ser Arg Thr Ala Ser Thr Lys Gly Pro
225                 230                 235                 240
Ser Val Phe Pro Leu Ala Pro Ser Ser Lys Ser Thr Ser Gly Gly Thr
                245                 250                 255
Ala Ala Leu Gly Cys Leu Val Lys Asp Tyr Phe Pro Glu Pro Val Thr
            260                 265                 270
Val Ser Trp Asn Ser Gly Ala Leu Thr Ser Gly Val His Thr Phe Pro
        275                 280                 285
Ala Val Leu Gln Ser Ser Gly Ser Leu Ser Ser Val Val Thr Val Pro
    290                 295                 300
Ser Ser Ser Leu Gly Thr Gln Thr Tyr Ile Cys Asn Val Asn His Lys
305                 310                 315                 320
Pro Ser Asn Thr Lys Val Asp Lys Lys Val Glu Pro Lys Ser Cys Asp
                325                 330                 335
Lys Thr His Thr Cys Pro Pro Cys Pro Ala Pro Glu Leu Leu Gly Gly
            340                 345                 350
Pro Ser Val Phe Leu Phe Pro Pro Lys Pro Lys Asp Thr Leu Met Ile
        355                 360                 365
Ser Arg Thr Pro Glu Val Thr Cys Val Val Val Asp Val Ser His Glu
    370                 375                 380
Asp Pro Glu Val Lys Phe Asn Trp Tyr Val Asp Gly Val Glu Val His
385                 390                 395                 400
Asn Ala Lys Thr Lys Pro Arg Glu Glu Gln Tyr Asn Asn Ala Ser Arg
                405                 410                 415
Val Val Ser Val Leu Thr Val Leu His Gln Asp Trp Leu Asn Gly Lys
            420                 425                 430
Glu Tyr Lys Cys Lys Val Ser Asn Lys Ala Leu Pro Ala Pro Ile Glu
        435                 440                 445
```

```
Lys Thr Ile Ser Lys Ala Lys Gly Gln Pro Arg Glu Pro Gln Val Tyr
        450                 455                 460

Thr Leu Pro Pro Ser Arg Asp Glu Leu Thr Lys Asn Gln Val Ser Leu
465                 470                 475                 480

Thr Cys Leu Val Lys Gly Phe Tyr Pro Ser Asp Ile Ala Val Glu Trp
                485                 490                 495

Glu Ser Asn Gly Gln Pro Glu Asn Asn Tyr Lys Thr Thr Pro Pro Val
                500                 505                 510

Leu Asp Ser Asp Gly Ser Phe Phe Lys Lys Leu Thr Val Asp Lys Ser
            515                 520                 525

Arg Trp Gln Gln Gly Asn Val Phe Ser Cys Ser Val Met His Glu Ala
        530                 535                 540

Leu His Asn His Tyr Thr Gln Lys Ser Leu Ser Leu Ser Pro Gly
545                 550                 555

<210> SEQ ID NO 531
<211> LENGTH: 338
<212> TYPE: PRT
<213> ORGANISM: Artificial Sequence
<220> FEATURE:
<223> OTHER INFORMATION: Synthetic Construct

<400> SEQUENCE: 531

Glu Ile Val Leu Thr Gln Ser Pro Asp Phe Leu Ser Val Thr Pro Lys
1               5                   10                  15

Glu Lys Val Thr Leu Thr Cys Arg Ala Ser Gln Ser Ile Gly Asn Asn
            20                  25                  30

Leu His Trp Tyr Gln Gln Lys Ser Asp Gln Ser Pro Lys Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Thr Ile Asn Ser Val Glu Ala
65                  70                  75                  80

Glu Asp Ala Ala Thr Tyr Phe Cys Gln Gln Ser Lys Ser Trp Pro Arg
                85                  90                  95

Thr Phe Gly Gly Gly Thr Lys Leu Glu Ile Lys Gly Gln Pro Lys Ala
            100                 105                 110

Ala Pro Asp Val Val Met Thr Gln Thr Pro Leu Ser Leu Ser Val Thr
        115                 120                 125

Pro Gly Gln Pro Ala Ser Ile Ser Cys Arg Ser Ser Gln Thr Ile Val
    130                 135                 140

His Ser Asn Ser Lys Thr Tyr Leu Glu Trp Tyr Leu Gln Lys Pro Gly
145                 150                 155                 160

Gln Ser Pro Gln Leu Leu Ile Tyr Lys Val Ser Asn Arg Phe Ser Gly
                165                 170                 175

Val Pro Asp Arg Phe Ser Gly Ser Gly Ser Gly Thr Asp Phe Thr Leu
            180                 185                 190

Lys Ile Ser Arg Val Glu Ala Glu Asp Val Gly Val Tyr Tyr Cys Phe
        195                 200                 205

Gln Gly Ser His Val Pro Leu Thr Phe Gly Ala Gly Thr Lys Leu Glu
    210                 215                 220

Ile Lys Thr Lys Gly Pro Ser Arg Thr Val Ala Ala Pro Ser Val Phe
225                 230                 235                 240

Ile Phe Pro Pro Ser Asp Glu Gln Leu Lys Ser Gly Thr Ala Ser Val
                245                 250                 255
```

Val Cys Leu Leu Asn Asn Phe Tyr Pro Arg Glu Ala Lys Val Gln Trp
            260                 265                 270

Lys Val Asp Asn Ala Leu Gln Ser Gly Asn Ser Gln Glu Ser Val Thr
            275                 280                 285

Glu Gln Asp Ser Lys Asp Ser Thr Tyr Ser Leu Ser Ser Thr Leu Thr
            290                 295                 300

Leu Ser Lys Ala Asp Tyr Glu Lys His Lys Val Tyr Ala Cys Glu Val
305                 310                 315                 320

Thr His Gln Gly Leu Ser Ser Pro Val Thr Lys Ser Phe Asn Arg Gly
            325                 330                 335

Glu Cys

<210> SEQ ID NO 532
<211> LENGTH: 559
<212> TYPE: PRT
<213> ORGANISM: Artificial Sequence
<220> FEATURE:
<223> OTHER INFORMATION: Synthetic Construct

<400> SEQUENCE: 532

Gln Val Gln Leu Val Gln Ser Gly Ala Glu Val Val Lys Pro Gly Ser
1               5                   10                  15

Ser Val Lys Val Ser Cys Glu Ala Ser Gly Phe Thr Phe Thr Asp Ser
            20                  25                  30

Val Ile Thr Trp Val Arg Gln Arg Pro Gly Gln Gly Leu Glu Trp Ile
        35                  40                  45

Gly Glu Ile Tyr Pro Gly Ser Gly Asn Phe Tyr Tyr Asn Glu Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Met Arg Arg Ser Ser Trp Gly Gln Gly Thr Leu Val Thr Val Ser
            100                 105                 110

Ser Ser Glu Val Gln Leu Val Glu Ser Gly Gly Gly Leu Val Gln Pro
        115                 120                 125

Gly Gly Ser Leu Arg Leu Ser Cys Ala Ala Ser Gly Phe Thr Phe Ser
130                 135                 140

Ser Tyr Thr Met Ser Trp Val Arg Gln Ala Pro Gly Lys Gly Leu Glu
145                 150                 155                 160

Trp Val Ala Thr Ile Ser Ser Gly Asp Asn Thr Tyr Tyr Pro Asp
            165                 170                 175

Ser Val Lys Gly Arg Phe Thr Ile Ser Arg Asp Asn Ser Lys Asn Thr
            180                 185                 190

Leu Tyr Leu Gln Met Ser Ser Leu Arg Ala Glu Asp Thr Ala Leu Tyr
        195                 200                 205

Tyr Cys Ala Arg Phe Asp Tyr Gly Ser Ser Leu Asp Ser Trp Gly Gln
    210                 215                 220

Gly Thr Thr Leu Thr Val Ser Ser Arg Thr Ala Ser Thr Lys Gly Pro
225                 230                 235                 240

Ser Val Phe Pro Leu Ala Pro Ser Ser Lys Ser Thr Ser Gly Gly Thr
                245                 250                 255

Ala Ala Leu Gly Cys Leu Val Lys Asp Tyr Phe Pro Glu Pro Val Thr
            260                 265                 270

```
Val Ser Trp Asn Ser Gly Ala Leu Thr Ser Gly Val His Thr Phe Pro
            275                 280                 285

Ala Val Leu Gln Ser Ser Gly Ser Leu Ser Ser Val Val Thr Val Pro
            290                 295                 300

Ser Ser Ser Leu Gly Thr Gln Thr Tyr Ile Cys Asn Val Asn His Lys
305                 310                 315                 320

Pro Ser Asn Thr Lys Val Asp Lys Lys Val Glu Pro Lys Ser Cys Asp
                325                 330                 335

Lys Thr His Thr Cys Pro Pro Cys Pro Ala Pro Glu Leu Leu Gly Gly
            340                 345                 350

Pro Ser Val Phe Leu Phe Pro Pro Lys Pro Lys Asp Thr Leu Met Ile
            355                 360                 365

Ser Arg Thr Pro Glu Val Thr Cys Val Val Val Asp Val Ser His Glu
370                 375                 380

Asp Pro Glu Val Lys Phe Asn Trp Tyr Val Asp Gly Val Glu Val His
385                 390                 395                 400

Asn Ala Lys Thr Lys Pro Arg Glu Glu Gln Tyr Asn Ala Ser Arg
                405                 410                 415

Val Val Ser Val Leu Thr Val Leu His Gln Asp Trp Leu Asn Gly Lys
            420                 425                 430

Glu Tyr Lys Cys Lys Val Ser Asn Lys Ala Leu Pro Ala Pro Ile Glu
            435                 440                 445

Lys Thr Ile Ser Lys Ala Lys Gly Gln Pro Arg Glu Pro Gln Val Tyr
            450                 455                 460

Thr Leu Pro Pro Ser Arg Asp Glu Leu Thr Lys Asn Gln Val Ser Leu
465                 470                 475                 480

Thr Cys Leu Val Lys Gly Phe Tyr Pro Ser Asp Ile Ala Val Glu Trp
            485                 490                 495

Glu Ser Asn Gly Gln Pro Glu Asn Asn Tyr Lys Thr Thr Pro Pro Val
            500                 505                 510

Leu Asp Ser Asp Gly Ser Phe Phe Lys Lys Leu Thr Val Asp Lys Ser
            515                 520                 525

Arg Trp Gln Gln Gly Asn Val Phe Ser Cys Ser Val Met His Glu Ala
            530                 535                 540

Leu His Asn His Tyr Thr Gln Lys Ser Leu Ser Leu Ser Pro Gly
545                 550                 555

<210> SEQ ID NO 533
<211> LENGTH: 338
<212> TYPE: PRT
<213> ORGANISM: Artificial Sequence
<220> FEATURE:
<223> OTHER INFORMATION: Synthetic Construct

<400> SEQUENCE: 533

Glu Ile Val Leu Thr Gln Ser Pro Asp Phe Leu Ser Val Thr Pro Gly
1               5                   10                  15

Glu Lys Val Thr Leu Thr Cys Arg Ala Ser Gln Ser Ile Ser Asn Tyr
            20                  25                  30

Leu His Trp Tyr Gln Gln Lys Ser Asp Gln Ser Pro Lys Leu Leu Ile
        35                  40                  45

Lys Tyr Ala Ser Gln Ser Ile Ser Gly Val Pro Ser Arg Phe Ser Gly
    50                  55                  60

Ser Gly Ser Gly Thr Asp Phe Thr Leu Thr Ile Ser Ser Val Glu Ala
65                  70                  75                  80
```

```
Glu Asp Phe Ala Thr Tyr Phe Cys Gln Gln Ser Lys Ser Trp Pro Arg
                 85                  90                  95

Thr Phe Gly Gly Gly Thr Lys Leu Glu Ile Lys Gly Gln Pro Lys Ala
            100                 105                 110

Ala Pro Asp Val Val Met Thr Gln Thr Pro Leu Ser Leu Ser Val Thr
            115                 120                 125

Pro Gly Gln Pro Ala Ser Ile Ser Cys Arg Ser Ser Gln Thr Ile Val
            130                 135                 140

His Ser Asn Ser Lys Thr Tyr Leu Glu Trp Tyr Leu Gln Lys Pro Gly
145                 150                 155                 160

Gln Ser Pro Gln Leu Leu Ile Tyr Lys Val Ser Asn Arg Phe Ser Gly
                165                 170                 175

Val Pro Asp Arg Phe Ser Gly Ser Gly Ser Gly Thr Asp Phe Thr Leu
            180                 185                 190

Lys Ile Ser Arg Val Glu Ala Glu Asp Val Gly Val Tyr Tyr Cys Phe
            195                 200                 205

Gln Gly Ser His Val Pro Leu Thr Phe Gly Ala Gly Thr Lys Leu Glu
            210                 215                 220

Ile Lys Thr Lys Gly Pro Ser Arg Thr Val Ala Ala Pro Ser Val Phe
225                 230                 235                 240

Ile Phe Pro Pro Ser Asp Glu Gln Leu Lys Ser Gly Thr Ala Ser Val
                245                 250                 255

Val Cys Leu Leu Asn Asn Phe Tyr Pro Arg Glu Ala Lys Val Gln Trp
            260                 265                 270

Lys Val Asp Asn Ala Leu Gln Ser Gly Asn Ser Gln Glu Ser Val Thr
            275                 280                 285

Glu Gln Asp Ser Lys Asp Ser Thr Tyr Ser Leu Ser Ser Thr Leu Thr
290                 295                 300

Leu Ser Lys Ala Asp Tyr Glu Lys His Lys Val Tyr Ala Cys Glu Val
            305                 310                 315                 320

Thr His Gln Gly Leu Ser Ser Pro Val Thr Lys Ser Phe Asn Arg Gly
                325                 330                 335

Glu Cys

<210> SEQ ID NO 534
<211> LENGTH: 5
<212> TYPE: PRT
<213> ORGANISM: Artificial Sequence
<220> FEATURE:
<223> OTHER INFORMATION: Synthetic Construct

<400> SEQUENCE: 534

Asp Lys Thr His Thr
1               5
```